US012796695B2

(12) United States Patent
Isoe et al.

(10) Patent No.: US 12,796,695 B2
(45) Date of Patent: Nov. 17, 2026

(54) COMPOSITIONS AND METHODS FOR MODULATING EGG DEVELOPMENT IN MOSQUITOES

(71) Applicant: Arizona Board of Regents on Behalf of The University of Arizona, Tucson, AZ (US)

(72) Inventors: Jun Isoe, Tucson, AZ (US); Roger Miesfeld, Tucson, AZ (US)

(73) Assignee: Arizona Board of Regents on Behalf of The University of Arizona, Tucson, AZ (US)

( * ) Notice: Subject to any disclaimer, the term of this patent is extended or adjusted under 35 U.S.C. 154(b) by 1542 days.

(21) Appl. No.: 17/289,590

(22) PCT Filed: Oct. 30, 2019

(86) PCT No.: PCT/US2019/058910

§ 371 (c)(1),
(2) Date: Apr. 28, 2021

(87) PCT Pub. No.: WO2020/092605

PCT Pub. Date: May 7, 2020

(65) Prior Publication Data

US 2021/0400988 A1 Dec. 30, 2021

Related U.S. Application Data

(60) Provisional application No. 62/752,880, filed on Oct. 30, 2018.

(51) Int. Cl.
*A01N 63/60* (2020.01)
*C12N 15/113* (2010.01)

(52) U.S. Cl.
CPC .......... *A01N 63/60* (2020.01); *C12N 15/1137* (2013.01); *C12N 2310/14* (2013.01); *C12N 2320/12* (2013.01)

(58) Field of Classification Search
CPC ........ A01N 63/60; A01N 57/16; A01N 25/26; C12N 15/1137; C12N 2310/14; C12N 2320/12; C12N 15/113
See application file for complete search history.

(56) References Cited

U.S. PATENT DOCUMENTS

| | | | |
|---|---|---|---|
| 5,034,506 A | 7/1991 | Summerton | |
| 5,487,994 A | 1/1996 | Chandrasegaran | |
| 5,506,337 A | 4/1996 | Summerton | |
| 5,786,571 A | 7/1998 | Bethel | |
| 7,067,617 B2 | 6/2006 | Barbas, III | |
| 7,868,222 B1 | 1/2011 | Dobson | |
| 8,080,648 B1 * | 12/2011 | Pridgeon | A01N 57/16 435/375 |
| 9,237,741 B2 | 1/2016 | Barrera | |
| 2007/0213269 A1 | 9/2007 | Barbas, III | |
| 2011/0145940 A1 | 6/2011 | Voytas | |
| 2016/0017529 A1 | 1/2016 | Kwak | |
| 2017/0051285 A1 * | 2/2017 | Paldi | A01K 67/68 |

FOREIGN PATENT DOCUMENTS

| | | |
|---|---|---|
| WO | 2002044321 | 7/2001 |
| WO | 2003016496 | 8/2002 |
| WO | 2011072246 | 6/2011 |
| WO | 2014018423 | 1/2014 |

OTHER PUBLICATIONS

Hammond, A. et al. "A CRISPR-Cas9 gene drive system targeting female reproduction in the malaria mosquito vector *Anopheles gambiae*". Nature Biotechnology, vol. 34, No. 1 (Jan. 2016), pp. 78-83) (Year: 2016).*

Hammond, A. et al. "A CRISPR-Cas9 gene drive system targeting female reproduction in the malaria mosquito vector *Anopheles gambia*". Nature Biotechnology, vol. 34 (2016), pp. 78-83. (Year: 2016).*

LeMosy, E.K. et al. "The Nudel protease is required for eggshell biogenesis in addition to embryonic patterning". Developmental Biology, vol. 217 (2000), pp. 352-361. (Year: 2000).*

Bryant, B. et al. "microRNA miR-275 is indispensable for blood digestion and egg development in the mosquito *Aedes aegypti*" Proceedings of the National Academy of Sciences USA, vol. 107 (2010), pp. 22391-22398. (Year: 2010).*

XM_021855380.1; NCBI reference sequence XM_021855380.1, Aedes aegypti uncharacterized LOC5576092, transcript variant X1, mRNA, published Jul. 20, 2017. (Year: 2017).*

Marangos, P. et al. "Prophase I arrest and progression to metaphase I in mouse oocytes are controlled by Emi1dependent regulation of APC-Cdh1." Journal of Cell Biology , vol. 176, No. 1 (2007), pp. 65-75. (Year: 2007).*

Shoji, S. et al. "The zinc-binding region (ZBR) fragment of Emi2 can inhibit APC/C by targeting its association with the coactivator Cdc20 and UBE2C-mediated ubiquitylation." FEBS. Openbio, vol. 4 (2014), pp. 689-703. (Year: 2014).*

Zhu,K. Y. et al. "Mechanisms, applications, and challenges of insect RNA interference". Annual Review of Entomology, vol. 65 (2020), pp. 293-311. (Year: 2020).*

(Continued)

*Primary Examiner* — Nancy J Leith
*Assistant Examiner* — Alexandra Geraldine Dace Denito
(74) *Attorney, Agent, or Firm* — Pabst Patent Group LLP

(57) ABSTRACT

Compositions and methods for reducing or inhibiting mosquito egg development are provided. Typically, the compositions include an effective amount of a compound that reduces or inhibits expression of a mosquito EOF1, Nasrat, Closca, Polehole Nudel, CATL3, DCE2, DCE4, or DCE5 gene, or a gene product thereof, for example EOF1 or Nudel mRNA or protein. The compound can be a functional nucleic acid such as antisense molecule, siRNA, miRNA, ribozymes, RN Ai, or external guide sequences, a gene editing composition, or a protease inhibitor. The disclosed methods typically include contacting mosquito cells with an effective amount of one or more of the disclosed compositions, and can be used to reduce or inhibit, egg development in an effective number of mosquitoes to reduce transmission of one or more infections or diseases.

13 Claims, 13 Drawing Sheets

Specification includes a Sequence Listing.

(56) References Cited

OTHER PUBLICATIONS

Vogel, E. et al. "RNA interference in insects: protecting beneficials and controlling pests". Frontiers in Physiology, vol. 9 (2019), p. 1912. (Year: 2019).*
Lam, J.K.W. et al. "siRNA versus miRNA as therapeutics for gene silencing". Molecular Therapy—Nucleic Acids, vol. 4 (2015), p. e252. (Year: 2015).*
Huang, Y-J. S. et al. "Biological control strategies for mosquito vectors of arboviruses". Insects, vol. 8 (2017), p. 21. (Year: 2017).*
PDF-NCBI-Aedes aegypti major royal jelly protein 5 (LOC5574004), mRNA-NCBI Reference Sequence: XM_021842318.1; Jul. 20, 2017. (Year: 2017).*
Adams, et al., "The genome sequence of *Drosophila melanogaster*", Science, 287(5461):2185-2195 (2000).
Airs, et al., "RNA Interference for Mosquito and Mosquito-Borne Disease Control", Insects, 8(1): 4 (2017); doi: 10.3390/insects8010004.
Alabaster, et al., "Deficiencies in acetyl-CoA carboxylase and fatty acid synthase 1 differentially affect eggshell formation and blood meal digestion in Aedes aegypti", Insect Biochem. Mol. Biol., 41(12):946-55 (2011).
Amenya, et al., "Proteomics reveals novel components of the Anopheles gambiae eggshell", J. Insect. Physiol., 56(10):1414-1419 (2010).
Aryan, et al., "Targeted genome editing in Aedes aegypti using TALENs", Methods, 69(1): 38-45 (2014).
Aryan et al., "Germline excision of transgenes in Aedes aegypti by homing endonucleases", Sci. Rep., 3:1603 (2013).
Benelli, et al., "Declining malaria, rising of dengue and Zika virus: insights for mosquito vector control", Parasitol Res., 115(5):1747-54 (2016).
Bhatt, et al., "The global distribution and burden of dengue", Nature, 496(7446):504-507 (2013).
Braasch, et al., "Locked nucleic acid (LNA): fine-tuning the recognition of DNA and RNA", Chem. Biol., 8(1):1-7 (2001).
Brown, et al., "Influence of the Length of Storage on *Aedes aegypti* (Diptera: Culicidae) Egg Viability", J. Med. Entomol., 54(2):489-491 (2016).
Carroll, "Genome engineering with targetable nucleases", Annu. Rev. Biochem., 83:409-439 (2014).
Cermak, et al., "Efficient design and assembly of custom TALEN and other TAL effector-based constructs for DNA targeting", Nucl. Acids Res., 39(12):e82 (2011); doi: 10.1093/nar/gkr218.
Clifton, et al., "Nutrient limitation results in juvenile hormone-mediated resorption of previtellogenic ovarian follicles in mosquitoes", J. Insect Physiol., 57(9):1274-1281 (2011).
Cong, "Multiplex genome engineering using CRISPR/Cas systems", Science, 15:339(6121):819-823 (2013).
Dandapani, et al., "Selecting, Acquiring, and Using Small Molecule Libraries for High-Throughput Screening", Curr. Protoc. Chem. Biol., 4:177-191 (2012).
Degennaro, et al., "orco mutant mosquitoes lose strong preference for humans and are not repelled by volatile Deet", Nature, 498(7455):487-491 (2013).
Edwards, et al., "Vitelline envelope genes of the yellow fever mosquito, *Aedes aegypti*", Insect Biochem Mol. Biol., 28(12):915-925 (1998).
Elbashir, et al., "RNA interference is mediated by 21and 22-nucleotide RNAs", Genes & Dev., 15:188-200 (2001a).
Elbashir, et al., "Duplexes of 21-nucleotide RNAs mediate RNA interference in cultured mammalian cells", Nature, 411(6836):494 498 (2001b).
Fakhouri, et al., "Minor proteins and enzymes of the *Drosophilia* eggshell matrix", Dev. Biol., 293(1):127-141 (2006).
Fang, et al., "Functional Expression and Characterization of Aedes aegypti Dopachrome Conversion Enzyme", Biochem. Biophys. Res. Commun., 290(1):287-293 (2002).
Fauci, et al., "Zika Virus in the Americas—Yet Another Arbovirus Threat", N. Engl. J. Med., 374(7):601-604 (2016).
Gantz, et al., "Highly efficient Cas9-mediated gene drive for population modification of the malaria vector mosquito *Anopheles stephensi*", PNAS, 112(49):E6736-E3743 (2015).
GenBank Accession: JO874789, "TSA: Aedes albopictus Aalb_ooctyte_rep_c529 mRNA sequence", retrieved from internet <https://www.ncbi.nlm.nih.gov/nuccore/JO874789> retrieved Feb. 7, 2020.
Grigoraki, et al., "Striking diflubenzuron resistance in Culex pipiens, the prime vector of West Nile Virus", Sci. Rep. 7(1):11699 (2017).
Hall, et al., "Sex Determination. A male-determining factor in the mosquito *Aedes aegypti*", Science, 348(6240):1268-70 (2015).
Hammond, et al., "A CRISPR-Cas9 gene drive system targeting female reproduction in the malaria mosquito vector *Anopheles gambiae*", Nature Biotechnology, 34(1):78-83 (2016).
Hammond, et al., "The creation and selection of mutations resistant to a gene drive over multiple generations in the malaria mosquito", PLoS Genet., 13(10):e1007039 (2017).
Hannon, "RNA interference", Nature, 418(6894):244-51 (2002).
Holt, et al., "The genome sequence of the malaria mosquito *Anopheles gambiae*", Science, 298(5591):129-149 (2002).
Isoe, et al., "Xanthine dehydrogenase-1 silencing in Aedes aegypti mosquitoes promotes a blood feeding-induced adulticidal activity", FASEB J, 31(6):2276-2286 (2017).
Isoe, et al., "COPI-mediated blood meal digestion in vector mosquitoes is independent of midgut ARF-GEF and ARF-GAP regulatory activities", Insect Biochem. Mol. Biol., 43(8):732-739 (2013).
Itokawa, et al., "Testing the causality between CYP9M10 and pyrethroid resistance using the TALEN and CRISPR/Cas9 technologies", Sci. Rep., 6:24652 (2016).
Jinek, et al., "A programmable dual-RNA-guided DNA endonuclease in adaptive bacterial immunity", Science, 337(6096):816-21 (2012).
Kim, et al., "Insertion and Deletion Mutants of Fokl Restriction Endonuclease", J. Biol. Chem., 269(50):31978-31982 (1994).
Kistler, et al., "Genome Engineering with CRISPR-Cas9 in the Mosquito *Aedes aegypti*", Cell Rep., 11(1):51-60 (2015).
Koch, et al., "Molecular and Biochemical Characterization of Chorion Peroxidases During Eggshell Formation in Aedes aegypti", The University of Arizona, 28 pages (2017).
Li, et al., "Egg chorion tanning in Aedes aegypti mosquito", Comp. Biochem. Physiol., 109(4):835-843 (1994).
Li, et al., "Major chorion proteins and their crosslinking during chorion hardening in Aedes aegypti mosquitoes", Insect Biochem. Mol. Biol., 36(12):954-964 (2006).
Li, et al., "Characterization of N-linked oligosaccharides in chorion peroxidase of Aedes aegypti mosquito", Protein Sci., 14(9):2370-2386 (2005).
Lobo, et al., "Germ line transformation of the yellow fever mosquito, *Aedes aegypti*, mediated by transpositional insertion of a piggyBac vector", Insect Mol. Biol., 11(2): 133-139 (2002).
Mathews, "A genetically modified organism could end malaria and save millions of lives—if we decide to use it" VOX (2018); ; retrieved from https://www.vox.com/science-and-health/2018/5/31/17344406/crispr-mosquito-malaria-gene-drive-editing-target-africa-regulation-gmo.
Marinotti, et al., "Development of a population suppression strain of the human malaria vector mosquito, *Anopheles stephensi*", Malar J., 12:142 (2011).
Marinotti, et al., "Integrated proteomic and transcriptomic analysis of the Aedes aegypti eggshell", BMC Dev. Biol., 14:15 (2014); retrieved from https://www.vox.com/science-and-health/2018/5/31/17344406/crispr-mosquito-malaria-gene-drive-editing-target-africa-regulation-gmo.
Martinez, et al., "Single-stranded antisense siRNAs guide target RNA cleavage in RNA", Cell, 110(5):563-74 (2002).
Mazzalupo, et al., "Effective disposal of nitrogen waste in blood-fed Aedes aegypti mosquitoes requires alanine aminotransferase", FASEB J, 30(1):111-120 (2016).
Mcmeniman, et al., "Multimodal integration of carbon dioxide and other sensory cues drives mosquito attraction to humans", Cell, 156(1):1060-1071 (2014).
Miller, et al., "A TALE nuclease architecture for efficient genome editing", Nature Biotechnol., 29(2):143-8 (2011).
Murray, et al., "Epidemiology of dengue: past, present and future prospects", Clin. Epidemiol., 5:299-309 (2013).

(56) References Cited

OTHER PUBLICATIONS

Needleman, et al., "A general method applicable to the search for similarities in the amino acid sequence of two proteins", J. Mol. Biol., 48(3):443-453 (1970).

Nene, et al., "Genome sequence of Aedes aegypti, a major arbovirus vector", Science, 316(5832):1718-1723 (2007).

Nykanen, et al., "ATP requirements and small interfering RNA structure in the RNA interference pathway", Cell, 107(3):309-21 (2001).

Raikhel, et al., "Molecular biology of mosquito vitellogenesis: from basic studies to genetic engineering of antipathogen immunity", Insect Biochem. Mol. Biol., 32(10):1275-1286 (2002).

Sandersjoo, et al., "Protease substrate profiling using bacterial display of self-blocking affinity proteins and flow-cytometric sorting", Biotechnol J., 12(1)::1600365 (2016); doi: 10.1002/BIOT.201600365.

Scaraffia, et al., "Discovery of an alternate metabolic pathway for urea synthesis in adult Aedes aegypti mosquitoes", PNAS, 105(2):518-523 (2008).

Stoddard, "Homing endonucleases from mobile group I introns: discovery to genome engineering", Mob. DNA., 5(1):7 (2014).

Suman, et al., "Differentiation of *Aedes aegypti* and *Aedes albopictus* (Diptera: Culicidae) with egg surface morphology and morphometrics using scanning electron microscopy", Arthropod. Struct. Dev., 40(5):479-483 (2011).

UniProKitB: AAEL012336-PA, "Aedes aegypti", Jul. 25, 2005, retrieved online <www.uniprot.org/uniprot/Q16ME2> retrieved on Feb. 17, 2020.

Uchida, et al., "Follicular epithelial cell apoptosis of atretic follicles within developing ovaries of the mosquito *Culex pipiens pallens*", J. Insect Physiol., 50(10):903-912 (2004).

Wang, et al., "Roles of F-box proteins in cancer", Nat. Rev. Cancer, 14(4):233-247 (2014).

International Search Report for PCT application PCT/US2019/58910 dated Mar. 9, 2020.

* cited by examiner

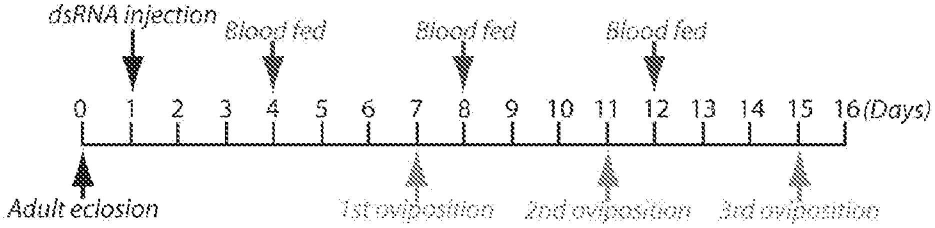
FIG. 2A
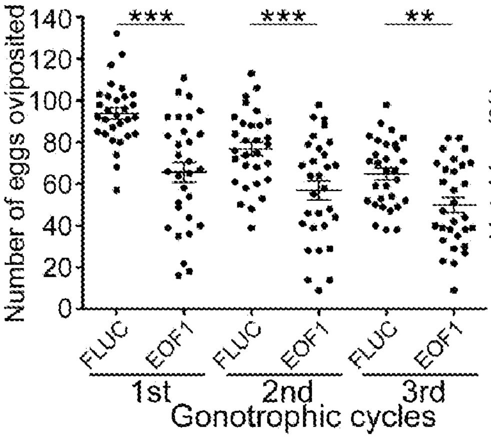
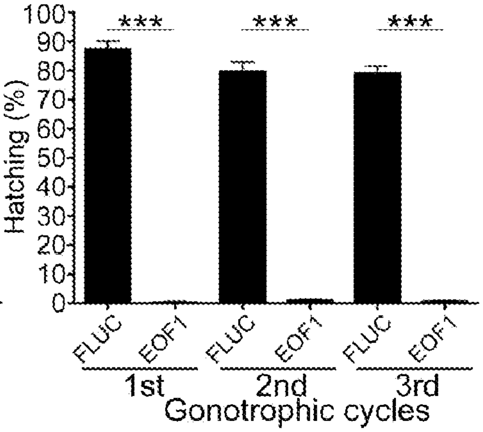
FIG. 2B
FIG. 2C
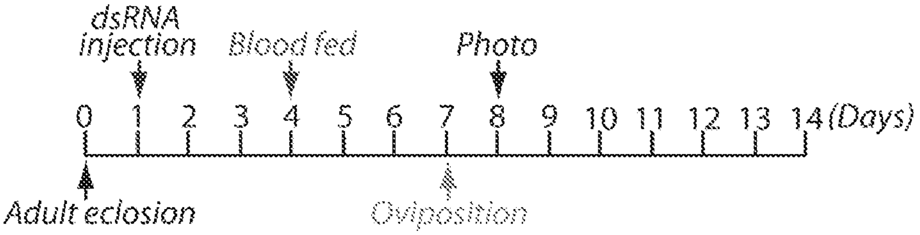
FIG. 2D
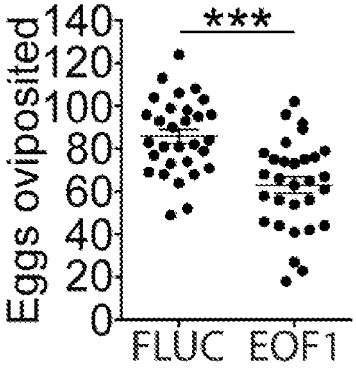
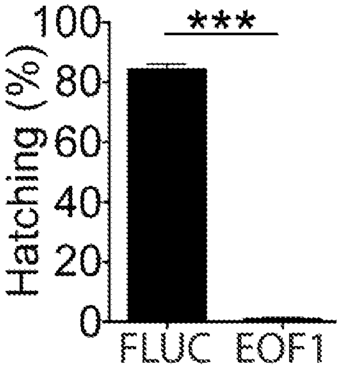
FIG. 2E
FIG. 2F

COMPOSITIONS AND METHODS FOR MODULATING EGG DEVELOPMENT IN MOSQUITOES

CROSS-REFERENCE TO RELATED APPLICATION

This application is a National Phase application under 35 U.S.C. § 371 of PCT/US2019/058910, filed Oct. 30, 2019, which claims the benefit of and priority to U.S. Provisional Application No. 62/752,880 filed Oct. 30, 2018, which are hereby incorporated by reference in their entireties.

REFERENCE TO SEQUENCE LISTING

The Sequence Listing submitted as a text file named "UA_18_216_PCT_ST25.txt," created on Oct. 30, 2019, and having a size of 474,688 bytes is hereby incorporated by reference pursuant to 37 C.F.R. § 1.52(e)(5).

FIELD OF THE INVENTION

The present invention relates to compounds and compositions for controlling mosquitoes, and methods of making and using thereof.

BACKGROUND OF THE INVENTION

Developing new strategies for vector control is becoming increasingly important as worldwide cases of *Aedes aegypti*-transmitted dengue and Zika virus infections have risen dramatically in the last decade (Murray, et al., *Clin Epidemiol* 5:299-309 (2013), Bhatt S, et al. Nature 496(7446): 504-507 (2013), Fauci, et al., *N Engl J Med* 374(7):601-604 (2016)). Metabolic regulation of blood meal metabolism in *Ae. aegypti* mosquitoes is being investigated as a strategy for identifying new protein targets that could be exploited for vector control (Isoe, et al., *Proc Natl Acad Sci USA,* 108 (24):E211-217 (2011), Isoe, et al., *Insect Biochem Mol Biol,* 39(12):903-912 (2009), Scaraffia, et al., *Proc Natl Acad Sci USA,* 105(2):518-523 (2008), Brandon, et al., *Insect Biochem Mol Biol,* 38(10):916-922 (2008), Alabaster, et al., *Insect Biochem Mol Biol,* 41(12):946-55 (2011), Rascon, et al., *BMC Biochem,* 12:43 (2011), Zhou, et al., *PLoS One,* 6(3):e18150 (2011), Isoe, et al., *Insect Biochem Mol Biol,* 43(8):732-739 (2013), Isoe, et al., *PLoS One,* 8(6):e65393 (2013), Mazzalupo, et al., *FASEB J,* 30(1):111-120 (2016), Isoe, et al., *FASEB J,* 31(6):2276-2286 (2017)). The approach has focused on biochemical processes that are likely to be required for completion of the gonotrophic cycle in blood-fed mosquitoes based on what is known about mosquito biology and metabolic regulation in other organisms. Specific genes in these chosen pathways were then systematically knocked down by microinjection of double-stranded RNA (dsRNA), and the resulting phenotypes were characterized in detail by molecular and biochemical approaches.

Other strategies for vector control include use of devices for the capture, detection, and control of insect vectors such as autocidal gravid ovitraps (see e.g., U.S. Pat. No. 9,237,741) and methods for artificially infecting mosquitoes to control the reproduction capability of the population (see e.g., U.S. Pat. No. 7,868,222). See also Pates H. and Curtis C., *Annu Rev Entomol.,* 50:53-70 (2005); Benelli G. and Mehlhorn H., *Parasitol Res.,* 115(5):1747-54 (2016); and Benelli G., *Parasitol Res.,* 114(8):2801-5 (2015).

The insect eggshell is important as a protective layer for embryonic development. Follicle development and eggshell formation in the *Ae. aegypti* mosquito are tightly regulated in response to blood feeding (Hagedorn, et al., *J Insect Physiol* 23(2):203-206 (1977), Lea, et al., *Physiol Entomol* 3(4):309-316 (1978), Clements, et al., *Physiol Entomol* 9(1):1-8 (1984), Raikhel, et al., *Insect Biochem Mol Biol* 32(10):1275-1286 (2002), Uchida, et al., *J Insect Physiol* 50(10):903-912 (2004), Clifton, et al., *J Insect Physiol* 57(9):1274-1281 (2011)). Once female mosquitoes acquire blood, follicle development is initiated via accumulation of vitellogenin yolk proteins. Mosquitoes contain ~100 ovarioles per ovary, which are composed of primary and secondary follicles and a germarium, and the ovarian follicles develop synchronously throughout oogenesis. A single layer of follicular epithelial cells surrounding the oocyte is mainly responsible for secreting a majority of eggshell structural components. The mosquito eggshell is made from different types of proteins including structural proteins, enzymes, odorant binding proteins, uncharacterized proteins of unknown function. *Ae. aegypti* eggshell melanization proteins were identified more than 20 years ago (Li, et al., *Comp Biochem Physiol* 109(4):835-843 (1994)), and several key eggshell enzymes have been well characterized (Ferdig, et. al., *Insect Mol Biol* 5(2):119-126 (1996), Han, et al., *Arch Biochem Biophys* 378(1):107-115 (2000), Johnson, et al., *Insect Biochem Mol Biol,* 31(11):1125-1135 (2001), Fang, et al., *Biochem Biophys Res Commun* 2002, 290(1):287-293 (2002), Kim, et al., *Insect Mol Biol* 14(2):185-194 (2005), Li, et al., *Protein Sci* 14(9):2370-2386 (2005), Li, et al., *Insect Biochem Mol Biol* 36(12):954-964 (2006)). Moreover, proteomic studies have been performed on purified mosquito eggshells to identify most of the abundant protein components (Amenya, et al., *J Insect Physiol,* 56(10):1414-1419 (2010), Marinotti, et al., *BMC Dev Biol* 2014, 14:15 (2014)). However, these descriptive studies have not identified essential eggshell proteins that are required for embryonic development.

Genomic sequences of *Drosophila melanogaster* (Adams, et al., *Science* 287(5461):2185-2195 (2000)), *Anopheles gambiae* (Holt, et al., *Science* 298(5591):129-149 (2002)), *Ae. aegypti* (Nene, et al., *Science* 316(5832):1718-1723 (2007)), and *Culex quinquefasciatus* (Arensburger, et al., *Science* 330(6000):86-88) have been completed. Many predicted putative proteins identified in the genome of mosquitoes are homologous to proteins of known function studied in other organisms. Proteins that are conserved in a wide variety of organisms are not ideal target molecules as vector control agents because of deleterious effects on non-target organisms, such as vertebrates, pollinating agricultural insects, and beneficial predators.

Mosquito-borne pathogens infect millions of people worldwide, and increasing insecticide resistance exacerbates this problem. A new generation of environmentally safe insecticides will be important to control insecticide-resistant mosquitoes (Marinotti, et al., *Anopheles stephensi.* Malar J. 12:142 (2011). As such, there is a growing demand for the identification of important proteins responsible for mosquito reproduction.

Thus, it is an object of the invention to provide compositions and methods for identifying mosquito-specific proteins important for embryonic development in *Ae. aegypti* mosquitoes, and compositions and methods for reducing expression or activity of these proteins in mosquitoes.

SUMMARY OF THE INVENTION

Compositions and methods for reducing or preventing mosquito embryos from completing embryogenesis and/or reaching the first larval instar, reducing, delaying, or otherwise disrupting eggshell formation and/or egg melanization, reducing egg survival, altering the follicular shape of eggs, increasing permeability of oocytes to water, reducing female fecundity, increasing an embryonic lethal phenotype, or any combination thereof are provided. The compositions can, for example, include an effective amount of a compound or compounds that reduces, inhibits, or prevents expression or activity of an eggshell formation, melanization, and/or crosslinking pathway having a mosquito Eggshell Organizing Factor 1 (EOF1) protein therein. In some embodiments, the pathway further includes one or more proteins selected from Nasrat, Closca, Polehole, Nudel, CATL3, DCE2, DCE4, and DCE5 therein.

Typically, the compositions include an effective amount of a compound that reduces, inhibits, or prevents expression and/or activity of a mosquito target gene selected from Eggshell Organizing Factor 1 (EOF1), Nasrat, Closca, Polehole, Nudel, CATL3, DCE2, DCE4, and DCE5, or a combination, or a gene product thereof, for example EOF1, Nasrat, Closca, Polehole, Nudel, CATL3, DCE2, DCE4, or DCE5 mRNA or EOF1 Nasrat, Closca, Polehole, Nudel, CATL3, DCE2, DCE4, or DCE5 protein. In preferred embodiments, the compound reduces, inhibits, or prevents expression and/or activity of a mosquito target gene selected from the group consisting of Eggshell Organizing Factor 1 (EOF1), Nasrat, Closca, Polehole, or Nudel, or a gene product thereof.

The EOF1 gene can, for example, encode the protein AAEL012336 (*Aedes aegypti*) (Genbank Accession number: EAT35499), or a homologous protein from another species of mosquito with at least 70, 75, 80, 85, 90, 95, 96, 97, 98, or 99 percent sequence identity to the protein AAEL012336 (*Aedes aegypti*) (Genbank Accession number: EAT35499).

The Nasrat gene can, for example, encode the protein AAEL008829 (*Aedes aegypti*) (Genbank Accession number: EAT39370), or a homologous protein from another species of mosquito with at least 70, 75, 80, 85, 90, 95, 96, 97, 98, 99 percent sequence identity to the protein AAEL008829 (*Aedes aegypti*) (Genbank Accession number: EAT39370.

The Closca gene can, for example, encode the protein AAEL000961 (*Aedes aegypti*) (Genbank Accession number: EAT47957), or a homologous protein of another species of mosquito with at least 70, 75, 80, 85, 90, 95, 96, 97, 98, 99 percent sequence identity to the protein AAEL000961 (*Aedes aegypti*) (Genbank Accession number: EAT47957).

The Polehole gene can, for example, encode the protein AAEL022628 (*Aedes aegypti*) (Genbank Accession number: EAT33906), or a homologous protein of another species of mosquito with at least 70, 75, 80, 85, 90, 95, 96, 97, 98, 99 percent sequence identity to the protein AAEL022628 (*Aedes aegypti*) (Genbank Accession number: EAT33906).

The Nudel gene can, for example, encode the protein AAEL016971 (*Aedes aegypti*) (Genbank Accession number: EJY57924), or a homologous protein of another species of mosquito with at least 70, 75, 80, 85, 90, 95, 96, 97, 98, 99 percent sequence identity to the protein AAEL016971 (*Aedes aegypti*) (Genbank Accession number: EJY57924).

The CATL3 gene can, for example, encode the protein AAEL002196 (*Aedes aegypti*) (Genbank Accession number: EAT46597), or a homologous protein of another species of mosquito with at least 70, 75, 80, 85, 90, 95, 96, 97, 98, 99 percent sequence identity to the protein AAEL002196 (*Aedes aegypti*) (Genbank Accession number: EAT46597).

The DCE2 gene can, for example, encode the protein AAEL006830 (*Aedes aegypti*) (Genbank Accession number: EAT41553), or a homologous protein of another species of mosquito with at least 70, 75, 80, 85, 90, 95, 96, 97, 98, 99 percent sequence identity to the protein AAEL006830 (*Aedes aegypti*) (Genbank Accession number: EAT41553).

The DCE4 gene can, for example, encode the protein AAEL007096 (*Aedes aegypti*) (Genbank Accession number: EAT41240), or a homologous protein of another species of mosquito with at least 70, 75, 80, 85, 90, 95, 96, 97, 98, 99 percent sequence identity to the protein AAEL007096 (*Aedes aegypti*) (Genbank Accession number: EAT41240). The DCE5 gene can, for example, encode the protein AAEL010848 (*Aedes aegypti*) (Genbank Accession number: EAT37145), or a homologous protein of another species of mosquito with at least 70, 75, 80, 85, 90, 95, 96, 97, 98, 99 percent sequence identity to the protein AAEL010848 (*Aedes aegypti*) (Genbank Accession number: EAT37145).

In some embodiments, the compound is a functional nucleic acid or a vector encoding a functional nucleic acid, or a gene editing composition or a vector encoding a gene editing composition. Functional nucleic acids include, for example, antisense molecules, siRNA, miRNA, ribozymes, RNAi, and external guide sequences. Exemplary gene editing compositions include, for example, CRISPR/Cas systems, Zinc Figure Nucleases, Transcription Activator-Like Effector Nucleases, triplex forming molecules, and donor oligonucleotides.

In some embodiments, the compound is a functional nucleic acid, particularly RNAi, e.g., double stranded RNAi, that targets an mRNA encoding the EOF1, Nasrat, Closca, Polehole, Nudel, CATL3, DCE2, DCE4, or DCE5 protein (e.g., any one of SEQ ID NOS:1, 183-190, or 200-219, or a sequence at least 85%, 90%, or 95% identical thereto). In particular embodiments, the composition is a functional nucleic acid, particularly RNAi, e.g., double stranded RNAi, that targets the mRNA corresponding to or encoded by the DNA sequence of any one of SEQ ID NOS:191-199 or 220-247, or a sequence at least 85%, 90%, or 95% identical thereto.

It is believed that Nudel serine protease associates with the Nasrat, Closca, and Polehole structural proteins in a common pathway that is itself controlled by EOF1, and that protease inhibitors that target Nudel can be used to control mosquito populations. Thus, in some embodiments, the compound is a protease inhibitor such as, but not limited to, a protein, a peptide, or small molecule. In preferred embodiments, the inhibitor is specific for a mosquito nudel. In some embodiments, the inhibitor is specific for *A. aegypti* mosquito nudel.

In some embodiments, the composition includes a biotic or abiotic system that mediates protection and/or uptake of the compound. For example, in some embodiments, the compound is expressed by a viral expression system, bacterial expression system, or yeast expression system. In some embodiments, the compound is encapsulated or dispersed in nanoparticles or microparticles. The particles can be, for example, polymeric or liposomal. The composition can include a carrier optionally including one or more additional inert ingredients.

The disclosed methods typically include contacting mosquito cells with an effective amount of one or more of the disclosed compositions. The mosquito cells are typically contacted in vivo in one or more adult, larvae, pupae, or embryonic mosquitoes. In some embodiments, the composition is administered in a manner suitable to reduce, inhibit, or prevent expression of the EOF1, Nasrat, Closca, Polehole, Nudel, CATL3, DCE2, DCE4, and/or DCE5 gene or a gene product thereof at least a few days, for example 2 days, 3 days, 4 days, or 5 days, prior to blood feeding in the first and/or second gonotrophic cycles; one day, two days, three days, or more after oviposition; or a combination thereof of in adult female mosquitoes.

In some embodiments, the mosquitoes contact a surface, such as water or vegetation or bait, previously treated with the composition and thereby contact the composition. The composition can also be administered by impregnated bed nets, spraying, and/or direct application to a water source.

In some embodiments, expression of the EOF1, Nasrat, Closca, Polehole, Nudel, CATL3, DCE2, DCE4, or DCE5 gene or a product thereof is reduced, inhibited, or prevented in an effective number of mosquitoes to reduce transmission of one or more infections or diseases such as West Nile Virus, La Crosse Encephalitis, Jamestown Canyon Virus, Western Equine Encephalitis, Eastern Equine Encephalitis, St. Louis Encephalitis, Chikungungya, Dengue Fever, Malaria, Yellow Fever, Zika Virus, or a combination thereof in, for example, humans.

Methods of identifying mosquito-specific target genes are also provided. The methods can include, for example, data mining and bioinformatic analysis to identify putative protein-coding and non-protein coding gene sequences that are only present in the genomes of one or more mosquitoes. In some embodiments, the cut-off for expected value threshold of, for example, about 1e−15 is used. The putative protein-coding gene sequences can be selected if a corresponding mRNA or orthologue thereof is present in a mosquito expressed sequence tag (EST) or expressed transcriptome shotgun assembly (TSA) database. In some embodiments, the gene sequences are further selected if they are not part of a multigene family, there is no corresponding homologue in one or more of phantom midges, true midges, crane fly, and sandflies within the suborder Nematocera, or a combination thereof.

Selected genes can be screened for activity. For example, functional nucleic acids designed to reduce, inhibit or prevent expression of the selected gene sequences or products thereof can be contacted with a mosquito. In some embodiments, the gene sequences are further selected when the functional nucleic acid causes a desirable phenotype in the mosquito. The desirable phenotype can be associated with, for example, morphogenesis, olfaction for host seeking, oviposition, blood feeding, digestion, reproduction, fertility, fecundity, embryogenesis, survival, insecticide resistance, larval development, pupal development, emergence, pathogen uptake, development, transmission, and combinations thereof.

Methods of identifying inhibitors of the disclosed proteins are also provided. In some embodiments, the protein is an enzyme, for example a mosquito Nudel, CATL3, and DCE2. The screen can include, for example, contacting a putative inhibitor with the enzyme in the presence and absence of a substrate of the enzyme, and selecting the putative inhibitor when activity of the enzyme's activity for the substrate is reduced in the presence of the inhibitor compared to the enzyme's activity for the substrate in the absence of the inhibitor. The steps can be repeated with a plurality of putative inhibitors. In some embodiments, the screen is a high throughput screen. The screen can be automated.

In some embodiments, the methods further include testing selected putative inhibitors in one or more in vitro or in vivo assay measuring eggshell formation, melanization, cross-linking or another egg development assay in mosquitoes. The putative inhibitor can be selected, for example, when it phenocopies an RNAi of one or more of EOF1, Nasrat, Closca, Polehole Nudel, CATL3, DCE2, DCE4, or DCE5. In some embodiments, The method the putative has little or more phenotypic effect on mammals, other insects, or a combination thereof, or the cells or proteins thereof, in the same or similar assays.

BRIEF DESCRIPTION OF THE DRAWINGS

FIG. 2A is a schematic diagram of experimental time course for dsRNA microinjection, blood feeding, and oviposition in the first three gonotrophic cycles. FIGS. 2B and 2C are bar graphs showing the effect of RNAi-EOF1 or -Fluc control on fecundity (2B) and viability (2C) according to the experimental scheme of 2A. FIG. 2D is a schematic diagram of experimental time course for dsRNA microinjection, blood feeding, and oviposition where microjection occurs one day after adult eclosion. FIGS. 2E and 2F are bar graphs showing the effect of RNAi-EOF1 or -Fluc control on fecundity (2E) and viability (2F) according to the experimental scheme of 2D.

FIG. 9A is a bar graph showing the effect of RNAi-Nasrat, -Closca, Polehole, -Nudel or -Fluc control on egg melanization. The assay was performed using follicles isolated from the indicated RNAi mosquitoes at 96 hours PBM Timing of dsRNA microinjection and blood feeding was identical to that shown in FIG. 5A. The follicles were photographed 5, 70 and 120 min after follicle dissection. Each bar corresponds to mean percentage egg melanization from 5 individual mosquitoes. The mean±SEM are shown as horizontal lines. Statistical significance is represented by stars above each column (unpaired student's t test; *P<0.001, P<0.01). FIG. 9B is a bar graph showing the results of an in vitro follicle melanization assay performed using a protease inhibitor cocktail (PI). The follicles were photographed 5, 70 and 120 min after the follicle dissection. Follicles were incubated with PI at 0, 10, or 20 minutes after follicle dissection. Each bar corresponds to mean percentage egg melanization from 5 individual mosquitoes. The mean±SEM are shown as horizontal lines. Statistical significance is represented by stars above each column (unpaired student's t test; ***P<0.001, NS not significant). Vectorbase ID: Nasrat (AAEL008829), Closca (AAEL000961), Polehole (AAEL022628), and Nudel (AAEL016971).

DETAILED DESCRIPTION OF THE INVENTION

I. Definitions

Figure 1A:
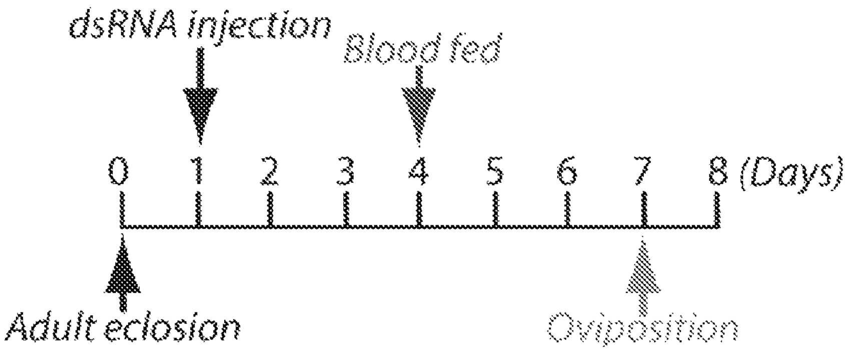
FIG. 1A is a schematic diagram of experimental time course for dsRNA microinjection, blood feeding, and oviposition.

As used herein, the term "isolated" describes a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" includes compounds that are within samples that are substantially enriched for the compound of interest and/or in which the compound of interest is partially or substantially purified. With respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "nucleic acid(s)" refers to any nucleic acid containing molecule, including, but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. In accordance with standard nomenclature, nucleic acid sequences are denominated by either a three letter, or single letter code as indicated as follows: adenine (Ade, A), thymine (Thy, T), guanine (Gua, G) cytosine (Cyt, C), uracil (Ura, U).

As used herein, the term "polynucleotide" refers to a chain of nucleotides of any length, regardless of modification (e.g., methylation).

As used herein, the term "gene" refers to a nucleic acid (e.g., DNA or RNA) sequence that including coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "nucleic acid molecule encoding" refers to the order or sequence of nucleotides along a strand of nucleotides. The order of these nucleotides determines the order of amino acids along the polypeptide (protein) chain.

As used herein, "heterologous" means derived from a different species.

As used herein, "homologous" means derived from the same species. For example, a homologous trait is any characteristic of organisms that is derived from a common ancestor. Homologous sequences can be orthologous or paralogous. Homologous sequences are orthologous if they were separated by a speciation event: when a species diverges into two separate species, the divergent copies of a single gene in the resulting species are said to be orthologous. Orthologs, or orthologous genes, are genes in different species that are similar to each other because they originated from a common ancestor. Homologous sequences are paralogous if they were separated by a gene duplication event: if a gene in an organism is duplicated to occupy two different positions in the same genome, then the two copies are paralogous.

As used herein, "autologous" means derived from self.

As used herein, "endogenous" means a substance that originates from within an organism, tissue, or cell.

As used herein, "exogenous" means a substances that originates from outside an organism, tissue, or cell.

As used herein a "recombinant protein" is a protein derived from recombinant DNA.

As used herein "recombinant DNA" refers to a DNA molecule that is extracted from different sources and chemically joined together; for example DNA including a gene from one source may be recombined with DNA from another source. Recombinant DNA can be all heterologous DNA or a combination of homologous and heterologous DNA. The recombinant DNA can be integrated into and expressed from a cell's chromosome, or can be expressed for an extra-chromosomal array such as a plasmid.

As used herein, the term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant," "mutant," or "mutated" polynucleotide or polypeptide contains at least one polynucleotide or polypeptide sequence alteration as compared to the polynucleotide or polypeptide sequence of the corresponding wild-type or parent polynucleotide or polypeptide. Mutations may be natural, deliberate, or accidental. Mutations include substitutions, deletions, and insertions.

As used herein, a "nucleic acid sequence alteration" can be, for example, a substitution, a deletion, or an insertion of one or more nucleotides. An "amino acid sequence alteration" can be, for example, a substitution, a deletion, or an insertion of one or more amino acids.

As used herein, "identity," as known in the art, is a relationship between two or more polynucleotide or polypeptide sequences, as determined by comparing the sequences. In the art, "identity" also means the degree of sequence relatedness between the polynucleotide or polypeptide as determined by the match between strings of such sequences. "Identity" can also mean the degree of sequence relatedness of a polynucleotide or polypeptide compared to the full-length of a reference polynucleotide or polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polynucleotides or polypeptides of the present disclosure.

By way of example, a polynucleotide or polypeptide sequence may be identical to the reference sequence, that is be 100% identical, or it may include up to a certain integer number of nucleotides or amino acid alterations as compared to the reference sequence such that the % identity is less than 100%. Such alterations are selected from: at least one deletion, substitution, including conservative and non-conservative substitution, or insertion, and wherein said alterations may occur at the 5' or 3' end of the polynucleotide, or amino- or carboxy-terminal positions of the reference polypeptide sequence or anywhere between those terminal positions, interspersed either individually among the nucleic acids or amino acids in the reference sequence or in one or more contiguous groups within the reference sequence. The number of nucleotide or amino acid alterations for a given % identity is determined by multiplying the total number of nucleic acids or amino acids in the reference polynucleotide or polypeptide by the numerical percent of the respective percent identity (divided by 100) and then subtracting that product from said total number of nucleic acids or amino acids in the reference polynucleotide or polypeptide.

As used herein, "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

As used herein, the term "effective amount" means a dosage sufficient to provide a desired physiologic or phenotypic effect.

As used herein, the phrase "gene editing composition(s)" refers to a group of technologies that give the practitioner the ability to change an organism's DNA. These compositions allow genetic material to be added, removed, or altered at particular locations in the genome.

As used herein, the term "small molecule" generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

II. Compositions

Female mosquitoes feed on blood to produce eggs, which are covered with eggshell. It has been discovered that EOF1 protein plays an important role in eggshell melanization and embryonic development. As discussed in the Examples below, nearly 100% of eggs oviposited by EOF1-deficient females had defective eggshell and non-viable egg phenotypes. It is believed that EOF1 has evolved within the Culicidae to affect eggshell formation and therefore maximize egg survival. Compositions and methods for directly and indirectly reducing, inhibiting, or otherwise interfering with an EOF1 gene or a gene product thereof are provided. In some embodiments, the inhibitors directly or indirectly reduce bioactivity, expression, location, activity, or a combination thereof of the EOF1 gene, mRNA, protein, or a combination thereof. In some embodiments, the compound is an inhibitory polypeptide; peptidomimetic; an inhibitory nucleic acid that targets genomic or expressed EOF1 nucleic acids or a vector that encodes a functional nucleic acid such as an inhibitory nucleic acid; or a gene editing composition or vector encoding a gene editing composition. The inhibitor can reduce the expression or bioavailability of a gene product of an EOF1 gene. Inhibition can be competitive, non-competitive, uncompetitive, or product inhibition. Thus, an inhibitor can directly inhibit EOF1, can inhibit another factor in a pathway that leads to induction, persistence, or amplification of EOF1 expression and/or activity, or a combination thereof.

It has also been discovered that other proteins play an important role in eggshell melanization and embryonic development. SDS PAGE analysis demonstrated that eggshells produced by EOF1 deficient mosquitoes lack certain high molecular weight proteins (over 200 kD) compared to eggshells produced by control mosquitoes. As shown in the Examples below, it was observed that RNAi against high molecular weight eggshell proteins Nasrat, Closca, Polehole and Nudel resulted in significant loss of egg melanization and embryo viability, which are similar phenotypes observed in EOF1-deficient eggs. RNAi knockdown of CATL3, DCE2, DCE4, and DCE5 in *Aedes aegypti* also resulted in an egg phenotype.

Thus, also provided are compositions and methods for directly and indirectly reducing, inhibiting, or otherwise interfering with a Nasrat, Closca, Polehole, Nudel, CATL3, DCE2, DCE4, or DCE5 gene or a gene product thereof. In some embodiments, the inhibitors directly or indirectly reduce bioactivity, expression, location, activity, or a combination thereof of the Nasrat, Closca, Polehole, Nudel, CATL3, DCE2, DCE4, or DCE5 gene, mRNA, protein, or a combination thereof. In some embodiments, the compound is an inhibitory polypeptide; peptidomimetic; an inhibitory nucleic acid that targets genomic or expressed Nasrat, Closca, Polehole, Nudel, CATL3, DCE2, DCE4, or DCE5 nucleic acids or a vector that encodes a functional nucleic acid such as an inhibitory nucleic acid; or a gene editing composition or vector encoding a gene editing composition. The compound can reduce the expression or bioavailability of a gene product of a Nasrat, Closca, Polehole, Nudel, CATL3, DCE2, DCE4, or DCE5 gene, or combinations thereof. Inhibition can be competitive, non-competitive, uncompetitive, or product inhibition. Thus, an inhibitor can directly inhibit Nasrat, Closca, Polehole Nudel, CATL3, DCE2, DCE4, and/or DCE5, can inhibit another factor in a pathway that leads to induction, persistence, or amplification of Nasrat, Closca, Polehole, Nudel, CATL3, DCE2, DCE4, and/or DCE5 expression and/or activity, or a combination thereof.

Typically the inhibitor is a compound that targets a EOF1, Nasrat, Closca, Polehole, Nudel, CATL3, DCE2, DCE4, or DCE5 gene or gene product thereof and reduces its expression, activity, or bioavailability. Exemplary EOF1, Nasrat, Closca, Polehole, Nudel, CATL3, DCE2, DCE4, and DCE5 targets, exemplary functional nucleic acids and gene editing compositions, small molecule inhibitors, and methods of use thereof are provided in more detail below.

A. Exemplary EOF1 Genes and Gene Products

The Examples below show that a putative *Aedes aegypti* protein referred to herein as EOF1 (also referred to herein and elsewhere as AAEL012336) is important for egg formation, egg melanization, and egg survival. Protein and nucleic acid sequences, and genomic mapping of the EOF1 gene, are known in the art for numerous species of mosquitoes. See, for example, Genbank accession numbers: EAT35499 (*Aedes aegypti*); XP_019565035 and AALF011550 (*Aedes albopictus*); and XP_001870696 and CPIJ010293 (*Culex quinquefasciatus*), and other in Table 1, the contents of all of which are specifically incorporated by reference in their entirety.

For example, the amino acid sequence of *Aedes aegypti* EOF1 is

```
MEESQQLQFP IRGNNNNKPL NVSGONDGSG QFTDSGYTSY
HSISASGSVA RSVLATIEED NEADSSFEEA RSSEDIFQMG
GGSNVLTPTT AASIERISNF HLTTPNSTGK PVGQHRGLVR
KPTFDNLFEQ YTPKKADYGP PCRTTQTPVR SDRKVELGSQ
TPRKNKASAK RKLGEFREKL YSDGDALELA PSRDLNDSLE
GDCKKLDQED ISPIYHTKRR RSSVIDLIRS STPKTASLRS
NFHVEVRENI DWDAVQQGKA SGROGKSRAL RKFQSFSPSK
MHSYKKRDVL QEKSVIANRR APFQRQDALR QVSLEQDLSK
QSTPQKAQES SLDKSFELPL EGLITPSKQS NLGVLLDAPI
LVQPSSEADF KESDLEQQIS QIPSFEECAY PQTPSKQTLS
LDDSGVIRHA PVCTEVNKSI PSILGTESPS FVSLSIPKTP
```

-continued

```
TSTNKSRNRL KRLSSTKKDK PRSKPPSPIH RAQPFIPGTY
RRPSYVNVER LNILKWLNEH DKDALGIVLD YLNDSDLVRV
VRVSTGWRDI IEHHRPSYRR LRAHFAREKE VKENLSFPSF
VSREGSLLGK TGGSLLSSFG DSSKEIAVSL PRQPFSLCNS
IDSNQSVGGE LRRSGSVQRS PPVSPSKRKF RENQKIASHL
KKSERLKPCP RCEKPSRVVL TKSSIKLAMA TGSLDSSTTR
TVASGKLDRS YTLPDSLMGS SATSMIAAAA LDCTSTTIGS
PQSPTNPDRI RRNLFSTSLL PRSQSVDART PVTRSPRRRR
STDVQGSSAS LLERKNGKTK SAEAIQCDYA VCSOKNCGFM
FCIKCLCEYH PSSVCKDLAP NSPSKEDEPA HNVACSKQSR
RSLLRLRK
```

(SEQ ID NO: 1, AAEL012336-PA [*Aedes aegypti*] GenBank: EAT35499).

A nucleic acid sequence for EOF1 is (SEQ ID NO: 191)

```
ATGGAAGAGTCCCAACAGCTGCAATTTCCCATCCGTGGCAACAACAACA
ATAAACCGCTCAATGTCAGCGGAGGGAATGACGGAAGTGGACAGTTCAC
CGATAGCGGATACACGTCGTATCATTCGATAAGTGCTTCCGGTTCGGTT
GCCCGGTCGGTGCTGGCCACAATCGAGGAGGATAATGAAGCGGACAGTA
GCTTCGAGGAGGCTCGATCCTCGGAAGATATCTTCCAGATGGGTGGGGG
CAGTAATGTCCTGACCCCTACCACTGCGGCCAGTATCGAGAGAATCTCA
AATTTCCACCTTACCACACCGAACAGTACGGGAAAACCGGTTGGACAAC
ATCGAGGTCTTGTCCGGAAACCGACATTTGATAATCTGTTTGAGCAATA
CACTCCGAAGAAAGCTGATTATGGACCTCCTTGCAGAACCACTCAAACC
CCTGTTCGATCAGATCGGAAAGTTGAGCTTGGCAGTCAAACACCCCGCA
AAAATAAGGCTTCAGCCAAACGCAAGCTCGGAGAATTCAGAGAGAAGCT
TTACTCCGATGGGGATGCACTGGAATTGGCACCTTCTCGTGACCTCAAT
GATTCCCTGGAAGGAGATTGTAAGAAGCTGGATCAAGAGGACATTTCAC
CGATCTACCATACAAAACGTCGCAGAAGCTCCGTCATTGATTTGATTCG
CTCCAGTACTCCGAAGACGGCAAGTCTCAGATCTAACTTCCACGTAGAA
GTCCGAGAGAACATCGATTGGGATGCAGTGCAGCAGGGAAAAGCTTCCG
GGCGCGGGGGTAAATCTCGCGCCTTACGCAAGTTTCAGAGCTTCAGTCC
CAGCAAAATGCACAGCTATAAGAAGCGAGATGTGCTGCAGGAAAAAATCG
GTCATAGCGAATCGTAGAGCCCCATTTCAACGGCAGGACGCCTTACGGC
AGGTTTCCCTGGAGCAAGATTTGTCCAAACAATCCACTCCACAAAAAGC
ACAAGAATCCTCATTGGACAAATCTTTTGAATTGCCTCTCGAGGGACTC
ATCACTCCGTCGAAGCAATCCAATCTCGGCGTTCTGCTGGACGCTCCGA
TTTTGGTTCAGCCGTCTTCCGAGGCGGACTTCAAGGAATCCGACCTTGA
GCAGCAAATATCGCAAATACCTTCGTTCGAAGAATGTGCCTATCCTCAG
ACTCCCAGCAAGCAAACCCTTTCGTTGGATGATTCCGGCGTCATTCGAC
ATGCTCCCGTGTGCACTGAGGTCAACAAGTCCATTCCGTCGATTCTTGG
```

-continued

```
CACCGAATCTCCATCTTTCGTCTCTCTAAGCATCCCCAAAACGCCAACA

TCAACCAACAAATCTCGCAACCGTCTCAAGCGTCTCTCTTCGACGAAAA

AGGACAAACCCCGTAGCAAGCCGCCTTCGCCAATCCATCGCGCCCAGCC

ATTCATTCCCGGAACGTATCGTCGTCCATCCTACGTGAACGTTGAGCGT

CTCAACATTCTCAAGTGGCTCAACGAGCATGACAAGGATGCGCTGGGGA

TAGTCCTGGATTATCTGAACGACAGCGATCTGGTTCGGGTGGTACGCGT

TTCCACCGGGTGGCGTGACATTATCGAACACCATCGGCCATCCTATCGG

CGTCTTCGAGCGCATTTTGCTCGGGAAAAGGAAGTCAAGGAGAATCTCA

GTTTTCCGTCGTTTGTATCGCGCGAAGGCAGCCTCCTGGGGAAAACCGG

AGGAAGTCTGCTGAGTAGCTTCGGCGACTCGTCGAAGGAGATTGCGGTA

TCGCTTCCTCGTCAGCCGTTCAGTTTGTGCAACTCGATCGACAGCAACC

AATCGGTTGGCGGCGAGCTGAGACGTTCGGGGTCGGTACAGAGGTCGCC

ACCGGTCAGCCCGTCCAAGAGGAAGTTCCGGGAGAACCAGAAGATTGCA

TCCCATCTGAAGAAATCGGAAAGACTGAAACCTTGCCCTCGCTGTGAAA

AGCCCAGCCGGGTGGTACTGACCAAATCGTCCATCAAGCTGGCCATGGC

CACGGGATCGCTAGACTCGTCTACCACCCGAACCGTGGCCAGCGGAAAG

CTGGATCGCTCCTATACGTTACCTGATTCCCTCATGGGCTCGTCGGCGA

CAAGCATGATCGCCGCTGCGGCACTCGACTGTACCTCAACCACCATCGG

CAGTCCCCAGTCACCTACCAATCCGGATCGCATCCGTAGGAATTTGTTC

TCGACCAGTTTGCTGCCCCGGTCCCAGTCTGTCGACGCGAGAACTCCGG

TGACTCGGAGTCCGCGTCGGCGCAGGTCCACAGATGTTCAGGGATCGTC

TGCGTCCCTGCTGGAGCGTAAAAACGGTAAGACTAAATCCGCCGAAGCG

ATTCAATGTGATTATGCCGTGTGCAGTGGCAAAAACTGCGGCTTCATGT

TCTGTATTAAGTGTTTGTGTGAGTACCATCCGAGTTCGGTGTGCAAGGA

CTTGGCCCCAAATTCGCCCAGTAAAGAGGACGAACCGGCACACAATGTG

GCATGTAGCAAGCAAAGCCGCCGATCGTTACTGCGACTGCGAAAGTAG.
```

Thus, in some embodiments, the EOF1 gene or gene product that is subject to inhibition has at least 50%, 60%, 70%, 80%, 85%, 90%, 95%, 96%, 97%, 98%, 99%, or 100% sequence identity with SEQ ID NO:1, or a nucleic acid sequence encoding SEQ ID NO:1, for example SEQ ID NO:191 or 239.

The EOF1 genes and proteins, or a homologue thereof, such as an orthologue or a paralogue, from other species of mosquito can be identified using, for example, BLASTN and/or BLASTP queries and/or sequence alignment techniques for global comparison. Exemplary species of mosquitoes that can be targeted are discussed in more detail below, and thus the EOF1 or homologue thereof can be from any of these species.

The sequences of any of the accession numbers disclosed herein can be used as query sequences to identify homologues and other related sequences. In some embodiments, a putative EOF1 protein, gene, or mRNA has at least 50%, 60%, 70%, 80%, 85%, 90%, 95%, 96%, 97%, 98%, 99%, or 100% sequence identity with the sequences of any of the accession numbers disclosed herein, such as EAT35499, and including nucleic acid sequences encoding amino acid sequences thereof. Preferably the sequence identity is over at least 50%, 60%, 70%, 80%, 85%, 90%, 95%, 96%, 97%, 98%, 99%, or 100% of the length of the query sequence. Thus, in some embodiments, the EOF1 gene or gene product that is subject to inhibition has at least 50%, 60%, 70%, 80%, 85%, 90%, 95%, 96%, 97%, 98%, 99%, or 100% sequence identity with the sequence of any of the EOF1 accession numbers disclosed herein, and including the amino acid sequence where the nucleic acid sequence is provided and the nucleic acid sequence where the amino acid sequence is provided.

B. Exemplary Other Target Genes and Gene Products

The Examples below show that the *Aedes aegypti* proteins Nasrat, Closca, Polehole, and Nude1 are important for egg melanization, egg survival and oocyte membrane permeability.

RNAi knockdown of CATL3, DCE2, DCE4, and DCE5 in *Aedes aegypti*, discussed in more detail in the experiments described below, also resulted in an egg phenotype. More specifically, CATL3: RNAi-CATL3 gravid females were not able to lay majority eggs on wet oviposition substrate. However, they laid eggs on water surface. A nearly 100% eggs were defective for a shape and viability.

DCE2: RNAi-CATL3 gravid females laid eggs that contain incompletely melanized eggshell.

DCE4: RNAi-DCE4 gravid females laid nearly all viable eggs. However, all eggs have a defective exochorion structure which is important for substrate attachment in nature.

DCE5: Nearly identical phenotypes are observed from those eggs laid by RNAi-DCE5 gravid females as was observed for RNAi-DCE4 and described above.

Protein and nucleic acid sequences, and genomic mapping of these genes are known in the art for various species of mosquitoes. See, for example, Vectorbase and Genbank accession numbers provided in Table 1, the contents of each of which are specifically incorporated by reference in their entirety.

Thus, in some embodiments, the gene or gene product that is subject to inhibition has at least 50%, 60%, 70%, 80%, 85%, 90%, 95%, 96%, 97%, 98%, 99%, or 100% sequence identity with any of the protein sequences disclosed in Table 1 (e.g., SEQ ID NOs:1, 183-190, and 200-219), or a nucleic acid sequence encoding any of the nucleic acid sequences disclosed in Table 1 (e.g., SEQ ID NOS:191-199 or 220-247).

For example, the amino acid sequence of *Aedes aegypti* Nasrat is

```
MNRLSFLFSTLFVIAAIQIKIETNAQVVQPAHTLPSNERPTSGPTKPAK

NGSPPLKIPTAKPSLGDAIKSLNDRILNDTDTPQDMLQHVRDSSFRNVF

HEAIDAKIVNPDLIRTLASVGKPLVNDYTRDTLLIESIREDINFTFGPN

VTWWETLELKKNEQHVIVGLSNSSIVILFEHFGEFKLQQEVLMETAPTA

FEIITVWDSVAETPVSCLIVATELQLIWYTMRPDTNFVLTEEWRWPLYK

MTTLIRGFKYRDIHMILLVGTHPNKQKSVSATLYEFNFEKQQFWLLQRL

DLAHACSTVGLVRVGREFLVAFPQHDKAMIYTLEAGEKYRGRFNLVANY

TSELVQTVGAFQVGRYAYIAIGGRSPQIVRYANGVFVSQRIPMEAMETV

EAYFEIPTPTYRDDFILLVQHKMLFSTHDLQRLDIFVWNGESFDLRSNI

PCYVEDELMDNEVSCMLDLYRPTGIVGSAIILRGKQVSMIVPRYQTHST

LFNLRIELLSAEHPIRQKTQEMRDTIDAFTKIFHYQDEVISEAYAAIAE
```

-continued

AEQTYDVPLLTLQNCSLGTVQADLVVQDSDFRWPSGKIMVGNRTWSHRD
TAVDVPAIARELEAEMALLSELEQQLNYTVRRHNDSFSLDLDQPLYVQG
RVEVGGALVTDDLYVRQLEEDPPLLRVVRQTGDDGMQELRVKDLKVRHL
NFETVNGILASDLVYNTGEKIELANALVVNSVLVAQNVILPKGGTVNGV
DLSESTVYFNCKNRRWDNLKFDSVEVLENVVAHETINGVKLDLAELDAR
FRQASEDMSDVLVTENLQLDGSLYVHSINGVPWSDIIHRIVLKNRPNRL
ADLKINGSLILQNDNVTVYHLNGLAFPMDYLLSSSPMESIVTGYKKFVN
ITNIEAMDVERTINGVDLQDIITLHDDQHIPGDVTIGELHVTERLEVKG
AIRGKHLDEFLDNPTLLQTTSIKAACHFKQLFVDGPVIVEGNLNGMDVD
AVLSDVVYDTEHTVTIEASKRIASAEFRDNVTISSNMVNEFKLDQFVTR
STEQELNVREINGNVFIRELQLDGLFDGLNATALDVSAVKLFGDQYTEA
SLIFKNRENALYPDVEANELKIMKTLNSKARSEYKDTDQEELVLTGQIS
LNHLHVDHLLLKGSSLEGPSKMINLVHLPTFDNLRFSLTRPQQVTAPFI
VNKLVVGSQIAAAYVNGRDFRGLKESIDRLDNFKNHLLQGSIPIENLHV
GGDLQVNMLNDVNFDALVKQVIWLNRPNRIPGTIRFLDPLMIIGNLTAR
GQVNNAVFGDFLEDVIRKSAGVAEFHGSITFMNGLVVEGNVNTESINNI
HMSELALRNDTIYLQGDVEILGDLFVEHLHVENHLNQEPIQNLLNSYSY
DDSKDVHTVKSDMYLYGAQIGALHIGGMLNQIPNVDAHLASVIRKDQNY
NFTKPLLFKNEVFFDQGFSATYLNQIDISNIQQDIVRINDPNPVEIEAE
VITFAEPIYADQLTIKGDMITTNLVGCNPDIWTSTGIMINRDAEIYAKT
FFSPGAFRTNHLRVDYMNGQPMNSLITLNTDQTIETTLLIHEMTITQPM
DVGGYVNGVTLPYERKNTLMTYGNQRVRLPTVFHTIRVLQSLTLPPILN
SKPFGPPVAIGPEMIIESPISFRHLIVDRLETEDMISGVDFNQWYENSL
WRKGRDHQTIEAKISARNVRFNGDVEGDGKINGVDIVDVVQRMKAAKKN
VEDQLLDYRSEMRSFCSNTKQLVDKSQSRMYFFKYFVQRQVINEHLPIV
SFHFFDHLGYNFLGVNMGCESHFYQWDPTGKAFVPIFKYYTGVVQEWNH
VVNGEEAIFLVTRSITELTQCEVAGLSVWLFTGVQLQLIWNTVDTASMQ
SVAADPAKSTSFYVLTPDVVVEYGVDGSTLEQWRLPKSALGYEFIPSKV
GLGLALSDSKLLVLLSNVNKTFEEDSTDLEMALFSSQSLHDRMKKTYSE
KLLNSTVSSEEVSDIIHPENISPLEEHSHFNNDTVIYVVEPETIDIPDP
PVSEDELSSETPIARDIPHGGILIADNQHFPERAKGDVVAFYAGPHNKK
RHLVAVSTVIHTVIQGDQDAIKIYTDIQTGKLYQVLPCHRPSHLTALEL
RDETILAFLEARQTVQIYIYRGMQGFVRLSNFKLTAPARAMAGVSLPQP
LTIRCKLHYLAIATEQNELIMLRAKTQGDCGLLVQVDCDDVE
(SEQ ID NO: 183, AAEL008829-PA [*Aedes aegypti*] GenBank: EAT39370).

A nucleic acid sequence for *Aedes aegypti* Nasrat is (SEQ ID NO: 192)
ATGAATAGGTTAAGCTTTCTTTTTTCGACGCTTTTCGTGATTGCAGCGA
TTCAGATTAAGATCGAGACTAACGCGCAGGTCGTCCAACCAGCGCATAC
CCTTCCTTCAAACGAGCGACCAACAAGTGGTCCAACAAAACCCGCCAAA -continued AATGGTTCCCCGCCGCTTAAAATCCCAACGGCCAAACCTAGTCTCGGTG
ACGCGATCAAGAGCCTCAATGATCGCATCCTGAATGACACGGACACTCC
GCAGGATATGCTCCAACACGTCCGAGATAGTTCGTTCCGAAACGTTTTC
CACGAGGCGATCGACGCCAAGATCGTCAATCCGGATCTCATCAGAACGC
TGGCTTCGGTCGGCAAACCGTTGGTCAATGACTACACCCGGGACACCCT
GCTGATCGAGTCGATCAGGGAAGACATTAACTTCACATTCGGGCCTAAT
GTCACTTGGTGGGAAACACTGGAGCTCAAGAGAACGAGCAGCACGTGAT
CGTGGGGTTGAGCAATAGCAGTATCGTTATTCTGTTTGAGCACTTTGGC
GAGTTCAAGCTACAGCAGGAGGTTCTGATGGAGACGGCGCCGACGGCTT
TCGAGATCATCACGGTTTGGGACTCGGTGGCGGAGACTCCGGTCAGCTG
TTTGATCGTGGCGACCGAGTTGCAGCTCATTTGGTACACGATGCGACCG
GATACGAATTTCGTTCTGACGGAGGAGTGGCGTTGGCCGCTTTATAAGA
TGACGACGTTGATTCGGGGATTCAAGTACCGGGATATTCACATGATCTT
GCTGGTGGGGACGCACCCGAACAAACAAAAATCCGTTTCGGCAACTCTT
TATGAGTTCAATTTTGAGAAGCAGCAGTTTTGGCTTCTGCAGCGGTTGG
ATCTTGCACATGCTTGTAGTACGGTTGGACTGGTGAGGGTTGGACGGGA
GTTTTTGGTGGCTTTTCCGCAGCATGATAAGGCCATGATTTACACTCTG
GAAGCCGGTGAGAAATATCGCGGAAGGTTCAATTTGGTAGCGAACTACA
CGTCGGAGTTGGTTCAGACGGTGGGGGCTTTTCAGGTCGGAAGGTATGC
CTATATTGCGATCGGGGGGAGATCGCCACAGATCGTGCGCTATGCCAAT
GGAGTGTTCGTGTCCCAGCGTATTCCAATGGAGGCGATGGAGACGGTTG
AGGCATACTTTGAAATACCGACTCCTACCTATCGGGATGACTTCATTCT
GCTGGTGCAGCACAAAATGCTTTTCTCAACGCACGATCTTCAGCGGTTG
GATATTTTTGTGTGGAACGGGGAGTCGTTTGATCTCCGAAGTAACATCC
CTTGCTACGTGGAAGACGAACTAATGGACAACGAAGTTTCGTGCATGCT
GGATCTGTACCGGCCGACCGGTATCGTCGGGTCTGCGATCATACTTCGG
GGCAAGCAGGTTTCGATGATCGTTCCTCGCTATCAGACTCATTCGACGC
TGTTCAACTTGCGTATCGAGCTGCTGTCCGCAGAGCACCCGATCAGGCA
GAAGACTCAGGAGATGCGGGACACGATCGATGCGTTTACCAAAATCTTC
CACTACCAAGACGAGGTGATCAGCGAAGCGTATGCGGCGATCGCCGAAG
CGGAGCAGACATATGATGTTCCACTGCTAACGCTGCAGAACTGTTCTCT
GGGGACAGTTCAGGCGGACTTGGTTGTGCAAGATTCGGACTTCCGGTGG
CCGAGCGGGAAGATCATGGTTGGTAACAGGACATGGTCGCATCGTGACA
CGGCGGTTGACGTTCCAGCGATCGCGCGAGAATTAGAGGCGGAGATGGC
GCTGTTGAGTGAGTTGGAGCAACAGCTGAACTACACGGTTCGACGACAC
AACGATAGCTTCTCGCTGGATTTGGATCAGCCGTTGTACGTGCAGGGTC
GAGTCGAGGTCGGAGGAGCTCTGGTTACGGATGATCTGTACGTAAGGCA
GCTGGAAGAAGATCCACCGTTGTTGCGGGTGGTCCGGCAAACCGGCGAT
GATGGTATGCAGGAGTTGCGGGTCAAAGATCTCAAAGTTCGTCATCTGA
ATTTGAAACCGTGAACGGAATTCTGGCGAGTGATCTCGTCTACAATAC -continued

GGGCGAGAAGATCGAGTTGGCCAACGCGCTGGTTGTGAACAGTGTGCTT

GTGGCGCAAAACGTGATCTTGCCCAAAGGCGGAACGGTCAACGGGGTAG

ATCTGAGCGAGTCAACGGTCTATTTCAACTGCAAGAATCGTCGGTGGGA

TAACTTGAAGTTCGATTCGGTGGAAGTGTTGGAGAATGTGGTAGCTCAC

GAAACGATCAACGGGGTGAAGCTTGACCTGGCGGAATTGGATGCTCGAT

TCAGGCAGGCAAGTGAAGACATGTCTGATGTGCTGGTAACGGAAAATCT

ACAACTAGATGGAAGTTTGTACGTCCATAGCATAAATGGCGTACCGTGG

AGTGACATTATCCATCGAATCGTGCTGAAGAACCGACCTAATCGGCTGG

CTGATCTGAAGATCAACGGAAGTCTGATTCTGCAGAACGACAACGTGAC

GGTTTACCATCTGAATGGGCTGGCCTTCCCAATGGATTATCTGCTCTCC

AGCAGTCCGATGGAGTCGATCGTGACCGGCTACAAGAAATTTGTGAACA

TTACGAACATCGAAGCCATGGACGTAGAACGCACGATCAACGGAGTTGA

CCTGCAGGACATTATCACCTTGCACGACGATCAGCACATCCCTGGTGAC

GTTACCATCGGTGAACTTCACGTAACCGAACGGCTGGAAGTCAAGGGAG

CTATCCGCGGCAAGCACTTGGATGAATTCCTGGACAACCCAACGCTGCT

GCAAACCACGTCGATCAAAGCCGCGTGCCATTTCAAGCAGCTCTTCGTC

GACGGACCGGTGATCGTGGAAGGCAATCTCAACGGCATGGATGTGGACG

CAGTGCTGTCGGATGTGGTCTACGACACGGAGCACACGGTCACGATCGA

GGCTTCCAAGCGAATTGCTTCGGCAGAGTTCCGCGACAATGTCACGATC

AGTTCTAATATGGTCAACGAGTTCAAACTGGATCAGTTTGTGACGCGCA

GCACCGAGCAGGAGCTGAACGTTCGGGAGATCAACGGAAACGTATTTAT

CCGCGAGTTGCAATTAGATGGGCTATTCGATGGACTGAATGCGACGGCT

TTGGATGTGAGCGCGGTGAAGTTGTTTGGCGATCAGTACACGGAAGCTT

CGTTGATCTTCAAGAATCGGGAGAATGCTCTGTACCCGGACGTGGAAGC

AAACGAGCTTAAGATTATGAAAACTCTGAACTCCAAAGCGAGAAGTGAA

TACAAGGATACGGATCAAGAAGAACTGGTTCTGACCGGGCAGATTAGTC

TGAACCATCTACATGTAGATCATTTGCTGTTGAAGGGATCGAGCTTAGA

GGGACCGTCCAAAATGATCAACTTGGTGCACTTACCGACCTTCGACAAC

CTTCGCTTCAGCTTGACGAGACCTCAACAGGTCACAGCACCGTTCATCG

TGAACAAACTTGTCGTGGGAAGTCAAATAGCGGCGGCTTACGTTAATGG

ACGAGACTTCCGGGGTCTGAAGGAGAGCATCGATCGCTTGGACAACTTC

AAGAACCACCTGCTACAGGGAAGTATTCCGATTGAGAATCTCCACGTTG

GAGGCGATCTGCAGGTCAACATGTTGAACGACGTAAACTTTGATGCGTT

GGTGAAGCAAGTCATCTGGTTGAACCGCCCCAACAGGATACCGGGAACG

ATCCGGTTCCTCGATCCTCTGATGATCATTGGAAATCTAACGGCACGGG

GACAGGTCAACAACGCCGTTTTCGGAGACTTTTTGGAAGATGTGATCCG

GAAATCGGCAGGAGTGGCGGAGTTTCACGGTTCAATTACATTCATGAAC

GGTTTGGTAGTCGAAGGCAACGTCAATACTGAGAGCATCAACAATATCC

ACATGAGTGAGCTGGCGTTGAGAAACGATACGATCTACTTGCAAGGTGA

CGTGGAAATCTTGGGAGACCTTTTCGTGGAGCATCTACACGTCGAGAAC

CATCTGAATCAGGAGCCCATTCAGAACCTCCTGAACTCGTACAGCTATG

-continued

ACGATTCCAAGGACGTTCACACGGTCAAAAGTGATATGTACCTGTATGG

TGCCCAAATCGGAGCGCTGCACATCGGAGGAATGCTGAACCAGATACCG

AACGTTGACGCCCACTTGGCATCGGTCATCCGCAAGGACCAAAACTACA

ACTTCACCAAGCCGCTGTTGTTCAAGAACGAAGTCTTCTTCGATCAAGG

TTTCTCGGCCACCTACCTCAACCAAATTGATATTTCAAATATCCAGCAA

GACATCGTTCGGATCAACGATCCGAACCCGGTAGAGATCGAAGCGGAAG

TGATCACGTTCGCCGAACCCATCTACGCTGATCAGTTGACCATCAAAGG

GGATATGATCACTACAAATCTCGTTGGGTGCAATCCGGACATCTGGACG

AGCACAGGAATCATGATCAATAGGGACGCCGAGATCTACGCGAAAACAT

TCTTCTCGCCGGGAGCCTTCCGTACGAATCATCTCCGCGTAGACTACAT

GAACGGACAACCGATGAACAGCCTGATCACGCTGAACACCGATCAGACG

ATCGAGACAACGCTGCTCATTCACGAGATGACAATTACACAGCCGATGG

ATGTCGGTGGATACGTCAACGGAGTTACGCTACCGTACGAACGCAAGAA

TACGCTCATGACATACGGCAACCAGCGGGTCCGCCTACCAACAGTCTTC

CACACGATCCGAGTCCTTCAATCGCTCACTCTCCCACCAATTCTGAACA

GTAAACCCTTCGGACCACCGGTCGCGATCGGACCCGAAATGATAATCGA

GTCCCCCATTTCCTTCCGACATCTCATCGTTGATCGGCTCGAGACGGAA

GACATGATCTCCGGGGTGGACTTCAACCAGTGGTACGAGAACAGTTTGT

GGCGTAAGGGCCGCGATCACCAGACCATCGAAGCGAAGATTTCAGCCCG

CAATGTGCGGTTCAACGGAGACGTGGAAGGCGACGGCAAGATCAACGGA

GTAGACATCGTGGACGTCGTGCAGCGAATGAAGGCCGCCAAGAAGAACG

TGGAAGATCAGCTACTGGACTACCGGTCGGAGATGCGATCGTTCTGCTC

CAACACCAAACAGCTGGTGGACAAATCCCAGAGCCGGATGTACTTCTTC

AAGTACTTCGTGCAGCGACAGGTGATCAATGAGCATCTACCGATCGTGT

CGTTCCACTTCTTCGATCACTTGGGGTACAATTTCCTGGGCGTGAACAT

GGGATGCGAGAGCCACTTCTACCAATGGGATCCGACTGGGAAGGCATTC

GTGCCGATTTTCAAATATTACACGGGAGTGGTGCAGGAATGGAACCACG

TGGTTAATGGCGAGGAAGCTATCTTCCTGGTGACGCGATCGATCACTGA

GCTTACGCAATGTGAAGTTGCGGGACTTAGCGTGTGGTTGTTCACGGGC

GTACAGCTGCAGCTGATTTGGAATACGGTGGACACCGCCTCGATGCAAT

CGGTAGCTGCCGATCCTGCGAAGTCGACAAGCTTCTATGTACTAACGCC

GGATGTTGTGGTGGAGTACGGCGTTGATGGAAGCACTTTGGAGCAGTGG

AGACTTCCAAAGAGCGCTTTGGGTTACGAATTCATCCCCAGTAAGGTCG

GACTTGGACTGGCCTTAAGCGATAGTAAGCTACTGGTTCTGCTTTCGAA

TGTGAACAAGACTTTCGAGGAGGATTCGACTGATCTTGAAATGGCGCTG

TTCTCTTCGCAATCGCTGCACGATCGCATGAAAAAGACGTATTCGGAAA

AGCTATTGAATTCTACGGTAAGCTCAGAAGAAGTCAGCGACATTATCCA

CCCAGAAAATATATCACCACTCGAAGAGCACTCACATTTCAACAACGAT

ACGGTGATCTATGTGGTTGAACCGGAGACAATCGACATACCGGATCCAC

CGGTAAGTGAAGATGAATTGTCTTCGGAGACACCGATCGCCAGAGACAT

-continued

TCCCCACGGAGGAATCCTGATTGCCGACAACCAGCACTTCCCCGAGAGA
GCCAAAGGGGACGTGGTGGCATTTTACGCTGGTCCGCACAACAAGAAGC
GCCATCTGGTGGCGGTGTCCACTGTGATTCACACAGTCATCCAAGGAGA
TCAGGACGCGATCAAGATCTACACCGACATCCAGACGGGCAAACTCTAC
CAGGTTCTACCCTGTCACCGTCCTTCGCATTTGACCGCCCTGGAACTGC
GGGACGAGACGATCCTCGCCTTCCTGGAAGCCCGGCAGACCGTGCAGAT
CTACATCTACCGGGGCATGCAGGGTTTCGTGCGGCTGAGCAACTTCAAG
CTGACGGCTCCGGCCAGGGCCATGGCCGGGGTTTCGCTGCCGCAGCCGT
TGACGATTCGATGCAAGCTGCACTACCTGGCGATCGCCACTGAGCAGAA
CGAACTGATCATGCTACGAGCCAAGACACAAGGTGACTGCGGACTGCTG
GTCCAGGTGGACTGCGATGATGTGGAGTGA

For example, the amino acid sequence of *Aedes aegypti* Closca is

MPETDLFDCQMCELANNIDDMVQCEGCTKWSHYGCVGFDDGKKEENWRC
AGCIAKSSSNSTGGDSNVQATDGQQKTRGSTGGAESISDLAQLNLKLLE
ERKAVLLREIELQHSTQLEQRKLQLEKEAWQAKYDILNAKCESTSSTVG
SSGLGNWISRMNQVAVSQYQQTSVSASTVTTSLNPRMRQQHTATGEGNA
TSVVTTSSRPGCSLYGSESTSFLPQITSTIALSANQPSSTYAVGQATSY
MGDFQPGVGANRPGSSTPVTSVNWVNPGANPTSSAQCLPPYVSSMEQLG
GHPMPSGYVSHPYQVTSSLNNFAPVGQVAFSQYAHSSVGSAENRYLKGF
RERGSIPVSFPIDICLLKVGRSVFGASLHIRKSKENYKNQTIVTFYKRQ
KGQFHKYKEYLAAQARHFDCISHASLGFVAVVNYYDNAANQEFPEAHPG
FDEGSPVFQIHEDGTTEIIQKFRQSNQNTVHMWTAGNHFYLTHTYINLN
ESVENVCPLYRWTGYHFDVIDELPCYNSINIEPFSIEQTLYIAIANQMN
DQSVEEDTFSDIFRFNYEQQRFEFHQKIYVYSVSDIAYFFLELGDVREH
YLITGNSRAGKETAIDKLDYDQHSIVYKFVEGYFVPVQKIELHQVKMFL
PVTHENGDFLLLIRCKGKPLLIYEYDGYKFVPSRIDYTRNAFSTGVSFM
RVYRHILNTSLIVIANKQSYGTTANLFTPIYGVENDLRDVYGQFISWCS
ETTHQLENVNLEEVYNKLAALPKISGSGARFEKDIEVKDSSVEKLRTKV
LHTKHFMFNQEAFDYLNNVNAQMKALKQKAKKLRSLIDDSLKLSEAMEV
RGDVRVPQVIAADGLIRDLEAKNVNDERVVPRVANQTKHEDVINVDRLI
IEDRLAVKFLNGYASETLLHTTDDLRSLEGVDLHAKAVEIRGELFVDKA
IDGVHVSADNVLLRGVDQVFTGRTLRATNFTVGNLVAKQLNSTDVGMIM
SYLDRVSEYDSAQKRTVESYPKKFKEIRVQDLEVSGLVNDVDIKYINKN
ALKIVGDQVITGSINFDNIVTRKLETPNKRLSGVDLNYLVMTEPTPDQQ
DFTVRQDVQFINPVYMENLHVDDRINHINVVDDQLQVLLKDPKEPQLIT
GTKSFDNVQLLGPIYLQGKINSSSLSKLNPVSTITQDVYLEGDFVITGD
VSIRQLLNTSNIYGSSKTFNFYDLYHHGLPLSAASANQNFVFKEPLVVH
HAFANNLNGVNPSDFIPIPSKKLQRITGRKIFNGDLTIRGDRVDAAMIN
DIDLKHLNRTILKKTGDQVVKGTIHFKELIASTVVAKTTLFEERPLSTL

-continued

LTVNTNQRIKSKVRCVNCKLTIHGDLSVGRMETHNKSRLFGYDLDFLFS
DTLHKSYAQPDSIAVTGGKGFYNVTVGELILLDQATINGVDLIGLKKIN
DPLEKDVIVEETLILKNPLHVRNVYFNGSINGVPAQEFGRTWLLNEYNQ
TFTAPQVFEHVAAEGMFVDGYFNGVKLEDLVQDIYFLDRSEHLPEAIFH
EGIVSYQPITVKGLVSGLNLATDVLLNYSPNRQYLKDVRIDGNLLVANR
IHVEHTLNGMNYAKLREYATSSGVERPMNVEVQGNVHFHLQPDVSQLNG
YSLEQLHREIWLTNRDEVLTGSYRFDNVHFGSYVHTKGPVNQLDLEEIV
HSYLSVSKPQNVTTPLVFKGPVELQKMATFDSINLEGLLKGAKESRGIN
IVDFDRYVLKKNVDQTITGKWVFHDAEVYGNLNLTTLNGLDIRRDILLN
HAEQVTFSGAKRIDNLRVHNLRCPDPCIIQGVDFSEWFANSVRLDRNHT
VEGVTYLEGATILGDIESRGPVNNVTFDPQSLLLKSVPQTLEGTLYLKT
KFPEHNLIYQSSIESLEVNSINGKDFNRFMDNLARVEEGKVTIDTPVTL
VQNLNAKNVDTGDSKMFDVNINQLLQEVEYGDQLSQYETKLRRLHMVGQ
SLVETLSTKTPYLSHYQPIKPLPGYFRSVVTITLPLSPMPIELLAAHVD
DGNRTAVEFYRWNKKDSQFHIAKGFPPITYPTLQITKTKRIVLGGVQNL
FVEYYDHSRHLYRQSILDLEAPDFTAPKKTPKFTSIYEFNSSLPRDIVA
LKVLDLDCVGLYSPHIDGLNVYCLQLENLVYYLKFHQLLTTPAVNQALH
LDGRLILLSRDSLLQVWRPRADYKLGLLQLIKIAHPTSLTVAKFEQQLF
IAINSDQALTEASAHHGSIEIWRDLRPQHHNSTFNKYQTILTKMPKQIQ
FSVLATTSELMLYTLTENPFHPLVIYRYEGVAGFREYLTSNALRTSSKR
FTVVKLDRKQRELLALVSDREVTWIEAVIKGR (SEQ ID NO: 184, AAEL000961-PA [*Aedes aegypti*] GenBank: EAT47957).

A nucleic acid sequence for *Aedes aegypti* Closca is (SEQ ID NO: 193)

ATGCCGGAGACCGATCTATTTGATTGCCAGATGTGCGAGCTCGCAAATA
ACATCGATGATATGGTGCAATGTGAGGGATGTACTAAGTGGTCGCATTA
TGGATGCGTCGGCTTTGACGATGGGAAAAAGGAAGAAAACTGGAGGTGT
GCCGGTTGTATTGCGAAATCATCTTCCAATAGCACCGGCGGAGATTCCA
ATGTTCAAGCTACCGACGGACAGCAGAAGACAAGAGGCTCTACAGGAGG
AGCAGAATCCATTAGTGATCTCGCACAGCTTAACCTTAAACTGTTAGAG
GAGCGCAAGGCCGTCCTGTTGAGGGAGATCGAACTGCAGCACTCAACTC
AGTTAGAACAACGTAAACTTCAGCTGGAGAAGGAGGCATGGCAAGCAAA
GTACGATATTCTCAACGCGAAATGTGAATCAACCAGTAGCACGGTAGGA
AGCAGCGGTCTCGGAAACTGGATAAGCCGTATGAATCAGGTCGCTGTCA
GCCAGTACCAACAAACATCCGTGTCGGCAAGTACGGTGACGACTTCATT
GAATCCCAGGATGAGACAGCAGCACACCGCTACTGGAGAAGGAAATGCG
ACATCAGTAGTAACGACGTCATCGCGACCAGGCTGTTCGCTGTATGGAA
GCGAATCGACATCCTTTCTTCCGCAAATTACTTCTACGATCGCCTTGTC
TGCAAATCAACCATCAAGTACGTATGCGGTGGGACAAGCAACCAGTTAT
ATGGGAGACTTCCAACCTGGAGTAGGAGCGAATCGTCCGGGATCATCGA
CGCCAGTGACCAGTGTAAATTGGGTCAACCCAGGGGCGAATCCAACCAG

-continued

CTCCGCCCAGTGTTTGCCACCATACGTCAGCTCGATGGAACAGCTAGGA
GGTCATCCGATGCCATCGGGATACGTAAGCCACCCGTACCAGGTAACCA
GTAGCTTAAATAATTTCGCACCAGTAGGCCAGGTAGCTTTTTCACAATA
TGCTCACAGTAGCGTAGGGTCAGCCGAAAATCGCTACCTCAAAGGTTTC
CGTGAGCGAGGATCCATACCGGTTAGCTTTCCCATCGATATCTGCTTGC
TTAAAGTGGGACGCTCCGTTTTCGGTGCATCACTGCATATTCGGAAATC
CAAGGAGAACTACAAGAACCAAACCATCGTAACGTTCTACAAGAGACAG
AAGGGACAGTTCCACAAGTACAAGGAGTACTTGGCGGCTCAAGCACGAC
ATTTCGACTGTATTTCGCACGCTTCGCTCGGGTTTGTCGCCGTGGTCAA
CTACTACGACAATGCGGCTAACCAAGAATTCCCGGAAGCTCATCCAGGG
TTCGACGAGGGGTCGCCCGTGTTTCAAATTCATGAGGACGGCACCACTG
AGATTATACAAAAGTTTCGACAATCCAATCAGAATACGGTTCACATGTG
GACTGCGGGGAACCATTTCTATCTGACGCACACGTACATCAATTTGAAC
GAAAGCGTTGAAAACGTTTGCCCTCTATATCGCTGGACCGGGTATCACT
TCGATGTGATCGATGAGCTGCCGTGCTACAATTCCATCAACATAGAACC
GTTCTCGATCGAGCAGACCCTGTACATCGCCATCGCCAATCAGATGAAC
GATCAGTCCGTCGAAGAGGACACCTTTTCCGACATCTTTCGGTTTAACT
ACGAACAGCAGAGGTTCGAGTTCCACCAGAAGATCTACGTCTACTCCGT
GTCGGATATAGCGTACTTCTTCCTGGAGTTGGGCGACGTTCGCGAACAC
TACTTAATCACGGGAAATTCGCGAGCCGGCAAGGAAACCGCGATCGATA
AGCTTGACTACGATCAGCATTCGATCGTGTACAAGTTCGTCGAGGGATA
CTTCGTGCCGGTGCAGAAGATCGAACTGCACCAGGTGAAGATGTTCCTG
CCCGTTACGCACGAGAACGGTGATTTCCTGCTACTGATCCGCTGCAAAG
GCAAGCCCCTGTTGATCTACGAGTACGATGGCTATAAGTTTGTACCTTC
GCGAATTGATTACACCCGGAATGCCTTTAGCACGGGAGTGTCGTTCATG
CGCGTCTATCGACACATTCTGAACACCAGTCTGATCGTGATCGCCAACA
AGCAAAGCTACGGGACTACGGCGAACCTGTTCACTCCTATCTACGGCGT
TGAGAATGATCTCCGGGATGTCTACGGGCAGTTTATATCGTGGTGTAGC
GAAACGACCCATCAGTTGGAGAACGTCAATCTGGAAGAGGTTTATAACA
AACTGGCTGCGCTGCCGAAGATTTCGGGTAGCGGTGCAAGGTTCGAGAA
GGATATAGAAGTCAAGGACTCGAGTGTGGAAAAGCTGAGGACTAAAGTT
TTACACACGAAGCACTTCATGTTCAACCAAGAAGCGTTCGATTATTTGA
ACAATGTGAATGCACAGATGAAGGCGTTGAAGCAGAAGGCGAAGAAACT
TCGTAGCTTGATCGATGACAGCCTGAAGTTGAGTGAAGCGATGGAAGTC
CGTGGGGACGTTAGGGTACCGCAGGTGATCGCGGCCGACGGATTGATAA
GGGATCTAGAAGCGAAGAATGTCAACGATGAGCGGGTGGTTCCCAGAGT
TGCGAATCAAACAAAACACGAAGATGTGATCAATGTAGATCGACTGATC
ATTGAAGACAGATTGGCGGTAAAGTTCTTGAACGGCTATGCCAGTGAAA
CACTGTTGCATACGACAGATGATCTTCGATCTTTGGAAGGAGTAGACTT
GCATGCAAAAGCGGTTGAAATACGCGGAGAGTTGTTCGTAGATAAGGCA

-continued

ATCGATGGTGTTCATGTGTCTGCGGACAATGTTCTACTTCGTGGCGTGG
ATCAGGTATTCACGGGAAGAACACTACGGGCCACGAACTTTACAGTGGG
TAATTTGGTGGCAAAGCAGCTTAACTCGACGGATGTTGGGATGATCATG
TCGTACCTGGATCGAGTATCAGAGTACGACAGCGCACAGAAAAGAACAG
TTGAAAGTTATCCGAAAAAGTTCAAAGAAATCAGAGTTCAAGATCTCGA
AGTCAGCGGTCTTGTGAATGATGTTGATATCAAATATATCAACAAGAAC
GCTTTGAAGATCGTTGGAGATCAAGTGATTACTGGTAGCATAAACTTCG
ATAATATCGTTACAAGGAAACTTGAAACTCCCAACAAACGACTATCTGG
AGTAGATTTGAACTACCTAGTCATGACCGAACCGACGCCGGATCAACAG
GATTTCACTGTACGACAAGACGTACAGTTCATCAACCCTGTGTACATGG
AGAACTTACACGTAGATGATCGCATCAACCACATCAACGTGGTTGACGA
TCAGCTGCAGGTACTGCTGAAGGACCCAAAGGAACCTCAACTCATCACC
GGTACCAAGTCGTTCGACAACGTCCAGCTTCTGGGGCCAATCTACCTTC
AGGGAAAAATCAACAGTAGTAGTTTGAGTAAATTGAATCCGGTTTCTAC
GATCACCCAAGACGTATATCTGGAAGGCGACTTTGTAATAACCGGAGAT
GTATCGATCAGACAACTGTTGAACACCTCCAACATATACGGATCGAGCA
AAACGTTCAACTTCTACGATTTGTATCACCATGGCCTTCCGCTAAGTGC
AGCTTCCGCCAATCAGAACTTCGTCTTCAAGGAACCTCTTGTTGTGCAT
CACGCGTTCGCCAACAATCTCAATGGTGTCAATCCGAGCGACTTCATCC
CAATACCTTCCAAAAAACTGCAGCGCATTACCGGGCGGAAGATATTCAA
CGGAGATCTAACCATACGTGGTGATCGAGTTGATGCTGCCATGATCAAT
GACATTGATTTAAAGCACTTGAATCGAACGATACTGAAAAAGACTGGCG
ATCAAGTGGTTAAGGGAACGATCCATTTCAAGGAATTGATCGCATCCAC
CGTAGTTGCGAAGACGACTCTGTTCGAGGAACGACCTCTGAGTACGCTC
CTTACCGTGAATACCAACCAACGCATCAAGTCGAAGGTACGCTGCGTAA
ACTGTAAACTGACGATCCACGGAGACCTGAGCGTCGGTCGAATGGAAAC
GCACAACAAATCCAGGCTATTCGGTTATGATCTGGATTTCCTGTTTTCT
GACACACTACACAAAAGTTACGCTCAGCCTGATTCGATTGCGGTAACTG
GCGGCAAGGGCTTCTACAACGTAACCGTTGGGGAACTCATACTGCTGGA
TCAAGCAACCATCAACGGAGTGGACCTGATTGGGCTGAAGAAGATCAAC
GATCCCCTCGAGAAGGATGTCATTGTGGAGGAAACGTTGATTTTGAAGA
ATCCTCTACACGTACGCAATGTGTACTTCAACGGATCGATCAACGGCGT
CCCGGCGCAAGAATTCGGACGCACGTGGCTGTTGAACGAGTACAACCAA
ACGTTCACGGCGCCGCAGGTCTTCGAGCACGTGGCAGCCGAGGGGATGT
TCGTCGATGGGTATTTCAATGGAGTCAAGCTGGAGGACTTGGTTCAGGA
CATCTATTTCTTGGATCGAAGCGAACATCTACCGGAGGCTATCTTTCAT
GAGGGGATTGTCTCCTATCAGCCAATCACCGTCAAGGGTCTCGTTTCCG
GTTTGAACCTGGCCACCGACGTGCTGTTGAACTACTCCCCAAATCGTCA
ATATCTCAAGGACGTACGAATCGATGGTAATCTGCTTGTGGCCAACCGG
ATACACGTGGAGCATACTTTGAACGGGATGAACTACGCTAAACTACGGG
AATACGCAACATCTAGTGGCGTTGAACGACCGATGAACGTGGAGGTTCA

-continued

AGGGAACGTTCATTTCCACCTTCAACCGGACGTTTCTCAGCTTAATGGG

TACAGCTTGGAACAGCTTCATCGGGAAATTTGGCTGACGAATCGAGATG

AAGTGCTCACGGGGTCATACCGCTTCGACAACGTTCACTTCGGCAGCTA

TGTTCATACTAAGGGTCCGGTGAACCAGCTGGATTTGGAGGAAATTGTA

CACAGCTACCTGAGTGTATCGAAGCCACAAAACGTGACTACACCGCTGG

TTTTCAAGGGACCGGTGGAGCTTCAGAAGATGGCAACATTCGATAGTAT

AAACCTGGAAGGACTGCTGAAGGGAGCGAAGGAGTCTCGAGGAATAAAT

ATCGTGGACTTTGATAGATACGTCCTCAAGAAGAACGTCGATCAAACCA

TTACTGGAAAATGGGTCTTCCATGATGCTGAAGTTTACGGAAACCTCAA

TTTGACCACCCTAAACGGCCTGGACATCAGACGGGACATCCTGTTGAAC

CACGCTGAGCAGGTAACGTTCTCTGGAGCCAAACGAATTGACAACCTTC

GAGTTCATAACCTCCGATGTCCGGATCCATGCATCATCCAAGGGGTGGA

CTTTAGCGAATGGTTCGCCAACTCTGTTCGTCTGGATCGGAACCATACC

GTCGAGGGCGTCACCTATCTGGAAGGGGCTACCATCCTGGGAGACATCG

AATCCCGTGGCCCAGTCAACAATGTTACGTTTGATCCTCAGAGTTTGCT

TCTGAAATCGGTTCCACAAACGCTGGAAGGTACCCTGTACCTTAAAACC

AAATTTCCAGAACACAACTTGATCTACCAGTCGTCGATCGAATCTTTGG

AGGTGAACTCCATCAACGGCAAGGATTTCAACCGGTTTATGGACAATCT

GGCACGTGTTGAGGAGGGTAAAGTAACGATAGATACCCCGGTAACGTTG

GTTCAGAACTTGAATGCCAAGAATGTCGATACGGGCGATAGTAAGATGT

TCGATGTGAACATCAACCAACTTCTGCAGGAAGTGGAATACGGCGATCA

GCTGAGCCAATACGAAACGAAGTTGCGACGGTTGCACATGGTTGGTCAA

TCCTTGGTGGAAACACTCAGTACCAAAACTCCTTATCTGAGTCACTATC

AACCGATAAAGCCTTTGCCGGGATACTTCCGTAGCGTAGTTACTATTAC

GTTACCCCTTTCACCAATGCCGATCGAGTTACTGGCTGCGCACGTGGAC

GACGGAAATCGTACGGCCGTTGAGTTCTACAGGTGGAACAAGAAGGATT

CGCAGTTCCATATTGCTAAAGGTTTTCCACCCATCACTTATCCGACCCT

TCAGATCACCAAGACGAAACGAATCGTCTTGGGTGGCGTGCAGAACCTC

TTCGTTGAATACTACGACCACAGCCGTCATCTGTATCGACAGTCCATCC

TTGACCTCGAAGCGCCGGACTTCACAGCACCTAAGAAGACACCGAAGTT

CACCTCGATCTACGAGTTCAACAGTTCACTACCCAGGGATATTGTGGCA

CTGAAGGTCTTGGATCTGGACTGCGTCGGACTCTACTCGCCTCACATCG

ATGGGCTAAACGTGTACTGCCTCCAGTTGGAGAATCTGGTGTACTACTT

GAAGTTCCATCAACTGCTTACCACGCCCGCCGTCAATCAAGCTCTTCAC

CTAGACGGACGATTGATCCTACTGAGCAGAGATAGCCTATTGCAAGTGT

GGCGACCACGGGCCGACTACAAACTAGGTCTCCTGCAGCTAATCAAAAT

AGCCCATCCGACTTCGCTAACCGTAGCCAAATTCGAGCAGCAGCTGTTC

ATCGCCATTAATTCGGACCAGGCACTGACCGAGGCGTCCGCCCATCACG

GTTCCATAGAGATTTGGCGCGATCTACGACCCCAGCATCACAACAGCAC

CTTCAACAAGTATCAAACCATCCTGACCAAGATGCCCAAGCAGATCCAG

-continued

TTCTCGGTCCTGGCAACCACTTCGGAACTGATGCTGTACACTTTGACGG

AGAATCCGTTCCACCCGTTGGTGATCTACCGCTACGAGGGTGTGGCCGG

ATTCCGCGAATATCTGACGAGCAACGCGCTGCGAACCAGCAGTAAGCGG

TTCACGGTGGTCAAACTGGATCGCAAACAGCGGGAACTGTTGGCGTTGG

TGAGCGATCGGGAAGTGACGTGGATCGAAGCTGTCATAAAGGGGAGGTA

G

For example, the amino acid sequence of *Aedes aegypti* Polehole is

MFMDYLNTIAVKEYFKLLTLKGDSDKAQQWEIGGSKTLQKGMAVDGKLN

VVHVNRLILDNILYNSARKTGPMNIAGLWNITKLATKYLATKQINGPAY

LMTSDIIVELYNKSLSQTYLKLEDVYTTGIVAQLLNIHRINIKEFLNRR

IAFNQCNIKKSISIHMIKTNEQYDLWKKLSDNSVQCK (SEQ ID NO: 185, AAEL022628-PA [*Aedes aegypti*] GenBank: EAT33906).

A nucleic acid sequence for *Aedes aegypti* Polehole is (SEQ ID NO: 194)

ATGATTCTTCCAAAGTGGTTACTGTTGTCGGCGATTGCGCTTCAGGTGG

CGTGGTGTTGGAATGGATTCAGTGATGGGGGCTCCGATTTGGATGTTCT

CATGCGGCGAAGGTTGGATCTCTTATCATCCGAGCGAAGGACTAGGCAA

GCTCCACAAGCGCATTCCCGTGAAACTGATACATCTCAGTATGATTTAA

CATTGCACCGTGTTAAGGTGAACCTAAACCGTACTGCTGCTGATCATCA

AATGTTGTTCACACGAGTTCGAAGCAGCGGAAATCTGTATCTCTACTCT

GGCAATCAAATCTCACGGGTCACGGTTGCCGAAACAGAGGTTAAGCTGG

TGCCTGTAGCTGCGACTTCTGATATACACGAGGAAGTTTCAGAATTCCA

GATTGAGGAACTTAAGGCAATTGACAACAAGACGACACTGATAGTCACT

GTCTCTCTGCCGGATCGGATGCATGTTTATCAAATATCGGGCAACTCGA

AGGGGAAAGTGTTAACAGTGAAAGCTATGCAAAGGATAAAGCGACCAGG

TCAAACCCATCAATCAGTTTTGGTGCAGTCGAAATCCAATTTGTTCCTG

ATCAGCGGTTATTCCGAAGCACGTTTCGGAAAAGTGGTAATTTATCGTT

GGTTGGACTTCCATTTTTCGTTGCGTGATGTCAAGGAAGTGGATCGCTG

TGACAAGCTTTTGGTATTCAGTGGTGATCAACTCGTTATTCTCGTACTG

GAAATGGCTGAATATCCGGAACGATCAGTGAATAATATTTTCATGCTTA

ACGATGAATTCAAGTTGGTTAAAACGCAAGAAATGTACTTTTTGTTCGA

TCGACTACCGCATTATGAGGTGGAAAATCAGTTCTACATTCTGCGATGT

CTTGCGTTAGATACGTGCTTTTTATATCGATGGAATGGTGAGAGCCTTT

TTCGTCGAGCCAGCAAAATATCATACGATCCCAGGAACATCGACATCAT

GGCCTCGGGTCATGGAATGATAGCAATGTCCCTCGAAAGAACACTCTAC

TTCTACGACAATCAGCCCCTGTTGAAAATTGCTGCTTCGTACGCTATCG

TAAACAGACGCGGCACAGTTACGGATAAACCTTTCCAGCTCGATCCACG

AGTTAGCGACATGTTTCTTTACAAGGAGGAAGCAACGGAAAAATTGTAT

CTCTGCATCCTGTACAACTCTGGTGCCAAATTGTTGGATATGGTCGAGA

-continued

TACAGTTGAATAAAGGAAGAAGCGCGCCCAGTCCAGGTGAGCAGTCCAA

TTTCAACGCTCTTAAAACGTGCCTTTTCCACATGAAAGATTTGGCGAAT

ATTCGTAAAAAGTGGATTGATTTAATCAAATACCAACTGAGCAAAACGC

TGCGCAGCTGCAAATCTACAGGTGTGCTTTCGCTGGCATCCAAAGTGTT

TTTAGCTGAATCCAATAAAGTTGATCGCATAGAAGTTGACGGAAATATC

GAAAACTCTCCCCAGGATCTATTGAAAGAGTGGAGTTCGACTAAAAAAA

GTTTAGCTGAAATGCATTCGCAGTCGCAAAATTTGTTCTATTTGAACCG

GATGAATACTGTGCAATCTAATATGAAAATTCAAGGAAATTTGCGAACA

AAATCGACACGAATGAAACACGTTAAGGTACACCATCCTCATTCAGGCC

GACCTGCTTATGTGCGACCCAAAAGGGATCTGCAATCTTCAAGAGTGAT

CACCTCCGCCATTGTCAACGCCAGAGAAGTAGTATACAATGGAAAAATG

TTTGCTTATACTCTAAGTCGTAACAACGTGAACTACGTTTCATCTCCTG

TCCATGTTGCAAATCTACATACGCAAAACGTGCACATCGGTTTGAATAC

CATTAACCGAATCCCAGTGGATCAAATGTTGTACAACGCTACCGATAAA

TTCGTAGAAAAAGGACACAAAGTTTTCAAAGCGATAGACACAAATACTC

TCAAAGTTTATCTCGTGAATGGGGAGAAAACAACACAGCAATTCTCTAG

CTTGCGAAATTTCGTCGTAACGGCCGGATCTGAAGCTCCTGTGAAATTG

TCTGGGGCACGTGGCGTCACAAATTTGATCGTCGGTGGAAAGCTGAATA

ACGTATCCTTAGATGATCTATTACATCAGTTATATTACGTGGACAAAAA

ATCGACAATCAACGGTAACGTTTTCTTGCGTGCACCTTCATACATCCGT

AATGTATATGCTCGAAGTCTGAATAGTTTCCCTACCAGCAACATTTTCG

ATTTGAGGACGAATCAAACAATTTCTGCCGTTGTACATCTCTCTCAAGT

GTACGCCCGAAATGTGTATAGTAAAACAATAAATGGAATAAACATTCCT

AAAGATGTCGCACTAATAAGCTCTGCGAAAACCATTAAAGCGGCAGTGG

CATCCAACTTCGTCGTCAAGAAAGATCTCACACTTTCCGCCGAAGACCA

GCACTTTACCAAACATGTTTTGGGCACAAAGGTGGAAGATTTCTCCCAA

ATTTACTCAGGACGTGTTTATCTGAAAGGATCCCTCAAGTTGAAACAGC

TTAACCTGGAGAATCAAAAAAGTCAACTGGTTTTGAATGGTTTCACAGC

CAGTCCGGATGTACAAAACCATTTCTGGATGAAACGTGTCGAACAGGAT

ATAGGTACCTTCACGTTCAATCGCAACGTTAAGGCTAGCCATCTGGTCT

GTGCAAAACTGAATTATAATCCAACGGTTAGCTATTTGAGGGGTGACCA

TTGGCCATCGCATCTGAACCTTGAAATGTCGAATGCTTATGTCCGAGGA

TTCATAAAAACCTATGCTACCACCCCCACTTTCTTACAACACATTTCCA

CTGAAGCCGTTCTGCGTGGATCCATGTCCACTGTGTCAGGCCGTAAAGT

CTTCACTGGTCAGCTTCATACCGATACCTTGGTTGCAGATGGAGTCGAT

GCAATCAACGTTCAAAGCTTGGCAACTGACTTCAGCACTATGGCGTTCC

TAGACGGAGTCAAAGAAATTGAACATTTCTCATCAGAGGAATGTTATAT

CGAGCTGCTCGGTGGATTGACATTGCAAGAGTACCAGAACGTCTCCTTC

AACGCTATAGTGGAGAGCACTGTAAATACGCACAACCCGCAAACTCTGG

AGTATTTGTTTCTGCCGGATATAAAAGTTGAACATTTCCGAGCAGCGCT

GATCAATGGAGTTAACGCAGAAGATTTCATAACCGAAATAGATAATTTT

-continued

ACGTATCGTGTAGATCCCTTCGCGGCGCAATTTAAAATCGATAACCTCA

TTGTTAAGAAAAACGTGATTTCCACCAGCCAAATGTTCATGGACTATTT

GAACACAATCGCTGTGAAGGAATATTTCAAACTGCTGACCCTAAAGGGT

GATAGTGACAAAGCGCAGCAGTGGGAAATCGGAGGCAGCAAAACCTTGC

AGAAAGGCATGGCCGTCGATGGAAAATTGAATGTGGTTCACGTAAATCG

GCTAATCCTAGTTAACATACTCTATAATTCTGCCAGGAAAACAGGTCCT

ATGAATATTGCGGGATTATGGAACATAACGAAACTGGCGACGAAGTACT

TGGCGACCAAACAAATAAACGATCTACCAATAAAACATTTGCAGAATTC

CAATTTGAAAAGCTTCAAAATTAAACACGACATTTCGGTTGGAACATTG

GCGATTTCTGCGAACATGCATGGTCATCTGTTTCCAAATAGTTCATCAG

TTTCGATGCCCCCAAATATCCAGATGCTGGCCAGTTTGACTGTCCATGG

ATCGTTTTTGCTGGAACATTGGAAGCCTGGAACACTCTTGTTCGATGTG

ATGTTATCAGCCGTAACTGGTTCAACGAATGTTTTTGATAAGAAGCTTG

TTTTCCGAGGACACCACGTTGAAATTGAGAAGTTACGAAACGAAGGCAA

AATTTTCAGCAAGAGCTGCAATTTTGTCAATTTGCTAATGGACTCAGTG

AAGAGAAGACAACCCAATCTCGTATTCAGCAGTCTCGGAAAAACGTTCA

GGGAAGTGGTTTGTCTTGGATCAGTGGCATCTAATGATTTAGTTACCGC

AACGCTGGTGAATGGAATCGATGTAATTCATTTGAATAGGAGCATTCAC

TCAGTTGGTCACCACCAGGAAATGATTAAATCGACAAAGTACTTTGAAG

AAGAAGTGAAGGTTGTGCAGTTGCTCTGTCATGACCAACTGGTGGACGG

TATTTATCCTAGCAATTTGGACCTTTACTCGGACGCAAGCCAGATGGTC

AAGAAACGGTATCAGTTTGAAAAACCCATTTCGGTCATCGGGAATTTGT

ACGTCGATGCAATCAACGATTTCTCGTTGCAACACTTCCTGGCGACTCG

CGTGGTGAAAAATAGGACGTATACGCAGGAATACCATCAGGAAAAGTCT

CAACAAGTAACAGGATTTATCACATTTTCGAACCTGGTTTTATCCGGTG

AATACAACACAGTTCACGTAGTCAACGGTATTCCTGTAAGCGAGATTGT

ATCCAGATCGTCCAATGAGCATCAGGTTATGGTTGAGACAAAGCATTTG

ACAGGCACCATTCAGCTTATTGGACCTACATCGGTCATGAAGTGTAACA

ACGTCTCTTTGTTGGATGCATACAAATCTAGCTTTAAAGCCAATTCTGC

AGAGATTGCTTTCAAAGACTTGATTTTTAATTCTAAAGGTGTTTTGCAA

AATGGTTTGACCATTGAAAACAAGCTGAATGGAGTATCAGTGCAGAAAA

TGATGAAGCTTCGGCTATCGTCGGTAGAGGAGCTGCTGCCATTGATTCC

AATAATCCAAGAGCAGATATCGGTCTCCAATAGAGCATACCTAACCAAC

AAACCAAAGGATTTACACATGTTGTACATAGAAAATATTCCGCTGGATG

AAAGAGGCACCATGGTCGGAAAGAGCGAAGGTCAACGGACCAATGAAGC

ATCTGATACTGTTAATTTCGAGAAATCCTGCAGTAATGGCATATATCGT

TTCAACGTTACTATTCGGCAGAAATCGTCCAACGGAGATATAAGTTCTG

CCAGAACCGTATTGGATGGAGTGATGATAAAATCCGATTGGATGGAAAT

AGCAAATAACGGCGAAATACAAACAATAGTCGTGTCACAAGTCGAAAAG

AATGCCAAGTACTTCCTACTTCTTTACGTCAATCGCAATGGAGAACTCA

-continued

```
GTGTTCAACAGGAACTTCCATTAAGCTCATCGGCGGCTGTATTCTACTT
CGTACACGTAAACGATTCAGCACTTTTGCTGGCAGTATCAGATTCACAC
CCCCTTCAACTGGGCCATTTGGCACCGAAACTCAAACTATTCCGCTATG
ATCCGGATGTAATGCGCTTCGTACATTTCAAAACGCTCAGTGGCCATTA
CAATGACGTTGTTGCTATCGATGTCGAGGACGTTATAATGTTTGCAGTT
TCAGAGCAAGGTTCTAACATGGTGGAAATATTTGTGCTGGACCGTTCCT
ACTCGGCGTTATTCCAAAAGCTTATCTTCGATTCGACTTTGGCGTCAAT
GAAAGCGTTCAAATTACAAGGATCCCCAGTTCTACAGATATCAACGGTC
GATAATTTGGTCTACGTTTACAATTACAGTATTCTTGAGGGCTGGCGGC
AGTTGTCGTACGGCAGGATTCCGTCTGACGTGAACTAA
```

For example, the amino acid sequence of *Aedes aegypti* Nude1 is

```
MNVPLNIQNLSGKRTSDDPDLEGAQLVCSFVGPSSTEKPLAGNDSMMLQ
SSQELFVSSTRARGHHRHCPRGKVPCADGIQCVLSSHLCDSRVDCFDGS
DESHCSCLSRLADKRRCDGYVDCPLAEDEMGCFGCDKFSFSCFNTFFEY
QASHHSETRCFTLIEKCDGFNNCMNRKDEQDCTMLVRDLRSPLAFAVGH
SVGVLHRNYKGKWYPVCHNPLNLAREACEAELGPADRDPVILQHHODLP
GPFIQPSPRSHHVFQPEFTDTCNGLINYVKCPAPKCGSSKQNEMENLRI
KIRGKRNATELVQIVGGTKAEPAAYPFIVGIFRDGKFHCGGSIFNERWI
VTAAHCCDNFPRHHYELRAGLLRRRSFSPQVQVSTVTHVFIHRGYSAQK
MINDISLMHSDRPFQYNRWVRPICLPDRHMTTNDRDWIWGPKPGTMCTA
VGWGALREHGGSPDHLMQVTVPILPFCKHKNDRDGLAICAAEMSGGHDA
CQGDSGGPFACISVSSPHEWYLAGVVSHGEGCARPNEPGVYTRVALFND
WIQRKTREVLTSSSTRQDCPGFQCSVGVSFCIPRQKRCNGKVDCLGGED
ELSCSLDQLLAESIQETTIATTPKNSTATSSTTAAATTEAVTSKIDFLA
```

-continued

```
ENSEASDPATTVTEASSTETANIETILTTIETVSAKDVSDGIFQVSTEA
TTVEINTTLDISSSSQNVSASPEKVEESTVDETTSSTTETSFTHPTTIE
SETTADSVTALMSETTSPSLPPNENNTTVDYTVTRSTDQTTNTPFTISP
TTDSLDDSSAAYSSSANDSEVNHSTTIEPKNTESSVHATTVIELISVES
TTNIEATSLADPSNASITTLSSDLVEETSSSSTTPSTPDSTSSTQPDSS
HSSTSSAPWMQINEAIANLKPRPPSTDRDMEMRQLELGDSVAATRTDNT
TSTTISTAPSAATDSTSSTPLSTTTVESSSTTHGDLEHSETQIEPVEAE
ATNASVEEHPFLREIHNLVEEKTRRLNQFRLSMHYLHTSLRNQTQDANE
TSYQYRRFKCSKIRQSINIAHHCDRIIDCEDGTDELRCTCRDYLKDKYD
FLICDGKTDCLDLTDEADCFSCTAGQFPCRMSKVCIDEKKLCDAIPDCP
LHEDELDCLALTDGHKVYFDANNLSEFKYEGLVTKNTNGTWDLICGAEI
NNKSVESIGKICSFLGFAGYESYYQTVLTPLVNETVDLDHQPLLIMSYR
NISSEPNCKALHITCAPFINATEHEISHFENQHKEQPVQVNIRPTHPIQ
NITSLTHITFQENAHIEFIENFGDDYDWPWNADIYLEGVFLCSAIIIEV
NWIVVDSSCMRMINLKNDYLSVVAGGAKSYLKISGPYEQVVRVDCYHFL
PEARVVMLHLAKNLTFTRHVLPTFIPEKNYNITDNQCLAVGQDKYGRTR
TLRVHMNMTNCEPEDHICYQLNPDNGIYHADHCYTENASRTGVVVCKSK
VSGWYPVGFYQNKHGLCGFNEVVKMISLKEFYTDIQHVLSHKKCDYEFP
EPLCDGVRCWHGKCIGHSLVCDNKMDCDDNFDERPEACNAINDTSTACL
PTQFRCGSHQCVDKSKFCDGRNDCGDLSDEPHECSCYTYLKVTDPSKIC
DGVRNCWDKSDENPRLCKCAKTSFRCGDSEVCIPYDHVCDDEIDCPGEE
DERYCYALQQNPAETNYGEVMQQSYGIWHSKCFPKDDKYDEQTIKEICH
RVGYQQVRKVYGRKVLPESRLRTSNRTHDPVDRLRGAATKAVAFNKFFK
VNINEKQAIFMKPSRPLYTLVNWDAEDEQKCDRLEINCGD (SEQ ID
NO: 186, AAEL016971-PA [Aedes aegypti] GenBank:
EJY57924).
```

A nucleic acid sequence for *Aedes aegypti* Nude1 is

```
                                                (SEQ ID NO: 195)
ATGAATGTTCCACTCAACATCCAAAATCTTTCCGGAAAAAGAACAAGTGACGATCCGGA
TCTAGAAGGAGCTCAACTGGTGTGTAGCTTCGTGGGACCATCTTCCACGGAGAAACCTT
TAGCTGGGAATGATTCGATGATGTTGCAATCATCACAGGAATTGTTTGTGAGCAGTACG
AGGGCTCGTGGCCACCATCGGCACTGTCCTCGAGGCAAGGTTCCCTGTGCAGATGGCAT
TCAGTGTGTTCTGAGTTCACATTTGTGTGACTCGCGGGTGGACTGTTTCGATGGAAGTG
ACGAATCGCACTGCTCGTGTTTGTCACGGTTGGCGGACAAACGGCGCTGTGATGGTTAC
GTAGACTGTCCTCTCGCGGAAGATGAGATGGGCTGCTTCGGATGTGACAAGTTCTCGTT
CTCGTGTTTCAATACGTTTTTTGAGTATCAGGCTTCGCATCATTCCGAGACAAGGTGCT
TTACGTTGATCGAGAAGTGTGATGGCTTCAACAACTGCATGAATCGGAAGGACGAACAG
GATTGTACGATGTTGGTGCGAGACTTGAGAAGTCCCCTGGCGTTTGCGGTTGGCCATTC
AGTGGGTGTCCTGCATCGGAACTACAAGGGTAAGTGGTATCCGGTTTGTCACAATCCGT
TGAATCTGGCACGAGAGGCTTGTGAAGCAGAACTTGGACCAGCGGATCGCGATCCGGTG
ATTCTGCAGCACCATGGAGATCTACCGGGACCATTTATTCAACCAAGTCCACGAAGTCA
```

-continued

TCACGTGTTCCAACCGGAGTTCACCGATACCTGTAACGGGTTGATCAACTACGTTAAGT

GTCCGGCACCGAAGTGTGGATCCAGCAAGCAGAACGAGATGGAAAATCTTCGTATTAAA

ATCCGTGGAAAGAGAAATGCTACAGAGTTAGTGCAGATCGTTGGCGGAACGAAAGCTGA

ACCGGCTGCTTACCCTTTTATTGTGGGAATATTCAGAGACGGGAAATTCCATTGCGGTG

GTAGCATCTTCAACGAACGTTGGATCGTAACGGCAGCTCACTGCTGTGACAACTTCCCA

AGGCACCATTACGAACTGCGAGCGGGTCTTCTCCGTAGACGTAGCTTCTCTCCTCAGGT

GCAGGTTTCAACGGTAACCCATGTGTTCATACACCGAGGATACAGCGCGCAAAAGATGA

TCAACGACATCAGTCTGATGCATTCGGACAGGCCTTTCCAGTACAACCGATGGGTAAGG

CCGATCTGTCTACCCGACCGACACATGACTACCAACGATCGGGATTGGATTTGGGGTCC

GAAACCGGGAACGATGTGTACGGCTGTTGGTTGGGGAGCACTCAGGGAGCACGGTGGAT

CACCTGATCATTTGATGCAGGTTACGGTCCCAATTCTACCGTTCTGTAAACATAAAAAT

GATCGCGATGGACTCGCTATTTGTGCTGCCGAAATGAGTGGAGGTCACGACGCCTGTCA

AGGTGACTCGGGAGGTCCATTTGCCTGCATTAGTGTCTCCAGTCCACATGAGTGGTATC

TGGCGGGAGTGGTTAGCCATGGAGAGGGCTGTGCTAGACCAAACGAGCCTGGCGTCTAT

ACGAGAGTTGCACTGTTCAACGACTGGATCCAAAGGAAAACTAGGGAAGTGCTTACTTC

GTCCTCTACGCGGCAGGATTGTCCCGGCTTCCAGTGCTCAGTTGGGGTATCGTTCTGCA

TACCGCGGCAGAAGCGGTGCAACGGGAAGGTAGATTGTCTTGGTGGAGAAGATGAACTA

AGCTGTTCGCTGGATCAACTGCTAGCTGAATCGATACAGGAAACAACCATAGCGACGAC

ACCAAAGAATAGTACTGCGACAAGTTCAACAACTGCTGCAGCTACTACAGAAGCTGTCA

CTTCGAAGATCGATTTCCTCGCGGAGAATTCTGAAGCATCGGATCCTGCTACTACCGTG

ACGGAAGCATCAAGCACTGAAACTGCTAATATTGAAACTATATTGACAACTATTGAGAC

AGTATCTGCTAAAGATGTAAGTGATGGTATTTTCCAAGTATCAACTGAGGCAACTACAG

TGGAAATAAATACTACCTTAGATATTAGCAGTTCATCGCAAAATGTTTCAGCTTCACCA

GAAAAAGTTGAAGAATCAACAGTGGACGAAACCACTTCATCCACAACTGAAACAAGCTT

CACACATCCAACAACGATTGAATCCGAAACTACAGCTGACAGTGTAACCGCTCTCATGT

CGGAAACTACCTCGCCATCTCTACCACCAAACGAAAACAACACTACAGTGGACTACACT

GTCACAAGATCTACTGATCAAACAACAAATACACCTTTTACAATATCCCCTACCACTGA

TTCCTTAGATGACTCATCTGCTGCTTACTCATCATCTGCAAACGATTCAGAAGTAAATC

ACAGTACAACGATAGAACCCAAGAACACAGAAAGTAGCGTACATGCAACGACAGTTATA

GAACTGATCTCGGTTGAATCTACTACCAATATCGAAGCAACGTCCTTAGCGGATCCCTC

AAATGCGTCAATCACAACGCTATCCTCCGATTTGGTCGAAGAAACTTCATCCTCGTCAA

CAACCCCGTCCACTCCAGATTCTACTTCATCAACTCAACCTGATTCCTCCCACAGCAGC

ACCTCAAGCGCTCCTTGGATGCAGATTAACGAAGCTATCGCAAATTTGAAACCTCGTCC

ACCTAGCACGGATCGCGATATGGAGATGCGTCAACTGGAATTGGGCGACAGCGTCGCAG

CGACTCGAACAGACAACACCACGTCGACAACTATCTCTACAGCTCCCAGTGCTGCAACC

GATTCCACCAGTTCCACACCGCTGTCAACCACCACGGTGGAAAGTTCCAGCACGACCCA

CGGCGATCTGGAACACAGCGAAACTCAAATCGAGCCCGTTGAAGCCGAAGCGACCAATG

CTTCTGTGGAGGAGCATCCATTTTTGCGCGAAATTCACAATCTGGTGGAGGAGAAAACC

CGTCGGTTGAACCAGTTCCGGTTGTCCATGCACTACCTGCACACATCGCTGAGGAACCA

AACGCAGGACGCGAACGAAACTTCCTACCAATACCGGCGGTTCAAGTGTTCTAAAATCC

GACAATCGATCAACATTGCGCACCATTGCGATCGGATCATCGACTGCGAAGACGGTACG

-continued

GACGAATTGCGGTGCACGTGTCGCGATTACCTGAAGGATAAGTACGACTTCCTGATCTG

TGACGGCAAAACGGATTGTTTGGATTTGACCGATGAAGCAGATTGCTTTTCTTGCACGG

CTGGACAGTTTCCTTGCCGAATGAGCAAAGTCTGCATCGACGAGAAGAAGCTGTGCGAT

GCGATTCCGGATTGTCCTCTGCATGAAGATGAGCTGGATTGTCTTGCCCTCACGGATGG

TCACAAGGTCTACTTTGATGCGAACAACCTCTCGGAATTCAAATACGAAGGGCTGGTCA

CTAAGAACACTAACGGAACGTGGGATCTGATCTGTGGAGCGGAGATCAATAACAAATCT

GTGGAATCGATTGGAAAAATCTGCTCTTTCTTGGGATTTGCTGGGTACGAAAGCTACTA

TCAAACCGTCCTAACACCACTGGTGAACGAAACGGTGGATTTGGATCATCAGCCGCTGC

TGATCATGTCGTATCGCAATATCTCATCGGAGCCAAACTGTAAGGCCCTCCATATAACC

TGTGCGCCATTCATCAATGCTACTGAACATGAGATCAGTCACTTCGAGAACCAACATAA

GGAACAACCAGTGCAAGTCAACATTCGTCCAACACATCCGATACAGAATATCACCTCTC

TAACGCACATCACCTTCCAAGAAAACGCTCACATCGAGTTCATCGAGAACTTCGGCGAT

GACTACGATTGGCCATGGAACGCCGACATCTACCTGGAAGGAGTGTTCCTGTGCAGTGC

GATCATCATCGAGGTCAACTGGATCGTGGTCGACAGTTCCTGCATGAGGATGATCAATC

TGAAGAACGATTACCTCTCCGTAGTGGCCGGTGGAGCCAAGTCATATCTGAAGATCTCC

GGACCATACGAACAGGTTGTTCGCGTGGATTGTTATCACTTTTTGCCCGAGGCACGCGT

TGTGATGCTTCATTTGGCGAAAAACTTGACCTTCACCAGGCATGTTCTGCCGACATTCA

TTCCGGAAAAGAACTATAACATTACGGATAACCAATGCCTCGCCGTTGGTCAGGACAAG

TATGGAAGAACGCGTACGTTACGAGTCCACATGAACATGACGAATTGCGAACCAGAGGA

CCATATCTGTTATCAGCTAAATCCAGATAACGGCATATACCATGCAGATCACTGCTATA

CCGAAAATGCATCACGTACTGGAGTCGTCGTTTGTAAGTCTAAGGTCTCGGGATGGTAT

CCAGTGGGCTTCTATCAGAACAAGCACGGCCTTTGCGGGTTCAACGAAGTCGTCAAAAT

GATCTCCCTGAAGGAATTCTACACTGACATTCAACATGTTTTGAGCCATAAGAAATGTG

ACTACGAATTTCCTGAGCCGCTTTGCGATGGAGTGAGGTGTTGGCATGGGAAATGTATT

GGCCATTCTTTGGTTTGTGATAACAAAATGGACTGCGACGACAACTTTGACGAGCGTCC

CGAAGCGTGCAATGCCATAAACGATACGTCAACTGCCTGTCTACCGACGCAGTTCCGTT

GCGGGAGCCATCAATGCGTTGATAAGAGCAAGTTCTGTGACGGGCGAAACGATTGCGGT

GATTTGTCGGATGAGCCACACGAATGCTCTTGCTACACTTATCTCAAGGTAACCGATCC

ATCTAAGATATGCGATGGCGTTCGCAACTGTTGGGACAAATCTGATGAGAATCCACGAC

TGTGCAAGTGTGCAAAAACGAGCTTCAGATGCGGCGACAGCGAAGTTTGTATTCCTTAC

GATCACGTCTGCGACGACGAGATCGACTGCCCCGGAGAAGAAGACGAACGATACTGCTA

TGCTCTACAGCAGAATCCAGCGGAGACCAACTACGGTGAAGTGATGCAACAAAGCTACG

GCATCTGGCACTCAAAGTGCTTCCCTAAGGACGATAAATACGACGAGCAAACGATCAAG

GAAATATGTCATCGCGTCGGATACCAACAGGTCCGGAAGGTCTACGGCAGAAAGGTGCT

TCCGGAGTCACGTCTGAGAACTTCCAATCGGACACATGATCCCGTCGATAGGTTACGCG

GCGCAGCAACCAAGGCAGTTGCGTTCAACAAATTCTTCAAAGTGAATATCAACGAAAAA

CAAGCGATCTTCATGAAACCCAGTAGGCCGTTGTACACTCTGGTCAACTGGGATGCCGA

AGACGAGCAGAAGTGCGATCGGTTAGAGATCAACTGTGGAGATTAA

For example, an amino acid sequence of *Aedes aegypti* CATL3 can be

MKKQLLWILSALIVAAGDIGERVDEGDVTNFDTFLGAYQKKYKAKYRMD

RRKRAFKKNMQEIEEHNANYEQGKSTFQMGVNELADMDKSSYLKKMVRM

TDAIDHRKLDVDFNDEMLQATNAFGEEFVQATQNSMPDSLDWRDKGFTT

MAVNQKTCGSCYAFSIGHALNGQIMRRIGRVEYVSTQQMVDCSTSAGNK

GCAGGSLRFTMQYLQNSQGIMRSSDYPYTSSSSKQSEYFQEEGRVGQKA

CKQQLASCKAPATKLVTSLVCRSHPIKQFSVSDSVQEWAVLDVVSGVSP

KEQLCRVTASHTVSLKNAE (SEQ ID NO: 187, AAEL002196-PA [*Aedes aegypti*] GenBank: EAT46597).

An amino acid sequence of *Aedes aegypti* CATL3 can also be

MKKQLLWILSALIVAAGDIGERVDEGDVTNFDTFLGAYQKKYKAKYRM

DRRKRAFKKNMQEIEEHNANYEQGKSTFQMGVNELADMDKSSYLKKMV

RMTDAIDHRKLDVDFNDEMLQATNAFGEEFVQATQNSMPDSLDWRDKG

FTTMAVNQKTCGSCYAFSIGHALNGQIMRRIGRVEYVSTQQMVDCSTS

AGNKGCAGGSLRFTMQYLQNSQGIMRSSDYPYTSSVSIIFRVLLVFLS

HFLQARAVSSRSISKKR (SEQ ID NO: 200, GenBank: XP_021703341))

A nucleic acid sequence for *Aedes aegypti* CATL3 is (SEQ ID NO: 196)

ATGAAGAAACAACTGCTGTGGATACTTTCTGCGCTGATAGTCGCTGCCG

GAGATATTGGCGAACGAGTGGATGAGGGTGATGTTACCAATTTTGACAC

ATTTTTGGGCGCGTACCAGAAGAAATACAAAGCCAAATACCGAATGGAC

CGAAGAAAGAGGGCTTTCAAGAAGAATATGCAGGAAATTGAAGAGCACA

ATGCTAATTACGAGCAAGGCAAAAGCACATTCCAGATGGGGGTCAACGA

ACTGGCTGATATGGACAAAAGCAGCTACCTGAAGAAGATGGTCCGAATG

ACGGACGCGATCGACCACCGGAAATTGGACGTGGACTTCAACGACGAAA

TGCTACAAGCCACGAATGCCTTCGGCGAAGAATTTGTGCAAGCCACACA

GAACAGCATGCCGGACAGTTTGGATTGGCGCGATAAAGGATTCACCACG

ATGGCCGTCAACCAGAAGACGTGTGGTTCCTGCTATGCTTTCAGCATTG

GACATGCCCTCAATGGACAGATTATGCGCCGTATTGGTCGGGTTGAGTA

TGTCAGTACCCAGCAGATGGTCGATTGTTCGACCAGTGCCGGCAATAAG

GGATGTGCTGGAGGATCTCTAAGGTTTACGATGCAGTACTTGCAGAATA

GCCAGGGTATCATGAGGAGTTCAGATTATCCGTACACTTCGTCGGTAAG

TATCATTTTCAGGGTGTTGTTGGTTTTCCTTTCTCATTTCCTGCAGGCC

AGAGCAGTAAGCAGTCGGAGTATTTCCAAGAAGAGGTAA

For example, the amino acid sequence of *Aedes aegypti* DCE2 is

MWKSSVVCLALLGVLGSVSGTTKLQERYSWRQLDFVFPNQQLKQQALAS

GDYVPTNGLPVGIERWENKLFVSVPRWKDGIPSTLNYIDMNQTPSGSPP

-continued

LIPYPSWANNVAGDCQNGLSTVYRIKADKCGRLWVLDTGTVGIGNTTQQ

LCPYALNIFDLKTNTRLRRYELRAEDTNQNIFIANIAIDMGRSCEDTFA

YMSDELGYGLIAYSFEKNKSWRFEHSFFFPDPLRGDFNVAGLNFQWGEE

GIFGMSLSPLQSDGFRTMYFSPLASHREFMVSTQVLRDEEGAEESFHKF

TYLKERGPNSHTTSRVMSETGLQLFNLIDQNAVGCWHSSLPYSPENHGI

VDRDDVELVFPADVKIDAEENVWVISDRMPVFLIAELDYSDVNFRIFTA

PLSTLVAGTVCDVRPSLRPGAIQSKFGGSDLSTYPGTTLLPVGYTQPIS

YTPSSYAPTVAPVTKYTAAPAYDHPTSHMYTTQEYPTTAKAYHFNKYHN

VEYQSHONGQADYHFGHGGHYHDHDHAHEYGHDHGYYGGGQRRHWGAGA

KKPEAWKQQLY (SEQ ID NO: 188, AAEL006830-PA [*Aedes aegypti*] GenBank: EAT41553).

A nucleic acid sequence for *Aedes aegypti* DCE2 is (SEQ ID NO: 197)

ATGTGGAAATCGTCGGTGGTGTGTTTGGCCCTTCTGGGGGTCCTGGGGT

CGGTTAGCGGAACGACGAAACTGCAGGAACGCTACAGCTGGCGTCAGTT

GGACTTTGTGTTCCCGAACCAGCAGCTGAAGCAGCAGGCCTTGGCCAGC

GGAGACTACGTGCCCACGAATGGACTCCCGGTCGGAATCGAACGCTGGG

AGAACAAGCTCTTTGTGTCGGTCCCAAGATGGAAGGATGGTATCCCGTC

CACCCTGAACTACATCGATATGAATCAGACCCCGTCCGGGTCGCCACCG

CTGATCCCTTACCCAAGCTGGGCCAACAACGTGGCCGGAGACTGTCAGA

ATGGCCTGTCGACCGTGTACCGTATCAAGGCTGACAAGTGTGGACGCCT

CTGGGTTCTGGACACCGGTACCGTCGGAATCGGAAACACCACCCAGCAG

CTGTGCCCGTACGCGTTGAACATCTTTGACCTTAAGACCAACACCCGTC

TGCGTCGGTATGAACTGCGTGCCGAAGACACCAACCAGAACACCTTCAT

CGCTAACATTGCCATCGACATGGGACGCAGCTGCGAGGACACCTTCGCC

TACATGTCCGATGAACTGGGCTACGGACTGATTGCCTACTCATTTGAGA

AGAACAAGTCCTGGCGGTTCGAGCATAGCTTCTTCTTCCCAGATCCTCT

ACGCGGAGACTTCAACGTTGCCGGTCTGAACTTCCAATGGGGTGAGGAA

GGTATCTTCGGAATGTCGCTTTCCCCCCTGCAATCCGATGGCTTCCGCA

CCATGTACTTCTCCCCGTTGGCCAGTCACCGTGAATTCATGGTCTCCAC

TCAGGTCCTGCGCGACGAAGAAGGTGCCGAAGAGAGCTTCCACAAGTTC

ACCTACCTGAAGGAACGAGGACCCAACAGCCATACTACATCCCGAGTCA

TGAGCGAAACCGGACTGCAGCTATTCAACTTGATTGACCAGAACGCCGT

CGGATGCTGGCATTCGTCGCTCCCTTACAGCCCTGAAAACCATGGAATC

GTCGACCGTGATGATGTGGAACTGGTCTTCCCAGCTGACGTCAAGATCG

ATGCCGAAGAGAACGTGTGGGTCATCTCCGACCGTATGCCAGTGTTCCT

CATCGCCGAGCTGGACTACAGTGATGTCAACTTCCGCATCTTCACCGCT

CCTCTGAGCACTCTGGTCGCTGGAACCGTCTGCGACGTTAGGCCTTCGC

TCCGACCAGGTGCCATCCAGTCCAAATTCGGTGGATCCGATCTGTCCAC

CTATCCAGGCACCACCCTTCTCCCAGTTGGCTACACTCAACCCATCAGC

-continued

TATACCCCGTCCTCGTACGCCCCAACCGTTGCCCCTGTCACCAAGTACA

CAGCCGCTCCAGCGTACGATCACCCAACCTCCCACATGTACACGACCCA

GGAATATCCGACGACCGCCAAGGCGTACCACTTCAACAAGTACCACAAC

GTAGAGTACCAATCGCATGGAAATGGTCAAGCTGACTACCACTTCGGAC

ACGGTGGACACTACCACGATCACGACCACGCCCATGAATACGGTCACGA

TCACGGATACTACGGCGGTGGTCAACGCCGTCATTGGGGAGCTGGCGCC

AAGAAGCCCGAAGCCTGGAAGCAGCAGCTGTACTAG

For example, the amino acid sequence of *Aedes aegypti* DCE4 is

MRGNILWLLAAVTQLTVTSVTAFANNSNAIYTWEGGRIEWPCPTTKRLV

KAAAKYTPKDIIAMACARSGDKTLCAMPRYRNSIPITLGQIYATKKGCD

VKFEPFPCWTEQEENNCNSLQSVIDIYATGDFVWVLDNGILNALRSPIQ

RCPAKIVVYEAKTGKKMKTINLGRYVTEKSRLQYMQVECLKGGQCFVYI

SDAGNNAIIIYDVSGGRGYRVVLPKAVHHGCRFRDVLYIFLSYHKDGTK

LFFTYLGGRRLFAIATDHLRKGHGGNIEDIGEKPGSFIYIGPDGATGVF

FREEGDSNVFFWDTKTCLKKSNFKLVFKSSEGLYATDVFPDHEINRFLI

LESDFPGYMEEKAGCGTLHQISLLDGATC (SEQ ID NO: 189, AAEL007096-PA [*Aedes aegypti*] GenBank: EAT41240).

A nucleic acid sequence for *Aedes aegypti* DCE4 is (SEQ ID NO: 198)

ATGCGAGGTAACATCCTTTGGCTGTTGGCTGCAGTGACGCAGCTGACGG

TGACCAGCGTTACGGCGTTCGCGAACAATTCAAATGCTATCTACACCTG

GGAAGGTGGCCGCATCGAGTGGCCATGCCCGACGACAAAGCGATTGGTT

AAGGCTGCTGCAAAGTACACTCCTAAGGATATCATCGCAATGGCTTGCG

CAAGAAGTGGCGACAAGACCCTCTGCGCGATGCCAAGATACCGAAATAG

TATTCCGATAACCCTGGGACAAATCTACGCAACAAAAAAGGGTTGTGAC

GTCAAGTTCGAACCTTTCCCGTGCTGGACTGAGCAAGAAGAGAACAACT

GCAATTCGCTACAGTCGGTTATTGACATCTACGCTACCGGTGACTTCGT

GTGGGTTCTGGACAATGGTATACTTAATGCATTGAGAAGTCCTATTCAA

AGATGCCCAGCGAAGATCGTGGTTTATGAAGCCAAAACGGGGAAAAAGA

TGAAGACGATAAACCTTGGCCGATACGTGACCGAGAAGTCTCGTCTCCA

GTATATGCAGGTCGAGTGCTTGAAGGGTGGCCAATGTTTCGTGTACATC

AGCGACGCTGGAAACAATGCAATTATCATTTACGACGTGTCTGGAGGTC

GTGGCTATCGTGTAGTACTGCCGAAAGCTGTGCATCACGGATGTAGATT

CCGCGACGTTCTGTACATTTTCTTGTCGTATCACAAGGATGGAACAAAA

CTATTTTTCACCTATCTGGGTGGACGACGACTATTCGCCATTGCTACGG

ATCACCTACGAAAAGGTCATGGCGGTAACATTGAAGATATCGGGGAAAA

GCCAGGGTCCTTCATTTACATCGGACCAGACGGAGCAACAGGTGTGTTT

TTCAGAGAGGAAGGCGATAGCAATGTATTCTTCTGGGACACAAAAACAT

GTCTCAAGAAGTCGAACTTCAAACTGGTGTTCAAGAGCAGTGAGGGATT

ATATGCAACGGATGTGTTCCCGGACCATGAAATCAATCGGTTCCTTATA

-continued

TTGGAGTCAGATTTTCCAGGTTATATGGAGGAGAAAGCTGGATGTGGTA

CACTGCATCAGATCTCCCTGCTTGACGGGGCTACTTGTTAA

For example, the amino acid sequence of *Aedes aegypti* DCE5 is

MWALDSGICNSLEQPIKRCTAKVIAFDLETDKTVKTVDLSDILKPHSRP

QYLVTDYSPNGFPYVYISDAEGAIIVLDIHHNKMYRVVLPRAISAGCGE

SDVLYLLLVRRPKNQNMVIFSYLCONKVYGIKSEFLRTGRGSSAIVELG

SKTKHSVLLGTDGSNGVILRYRSESELYKWNTDQPYKECNFELVQLAEE

CRLSTHVAPGGKDALMYSLSSNVADYLNHTCGAGGASARLKYISKECED

DCY (SEQ ID NO: 190, AAEL010848-PA [*Aedes aegypti*] GenBank: EAT37145).

A nucleic acid sequence for *Aedes aegypti* DCE5 is (SEQ ID NO: 199)

ATGTGGGCCCTCGACTCAGGCATTTGCAACTCTTTGGAGCAACCCATAA

AACGCTGCACAGCAAAGGTGATAGCGTTTGACCTGGAAACAGATAAAAC

AGTGAAAACGGTGGATCTAAGCGACATTCTGAAGCCACACTCCAGACCA

CAGTACCTTGTGACGGATTATTCGCCCAATGGATTCCCGTACGTCTACA

TTAGCGACGCTGAAGGTGCCATCATCGTACTGGACATCCACCACAACAA

GATGTACCGAGTGGTGCTACCACGTGCCATTTCTGCTGGCTGTGGCGAA

TCGGATGTCCTATATTTACTGCTGGTACGAAGACCCAAAAACCAAAACA

TGGTCATATTCTCGTATCTGTGCGGAAACAAGGTCTACGGTATCAAATC

GGAATTTCTGCGCACGGGACGAGGCTCGAGTGCTATCGTAGAGCTCGGT

AGCAAGACTAAGCATTCTGTTTTGCTCGGGACGGACGGAAGCAACGGTG

TTATTCTGAGGTATAGAAGCGAAAGCGAACTCTACAAATGGAACACTGA

TCAACCGTACAAGGAGTGTAACTTCGAATTGGTTCAACTTGCGGAGGAG

TGTCGCTTGAGCACGCATGTCGCCCCTGGAGGAAAAGATGCTCTGATGT

ACTCATTGTCATCCAATGTGGCCGATTACTTAAATCACACCTGTGGCGC

AGGAGGTGCTTCAGCTCGACTCAAATATATAAGTAAAGAATGTGAAGAT

GATTGTTATTAA

For any of the disclosed genes and proteins (e.g., Nasrat, Closca, Polehole, Nudel, CATL3, DCE2, DCE4, DCE5), or a homologue thereof, such as an orthologue or a paralogue, from other species of mosquito can be identified using, for example, BLASTN and/or BLASTP queries and/or sequence alignment techniques for global comparison. Exemplary species of mosquitoes that can be targeted are discussed in more detail below, and thus the Nasrat, Closca, Polehole, Nudel, CATL3, DCE2, DCE4, DCE5 or homologue thereof can be from any of these species.

Vectorbank and Genbank accession numbers, and sequence identifiers for EOF1, Nasrat, Closca, Polehole, Nudel, CATL3, DCE2, DCE4, and DCE5 protein and nucleic acid sequences in various species of mosquitoes are provided in Table 1, below. All the Vectorbank and Genbank accession numbers, including all sequences they provide, in Table 1 and provided elsewhere herein are specifically incorporated by reference herein in their entireties.

The sequences of any of the accession numbers disclosed herein can be used as query sequences to identify homologues and other related sequences. In some embodiments, a putative EOF 1, Nasrat, Closca, Polehole, Nudel, CATL3, DCE2, DCE4, or DCE5 has at least 50%, 60%, 70%, 80%, 85%, 90%, 95%, 96%, 97%, 98%, 99%, or 100% sequence identity with the sequences of any of the accession numbers or sequence identifiers disclosed in Table 1, and including nucleic acid sequences encoding amino acid sequences thereof. Preferably the sequence identity is over at least 50%, 60%, 70%, 80%, 85%, 90%, 95%, 96%, 97%, 98%, 99%, or 100% of the length of the query sequence. Thus, in some embodiments, the EOF1, Nasrat, Closca, Polehole, Nudel, CATL3, DCE2, DCE4, or DCE5 gene or gene product that is subject to inhibition has at least 50%, 60%, 70%, 80%, 85%, 90%, 95%, 96%, 97%, 98%, 99%, or 100% sequence identity with the sequence of any of the accession numbers or sequence identifiers disclosed in Table 1, and including the amino acid sequence where the nucleic acid sequence is provided and the nucleic acid sequence where the amino acid sequence is provided.

TABLE 1

Target Sequences

| Target | Species | Vectorbase # | Genbank protein # | Amino Acid SEQ ID NO: | Genbank nucleotide # | Nucleic Acid SEQ ID NO: |
|---|---|---|---|---|---|---|
| EOF1 | *Aedes aegypti* | AAEL012336 | EAT35499 | 1 | XM_021855381 | 191, 239 |
| | *Aedes albopictus* | NA | KXJ75527.1 | 201 | XM_019701144.2 | 220 |
| | *Anopheles gambiae* | AGAP011495 | XP_001237976.2 | 210 | XM_001237975.2 | 229 |
| | *Culex quinquefasciatus* | CPIJ010293 | XP_001870696 | 219 | XM_001870661.1 | 238 |
| Nasrat | *Aedes aegypti* | AAEL008829 | EAT39370 | 183 | XM_001659527.2 | 192, 240 |
| | *Aedes albopictus* | NA | KXJ83088.1 | 202 | XM_019692618.2 | 201 |
| | *Anopheles gambiae* | AGAP003290 | XP_307796.5 | 211 | XM_307796.5 | 230 |
| Closca | *Aedes aegypti* | AAEL000961 | EAT47957 | 184 | XM_021852861.1 | 193, 241 |
| | *Aedes albopictus* | NA | XP_029731592.1 | 203 | XM_029875732.1 | 222 |
| | *Anopheles gambiae* | AGAP011897 | XP_320629.4 | 212 | XM_320629.4 | 231 |
| Polehole | *Aedes aegypti* | AAEL022628 | EAT33906 | 185 | XM_021856944.1 | 194, 242 |
| | *Aedes albopictus* | NA | XP_019549605.1 | 204 | XR_003892964.1 | 223 |
| | *Anopheles gambiae* | undetected | undetected | 213 | undetected | 232 |
| Nudel | *Aedes aegypti* | AAEL016971 | EJY57924 | 186 | XM_011495306.2 | 195, 243 |
| | *Aedes albopictus* | NA | XP_029725264.1 | 205 | XM_029869404.1 | 224 |
| | *Anopheles gambiae* | AGAP007280 | XP_308537.4 | 214 | XM_308537.4 | 233 |
| CATL3 | *Aedes aegypti* | AAEL002196 | EAT46597 | 187, 200 | XM_021847649.1 | 196, 244 |
| | *Aedes albopictus* | NA | XP_029727064.1 | 206 | XM_029871204.1 | 225 |
| | *Anopheles gambiae* | AGAP001960 | XP_321102.4 | 215 | XM_321102.5 | 234 |
| DCE2 | *Aedes aegypti* | AAEL006830 | EAT41553 | 188 | XM_001658016.2 | 197, 245 |
| | *Aedes albopictus* | NA | XP_019530244.1 | 207 | XM_029854936.1 | 226 |
| | *Anopheles gambiae* | AGAP000879 | XP_316854.4 | 216 | XM_316854.5 | 235 |
| DCE4 | *Aedes aegypti* | AAEL007096 | EAT41240 | 189 | XM_001658061.2 | 198, 246 |
| | *Aedes albopictus* | NA | XP_019531502.1 | 208 | MH936662.1 | 227 |
| | *Anopheles gambiae* | AGAP005959 | XP_315999.4 | 217 | XM_315999.4 | 236 |
| DCE5 | *Aedes aegypti* | AAEL010848 | EAT37145 | 190 | XM_021842318.1 | 199, 247 |
| | *Aedes albopictus* | NA | XP_019531562.2 | 209 | XM_019676017.2 | 228 |
| | *Anopheles gambiae* | AGAP005958 | XP_315998.4 | 218 | XM_315998.4 | 237 |

B. Inhibitors of Target Genes/Gene Products

The disclosed inhibitors of target genes/gene products such as EOF1, Nasrat, Closca, Polehole, Nudel, CATL3, DCE2, DCE4, or DCE5 are typically functional nucleic acids or a gene editing composition. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, ribozymes, RNAi, external guide sequences, RNA interference. Gene editing compositions facilitate a change in an organism's DNA. Gene editing compositions include, for example, CRISPR/Cas and other nuclease-based systems as well as triplex forming molecules and donor oligonucleotides.

The EOF1 inhibitor compounds can act as effectors, inhibitors, modulators, and stimulators of a specific activity possessed by a target molecule, or the functional nucleic acid molecules can possess a de novo activity independent of any other molecules. The compounds may interact with any macromolecule, such as DNA, RNA, polypeptides, or carbohydrate chains. Thus, compounds can interact with the mRNA or the genomic DNA of a target polypeptide or they can interact with the polypeptide itself. Often the compounds are designed to interact with other nucleic acids based on sequence homology between the target molecule and the compound. In other situations, the specific recognition between the EOF1, Nasrat, Closca, Polehole, Nudel, CATL3, DCE2, DCE4, or DCE5 inhibitor compound and the target molecule is not based on sequence homology between the compound and the target molecule, but rather is based on the formation of tertiary structure that allows specific recognition to take place.

Therefore the compositions can include one or more functional nucleic acids or gene editing compositions designed to reduce expression of an EOF1 gene, or a gene product thereof. The compositions can include one or more functional nucleic acids or gene editing compositions designed to reduce expression of a Nasrat, Closca, Polehole, Nudel, CATL3, DCE2, DCE4, or DCE5 gene, or a gene product thereof. In preferred embodiments, the compositions can include one or more functional nucleic acids or gene editing compositions designed to reduce expression of an EOF1, Nasrat, Closca, Polehole, or Nudel gene, or a gene product thereof.

In some embodiments, the composition is a functional nucleic acid such as a siRNA or RNAi or others described in more detail elsewhere herein that inhibits or otherwise reduces expression of a nucleic acid encoding a protein according to an accession number or sequence identifier of Table 1.

In some embodiments, the composition is a functional nucleic acid such as a siRNA or RNAi or others described in more detail elsewhere herein that inhibits or otherwise reduces expression of a nucleic acid according to an accession number or sequence identifier of Table 1.

For example, in some embodiments, the composition is a functional nucleic acid, particularly RNAi, e.g., double stranded RNAi, that targets an mRNA encoding the EOF1, Nasrat, Closca, Polehole, Nudel, CATL3, DCE2, DCE4, or DCE5 protein (e.g., any one of SEQ ID NOS:1, 183-190, or 200-219, or a sequence at least 85%, 90%, or 95% identical thereto). In particular embodiments, the composition is a functional nucleic acid, particularly RNAi, e.g., double stranded RNAi, that targets the mRNA corresponding to or encoded by the DNA sequence of any one of SEQ ID NOS:191-199 or 220-247, or a sequence at least 85%, 90%, or 95% identical thereto.

In some embodiments, the RNAi comprise and RNAi sequence provided herein, for example in the experiments below.

1. Functional Nucleic Acids a. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

b. Ribozymes

The functional nucleic acids can be ribozymes. Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

c. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

d. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors including shRNA are available, such as, for example, Imgenex's GENESUPPRESSOR™ Construction Kits and Invitrogen's BLOCK-IT™ inducible RNAi plasmid and lentivirus vectors.

In some embodiments, the functional nucleic acid is siRNA, shRNA, miRNA. In some embodiments, the composition includes a vector expressing the functional nucleic acid. Methods of making and using vectors for in vivo expression of functional nucleic acids such as antisense oligonucleotides, siRNA, shRNA, miRNA, EGSs, and ribozymes, are known in the art.

2. Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide. The compositions can be used, for example, to reduce or otherwise modify expression of an EOF1, Nasrat, Closca, Polehole, Nudel, CATL3, DCE2, DCE4, or DCE5.

a. Strand Break Inducing Elements i. CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as EOF1, Nasrat, Closca, Polehole, Nudel, CATL3, DCE2, DCE4, or DCE5) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

ii. Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-

31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe (sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

iii. Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). US Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of Fold nuclease. The resulting TALENs were shown to induce gene modification in immortalized human cells. General design principles for TALE binding domains can be found in, for example, WO 2011/072246.

b. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

c. Triplex Forming Oligonucleotides

The compound can be triplex forming molecules. Triplex forming molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Triplex forming molecules are often used in combination with a mutagen or a donor oligonucleotide such as those described above.

3. Oligonucleotide Composition

The functional nucleic acids and gene editing compositions can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i−1 phosphate in the purine strand of the duplex.

In some embodiments, the oligonucleotide is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

c. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.,* 52:4202, (1987)), and uncharged morpholino-based polymers having achiral intersubunit linkages (see, e.g., U.S. Pat. No. 5,034, 506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., *Chem. Biol.,* 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the compounds can be single stranded or double stranded.

4. Protease Inhibitors

The disclosed inhibitors of target genes or gene products can be one or more protease inhibitors. For example, in particular embodiments, the inhibitor of a disclosed gene product, particularly the Nudel gene product, is a protease inhibitor or a cocktail of two or more protease inhibitors.

Protease inhibitors are molecules that block, reduce or otherwise limit the activity of proteases. Typically, a protease inhibitor functions on classes of proteases with similar mechanisms of action. Protease inhibitors can be proteins, peptides, or small molecules. In some embodiments, the protease inhibitor is an antibody or functional fragment thereof. The protease inhibitors can be naturally occurring or synthetic. Naturally occurring protease inhibitors are usually proteins or peptides. Protease inhibitors used in experimental studies or thug development are often synthetic peptide-like or small molecules.

Protease inhibitors can work in many different ways to inhibit the action of proteases. These inhibitors can be classified by the type of proteases they inhibit and the mechanism by which they inhibit the protease enzyme. Reversible inhibitors usually bind to the protease with multiple non-covalent interactions, without any change to the inhibitor itself. These inhibitors can be removed by dilution or dialysis. Reversible inhibitors include competitive inhibitors (which compete with substrates for access to the active site), uncompetitive inhibitors (which bind to the protease only when it is already attached to a substrate), and non-competitive inhibitors (bind to the protease with similar affinities, regardless of the presence of a bound substrate; typically inhibit protease activity through an allosteric mechanism). Irreversible protease inhibitors function by specifically altering the active site of its specific target protease, often through the covalent bond formation. They can also be called inactivators. Upon binding to the inhibitor, a protease's active site is altered, and it can no longer perform peptide bond hydrolysis. Some of such inhibitors do not actually covalently bind to the protease, but interact with such a high affinity, that they are not easily removed, Suicide inhibitors, typically analogs of the substrate, are irreversible inhibitors that covalently bind to proteases. An example of a suicide protease inhibitor is the serpin family of proteins, which play a role in blood coagulation and inflammation.

Many different protease inhibitors are commercially available. Protease inhibitors can be in liquid form or solid form (e.g., tablets). Protease inhibitors can be used individually or as a cocktail containing multiple protease inhibitors in defined concentrations. Protease inhibitor cocktails are often used for their reliability and reproducibility.

In preferred embodiments, the protease inhibitor is specific to a particular protease (e.g., Nudel) or to one or more general classes of proteases (e.g., serine proteases).

Exemplary protease inhibitors include, but are not limited to, AEBSF/Pefabloc, Aprotinin, Bestatin, E-64, EDTA, EGTA, GM 6001, Leupeptin, Pepstatin, PMSF, and valine-pyrrolidide. MilliporeSigma, STEMCELL Technologies, and Thermo Fisher are common vendors for protease inhibitors.

III. Methods of Use

Methods of inhibiting target genes or gene products such as EOF1, Nasrat, Closca, Polehole, Nudel, CATL3, DCE2, DCE4, or DCE5 are provided. The methods typically include contacting mosquito cells with an effective amount of an inhibitor, such as a functional nucleic acid, gene editing composition or protease inhibitor specific for one or more target gene or gene product (e.g., EOF1, Nasrat, Closca, Polehole, Nudel, CATL3, DCE2, DCE4, or DCE5) to reduce expression, activity, or bioavailability of the gene or a gene product thereof (e.g., EOF1, Nasrat, Closca, Polehole, Nudel, CATL3, DCE2, DCE4, or DCE5). The functional nucleic acid or gene editing composition can be introduced into the mosquito cells in any manner and at any time suitable to reduce, inhibit, or interfere with a target gene or gene product, e.g. EOF1, Nasrat, Closca, Polehole, Nudel, CATL3, DCE2, DCE4, or DCE5. The contacting can be in vivo. Thus, for example, in some embodiments, the compositions are introduced into mosquito cells during or after the composition is contacted with or administered to live mosquitoes. The mosquitoes can be at any stages of development. For example, the mosquitoes can be embryonic, larval, pupal, adult, etc. In some embodiments, the mosquito cells are eggs that can be contacted inside or outside of the mother.

Preferably the EOF1-, Nasrat-, Closca-, Polehole-, Nudel-, CATL3-, DCE2-, DCE4-, or DCE5-inhibiting compositions are contacted with mosquito cells in an effective amount to induce one or more desired physiologic or phenotypic effects in the treated mosquito or cells thereof. For example, in some embodiments, the level of alternation to EOF1-, Nasrat-, Closca-, Polehole-, Nudel-, CATL3-, DCE2-, DCE4-, or DCE5 gene or gene product activity is sufficient to reduce or prevent embryos from completing embryogenesis and/or reaching the first larval instar; reduces, delays, or otherwise disrupts eggshell formation and/or egg melanization, reduces egg survival, alters the follicular shape of eggs, increases permeability of oocytes to water, reduces female fecundity, leads to an embryonic lethal phenotype, or any combination thereof.

The disclosed methods can be used to prevent the spread of mosquito-borne illnesses. Mosquito-borne illnesses include, but are not limited to, mosquito vectored diseases such as protozoan diseases, i.e., malaria, filarial diseases such as dog heartworm, and viruses such as Dengue, encephalitis, West Nile virus, rift valley fever, and yellow fever, as well as severe skin irritation through an allergic reaction to the mosquito's saliva.

A. Methods of Inhibiting Target Genes/Gene Products in Mosquitoes

Methods of genetic manipulation of mosquitoes including the effective amount of nucleic acids needed, methods of administration, and timing of administration can be selected by the practitioner based on the particular compounds and methods chosen.

For example, an RNAi-based method is exemplified in the experiments described below, and typically involves introducing dsRNA into mosquito cells. See, e.g., Airs and Bartholomay, *Insects.* 2017 March; 8(1): 4 and references cited therein, which is specifically incorporated by reference in its entirety. Airs and Bartholomy, supra, which discusses that RNAi can be delivered to mosquitoes from embryo through adulthood and provides diverse examples of both (A) delivery systems and (B) RNAi trigger molecules (see also FIG. 2) that can be employed to suppress genes in mosquitoes. Examples shown include: (1) naked RNAi triggers such as dsRNA, siRNA, or chemically modified siRNA (star shape); (2) transfection agents with dsRNA or shRNA expressing plasmids; (3) nanoparticles of abiotic or biotic origin in combination with dsRNA or plasmids; (4) viral expression systems carrying dsRNA or ssRNA that is converted to dsRNA in the cell; (5) bacterial expression systems containing dsRNA or shRNA plasmids; and (6) yeast expression systems containing dsRNA or shRNA plasmids.

In some embodiments, the method includes administering mosquitoes a functional nucleic acid, particularly RNAi, e.g., double stranded RNAi that targets an mRNA encoding the EOF1, Nasrat, Closca, Polehole, Nudel, CATL3, DCE2, DCE4, or DCE5 protein (e.g., any one of SEQ ID NOS:1, 183-190, or 200-219, or a sequence at least 85%, 90%, or 95% identical thereto). In particular embodiments, the composition is a functional nucleic acid, particularly RNAi, e.g., double stranded RNAi that targets the mRNA corresponding to the cDNA sequence of any one of SEQ ID NOS:191-199 or 220-247 or a sequence at least 85%, 90%, or 95% identical thereto.

Techniques for gene modification in mosquitoes is also well known, published examples including transposon-mediated transgenesis (Coates *Proc. Natl. Acad. Sci. USA.* 1998; 95: 3748-3751; Lobo et al., *Insect Mol. Biol.* 2002; 11: 133-139) and loss-of-function gene editing with zinc-finger nucleases (ZFNs) (DeGennaro et al., *Nature.* 2013; 498: 487-491; Liesch et al., *PLoS Negl. Trop. Dis.* 2013; 7: e2486, McMeniman et al., *Cell.* 2014; 156: 1060-1071), TAL-effector nucleases (TALENS) (Aryan et al., *PLoS ONE.* 2013; 8: e60082, Aryan et al., *Methods.* 2014; 69: 38-45), and homing endonuclease genes (HEGs) (Aryan et al., *Sci. Rep.* 2013; 3: 1603). ZFNs and TALENs are modular DNA-binding proteins tethered to a non-specific FokI DNA nuclease (Carroll, *Annu. Rev. Biochem.* 2014; 83: 409-439), while HEGs are naturally occurring endonucleases that can be reengineered to target new sequences (Stoddard, *Mob. DNA.* 2014; 5: 7 (2014)). Targeting specificity by these reagents is conferred by context-sensitive protein-DNA-binding interactions.

The CRISPR/Cas9-based genome editing methodology and gene-drive systems have also been employed in mosquitoes. See, for example, Basu, et al., Proc *Natl Acad Sci USA.* 2015; 112(13):4038-43. pmid:25775608; Dong, et al., *PLoS One.* 2015; 10(3): e0122353. pmid:25815482; Kistler, et al., *Cell Rep.* 2015; 11(1):51-60. pmid:25818303; Hall, et al., *Science.* 2015; 348(6240):1268-70. pmid:25999371; Itokawa, et al., *Sci Rep.* 2016; 6:24652. pmid:27095599; and Grigoraki, et al., *Sci Rep.* 2017; 7(1):11699. pmid: 28916816, which exemplify CRIPSR/Cas9 gene editing in *Aedes aegypti, Anopheles stephensi*, and *Culex* mosquitoes. Furthermore, Kistler and colleagues (Kistler, et al., *Cell Rep.* 2015; 11(1):51-60. pmid:25818303) have established a comprehensive protocol for CRISPR/Cas9 gene editing in *Aedes* mosquitoes through embryonic delivery of in vitro-synthesized guide RNA (sgRNA) and recombinant Cas9 protein. CRISPR/Cas9 mediated somatic disruption of a male-determining gene in *Aedes* mosquitoes has produced males with feminized genitalia (Hall, et al., *Science.* 2015; 348(6240): 1268-70. pmid:25999371), and Cas9-mediated gene drive technology has also proven promising for population modification of both Asian and African malaria vector mosquitoes, *A. stephensi* and *A. gambiae*, respectively (Gantz, et al., *Proc Natl Acad Sci USA.* 2015; 112(49):E6736-43. pmid: 26598698; Hammond, et al., *Nat Biotechnol.* 2016; 34(1): 78-83. pmid:26641531; Hammond, et al., *PLoS Genet.* 2017; 13(10):e1007039. pmid:28976972).

As disclosed herein, EOF1 is expressed by females and is important for eggshell development. It is not believed to be essential in males. One preferred strategy is to use CRISPR-Cas endonuclease (or another nucleases such as zinc finger nucleases or a TALENs) constructs that function as gene drive systems to reduce or completely eliminate egg development or egg fitness in females. Because the eggshell development is not essential to male fitness, genetically modified males can be released and serve that carriers that introduce the reduced fertility to one or more generations of females. See, e.g., Mathews, "A genetically modified organism could end malaria and save millions of lives—if we decide to use it," VOX, updated Sep. 26, 2018; Kyrou, et al., "A CRISPR-Cas9 gene drive targeting doublesex causes complete population suppression in caged *Anopheles gambiae* mosquitoes," *Nature Biotechnology*, published online 24 Sep. 2018; doi:10.1038/nbt.4245; Hammond, et al., "A CRISPR-Cas9 gene drive system targeting female reproduction in the malaria mosquito vector *Anopheles gambiae,"* *Nature Biotechnology,* 34:78-83 (2016).

The target for gene modification can be any one or more of the genes encoding an EOF1, Nasrat, Closca, Polehole, Nudel, CATL3, DCE2, DCE4, or DCE5 protein (e.g., any one of SEQ ID NOS:1, 183-190, or 200-219, or a sequence at least 85%, 90%, or 95% identical thereto.

B. Pesticide Compositions

Other (or inert) ingredients may be included in the composition to aid in the application of the compound (e.g. functional nucleic acid, gene editing composition, protease inhibitor, etc.), also referred to the active agent with respect to the composition. Typically, the other ingredients do not eliminate (e.g., through degradation) the compound. Thus, preferably the other ingredients are of a composition and/or are used in a concentration compatible with the target gene or gene product (e.g., EOF1, Nasrat, Closca, Polehole, Nudel, CATL3, DCE2, DCE4, or DCE5) inhibitor compound.

In some embodiments, the composition includes a delivery vehicle to enhance stability, transfectability, or a combination thereof. For example in some embodiments, the compound is delivered via a liposome. Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. This disclosed compositions and methods can be used in conjunction with any of these or other commonly used gene transfer methods.

In some embodiments, the delivery vehicle is incorporated into or encapsulated by a nanoparticle, microparticle, micelle, synthetic lipoprotein particle, or carbon nanotube. For example, the compositions can be incorporated into a vehicle such as polymeric particles which provide controlled release of the compound. In some embodiments, release of the compound is controlled by diffusion of the compound out of the particles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for compound containing particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

The compound can be incorporated into materials which are insoluble in aqueous solution or slowly soluble in aqueous solution, but are capable of degrading by means including enzymatic degradation, surfactant action, and/or mechanical erosion. As used herein, the term "slowly soluble in water" refers to materials that are not dissolved in water within a period of 30 minutes. Preferred examples include fats, fatty substances, waxes, waxlike substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

Other ingredients include but are not limited to, solvents, carriers, adjuvants, or any other compound, besides the active ingredient. There are many types of other ingredients: solvents are liquids that dissolve the active ingredient, carriers are liquids or solid chemicals that are added to a pesticide product to aid in the delivery of the active ingredient, and adjuvants often help make the pesticide stick to or spread out on the application surface (i.e., leaves). Other adjuvants aid in the mixing of some compositions when they are diluted for application.

The compound may be applied as a solid, such as in the form of pellets or flakes. For example, the compound may be included in a solid pellet that is introduced into a water source.

The compound may be dissolved or dispersed in a continuous phase. The continuous phase typically contains a surfactant wetting agent, e.g. alkyl/aryl polyether alcohols, polyethylene oxide esters (or ethers) of fatty acids, alkyl/aryl sulfonates, alkyl sulfates and the like. The surfactant is preferably present in the amount of about 0.1% up to about 5% vol/vol of the composition. These surface active agents are well known in the art for use in preparing dispersions of insecticides. In the continuous phase of the composition, the surfactants assist in causing the solution droplets to spread out on waxy leaves and penetrate the waxy protective coating on the insects and their eggs.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

In some embodiments, the compositions can include one or more carriers and/or diluents such as, for example, any solid or liquid carrier or diluent that is commonly used in pesticidal, agricultural, or horticultural compositions. Those skilled in the art will recognize that these components in a composition are typically referred to as "inert ingredients" and are regulated by governmental agencies, such as the U.S. Environmental Protection Agency (EPA). Suitably, any included additional carrier or diluent will not reduce the insecticidal efficacy of the composition, relative to the efficacy of the composition in the absence of the additional component. Carriers and diluents can include, for example, solvents (e.g., water, alcohols, petroleum distillates, acids, and esters); vegetable oil (including but not limited to methylated vegetable oil); and/or plant-based oils as well as ester derivatives thereof (e.g., wintergreen oil, cedarwood oil, rosemary oil, peppermint oil, geraniol, rose oil, palmarosa oil, citronella oil, citrus oils (e.g., lemon, lime, and orange), dillweed oil, corn oil, sesame oil, soybean oil, palm oil, vegetable oil, olive oil, peanut oil, and canola oil). The composition can include varying amounts of other components such as, for example, fatty acids and fatty acid esters of plant oils (e.g., methyl palmitate/oleate/linoleate), and other auxiliary ingredients such as, for example, emulsifiers, dispersants, stabilizers, suspending agents, penetrants, coloring agents/dyes, UV-absorbing agents, and fragrances, as necessary or desired. The compositions may include a carrier or diluent in an amount of at least about 1%, at least about 2%, or at least about 5% by weight of the composition. The compositions may include a carrier or diluent in an amount of less than about 30%, less than about 25%, or less than about 20% by weight of the composition. The compositions may include carrier or diluent in an amount of about 1% to about 30%, about 2% to about 25%, or about 5% to about 20% by weight of the composition. Components other than mineral oil and coconut oil can be included in the compositions in any amount as long as the composition provides some amount of insecticidal efficacy.

C. Methods of Administration

The methods of administration can also be selected based on the desired target species and life stage with consideration for environmental and abiotic factors including: UV, ribonucleases, microbes, dissipation and dilution in aqueous environs and on solid substrates. Methods of delivering RNAi to mosquitoes are described in Airs and Barholomay, et al., *Insects*. 2017 March; 8(1): 4, doi: 10.3390/insects8010004, which is specifically incorporated by reference in its entirety, as well as references cited therein, and such methods may also be useful for other types of nucleic acid compounds.

Infrastructure and techniques for a variety of interventions already exist to deliver chemical and biological pesticides to vector mosquitoes, including, for example, topical and contact applications for adults (e.g., aerial and residual spraying and long-lasting insecticidal nets (LLINs)) and per os or contact applications for aquatic stages.

Suitable methods include contacting a mosquito or population of mosquitoes with an effective amount of a composition as described above. Contacting includes contacting an insect directly or indirectly. For example, compositions described herein may be applied to a surface and an insect may subsequently or concurrently contact the surface and the composition. In some embodiments, compositions may be applied to a surface. In some embodiments, compositions may form a coating or film on a surface. In some embodiments, methods include forming a coating or film on a surface.

Surfaces may include, but are not limited to, surfaces of liquid such as bodies of water or other aquatic mosquito breeding sites. Examples of bodies of water and application sites include, without limitation, salt marshes, freshwater aquatic environments, storm water drainage areas, sewers and catch basins, woodland pools, snow pools, roadside ditches, retention ponds, freshwater dredge spoils, tire tracks, rock holes, pot holes, and similar areas subject to holding water; natural and manmade aquatic sites, fish ponds, ornamental ponds, fountains, and other artificial water-holding containers or tanks; flooded crypts, transformer vaults, abandoned swimming pools, construction, and other natural or manmade depressions; stream eddies, creek edges, detention ponds, freshwater swamps and marshes including mixed hardwood swamps, cattail marshes, common reed wetlands, water hyacinth ponds, and similar freshwater areas with emergent vegetation; brackish water swamps, marshes, and intertidal areas; sewage effluent, sewers, sewage lagoons, cesspools, oxidation ponds, septic ditches, and septic tanks; animal waste lagoons, settling ponds, livestock runoff lagoons, and wastewater impoundments associated with fruit and vegetable processing; and similar areas. Other examples include, without limitation, dormant rice fields (for application during the interval between harvest and preparation of the field for the next cropping cycle), standing water within pastures/hay fields, rangeland, orchards, and citrus groves where mosquito breeding occurs.

In some embodiments, the methods described herein include any known route, apparatus, and/or mechanism for the delivery or application of the compositions. In some embodiments, the method includes applying the compositions via a sprayer. Traditional pesticide sprayers in the pest control markets are typically operated manually or electrically or are gas-controlled and use maximum pressures ranging from 15 to 500 psi generating flow rates from 1 gpm to 40 gpm.

Certain steps can be taken to increase the delivery of nucleic acids to the desired mosquito or mosquito cells, and reduce environmental degradation of the composition. For example, RNAi knockdown in larvae by per os exposure is efficacious using scalable bacterial and yeast expression systems, demonstrating potential for RNAi in larval control applications. Interventions have also been explored to provide oral applications to adults in the form of Attractive Toxic Sugar Baits (ATSB): formulations that can include, for example, simple sucrose solutions and complex mixtures of fruit sugars with minimal effects on non-target organisms. Formulations can be delivered either via spraying on, for example, plant sources or in bait stations. Spray formulations have proven effective on flowering and non-flowering plants in arid and wet climates, and bait stations placed near breeding sites (referred to as Attractive Baited Oviposition Trap (ABOT)) or indoors can attract and vector species in proximity to people. Although ATSB have not been studied in conjunction with RNAi, successful gene silencing by oral exposure routes has been documented using sucrose meals and artificial blood meals demonstrating the potential of utilizing these approaches to deploy nucleic acid compounds to mosquitoes.

In both baited strategies and more traditional insecticidal delivery approaches (ultra-low volume or residual sprays, or LLINs), nucleic acid compositions may be more efficacious in combination with biotic (e.g., a virus, yeast or bacterial expression system) or abiotic (e.g., nanoparticles, liposomes, PRINT, etc.) systems that mediate both protection and uptake of nucleic acids. As discussed above, in some embodiments, the nucleic acids or vectors encoding them include chemically modified nucleotides that increase their stability and/or otherwise reduce degradation.

In some embodiments, the compositions are delivered directly to mosquitoes using conventional impregnated bed nets, spraying, and/or direct application to a water source. These methods of administration are often preferred for use in areas with high transmission rates of mosquito-borne diseases.

As discussed in the examples below, EOF1, Nasrat, Closca, Polehole, and Nude1 play important roles in eggshell melanization and embryonic development. In some embodiments, the compound is administered in a method suitable to reduce, inhibit, or prevent expression of the EOF1, Nasrat, Closca, Polehole, Nudel, CATL3, DCE2, DCE4, or DCE5 gene or a product thereof in female mosquitoes at least a few days prior to blood feeding in the first and/or second (preferably both) gonotrophic cycles; about one and about three days after oviposition; or a combination thereof in order to induce EOF1, Nasrat, Closca, Polehole, Nudel, CATL3, DCE2, DCE4, or DCE5 depletion and produce defective egg phenotypes. For example, in some embodiments, the compound is administered at between about 2 days and 5 days prior to blood feeding in the first and/or second (preferably both) gonotrophic cycles (e.g., about 2 days, about 3 days, about 4 days, about 5 days, or a combination thereof). In some embodiments, the compound is administered about one, about two, about three days, or a combination thereof after oviposition. Thus, in some embodiments, the compound administered at, or around, these time. In other embodiments, the compound is administered at an earlier time, but the compound is still effective to reduce, inhibit, or prevent expression of the EOF1, Nasrat, Closca, Polehole, Nudel, CATL3, DCE2, DCE4, or DCE5 gene or a product thereof during these periods.

In some embodiments, the compound is administered up to, along with, or after a blood feeding, particularly wherein the compound targets Nudel.

D. Diseases to Be Treated and Mosquitoes to be Targeted

The compounds described herein may be administered to reduce or prevent the spread or transmission of diseases, illnesses, and infections caused by mosquitoes in a population of animals, for example, humans. Such diseases and infections include, but are not limited to, West Nile Virus, La Crosse Encephalitis, Jamestown Canyon Virus, Western Equine Encephalitis, Eastern Equine Encephalitis, St. Louis Encephalitis, Chikungungya, Dengue Fever, Malaria, Yellow Fever, and Zika Virus.

Mosquitoes that can be target of the disclosed compositions and methods include, but are not limited to, *Aedes* (*Stegomyia*) spp., including *Aedes aegypti, Aedes albopictus, Aedes* polynesiensis and other members of the *Aedes scutellaris, Anopheles dirus, Anopheles minimus, Anopheles philippinensis*, and *Anopheles sundaicus, Culiseta melanura, Culiseta morsitans, Aedes atlanticus, Culiseta particeps, Aedesatropalpus, Deinocerites cancer, Aedes canadensis, Mansonia titillans, Aedes cantator, Orthopodomyia signifera, Aedes cinereus, Psorophora ciliate, Aedes condolescens, Psorophora columbiae, Aedes dorsalis, Psorophora ferox, Aedes dupreei, Psorophora howardii, Aedes epactius, Uranotaenia sapphirina, Aedes fitchii, Aedes fulvus pallens, Aedes grossbecki, Aedes infirmatus, Aedes japonicas, Aedes melanimon, Aedes nigromaculis, Aedes provocans, Aedes sollicitans, Aedes squamiger, Aedes sticticus, Aedes stimulans, Aedes taeniorhynchus, Aedes triseriatus, Aedes trivittatus, Aedes vexans, Anopheles atropos, Anopheles barberi, Anopheles bradleyi/crucians, Anopheles franciscanus, Anopheles freebomi, Anopheles hermsi, Anopheles punctipennis, Anopheles quadrimaculatus, Anopheles walker, Coquillettidia perturbans, Culex apicalis, Culex bahamensis, Culex coronator, Culex erraticus, Culex erythrothorax, Culex nigripalpus, Culex pipiens, Culex quinquefasciatus, Culex restuans, Culex salinarius, Culex stigmatosoma, Culex tarsalis, Culex territans, Culex thriambus, Culiseta incidens, Culiseta impatiens*, and *Culiseta inornata*.

As discussed in more detail below, EOF1 may be involved in the specification of the outer chorionic area surrounded by the exochorionic network in *Ae. aegypti* mosquitoes. Thus, inhibiting EOF1 expression or reducing its activity for mosquito population control and disease transmission may be most effective in mosquito species in which EOF1 or a variant or homologue related thereto plays this role. In some embodiments, the mosquitoes that are the target of the disclosed compositions and methods have EOF1 protein or a variant or homologue thereof in their eggshells or otherwise express the protein during their eggshell development program. Conversely, mosquitoes, insects, and other animals that do not have EOF1 protein or a variant or homologue thereof in their eggshells or otherwise express the protein during their eggshell development program may not be preferred targets of the disclosed compositions and methods, and may not be strongly affected by them.

The Examples show that Nasrat, Closca, Polehole, and Nude1 are important for egg melanization, egg viability, and oocyte permeability. Thus, inhibiting Nasrat, Closca, Polehole, Nude1 or other gene (e.g., CATL3, DCE2, DCE4, or DCE5) expression or reducing Nasrat, Closca, Polehole, Nudel, or other gene (e.g., CATL3, DCE2, DCE4, or DCE5) activity for mosquito population control and disease transmission may be most effective in mosquito species in which Nasrat, Closca, Polehole, Nudel, or other gene (e.g., CATL3, DCE2, DCE4, or DCE5) or a variant or homologue related thereto plays these or similar roles. In some embodiments, the mosquitoes that are the target of the disclosed compositions and methods have Nasrat, Closca, Polehole, Nudel, or CATL3, DCE2, DCE4, and/or DCE5 proteins or a variant or homologue thereof in their eggshells or ovaries or otherwise express the protein during their eggshell development program. Conversely, mosquitoes, insects, and other animals that do not have Nasrat, Closca, Polehole, Nudel, CATL3, DCE2, DCE4, and DCE5 protein or a variant or homologue thereof in their eggshells or ovaries or otherwise express the protein during their eggshell development program may not be preferred targets of the disclosed compositions and methods, and may not be strongly affected by them.

IV. Kits

Kits containing compositions are also provided. The compositions may be packaged in any suitable container or source structure affording a desired supply of the composition for its intended purpose. For example, the compositions may be packaged in an aerosol container, as a fogger or spray unit, for fogging, misting or spraying of the pest-control composition to a desired locus of use. The composition alternatively can be packaged in a container equipped with a hand pump dispenser unit or other applicator, administration or dispensing elements. These embodiments are particularly useful for application of the compositions in areas inhabited by blood-ingesting pests that are vectors of human pathogens, such as mosquitoes.

V. Screens for Mosquito-Specific Genes

A. Gene Target Identification In Silico

Methods for identifying mosquito lineage-specific genes are also provided. Data mining and bioinformatic analysis can be carried out using a database such as GenBank database to identify putative protein-coding and non-protein coding sequences that are only present in the genomes of one or more mosquitoes such as those discussed herein. A cut-off for expected value threshold of, for example, about 1e−15, can be used to help identify mosquito-specific genes.

In some embodiments, mosquito-specific putative genes without corresponding mRNA (or orthologue thereof) in an expressed sequence tag (EST) or expressed transcriptome shotgun assembly (TSA) database are excluded to enhance for selection of protein-coding genes.

In some embodiments, genes that appear to be members of a multigene family can be excluded due to possible functional redundancy with other gene family members.

In some embodiments, putative genes identified according to the foregoing steps are excluded if a corresponding homologue is found in one or more evolutionarily closely related organisms within the suborder Nematocera such as phantom midges, true midges, crane fly, and sandflies. Preferably, the gene is absent from all of the foregoing evolutionarily closely related organisms.

B. Validating Gene Targets Identified In Silico

Once one or more mosquito-specific genes are identified according to one or more of the foregoing methods, functional nucleic acids can be designed to target the mosquito-specific genes. Desirable mosquito-specific genes can be selected when the functional nucleic acid is contacted with mosquitoes or mosquito cells, inhibits, reduces or prevent expression of the mosquito-specific gene, and leads to a desirable phenotype. Desirable phenotypes can be those that effect mosquito survival, fecundity, behavior, and/or vector status, and can target a range of pathways and functions including, but not limited to, morphogenesis, olfaction for host seeking and oviposition, blood feeding, digestion, reproduction, fertility, fecundity, embryogenesis, survival, insecticide resistance, larval development, pupal development, emergence, pathogen uptake, development, and/or transmission. Phenotypes and other molecular cues that can be used to screen for desirable phenotypes are well know in the art and exemplified below with respect egg maturation and embryogenesis.

Target genes identified in this manner can become targets of mosquito control compositions and methods analogous to those disclosed herein for targeting EOF1, Nasrat, Closca, Polehole, Nudel, CATL3, DCE2, DCE4, and/or DCE5 and eventually lead to a decrease in the mosquito population and thus lower the transmission of mosquito-borne viral infections.

VI. Screens for Enzyme Inhibitors

Methods for identifying inhibitors of target proteins, particularly enzymes, suitable for use in accordance with the disclosed compositions are also provided.

Insecticide resistance by mosquitoes has been a serious problem worldwide. A new generation of environmentally safe insecticides will be important to control mosquito populations in areas of high rates of disease transmission. Screens are provided to focus on the characterization of evolutionarily-diverged, yet important, mosquito eggshell enzymes, which can be targeted by small molecule inhibitors with the potential to be next generation biosafe mosquitocides.

As illustrated in the experiments below, numerous new eggshell target proteins have been identified. For example, experiments show that evolutionarily-diverged Nudel serine protease could be a potential downstream effector of EOF1, DCE2 enzymes are required for eggshell melanization and egg viability, and the evolutionarily-diverged protein most closely related to CATL3 cysteine proteases, plays a key role in ovarian follicles controlling eggshell melanization and dorso-ventral axis formation.

Thus, screening methods, preferably high throughput screening, of agents, preferably small molecule agents (e.g., small molecule libraries) to identify inhibitory molecules that target any of the disclosed proteins, and preferably DCE2, Nudel, or CATL3, most preferably Nudel are provided.

Typically, recombinant protein is expressed in vitro. For example, biochemically active protein can be overexpressed in baculovirus insect cell expression system and in *Escherichia coli.*

In an exemplary protocol, DNA encoding the target protein can be codon-optimized for e.g., *Trichoplusia ni*. The protein encoding sequence is synthesized and inserted into an expression vector, e.g., the Bac-to-Bac® HT Vector (Thermo). The target protein expression vector can be co-transformed into *E. coli* competent cells, along with baculoviral DNA and helper DNA. After a transposition, the recombinant baculovirus containing DCE2 can be purified and transfected into, e.g., High Five™ *Trichoplusia ni* insect cell line (Thermo), which are preferred cells for secreted protein expression.

In another exemplary embodiment, DNA encoding the target protein and optionally a purification tag, e.g., an N-terminal 6× histidine tag, can be synthesized and cloned into e.g., the pET28b expression vector (Eurofins Genomics). These open reading frames can be *E. coli* codon-optimized in order to efficiently express in the bacterial system. Protein expression and enzyme activity assays can be improved by starting with ARCTICEXPRESS™ (Agilent) competent cells and altering the bacterial growth conditions to overexpress soluble and enzymatically-active target protein. Once soluble expression is achieved, the enzyme can be purified e.g., with a Nickel HisTRAP column using an AKTA Pure L1 FPLC.

Activation conditions can be tested using various pH buffer conditions, followed by activity and substrate specificity determination studies using enzyme substrates. Substrates may be commercially available and/or can be identified using proteomic, screening approaches such as those described in Bredemeyer, et al., PNAS, 101 (32) 11785-11790 (2004), Sandersjoo, et al., *Biotechnol J.,* 12(1). doi: 10.1002/biot.201600365 (2017), or a screening service.

The soluble recombinant protein can be incubated in the reaction mixture with substrate, and enzymatic activity measured. A high throughput activity screening assay with automated handling of chemical samples can be performed (e.g., by Blomek FX (Beckman Coulter)). These studies can include measuring a change in absorbance over time using a microplate spectrophotometer as a reflection of enzyme activity.

Many high quality, small molecule libraries are commercially available and are suitable for the disclosed screens. Examples include CHEMBRIDGE™ EXPRESS-Pick Collection Stock and CORE library Stock. See Dandapani S., *Curr Protoc Chem Biol.,* 4:177-191 (2012) for examples of available small molecule libraries. It is contemplated that a high-throughput screening of small molecule libraries against target enzymes will identify inhibitory molecules, which can be further modified (e.g., to increase specificity and activity) if desired.

Promising inhibitory molecules can be further validated in secondary screens.

The positive compounds can be further evaluated for their effect on target protein activity and eggshell phenotypes using in vitro and/or in vivo assays, including any one or more of the assays described herein, and leading to any one or more of the phenotypes described herein. Assay may include, for example, microinjection and/or topical application of putative inhibitors to mosquitoes, particularly female mosquitoes. In some embodiments, putative inhibitors are tested for their effect on egg melanization, egg viability, oocyte permeability, or other egg or developmental phenotypes discussed herein, by applying or feeding the putative inhibitor to mosquitoes or applying it directly to eggs. In some embodiments, an inhibitor is selected when it generates an egg phenotype the same or similar to knockdown of EOF1, Nasrat, Closca, Polehole, Nudel, CATL3, DCE2, DCE4, and/or DCE5.

In some embodiments, the compounds are also tested on alternative species of mosquitoes, insects, and/or other animals including mammals such as mice and humans. In some embodiments, the compound that are insect-specific, mosquito-specific, and/or specific for a specific species or group of species of mosquitoes are selected. For example, in some embodiments, the compounds have reduced activity in mammals and/or other non-mosquito insects.

In some embodiments, putative protease inhibitors are tested for their effect on egg melanization, egg viability, oocyte permeability, or other egg or developmental phenotypes discussed herein, by applying or feeding the putative inhibitor to mosquitoes or applying it directly to eggs. In some embodiments, a putative protease inhibitor is selected when it generates an egg phenotype the same or similar to knockdown of EOF1, Nasrat, Closca, Polehole, Nudel, CATL3, DCE2, DCE4, and/or DCE5.

EXAMPLES

Example 1: EOF1 is an Important Protein for Viable Embryos

Materials and Methods

Mosquitoes

Most of the experiments were carried out using *Ae. aegypti* mosquitoes (Rockefeller strain) and reared as previously described (Isoe, et al., *Insect Biochem Mol Biol* 39(12):903-912 (2009)). For comparison, Ae. *aegypti* mosquitoes (Tucson strain) were colonized from Tucson, Arizona (Brown, et al., *J Med Entomol* 54(2):489-491 (2016)). *Aedes albopictus* (Gainesville strain, MRA-804) was obtained from CDC/MR4. Using an artificial glass feeder, female mosquitoes were allowed to feed on an expired human blood donated by American Red Cross. Only fully engorged female mosquitoes were used.

Identification of Mosquito-Specific Putative Genes

Data mining and bioinformatic analysis were carried out using the GenBank database to identify putative protein-coding sequences that are only present in the genomes of *Aedes, Culex*, and *Anopheles* mosquitoes using a cut-off for expected value threshold of 1e−15. Mosquito-specific putative genes without corresponding mRNA in *Ae. aegypti* expressed sequence tags (EST) or expressed orthologs in the *Ae. albopictus* transcriptome shotgun assembly (TSA) database were excluded for further RNAi screening. Also excluded were genes that appear to be members of a multigene family due to possible functional redundancy with other gene family members.

dsRNA Synthesis and Microinjection

RNA interference (RNAi) was carried out to knock down *Ae. aegypti* mosquito genes. Each gene-specific forward and reverse oligonucleotide primer was designed using a NetPrimer web-based primer analysis tool. T7 RNA polymerase promoter sequence, TAATACGACTCACTATAGGGAGA (SEQ ID NO: 117), was added to the 5' end of each primer (Table 2). All primers were purchased from Eurofins Genomics (Louisville, KY). PCR was performed using Taq 2× Master Mix (NEB, Ipswich, MA) with mosquito whole body cDNA as a template, and the amplified PCR products were cloned into the pGEM-T easy vector (Promega Madison, WI) for DNA sequence verification using an ABI 377 automated sequencer (Applied Biosystems, Foster City, CA). dsRNA was synthesized by in vitro transcription using HiScribe™ T7 Quick High Yield RNA Synthesis Kit (NEB). Cold anesthetized female mosquitoes were injected with 2.0 μg dsRNA using a NANOJECT II™ microinjector (Drummond Scientific Company, Broomall, PA). Mosquitoes were maintained on 10% sucrose throughout the experiments.

Mosquito Egg Hatching Assay

Eggs laid on oviposition papers remained wet for three days before drying at 28° C. Eggs (about 7 days old) on oviposition paper were submerged in water, vacuumed using a Speed Vac for 10 minutes, and allowed to hatch for 2 days. First instar larvae were counted.

Bleach Assay

A bleach assay was performed to determine viability of 4-day old *Ae. aegypti* eggs from RNAi studies. Eggs on oviposition paper were soaked in 12% bleach at room temperature. A gradual progress of dechorionation of eggshell was observed under a microscope. Light microscopic images of eggs deposited from RNAi-Fluc and -EOF1 females prior to and after the addition of bleach were taken at X49 magnification (Nikon, SMZ-10A).

Statistical Analysis

Statistical analyses were performed using GRAPHPAD PRISM® Software (GraphPad, La Jolla, CA). Statistical significance for fecundity, viability, and RNAi knockdown efficiency was analyzed using an unpaired Student's t-test. P values of ≤0.05 were considered significantly different. All experiments were performed from at least three independent cohorts.

Results

Data mining and bioinformatic analysis was performed using the GenBank database to identify putative protein-coding sequences that are only present in the genomes of *Aedes, Culex*, and *Anopheles* mosquitoes using a cut-off for expected value threshold of 1e−15. Importantly, the mosquito lineage-specific genes identified (Table 2) were found to be completely absent in evolutionarily closely related organisms, such as phantom midges, true midges, crane fly, and sandflies within the suborder Nematocera, and thus, these genes are not present in other known animals, plants, fungi, and bacteria species.

In order to focus on genes that are expressed and likely to encode proteins that could potentially serve as vector control targets, genes without corresponding mRNA in *Ae. aegypti* expressed sequence tags or expressed orthologs in the *Ae. albopictus* transcriptome shotgun assembly database were excluded. Also excluded were mosquito lineage-specific genes that appear to be members of a multigene family because RNAi knockdown phenotypes may not be immediately identifiable due to possible functional redundancy with other gene family members. This highly selected subset of hypothetical mosquito lineage-specific proteins may have therefore evolved independently and advantageously within the family Culicidae.

Systematic RNAi screening of mosquito-specific genes was performed by directly microinjecting the corresponding dsRNA into female *Ae. aegypti* mosquitoes 3 days prior to blood feeding (FIG. 1A), and the blood fed female mosquitoes were individually analyzed for their egg phenotypes, fecundity and viability. Among 40 mosquito-specific genes screened (Table 2), utilizing this experimental approach led to the identification of eggshell organizing factor 1 (EOF1, AAEL012336), which, upon RNAi knockdown, plays an important role in the strength and structural integrity of the forming eggshell, as well as its melanization.

To investigate if EOF1 has evolved within the family Culicidae to affect eggshell formation and melanization and therefore maximize egg survival, EOF1 was further characterized in mosquitoes. EOF1 sequences found in *Aedes, Culex*, and *Anopheles* mosquito species contain an F-box functional motif, and members of the F-box protein family are in general characterized by ~50 amino acid F-box motif that interacts with a highly conserved SKP1 protein in the E3 ubiquitin ligase SCF complex (Wang, et al., *Nat Rev Cancer* 14(4):233-247 (2014)), indicating that EOF1 may function intracellularly. Recent proteomic analysis has identified over 100 mosquito eggshell proteins (Amenya, et al., *J Insect Physiol* 56(10):1414-1419 (2010), Marinotti, et al., *BMC Dev Biol* 2014, 14:15), and some of these proteins identified are enzymes that may potentially be involved in catalyzing eggshell melanization and cross-linking reactions (Ferdig, et. al., *Insect Mol Biol* 5(2):119-126 (1996), Han, et al., *Arch Biochem Biophys* 378(1):107-115 (2000), Johnson, et al., *Insect Biochem Mol Biol,* 31(11):1125-1135 (2001), Fang, et al., *Biochem Biophys Res Commun* 2002, 290(1):287-293 (2002), Kim, et al., *Insect Mol Biol* 14(2):185-194 (2005), Li, et al., *Protein Sci* 14(9):2370-2386 (2005), Li, et al., *Insect Biochem Mol Biol* 36(12):954-964 (2006)). However, EOF1 was not previously identified in these mosquito eggshell proteomic studies, indicating that EOF1 may be an upstream regulatory factor of eggshell proteins.

Figure 1B:
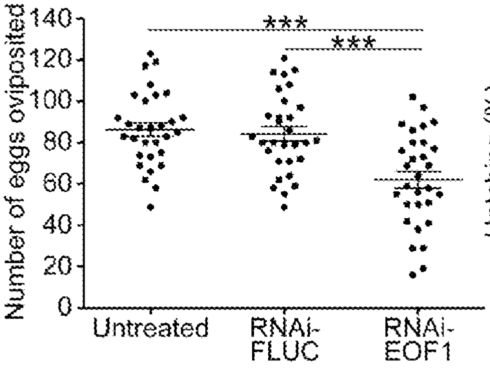
FIG. 1B is a dot plot showing the effect of RNAi-EOF1 or -Fluc control on *Ae. aegypti* fecundity examined by counting the number of eggs laid by each individual female. Note that 25% of fully blood-fed RNAi-EOF1 females did not produce mature follicles. Each dot represents the number of eggs oviposited by an individual mosquito. The mean±SEM are shown as horizontal lines, and statistical significance is represented by stars above each column (unpaired Student's t test; *P<0.001).
Figure 1C:
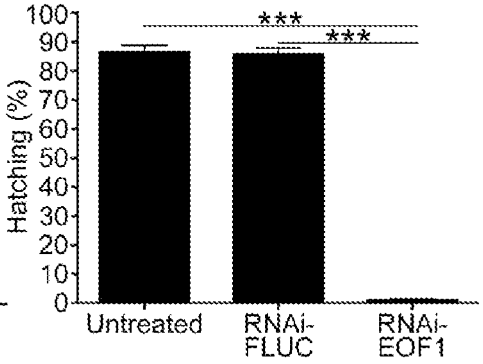
FIG. 1C is a bar graph showing the viability of these eggs was determined. A significant reduction in the percentage of egg hatching was observed in RNAi-EOF1 mosquitoes. Each bar corresponds to egg viability from 15 individual mosquitoes from three groups.
Figure 1D:
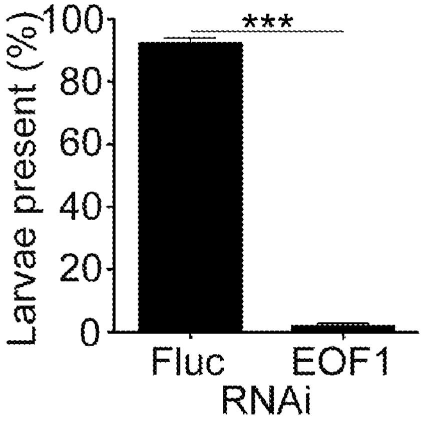
FIG. 1**D is a bar graph showing larvae present in control and RNAi-EOF1 as measured following a bleaching test.

The RNAi-EOF1 had a significant adverse impact on eggshell formation and egg viability. Single mosquito analysis showed that phenotypes associated with RNAi-EOF1 range from totally non-melanized, collapsed to truncated, melanized eggs, while untreated and RNAi-Fluc control laid eggs that exhibit uniformly elongated and melanized patterns. Single mosquito analysis also showed that fecundity and viability from eggs of RNAi-EOF1 females are strongly affected by reduced EOF1 function through RNAi (FIGS. 1B and 1C). A bleach test was performed to determine viability of 4-day old eggs from RNAi studies, and confirmed that mosquito-specific EOF1 is required for embryonic development in *Ae. aegypti* mosquitoes (FIG. 1D). Light microscopic images were taken from RNAi-Fluc and -EOF1 females immediately prior to the addition of bleach (0 min). Partially melanized eggs were frequently observed from EOF1 deficient mosquitoes collapsed prior to bleach application. Representative photos were taken 2, 50, 60, 70, and 80 min post bleach application. The exochorionic structures including exochorionic network become invisible immediately upon bleach application (2 min). Eyes of the first instar larvae present in eggs, indicated with white circles, have begun to appear through the partially dechorionated eggshell at 50 min post-bleach application, while weakly melanized eggs from EOF1-deficient mosquito disappeared. Eggshell was nearly removed by 80 min after bleach treatment, exposing the fully developed first instar larvae. Bleach treatment (10%) gently dechorionates eggshell with minimal adverse effects on the embryos due to the presence of the extraembryonic serosal cuticle. Overall, the bleach studies showed that eggs from RNAi-Fluc mosquitoes had 92.2% of developed first instar larvae, while 1.8% of egg deposited by RNAi-EOF1 mosquitoes successfully completed embryogenesis to reach the first larval instar (FIG. 1D). The mean±SEM are shown as horizontal lines, and the statistical significance is represented by stars above each column (unpaired Student's t test; ***P<0.001). Eggs were observed using a light microscope at X49 magnification (Nikon, SMZ-10A).

In the majority of eggs laid by EOF1-deficient mosquitoes, embryos fail to complete embryogenesis and reach the first larval instar. A recently colonized *Ae. aegypti* Tucson strain from wild populations (Brown, et al., *J Med Entomol,* 54(2):489-491 (2016)) also exhibited similar defective egg and embryo phenotypes associated with RNAi-EOF1. Thus, EOF1 protein is important for complete eggshell formation and embryonic development in *Ae. aegypti* mosquitoes.

Anautogenous female mosquitoes can undergo multiple gonotrophic cycles by repeating blood feeding, vitellogenesis, and oviposition events. Because EOF1 plays an important role in eggshell formation, experiments were designed to investigate how long the RNAi knockdown effect of EOF1 lasts from a single dsRNA microinjection. The effect of EOF1 deficiency on eggs was examined in three consecutive gonotrophic cycles in individual containers. Eggshell melanization, fecundity (FIG. 2B), and viability (FIG. 2C) phenotypes are profoundly altered in EOF1-deficient mosquitoes during the first three gonotrophic cycles. Therefore, the data demonstrate that the RNAi-EOF1 effect from a single dsRNA injection remains substantial for the second and even the third gonotrophic cycles.

Figure 2G:
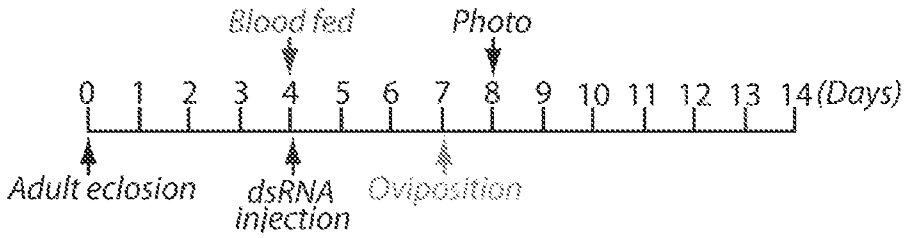
FIG. 2G is a schematic diagram of experimental time course for dsRNA microinjection, blood feeding, and oviposition where microjection occurs immediately after blood feeding.
Figure 2H:
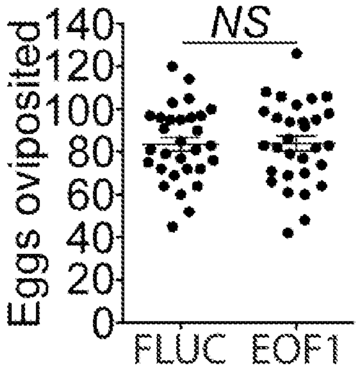
FIGS. 2H and 2I are bar graphs showing the effect of RNAi-EOF1 or -Fluc control on fecundity (2H) and viability (2I) according to the experimental scheme of 2G.
Figure 2I:
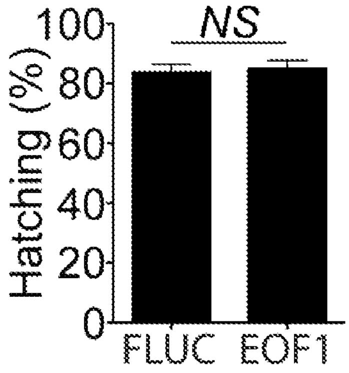
Figure 2J:
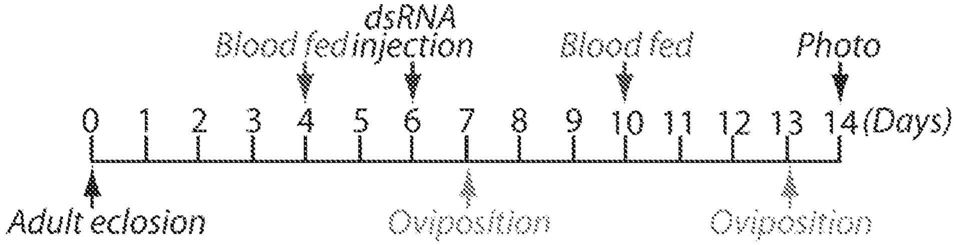
FIG. 2J is a schematic diagram of experimental time course for dsRNA microinjection, blood feeding, and oviposition where microjection occurs 48 hours post blood meal and before oviposition.
Figure 2K:
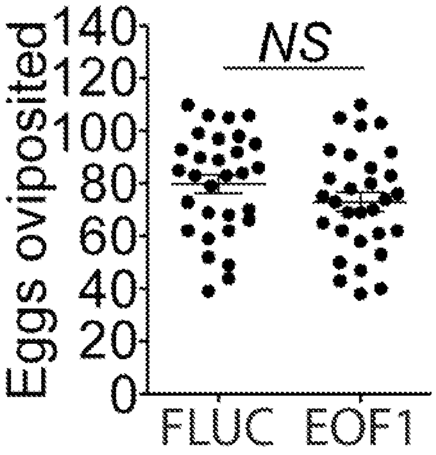
FIGS. 2K and 2L are bar graphs showing the effect of RNAi-EOF1 or -Fluc control on fecundity (2K) and viability (2L) according to the experimental scheme of 2J.
Figure 2L:
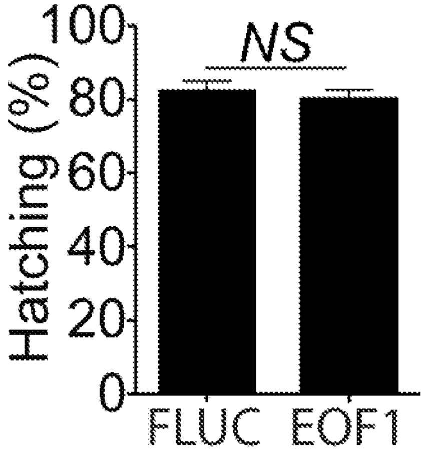
Figure 2M:
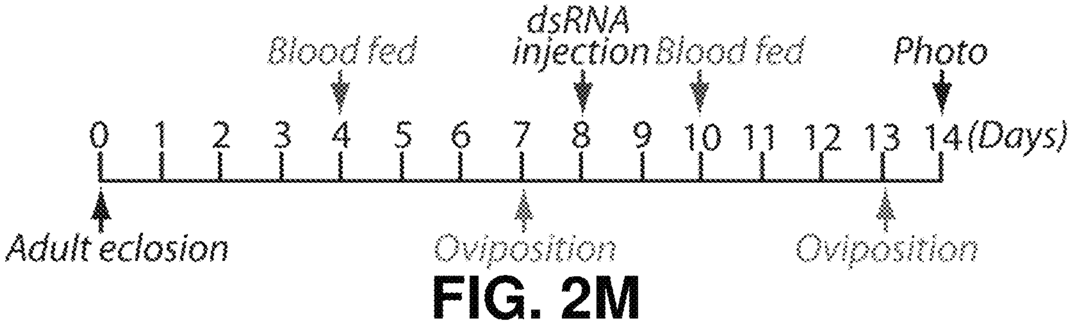
FIG. 2M is a schematic diagram of experimental time course for dsRNA microinjection, blood feeding, and oviposition where microjection occurs one day after oviposition.
Figure 2N:
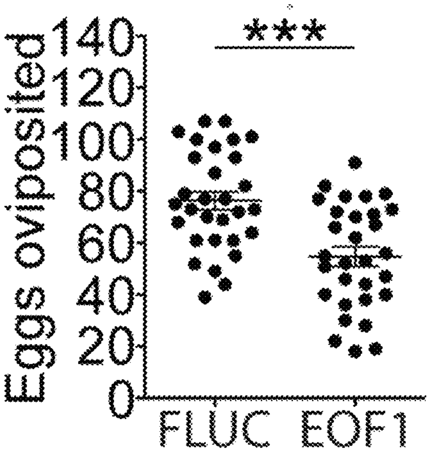
FIGS. 2N and 2O are bar graphs showing the effect of RNAi-EOF1 or -Fluc control on fecundity (2N) and viability (2O) according to the experimental scheme of 2M. The schematic images show an oviposition experimental setup. The effect of RNAi-EOF1 or -Fluc control on *Ae. aegypti* fecundity was examined by counting the number of eggs laid by each individual female. Each dot represents the number of eggs oviposited by an individual mosquito. Viability of these eggs was determined. Each bar corresponds to egg viability from 15 individual mosquitoes from three groups. The mean±SEM are shown as horizontal lines. Statistical significance is represented by stars above each column (unpaired student's t test; ***P<0.001, NS not significant).
Figure 2O:
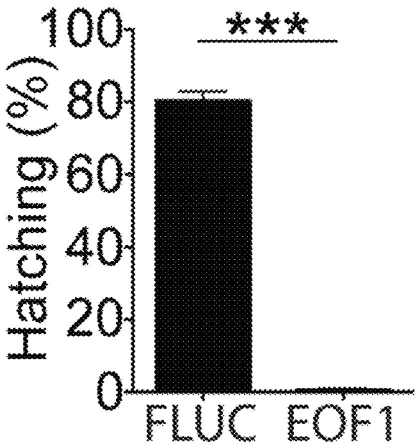

Furthermore, the timing of dsRNA microinjection is important. The dsRNA has to be microinjected few days prior to blood feeding in both the first and second gonotrophic cycles in order to induce RNAi-mediated EOF1 depletion and produce defective egg phenotypes (FIG. 2D-2O). Mosquitoes injected with dsRNA-EOF1 at one day after adult eclosion produced inviable eggs (FIGS. 2D-2F). Mosquitoes were also injected with dsRNA-EOF1 immediately after blood feeding. These females laid eggs that show no difference in fecundity and viability compared to RNAi-Fluc control mosquitoes (FIG. 2G-2I). Mosquitoes injected with dsRNA-EOF1 48 hours post blood meal and before oviposition oviposited normal eggs (FIG. 2J-2L). Mosquitoes injected with dsRNA-EOF1 at one day after oviposition resulted in the production of inviable eggs (FIG. 2M-2O).

Example 2: EOF1 Expression Pattern

Materials and Methods

Pattern of EOF1 Gene Expression by qPCR

Using TRIZOL™ (RNA extraction reagent), total RNA was extracted from larvae, pupae and male adults as well as five tissues including thorax, fat body, midgut, ovaries, and Malpighian tubules dissected from sugar-fed at 3 day post eclosion and blood-fed female mosquitoes at 24 and 48 h PBM. First strand cDNA was synthesized from pools of total RNA using an oligo-(dT) 20 primer and reverse transcriptase. qPCR was carried out with the corresponding cDNA, EOF1 or Ribosomal protein S7 gene-specific primers (Table 3), PERFECTA SYBR® Green FastMix, and ROX™ (reaction cocktail) (Quanta BioSciences, Gaithersburg, MD) on the 7300 Real-Time PCR System (Applied Biosystems).

Preparation of Enriched Mosquito Eggshell

Female mosquitoes were injected with dsRNA at 1 day post adult emergence, and ovaries were dissected in 1×PBS at 96 hour PBM. The dissected ovaries were thoroughly homogenized (40 strokes) in ice cold 1×PBS using Dounce homogenizers (B pestle). The eggshells were allowed to settle down to the bottom of the homogenizer on ice. The top cloudy fraction was gently aspirated, and the washing step with ice cold 1×PBS for the eggshells was repeated four times or until the solution was completely cleared.

Subsequently, the eggshell was homogenized (20 strokes) in ice cold 1×PBS using A pestle. The eggshell proteins were subjected to SDS-PAGE and stained with GELCODE™ Blue reagent (stain).

SDS-PAGE and Western Blot Analysis

Mosquito ovaries were dissected in 1×PBS under a dissecting microscope and homogenized in lysis buffer (12 mM sodium deoxycholate, 0.2% SDS, 1% triton X-100 TRITON™ X-100 (non-ionic surfactant), complete mini-EDTA-free protease inhibitor, Roche Applied Science, Indianapolis, IN). Protein extracts were resolved on SDS-PAGE using a 12% acrylamide separation gel and a 3% stacking gel. The resolved proteins were either stained with GELCODE™ Blue reagent (stain) (Thermo Scientific, Waltham, MA) or electrophoretically blotted to a nitrocellulose membrane (LI-COR, Lincoln, NE) for Western Blot analysis. The membranes were blocked with 4% nonfat dry milk and incubated with each primary antibody in 4% non-fat milk in PBS containing 0.1% Tween 20. The EOF1 rabbit polyclonal antibody was generated by GenScript Corporation (Piscataway, NJ) based on an antigenic peptide (LAPNSPSKEDEPAH). The anti-a-tubulin monoclonal antibody from Developmental Studies Hybridoma Bank (University of Iowa, Iowa City, IA) was used as loading controls for ovaries. The dilutions of the primary antibodies were as follows: EOF1 (1:3,000) and a-tubulin (1:2,000). The secondary antibodies were either IRDye 800CW goat anti-rabbit secondary antibody (1:10,000; LI-COR) or IRDye 800CW goat anti-mouse secondary antibody (1:10,000; LI-COR). The protein bands were visualized with an Odyssey Infrared Imaging System (LI-COR).

Fluorescence In Situ Hybridization (FISH)

mRNA distribution of EOF1 and vitelline envelopes (15a1, 15a2, and 15a3) in *Ae. aegypti* primary follicles was determined using whole-mount fluorescent in situ hybridization. Primary follicles were isolated from ovaries of untreated female mosquitoes at 36 hours PBM fixed with 4% paraformaldehyde. After washing with 1×PBS, the follicle samples were dehydrated with ethanol (ETOH) in water through a graded series for 10 min each in 10, 30, 50, 70, 90% ETOH and 3 times 30 min each in 100% ETOH at room temperature. The samples were hydrated with 1×PBS in ETOH through a graded.

Measuring Knockdown Efficiency of RNAi-EOF1

Knockdown efficiency of RNAi was verified by real-time qPCR using gene-specific primers (Table 3). cDNA was synthesized from DNase I-treated total RNA isolated from ovaries of individual dsRNA-injected mosquitoes at 48 hours PBM. Normalization was done using the ribosomal protein S7 transcript levels as an internal control, and the knockdown efficiency of RNAi-EOF1 was compared using Fluc dsRNA injected mosquitoes as a control. RNAi knockdown level of EOF1 protein was also determined by Western Blot analysis using an EOF1-specific polyclonal antibody.

Ovarian protein extracts were isolated from 8 individual mosquitoes from RNAi-Fluc or RNAi-EOF1 mosquitoes at 48 hours PBM. α-tubulin was used as an internal control.

Results

Figure 3A:
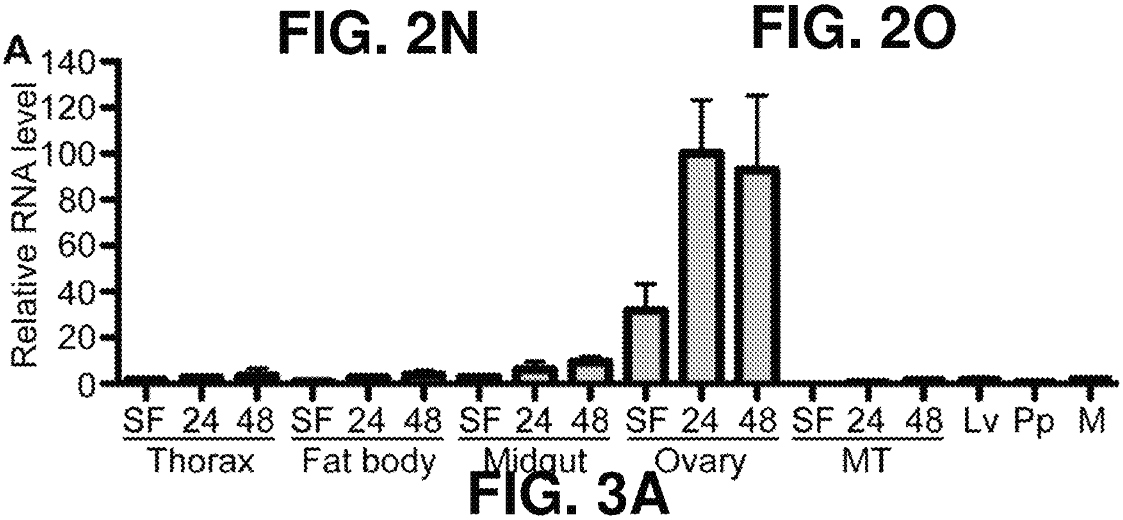
FIG. 3A is a bar graph showing tissue-specific and developmental expression pattern of EOF1 during the first gonotrophic cycle of *Aedes aegypti* mosquitoes. EOF1 gene expression was analyzed by qPCR using cDNAs prepared from various tissues. Tissues include thorax, fat body, midgut, ovary, and Malphigian tubules (MT) in sugar-fed only (SF) and 24 and 48 hours post blood meal (PBM), as well as larvae (Lv) pupae (Pp), and adult males (M). The pattern demonstrates the ovary-specific EOF1 expression in *Ae. aegypti* mosquitoes. The EOF1 expression levels were normalized to S7 ribosomal protein transcript levels in the same cDNA samples. Data were collected from three different mosquito cohorts.
Figure 3B:
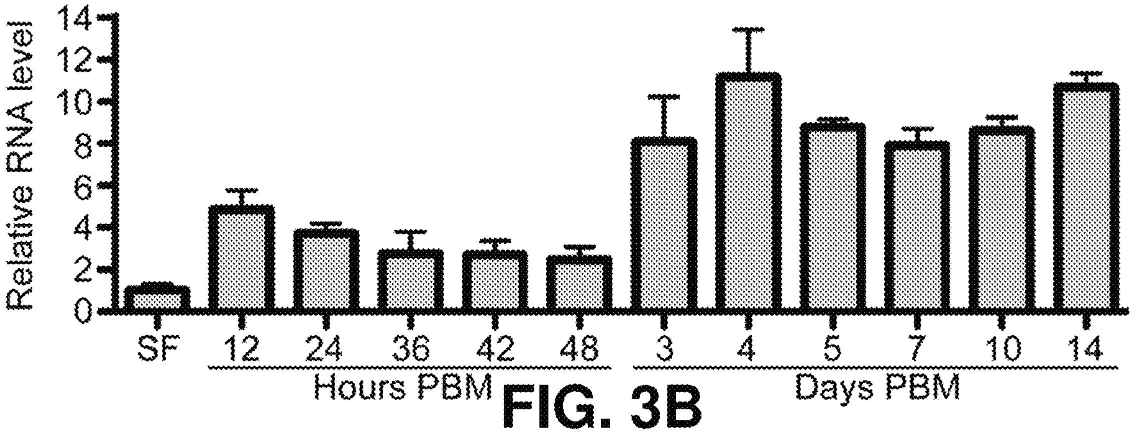
FIG. 3B is a bar graph showing detailed EOF1 gene expression in ovaries and follicles analyzed by qPCR using cDNAs from mosquito ovaries or follicles. Samples from SF to 36 hours PBM include entire ovaries, whereas those from 48 hours to 14 days PBM include only follicles isolated from ovaries. Experiments were performed in triplicate.

Since little is known about this mosquito-specific EOF1 gene except for the phenotypes associated with RNAi, the expression pattern of EOF1 was investigated at the mRNA level in untreated *Ae. aegypti* by quantitative real-time PCR (qPCR). Five tissues including thorax, fat body, midgut, ovaries, and Malpighian tubules were dissected from sugar-fed at 3 day post eclosion and blood-fed female mosquitoes at 24 and 48 h PBM. The mRNA expression in whole body of mixed sex samples of 4th instar larvae and pupae and adult male mosquitoes was also investigated. EOF1 is predominantly expressed in ovaries, and the expression is upregulated in the ovaries by blood feeding (FIG. 3A).

qPCR results also indicate that mRNA encoding EOF1 is not strongly detected from larvae, pupae and adult male mosquitoes. Next, the pattern of EOF1 expression during the first gonotrophic cycle was examined in detail. Ovaries were isolated at various time points PBM. In ovary samples after 36 h PBM, the primary follicles were carefully isolated from ovaries to exclude non-follicle ovarian cell types such as muscles and trachea. qPCR data show that EOF1 mRNA expression is up-regulated in response to blood feeding, and the levels remain even high at 14 days PBM (FIG. 3B). Since follicular epithelial cells and nurse cells in the primary follicles undergo apoptosis by around 72 h PBM, mRNAs encoding EOF1 may likely originate from the unfertilized mature oocytes. EOF1 mRNA distribution in primary follicles was further determined using whole-mount Fluorescent in situ hybridization (FISH). FISH analysis shows that while three vitelline envelope genes (Edwards, et al., *Insect Biochem Mol Biol* 28(12):915-925 (1998)) were exclusively expressed in the follicular epithelial cells, EOF1 mRNA transcripts are present in oocyte and nurse cells of primary follicles and weakly expressed in the secondary follicle, while mRNAs encoding three vitelline envelope proteins are restricted in follicular epithelial cells of primary follicles. Western blot protein analysis confirmed that EOF1 expression is induced in ovaries in response to blood feeding.

Figure 3C:
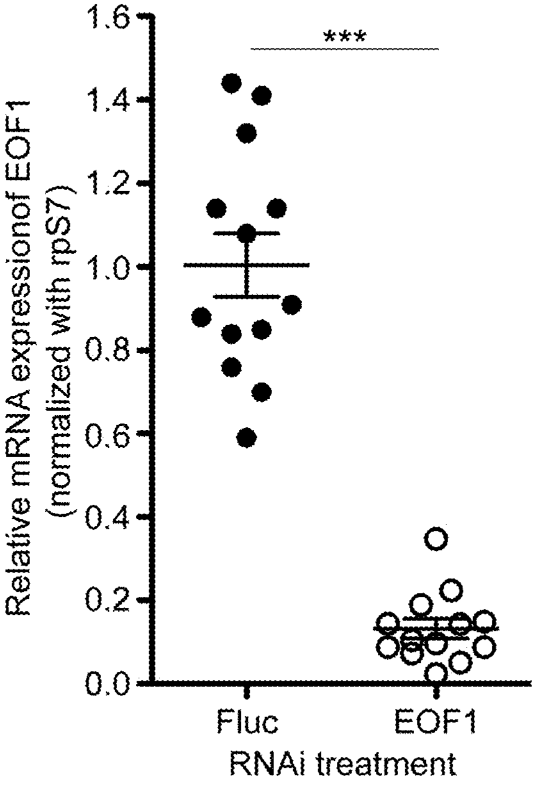
FIG. 3C is a dot plot showing the results of single mosquito qPCR analysis performed to measure the relative RNAi knockdown level of EOF1 transcript in ovaries. The mean±SEM are shown as horizontal lines. Statistical significance is represented by asterisks above the column (unpaired student's t test; ***P<0.001).

RNAi knockdown level of EOF1 mRNA and protein was confirmed by qPCR and Western Blot, respectively (FIG. 3C). Single mosquito qPCR analysis was performed to measure the relative RNAi knockdown level of EOF1 transcript in ovaries. Mosquitoes were microinjected with 2.2 μg of dsRNA-EOF1 or -Fluc three days prior to blood feeding, and a pair of ovaries was dissected from 13 individual mosquitoes from both groups at 48 hours PBM. EOF1 transcript levels were normalized to S7 ribosomal protein transcript levels in the same cDNA samples (FIG. 3C).

Example 3: Follicle Development in EOF1-Deficient Females

Materials and Methods

Apoptosis Assay for Ovarian Follicles Using Confocal Laser Microscopy

Female *Ae. aegypti* mosquitoes were microinjected with dsRNA at 1 day post adult emergence, and ovaries at 36 hour PBM were removed in 1×PBS under a dissecting microscope and immediately incubated with tissue culture media (Medium 199, Thermo Fisher Scientific) containing a caspase inhibitor (SR FLICA® Poly Caspase Assay Kit, ImmunoChemistry Technologies, Bloomington, MN) at 37° C. in the dark for 1 hour. The ovaries were washed with 1×PBS, fixed with 4% paraformaldehyde, quenched with 25 mM glycine, permeabilized with 0.5% Triton X100, and stained with ACTI-STAIN™ 488 phalloidin (Cytoskeleton Inc, Denver, CO) overnight at 4° C. After washing with 1×PBS, the whole ovaries were mounted on a glass slide using PROLONG™ Gold Antifade reagent (Thermo Fisher Scientific). Immunofluorescence and light microscopic images of the ovaries were captured using a Spinning Disk Confocal Laser Microscope (Intelligent Imaging Innovations, Denver, CO) in the Keck Imaging Center at the University of Arizona.

Rhodamine B and Neutral Red Mosquito Follicle Permeability Assay

The assay has an advantage that it can quickly assess whether follicles within the ovaries may contain defective eggshell prior to oviposition. Individual follicles of untreated, RNAi-Fluc, or -EOF1 mosquitoes at 96 hour PBM were dissected and gently separated from the ovaries, and transferred to glass scintillation vials. Rhodamine B (final concentration of 1 mM in H2O, Sigma) and neutral red (0.5%, Sigma) was used to stain primary follicles for 10 min on a rocking shaker and thoroughly rinsed with H2O. The stained primary follicles were photographed with a Coolpix 4300 (Nikon).

Results

EOF1-deficient female mosquitoes had low fecundity (FIG. 1B) and laid eggs that are defective in eggshell formation, leading to the embryonic lethal phenotype (FIG. 1C). Experiments were designed to determine if primary follicles of EOF1-deficient mosquitoes undergo cell death, removing severely affected follicles within the ovaries. Ovarian follicle phenotypes associated with EOF1 gene suppression were examined by RNAi in *Ae. aegypti* mosquitoes. Representative ovaries at 36 h PBM showed that RNAi-EOF1 ovaries contain follicles that undergo caspase-mediated apoptosis, while these dying follicles were not observed in untreated or RNAi-Fluc control ovaries. The caspase activity was also observed to be more concentrated in the oocytes than in the follicular epithelial cells.

*Representative mature ovaries were dissected from abdomen of dsRNA injected mosquitoes and photographed at 96 h PBM. While all RNAi-Fluc control mature follicles in ovaries have not initiated melanization, it was frequently observed that some follicles isolated from RNAi-EOF1 were already partially melanized in the ovaries. The partially melanized phenotype in EOF1-deficient ovaries was accompanied by a loss of structural integrity, and thus it was believed that decreased chorionic osmotic control results in this alteration of egg shape. To determine whether the water permeability of the mosquito eggshells was affected in response to EOF1 knockdown, two chemical markers, rhodamine B and neutral red, were employed to stain ovarian follicles. Significant differences in the permeability of both markers in ovaries were observed. While the follicles from both untreated and RNAi-Fluc mosquitoes were only slightly stained, the majority of follicles from RNAi-EOF1 mosquitoes were strongly stained with the markers. Since follicular epithelial cells have been already shed around 72 h PBM, there is a single oocyte present in each follicle at this developmental stage (96 h PBM). The reduction of EOF1 expression in female mosquitoes resulted in defective eggshells, leading to increased permeability of water into oocytes and altered follicular shape.

Example 4: Ultrastructure Analysis of Mosquito Eggs

Materials and Methods

Ultrastructural Study of Eggshell by SEM

The ovaries were dissected from mosquitoes injected with Fluc control dsRNA and EOF1 dsRNA at 96 h PBM. Each follicle was carefully separated from the ovaries in 1×PBS under a dissecting microscope. The mature follicles were fixed in 2.5% glutaraldehyde in 0.1 M PIPES for 1 hour at room temperature and washed twice in PIPES. The follicles were then post-fixed in 1% osmium tetroxide in PIPES for 1 hour and washed twice in deionized water for 10 min each. The follicles were dehydrated with ethanol (ETOH) in water through a graded series for 10 min each in 10, 30, 50, 70, 90% ETOH and 3 times 30 min each in 100% ETOH at room temperature. The samples were dried with hexamethyldisilazane (HMDS, Electron Microscopy Sciences, Hatfield, PA) in ETOH through a graded series for 20 min each in 25, 50, 75, and 100% HMDS at room temperature. The follicle samples were air-dried under a fume hood overnight at room temperature for SEM analysis. The dried samples were metallized with gold using Hummer 6.2 Sputter System (Anatech USA, Union City, CA). Inspect-S scanning electron microscope (FEI, Hillsboro, OR) was used to compare the ultrastructural characteristics of the ovarian follicles of females injected with Fluc and EOF1 dsRNA.

Results

EOF1-deficient mosquitoes oviposited eggs with different degrees of eggshell melanization phenotypes that include non-melanized, partially melanized and melanized eggs. Since nearly 100% of eggs oviposited from RNAi-EOF1 females did not undergo complete embryogenesis (FIGS. 1C and 2C), it was believed that the defective eggshell may be the primary cause of embryonic death. Light microscopy images of eggs from *Ae. aegypti* RNAi-Fluc and -EOF1 mosquitoes revealed that EOF1 may be involved in the specification of the outer chorionic area (OCA) surrounded by the exochorionic network (EN). Next, the effect of RNAi-EOF1 on the ultrastructure of eggs was examined in detail by scanning electron microscopy (SEM). A very similar *Ae. aegypti* eggshell ultrastructure to other SEM studies was observed (Suman, et al., *Arthropod Struct* Dev 40(5):479-483 (2011), Faull, et al., *Arthropod Struct Dev* 45(3):273-280 (2016)). An exochorion outermost layer of the eggshell is characterized by the presence of a single protruding central tubercle (CT) and several peripheral minute tubercles (PT) in the OCA. However, SEM images showed that OCA in RNAi-EOF1 eggs is about 6 times larger than eggs of control mosquitoes, indicating that EOF1 may be involved in specifying the size of OCA. Each OCA also contained multiple miniaturized CT-like structures also surrounded by EN-like structures instead of one predominant CT. Thus, EOF1 may act as an upstream factor to control eggshell surface patterning in *Ae. aegypti*.

Through RNAi screening of putative mosquito-specific genes in Ae. *aegypti*, EOF1 was identified as an important protein for eggshell formation and melanization. Since eggshell components are directly secreted into the extracellular space between the oocyte and the surrounding follicular epithelial cells, intimate communication between these cells within each ovariole may exist throughout the follicle maturation, eventually leading to follicular epithelial cell shedding, ovulation, and oviposition. In general, mature follicles from mosquitoes do not undergo premature melanization within the ovaries, and gravid females can hold their mature follicles for a long period of time under adverse environmental conditions and still lay viable eggs which become melanized after oviposition. Thus, the timing of eggshell melanization may likely be tightly regulated and catalyzed by specific enzymes, and their synthesis, secretion, and activation may be important for proper melanization and thus survival of embryos.

Figure 4A:
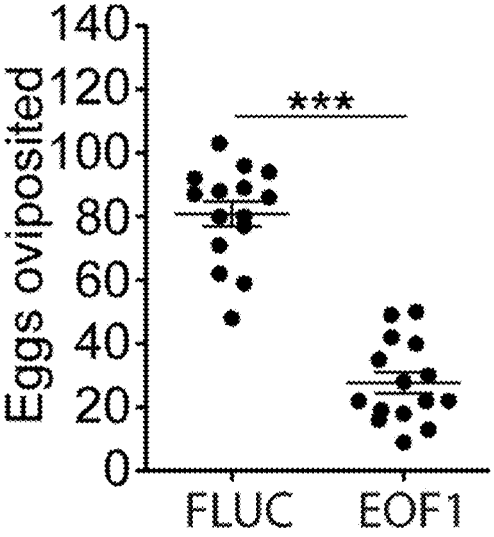
FIG. 4A is a dot plot showing the effect of RNAi-EOF1 or -Fluc control on *Ae. albopictus* fecundity examined by counting the number of eggs laid by each individual female. Each dot represents the number of eggs oviposited by an individual mosquito. The mean±SEM are shown as horizontal lines. Statistical significance is represented by stars above each column (unpaired student's t test; *P<0.001).
Figure 4B:
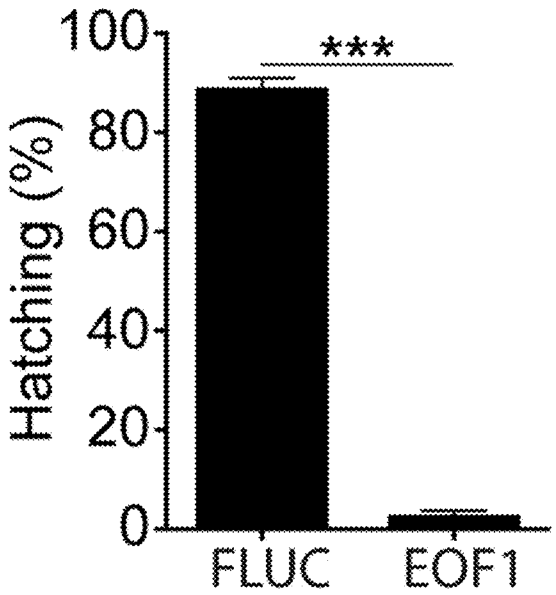
FIG. 4**B is a bar graph showing the viability of these eggs was also determined. Each bar corresponds to egg viability from 15 individual mosquitoes from three groups.

A possible explanation for aberrant partial melanization of follicles within the EOF1-deficient ovaries prior to an oviposition event is that a loss of EOF1 function may alter hemolymph permeability of eggshell, affecting a delicate chemical balance within the oocytes, which in turn trigger other eggshell components to prematurely initiate eggshell melanization processes. In addition to *Ae. aegypti*, EOF1 was confirmed to play an important role in eggshell formation in *Ae. albopictus* (FIGS. 4A and 4B). Mosquitoes were injected with dsRNA at one day after adult eclosion, and the effect of RNAi-EOF1 or -Fluc control on *Ae. albopictus* fecundity (FIG. 4A) was examined by counting the number of eggs laid by each individual female. Knockdown of EOF1 in *Ae. albopictus* females led to the production of non-melanized abnormal eggs. Note that 55.9% of fully bloodfed RNAi-EOF1 females did not produce mature follicles, and the results are not included in the analysis. Viability of these eggs was also determined (FIG. 4B).

SDS-PAGE analysis shows that enriched eggshell proteins from EOF1 deficient eggs slightly differ those from RNAi-Fluc control, and thus an identification of the downstream EOF1-dependent eggshell proteins may lead to a better understanding of molecular mechanisms for mosquito eggshell formation. Based on the presence of a conserved F-box motif in EOF1, one possibility is that EOF1 is required in the ubiquitin pathway for controlled degradation of one or more proteins that regulate proper timing of eggshell development. Dysregulation of stage-specific ordered events in RNAi-EOF1 injected mosquitoes could lead to collapse of the developmental program at all downstream control points. The finding that RNAi-EOF1 phenotypes are observed three gonotrophic cycles beyond the time of injection, indicates that the EOF1 protein may not be resynthesized at the onset of each gonotrophic cycle, but rather establishes the eggshell development program when the reproductive phase is initiated in the female mosquito. Another possibility is that RNAi effects are particularly long-lasting in ovary tissues and continue to abrogate EOF1 synthesis at each gonotrophic cycle.

TABLE 2

Gene-specific Primers Used to Amplify DNA Templates for dsDNA Synthesis

| GenBank | Vectorbase | Forward primer[1] (5' - 3') | SEQ ID No. | Reverse primer[1] (5' - 3') | SEQ ID No. | Genome[2] |
|---|---|---|---|---|---|---|
| EA137576 | AAEL010447 | GTCAATAACGTGGGTAGCAAT | 182 | CCGAGGATCTCAGCAATATGT | 41 | Ae Cx An |
| EA137892 | AAEL010160 | GAGCAGGAAGCTCAAGAATG | 2 | ccgctgcacaactcgTCAAT | 42 | Ae Cx An |
| EA139432 | AAEL008778 | CCAAGAACACATACCAGACATCA | 3 | ACTTCGTCCTTGATGCTCAC | 43 | Ae Cx An |
| EA139736 | AAEL008480 | TGCCAGCCGAAGATGACATG | 4 | TTGGCGATGGCACCACTGCT | 44 | Ae Cx |
| EA139797 | AAEL008422 | CGCTTGACCAGGAAAGTGAT | 5 | GGGATGTCGGTGATTCATCT | 45 | Ae Cx An |
| EA139842 | AAEL008395 | TTCAATCCAAAGACTTGGTTGC | 6 | CGGAATGTAGATTGGGTTCTG | 46 | Ae Cx An |
| EA139835 | AAEL008376 | CTTCCACAGTTTGCCGACCA | 7 | CGCCTGACCAGCATCTGCAA | 47 | Ae Cx An |
| EA140495 | AAEL007782 | TGCGATGTTCGGTGTGCAA | 8 | GTGGCTCTTCCTTCTCTCG | 48 | Ae Cx An |
| EA140792 | AAEL007493 | catcaggagggaacATGGAA | 9 | TAGGCTGCTGGTCGGTTGAT | 49 | Ae Cx An |
| EA132510 | AAEL015457 | CCTACGAAGATAAACGCATCC | 10 | cctgtctcggtgctacaTCA | 50 | Ae Cx An |
| EA133716 | AAEL014008 | GATGATCCGAACGTGAGCTAC | 11 | GCTTATCCGACTATCGAAGGA | 51 | Ae Cx |
| EA133725 | AAEL014000 | ATGTCGAGCCACAACTGGAC | 12 | TCCATCAGCCTCAGCTTCAA | 52 | Ae Cx |
| EA144872 | AAEL003811 | TGGGGATGCATTTGGCGGAA | 13 | CCTTCGTAGATGAGCACGTT | 53 | Ae Cx |
| EA144869 | AAEL003798 | GGAAAACCTATCATCCACGAGG | 14 | TCGTGTTCCTCAGTCTTGAC | 54 | Ae Cx An |
| EA145024 | AAEL003656 | GATCGGAGCAAAATGAGTCAAG | 15 | CTCAACAATTGCTGCGCTCG | 55 | Ae Cx |
| EA145012 | AAEL003667 | CGAGAGAGGCTTTCCTTGAAC | 16 | GAAGCATATGACTAGAAGAAGCAC | 56 | Ae Cx An |
| EA141389 | AAEL006962 | GCAGGAATTTGCCAAGATGTG | 17 | GCATTCTTGAGCGCCTGAAG | 57 | Ae Cx |
| EA134247 | AAEL013484 | gatcATGTCGTCACTCATGGA | 18 | GACACTTTGTCTTGCGACGA | 58 | Ae Cx |
| EA134512 | AAEL013257 | CGCCGTCTAGGGCAGTCGAA | 19 | TCTGTGTCTCCTCGTGTGCC | 59 | Ae Cx An |
| EA134542 | AAEL013231 | GGGTCTAAGGGTTTGGAAAG | 20 | GCGTGATGGAGCTTATGATC | 60 | Ae Cx |

TABLE 2-continued

Gene-specific Primers Used to Amplify DNA Templates for dsDNA Synthesis

| GenBank | Vectorbase | Forward primer[1] (5' - 3') | SEQ ID No. | Reverse primer[1] (5' - 3') | SEQ ID No. | Genome[2] |
|---|---|---|---|---|---|---|
| EA134665 | AAEL013122 | AACCCACCGATAACGACTTG | 21 | GAATCGTCCGTTGGACACAT | 61 | Ae Cx An |
| EA134734 | AAEL013051 | CGGTGCAAAGCCTCAGAAGAAGT | 22 | GAGGAATCGCCGCTGCTTTG | 62 | Ae Cx |
| EA145618 | AAEL003113 | GAATAGATATTGGTTTACCGATG | 23 | AGTCCACTGCCGATAGCTAG | 63 | Ae Cx An |
| EA145636 | AAEL003107 | CAGTGGATGGGACTGTTCAA | 24 | TGCTTCCGACGAAGGCACTC | 64 | Ae Cx |
| EA134953 | AAEL012849 | GATCAACCAGGTACGTTTGACT | 25 | TACAAGCTGGCGTTGACCGA | 65 | Ae Cx |
| EA145776 | AAEL002968 | AGTGGAGTAATCATGCAGCACAA | 26 | GACTGCCATTGCTGGAACAA | 66 | Ae Cx |
| EA141456 | AAEL006896 | GCTGAAACCCGTTCCTTATC | 27 | gaaacccatcTCAATCACGCTT | 67 | Ae Cx |
| EA145810 | AAEL002939 | CGGTAACATTTACCCTGCGGTT | 28 | TGGTTGATGCTGGATTGACTTGT | 68 | Ae Cx An |
| EA135499 | AAEL012336 | AGCCCGTCCAAGAGGAAGTT | 29 | CTCGGATGGTACTCACACAA | 69 | Ae Cx An |
| EA137173 | AAEL010799 | gtgtggaagttgtgccaaattgc | 30 | ATGTAGCGGTTCTGTTCCTCAT | 70 | Ae Cx An |
| EA145839 | AAEL002889 | TTCGCTGCACTACTCGTGCT | 31 | CTTACACAACAGTGTCCACTC | 71 | Ae Cx |
| EA135369 | AAEL012453 | GATGCTGGCACATGGCAAGA | 32 | CGATACTGGCTGAATCCGTA | 72 | Ae Cx |
| EA135414 | AAEL012414 | GAGGATGACATGGAGTTCGA | 33 | GCTTTGAGCAGCTTCTCTGA | 73 | Ae Cx |
| EA145942 | AAEL002828 | GAACAAGAATGCGATGCTATAA | 34 | CGTCAACACATTCATCCTCGAT | 74 | Ae Cx |
| EA145936 | AAEL002840 | GAGTTCTACTCGCCAAGTGC | 35 | CCTCGGCAGCACCTTTCTT | 75 | Ae Cx |
| EA135439 | AAEL012398 | ACGGTACAATGTGGCGAGAC | 36 | CCAATAATGGGATCGGAACG | 76 | Ae Cx An |
| EA135654 | AAEL012188 | TGGATACGGTTGATCGAGCT | 37 | ACGAATCTCGGCTGCTCGAT | 77 | Ae Cx |
| EA146193 | AAEL002586 | GATGACTTGGATGACGATATTC | 38 | GTCATCTTTCCGTAGCATCTC | 78 | Ae Cx An |
| EA148655 | AAEL000312 | GAAAGTGAGGATAGTAGTTCG | 39 | GGGATGTCAACTTTATCGTCGA | 79 | Ae Cx An |
| EA136304 | AAEL011598 | ATACTAGTGCGGTCACCCAA | 40 | CCACAGCAGACTGATATCGGA | 80 | Ae Cx An |

[1]T7 promoter sequence (5' TAATACGACTCACTATAGGGAGA 3'; SEQ ID NO: 117) was added in 5' of each RNAi primer.
[2]Presence of mosquito-specific putative genes in genomes of Aedes (Ae), Culex (Cx), and Anopheles (An) mosquito species. Lower letters for oligonucleotide sequences are present in either at 5' or 3' UTR.

TABLE 3

Gene-specific Primers for DNA Template Used in In Situ Hybridization Probe Synthesis

| Genes template | Probe | Forward primer (5' - 3') | SEQ ID No. | Reverse primer (5' - 3') | SEQ ID No. |
|---|---|---|---|---|---|
| EOF1 | sense | *AGCCCGTCCAAGAGGAAGTT | 81 | CTCGGATGGTACTCACACAA | 89 |
| EA135439 | anti-sense | AGCCCGTCCAAGAGGAAGTT | 82 | *CTCGGATGGTACTCACACAA | 90 |
| 15a1 | sense | *TTCCCATCCAACTCAGTAACCAT | 83 | TTCCGCTGCATCTTCAAGAG | 91 |
| XP_001663218 | anti-sense | TTCCCATCCAACTCAGTAACCAT | 84 | *TTCCGCTGCATCTTCAAGAG | 92 |
| 15a2 | sense | *CCAGCGTGGTACAACAGTAAATC | 85 | CCGTTCCTTGGTCCTGGTTC | 93 |
| XP_011493693 | anti-sense | CCAGCGTGGTACAACAGTAAATC | 86 | *CCGTTCCTTGGTCCTGGTTC | 94 |
| 15a3 | sense | *CGGAAGGAATCCATCCAACTT | 87 | CAGTCCAATCGATGATCCGC | 95 |
| XP_001649022 | anti-sense | CGGAAGGAATCCATCCAACTT | 88 | *CAGTCCAATCGATGATCCGC | 96 |

*T7 promoter sequence (5' TAATACGACTCACTATAGGGAGA 3' SEQ ID NO: 117) was added in 5' end of each primer.

TABLE 4

| Gene-specific Primers for RNAi and qPCR | | | | | |
|---|---|---|---|---|---|
| Gen Bank ID | | Forward primer (5' - 3') | SEQ ID No. | Reverse primer (5' - 3') | SEQ ID No. |
| *Aedes aegypti* | RNAi | AGCCCGTCCAAGAGGAAGTT | 97 | CTCGGATGGTACTCACACAA | 107 |
| EOF1:EA135499 | qPCR | CTGCGGCTTCATGTTCTGTAT | 98 | CTTGCTACATGCCACATTGTG | 108 |
| RPS7:AY380336 | qPCR | ACCGCCGTCTACGATGCCA | 99 | ATGGTGGTCTGCTGGTTCTT | 109 |
| *Aedes albopictus* | RNAi | CAAACCGCTCAATGTCAGTGG | 100 | GTACTCGAACGAATCAAGTCAA | 110 |
| EOF1:XP_019565035 | qPCR | TATCATGCCAAGCGTCGCC | 101 | CGCATCCCAATCGATATTCTC | 111 |
| RPS7:XP_019538251 | qPCR | CCTGATGCGTTCGAGGGTCA | 102 | CGGGTGATATACAGATCACG | 112 |
| *Culex quinquefasciatus* | RNAi | CGAACTTCCACCTGACCACGC | 103 | GGGCTGAAGGACTGGAACTT | 113 |
| EOF1:XP_001870696 | qPCR | TCCAACTTCCACGTTGAAGC | 104 | CGCTTGCGATAGCTGTGCAT | 114 |
| RPS7:XP_001848154 | qPCR | CGTGAGATCGAGTTCAACAACA | 105 | GTGCTTGCCGGAGAACTTCTT | 115 |
| Contrtol Luciferase:U47295 | RNAi | AGCACTCTGATTGACAAATACGA | 106 | AGTTCACCGGCGTCATCGTC | 116 |

Vectobase ID for *Aedes albopictus* EOF1: AALF011550, *Culex quinquefasciatus* EOF1: CP11010293.

Example 5: Nasrat, Closca, Polehole and Nude1 are Important Eggshell Proteins

Materials and Methods

DsRNA synthesis and microinjection, mosquito egg hatching assay, qPCR, SDS-PAGE and western blot, Rhodamine B follicle permeability assay, microscopy, and statistical analysis were performed generally as described above in Examples 1-4, except using gene-specific primers for qPCR and dsRNA template synthesis by PCR for the new targets.

In Vitro Mosquito Follicle Melanization Assays RNAi

Briefly, ovaries were dissected from these dsRNA injected mosquitoes at 96 h post blood meal. The mature follicles were isolated from the ovaries, transferred to oviposition paper wetted with water, and photographed periodically to determine a time required for eggshell melanization.

Protease Inhibitor

Ovaries from female mosquitoes at 96 hours PBM were dissected and placed in water containing protease inhibitors at different time after ovary dissection. Individual follicles were then separated, transferred onto oviposition paper, continuously soaked with water containing the protease inhibitors, and monitored for eggshell melanization. The control follicles were soaked with water without protease inhibitors.

Eggshell Isolation and Eggshell Protein Identification dsRNA samples were microinjected into the mosquito thorax three days prior to blood feeding. dsRNA injected mosquitoes were allowed to feed on blood until fully engorged. Ovaries were dissected from dsRNA injected mosquitoes 4 days post blood meal. Primary follicles were purified from dissected ovaries. The primary follicles were homogenized using a dounce homogenizer to remove oocyte cytosolic and membrane contents, and eggshell was filtered through a mesh strainer (40 μm) to obtain enriched eggshell. Trypsin-digested eggshell proteins were subjected to LC-MS/MS using the Q EXACTIVE™ hybrid quadrupole-ORBITRAP™ mass spectrometer.

Results

Since EOF-1 is expressed in the mosquito ovaries, but is not itself a component of the mature eggshell, experiments were designed to test if EOF-1 is a regulatory protein that controls the synthesis and secretion of eggshell proteins from follicular epithelial cells. Indeed, SDS PAGE analysis of eggshell proteins demonstrated that eggshells produced by EOF1 deficient mosquitoes lack certain high molecular weight proteins (over 200 kD) compared to eggshells produced by control mosquitoes, which may represent downstream targets in an EOF1-regulated pathway.

An RNAi screen was performed to identify new important eggshell proteins in *Aedes aegypti* mosquitoes. Mosquitoes were either untreated (uninjected control) or injected with RNAi targeting 32 eggshell genes, firefly luciferase (injected control), or EOF1 (AAEL012336). Results of the screen indicated that RNAi against AAEL000961, AAEL002196, AAEL006830, AAEL007096, AAEL008829, and AAEL010848 resulted in defective eggshells compared to untreated (uninjected) control (see Table 5).

TABLE 5

| RNAi screening of *Aedes aegypti* eggshell proteins. | | | |
|---|---|---|---|
| Vectorbase ID | GenBank ID | Putative functions | RNAi egg phenotypes |
| AAEL000064 | EAT48898 | Dopachrome converting enzyme, DCE1 | NO |
| AAEL000361 | EAT48607 | Trypsin inhibitor-like/serpin | NO |
| AAEL000363 | EAT48611 | Myosin inhibitor-like/serpin | NO |
| AAEL000375 | EAT48605 | Myosin inhibitor-like/serpin | NO |
| AAEL000507 | EAT48446 | Chorion peroxidase | NO |
| AAEL000961 | EAT47957 | Closca | YES |
| AAEL002198 | EAT46597 | Cysteine proteinase L-like, CATL3 | YES |
| AAEL002382 | EAT46452 | Unknown | NO |

TABLE 5-continued

RNAi screening of *Aedes aegypti* eggshell proteins.

| Vectorbase ID | GenBank ID | Putative functions | RNAi egg phenotypes |
|---|---|---|---|
| AAEL003110 | EAT45849 | Chitinase domain | NO |
| AAEL004202 | EAT44412 | Unknown | NO |
| AAEL004336 | EAT44219 | Chorion peroxidase | NO |
| AAEL004390 | EAT44218 | Chorion peroxidase | NO |
| AAEL004401 | EAT44216 | Chorion peroxidase | NO |
| AAEL005098 | EAT43477 | Trypsin inhibitor-like/serpin | NO |
| AAEL005648 | EAT42848 | Clip-domain serine protease | NO |
| AAEL005861 | EAT42645 | Vacuolar sorting protein | NO |
| AAEL006830 | EAT41553 | Dopachrome converting enzyme, DCE2 | YES |
| AAEL006985 | EAT41324 | Dopachrome converting enzyme, DCE3 | NO |
| AAEL007096 | EAT41240 | Dopachrome converting enzyme, DCE4 | YES |
| AAEL007415 | EAT40867 | Laccase-like multicopper oxidases | NO |
| AAEL007641 | EAT40646 | Transglutaminase | NO |
| AAEL006829 | EAT39370 | Nasrat | YES |
| AAEL009290 | EAT38853 | Unknown | NO |
| AAEL009452 | EAT38674 | Unknown | NO |
| AAEL009748 | EAT38349 | Unknown | NO |
| AAEL010544 | EAT37465 | Unknown | NO |
| AAEL010848 | EAT37145 | Dopachrome converting enzyme, DCE5 | YES |
| AAEL011238 | EAT36701 | Trypsin inhibitor-like/serpin | NO |
| AAEL012586 | EAT35235 | Unknown | NO |
| AAEL013936 | EAT33799 | Myosin inhibitor-like/serpin | NO |
| AAEL015203 | EAT32616 | Unknown | NO |
| AAEL017467 | EJY57339 | Chorion peroxidase | NO |

To further explore this possibility, RNAi knockdown analysis of six genes encoding eggshell proteins with high molecular weight was performed to determine if deficiencies in these proteins phenocopy the EOFI deficient phenotype of producing defective eggshells. It was observed that RNAi against nasrat (248 kD), closca (264 kD), polehole (214 kD) and nudel (285 kD) resulted in significant loss of egg melanization and embryo viability phenotypes (FIG. 5C-5D), which are similar phenotypes observed in EOF1-deficient eggs. All four of these proteins have been studied in *Drosophila melanogaster*, which showed that nasrat, closca, and polehole are structural proteins that associated with a nudel serine protease in the perivitelline space (between eggshell and oocyte plasma membrane) of developing ovarian follicles.

Mosquito nasrat, closca, pole hole, and nudel proteins have diverged significantly from *D. melanogaster* orthologs (below 30% sequence identity), indicating that their functional overlap is not conserved structurally and thereby provides an opportunity for mosquito-selective targeting.

The tissue-specific and developmental expression pattern of these genes during the first gonotrophic cycle was investigated at the mRNA level in untreated *Ae. aegypti* by quantitative real-time PCR (qPCR). Five tissues including thorax, fat body, midgut, ovaries, and Malpighian tubules were dissected from sugar-fed only (SF) and blood-fed mosquitoes at 24 and 48 hours post blood meal (PBM). The mRNA expression in larvae, pupae and adult male mosquitoes was also investigated. The tissue expression study demonstrated that Nasrat, Closca, and Polehole were predominantly expressed in ovaries, while Nudel transcripts were significantly observed in whole body male mosquitoes (FIGS. 6A-6D).

Figure 7A:
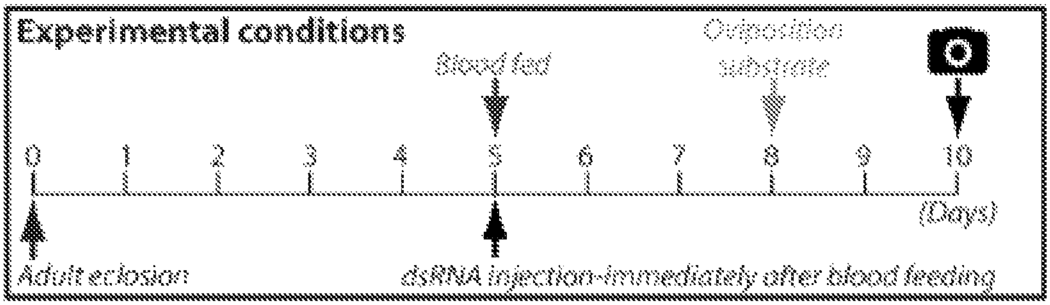
FIG. 7A is a schematic diagram of experimental time course for dsRNA microinjection, blood feeding, and oviposition in the first gonotrophic cycle. Mosquitoes were microinjected with dsRNA immediately after blood feeding.
Figure 7B:
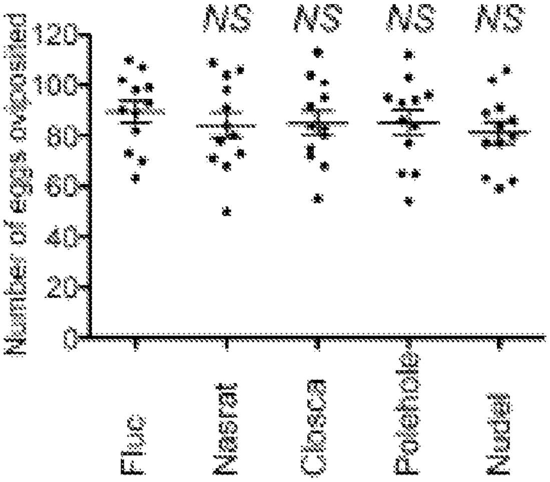
FIG. 7B is a dot plot showing the effect of RNAi against the indicated genes or Fluc (control) on *Ae. aegypti* fecundity examined by counting the number of eggs laid by each individual female. Each dot represents the number of eggs oviposited by an individual mosquito.
Figure 7C:
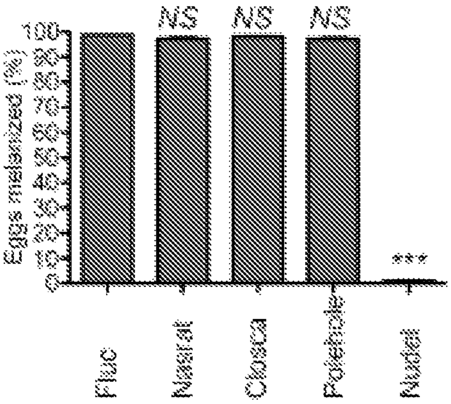
FIG. 7C is a bar graph showing the percentage melanization of the eggs. Melanization of the eggs was examined under a light microscope.
Figure 7D:
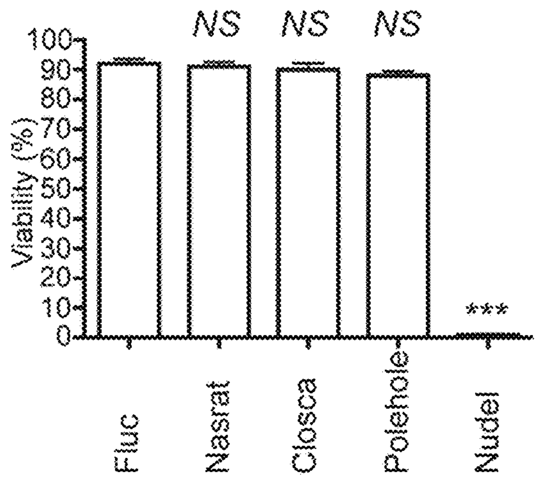
FIG. 7D is a bar graph showing the effect of RNAi on egg viability. Viability of the eggs was determined by hatching eggs one week after oviposition. Each bar corresponds to egg viability from 15 individual mosquitoes from three groups. The mean±SEM are shown as horizontal lines. Statistical significance is represented by stars above each column (unpaired student's t test; ***P<0.001, NS not significant). Vectorbase ID: Nasrat (AAEL008829), Closca (AAEL000961), Polehole (AAEL022628), and Nudel (AAEL016971).

To further explore the effects of timing of dsRNA injection on phenotype, the reproductive phenotypes associated with RNAi treatment immediately after feeding in the first gonotrophic cycle were investigated (FIG. 7A). It was observed that female mosquitoes with dsRNA-Nasrat, -Closca, or -Polehole laid eggs that showed no difference in fecundity (FIG. 7B), melanization (FIG. 7C), and viability (FIG. 7D) compared to RNAi-Fluc control mosquitoes. However, females microinjected with dsRNA-Nudel immediately after blood feeding showed adversely affected eggshell melanization and viability (FIGS. 7C-7D).

Figure 8A:
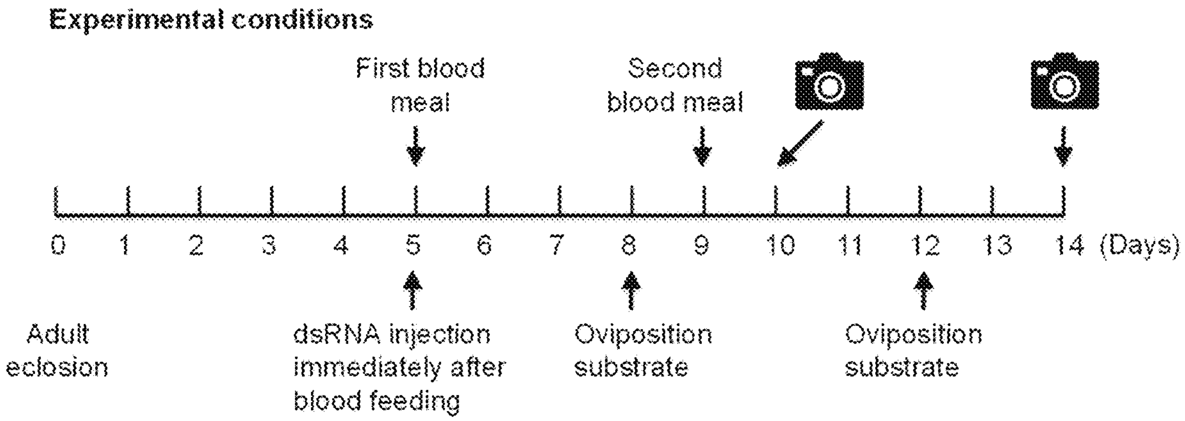
FIG. 8A is a schematic diagram of experimental time course for dsRNA microinjection, blood feeding, and oviposition in the first and second gonotrophic cycles.
Figure 8B:
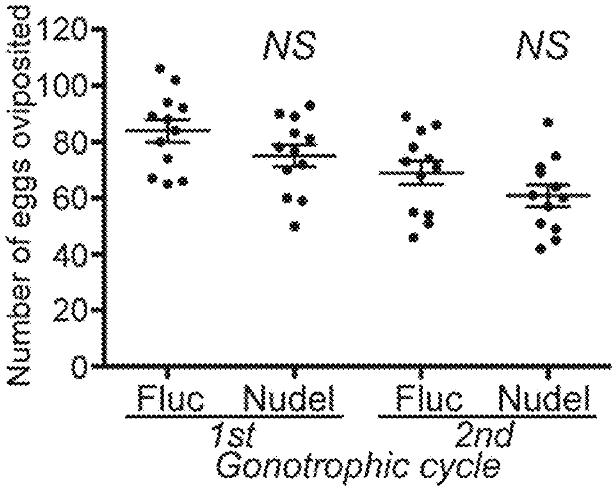
FIG. 8B is a dot plot showing the effect on fecundity in mosquitoes microinjected with dsRNA-Fluc and dsRNA-Nudel. Fecundity was examined by counting the number of eggs laid by each individual female. Each dot represents the number of eggs oviposited by an individual mosquito.
Figure 8C:
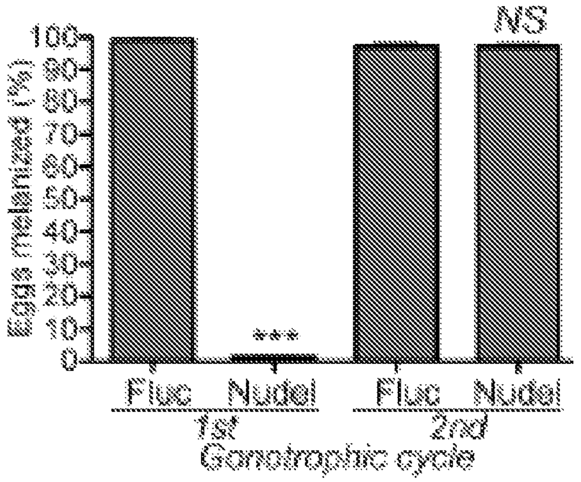
FIGS. 8C-8D are bar graphs showing the percentage melanization (FIG. 8C) and egg viability (FIG. 8D) during the first and second gonotrophic cycles. Melanization of the eggs was examined under a light microscope. Viability of the eggs was determined by hatching eggs one week after oviposition. Each bar corresponds to egg viability from 15 individual mosquitoes from three groups. The mean±SEM are shown as horizontal lines. Statistical significance is represented by stars above each column (unpaired student's t test; ***P<0.001, NS not significant).
Figure 8D:
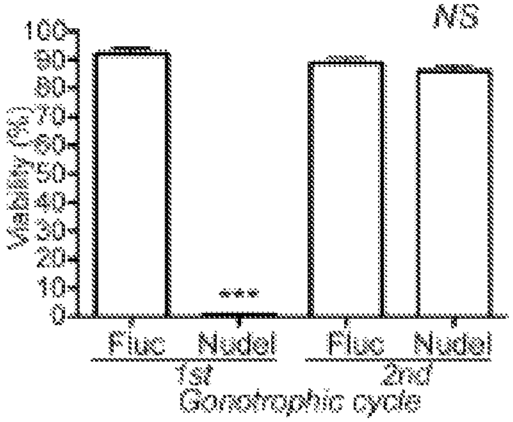

It was observed that eggs from the second gonotrophic cycle were not affected when females were microinjected with dsRNA-Nudel prior or at the blood feeding. In contrast to the first gonotrophic cycle, dsRNA-Nudel did not significantly affect melanization (FIG. 8C) and viability (FIG. 8D) of eggs in the second gonotrophic cycle.

RNAi-Nudel *Ae. aegypti* female mosquitoes laid melanization defective eggs, thus leading to embryonic death. Experiments were designed to test a model in which activation of Nudel serine protease in wildtype mosquitoes is tightly regulated in time and space in eggs such that Nudel in eggshell may be inactive prior to oviposition and becomes active as soon as female mosquitoes oviposit eggs in order to proteolytically regulate enzymes involved in the melanization and cross-linking. In vitro mosquito follicle melanization experiments were designed to determine the time required for melanization of primary follicles isolated from RNAi-mosquitoes.

Figure 5A:
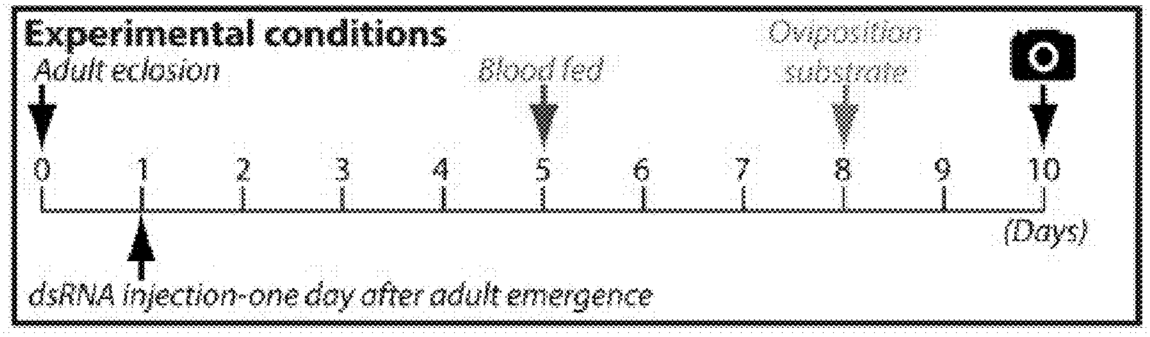
FIG. 5A is a schematic diagram of experimental time course for dsRNA microinjection, blood feeding, and oviposition in the first gonotrophic cycle.
Figure 5B:
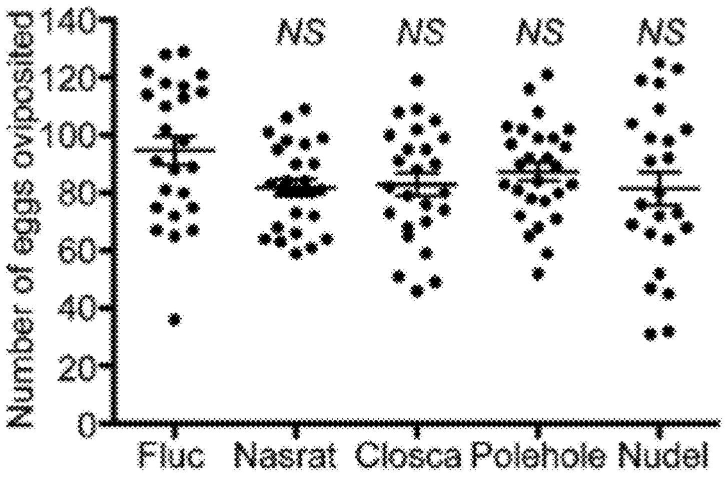
FIG. 5B is a dot plot showing the effect of RNAi against the indicated genes or Fluc (control) on *Ae. aegypti* fecundity examined by counting the number of eggs oviposited by each individual female (represented by each dot).
Figure 5C:
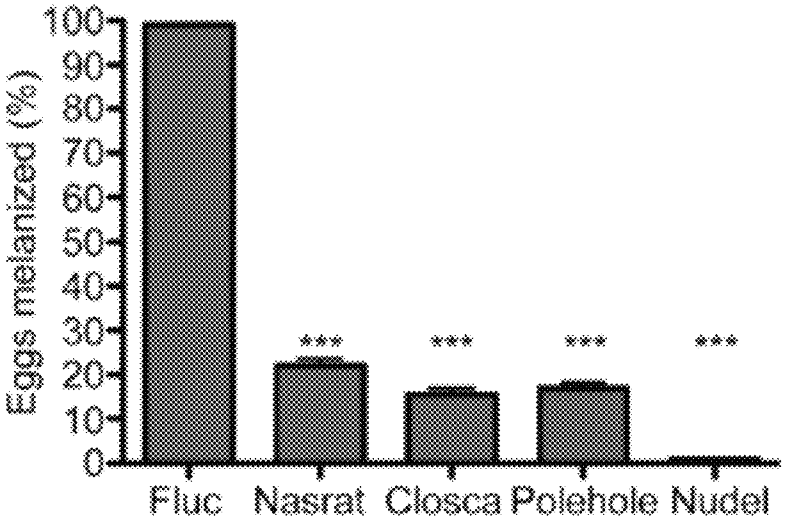
FIG. 5C is a bar graph showing the percentage melanization of these eggs determined by examination under a light microscope.
Figure 5D:
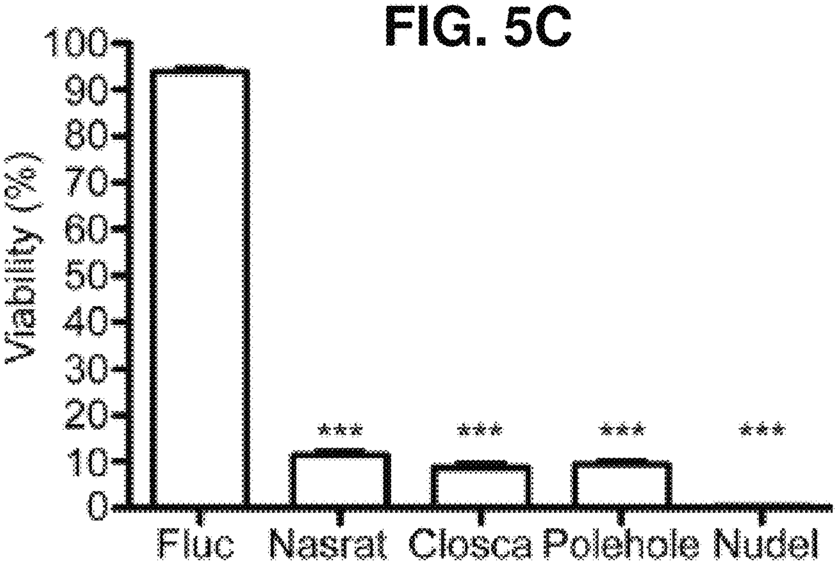
FIG. 5D is a bar graph showing the effect of RNAi on viability of these eggs determined by hatching eggs one week after oviposition. Each bar corresponds to egg viability from 15 individual mosquitoes from three groups. Vectorbase ID: Nasrat (AAEL008829), Closca (AAEL000961), Polehole (AAEL022628), and Nudel (AAEL016971). The mean±SEM are shown as horizontal lines. Statistical significance is represented by stars above each column (unpaired student's t test; ***P<0.001, NS not significant).
Figure 6A:
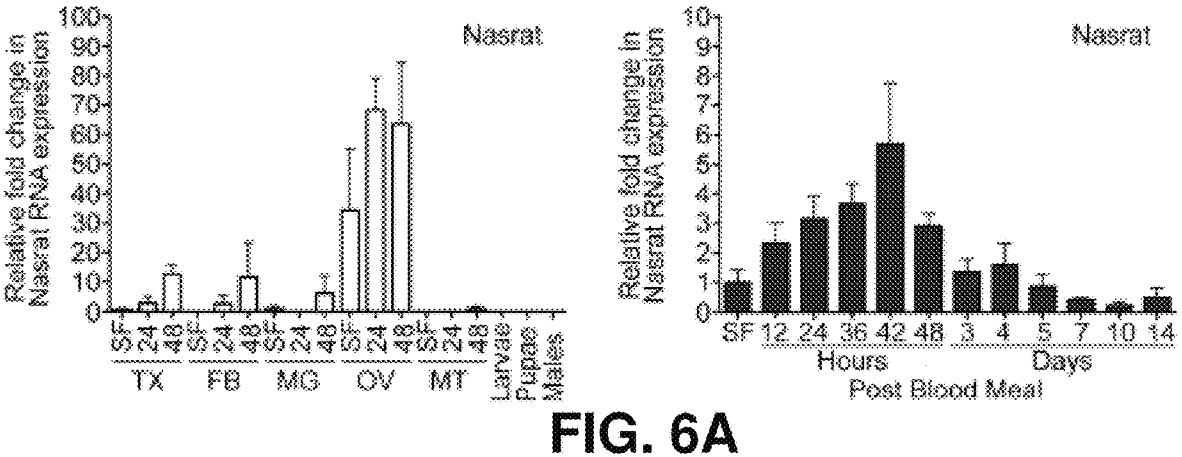
FIGS. 6A-6D are bar graphs showing tissue-specific and developmental expression pattern of Nasrat (FIG. 6A), Closca (FIG. 6B), Polehole (FIG. 6C) and Nudel (FIG. 6D) during the first gonotrophic cycle of *Aedes aegypti* mosquitoes. Gene expression was analyzed by qPCR using cDNAs prepared from various tissues. Tissues include thorax (TX), fat body (FB), midgut (MG), ovary (OV), and Malphigian tubules (MT) in sugar-fed only (SF) and 24 and 48 hours post blood meal (PBM), as well as larvae (Lv), pupae (Pp), and adult males (M). Detailed gene expression in mosquito ovaries or follicles in the first gonotrophic cycle was also analyzed by qPCR. Samples from SF to 36 hours PBM include entire ovaries, whereas those from 48 hours to 14 days PBM include only primary follicles isolated from ovaries. Expression levels were normalized to S7 ribosomal protein transcript levels in the same cDNA samples. Data were collected from three different mosquito cohorts. The mean±SE are shown as horizontal lines. Vectorbase ID: Nasrat (AAEL008829), Closca (AAEL000961), Polehole (AAEL022628), and Nudel (AAEL016971).
Figure 6B:
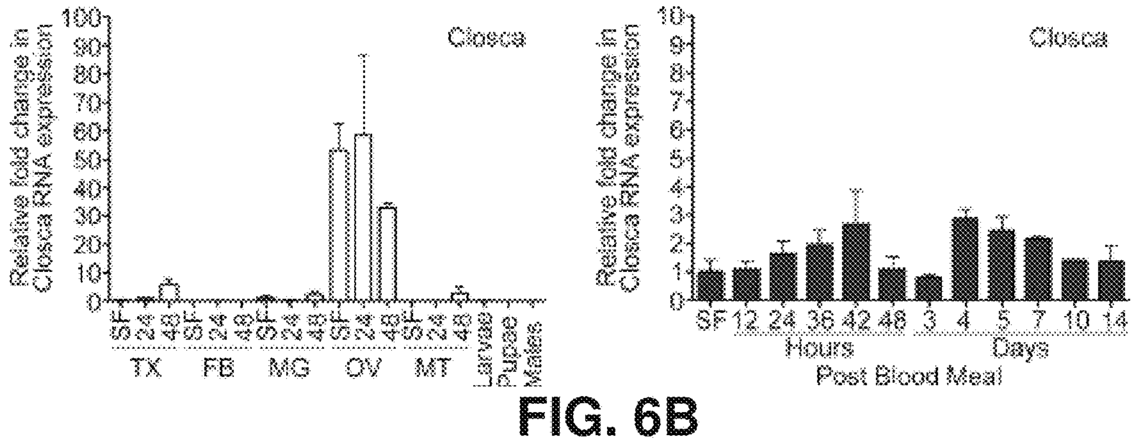
Figure 6C:
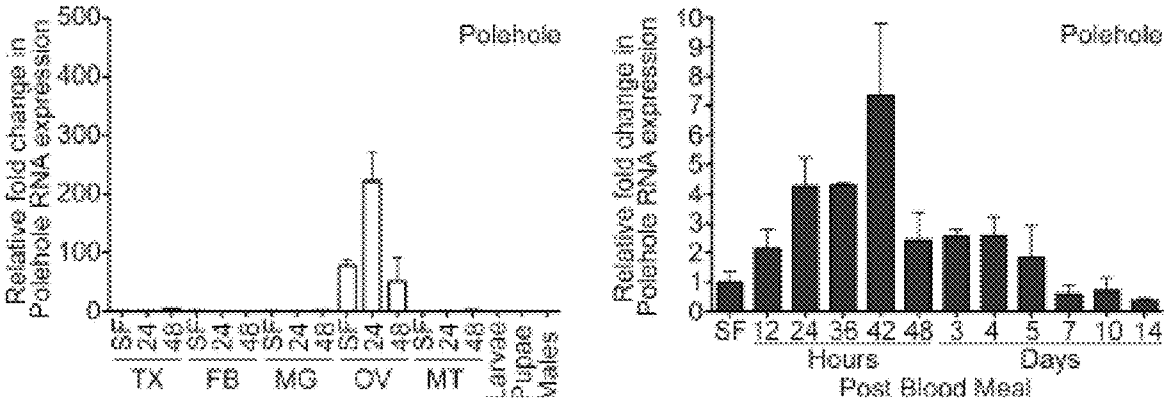
Figure 6D:
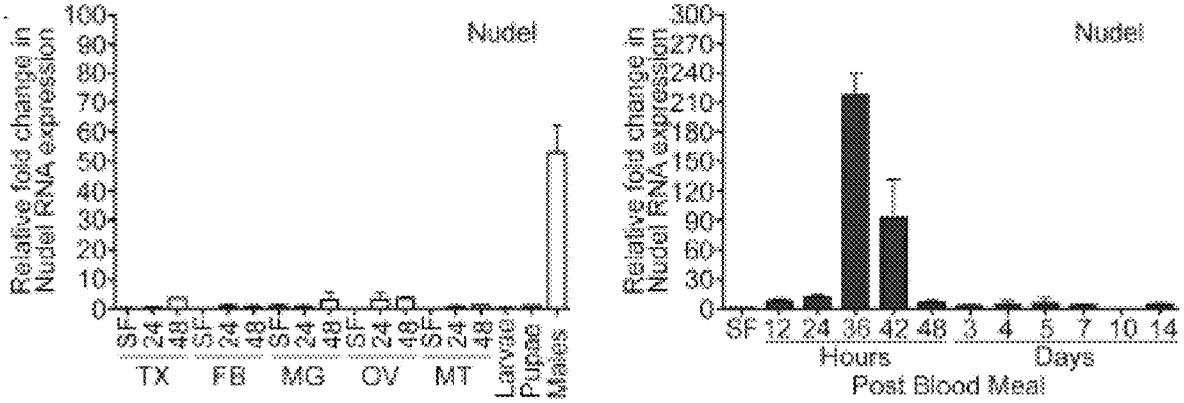
Figure 9A:
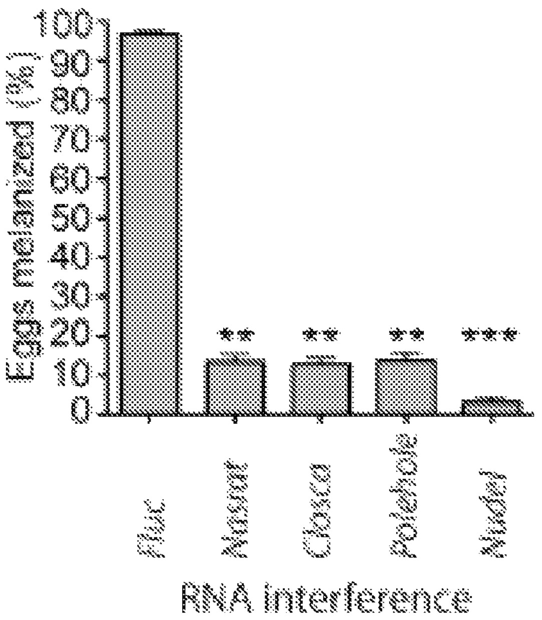
FIGS. 9A and 9B are bar graphs showing results from in vitro egg melanization assays.

Thus, to further investigate the effects of RNAi-Nasrat, -Closca, -Polehole, and -Nudel, an in vitro follicle melanization assay was conducted using follicles isolated from RNAi mosquitoes at 96 hours PBM Timing of dsRNA microinjection and blood feeding were identical to those shown in FIG. 5A. The follicles were photographed 5, 70 and 120 minutes after follicle dissection. Compared to Fluc control, individual knockdown of Nasrat, Closca, Polehole and Nudel was observed to significantly reduce egg melanization, with Nudel knockdown demonstrating the largest reduction (FIG. 9A). Melanization of follicles from RNAi-Fluc controls was initiated approximately at 70 min and completed by approximately 3 hours after the ovary dissection. In contrast, the majority of follicles from RNAi against Nasrat, Closca, Polehole, and Nudel mosquitoes did not undergo melanizataion within 3-hours experimental period and never further melanized even at 24 hours after the beginning of experiments, indicating that proteolytic activity of Nude1 serine protease may be needed for eggshell melanization in mosquitoes.

Figure 9B:
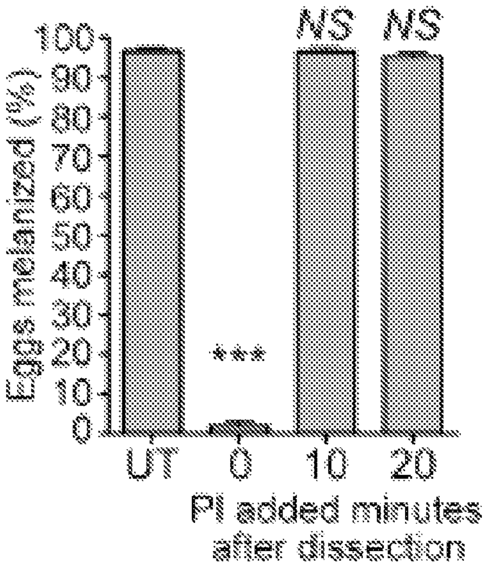

Next, experiments were designed to test whether active protease(s) are important during eggshell melanization. To determine a role of proteases on eggshell melanization, an in vitro follicle melanization assay was performed using a protease inhibitor cocktail (PI) (PI, Complete Mini, EDTA-free, Roche). Dissected matured mosquito follicles were treated with protease inhibitors. Follicles were incubated with PI at 0, 10, or 20 minutes after follicle dissection. The follicles were photographed 5, 70 and 120 min after the follicle dissection. Compared to untreated control, a significant reduction in egg melanization was only observed upon immediate treatment with PI after follicle dissection (i.e., the 0 minute time point; FIG. 9B).

The protease inhibitor cocktail totally inhibited melanization of wild-type mature follicles only when they were treated with PI (PI, Complete Mini, EDTA-free, Roche) during dissection. On the contrary, the cohort follicles treated with PI at 10 or 20 min after dissection were able to undergo normal eggshell melanization, which is similar to those control wild-type follicles soaked with water without PI. Thus, some proteases present in eggshell are likely important and activated immediately after contacting with water in order to regulate enzymes necessary for eggshell melanization in *Ae. aegypti*. Thus, it was concluded that Nude1 protease may play a significant role in mosquito eggshell melanization.

To determine whether the water permeability of the mosquito eggshells was affected in response to Nasrat, Closca, Polehole, or Nude1 knockdown, a rhodamine B permeability assay was employed to stain ovarian follicles. Significant differences in the permeability were observed. The follicle permeability assay showed that a strong Rhodamine B cellular uptake was observed in primary follicles isolated from RNAi-Nasrat, -Closca, -Polehole, and -Nude1 female mosquitoes, whereas the follicles from RNAi-Fluc control mosquitoes were not stained.

Figure 10:
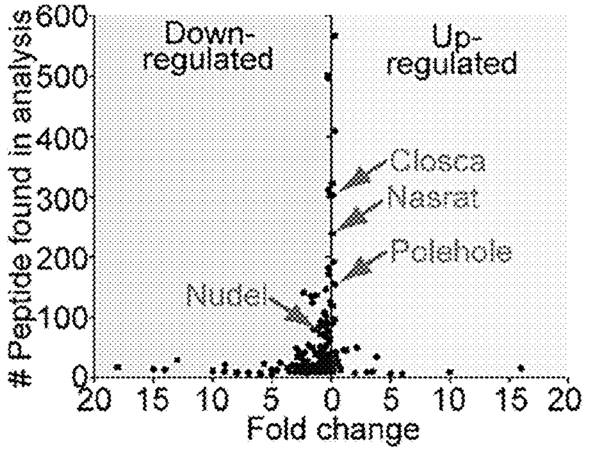
FIG. 10 is a plot showing eggshell peptide abundance fold changes in response to RNAi-EOF1 (AAEL012336) are shown in comparison with RNAi-Fluc control. Two independent biological replicates from both RNAi-Fluc and RNAi-EOF1 were used in the proteomic analysis.

Polehole, Nasrat, Closca, and Nude1 protein expressions (Eggshell peptide abundance fold changes) were also analyszed in response to RNAi-EOF1 (AAEL012336) in comparison with RNAi-Fluc control (FIG. 10).

Collectively, these results indicate that Nasrat, Closca, Polehole, and Nude1 are important for eggshell melanization and oocyte membrane permeability.

Figure 11:
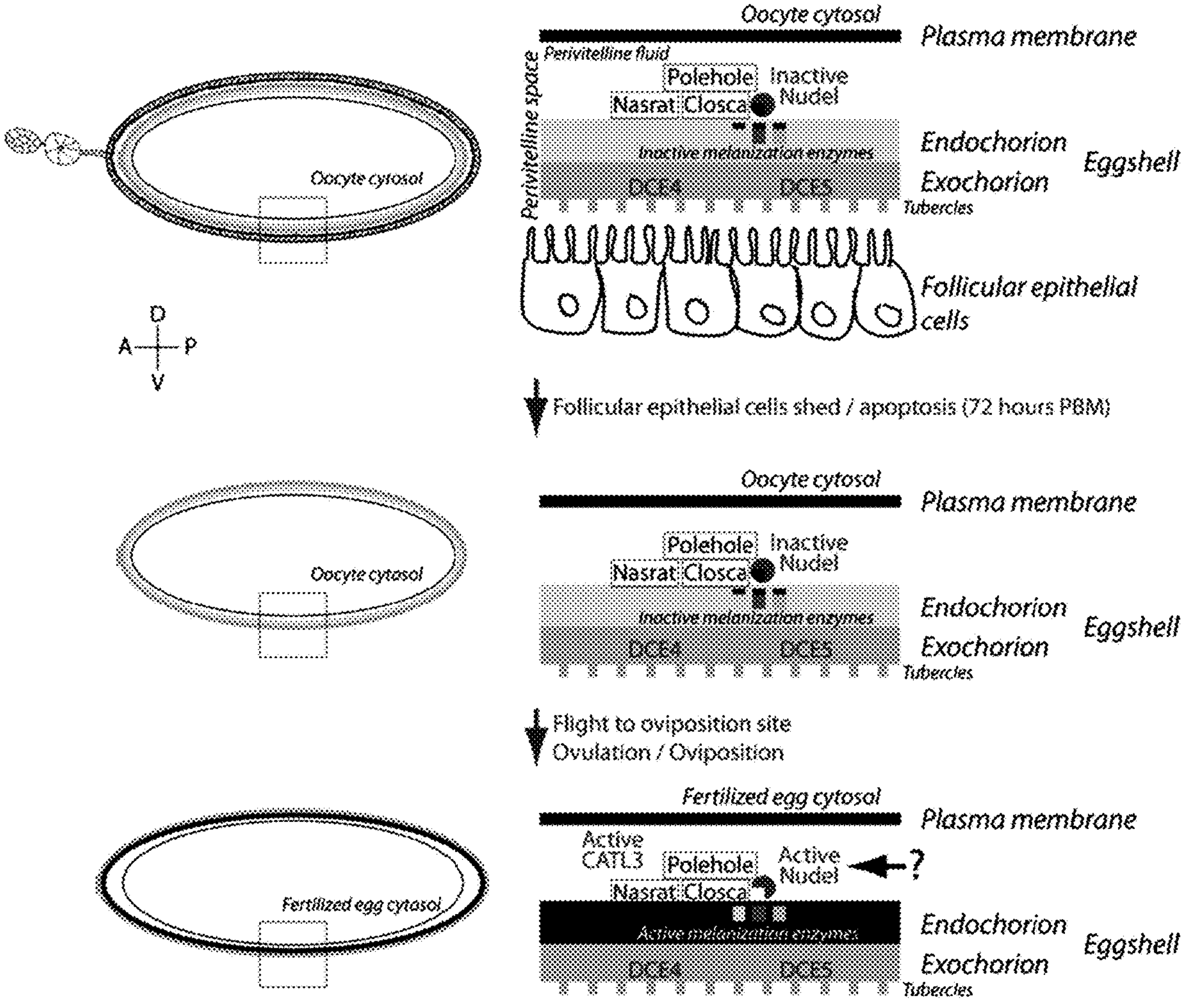
FIG. 11 is a proposed three stage model for involvement of specific proteins during eggshell formation and melanization in *Aedes aegypti* mosquitoes.

Based on the above results, a three-stage model for involvement of specific proteins during eggshell formation and melanization in *Aedes aegypti* mosquitoes is proposed (FIG. 11). In stage A, a primary follicle in the ovariole reaches maturity, and an extracellular eggshell matrix completely forms between oocyte and follicular epithelial cells around 48 hours post blood meal (PBM). Enzymes involved in eggshell melanization and cross-linking may be likely inactive. In stage B, as the follicles initiate migration into an inner oviduct, the surrounding follicular epithelia shed with the secondary follicle and germarium in the ovariole. The enzymes involved in eggshell melanization and cross-linking may be still inactive forms within the inner, lateral, and common oviducts. In stage C, once the eggs are deposited onto a dump substrate, eggs briefly uptake surrounding water and activate the melanization and cross-linking enzymes through the activity of Nude1 and/or CATL3.

It is believed that the *Ae. aegypti* nudel serine protease associates with the nasrat, closca, and polehole structural proteins in a common pathway that is itself controlled by EOF1. Inhibitor assays confirmed that proteases, e.g., serine proteases, are necessary for initiating melanization processes in *Ae. aegypti* mosquito eggs. It is believed that the *Ae. aegypti* nudel serine protease may function in a nasrat/closca/polehole protein complex to proteolytically regulate activities of secreted downstream target enzymes in the eggshell, including prophenol oxidases, dopachrome conversion enzymes, laccase, chorion peroxidases, and transglutaminases, which are known to be directly involved in mosquito eggshell maturation. It is contemplated that small inhibitory molecules targeting highly diverged mosquito nudel protease can be used in compositions and methods to specifically and safely control mosquito populations.

TABLE 6

Primers used for RNAi screening.

| Vectorbase ID | Gene-specific RNAi primers (5' - 3') | | SEQ ID No. | Vectorbase ID | Gene-specific RNAi primers (5' - 3') | | SEQ ID No. |
|---|---|---|---|---|---|---|---|
| AAEL000064 | Forward | TGCTGCGCCTCGTGTTCTT | 118 | AAEL006985 | Forward | CTCCCGGTTGGAATCGAAAG | 152 |
| | Reverse | CGGAGATGTAGACGAAGACCTT | 119 | | Reverse | GTCCGTAGTCCAGTTCATTGG | 153 |
| AAEL000361 | Forward | GTAGCGATTGTIGTICTAGCG | 120 | AAEL007096 | Forward | GCAAGAAGTGGCGACAAGAC | 154 |
| | Reverse | GGCGTAAGTAACTTGCACACGG | 121 | | Reverse | CGTCCACCCAGATAGGTGAA | 155 |
| AAEL000363 | Forward | CCCTGTGCCGACCCAAACGA | 122 | AAEL007415 | Forward | TCAGTGCCGACCAGCAAGT | 156 |
| | Reverse | CGGTGTGGTCGTAGTAATACA | 123 | | Reverse | CTGAGATTGTCTTGTTGGACTTC | 157 |
| AAEL000375 | Forward | ATGCAGCTTCCAATATGTGCTAT | 124 | AAEL007641 | Forward | CGCTCGCAACGTGCATTGG | 158 |
| | Reverse | GCGGCTTCGGCGTAGGCTT | 125 | | Reverse | GGACACCACGCACGCTGCAA | 159 |
| AAEL000507 | Forward | TACAGCTCTGCGTGCATCTG | 126 | AAEL008829 | Forward | GAGCCCATTCAGAACCTCCT | 160 |
| | Reverse | CCACAATCGGTCTTCGTCAG | 127 | | Reverse | AGCGTAACTCCGTTGACGTA | 161 |
| AAEL000961 | Forward | GGCAAGGGCTTCTACAACGT | 128 | AAEL009290 | Forward | ATCGAGGGATTGATGGAAGG | 162 |
| | Reverse | CCGTTCAAAGTATGCTCCAC | 129 | | Reverse | CCGTCCGAGTAGTGGATCGC | 163 |
| AAEL002196 | Forward | TGAAGAAACAACTGCTGTGG | 130 | AAEL009452 | Forward | GTCCTCCATCTCTTTGGTGA | 164 |
| | Reverse | CCATCTGCTGGGTACTGAC | 131 | | Reverse | TCACCAACCAGCTCTTCTCG | 165 |
| AAEL002382 | Forward | GCCCATGTGAACTTCCCTTGCC | 132 | AAEL009746 | Forward | CAGCCTACATCGTTGACCTA | 166 |
| | Reverse | GATACCTCGCCCTGTTGAAC | 133 | | Reverse | TGTCGAAGCACAACCGATGGTT | 167 |

TABLE 6-continued

Primers used for RNAi screening.

| Vectorbase ID | Gene-specific RNAi primers (5' - 3') | | SEQ ID No. | Vectorbase ID | Gene-specific RNAi primers (5' - 3') | | SEQ ID No. |
|---|---|---|---|---|---|---|---|
| AAEL003110 | Forward | TCCAACCAGGAGTCGAGTGA | 134 | AAEL010544 | Forward | CAGCGGGATCAGAACCAGGAT | 168 |
| | Reverse | CGCCAATTCCACCGAGTTG | 135 | | Reverse | CATAAGATCCGTCAGACCGTC | 169 |
| AAEL004202 | Forward | TCCTACGGCGAAGCTGGTTC | 136 | AAEL010848 | Forward | GCCCTCGACTCAGGCATTTG | 170 |
| | Reverse | GACTCTCGTTTGTCTGCTTC | 137 | | Reverse | TGCGTGCTCAAGCGACACTC | 171 |
| AAEL004386 | Forward | TGAGGGAACACAACCGACTA | 138 | AAEL011238 | Forward | CAACCAGTTGATGGCAGGATAC | 172 |
| | Reverse | TAAACCTGTGCCAAGAGTGC | 139 | | Reverse | CCGTTGTGCTTCACATAACC | 173 |
| AAEL004390 | Forward | TGAGGGAACACAACCGACTA | 140 | AAEL012586 | Forward | GCCGACAGGGACCGATGATG | 174 |
| | Reverse | TAAACTCGCGCCAGAAGAGC | 141 | | Reverse | GCCGAAATGTTGATCTTGTGTAC | 175 |
| AAEL004401 | Forward | CCACACTGGTCTGACGACAT | 142 | AAEL013936 | Forward | TTAGCAATAGTTTCTCACTGCCA | 176 |
| | Reverse | CGCCTACGTAAAGATCGACGT | 143 | | Reverse | GCCTGTGGGCTTCGATTGG | 177 |
| AAEL005098 | Forward | ATGAAGTTGGCAATCATTTGTGT | 144 | AAEL015203 | Forward | GTGTTGGTGCCGAAGAAGAG | 178 |
| | Reverse | GCTCCAGGACAATCGCACAG | 145 | | Reverse | TAGCACTTCAACTCGGATGACTT | 179 |
| AAEL005648 | Forward | GCCAAAGCCGATAGCCATC | 146 | AAEL017467 | Forward | TACAGCTCTGCGTGCATCTG | 180 |
| | Reverse | CTAGGCATGTTGAGAGCACC | 147 | | Reverse | CCACAATCGGTCTTCGTCAG | 181 |
| AAEL005861 | Forward | TGTGATGGCGATGACGACTG | 148 | AAEL012336 | Forward | AGCCCGTCCAAGAGGAAGTT | 29 |
| | Reverse | CTCATCACTTCCATCCTTGCA | 149 | (EOF1) | Reverse | CTCGGATGGTACTCACACAA | 69 |
| AAEL006830 | Forward | TGTGGAAATCGTCGGTGGT | 150 | U47295 | Forward | AGCACTCTGATTGACAAATACGA | 106 |
| | Reverse | TGTAGGCGAAGGTGTCCTC | 151 | (Luciferase) | Reverse | AGTTCACCGGCGTCATCGTC | 116 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising an effective amount of a compound or compounds that reduce(s) or inhibit(s) expression or activity of an eggshell formation, melanization, and/or crosslinking pathway comprising a mosquito Eggshell Organizing Factor 1 (EOF1) protein and optionally one or more proteins selected from Nasrat, Closca, Polehole, Nudel, CATL3, DCE2, DCE4, and DCE5, wherein the compound or compounds reduce(s) or inhibit(s) expression or activity of one or more mosquito target genes selected from the group consisting of EOF1, Nasrat, Closca, CATL3, DCE2, DCE4, and DCE5, or gene products thereof, wherein the compound or compounds comprise(s) one or more species of double stranded RNAs or vectors encoding the same, wherein the one or more species of double stranded RNA comprises a sequence transcribable from a double stranded DNA template amplicon formed by amplification using a primer pair annealed to and extended from a corresponding double stranded target gene sequence according to:

| Target Gene | Target Gene Encodes the Protein Sequence | Gene-specific double stranded RNA primers (5'-3') | Primer SEQ ID No. |
|---|---|---|---|
| EOF1 | AAEL012336 | Forward AGCCCGTCCAAGAGGAAGTT | 29 |
| | (SEQ ID NO: 1) | Reverse CTCGGATGGTACTCACACAA | 69 |
| Nasrat | AAEL008829 | Forward GAGCCCATTCAGAACCTCCT | 160 |
| | (SEQ ID NO: 183) | Reverse AGCGTAACTCCGTTGACGTA | 161 |
| Closca | AAEL000961 | Forward GGCAAGGGCTTCTACAACGT | 128 |
| | (SEQ ID NO: 184) | Reverse CCGTTCAAAGTATGCTCCAC | 129 |
| CATL3 | AAEL002196 | Forward TGAAGAAACAACTGCTGTGG | 130 |
| | (SEQ ID NOS: 187 or 200) | Reverse CCATCTGCTGGGTACTGAC | 131 |
| DCE2 | AAEL006830 | Forward TGTGGAAATCGTCGGTGGT | 150 |
| | (SEQ ID NO: 188) | Reverse TGTAGGCGAAGGTGTCCTC | 151 |
| DCE4 | AAEL007096 | Forward GCAAGAAGTGGCGACAAGAC | 154 |
| | (SEQ ID NO: 189) | Reverse CGTCCACCCAGATAGGTGAA | 155 |
| DCE5 | AAEL010848 | Forward GCCCTCGACTCAGGCATTTG | 170 |
| | (SEQ ID NO: 190) | Reverse TGCGTGCTCAAGCGACACTC | 171 |

wherein the species of double stranded RNAs target one or more of the mRNA encoded by the nucleic acid of SEQ ID NO: 191, 220, 229, 238, 239, 192, 230, 240,193, 222, 231, 241,196, 225, 234, 244, 197, 226, 235, 245, 198, 227, 236, 246, 199, 228, 237, or 247.

2. The composition of claim 1, comprising the compound or compounds that reduce(s) or inhibit(s) expression or activity of the mosquito target gene EOF1 or gene products thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| EOF1 | AAEL012336 (SEQ ID NO: 1) | Forward AGCCCGTCCAAGAGGAAGTT | 29 |
| | | Reverse CTCGGATGGTACICACACAA | 69 |

wherein the species of double stranded RNAs target one or more of the mRNA encoded by the nucleic acid of SEQ ID NO: 191, 220, 229, 238, and 239.

3. The composition of claim 1, comprising the compound or compounds that reduce(s) or inhibit(s) expression or activity of the mosquito target gene Nasrat or gene products thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| Nasrat | AAEL008829 (SEQ ID NO: 183) | Forward GAGCCCATTCAGAACCTCCT | 160 |
| | | Reverse AGCGTAACTCCGTTGACGTA | 161 |

wherein the species of double stranded RNAs target one or more of the mRNA encoded by the nucleic acid of SEQ ID NO: 192, 230, and 240.

4. The composition of claim 1, comprising the compound or compounds that reduce(s) or inhibit(s) expression or activity of the mosquito target gene Closca or gene product thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| Closca | AAEL000961 (SEQ ID NO: 184) | Forward GGCAAGGGCTICTACAACGT | 128 |
| | | Reverse CCGTTCAAAGTATGCTCCAC | 129 |

wherein the species of double stranded RNAs target one or more of the mRNA encoded by the nucleic acid of SEQ ID NO: 193, 222, 231, and 241.

5. The composition of claim 1, comprising the compound or compounds that reduce(s) or inhibit(s) expression or activity of the mosquito target gene CATL3 or gene products thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| CATL3 | AAEL002196 | Forward TGAAGAAACAACTGCTGTGG | 130 |
| | (SEQ ID NOS: 187 or 200) | Reverse CCATCTGCTGGGTACTGAC | 131 |

wherein the species of double stranded RNAs target one or more of the mRNA encoded by the nucleic acid of SEQ ID NO: 196, 225, 234, or 244.

6. The composition of claim 1, comprising the compound or compounds that reduce(s) or inhibit(s) expression or activity of the mosquito target gene DCE2 or gene products thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| DCE2 | AAEL006830 | Forward TGTGGAAATCGTCGGTGGT | 150 |
| | (SEQ ID NO: 188) | Reverse TGTAGGCGAAGGTGTCCTC | 151 |

wherein the species of double stranded RN As target one or more of the mRNA encoded by the nucleic acid of SEQ ID NO: 197, 226, 235, and 245.

7. The composition of claim 1, comprising the compound or compounds that reduce(s) or inhibit(s) expression or activity of the mosquito target gene DCE4 or gene products thereof, wherein the one or more species of double stranded RNA comprises the sequence transcribable from the double stranded DNA template amplicon formed by amplification using the primer pair annealed to and extended from the corresponding double stranded target gene sequence according to:

| Target Gene | Target Gene Encodes the Protein Sequence | Gene-specific RNAi primers (5'-3') | Primer SEQ ID No. |
|---|---|---|---|
| DCE4 | AAEL007096 | Forward GCAAGAAGTGGCGACAAGAC | 154 |
| | (SEQ ID NO: 189) | Reverse CGTCCACCCAGATAGGTGAA | 155 |

wherein the species of double stranded RNAs target one or more of the mRNA encoded by the nucleic acid of SEQ ID NO: 198, 227, 236 or 246.

8. The composition of claim 1, comprising the compound or compounds that reduce(s) or inhibit(s) expression or activity of the mosquito target gene DCE5 or gene products thereof, wherein the one or more species of double stranded RNA comprises the sequence transcribable from the double stranded DNA template amplicon formed by amplification using the primer pair annealed to and extended from the corresponding double stranded target gene sequence according to

| Target Gene | Target Gene Encodes the Protein Sequence | Gene-specific RNAi primers (5'-3') | Primer SEQ ID No. |
|---|---|---|---|
| DCE5 | AAEL010848 (SEQ ID NO: 190) | Forward GCCCTCGACTCAGGCATTTG | 170 |
| | | Reverse TGCGTGCTCAAGCGACACTC | 171 |

wherein the species of double stranded RNAs target one or more of the mRNA encoded by the nucleic acid of SEQ ID NO: 199, 228, 237, or 247.

9. A method of reducing or inhibiting expression of one or more mosquito target genes selected from the group consisting of Eggshell Organizing Factor 1 (EOF1), Nasrat, Closca, Polehole, Nudel, CATL3, DCE2, DCE4, and DCE5, or a gene product thereof comprising contacting mosquito cells with the composition of claim 1.

10. The method of claim 9, wherein the mosquito cells are contact in vivo in embryonic, larval, pupal, or adult mosquitoes, or a combination thereof.

11. The method of claim 10, wherein the mosquitoes comprise adult females.

12. The method of claim 11, wherein the composition is administered in a manner suitable to reduce, or inhibit expression of one or more of EOF1, Nasrat, Closca, Polehole Nudel, CATL3, DCE2, DCE4, or DCE5 genes or products thereof at about 2 or about 5 days prior to blood feeding in the first and/or second gonotrophic cycles; about one to about three days after oviposition; or a combination thereof in the adult females.

13. The method of claim 9, wherein the mosquitoes contact a surface previously treated with the composition and thereby contact the composition.

* * * * *

SEQUENCE LISTING

<160> NUMBER OF SEQ ID NOS: 247

<210> SEQ ID NO 1
<211> LENGTH: 848
<212> TYPE: PRT
<213> ORGANISM: Aedes aegypti

<400> SEQUENCE: 1

Met Glu Glu Ser Gln Gln Leu Gln Phe Pro Ile Arg Gly Asn Asn Asn
1 5 10 15

Asn Lys Pro Leu Asn Val Ser Gly Gly Asn Asp Gly Ser Gly Gln Phe
20 25 30

Thr Asp Ser Gly Tyr Thr Ser Tyr His Ser Ile Ser Ala Ser Gly Ser
35 40 45

Val Ala Arg Ser Val Leu Ala Thr Ile Glu Glu Asp Asn Glu Ala Asp
50 55 60

Ser Ser Phe Glu Glu Ala Arg Ser Ser Glu Asp Ile Phe Gln Met Gly
65 70 75 80

Gly Gly Ser Asn Val Leu Thr Pro Thr Thr Ala Ala Ser Ile Glu Arg
85 90 95

Ile Ser Asn Phe His Leu Thr Thr Pro Asn Ser Thr Gly Lys Pro Val
100 105 110

Gly Gln His Arg Gly Leu Val Arg Lys Pro Thr Phe Asp Asn Leu Phe

-continued

```
        115                 120                 125

Glu Gln Tyr Thr Pro Lys Lys Ala Asp Tyr Gly Pro Pro Cys Arg Thr
    130                 135                 140

Thr Gln Thr Pro Val Arg Ser Asp Arg Lys Val Glu Leu Gly Ser Gln
145                 150                 155                 160

Thr Pro Arg Lys Asn Lys Ala Ser Ala Lys Arg Lys Leu Gly Glu Phe
                165                 170                 175

Arg Glu Lys Leu Tyr Ser Asp Gly Asp Ala Leu Glu Leu Ala Pro Ser
            180                 185                 190

Arg Asp Leu Asn Asp Ser Leu Glu Gly Asp Cys Lys Lys Leu Asp Gln
        195                 200                 205

Glu Asp Ile Ser Pro Ile Tyr His Thr Lys Arg Arg Arg Ser Ser Val
    210                 215                 220

Ile Asp Leu Ile Arg Ser Ser Thr Pro Lys Thr Ala Ser Leu Arg Ser
225                 230                 235                 240

Asn Phe His Val Glu Val Arg Glu Asn Ile Asp Trp Asp Ala Val Gln
                245                 250                 255

Gln Gly Lys Ala Ser Gly Arg Gly Gly Lys Ser Arg Ala Leu Arg Lys
            260                 265                 270

Phe Gln Ser Phe Ser Pro Ser Lys Met His Ser Tyr Lys Lys Arg Asp
        275                 280                 285

Val Leu Gln Glu Lys Ser Val Ile Ala Asn Arg Arg Ala Pro Phe Gln
    290                 295                 300

Arg Gln Asp Ala Leu Arg Gln Val Ser Leu Glu Gln Asp Leu Ser Lys
305                 310                 315                 320

Gln Ser Thr Pro Gln Lys Ala Gln Glu Ser Ser Leu Asp Lys Ser Phe
                325                 330                 335

Glu Leu Pro Leu Glu Gly Leu Ile Thr Pro Ser Lys Gln Ser Asn Leu
            340                 345                 350

Gly Val Leu Leu Asp Ala Pro Ile Leu Val Gln Pro Ser Ser Glu Ala
        355                 360                 365

Asp Phe Lys Glu Ser Asp Leu Glu Gln Gln Ile Ser Gln Ile Pro Ser
    370                 375                 380

Phe Glu Glu Cys Ala Tyr Pro Gln Thr Pro Ser Lys Gln Thr Leu Ser
385                 390                 395                 400

Leu Asp Asp Ser Gly Val Ile Arg His Ala Pro Val Cys Thr Glu Val
                405                 410                 415

Asn Lys Ser Ile Pro Ser Ile Leu Gly Thr Glu Ser Pro Ser Phe Val
            420                 425                 430

Ser Leu Ser Ile Pro Lys Thr Pro Thr Ser Thr Asn Lys Ser Arg Asn
        435                 440                 445

Arg Leu Lys Arg Leu Ser Ser Thr Lys Lys Asp Lys Pro Arg Ser Lys
    450                 455                 460

Pro Pro Ser Pro Ile His Arg Ala Gln Pro Phe Ile Pro Gly Thr Tyr
465                 470                 475                 480

Arg Arg Pro Ser Tyr Val Asn Val Glu Arg Leu Asn Ile Leu Lys Trp
                485                 490                 495

Leu Asn Glu His Asp Lys Asp Ala Leu Gly Ile Val Leu Asp Tyr Leu
            500                 505                 510

Asn Asp Ser Asp Leu Val Arg Val Val Arg Val Ser Thr Gly Trp Arg
        515                 520                 525

Asp Ile Ile Glu His His Arg Pro Ser Tyr Arg Arg Leu Arg Ala His
    530                 535                 540
```

```
Phe Ala Arg Glu Lys Glu Val Lys Glu Asn Leu Ser Phe Pro Ser Phe
545                 550                 555                 560

Val Ser Arg Glu Gly Ser Leu Leu Gly Lys Thr Gly Gly Ser Leu Leu
                565                 570                 575

Ser Ser Phe Gly Asp Ser Ser Lys Glu Ile Ala Val Ser Leu Pro Arg
            580                 585                 590

Gln Pro Phe Ser Leu Cys Asn Ser Ile Asp Ser Asn Gln Ser Val Gly
        595                 600                 605

Gly Glu Leu Arg Arg Ser Gly Ser Val Gln Arg Ser Pro Pro Val Ser
    610                 615                 620

Pro Ser Lys Arg Lys Phe Arg Glu Asn Gln Lys Ile Ala Ser His Leu
625                 630                 635                 640

Lys Lys Ser Glu Arg Leu Lys Pro Cys Pro Arg Cys Glu Lys Pro Ser
                645                 650                 655

Arg Val Val Leu Thr Lys Ser Ser Ile Lys Leu Ala Met Ala Thr Gly
            660                 665                 670

Ser Leu Asp Ser Ser Thr Thr Arg Thr Val Ala Ser Gly Lys Leu Asp
        675                 680                 685

Arg Ser Tyr Thr Leu Pro Asp Ser Leu Met Gly Ser Ser Ala Thr Ser
    690                 695                 700

Met Ile Ala Ala Ala Ala Leu Asp Cys Thr Ser Thr Thr Ile Gly Ser
705                 710                 715                 720

Pro Gln Ser Pro Thr Asn Pro Asp Arg Ile Arg Arg Asn Leu Phe Ser
                725                 730                 735

Thr Ser Leu Leu Pro Arg Ser Gln Ser Val Asp Ala Arg Thr Pro Val
            740                 745                 750

Thr Arg Ser Pro Arg Arg Arg Arg Ser Thr Asp Val Gln Gly Ser Ser
        755                 760                 765

Ala Ser Leu Leu Glu Arg Lys Asn Gly Lys Thr Lys Ser Ala Glu Ala
    770                 775                 780

Ile Gln Cys Asp Tyr Ala Val Cys Ser Gly Lys Asn Cys Gly Phe Met
785                 790                 795                 800

Phe Cys Ile Lys Cys Leu Cys Glu Tyr His Pro Ser Ser Val Cys Lys
                805                 810                 815

Asp Leu Ala Pro Asn Ser Pro Ser Lys Glu Asp Glu Pro Ala His Asn
            820                 825                 830

Val Ala Cys Ser Lys Gln Ser Arg Arg Ser Leu Leu Arg Leu Arg Lys
        835                 840                 845
```

<210> SEQ ID NO 2
<211> LENGTH: 20
<212> TYPE: DNA
<213> ORGANISM: Artificial Sequence
<220> FEATURE:
<223> OTHER INFORMATION: Forward primer

<400> SEQUENCE: 2
gagcaggaag ctcaagaatg 20

<210> SEQ ID NO 3
<211> LENGTH: 23
<212> TYPE: DNA
<213> ORGANISM: Artificial Sequence
<220> FEATURE:
<223> OTHER INFORMATION: Forward primer

<400> SEQUENCE: 3
ccaagaacac ataccagaca tca 23

<210> SEQ ID NO 4
<211> LENGTH: 20
<212> TYPE: DNA
<213> ORGANISM: Artificial Sequence
<220> FEATURE:
<223> OTHER INFORMATION: Forward primer

<400> SEQUENCE: 4
tgccagccga agatgacatg 20

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
cgcttgacca ggaaagtgat 20

<210> SEQ ID NO 6
<211> LENGTH: 22
<212> TYPE: DNA
<213> ORGANISM: Artificial Sequence
<220> FEATURE:
<223> OTHER INFORMATION: Forward primer

<400> SEQUENCE: 6
ttcaatccaa agacttggtt gc 22

<210> SEQ ID NO 7
<211> LENGTH: 20
<212> TYPE: DNA
<213> ORGANISM: Artificial Sequence
<220> FEATURE:
<223> OTHER INFORMATION: Forward primer

<400> SEQUENCE: 7
cttccacagt ttgccgacca 20

<210> SEQ ID NO 8
<211> LENGTH: 19
<212> TYPE: DNA
<213> ORGANISM: Artificial Sequence
<220> FEATURE:
<223> OTHER INFORMATION: Forward primer

<400> SEQUENCE: 8
tgcgatgttc ggtgtgcaa 19

<210> SEQ ID NO 9
<211> LENGTH: 20
<212> TYPE: DNA
<213> ORGANISM: Artificial Sequence
<220> FEATURE:
<223> OTHER INFORMATION: Forward primer

<400> SEQUENCE: 9
catcaggagg gaacatggaa 20

<210> SEQ ID NO 10
<211> LENGTH: 21
<212> TYPE: DNA

```
<213> ORGANISM: Artificial Sequence
<220> FEATURE:
<223> OTHER INFORMATION: Forward primer

<400> SEQUENCE: 10

cctacgaaga taaacgcatc c                                             21


<210> SEQ ID NO 11
<211> LENGTH: 21
<212> TYPE: DNA
<213> ORGANISM: Artificial Sequence
<220> FEATURE:
<223> OTHER INFORMATION: Forward primer

<400> SEQUENCE: 11

gatgatccga acgtgagcta c                                             21


<210> SEQ ID NO 12
<211> LENGTH: 20
<212> TYPE: DNA
<213> ORGANISM: Artificial Sequence
<220> FEATURE:
<223> OTHER INFORMATION: Forward primer

<400> SEQUENCE: 12

atgtcgagcc acaactggac                                               20


<210> SEQ ID NO 13
<211> LENGTH: 20
<212> TYPE: DNA
<213> ORGANISM: Artificial Sequence
<220> FEATURE:
<223> OTHER INFORMATION: Forward primer

<400> SEQUENCE: 13

tggggatgca tttggcggaa                                               20


<210> SEQ ID NO 14
<211> LENGTH: 22
<212> TYPE: DNA
<213> ORGANISM: Artificial Sequence
<220> FEATURE:
<223> OTHER INFORMATION: Forward primer

<400> SEQUENCE: 14

ggaaaaccta tcatccacga gg                                            22


<210> SEQ ID NO 15
<211> LENGTH: 22
<212> TYPE: DNA
<213> ORGANISM: Artificial Sequence
<220> FEATURE:
<223> OTHER INFORMATION: Forward primer

<400> SEQUENCE: 15

gatcggagca aaatgagtca ag                                            22


<210> SEQ ID NO 16
<211> LENGTH: 21
<212> TYPE: DNA
<213> ORGANISM: Artificial Sequence
<220> FEATURE:
<223> OTHER INFORMATION: Forward primer

<400> SEQUENCE: 16

cgagagaggc tttccttgaa c                                             21
```

<210> SEQ ID NO 17
<211> LENGTH: 21
<212> TYPE: DNA
<213> ORGANISM: Artificial Sequence
<220> FEATURE:
<223> OTHER INFORMATION: Forward primer

<400> SEQUENCE: 17
gcaggaattt gccaagatgt g 21

<210> SEQ ID NO 18
<211> LENGTH: 21
<212> TYPE: DNA
<213> ORGANISM: Artificial Sequence
<220> FEATURE:
<223> OTHER INFORMATION: Forward primer

<400> SEQUENCE: 18
gatcatgtcg tcactcatgg a 21

<210> SEQ ID NO 19
<211> LENGTH: 20
<212> TYPE: DNA
<213> ORGANISM: Artificial Sequence
<220> FEATURE:
<223> OTHER INFORMATION: Forward primer

<400> SEQUENCE: 19
cgccgtctag ggcagtcgaa 20

<210> SEQ ID NO 20
<211> LENGTH: 20
<212> TYPE: DNA
<213> ORGANISM: Artificial Sequence
<220> FEATURE:
<223> OTHER INFORMATION: Forward primer

<400> SEQUENCE: 20
gggtctaagg gtttggaaag 20

<210> SEQ ID NO 21
<211> LENGTH: 20
<212> TYPE: DNA
<213> ORGANISM: Artificial Sequence
<220> FEATURE:
<223> OTHER INFORMATION: Forward primer

<400> SEQUENCE: 21
aacccaccga taacgacttg 20

<210> SEQ ID NO 22
<211> LENGTH: 23
<212> TYPE: DNA
<213> ORGANISM: Artificial Sequence
<220> FEATURE:
<223> OTHER INFORMATION: Forward primer

<400> SEQUENCE: 22
cggtgcaaag cctcagaaga agt 23

<210> SEQ ID NO 23
<211> LENGTH: 23
<212> TYPE: DNA
<213> ORGANISM: Artificial Sequence
<220> FEATURE:

<223> OTHER INFORMATION: Forward primer

<400> SEQUENCE: 23
gaatagatat tggtttaccg atg 23

<210> SEQ ID NO 24
<211> LENGTH: 20
<212> TYPE: DNA
<213> ORGANISM: Artificial Sequence
<220> FEATURE:
<223> OTHER INFORMATION: Forward primer

<400> SEQUENCE: 24
cagtggatgg gactgttcaa 20

<210> SEQ ID NO 25
<211> LENGTH: 22
<212> TYPE: DNA
<213> ORGANISM: Artificial Sequence
<220> FEATURE:
<223> OTHER INFORMATION: Forward primer

<400> SEQUENCE: 25
gatcaaccag gtacgtttga ct 22

<210> SEQ ID NO 26
<211> LENGTH: 23
<212> TYPE: DNA
<213> ORGANISM: Artificial Sequence
<220> FEATURE:
<223> OTHER INFORMATION: Forward primer

<400> SEQUENCE: 26
agtggagtaa tcatgcagca caa 23

<210> SEQ ID NO 27
<211> LENGTH: 20
<212> TYPE: DNA
<213> ORGANISM: Artificial Sequence
<220> FEATURE:
<223> OTHER INFORMATION: Forward primer

<400> SEQUENCE: 27
gctgaaaccc gttccttatc 20

<210> SEQ ID NO 28
<211> LENGTH: 22
<212> TYPE: DNA
<213> ORGANISM: Artificial Sequence
<220> FEATURE:
<223> OTHER INFORMATION: Forward primer

<400> SEQUENCE: 28
cggtaacatt taccctgcgg tt 22

<210> SEQ ID NO 29
<211> LENGTH: 20
<212> TYPE: DNA
<213> ORGANISM: Artificial Sequence
<220> FEATURE:
<223> OTHER INFORMATION: Forward primer

<400> SEQUENCE: 29
agcccgtcca agaggaagtt 20

<210> SEQ ID NO 30
<211> LENGTH: 23
<212> TYPE: DNA
<213> ORGANISM: Artificial Sequence
<220> FEATURE:
<223> OTHER INFORMATION: Forward primer

<400> SEQUENCE: 30
gtgtggaagt tgtgccaaat tgc 23

<210> SEQ ID NO 31
<211> LENGTH: 20
<212> TYPE: DNA
<213> ORGANISM: Artificial Sequence
<220> FEATURE:
<223> OTHER INFORMATION: Forward primer

<400> SEQUENCE: 31
ttcgctgcac tactcgtgct 20

<210> SEQ ID NO 32
<211> LENGTH: 20
<212> TYPE: DNA
<213> ORGANISM: Artificial Sequence
<220> FEATURE:
<223> OTHER INFORMATION: Forward primer

<400> SEQUENCE: 32
gatgctggca catggcaaga 20

<210> SEQ ID NO 33
<211> LENGTH: 20
<212> TYPE: DNA
<213> ORGANISM: Artificial Sequence
<220> FEATURE:
<223> OTHER INFORMATION: Forward primer

<400> SEQUENCE: 33
gaggatgaca tggagttcga 20

<210> SEQ ID NO 34
<211> LENGTH: 22
<212> TYPE: DNA
<213> ORGANISM: Artificial Sequence
<220> FEATURE:
<223> OTHER INFORMATION: Forward primer

<400> SEQUENCE: 34
gaacaagaat gcgatgctat aa 22

<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35
gagttctact cgccaagtgc 20

<210> SEQ ID NO 36
<211> LENGTH: 20
<212> TYPE: DNA
<213> ORGANISM: Artificial Sequence
<220> FEATURE:
<223> OTHER INFORMATION: Forward primer

<400> SEQUENCE: 36
acggtacaat gtggcgagac 20

<210> SEQ ID NO 37
<211> LENGTH: 20
<212> TYPE: DNA
<213> ORGANISM: Artificial Sequence
<220> FEATURE:
<223> OTHER INFORMATION: Forward primer

<400> SEQUENCE: 37
tggatacggt tgatcgagct 20

<210> SEQ ID NO 38
<211> LENGTH: 22
<212> TYPE: DNA
<213> ORGANISM: Artificial Sequence
<220> FEATURE:
<223> OTHER INFORMATION: Forward primer

<400> SEQUENCE: 38
gatgacttgg atgacgatat tc 22

<210> SEQ ID NO 39
<211> LENGTH: 21
<212> TYPE: DNA
<213> ORGANISM: Artificial Sequence
<220> FEATURE:
<223> OTHER INFORMATION: Forward primer

<400> SEQUENCE: 39
gaaagtgagg atagtagttc g 21

<210> SEQ ID NO 40
<211> LENGTH: 20
<212> TYPE: DNA
<213> ORGANISM: Artificial Sequence
<220> FEATURE:
<223> OTHER INFORMATION: Forward primer

<400> SEQUENCE: 40
atactagtgc ggtcacccaa 20

<210> SEQ ID NO 41
<211> LENGTH: 21
<212> TYPE: DNA
<213> ORGANISM: Artificial Sequence
<220> FEATURE:
<223> OTHER INFORMATION: Reverse primer

<400> SEQUENCE: 41
ccgaggatct cagcaatatg t 21

<210> SEQ ID NO 42
<211> LENGTH: 20
<212> TYPE: DNA
<213> ORGANISM: Artificial Sequence
<220> FEATURE:
<223> OTHER INFORMATION: Reverse primer

<400> SEQUENCE: 42
ccgctgcaca actcgtcaat 20

<210> SEQ ID NO 43
<211> LENGTH: 20

<212> TYPE: DNA
<213> ORGANISM: Artificial Sequence
<220> FEATURE:
<223> OTHER INFORMATION: Reverse primer

<400> SEQUENCE: 43
acttcgtcct tgatgctcac 20

<210> SEQ ID NO 44
<211> LENGTH: 20
<212> TYPE: DNA
<213> ORGANISM: Artificial Sequence
<220> FEATURE:
<223> OTHER INFORMATION: Reverse primer

<400> SEQUENCE: 44
ttggcgatgg caccactgct 20

<210> SEQ ID NO 45
<211> LENGTH: 20
<212> TYPE: DNA
<213> ORGANISM: Artificial Sequence
<220> FEATURE:
<223> OTHER INFORMATION: Reverse primer

<400> SEQUENCE: 45
gggatgtcgg tgattcatct 20

<210> SEQ ID NO 46
<211> LENGTH: 21
<212> TYPE: DNA
<213> ORGANISM: Artificial Sequence
<220> FEATURE:
<223> OTHER INFORMATION: Reverse primer

<400> SEQUENCE: 46
cggaatgtag attgggttct g 21

<210> SEQ ID NO 47
<211> LENGTH: 20
<212> TYPE: DNA
<213> ORGANISM: Artificial Sequence
<220> FEATURE:
<223> OTHER INFORMATION: Reverse primer

<400> SEQUENCE: 47
cgcctgacca gcatctgcaa 20

<210> SEQ ID NO 48
<211> LENGTH: 19
<212> TYPE: DNA
<213> ORGANISM: Artificial Sequence
<220> FEATURE:
<223> OTHER INFORMATION: Reverse primer

<400> SEQUENCE: 48
gtggctcttc cttctctcg 19

<210> SEQ ID NO 49
<211> LENGTH: 20
<212> TYPE: DNA
<213> ORGANISM: Artificial Sequence
<220> FEATURE:
<223> OTHER INFORMATION: Reverse primer

<400> SEQUENCE: 49
taggctgctg gtcggttgat 20

<210> SEQ ID NO 50
<211> LENGTH: 20
<212> TYPE: DNA
<213> ORGANISM: Artificial Sequence
<220> FEATURE:
<223> OTHER INFORMATION: Reverse primer

<400> SEQUENCE: 50
cctgtctcgg tgctacatca 20

<210> SEQ ID NO 51
<211> LENGTH: 21
<212> TYPE: DNA
<213> ORGANISM: Artificial Sequence
<220> FEATURE:
<223> OTHER INFORMATION: Reverse primer

<400> SEQUENCE: 51
gcttatccga ctatcgaagg a 21

<210> SEQ ID NO 52
<211> LENGTH: 20
<212> TYPE: DNA
<213> ORGANISM: Artificial Sequence
<220> FEATURE:
<223> OTHER INFORMATION: Reverse primer

<400> SEQUENCE: 52
tccatcagcc tcagcttcaa 20

<210> SEQ ID NO 53
<211> LENGTH: 20
<212> TYPE: DNA
<213> ORGANISM: Artificial Sequence
<220> FEATURE:
<223> OTHER INFORMATION: Reverse primer

<400> SEQUENCE: 53
ccttcgtaga tgagcacgtt 20

<210> SEQ ID NO 54
<211> LENGTH: 20
<212> TYPE: DNA
<213> ORGANISM: Artificial Sequence
<220> FEATURE:
<223> OTHER INFORMATION: Reverse primer

<400> SEQUENCE: 54
tcgtgttcct cagtcttgac 20

<210> SEQ ID NO 55
<211> LENGTH: 20
<212> TYPE: DNA
<213> ORGANISM: Artificial Sequence
<220> FEATURE:
<223> OTHER INFORMATION: Reverse primer

<400> SEQUENCE: 55
ctcaacaatt gctgcgctcg 20

<210> SEQ ID NO 56
<211> LENGTH: 24
<212> TYPE: DNA
<213> ORGANISM: Artificial Sequence
<220> FEATURE:
<223> OTHER INFORMATION: Reverse primer

<400> SEQUENCE: 56
gaagcatatg actagaagaa gcac 24

<210> SEQ ID NO 57
<211> LENGTH: 20
<212> TYPE: DNA
<213> ORGANISM: Artificial Sequence
<220> FEATURE:
<223> OTHER INFORMATION: Reverse primer

<400> SEQUENCE: 57
gcattcttga gcgcctgaag 20

<210> SEQ ID NO 58
<211> LENGTH: 20
<212> TYPE: DNA
<213> ORGANISM: Artificial Sequence
<220> FEATURE:
<223> OTHER INFORMATION: Reverse primer

<400> SEQUENCE: 58
gacactttgt cttgcgacga 20

<210> SEQ ID NO 59
<211> LENGTH: 20
<212> TYPE: DNA
<213> ORGANISM: Artificial Sequence
<220> FEATURE:
<223> OTHER INFORMATION: Reverse primer

<400> SEQUENCE: 59
tctgtgtctc ctcgtgtgcc 20

<210> SEQ ID NO 60
<211> LENGTH: 20
<212> TYPE: DNA
<213> ORGANISM: Artificial Sequence
<220> FEATURE:
<223> OTHER INFORMATION: Reverse primer

<400> SEQUENCE: 60
gcgtgatgga gcttatgatc 20

<210> SEQ ID NO 61
<211> LENGTH: 20
<212> TYPE: DNA
<213> ORGANISM: Artificial Sequence
<220> FEATURE:
<223> OTHER INFORMATION: Reverse primer

<400> SEQUENCE: 61
gaatcgtccg ttggacacat 20

<210> SEQ ID NO 62
<211> LENGTH: 20
<212> TYPE: DNA
<213> ORGANISM: Artificial Sequence
<220> FEATURE:
<223> OTHER INFORMATION: Reverse primer

<400> SEQUENCE: 62
gaggaatcgc cgctgctttg 20

<210> SEQ ID NO 63
<211> LENGTH: 20
<212> TYPE: DNA
<213> ORGANISM: Artificial Sequence
<220> FEATURE:
<223> OTHER INFORMATION: Reverse primer

<400> SEQUENCE: 63
agtccactgc cgatagctag 20

<210> SEQ ID NO 64
<211> LENGTH: 20
<212> TYPE: DNA
<213> ORGANISM: Artificial Sequence
<220> FEATURE:
<223> OTHER INFORMATION: Reverse primer

<400> SEQUENCE: 64
tgcttccgac gaaggcactc 20

<210> SEQ ID NO 65
<211> LENGTH: 20
<212> TYPE: DNA
<213> ORGANISM: Artificial Sequence
<220> FEATURE:
<223> OTHER INFORMATION: Reverse primer

<400> SEQUENCE: 65
tacaagctgg cgttgaccga 20

<210> SEQ ID NO 66
<211> LENGTH: 20
<212> TYPE: DNA
<213> ORGANISM: Artificial Sequence
<220> FEATURE:
<223> OTHER INFORMATION: Reverse primer

<400> SEQUENCE: 66
gactgccatt gctggaacaa 20

<210> SEQ ID NO 67
<211> LENGTH: 22
<212> TYPE: DNA
<213> ORGANISM: Artificial Sequence
<220> FEATURE:
<223> OTHER INFORMATION: Reverse primer

<400> SEQUENCE: 67
gaaacccatc tcaatcacgc tt 22

<210> SEQ ID NO 68
<211> LENGTH: 23
<212> TYPE: DNA
<213> ORGANISM: Artificial Sequence
<220> FEATURE:
<223> OTHER INFORMATION: Reverse primer

<400> SEQUENCE: 68
tggttgatgc tggattgact tgt 23

<210> SEQ ID NO 69
<211> LENGTH: 20
<212> TYPE: DNA
<213> ORGANISM: Artificial Sequence
<220> FEATURE:
<223> OTHER INFORMATION: Reverse primer

<400> SEQUENCE: 69
ctcggatggt actcacacaa 20

<210> SEQ ID NO 70
<211> LENGTH: 22
<212> TYPE: DNA
<213> ORGANISM: Artificial Sequence
<220> FEATURE:
<223> OTHER INFORMATION: Reverse primer

<400> SEQUENCE: 70
atgtagcggt tctgttcctc at 22

<210> SEQ ID NO 71
<211> LENGTH: 21
<212> TYPE: DNA
<213> ORGANISM: Artificial Sequence
<220> FEATURE:
<223> OTHER INFORMATION: Reverse primer

<400> SEQUENCE: 71
cttacacaac agtgtccact c 21

<210> SEQ ID NO 72
<211> LENGTH: 20
<212> TYPE: DNA
<213> ORGANISM: Artificial Sequence
<220> FEATURE:
<223> OTHER INFORMATION: Reverse primer

<400> SEQUENCE: 72
cgatactggc tgaatccgta 20

<210> SEQ ID NO 73
<211> LENGTH: 20
<212> TYPE: DNA
<213> ORGANISM: Artificial Sequence
<220> FEATURE:
<223> OTHER INFORMATION: Reverse primer

<400> SEQUENCE: 73
gctttgagca gcttctctga 20

<210> SEQ ID NO 74
<211> LENGTH: 22
<212> TYPE: DNA
<213> ORGANISM: Artificial Sequence
<220> FEATURE:
<223> OTHER INFORMATION: Reverse primer

<400> SEQUENCE: 74
cgtcaacaca ttcatcctcg at 22

<210> SEQ ID NO 75
<211> LENGTH: 19
<212> TYPE: DNA
<213> ORGANISM: Artificial Sequence
<220> FEATURE:
<223> OTHER INFORMATION: Reverse primer

<400> SEQUENCE: 75
cctcggcagc acctttctt 19

<210> SEQ ID NO 76

<211> LENGTH: 20
<212> TYPE: DNA
<213> ORGANISM: Artificial Sequence
<220> FEATURE:
<223> OTHER INFORMATION: Reverse primer

<400> SEQUENCE: 76
ccaataatgg gatcggaacg 20

<210> SEQ ID NO 77
<211> LENGTH: 20
<212> TYPE: DNA
<213> ORGANISM: Artificial Sequence
<220> FEATURE:
<223> OTHER INFORMATION: Reverse primer

<400> SEQUENCE: 77
acgaatctcg gctgctcgat 20

<210> SEQ ID NO 78
<211> LENGTH: 21
<212> TYPE: DNA
<213> ORGANISM: Artificial Sequence
<220> FEATURE:
<223> OTHER INFORMATION: Reverse primer

<400> SEQUENCE: 78
gtcatctttc cgtagcatct c 21

<210> SEQ ID NO 79
<211> LENGTH: 22
<212> TYPE: DNA
<213> ORGANISM: Artificial Sequence
<220> FEATURE:
<223> OTHER INFORMATION: Reverse primer

<400> SEQUENCE: 79
gggatgtcaa ctttatcgtc ga 22

<210> SEQ ID NO 80
<211> LENGTH: 21
<212> TYPE: DNA
<213> ORGANISM: Artificial Sequence
<220> FEATURE:
<223> OTHER INFORMATION: Reverse primer

<400> SEQUENCE: 80
ccacagcaga ctgatatcgg a 21

<210> SEQ ID NO 81
<211> LENGTH: 20
<212> TYPE: DNA
<213> ORGANISM: Artificial Sequence
<220> FEATURE:
<223> OTHER INFORMATION: Forward primer

<400> SEQUENCE: 81
agcccgtcca agaggaagtt 20

<210> SEQ ID NO 82
<211> LENGTH: 20
<212> TYPE: DNA
<213> ORGANISM: Artificial Sequence
<220> FEATURE:
<223> OTHER INFORMATION: Forward primer

<400> SEQUENCE: 82
agcccgtcca agaggaagtt 20

<210> SEQ ID NO 83
<211> LENGTH: 23
<212> TYPE: DNA
<213> ORGANISM: Artificial Sequence
<220> FEATURE:
<223> OTHER INFORMATION: Forward primer

<400> SEQUENCE: 83
ttcccatcca actcagtaac cat 23

<210> SEQ ID NO 84
<211> LENGTH: 23
<212> TYPE: DNA
<213> ORGANISM: Artificial Sequence
<220> FEATURE:
<223> OTHER INFORMATION: Forward primer

<400> SEQUENCE: 84
ttcccatcca actcagtaac cat 23

<210> SEQ ID NO 85
<211> LENGTH: 23
<212> TYPE: DNA
<213> ORGANISM: Artificial Sequence
<220> FEATURE:
<223> OTHER INFORMATION: Forward primer

<400> SEQUENCE: 85
ccagcgtggt acaacagtaa atc 23

<210> SEQ ID NO 86
<211> LENGTH: 23
<212> TYPE: DNA
<213> ORGANISM: Artificial Sequence
<220> FEATURE:
<223> OTHER INFORMATION: Forward primer

<400> SEQUENCE: 86
ccagcgtggt acaacagtaa atc 23

<210> SEQ ID NO 87
<211> LENGTH: 21
<212> TYPE: DNA
<213> ORGANISM: Artificial Sequence
<220> FEATURE:
<223> OTHER INFORMATION: Forward primer

<400> SEQUENCE: 87
cggaaggaat ccatccaact t 21

<210> SEQ ID NO 88
<211> LENGTH: 21
<212> TYPE: DNA
<213> ORGANISM: Artificial Sequence
<220> FEATURE:
<223> OTHER INFORMATION: Forward primer

<400> SEQUENCE: 88
cggaaggaat ccatccaact t 21

<210> SEQ ID NO 89
<211> LENGTH: 20
<212> TYPE: DNA

<213> ORGANISM: Artificial Sequence
<220> FEATURE:
<223> OTHER INFORMATION: Reverse primer

<400> SEQUENCE: 89
ctcggatggt actcacacaa 20

<210> SEQ ID NO 90
<211> LENGTH: 20
<212> TYPE: DNA
<213> ORGANISM: Artificial Sequence
<220> FEATURE:
<223> OTHER INFORMATION: Reverse primer

<400> SEQUENCE: 90
ctcggatggt actcacacaa 20

<210> SEQ ID NO 91
<211> LENGTH: 20
<212> TYPE: DNA
<213> ORGANISM: Artificial Sequence
<220> FEATURE:
<223> OTHER INFORMATION: Reverse primer

<400> SEQUENCE: 91
ttccgctgca tcttcaagag 20

<210> SEQ ID NO 92
<211> LENGTH: 20
<212> TYPE: DNA
<213> ORGANISM: Artificial Sequence
<220> FEATURE:
<223> OTHER INFORMATION: Reverse primer

<400> SEQUENCE: 92
ttccgctgca tcttcaagag 20

<210> SEQ ID NO 93
<211> LENGTH: 20
<212> TYPE: DNA
<213> ORGANISM: Artificial Sequence
<220> FEATURE:
<223> OTHER INFORMATION: Reverse primer

<400> SEQUENCE: 93
ccgttccttg gtcctggttc 20

<210> SEQ ID NO 94
<211> LENGTH: 20
<212> TYPE: DNA
<213> ORGANISM: Artificial Sequence
<220> FEATURE:
<223> OTHER INFORMATION: Reverse primer

<400> SEQUENCE: 94
ccgttccttg gtcctggttc 20

<210> SEQ ID NO 95
<211> LENGTH: 20
<212> TYPE: DNA
<213> ORGANISM: Artificial Sequence
<220> FEATURE:
<223> OTHER INFORMATION: Reverse primer

<400> SEQUENCE: 95
cagtccaatc gatgatccgc 20

<210> SEQ ID NO 96
<211> LENGTH: 20
<212> TYPE: DNA
<213> ORGANISM: Artificial Sequence
<220> FEATURE:
<223> OTHER INFORMATION: Reverse primer

<400> SEQUENCE: 96
cagtccaatc gatgatccgc 20

<210> SEQ ID NO 97
<211> LENGTH: 20
<212> TYPE: DNA
<213> ORGANISM: Artificial Sequence
<220> FEATURE:
<223> OTHER INFORMATION: Forward primer

<400> SEQUENCE: 97
agcccgtcca agaggaagtt 20

<210> SEQ ID NO 98
<211> LENGTH: 21
<212> TYPE: DNA
<213> ORGANISM: Artificial Sequence
<220> FEATURE:
<223> OTHER INFORMATION: Forward primer

<400> SEQUENCE: 98
ctgcggcttc atgttctgta t 21

<210> SEQ ID NO 99
<211> LENGTH: 19
<212> TYPE: DNA
<213> ORGANISM: Artificial Sequence
<220> FEATURE:
<223> OTHER INFORMATION: Forward primer

<400> SEQUENCE: 99
accgccgtct acgatgcca 19

<210> SEQ ID NO 100
<211> LENGTH: 21
<212> TYPE: DNA
<213> ORGANISM: Artificial Sequence
<220> FEATURE:
<223> OTHER INFORMATION: Forward primer

<400> SEQUENCE: 100
caaaccgctc aatgtcagtg g 21

<210> SEQ ID NO 101
<211> LENGTH: 19
<212> TYPE: DNA
<213> ORGANISM: Artificial Sequence
<220> FEATURE:
<223> OTHER INFORMATION: Forward primer

<400> SEQUENCE: 101
tatcatgcca agcgtcgcc 19

<210> SEQ ID NO 102
<211> LENGTH: 20
<212> TYPE: DNA
<213> ORGANISM: Artificial Sequence
<220> FEATURE:

<223> OTHER INFORMATION: Forward primer

<400> SEQUENCE: 102
cctgatgcgt tcgagggtca 20

<210> SEQ ID NO 103
<211> LENGTH: 21
<212> TYPE: DNA
<213> ORGANISM: Artificial Sequence
<220> FEATURE:
<223> OTHER INFORMATION: Forward primer

<400> SEQUENCE: 103
cgaacttcca cctgaccacg c 21

<210> SEQ ID NO 104
<211> LENGTH: 20
<212> TYPE: DNA
<213> ORGANISM: Artificial Sequence
<220> FEATURE:
<223> OTHER INFORMATION: Forward primer

<400> SEQUENCE: 104
tccaacttcc acgttgaagc 20

<210> SEQ ID NO 105
<211> LENGTH: 22
<212> TYPE: DNA
<213> ORGANISM: Artificial Sequence
<220> FEATURE:
<223> OTHER INFORMATION: Forward primer

<400> SEQUENCE: 105
cgtgagatcg agttcaacaa ca 22

<210> SEQ ID NO 106
<211> LENGTH: 23
<212> TYPE: DNA
<213> ORGANISM: Artificial Sequence
<220> FEATURE:
<223> OTHER INFORMATION: Forward primer

<400> SEQUENCE: 106
agcactctga ttgacaaata cga 23

<210> SEQ ID NO 107
<211> LENGTH: 20
<212> TYPE: DNA
<213> ORGANISM: Artificial Sequence
<220> FEATURE:
<223> OTHER INFORMATION: Reverse primer

<400> SEQUENCE: 107
ctcggatggt actcacacaa 20

<210> SEQ ID NO 108
<211> LENGTH: 21
<212> TYPE: DNA
<213> ORGANISM: Artificial Sequence
<220> FEATURE:
<223> OTHER INFORMATION: Reverse primer

<400> SEQUENCE: 108
cttgctacat gccacattgt g 21

<210> SEQ ID NO 109
<211> LENGTH: 20
<212> TYPE: DNA
<213> ORGANISM: Artificial Sequence
<220> FEATURE:
<223> OTHER INFORMATION: Reverse primer

<400> SEQUENCE: 109
atggtggtct gctggttctt 20

<210> SEQ ID NO 110
<211> LENGTH: 22
<212> TYPE: DNA
<213> ORGANISM: Artificial Sequence
<220> FEATURE:
<223> OTHER INFORMATION: Reverse primer

<400> SEQUENCE: 110
gtactcgaac gaatcaagtc aa 22

<210> SEQ ID NO 111
<211> LENGTH: 21
<212> TYPE: DNA
<213> ORGANISM: Artificial Sequence
<220> FEATURE:
<223> OTHER INFORMATION: Reverse primer

<400> SEQUENCE: 111
cgcatcccaa tcgatattct c 21

<210> SEQ ID NO 112
<211> LENGTH: 20
<212> TYPE: DNA
<213> ORGANISM: Artificial Sequence
<220> FEATURE:
<223> OTHER INFORMATION: Reverse primer

<400> SEQUENCE: 112
cgggtgatat acagatcacg 20

<210> SEQ ID NO 113
<211> LENGTH: 20
<212> TYPE: DNA
<213> ORGANISM: Artificial Sequence
<220> FEATURE:
<223> OTHER INFORMATION: Reverse primer

<400> SEQUENCE: 113
gggctgaagg actggaactt 20

<210> SEQ ID NO 114
<211> LENGTH: 20
<212> TYPE: DNA
<213> ORGANISM: Artificial Sequence
<220> FEATURE:
<223> OTHER INFORMATION: Reverse primer

<400> SEQUENCE: 114
cgcttgcgat agctgtgcat 20

<210> SEQ ID NO 115
<211> LENGTH: 21
<212> TYPE: DNA
<213> ORGANISM: Artificial Sequence
<220> FEATURE:
<223> OTHER INFORMATION: Reverse primer

<400> SEQUENCE: 115
gtgcttgccg gagaacttct t 21

<210> SEQ ID NO 116
<211> LENGTH: 20
<212> TYPE: DNA
<213> ORGANISM: Artificial Sequence
<220> FEATURE:
<223> OTHER INFORMATION: Reverse primer

<400> SEQUENCE: 116
agttcaccgg cgtcatcgtc 20

<210> SEQ ID NO 117
<211> LENGTH: 23
<212> TYPE: DNA
<213> ORGANISM: Artificial Sequence
<220> FEATURE:
<223> OTHER INFORMATION: T7 RNA polymerase promoter sequence

<400> SEQUENCE: 117
taatacgact cactataggg aga 23

<210> SEQ ID NO 118
<211> LENGTH: 19
<212> TYPE: DNA
<213> ORGANISM: Artificial Sequence
<220> FEATURE:
<223> OTHER INFORMATION: Forward primer

<400> SEQUENCE: 118
tgctgcgcct cgtgttctt 19

<210> SEQ ID NO 119
<211> LENGTH: 22
<212> TYPE: DNA
<213> ORGANISM: Artificial Sequence
<220> FEATURE:
<223> OTHER INFORMATION: Reverse primer

<400> SEQUENCE: 119
cggagatgta gacgaagacc tt 22

<210> SEQ ID NO 120
<211> LENGTH: 21
<212> TYPE: DNA
<213> ORGANISM: Artificial Sequence
<220> FEATURE:
<223> OTHER INFORMATION: Forward primer

<400> SEQUENCE: 120
gtagcgattg ttgttctagc g 21

<210> SEQ ID NO 121
<211> LENGTH: 22
<212> TYPE: DNA
<213> ORGANISM: Artificial Sequence
<220> FEATURE:
<223> OTHER INFORMATION: Reverse primer

<400> SEQUENCE: 121
ggcgtaagta acttgcacac gg 22

<210> SEQ ID NO 122
<211> LENGTH: 20

<212> TYPE: DNA
<213> ORGANISM: Artificial Sequence
<220> FEATURE:
<223> OTHER INFORMATION: Forward primer

<400> SEQUENCE: 122
ccctgtgccg acccaaacga 20

<210> SEQ ID NO 123
<211> LENGTH: 21
<212> TYPE: DNA
<213> ORGANISM: Artificial Sequence
<220> FEATURE:
<223> OTHER INFORMATION: Reverse primer

<400> SEQUENCE: 123
cggtgtggtc gtagtaatac a 21

<210> SEQ ID NO 124
<211> LENGTH: 23
<212> TYPE: DNA
<213> ORGANISM: Artificial Sequence
<220> FEATURE:
<223> OTHER INFORMATION: Forward primer

<400> SEQUENCE: 124
atgcagcttc caatatgtgc tat 23

<210> SEQ ID NO 125
<211> LENGTH: 19
<212> TYPE: DNA
<213> ORGANISM: Artificial Sequence
<220> FEATURE:
<223> OTHER INFORMATION: Reverse primer

<400> SEQUENCE: 125
gcggcttcgg cgtaggctt 19

<210> SEQ ID NO 126
<211> LENGTH: 20
<212> TYPE: DNA
<213> ORGANISM: Artificial Sequence
<220> FEATURE:
<223> OTHER INFORMATION: Forward primer

<400> SEQUENCE: 126
tacagctctg cgtgcatctg 20

<210> SEQ ID NO 127
<211> LENGTH: 20
<212> TYPE: DNA
<213> ORGANISM: Artificial Sequence
<220> FEATURE:
<223> OTHER INFORMATION: Reverse primer

<400> SEQUENCE: 127
ccacaatcgg tcttcgtcag 20

<210> SEQ ID NO 128
<211> LENGTH: 20
<212> TYPE: DNA
<213> ORGANISM: Artificial Sequence
<220> FEATURE:
<223> OTHER INFORMATION: Forward primer

<400> SEQUENCE: 128
ggcaagggct tctacaacgt 20

<210> SEQ ID NO 129
<211> LENGTH: 20
<212> TYPE: DNA
<213> ORGANISM: Artificial Sequence
<220> FEATURE:
<223> OTHER INFORMATION: Reverse primer

<400> SEQUENCE: 129
ccgttcaaag tatgctccac 20

<210> SEQ ID NO 130
<211> LENGTH: 20
<212> TYPE: DNA
<213> ORGANISM: Artificial Sequence
<220> FEATURE:
<223> OTHER INFORMATION: Forward primer

<400> SEQUENCE: 130
tgaagaaaca actgctgtgg 20

<210> SEQ ID NO 131
<211> LENGTH: 19
<212> TYPE: DNA
<213> ORGANISM: Artificial Sequence
<220> FEATURE:
<223> OTHER INFORMATION: Reverse primer

<400> SEQUENCE: 131
ccatctgctg ggtactgac 19

<210> SEQ ID NO 132
<211> LENGTH: 22
<212> TYPE: DNA
<213> ORGANISM: Artificial Sequence
<220> FEATURE:
<223> OTHER INFORMATION: Forward primer

<400> SEQUENCE: 132
gcccatgtga acttcccttg cc 22

<210> SEQ ID NO 133
<211> LENGTH: 20
<212> TYPE: DNA
<213> ORGANISM: Artificial Sequence
<220> FEATURE:
<223> OTHER INFORMATION: Reverse primer

<400> SEQUENCE: 133
gatacctcgc cctgttgaac 20

<210> SEQ ID NO 134
<211> LENGTH: 20
<212> TYPE: DNA
<213> ORGANISM: Artificial Sequence
<220> FEATURE:
<223> OTHER INFORMATION: Forward primer

<400> SEQUENCE: 134
tccaaccagg agtcgagtga 20

<210> SEQ ID NO 135
<211> LENGTH: 19
<212> TYPE: DNA
<213> ORGANISM: Artificial Sequence
<220> FEATURE:
<223> OTHER INFORMATION: Reverse primer

<400> SEQUENCE: 135
cgccaattcc accgagttg 19

<210> SEQ ID NO 136
<211> LENGTH: 20
<212> TYPE: DNA
<213> ORGANISM: Artificial Sequence
<220> FEATURE:
<223> OTHER INFORMATION: Forward primer

<400> SEQUENCE: 136
tcctacggcg aagctggttc 20

<210> SEQ ID NO 137
<211> LENGTH: 20
<212> TYPE: DNA
<213> ORGANISM: Artificial Sequence
<220> FEATURE:
<223> OTHER INFORMATION: Reverse primer

<400> SEQUENCE: 137
gactctcgtt tgtctgcttc 20

<210> SEQ ID NO 138
<211> LENGTH: 20
<212> TYPE: DNA
<213> ORGANISM: Artificial Sequence
<220> FEATURE:
<223> OTHER INFORMATION: Forward primer

<400> SEQUENCE: 138
tgagggaaca caaccgacta 20

<210> SEQ ID NO 139
<211> LENGTH: 20
<212> TYPE: DNA
<213> ORGANISM: Artificial Sequence
<220> FEATURE:
<223> OTHER INFORMATION: Reverse primer

<400> SEQUENCE: 139
taaacctgtg ccaagagtgc 20

<210> SEQ ID NO 140
<211> LENGTH: 20
<212> TYPE: DNA
<213> ORGANISM: Artificial Sequence
<220> FEATURE:
<223> OTHER INFORMATION: Forward primer

<400> SEQUENCE: 140
tgagggaaca caaccgacta 20

<210> SEQ ID NO 141
<211> LENGTH: 20
<212> TYPE: DNA
<213> ORGANISM: Artificial Sequence
<220> FEATURE:
<223> OTHER INFORMATION: Reverse primer

<400> SEQUENCE: 141
taaactcgcg ccagaagagc 20

<210> SEQ ID NO 142
<211> LENGTH: 20
<212> TYPE: DNA
<213> ORGANISM: Artificial Sequence
<220> FEATURE:
<223> OTHER INFORMATION: Forward primer

<400> SEQUENCE: 142
ccacactggt ctgacgacat 20

<210> SEQ ID NO 143
<211> LENGTH: 21
<212> TYPE: DNA
<213> ORGANISM: Artificial Sequence
<220> FEATURE:
<223> OTHER INFORMATION: Reverse primer

<400> SEQUENCE: 143
cgcctacgta aagatcgacg t 21

<210> SEQ ID NO 144
<211> LENGTH: 23
<212> TYPE: DNA
<213> ORGANISM: Artificial Sequence
<220> FEATURE:
<223> OTHER INFORMATION: Forward primer

<400> SEQUENCE: 144
atgaagttgg caatcatttg tgt 23

<210> SEQ ID NO 145
<211> LENGTH: 20
<212> TYPE: DNA
<213> ORGANISM: Artificial Sequence
<220> FEATURE:
<223> OTHER INFORMATION: Reverse primer

<400> SEQUENCE: 145
gctccaggac aatcgcacag 20

<210> SEQ ID NO 146
<211> LENGTH: 19
<212> TYPE: DNA
<213> ORGANISM: Artificial Sequence
<220> FEATURE:
<223> OTHER INFORMATION: Forward primer

<400> SEQUENCE: 146
gccaaagccg atagccatc 19

<210> SEQ ID NO 147
<211> LENGTH: 20
<212> TYPE: DNA
<213> ORGANISM: Artificial Sequence
<220> FEATURE:
<223> OTHER INFORMATION: Reverse primer

<400> SEQUENCE: 147
ctaggcatgt tgagagcacc 20

<210> SEQ ID NO 148
<211> LENGTH: 20
<212> TYPE: DNA
<213> ORGANISM: Artificial Sequence
<220> FEATURE:
<223> OTHER INFORMATION: Forward primer

<400> SEQUENCE: 148
tgtgatggcg atgacgactg 20

<210> SEQ ID NO 149
<211> LENGTH: 21
<212> TYPE: DNA
<213> ORGANISM: Artificial Sequence
<220> FEATURE:
<223> OTHER INFORMATION: Reverse primer

<400> SEQUENCE: 149
ctcatcactt ccatccttgc a 21

<210> SEQ ID NO 150
<211> LENGTH: 19
<212> TYPE: DNA
<213> ORGANISM: Artificial Sequence
<220> FEATURE:
<223> OTHER INFORMATION: Forward primer

<400> SEQUENCE: 150
tgtggaaatc gtcggtggt 19

<210> SEQ ID NO 151
<211> LENGTH: 19
<212> TYPE: DNA
<213> ORGANISM: Artificial Sequence
<220> FEATURE:
<223> OTHER INFORMATION: Reverse primer

<400> SEQUENCE: 151
tgtaggcgaa ggtgtcctc 19

<210> SEQ ID NO 152
<211> LENGTH: 20
<212> TYPE: DNA
<213> ORGANISM: Artificial Sequence
<220> FEATURE:
<223> OTHER INFORMATION: Forward primer

<400> SEQUENCE: 152
ctcccggttg gaatcgaaag 20

<210> SEQ ID NO 153
<211> LENGTH: 21
<212> TYPE: DNA
<213> ORGANISM: Artificial Sequence
<220> FEATURE:
<223> OTHER INFORMATION: Reverse primer

<400> SEQUENCE: 153
gtccgtagtc cagttcattg g 21

<210> SEQ ID NO 154
<211> LENGTH: 20
<212> TYPE: DNA
<213> ORGANISM: Artificial Sequence
<220> FEATURE:
<223> OTHER INFORMATION: Forward primer

<400> SEQUENCE: 154
gcaagaagtg gcgacaagac 20

<210> SEQ ID NO 155

<211> LENGTH: 20
<212> TYPE: DNA
<213> ORGANISM: Artificial Sequence
<220> FEATURE:
<223> OTHER INFORMATION: Reverse primer

<400> SEQUENCE: 155
cgtccaccca gataggtgaa 20

<210> SEQ ID NO 156
<211> LENGTH: 19
<212> TYPE: DNA
<213> ORGANISM: Artificial Sequence
<220> FEATURE:
<223> OTHER INFORMATION: Forward primer

<400> SEQUENCE: 156
tcagtgccga ccagcaagt 19

<210> SEQ ID NO 157
<211> LENGTH: 23
<212> TYPE: DNA
<213> ORGANISM: Artificial Sequence
<220> FEATURE:
<223> OTHER INFORMATION: Reverse primer

<400> SEQUENCE: 157
ctgagattgt cttgttggac ttc 23

<210> SEQ ID NO 158
<211> LENGTH: 19
<212> TYPE: DNA
<213> ORGANISM: Artificial Sequence
<220> FEATURE:
<223> OTHER INFORMATION: Forward primer

<400> SEQUENCE: 158
cgctcgcaac gtgcattgg 19

<210> SEQ ID NO 159
<211> LENGTH: 20
<212> TYPE: DNA
<213> ORGANISM: Artificial Sequence
<220> FEATURE:
<223> OTHER INFORMATION: Reverse primer160

<400> SEQUENCE: 159
ggacaccacg cacgctgcaa 20

<210> SEQ ID NO 160
<211> LENGTH: 20
<212> TYPE: DNA
<213> ORGANISM: Artificial Sequence
<220> FEATURE:
<223> OTHER INFORMATION: Forward primer

<400> SEQUENCE: 160
gagcccattc agaacctcct 20

<210> SEQ ID NO 161
<211> LENGTH: 20
<212> TYPE: DNA
<213> ORGANISM: Artificial Sequence
<220> FEATURE:
<223> OTHER INFORMATION: Reverse primer

<400> SEQUENCE: 161
agcgtaactc cgttgacgta 20

<210> SEQ ID NO 162
<211> LENGTH: 20
<212> TYPE: DNA
<213> ORGANISM: Artificial Sequence
<220> FEATURE:
<223> OTHER INFORMATION: Forward primer

<400> SEQUENCE: 162
atcgagggat tgatggaagg 20

<210> SEQ ID NO 163
<211> LENGTH: 20
<212> TYPE: DNA
<213> ORGANISM: Artificial Sequence
<220> FEATURE:
<223> OTHER INFORMATION: Reverse primer

<400> SEQUENCE: 163
ccgtccgagt agtggatcgc 20

<210> SEQ ID NO 164
<211> LENGTH: 20
<212> TYPE: DNA
<213> ORGANISM: Artificial Sequence
<220> FEATURE:
<223> OTHER INFORMATION: Forward primer

<400> SEQUENCE: 164
gtcctccatc tctttggtga 20

<210> SEQ ID NO 165
<211> LENGTH: 20
<212> TYPE: DNA
<213> ORGANISM: Artificial Sequence
<220> FEATURE:
<223> OTHER INFORMATION: Reverse primer

<400> SEQUENCE: 165
tcaccaacca gctcttctcg 20

<210> SEQ ID NO 166
<211> LENGTH: 20
<212> TYPE: DNA
<213> ORGANISM: Artificial Sequence
<220> FEATURE:
<223> OTHER INFORMATION: Forward primer

<400> SEQUENCE: 166
cagcctacat cgttgaccta 20

<210> SEQ ID NO 167
<211> LENGTH: 22
<212> TYPE: DNA
<213> ORGANISM: Artificial Sequence
<220> FEATURE:
<223> OTHER INFORMATION: Reverse primer

<400> SEQUENCE: 167
tgtcgaagca caaccgatgg tt 22

<210> SEQ ID NO 168
<211> LENGTH: 21
<212> TYPE: DNA

<213> ORGANISM: Artificial Sequence
<220> FEATURE:
<223> OTHER INFORMATION: Forward primer

<400> SEQUENCE: 168
cagcgggatc agaaccagga t 21

<210> SEQ ID NO 169
<211> LENGTH: 21
<212> TYPE: DNA
<213> ORGANISM: Artificial Sequence
<220> FEATURE:
<223> OTHER INFORMATION: Reverse primer

<400> SEQUENCE: 169
cataagatcc gtcagaccgt c 21

<210> SEQ ID NO 170
<211> LENGTH: 20
<212> TYPE: DNA
<213> ORGANISM: Artificial Sequence
<220> FEATURE:
<223> OTHER INFORMATION: Forward primer

<400> SEQUENCE: 170
gccctcgact caggcatttg 20

<210> SEQ ID NO 171
<211> LENGTH: 20
<212> TYPE: DNA
<213> ORGANISM: Artificial Sequence
<220> FEATURE:
<223> OTHER INFORMATION: Reverse primer

<400> SEQUENCE: 171
tgcgtgctca agcgacactc 20

<210> SEQ ID NO 172
<211> LENGTH: 22
<212> TYPE: DNA
<213> ORGANISM: Artificial Sequence
<220> FEATURE:
<223> OTHER INFORMATION: Forward primer

<400> SEQUENCE: 172
caaccagttg atggcaggat ac 22

<210> SEQ ID NO 173
<211> LENGTH: 20
<212> TYPE: DNA
<213> ORGANISM: Artificial Sequence
<220> FEATURE:
<223> OTHER INFORMATION: Reverse primer

<400> SEQUENCE: 173
ccgttgtgct tcacataacc 20

<210> SEQ ID NO 174
<211> LENGTH: 20
<212> TYPE: DNA
<213> ORGANISM: Artificial Sequence
<220> FEATURE:
<223> OTHER INFORMATION: Forward primer

<400> SEQUENCE: 174
gccgacaggg accgatgatg 20

<210> SEQ ID NO 175
<211> LENGTH: 23
<212> TYPE: DNA
<213> ORGANISM: Artificial Sequence
<220> FEATURE:
<223> OTHER INFORMATION: Reverse primer

<400> SEQUENCE: 175
gccgaaatgt tgatcttgtg tac 23

<210> SEQ ID NO 176
<211> LENGTH: 23
<212> TYPE: DNA
<213> ORGANISM: Artificial Sequence
<220> FEATURE:
<223> OTHER INFORMATION: Forward primer

<400> SEQUENCE: 176
ttagcaatag tttctcactg cca 23

<210> SEQ ID NO 177
<211> LENGTH: 19
<212> TYPE: DNA
<213> ORGANISM: Artificial Sequence
<220> FEATURE:
<223> OTHER INFORMATION: Reverse primer

<400> SEQUENCE: 177
gcctgtgggc ttcgattgg 19

<210> SEQ ID NO 178
<211> LENGTH: 20
<212> TYPE: DNA
<213> ORGANISM: Artificial Sequence
<220> FEATURE:
<223> OTHER INFORMATION: Forward primer

<400> SEQUENCE: 178
gtgttggtgc cgaagaagag 20

<210> SEQ ID NO 179
<211> LENGTH: 23
<212> TYPE: DNA
<213> ORGANISM: Artificial Sequence
<220> FEATURE:
<223> OTHER INFORMATION: Reverse primer

<400> SEQUENCE: 179
tagcacttca actcggatga ctt 23

<210> SEQ ID NO 180
<211> LENGTH: 20
<212> TYPE: DNA
<213> ORGANISM: Artificial Sequence
<220> FEATURE:
<223> OTHER INFORMATION: Forward primer

<400> SEQUENCE: 180
tacagctctg cgtgcatctg 20

<210> SEQ ID NO 181
<211> LENGTH: 20
<212> TYPE: DNA
<213> ORGANISM: Artificial Sequence
<220> FEATURE:

<223> OTHER INFORMATION: Reverse primer

<400> SEQUENCE: 181
ccacaatcgg tcttcgtcag 20

<210> SEQ ID NO 182
<211> LENGTH: 21
<212> TYPE: DNA
<213> ORGANISM: Artificial Sequence
<220> FEATURE:
<223> OTHER INFORMATION: Forward primer

<400> SEQUENCE: 182
gtcaataacg tgggtagcaa t 21

<210> SEQ ID NO 183
<211> LENGTH: 2198
<212> TYPE: PRT
<213> ORGANISM: Aedes aegypti

<400> SEQUENCE: 183

Met Asn Arg Leu Ser Phe Leu Phe Ser Thr Leu Phe Val Ile Ala Ala
1 5 10 15

Ile Gln Ile Lys Ile Glu Thr Asn Ala Gln Val Val Gln Pro Ala His
20 25 30

Thr Leu Pro Ser Asn Glu Arg Pro Thr Ser Gly Pro Thr Lys Pro Ala
35 40 45

Lys Asn Gly Ser Pro Pro Leu Lys Ile Pro Thr Ala Lys Pro Ser Leu
50 55 60

Gly Asp Ala Ile Lys Ser Leu Asn Asp Arg Ile Leu Asn Asp Thr Asp
65 70 75 80

Thr Pro Gln Asp Met Leu Gln His Val Arg Asp Ser Ser Phe Arg Asn
85 90 95

Val Phe His Glu Ala Ile Asp Ala Lys Ile Val Asn Pro Asp Leu Ile
100 105 110

Arg Thr Leu Ala Ser Val Gly Lys Pro Leu Val Asn Asp Tyr Thr Arg
115 120 125

Asp Thr Leu Leu Ile Glu Ser Ile Arg Glu Asp Ile Asn Phe Thr Phe
130 135 140

Gly Pro Asn Val Thr Trp Trp Glu Thr Leu Glu Leu Lys Lys Asn Glu
145 150 155 160

Gln His Val Ile Val Gly Leu Ser Asn Ser Ser Ile Val Ile Leu Phe
165 170 175

Glu His Phe Gly Glu Phe Lys Leu Gln Gln Glu Val Leu Met Glu Thr
180 185 190

Ala Pro Thr Ala Phe Glu Ile Ile Thr Val Trp Asp Ser Val Ala Glu
195 200 205

Thr Pro Val Ser Cys Leu Ile Val Ala Thr Glu Leu Gln Leu Ile Trp
210 215 220

Tyr Thr Met Arg Pro Asp Thr Asn Phe Val Leu Thr Glu Glu Trp Arg
225 230 235 240

Trp Pro Leu Tyr Lys Met Thr Thr Leu Ile Arg Gly Phe Lys Tyr Arg
245 250 255

Asp Ile His Met Ile Leu Leu Val Gly Thr His Pro Asn Lys Gln Lys
260 265 270

Ser Val Ser Ala Thr Leu Tyr Glu Phe Asn Phe Glu Lys Gln Gln Phe
275 280 285

-continued

```
Trp Leu Leu Gln Arg Leu Asp Leu Ala His Ala Cys Ser Thr Val Gly
    290                 295                 300

Leu Val Arg Val Gly Arg Glu Phe Leu Val Ala Phe Pro Gln His Asp
305                 310                 315                 320

Lys Ala Met Ile Tyr Thr Leu Glu Ala Gly Glu Lys Tyr Arg Gly Arg
                325                 330                 335

Phe Asn Leu Val Ala Asn Tyr Thr Ser Glu Leu Val Gln Thr Val Gly
            340                 345                 350

Ala Phe Gln Val Gly Arg Tyr Ala Tyr Ile Ala Ile Gly Gly Arg Ser
        355                 360                 365

Pro Gln Ile Val Arg Tyr Ala Asn Gly Val Phe Val Ser Gln Arg Ile
    370                 375                 380

Pro Met Glu Ala Met Glu Thr Val Glu Ala Tyr Phe Glu Ile Pro Thr
385                 390                 395                 400

Pro Thr Tyr Arg Asp Asp Phe Ile Leu Leu Val Gln His Lys Met Leu
                405                 410                 415

Phe Ser Thr His Asp Leu Gln Arg Leu Asp Ile Phe Val Trp Asn Gly
            420                 425                 430

Glu Ser Phe Asp Leu Arg Ser Asn Ile Pro Cys Tyr Val Glu Asp Glu
        435                 440                 445

Leu Met Asp Asn Glu Val Ser Cys Met Leu Asp Leu Tyr Arg Pro Thr
    450                 455                 460

Gly Ile Val Gly Ser Ala Ile Ile Leu Arg Gly Lys Gln Val Ser Met
465                 470                 475                 480

Ile Val Pro Arg Tyr Gln Thr His Ser Thr Leu Phe Asn Leu Arg Ile
                485                 490                 495

Glu Leu Leu Ser Ala Glu His Pro Ile Arg Gln Lys Thr Gln Glu Met
            500                 505                 510

Arg Asp Thr Ile Asp Ala Phe Thr Lys Ile Phe His Tyr Gln Asp Glu
        515                 520                 525

Val Ile Ser Glu Ala Tyr Ala Ala Ile Ala Glu Ala Glu Gln Thr Tyr
    530                 535                 540

Asp Val Pro Leu Leu Thr Leu Gln Asn Cys Ser Leu Gly Thr Val Gln
545                 550                 555                 560

Ala Asp Leu Val Val Gln Asp Ser Asp Phe Arg Trp Pro Ser Gly Lys
                565                 570                 575

Ile Met Val Gly Asn Arg Thr Trp Ser His Arg Asp Thr Ala Val Asp
            580                 585                 590

Val Pro Ala Ile Ala Arg Glu Leu Glu Ala Glu Met Ala Leu Leu Ser
        595                 600                 605

Glu Leu Glu Gln Gln Leu Asn Tyr Thr Val Arg Arg His Asn Asp Ser
    610                 615                 620

Phe Ser Leu Asp Leu Asp Gln Pro Leu Tyr Val Gln Gly Arg Val Glu
625                 630                 635                 640

Val Gly Gly Ala Leu Val Thr Asp Asp Leu Tyr Val Arg Gln Leu Glu
                645                 650                 655

Glu Asp Pro Pro Leu Leu Arg Val Val Arg Gln Thr Gly Asp Asp Gly
            660                 665                 670

Met Gln Glu Leu Arg Val Lys Asp Leu Lys Val Arg His Leu Asn Phe
        675                 680                 685

Glu Thr Val Asn Gly Ile Leu Ala Ser Asp Leu Val Tyr Asn Thr Gly
    690                 695                 700
```

```
Glu Lys Ile Glu Leu Ala Asn Ala Leu Val Val Asn Ser Val Leu Val
705                 710                 715                 720

Ala Gln Asn Val Ile Leu Pro Lys Gly Gly Thr Val Asn Gly Val Asp
                725                 730                 735

Leu Ser Glu Ser Thr Val Tyr Phe Asn Cys Lys Asn Arg Arg Trp Asp
            740                 745                 750

Asn Leu Lys Phe Asp Ser Val Glu Val Leu Glu Asn Val Val Ala His
        755                 760                 765

Glu Thr Ile Asn Gly Val Lys Leu Asp Leu Ala Glu Leu Asp Ala Arg
    770                 775                 780

Phe Arg Gln Ala Ser Glu Asp Met Ser Asp Val Leu Val Thr Glu Asn
785                 790                 795                 800

Leu Gln Leu Asp Gly Ser Leu Tyr Val His Ser Ile Asn Gly Val Pro
                805                 810                 815

Trp Ser Asp Ile Ile His Arg Ile Val Leu Lys Asn Arg Pro Asn Arg
            820                 825                 830

Leu Ala Asp Leu Lys Ile Asn Gly Ser Leu Ile Leu Gln Asn Asp Asn
        835                 840                 845

Val Thr Val Tyr His Leu Asn Gly Leu Ala Phe Pro Met Asp Tyr Leu
    850                 855                 860

Leu Ser Ser Ser Pro Met Glu Ser Ile Val Thr Gly Tyr Lys Lys Phe
865                 870                 875                 880

Val Asn Ile Thr Asn Ile Glu Ala Met Asp Val Glu Arg Thr Ile Asn
                885                 890                 895

Gly Val Asp Leu Gln Asp Ile Ile Thr Leu His Asp Asp Gln His Ile
            900                 905                 910

Pro Gly Asp Val Thr Ile Gly Glu Leu His Val Thr Glu Arg Leu Glu
        915                 920                 925

Val Lys Gly Ala Ile Arg Gly Lys His Leu Asp Glu Phe Leu Asp Asn
    930                 935                 940

Pro Thr Leu Leu Gln Thr Thr Ser Ile Lys Ala Ala Cys His Phe Lys
945                 950                 955                 960

Gln Leu Phe Val Asp Gly Pro Val Ile Val Glu Gly Asn Leu Asn Gly
                965                 970                 975

Met Asp Val Asp Ala Val Leu Ser Asp Val Val Tyr Asp Thr Glu His
            980                 985                 990

Thr Val Thr Ile Glu Ala Ser Lys  Arg Ile Ala Ser Ala  Glu Phe Arg
        995                 1000                1005

Asp Asn  Val Thr Ile Ser Ser  Asn Met Val Asn Glu  Phe Lys Leu
    1010                1015                1020

Asp Gln  Phe Val Thr Arg Ser  Thr Glu Gln Glu Leu  Asn Val Arg
    1025                1030                1035

Glu Ile  Asn Gly Asn Val Phe  Ile Arg Glu Leu Gln  Leu Asp Gly
    1040                1045                1050

Leu Phe  Asp Gly Leu Asn Ala  Thr Ala Leu Asp Val  Ser Ala Val
    1055                1060                1065

Lys Leu  Phe Gly Asp Gln Tyr  Thr Glu Ala Ser Leu  Ile Phe Lys
    1070                1075                1080

Asn Arg  Glu Asn Ala Leu Tyr  Pro Asp Val Glu Ala  Asn Glu Leu
    1085                1090                1095

Lys Ile  Met Lys Thr Leu Asn  Ser Lys Ala Arg Ser  Glu Tyr Lys
    1100                1105                1110

Asp Thr  Asp Gln Glu Glu Leu  Val Leu Thr Gly Gln  Ile Ser Leu
```

```
    1115                1120                1125

Asn His  Leu His Val Asp His  Leu Leu Leu Lys Gly  Ser Ser Leu
    1130                1135                1140

Glu Gly  Pro Ser Lys Met Ile  Asn Leu Val His Leu  Pro Thr Phe
    1145                1150                1155

Asp Asn  Leu Arg Phe Ser Leu  Thr Arg Pro Gln Gln  Val Thr Ala
    1160                1165                1170

Pro Phe  Ile Val Asn Lys Leu  Val Val Gly Ser Gln  Ile Ala Ala
    1175                1180                1185

Ala Tyr  Val Asn Gly Arg Asp  Phe Arg Gly Leu Lys  Glu Ser Ile
    1190                1195                1200

Asp Arg  Leu Asp Asn Phe Lys  Asn His Leu Leu Gln  Gly Ser Ile
    1205                1210                1215

Pro Ile  Glu Asn Leu His Val  Gly Gly Asp Leu Gln  Val Asn Met
    1220                1225                1230

Leu Asn  Asp Val Asn Phe Asp  Ala Leu Val Lys Gln  Val Ile Trp
    1235                1240                1245

Leu Asn  Arg Pro Asn Arg Ile  Pro Gly Thr Ile Arg  Phe Leu Asp
    1250                1255                1260

Pro Leu  Met Ile Ile Gly Asn  Leu Thr Ala Arg Gly  Gln Val Asn
    1265                1270                1275

Asn Ala  Val Phe Gly Asp Phe  Leu Glu Asp Val Ile  Arg Lys Ser
    1280                1285                1290

Ala Gly  Val Ala Glu Phe His  Gly Ser Ile Thr Phe  Met Asn Gly
    1295                1300                1305

Leu Val  Val Glu Gly Asn Val  Asn Thr Glu Ser Ile  Asn Asn Ile
    1310                1315                1320

His Met  Ser Glu Leu Ala Leu  Arg Asn Asp Thr Ile  Tyr Leu Gln
    1325                1330                1335

Gly Asp  Val Glu Ile Leu Gly  Asp Leu Phe Val Glu  His Leu His
    1340                1345                1350

Val Glu  Asn His Leu Asn Gln  Glu Pro Ile Gln Asn  Leu Leu Asn
    1355                1360                1365

Ser Tyr  Ser Tyr Asp Asp Ser  Lys Asp Val His Thr  Val Lys Ser
    1370                1375                1380

Asp Met  Tyr Leu Tyr Gly Ala  Gln Ile Gly Ala Leu  His Ile Gly
    1385                1390                1395

Gly Met  Leu Asn Gln Ile Pro  Asn Val Asp Ala His  Leu Ala Ser
    1400                1405                1410

Val Ile  Arg Lys Asp Gln Asn  Tyr Asn Phe Thr Lys  Pro Leu Leu
    1415                1420                1425

Phe Lys  Asn Glu Val Phe Phe  Asp Gln Gly Phe Ser  Ala Thr Tyr
    1430                1435                1440

Leu Asn  Gln Ile Asp Ile Ser  Asn Ile Gln Gln Asp  Ile Val Arg
    1445                1450                1455

Ile Asn  Asp Pro Asn Pro Val  Glu Ile Glu Ala Glu  Val Ile Thr
    1460                1465                1470

Phe Ala  Glu Pro Ile Tyr Ala  Asp Gln Leu Thr Ile  Lys Gly Asp
    1475                1480                1485

Met Ile  Thr Thr Asn Leu Val  Gly Cys Asn Pro Asp  Ile Trp Thr
    1490                1495                1500

Ser Thr  Gly Ile Met Ile Asn  Arg Asp Ala Glu Ile  Tyr Ala Lys
    1505                1510                1515
```

```
Thr Phe  Phe Ser Pro Gly Ala  Phe Arg Thr Asn His  Leu Arg Val
    1520                 1525                 1530

Asp Tyr  Met Asn Gly Gln Pro  Met Asn Ser Leu Ile  Thr Leu Asn
    1535                 1540                 1545

Thr Asp  Gln Thr Ile Glu Thr  Thr Leu Leu Ile His  Glu Met Thr
    1550                 1555                 1560

Ile Thr  Gln Pro Met Asp Val  Gly Gly Tyr Val Asn  Gly Val Thr
    1565                 1570                 1575

Leu Pro  Tyr Glu Arg Lys Asn  Thr Leu Met Thr Tyr  Gly Asn Gln
    1580                 1585                 1590

Arg Val  Arg Leu Pro Thr Val  Phe His Thr Ile Arg  Val Leu Gln
    1595                 1600                 1605

Ser Leu  Thr Leu Pro Pro Ile  Leu Asn Ser Lys Pro  Phe Gly Pro
    1610                 1615                 1620

Pro Val  Ala Ile Gly Pro Glu  Met Ile Ile Glu Ser  Pro Ile Ser
    1625                 1630                 1635

Phe Arg  His Leu Ile Val Asp  Arg Leu Glu Thr Glu  Asp Met Ile
    1640                 1645                 1650

Ser Gly  Val Asp Phe Asn Gln  Trp Tyr Glu Asn Ser  Leu Trp Arg
    1655                 1660                 1665

Lys Gly  Arg Asp His Gln Thr  Ile Glu Ala Lys Ile  Ser Ala Arg
    1670                 1675                 1680

Asn Val  Arg Phe Asn Gly Asp  Val Glu Gly Asp Gly  Lys Ile Asn
    1685                 1690                 1695

Gly Val  Asp Ile Val Asp Val  Val Gln Arg Met Lys  Ala Ala Lys
    1700                 1705                 1710

Lys Asn  Val Glu Asp Gln Leu  Leu Asp Tyr Arg Ser  Glu Met Arg
    1715                 1720                 1725

Ser Phe  Cys Ser Asn Thr Lys  Gln Leu Val Asp Lys  Ser Gln Ser
    1730                 1735                 1740

Arg Met  Tyr Phe Phe Lys Tyr  Phe Val Gln Arg Gln  Val Ile Asn
    1745                 1750                 1755

Glu His  Leu Pro Ile Val Ser  Phe His Phe Phe Asp  His Leu Gly
    1760                 1765                 1770

Tyr Asn  Phe Leu Gly Val Asn  Met Gly Cys Glu Ser  His Phe Tyr
    1775                 1780                 1785

Gln Trp  Asp Pro Thr Gly Lys  Ala Phe Val Pro Ile  Phe Lys Tyr
    1790                 1795                 1800

Tyr Thr  Gly Val Val Gln Glu  Trp Asn His Val Val  Asn Gly Glu
    1805                 1810                 1815

Glu Ala  Ile Phe Leu Val Thr  Arg Ser Ile Thr Glu  Leu Thr Gln
    1820                 1825                 1830

Cys Glu  Val Ala Gly Leu Ser  Val Trp Leu Phe Thr  Gly Val Gln
    1835                 1840                 1845

Leu Gln  Leu Ile Trp Asn Thr  Val Asp Thr Ala Ser  Met Gln Ser
    1850                 1855                 1860

Val Ala  Ala Asp Pro Ala Lys  Ser Thr Ser Phe Tyr  Val Leu Thr
    1865                 1870                 1875

Pro Asp  Val Val Val Glu Tyr  Gly Val Asp Gly Ser  Thr Leu Glu
    1880                 1885                 1890

Gln Trp  Arg Leu Pro Lys Ser  Ala Leu Gly Tyr Glu  Phe Ile Pro
    1895                 1900                 1905
```

Ser Lys Val Gly Leu Gly Leu Ala Leu Ser Asp Ser Lys Leu Leu
1910 1915 1920

Val Leu Leu Ser Asn Val Asn Lys Thr Phe Glu Glu Asp Ser Thr
1925 1930 1935

Asp Leu Glu Met Ala Leu Phe Ser Ser Gln Ser Leu His Asp Arg
1940 1945 1950

Met Lys Lys Thr Tyr Ser Glu Lys Leu Leu Asn Ser Thr Val Ser
1955 1960 1965

Ser Glu Glu Val Ser Asp Ile Ile His Pro Glu Asn Ile Ser Pro
1970 1975 1980

Leu Glu Glu His Ser His Phe Asn Asn Asp Thr Val Ile Tyr Val
1985 1990 1995

Val Glu Pro Glu Thr Ile Asp Ile Pro Asp Pro Pro Val Ser Glu
2000 2005 2010

Asp Glu Leu Ser Ser Glu Thr Pro Ile Ala Arg Asp Ile Pro His
2015 2020 2025

Gly Gly Ile Leu Ile Ala Asp Asn Gln His Phe Pro Glu Arg Ala
2030 2035 2040

Lys Gly Asp Val Val Ala Phe Tyr Ala Gly Pro His Asn Lys Lys
2045 2050 2055

Arg His Leu Val Ala Val Ser Thr Val Ile His Thr Val Ile Gln
2060 2065 2070

Gly Asp Gln Asp Ala Ile Lys Ile Tyr Thr Asp Ile Gln Thr Gly
2075 2080 2085

Lys Leu Tyr Gln Val Leu Pro Cys His Arg Pro Ser His Leu Thr
2090 2095 2100

Ala Leu Glu Leu Arg Asp Glu Thr Ile Leu Ala Phe Leu Glu Ala
2105 2110 2115

Arg Gln Thr Val Gln Ile Tyr Ile Tyr Arg Gly Met Gln Gly Phe
2120 2125 2130

Val Arg Leu Ser Asn Phe Lys Leu Thr Ala Pro Ala Arg Ala Met
2135 2140 2145

Ala Gly Val Ser Leu Pro Gln Pro Leu Thr Ile Arg Cys Lys Leu
2150 2155 2160

His Tyr Leu Ala Ile Ala Thr Glu Gln Asn Glu Leu Ile Met Leu
2165 2170 2175

Arg Ala Lys Thr Gln Gly Asp Cys Gly Leu Leu Val Gln Val Asp
2180 2185 2190

Cys Asp Asp Val Glu
2195

<210> SEQ ID NO 184
<211> LENGTH: 2335
<212> TYPE: PRT
<213> ORGANISM: Aedes aegypti (Closca)

<400> SEQUENCE: 184

Met Pro Glu Thr Asp Leu Phe Asp Cys Gln Met Cys Glu Leu Ala Asn
1 5 10 15

Asn Ile Asp Asp Met Val Gln Cys Glu Gly Cys Thr Lys Trp Ser His
20 25 30

Tyr Gly Cys Val Gly Phe Asp Asp Gly Lys Lys Glu Glu Asn Trp Arg
35 40 45

Cys Ala Gly Cys Ile Ala Lys Ser Ser Ser Asn Ser Thr Gly Gly Asp
50 55 60

```
Ser Asn Val Gln Ala Thr Asp Gly Gln Gln Lys Thr Arg Gly Ser Thr
65                  70                  75                  80

Gly Gly Ala Glu Ser Ile Ser Asp Leu Ala Gln Leu Asn Leu Lys Leu
                85                  90                  95

Leu Glu Glu Arg Lys Ala Val Leu Leu Arg Glu Ile Glu Leu Gln His
            100                 105                 110

Ser Thr Gln Leu Glu Gln Arg Lys Leu Gln Leu Glu Lys Glu Ala Trp
        115                 120                 125

Gln Ala Lys Tyr Asp Ile Leu Asn Ala Lys Cys Glu Ser Thr Ser Ser
    130                 135                 140

Thr Val Gly Ser Ser Gly Leu Gly Asn Trp Ile Ser Arg Met Asn Gln
145                 150                 155                 160

Val Ala Val Ser Gln Tyr Gln Gln Thr Ser Val Ser Ala Ser Thr Val
                165                 170                 175

Thr Thr Ser Leu Asn Pro Arg Met Arg Gln Gln His Thr Ala Thr Gly
            180                 185                 190

Glu Gly Asn Ala Thr Ser Val Val Thr Thr Ser Ser Arg Pro Gly Cys
        195                 200                 205

Ser Leu Tyr Gly Ser Glu Ser Thr Ser Phe Leu Pro Gln Ile Thr Ser
    210                 215                 220

Thr Ile Ala Leu Ser Ala Asn Gln Pro Ser Ser Thr Tyr Ala Val Gly
225                 230                 235                 240

Gln Ala Thr Ser Tyr Met Gly Asp Phe Gln Pro Gly Val Gly Ala Asn
                245                 250                 255

Arg Pro Gly Ser Ser Thr Pro Val Thr Ser Val Asn Trp Val Asn Pro
            260                 265                 270

Gly Ala Asn Pro Thr Ser Ser Ala Gln Cys Leu Pro Pro Tyr Val Ser
        275                 280                 285

Ser Met Glu Gln Leu Gly Gly His Pro Met Pro Ser Gly Tyr Val Ser
    290                 295                 300

His Pro Tyr Gln Val Thr Ser Ser Leu Asn Asn Phe Ala Pro Val Gly
305                 310                 315                 320

Gln Val Ala Phe Ser Gln Tyr Ala His Ser Ser Val Gly Ser Ala Glu
                325                 330                 335

Asn Arg Tyr Leu Lys Gly Phe Arg Glu Arg Gly Ser Ile Pro Val Ser
            340                 345                 350

Phe Pro Ile Asp Ile Cys Leu Leu Lys Val Gly Arg Ser Val Phe Gly
        355                 360                 365

Ala Ser Leu His Ile Arg Lys Ser Lys Glu Asn Tyr Lys Asn Gln Thr
    370                 375                 380

Ile Val Thr Phe Tyr Lys Arg Gln Lys Gly Gln Phe His Lys Tyr Lys
385                 390                 395                 400

Glu Tyr Leu Ala Ala Gln Ala Arg His Phe Asp Cys Ile Ser His Ala
                405                 410                 415

Ser Leu Gly Phe Val Ala Val Val Asn Tyr Tyr Asp Asn Ala Ala Asn
            420                 425                 430

Gln Glu Phe Pro Glu Ala His Pro Gly Phe Asp Glu Gly Ser Pro Val
        435                 440                 445

Phe Gln Ile His Glu Asp Gly Thr Thr Glu Ile Ile Gln Lys Phe Arg
    450                 455                 460

Gln Ser Asn Gln Asn Thr Val His Met Trp Thr Ala Gly Asn His Phe
465                 470                 475                 480
```

```
Tyr Leu Thr His Thr Tyr Ile Asn Leu Asn Glu Ser Val Glu Asn Val
                485                 490                 495

Cys Pro Leu Tyr Arg Trp Thr Gly Tyr His Phe Asp Val Ile Asp Glu
            500                 505                 510

Leu Pro Cys Tyr Asn Ser Ile Asn Ile Glu Pro Phe Ser Ile Glu Gln
        515                 520                 525

Thr Leu Tyr Ile Ala Ile Ala Asn Gln Met Asn Asp Gln Ser Val Glu
    530                 535                 540

Glu Asp Thr Phe Ser Asp Ile Phe Arg Phe Asn Tyr Glu Gln Gln Arg
545                 550                 555                 560

Phe Glu Phe His Gln Lys Ile Tyr Val Tyr Ser Val Ser Asp Ile Ala
                565                 570                 575

Tyr Phe Phe Leu Glu Leu Gly Asp Val Arg Glu His Tyr Leu Ile Thr
            580                 585                 590

Gly Asn Ser Arg Ala Gly Lys Glu Thr Ala Ile Asp Lys Leu Asp Tyr
        595                 600                 605

Asp Gln His Ser Ile Val Tyr Lys Phe Val Glu Gly Tyr Phe Val Pro
    610                 615                 620

Val Gln Lys Ile Glu Leu His Gln Val Lys Met Phe Leu Pro Val Thr
625                 630                 635                 640

His Glu Asn Gly Asp Phe Leu Leu Leu Ile Arg Cys Lys Gly Lys Pro
                645                 650                 655

Leu Leu Ile Tyr Glu Tyr Asp Gly Tyr Lys Phe Val Pro Ser Arg Ile
            660                 665                 670

Asp Tyr Thr Arg Asn Ala Phe Ser Thr Gly Val Ser Phe Met Arg Val
        675                 680                 685

Tyr Arg His Ile Leu Asn Thr Ser Leu Ile Val Ile Ala Asn Lys Gln
    690                 695                 700

Ser Tyr Gly Thr Thr Ala Asn Leu Phe Thr Pro Ile Tyr Gly Val Glu
705                 710                 715                 720

Asn Asp Leu Arg Asp Val Tyr Gly Gln Phe Ile Ser Trp Cys Ser Glu
                725                 730                 735

Thr Thr His Gln Leu Glu Asn Val Asn Leu Glu Glu Val Tyr Asn Lys
            740                 745                 750

Leu Ala Ala Leu Pro Lys Ile Ser Gly Ser Gly Ala Arg Phe Glu Lys
        755                 760                 765

Asp Ile Glu Val Lys Asp Ser Ser Val Glu Lys Leu Arg Thr Lys Val
    770                 775                 780

Leu His Thr Lys His Phe Met Phe Asn Gln Glu Ala Phe Asp Tyr Leu
785                 790                 795                 800

Asn Asn Val Asn Ala Gln Met Lys Ala Leu Lys Gln Lys Ala Lys Lys
                805                 810                 815

Leu Arg Ser Leu Ile Asp Asp Ser Leu Lys Leu Ser Glu Ala Met Glu
            820                 825                 830

Val Arg Gly Asp Val Arg Val Pro Gln Val Ile Ala Ala Asp Gly Leu
        835                 840                 845

Ile Arg Asp Leu Glu Ala Lys Asn Val Asn Asp Glu Arg Val Val Pro
    850                 855                 860

Arg Val Ala Asn Gln Thr Lys His Glu Asp Val Ile Asn Val Asp Arg
865                 870                 875                 880

Leu Ile Ile Glu Asp Arg Leu Ala Val Lys Phe Leu Asn Gly Tyr Ala
                885                 890                 895

Ser Glu Thr Leu Leu His Thr Thr Asp Asp Leu Arg Ser Leu Glu Gly
```

```
            900                 905                 910

Val Asp Leu His Ala Lys Ala Val Glu Ile Arg Gly Glu Leu Phe Val
        915                 920                 925

Asp Lys Ala Ile Asp Gly Val His Val Ser Ala Asp Asn Val Leu Leu
    930                 935                 940

Arg Gly Val Asp Gln Val Phe Thr Gly Arg Thr Leu Arg Ala Thr Asn
945                 950                 955                 960

Phe Thr Val Gly Asn Leu Val Ala Lys Gln Leu Asn Ser Thr Asp Val
                965                 970                 975

Gly Met Ile Met Ser Tyr Leu Asp Arg Val Ser Glu Tyr Asp Ser Ala
            980                 985                 990

Gln Lys Arg Thr Val Glu Ser Tyr  Pro Lys Lys Phe Lys  Glu Ile Arg
        995                 1000                1005

Val Gln  Asp Leu Glu Val Ser  Gly Leu Val Asn Asp  Val Asp Ile
    1010                1015                1020

Lys Tyr  Ile Asn Lys Asn Ala  Leu Lys Ile Val Gly  Asp Gln Val
    1025                1030                1035

Ile Thr  Gly Ser Ile Asn Phe  Asp Asn Ile Val Thr  Arg Lys Leu
    1040                1045                1050

Glu Thr  Pro Asn Lys Arg Leu  Ser Gly Val Asp Leu  Asn Tyr Leu
    1055                1060                1065

Val Met  Thr Glu Pro Thr Pro  Asp Gln Gln Asp Phe  Thr Val Arg
    1070                1075                1080

Gln Asp  Val Gln Phe Ile Asn  Pro Val Tyr Met Glu  Asn Leu His
    1085                1090                1095

Val Asp  Asp Arg Ile Asn His  Ile Asn Val Val Asp  Asp Gln Leu
    1100                1105                1110

Gln Val  Leu Leu Lys Asp Pro  Lys Glu Pro Gln Leu  Ile Thr Gly
    1115                1120                1125

Thr Lys  Ser Phe Asp Asn Val  Gln Leu Leu Gly Pro  Ile Tyr Leu
    1130                1135                1140

Gln Gly  Lys Ile Asn Ser Ser  Ser Leu Ser Lys Leu  Asn Pro Val
    1145                1150                1155

Ser Thr  Ile Thr Gln Asp Val  Tyr Leu Glu Gly Asp  Phe Val Ile
    1160                1165                1170

Thr Gly  Asp Val Ser Ile Arg  Gln Leu Leu Asn Thr  Ser Asn Ile
    1175                1180                1185

Tyr Gly  Ser Ser Lys Thr Phe  Asn Phe Tyr Asp Leu  Tyr His His
    1190                1195                1200

Gly Leu  Pro Leu Ser Ala Ala  Ser Ala Asn Gln Asn  Phe Val Phe
    1205                1210                1215

Lys Glu  Pro Leu Val Val His  His Ala Phe Ala Asn  Asn Leu Asn
    1220                1225                1230

Gly Val  Asn Pro Ser Asp Phe  Ile Pro Ile Pro Ser  Lys Lys Leu
    1235                1240                1245

Gln Arg  Ile Thr Gly Arg Lys  Ile Phe Asn Gly Asp  Leu Thr Ile
    1250                1255                1260

Arg Gly  Asp Arg Val Asp Ala  Ala Met Ile Asn Asp  Ile Asp Leu
    1265                1270                1275

Lys His  Leu Asn Arg Thr Ile  Leu Lys Lys Thr Gly  Asp Gln Val
    1280                1285                1290

Val Lys  Gly Thr Ile His Phe  Lys Glu Leu Ile Ala  Ser Thr Val
    1295                1300                1305
```

```
Val Ala  Lys Thr Thr Leu Phe  Glu Glu Arg Pro Leu  Ser Thr Leu
    1310                 1315                 1320

Leu Thr  Val Asn Thr Asn Gln  Arg Ile Lys Ser Lys  Val Arg Cys
    1325                 1330                 1335

Val Asn  Cys Lys Leu Thr Ile  His Gly Asp Leu Ser  Val Gly Arg
    1340                 1345                 1350

Met Glu  Thr His Asn Lys Ser  Arg Leu Phe Gly Tyr  Asp Leu Asp
    1355                 1360                 1365

Phe Leu  Phe Ser Asp Thr Leu  His Lys Ser Tyr Ala  Gln Pro Asp
    1370                 1375                 1380

Ser Ile  Ala Val Thr Gly Gly  Lys Gly Phe Tyr Asn  Val Thr Val
    1385                 1390                 1395

Gly Glu  Leu Ile Leu Leu Asp  Gln Ala Thr Ile Asn  Gly Val Asp
    1400                 1405                 1410

Leu Ile  Gly Leu Lys Lys Ile  Asn Asp Pro Leu Glu  Lys Asp Val
    1415                 1420                 1425

Ile Val  Glu Glu Thr Leu Ile  Leu Lys Asn Pro Leu  His Val Arg
    1430                 1435                 1440

Asn Val  Tyr Phe Asn Gly Ser  Ile Asn Gly Val Pro  Ala Gln Glu
    1445                 1450                 1455

Phe Gly  Arg Thr Trp Leu Leu  Asn Glu Tyr Asn Gln  Thr Phe Thr
    1460                 1465                 1470

Ala Pro  Gln Val Phe Glu His  Val Ala Ala Glu Gly  Met Phe Val
    1475                 1480                 1485

Asp Gly  Tyr Phe Asn Gly Val  Lys Leu Glu Asp Leu  Val Gln Asp
    1490                 1495                 1500

Ile Tyr  Phe Leu Asp Arg Ser  Glu His Leu Pro Glu  Ala Ile Phe
    1505                 1510                 1515

His Glu  Gly Ile Val Ser Tyr  Gln Pro Ile Thr Val  Lys Gly Leu
    1520                 1525                 1530

Val Ser  Gly Leu Asn Leu Ala  Thr Asp Val Leu Leu  Asn Tyr Ser
    1535                 1540                 1545

Pro Asn  Arg Gln Tyr Leu Lys  Asp Val Arg Ile Asp  Gly Asn Leu
    1550                 1555                 1560

Leu Val  Ala Asn Arg Ile His  Val Glu His Thr Leu  Asn Gly Met
    1565                 1570                 1575

Asn Tyr  Ala Lys Leu Arg Glu  Tyr Ala Thr Ser Ser  Gly Val Glu
    1580                 1585                 1590

Arg Pro  Met Asn Val Glu Val  Gln Gly Asn Val His  Phe His Leu
    1595                 1600                 1605

Gln Pro  Asp Val Ser Gln Leu  Asn Gly Tyr Ser Leu  Glu Gln Leu
    1610                 1615                 1620

His Arg  Glu Ile Trp Leu Thr  Asn Arg Asp Glu Val  Leu Thr Gly
    1625                 1630                 1635

Ser Tyr  Arg Phe Asp Asn Val  His Phe Gly Ser Tyr  Val His Thr
    1640                 1645                 1650

Lys Gly  Pro Val Asn Gln Leu  Asp Leu Glu Glu Ile  Val His Ser
    1655                 1660                 1665

Tyr Leu  Ser Val Ser Lys Pro  Gln Asn Val Thr Thr  Pro Leu Val
    1670                 1675                 1680

Phe Lys  Gly Pro Val Glu Leu  Gln Lys Met Ala Thr  Phe Asp Ser
    1685                 1690                 1695
```

```
Ile Asn  Leu Glu Gly Leu Leu  Lys Gly Ala Lys Glu  Ser Arg Gly
    1700                 1705                 1710

Ile Asn  Ile Val Asp Phe Asp  Arg Tyr Val Leu Lys  Lys Asn Val
    1715                 1720                 1725

Asp Gln  Thr Ile Thr Gly Lys  Trp Val Phe His Asp  Ala Glu Val
    1730                 1735                 1740

Tyr Gly  Asn Leu Asn Leu Thr  Thr Leu Asn Gly Leu  Asp Ile Arg
    1745                 1750                 1755

Arg Asp  Ile Leu Leu Asn His  Ala Glu Gln Val Thr  Phe Ser Gly
    1760                 1765                 1770

Ala Lys  Arg Ile Asp Asn Leu  Arg Val His Asn Leu  Arg Cys Pro
    1775                 1780                 1785

Asp Pro  Cys Ile Ile Gln Gly  Val Asp Phe Ser Glu  Trp Phe Ala
    1790                 1795                 1800

Asn Ser  Val Arg Leu Asp Arg  Asn His Thr Val Glu  Gly Val Thr
    1805                 1810                 1815

Tyr Leu  Glu Gly Ala Thr Ile  Leu Gly Asp Ile Glu  Ser Arg Gly
    1820                 1825                 1830

Pro Val  Asn Asn Val Thr Phe  Asp Pro Gln Ser Leu  Leu Leu Lys
    1835                 1840                 1845

Ser Val  Pro Gln Thr Leu Glu  Gly Thr Leu Tyr Leu  Lys Thr Lys
    1850                 1855                 1860

Phe Pro  Glu His Asn Leu Ile  Tyr Gln Ser Ser Ile  Glu Ser Leu
    1865                 1870                 1875

Glu Val  Asn Ser Ile Asn Gly  Lys Asp Phe Asn Arg  Phe Met Asp
    1880                 1885                 1890

Asn Leu  Ala Arg Val Glu Glu  Gly Lys Val Thr Ile  Asp Thr Pro
    1895                 1900                 1905

Val Thr  Leu Val Gln Asn Leu  Asn Ala Lys Asn Val  Asp Thr Gly
    1910                 1915                 1920

Asp Ser  Lys Met Phe Asp Val  Asn Ile Asn Gln Leu  Leu Gln Glu
    1925                 1930                 1935

Val Glu  Tyr Gly Asp Gln Leu  Ser Gln Tyr Glu Thr  Lys Leu Arg
    1940                 1945                 1950

Arg Leu  His Met Val Gly Gln  Ser Leu Val Glu Thr  Leu Ser Thr
    1955                 1960                 1965

Lys Thr  Pro Tyr Leu Ser His  Tyr Gln Pro Ile Lys  Pro Leu Pro
    1970                 1975                 1980

Gly Tyr  Phe Arg Ser Val Val  Thr Ile Thr Leu Pro  Leu Ser Pro
    1985                 1990                 1995

Met Pro  Ile Glu Leu Leu Ala  Ala His Val Asp Asp  Gly Asn Arg
    2000                 2005                 2010

Thr Ala  Val Glu Phe Tyr Arg  Trp Asn Lys Lys Asp  Ser Gln Phe
    2015                 2020                 2025

His Ile  Ala Lys Gly Phe Pro  Pro Ile Thr Tyr Pro  Thr Leu Gln
    2030                 2035                 2040

Ile Thr  Lys Thr Lys Arg Ile  Val Leu Gly Gly Val  Gln Asn Leu
    2045                 2050                 2055

Phe Val  Glu Tyr Tyr Asp His  Ser Arg His Leu Tyr  Arg Gln Ser
    2060                 2065                 2070

Ile Leu  Asp Leu Glu Ala Pro  Asp Phe Thr Ala Pro  Lys Lys Thr
    2075                 2080                 2085

Pro Lys  Phe Thr Ser Ile Tyr  Glu Phe Asn Ser Ser  Leu Pro Arg
```

2090 2095 2100

Asp Ile Val Ala Leu Lys Val Leu Asp Leu Asp Cys Val Gly Leu
2105 2110 2115

Tyr Ser Pro His Ile Asp Gly Leu Asn Val Tyr Cys Leu Gln Leu
2120 2125 2130

Glu Asn Leu Val Tyr Tyr Leu Lys Phe His Gln Leu Leu Thr Thr
2135 2140 2145

Pro Ala Val Asn Gln Ala Leu His Leu Asp Gly Arg Leu Ile Leu
2150 2155 2160

Leu Ser Arg Asp Ser Leu Leu Gln Val Trp Arg Pro Arg Ala Asp
2165 2170 2175

Tyr Lys Leu Gly Leu Leu Gln Leu Ile Lys Ile Ala His Pro Thr
2180 2185 2190

Ser Leu Thr Val Ala Lys Phe Glu Gln Gln Leu Phe Ile Ala Ile
2195 2200 2205

Asn Ser Asp Gln Ala Leu Thr Glu Ala Ser Ala His His Gly Ser
2210 2215 2220

Ile Glu Ile Trp Arg Asp Leu Arg Pro Gln His His Asn Ser Thr
2225 2230 2235

Phe Asn Lys Tyr Gln Thr Ile Leu Thr Lys Met Pro Lys Gln Ile
2240 2245 2250

Gln Phe Ser Val Leu Ala Thr Thr Ser Glu Leu Met Leu Tyr Thr
2255 2260 2265

Leu Thr Glu Asn Pro Phe His Pro Leu Val Ile Tyr Arg Tyr Glu
2270 2275 2280

Gly Val Ala Gly Phe Arg Glu Tyr Leu Thr Ser Asn Ala Leu Arg
2285 2290 2295

Thr Ser Ser Lys Arg Phe Thr Val Val Lys Leu Asp Arg Lys Gln
2300 2305 2310

Arg Glu Leu Leu Ala Leu Val Ser Asp Arg Glu Val Thr Trp Ile
2315 2320 2325

Glu Ala Val Ile Lys Gly Arg
2330 2335

<210> SEQ ID NO 185
<211> LENGTH: 184
<212> TYPE: PRT
<213> ORGANISM: Aedes aegypti (Polehole)

<400> SEQUENCE: 185

Met Phe Met Asp Tyr Leu Asn Thr Ile Ala Val Lys Glu Tyr Phe Lys
1 5 10 15

Leu Leu Thr Leu Lys Gly Asp Ser Asp Lys Ala Gln Gln Trp Glu Ile
20 25 30

Gly Gly Ser Lys Thr Leu Gln Lys Gly Met Ala Val Asp Gly Lys Leu
35 40 45

Asn Val Val His Val Asn Arg Leu Ile Leu Asp Asn Ile Leu Tyr Asn
50 55 60

Ser Ala Arg Lys Thr Gly Pro Met Asn Ile Ala Gly Leu Trp Asn Ile
65 70 75 80

Thr Lys Leu Ala Thr Lys Tyr Leu Ala Thr Lys Gln Ile Asn Gly Pro
85 90 95

Ala Tyr Leu Met Thr Ser Asp Ile Ile Val Glu Leu Tyr Asn Lys Ser
100 105 110

```
Leu Ser Gln Thr Tyr Leu Lys Leu Glu Asp Val Tyr Thr Thr Gly Ile
        115                 120                 125

Val Ala Gln Leu Leu Asn Ile His Arg Ile Asn Ile Lys Glu Phe Leu
    130                 135                 140

Asn Arg Arg Ile Ala Phe Asn Gln Cys Asn Ile Lys Lys Ser Ile Ser
145                 150                 155                 160

Ile His Met Ile Lys Thr Asn Glu Gln Tyr Asp Leu Trp Lys Lys Leu
                165                 170                 175

Ser Asp Asn Ser Val Gln Cys Lys
            180


<210> SEQ ID NO 186
<211> LENGTH: 1804
<212> TYPE: PRT
<213> ORGANISM: Aedes aegypti (Nudel)

<400> SEQUENCE: 186

Met Asn Val Pro Leu Asn Ile Gln Asn Leu Ser Gly Lys Arg Thr Ser
1               5                   10                  15

Asp Asp Pro Asp Leu Glu Gly Ala Gln Leu Val Cys Ser Phe Val Gly
            20                  25                  30

Pro Ser Ser Thr Glu Lys Pro Leu Ala Gly Asn Asp Ser Met Met Leu
        35                  40                  45

Gln Ser Ser Gln Glu Leu Phe Val Ser Ser Thr Arg Ala Arg Gly His
    50                  55                  60

His Arg His Cys Pro Arg Gly Lys Val Pro Cys Ala Asp Gly Ile Gln
65                  70                  75                  80

Cys Val Leu Ser Ser His Leu Cys Asp Ser Arg Val Asp Cys Phe Asp
                85                  90                  95

Gly Ser Asp Glu Ser His Cys Ser Cys Leu Ser Arg Leu Ala Asp Lys
            100                 105                 110

Arg Arg Cys Asp Gly Tyr Val Asp Cys Pro Leu Ala Glu Asp Glu Met
        115                 120                 125

Gly Cys Phe Gly Cys Asp Lys Phe Ser Phe Ser Cys Phe Asn Thr Phe
    130                 135                 140

Phe Glu Tyr Gln Ala Ser His His Ser Glu Thr Arg Cys Phe Thr Leu
145                 150                 155                 160

Ile Glu Lys Cys Asp Gly Phe Asn Asn Cys Met Asn Arg Lys Asp Glu
                165                 170                 175

Gln Asp Cys Thr Met Leu Val Arg Asp Leu Arg Ser Pro Leu Ala Phe
            180                 185                 190

Ala Val Gly His Ser Val Gly Val Leu His Arg Asn Tyr Lys Gly Lys
        195                 200                 205

Trp Tyr Pro Val Cys His Asn Pro Leu Asn Leu Ala Arg Glu Ala Cys
    210                 215                 220

Glu Ala Glu Leu Gly Pro Ala Asp Arg Asp Pro Val Ile Leu Gln His
225                 230                 235                 240

His Gly Asp Leu Pro Gly Pro Phe Ile Gln Pro Ser Pro Arg Ser His
                245                 250                 255

His Val Phe Gln Pro Glu Phe Thr Asp Thr Cys Asn Gly Leu Ile Asn
            260                 265                 270

Tyr Val Lys Cys Pro Ala Pro Lys Cys Gly Ser Ser Lys Gln Asn Glu
        275                 280                 285

Met Glu Asn Leu Arg Ile Lys Ile Arg Gly Lys Arg Asn Ala Thr Glu
    290                 295                 300
```

```
Leu Val Gln Ile Val Gly Gly Thr Lys Ala Glu Pro Ala Ala Tyr Pro
305                 310                 315                 320

Phe Ile Val Gly Ile Phe Arg Asp Gly Lys Phe His Cys Gly Gly Ser
                325                 330                 335

Ile Phe Asn Glu Arg Trp Ile Val Thr Ala Ala His Cys Cys Asp Asn
            340                 345                 350

Phe Pro Arg His His Tyr Glu Leu Arg Ala Gly Leu Leu Arg Arg Arg
        355                 360                 365

Ser Phe Ser Pro Gln Val Gln Val Ser Thr Val Thr His Val Phe Ile
    370                 375                 380

His Arg Gly Tyr Ser Ala Gln Lys Met Ile Asn Asp Ile Ser Leu Met
385                 390                 395                 400

His Ser Asp Arg Pro Phe Gln Tyr Asn Arg Trp Val Arg Pro Ile Cys
                405                 410                 415

Leu Pro Asp Arg His Met Thr Thr Asn Asp Arg Asp Trp Ile Trp Gly
            420                 425                 430

Pro Lys Pro Gly Thr Met Cys Thr Ala Val Gly Trp Gly Ala Leu Arg
        435                 440                 445

Glu His Gly Gly Ser Pro Asp His Leu Met Gln Val Thr Val Pro Ile
    450                 455                 460

Leu Pro Phe Cys Lys His Lys Asn Asp Arg Asp Gly Leu Ala Ile Cys
465                 470                 475                 480

Ala Ala Glu Met Ser Gly Gly His Asp Ala Cys Gln Gly Asp Ser Gly
                485                 490                 495

Gly Pro Phe Ala Cys Ile Ser Val Ser Ser Pro His Glu Trp Tyr Leu
            500                 505                 510

Ala Gly Val Val Ser His Gly Glu Gly Cys Ala Arg Pro Asn Glu Pro
        515                 520                 525

Gly Val Tyr Thr Arg Val Ala Leu Phe Asn Asp Trp Ile Gln Arg Lys
    530                 535                 540

Thr Arg Glu Val Leu Thr Ser Ser Ser Thr Arg Gln Asp Cys Pro Gly
545                 550                 555                 560

Phe Gln Cys Ser Val Gly Val Ser Phe Cys Ile Pro Arg Gln Lys Arg
                565                 570                 575

Cys Asn Gly Lys Val Asp Cys Leu Gly Gly Glu Asp Glu Leu Ser Cys
            580                 585                 590

Ser Leu Asp Gln Leu Leu Ala Glu Ser Ile Gln Glu Thr Thr Ile Ala
        595                 600                 605

Thr Thr Pro Lys Asn Ser Thr Ala Thr Ser Ser Thr Thr Ala Ala Ala
    610                 615                 620

Thr Thr Glu Ala Val Thr Ser Lys Ile Asp Phe Leu Ala Glu Asn Ser
625                 630                 635                 640

Glu Ala Ser Asp Pro Ala Thr Thr Val Thr Glu Ala Ser Ser Thr Glu
                645                 650                 655

Thr Ala Asn Ile Glu Thr Ile Leu Thr Thr Ile Glu Thr Val Ser Ala
            660                 665                 670

Lys Asp Val Ser Asp Gly Ile Phe Gln Val Ser Thr Glu Ala Thr Thr
        675                 680                 685

Val Glu Ile Asn Thr Thr Leu Asp Ile Ser Ser Ser Ser Gln Asn Val
    690                 695                 700

Ser Ala Ser Pro Glu Lys Val Glu Glu Ser Thr Val Asp Glu Thr Thr
705                 710                 715                 720
```

```
Ser Ser Thr Thr Glu Thr Ser Phe Thr His Pro Thr Thr Ile Glu Ser
                725                 730                 735

Glu Thr Thr Ala Asp Ser Val Thr Ala Leu Met Ser Glu Thr Thr Ser
            740                 745                 750

Pro Ser Leu Pro Pro Asn Glu Asn Asn Thr Thr Val Asp Tyr Thr Val
        755                 760                 765

Thr Arg Ser Thr Asp Gln Thr Thr Asn Thr Pro Phe Thr Ile Ser Pro
    770                 775                 780

Thr Thr Asp Ser Leu Asp Asp Ser Ser Ala Ala Tyr Ser Ser Ser Ala
785                 790                 795                 800

Asn Asp Ser Glu Val Asn His Ser Thr Thr Ile Glu Pro Lys Asn Thr
                805                 810                 815

Glu Ser Ser Val His Ala Thr Thr Val Ile Glu Leu Ile Ser Val Glu
            820                 825                 830

Ser Thr Thr Asn Ile Glu Ala Thr Ser Leu Ala Asp Pro Ser Asn Ala
        835                 840                 845

Ser Ile Thr Thr Leu Ser Ser Asp Leu Val Glu Glu Thr Ser Ser Ser
    850                 855                 860

Ser Thr Thr Pro Ser Thr Pro Asp Ser Thr Ser Ser Thr Gln Pro Asp
865                 870                 875                 880

Ser Ser His Ser Ser Thr Ser Ser Ala Pro Trp Met Gln Ile Asn Glu
                885                 890                 895

Ala Ile Ala Asn Leu Lys Pro Arg Pro Pro Ser Thr Asp Arg Asp Met
            900                 905                 910

Glu Met Arg Gln Leu Glu Leu Gly Asp Ser Val Ala Ala Thr Arg Thr
        915                 920                 925

Asp Asn Thr Thr Ser Thr Thr Ile Ser Thr Ala Pro Ser Ala Ala Thr
    930                 935                 940

Asp Ser Thr Ser Ser Thr Pro Leu Ser Thr Thr Thr Val Glu Ser Ser
945                 950                 955                 960

Ser Thr Thr His Gly Asp Leu Glu His Ser Glu Thr Gln Ile Glu Pro
                965                 970                 975

Val Glu Ala Glu Ala Thr Asn Ala Ser Val Glu Glu His Pro Phe Leu
            980                 985                 990

Arg Glu Ile His Asn Leu Val Glu  Glu Lys Thr Arg Arg  Leu Asn Gln
        995                 1000                1005

Phe Arg  Leu Ser Met His Tyr  Leu His Thr Ser Leu  Arg Asn Gln
    1010                1015                1020

Thr Gln  Asp Ala Asn Glu Thr  Ser Tyr Gln Tyr Arg  Arg Phe Lys
    1025                1030                1035

Cys Ser  Lys Ile Arg Gln Ser  Ile Asn Ile Ala His  His Cys Asp
    1040                1045                1050

Arg Ile  Ile Asp Cys Glu Asp  Gly Thr Asp Glu Leu  Arg Cys Thr
    1055                1060                1065

Cys Arg  Asp Tyr Leu Lys Asp  Lys Tyr Asp Phe Leu  Ile Cys Asp
    1070                1075                1080

Gly Lys  Thr Asp Cys Leu Asp  Leu Thr Asp Glu Ala  Asp Cys Phe
    1085                1090                1095

Ser Cys  Thr Ala Gly Gln Phe  Pro Cys Arg Met Ser  Lys Val Cys
    1100                1105                1110

Ile Asp  Glu Lys Lys Leu Cys  Asp Ala Ile Pro Asp  Cys Pro Leu
    1115                1120                1125

His Glu  Asp Glu Leu Asp Cys  Leu Ala Leu Thr Asp  Gly His Lys
```

```
    1130                1135                1140

Val Tyr  Phe Asp Ala Asn Asn  Leu Ser Glu Phe Lys  Tyr Glu Gly
    1145                1150                1155

Leu Val  Thr Lys Asn Thr Asn  Gly Thr Trp Asp Leu  Ile Cys Gly
    1160                1165                1170

Ala Glu  Ile Asn Asn Lys Ser  Val Glu Ser Ile Gly  Lys Ile Cys
    1175                1180                1185

Ser Phe  Leu Gly Phe Ala Gly  Tyr Glu Ser Tyr Tyr  Gln Thr Val
    1190                1195                1200

Leu Thr  Pro Leu Val Asn Glu  Thr Val Asp Leu Asp  His Gln Pro
    1205                1210                1215

Leu Leu  Ile Met Ser Tyr Arg  Asn Ile Ser Ser Glu  Pro Asn Cys
    1220                1225                1230

Lys Ala  Leu His Ile Thr Cys  Ala Pro Phe Ile Asn  Ala Thr Glu
    1235                1240                1245

His Glu  Ile Ser His Phe Glu  Asn Gln His Lys Glu  Gln Pro Val
    1250                1255                1260

Gln Val  Asn Ile Arg Pro Thr  His Pro Ile Gln Asn  Ile Thr Ser
    1265                1270                1275

Leu Thr  His Ile Thr Phe Gln  Glu Asn Ala His Ile  Glu Phe Ile
    1280                1285                1290

Glu Asn  Phe Gly Asp Asp Tyr  Asp Trp Pro Trp Asn  Ala Asp Ile
    1295                1300                1305

Tyr Leu  Glu Gly Val Phe Leu  Cys Ser Ala Ile Ile  Ile Glu Val
    1310                1315                1320

Asn Trp  Ile Val Val Asp Ser  Ser Cys Met Arg Met  Ile Asn Leu
    1325                1330                1335

Lys Asn  Asp Tyr Leu Ser Val  Val Ala Gly Gly Ala  Lys Ser Tyr
    1340                1345                1350

Leu Lys  Ile Ser Gly Pro Tyr  Glu Gln Val Val Arg  Val Asp Cys
    1355                1360                1365

Tyr His  Phe Leu Pro Glu Ala  Arg Val Val Met Leu  His Leu Ala
    1370                1375                1380

Lys Asn  Leu Thr Phe Thr Arg  His Val Leu Pro Thr  Phe Ile Pro
    1385                1390                1395

Glu Lys  Asn Tyr Asn Ile Thr  Asp Asn Gln Cys Leu  Ala Val Gly
    1400                1405                1410

Gln Asp  Lys Tyr Gly Arg Thr  Arg Thr Leu Arg Val  His Met Asn
    1415                1420                1425

Met Thr  Asn Cys Glu Pro Glu  Asp His Ile Cys Tyr  Gln Leu Asn
    1430                1435                1440

Pro Asp  Asn Gly Ile Tyr His  Ala Asp His Cys Tyr  Thr Glu Asn
    1445                1450                1455

Ala Ser  Arg Thr Gly Val Val  Val Cys Lys Ser Lys  Val Ser Gly
    1460                1465                1470

Trp Tyr  Pro Val Gly Phe Tyr  Gln Asn Lys His Gly  Leu Cys Gly
    1475                1480                1485

Phe Asn  Glu Val Val Lys Met  Ile Ser Leu Lys Glu  Phe Tyr Thr
    1490                1495                1500

Asp Ile  Gln His Val Leu Ser  His Lys Lys Cys Asp  Tyr Glu Phe
    1505                1510                1515

Pro Glu  Pro Leu Cys Asp Gly  Val Arg Cys Trp His  Gly Lys Cys
    1520                1525                1530
```

Ile Gly His Ser Leu Val Cys Asp Asn Lys Met Asp Cys Asp Asp
1535 1540 1545

Asn Phe Asp Glu Arg Pro Glu Ala Cys Asn Ala Ile Asn Asp Thr
1550 1555 1560

Ser Thr Ala Cys Leu Pro Thr Gln Phe Arg Cys Gly Ser His Gln
1565 1570 1575

Cys Val Asp Lys Ser Lys Phe Cys Asp Gly Arg Asn Asp Cys Gly
1580 1585 1590

Asp Leu Ser Asp Glu Pro His Glu Cys Ser Cys Tyr Thr Tyr Leu
1595 1600 1605

Lys Val Thr Asp Pro Ser Lys Ile Cys Asp Gly Val Arg Asn Cys
1610 1615 1620

Trp Asp Lys Ser Asp Glu Asn Pro Arg Leu Cys Lys Cys Ala Lys
1625 1630 1635

Thr Ser Phe Arg Cys Gly Asp Ser Glu Val Cys Ile Pro Tyr Asp
1640 1645 1650

His Val Cys Asp Asp Glu Ile Asp Cys Pro Gly Glu Glu Asp Glu
1655 1660 1665

Arg Tyr Cys Tyr Ala Leu Gln Gln Asn Pro Ala Glu Thr Asn Tyr
1670 1675 1680

Gly Glu Val Met Gln Gln Ser Tyr Gly Ile Trp His Ser Lys Cys
1685 1690 1695

Phe Pro Lys Asp Asp Lys Tyr Asp Glu Gln Thr Ile Lys Glu Ile
1700 1705 1710

Cys His Arg Val Gly Tyr Gln Gln Val Arg Lys Val Tyr Gly Arg
1715 1720 1725

Lys Val Leu Pro Glu Ser Arg Leu Arg Thr Ser Asn Arg Thr His
1730 1735 1740

Asp Pro Val Asp Arg Leu Arg Gly Ala Ala Thr Lys Ala Val Ala
1745 1750 1755

Phe Asn Lys Phe Phe Lys Val Asn Ile Asn Glu Lys Gln Ala Ile
1760 1765 1770

Phe Met Lys Pro Ser Arg Pro Leu Tyr Thr Leu Val Asn Trp Asp
1775 1780 1785

Ala Glu Asp Glu Gln Lys Cys Asp Arg Leu Glu Ile Asn Cys Gly
1790 1795 1800

Asp

<210> SEQ ID NO 187
<211> LENGTH: 313
<212> TYPE: PRT
<213> ORGANISM: Aedes aegypti (CATL3)

<400> SEQUENCE: 187

Met Lys Lys Gln Leu Leu Trp Ile Leu Ser Ala Leu Ile Val Ala Ala
1 5 10 15

Gly Asp Ile Gly Glu Arg Val Asp Glu Gly Asp Val Thr Asn Phe Asp
20 25 30

Thr Phe Leu Gly Ala Tyr Gln Lys Lys Tyr Lys Ala Lys Tyr Arg Met
35 40 45

Asp Arg Arg Lys Arg Ala Phe Lys Lys Asn Met Gln Glu Ile Glu Glu
50 55 60

His Asn Ala Asn Tyr Glu Gln Gly Lys Ser Thr Phe Gln Met Gly Val
65 70 75 80

Asn Glu Leu Ala Asp Met Asp Lys Ser Ser Tyr Leu Lys Lys Met Val
85 90 95

Arg Met Thr Asp Ala Ile Asp His Arg Lys Leu Asp Val Asp Phe Asn
100 105 110

Asp Glu Met Leu Gln Ala Thr Asn Ala Phe Gly Glu Glu Phe Val Gln
115 120 125

Ala Thr Gln Asn Ser Met Pro Asp Ser Leu Asp Trp Arg Asp Lys Gly
130 135 140

Phe Thr Thr Met Ala Val Asn Gln Lys Thr Cys Gly Ser Cys Tyr Ala
145 150 155 160

Phe Ser Ile Gly His Ala Leu Asn Gly Gln Ile Met Arg Arg Ile Gly
165 170 175

Arg Val Glu Tyr Val Ser Thr Gln Gln Met Val Asp Cys Ser Thr Ser
180 185 190

Ala Gly Asn Lys Gly Cys Ala Gly Gly Ser Leu Arg Phe Thr Met Gln
195 200 205

Tyr Leu Gln Asn Ser Gln Gly Ile Met Arg Ser Ser Asp Tyr Pro Tyr
210 215 220

Thr Ser Ser Ser Ser Lys Gln Ser Glu Tyr Phe Gln Glu Glu Gly Arg
225 230 235 240

Val Gly Gln Lys Ala Cys Lys Gln Gln Leu Ala Ser Cys Lys Ala Pro
245 250 255

Ala Thr Lys Leu Val Thr Ser Leu Val Cys Arg Ser His Pro Ile Lys
260 265 270

Gln Phe Ser Val Ser Asp Ser Val Gln Glu Trp Ala Val Leu Asp Val
275 280 285

Val Ser Gly Val Ser Pro Lys Glu Gln Leu Cys Arg Val Thr Ala Ser
290 295 300

His Thr Val Ser Leu Lys Asn Ala Glu
305 310

<210> SEQ ID NO 188
<211> LENGTH: 550
<212> TYPE: PRT
<213> ORGANISM: Aedes aegypti (DCE2)

<400> SEQUENCE: 188

Met Trp Lys Ser Ser Val Val Cys Leu Ala Leu Leu Gly Val Leu Gly
1 5 10 15

Ser Val Ser Gly Thr Thr Lys Leu Gln Glu Arg Tyr Ser Trp Arg Gln
20 25 30

Leu Asp Phe Val Phe Pro Asn Gln Gln Leu Lys Gln Gln Ala Leu Ala
35 40 45

Ser Gly Asp Tyr Val Pro Thr Asn Gly Leu Pro Val Gly Ile Glu Arg
50 55 60

Trp Glu Asn Lys Leu Phe Val Ser Val Pro Arg Trp Lys Asp Gly Ile
65 70 75 80

Pro Ser Thr Leu Asn Tyr Ile Asp Met Asn Gln Thr Pro Ser Gly Ser
85 90 95

Pro Pro Leu Ile Pro Tyr Pro Ser Trp Ala Asn Asn Val Ala Gly Asp
100 105 110

Cys Gln Asn Gly Leu Ser Thr Val Tyr Arg Ile Lys Ala Asp Lys Cys
115 120 125

Gly Arg Leu Trp Val Leu Asp Thr Gly Thr Val Gly Ile Gly Asn Thr

-continued

```
    130                 135                 140

Thr Gln Gln Leu Cys Pro Tyr Ala Leu Asn Ile Phe Asp Leu Lys Thr
145                 150                 155                 160

Asn Thr Arg Leu Arg Arg Tyr Glu Leu Arg Ala Glu Asp Thr Asn Gln
                165                 170                 175

Asn Thr Phe Ile Ala Asn Ile Ala Ile Asp Met Gly Arg Ser Cys Glu
            180                 185                 190

Asp Thr Phe Ala Tyr Met Ser Asp Glu Leu Gly Tyr Gly Leu Ile Ala
        195                 200                 205

Tyr Ser Phe Glu Lys Asn Lys Ser Trp Arg Phe Glu His Ser Phe Phe
    210                 215                 220

Phe Pro Asp Pro Leu Arg Gly Asp Phe Asn Val Ala Gly Leu Asn Phe
225                 230                 235                 240

Gln Trp Gly Glu Glu Gly Ile Phe Gly Met Ser Leu Ser Pro Leu Gln
                245                 250                 255

Ser Asp Gly Phe Arg Thr Met Tyr Phe Ser Pro Leu Ala Ser His Arg
            260                 265                 270

Glu Phe Met Val Ser Thr Gln Val Leu Arg Asp Glu Glu Gly Ala Glu
        275                 280                 285

Glu Ser Phe His Lys Phe Thr Tyr Leu Lys Glu Arg Gly Pro Asn Ser
    290                 295                 300

His Thr Thr Ser Arg Val Met Ser Glu Thr Gly Leu Gln Leu Phe Asn
305                 310                 315                 320

Leu Ile Asp Gln Asn Ala Val Gly Cys Trp His Ser Ser Leu Pro Tyr
                325                 330                 335

Ser Pro Glu Asn His Gly Ile Val Asp Arg Asp Asp Val Glu Leu Val
            340                 345                 350

Phe Pro Ala Asp Val Lys Ile Asp Ala Glu Glu Asn Val Trp Val Ile
        355                 360                 365

Ser Asp Arg Met Pro Val Phe Leu Ile Ala Glu Leu Asp Tyr Ser Asp
    370                 375                 380

Val Asn Phe Arg Ile Phe Thr Ala Pro Leu Ser Thr Leu Val Ala Gly
385                 390                 395                 400

Thr Val Cys Asp Val Arg Pro Ser Leu Arg Pro Gly Ala Ile Gln Ser
                405                 410                 415

Lys Phe Gly Gly Ser Asp Leu Ser Thr Tyr Pro Gly Thr Thr Leu Leu
            420                 425                 430

Pro Val Gly Tyr Thr Gln Pro Ile Ser Tyr Thr Pro Ser Ser Tyr Ala
        435                 440                 445

Pro Thr Val Ala Pro Val Thr Lys Tyr Thr Ala Ala Pro Ala Tyr Asp
    450                 455                 460

His Pro Thr Ser His Met Tyr Thr Thr Gln Glu Tyr Pro Thr Thr Ala
465                 470                 475                 480

Lys Ala Tyr His Phe Asn Lys Tyr His Asn Val Glu Tyr Gln Ser His
                485                 490                 495

Gly Asn Gly Gln Ala Asp Tyr His Phe Gly His Gly Gly His Tyr His
            500                 505                 510

Asp His Asp His Ala His Glu Tyr Gly His Asp His Gly Tyr Tyr Gly
        515                 520                 525

Gly Gly Gln Arg Arg His Trp Gly Ala Gly Ala Lys Lys Pro Glu Ala
    530                 535                 540

Trp Lys Gln Gln Leu Tyr
545                 550
```

<210> SEQ ID NO 189
<211> LENGTH: 372
<212> TYPE: PRT
<213> ORGANISM: Aedes aegypti (DCE4)

<400> SEQUENCE: 189

```
Met Arg Gly Asn Ile Leu Trp Leu Leu Ala Ala Val Thr Gln Leu Thr
1               5                   10                  15

Val Thr Ser Val Thr Ala Phe Ala Asn Asn Ser Asn Ala Ile Tyr Thr
            20                  25                  30

Trp Glu Gly Gly Arg Ile Glu Trp Pro Cys Pro Thr Thr Lys Arg Leu
        35                  40                  45

Val Lys Ala Ala Ala Lys Tyr Thr Pro Lys Asp Ile Ile Ala Met Ala
    50                  55                  60

Cys Ala Arg Ser Gly Asp Lys Thr Leu Cys Ala Met Pro Arg Tyr Arg
65                  70                  75                  80

Asn Ser Ile Pro Ile Thr Leu Gly Gln Ile Tyr Ala Thr Lys Lys Gly
                85                  90                  95

Cys Asp Val Lys Phe Glu Pro Phe Pro Cys Trp Thr Glu Gln Glu Glu
            100                 105                 110

Asn Asn Cys Asn Ser Leu Gln Ser Val Ile Asp Ile Tyr Ala Thr Gly
        115                 120                 125

Asp Phe Val Trp Val Leu Asp Asn Gly Ile Leu Asn Ala Leu Arg Ser
    130                 135                 140

Pro Ile Gln Arg Cys Pro Ala Lys Ile Val Val Tyr Glu Ala Lys Thr
145                 150                 155                 160

Gly Lys Lys Met Lys Thr Ile Asn Leu Gly Arg Tyr Val Thr Glu Lys
                165                 170                 175

Ser Arg Leu Gln Tyr Met Gln Val Glu Cys Leu Lys Gly Gly Gln Cys
            180                 185                 190

Phe Val Tyr Ile Ser Asp Ala Gly Asn Asn Ala Ile Ile Ile Tyr Asp
        195                 200                 205

Val Ser Gly Gly Arg Gly Tyr Arg Val Val Leu Pro Lys Ala Val His
    210                 215                 220

His Gly Cys Arg Phe Arg Asp Val Leu Tyr Ile Phe Leu Ser Tyr His
225                 230                 235                 240

Lys Asp Gly Thr Lys Leu Phe Phe Thr Tyr Leu Gly Gly Arg Arg Leu
                245                 250                 255

Phe Ala Ile Ala Thr Asp His Leu Arg Lys Gly His Gly Gly Asn Ile
            260                 265                 270

Glu Asp Ile Gly Glu Lys Pro Gly Ser Phe Ile Tyr Ile Gly Pro Asp
        275                 280                 285

Gly Ala Thr Gly Val Phe Phe Arg Glu Glu Gly Asp Ser Asn Val Phe
    290                 295                 300

Phe Trp Asp Thr Lys Thr Cys Leu Lys Lys Ser Asn Phe Lys Leu Val
305                 310                 315                 320

Phe Lys Ser Ser Glu Gly Leu Tyr Ala Thr Asp Val Phe Pro Asp His
                325                 330                 335

Glu Ile Asn Arg Phe Leu Ile Leu Glu Ser Asp Phe Pro Gly Tyr Met
            340                 345                 350

Glu Glu Lys Ala Gly Cys Gly Thr Leu His Gln Ile Ser Leu Leu Asp
        355                 360                 365

Gly Ala Thr Cys
```

370

<210> SEQ ID NO 190
<211> LENGTH: 248
<212> TYPE: PRT
<213> ORGANISM: Aedes aegypti (DCE5)

<400> SEQUENCE: 190

Met Trp Ala Leu Asp Ser Gly Ile Cys Asn Ser Leu Glu Gln Pro Ile
1 5 10 15

Lys Arg Cys Thr Ala Lys Val Ile Ala Phe Asp Leu Glu Thr Asp Lys
20 25 30

Thr Val Lys Thr Val Asp Leu Ser Asp Ile Leu Lys Pro His Ser Arg
35 40 45

Pro Gln Tyr Leu Val Thr Asp Tyr Ser Pro Asn Gly Phe Pro Tyr Val
50 55 60

Tyr Ile Ser Asp Ala Glu Gly Ala Ile Ile Val Leu Asp Ile His His
65 70 75 80

Asn Lys Met Tyr Arg Val Val Leu Pro Arg Ala Ile Ser Ala Gly Cys
85 90 95

Gly Glu Ser Asp Val Leu Tyr Leu Leu Leu Val Arg Arg Pro Lys Asn
100 105 110

Gln Asn Met Val Ile Phe Ser Tyr Leu Cys Gly Asn Lys Val Tyr Gly
115 120 125

Ile Lys Ser Glu Phe Leu Arg Thr Gly Arg Gly Ser Ser Ala Ile Val
130 135 140

Glu Leu Gly Ser Lys Thr Lys His Ser Val Leu Leu Gly Thr Asp Gly
145 150 155 160

Ser Asn Gly Val Ile Leu Arg Tyr Arg Ser Glu Ser Glu Leu Tyr Lys
165 170 175

Trp Asn Thr Asp Gln Pro Tyr Lys Glu Cys Asn Phe Glu Leu Val Gln
180 185 190

Leu Ala Glu Glu Cys Arg Leu Ser Thr His Val Ala Pro Gly Gly Lys
195 200 205

Asp Ala Leu Met Tyr Ser Leu Ser Ser Asn Val Ala Asp Tyr Leu Asn
210 215 220

His Thr Cys Gly Ala Gly Gly Ala Ser Ala Arg Leu Lys Tyr Ile Ser
225 230 235 240

Lys Glu Cys Glu Asp Asp Cys Tyr
245

<210> SEQ ID NO 191
<211> LENGTH: 2547
<212> TYPE: DNA
<213> ORGANISM: Aedes aegypti

<400> SEQUENCE: 191
atggaagagt cccaacagct gcaatttccc atccgtggca acaacaacaa taaaccgctc 60
aatgtcagcg gagggaatga cggaagtgga cagttcaccg atagcggata cacgtcgtat 120
cattcgataa gtgcttccgg ttcggttgcc cggtcggtgc tggccacaat cgaggaggat 180
aatgaagcgg acagtagctt cgaggaggct cgatcctcgg aagatatctt ccagatgggt 240
gggggcagta atgtcctgac ccctaccact gcggccagta tcgagagaat ctcaaatttc 300
caccttacca caccgaacag tacgggaaaa ccggttggac aacatcgagg tcttgtccgg 360
aaaccgacat ttgataatct gtttgagcaa tacactccga agaaagctga ttatggacct 420

```
ccttgcagaa ccactcaaac ccctgttcga tcagatcgga aagttgagct tggcagtcaa    480
acaccccgca aaaataaggc ttcagccaaa cgcaagctcg gagaattcag agagaagctt    540
tactccgatg ggatgcact ggaattggca ccttctcgtg acctcaatga ttccctggaa    600
ggagattgta agaagctgga tcaagaggac atttcaccga tctaccatac aaaacgtcgc    660
agaagctccg tcattgattt gattcgctcc agtactccga agacggcaag tctcagatct    720
aacttccacg tagaagtccg agagaacatc gattgggatg cagtgcagca gggaaaagct    780
tccgggcgcg gggtaaatc tcgcgcctta cgcaagtttc agagcttcag tcccagcaaa    840
atgcacagct ataagaagcg agatgtgctg caggaaaaat cggtcatagc gaatcgtaga    900
gccccatttc aacggcagga cgccttacgg caggtttccc tggagcaaga tttgtccaaa    960
caatccactc cacaaaaagc acaagaatcc tcattggaca aatcttttga attgcctctc   1020
gagggactca tcactccgtc gaagcaatcc aatctcggcg ttctgctgga cgctccgatt   1080
ttggttcagc cgtcttccga ggcggacttc aaggaatccg accttgagca gcaaatatcg   1140
caaatacctt cgttcgaaga atgtgcctat cctcagactc ccagcaagca aacccttttcg   1200
ttggatgatt ccggcgtcat tcgacatgct cccgtgtgca ctgaggtcaa caagtccatt   1260
ccgtcgattc ttggcaccga atctccatct ttcgtctctc taagcatccc caaaacgcca   1320
acatcaacca acaaatctcg caaccgtctc aagcgtctct cttcgacgaa aaaggacaaa   1380
ccccgtagca agccgccttc gccaatccat cgcgcccagc cattcattcc cggaacgtat   1440
cgtcgtccat cctacgtgaa cgttgagcgt ctcaacattc tcaagtggct caacgagcat   1500
gacaaggatg cgctggggat agtcctggat tatctgaacg acagcgatct ggttcgggtg   1560
gtacgcgttt ccaccgggtg gcgtgacatt atcgaacacc atcggccatc ctatcggcgt   1620
cttcgagcgc attttgctcg ggaaaaggaa gtcaaggaga atctcagttt tccgtcgttt   1680
gtatcgcgcg aaggcagcct cctggggaaa accggaggaa gtctgctgag tagcttcggc   1740
gactcgtcga aggagattgc ggtatcgctt cctcgtcagc cgttcagttt gtgcaactcg   1800
atcgacagca accaatcggt tggcggcgag ctgagacgtt cggggtcggt acagaggtcg   1860
ccaccggtca gcccgtccaa gaggaagttc cgggagaacc agaagattgc atcccatctg   1920
aagaaatcgg aaagactgaa accttgccct cgctgtgaaa agcccagccg ggtggtactg   1980
accaaatcgt ccatcaagct ggccatggcc acgggatcgc tagactcgtc taccacccga   2040
accgtggcca gcggaaagct ggatcgctcc tatacgttac ctgattccct catgggctcg   2100
tcggcgacaa gcatgatcgc cgctgcggca ctcgactgta cctcaaccac catcggcagt   2160
ccccagtcac ctaccaatcc ggatcgcatc cgtaggaatt tgttctcgac cagtttgctg   2220
ccccggtccc agtctgtcga cgcgagaact ccggtgactc ggagtccgcg tcggcgcagg   2280
tccacagatg ttcagggatc gtctgcgtcc ctgctggagc gtaaaaacgg taagactaaa   2340
tccgccgaag cgattcaatg tgattatgcc gtgtgcagtg gcaaaaactg cggcttcatg   2400
ttctgtatta agtgtttgtg tgagtaccat ccgagttcgg tgtgcaagga cttggcccca   2460
aattcgccca gtaaagagga cgaaccggca cacaatgtgg catgtagcaa gcaaagccgc   2520
cgatcgttac tgcgactgcg aaagtag                                       2547
```

<210> SEQ ID NO 192
<211> LENGTH: 6597
<212> TYPE: DNA
<213> ORGANISM: Aedes aegypti

<400> SEQUENCE: 192
atgaataggt taagctttct tttttcgacg cttttcgtga ttgcagcgat tcagattaag 60
atcgagacta acgcgcaggt cgtccaacca gcgcataccc ttccttcaaa cgagcgacca 120
acaagtggtc caacaaaacc cgccaaaaat ggttccccgc cgcttaaaat cccaacggcc 180
aaacctagtc tcggtgacgc gatcaagagc ctcaatgatc gcatcctgaa tgacacggac 240
actccgcagg atatgctcca acacgtccga gatagttcgt tccgaaacgt tttccacgag 300
gcgatcgacg ccaagatcgt caatccggat ctcatcagaa cgctggcttc ggtcggcaaa 360
ccgttggtca atgactacac ccgggacacc ctgctgatcg agtcgatcag ggaagacatt 420
aacttcacat tcgggcctaa tgtcacttgg tgggaaacac tggagctcaa gaagaacgag 480
cagcacgtga tcgtggggtt gagcaatagc agtatcgtta ttctgtttga gcactttggc 540
gagttcaagc tacagcagga ggttctgatg gagacggcgc cgacggcttt cgagatcatc 600
acggtttggg actcggtggc ggagactccg gtcagctgtt tgatcgtggc gaccgagttg 660
cagctcattt ggtacacgat gcgaccggat acgaatttcg ttctgacgga ggagtggcgt 720
tggccgcttt ataagatgac gacgttgatt cggggattca agtaccggga tattcacatg 780
atcttgctgg tggggacgca cccgaacaaa caaaaatccg tttcggcaac tctttatgag 840
ttcaattttg agaagcagca gttttggctt ctgcagcggt tggatcttgc acatgcttgt 900
agtacggttg gactggtgag ggttggacgg gagtttttgg tggcttttcc gcagcatgat 960
aaggccatga tttacactct ggaagccggt gagaaatatc gcggaaggtt caatttggta 1020
gcgaactaca cgtcggagtt ggttcagacg gtgggggctt ttcaggtcgg aaggtatgcc 1080
tatattgcga tcggggggag atcgccacag atcgtgcgct atgccaatgg agtgttcgtg 1140
tcccagcgta ttccaatgga ggcgatggag acggttgagg catactttga aataccgact 1200
cctacctatc gggatgactt cattctgctg gtgcagcaca aaatgctttt ctcaacgcac 1260
gatcttcagc ggttggatat ttttgtgtgg aacggggagt cgtttgatct ccgaagtaac 1320
atcccttgct acgtggaaga cgaactaatg gacaacgaag tttcgtgcat gctggatctg 1380
taccggccga ccggtatcgt cgggtctgcg atcatacttc ggggcaagca ggtttcgatg 1440
atcgttcctc gctatcagac tcattcgacg ctgttcaact tgcgtatcga gctgctgtcc 1500
gcagagcacc cgatcaggca gaagactcag gagatgcggg acacgatcga tgcgtttacc 1560
aaaatcttcc actaccaaga cgaggtgatc agcgaagcgt atgcggcgat cgccgaagcg 1620
gagcagacat atgatgttcc actgctaacg ctgcagaact gttctctggg gacagttcag 1680
gcggacttgg ttgtgcaaga ttcggacttc cggtggccga gcgggaagat catggttggt 1740
aacaggacat ggtcgcatcg tgacacggcg gttgacgttc cagcgatcgc gcgagaatta 1800
gaggcggaga tggcgctgtt gagtgagttg gagcaacagc tgaactacac ggttcgacga 1860
cacaacgata gcttctcgct ggatttggat cagccgttgt acgtgcaggg tcgagtcgag 1920
gtcggaggag ctctggttac ggatgatctg tacgtaaggc agctggaaga agatccaccg 1980
ttgttgcggg tggtccggca aaccggcgat gatggtatgc aggagttgcg ggtcaaagat 2040
ctcaaagttc gtcatctgaa ttttgaaacc gtgaacggaa ttctggcgag tgatctcgtc 2100
tacaatacgg gcgagaagat cgagttggcc aacgcgctgg ttgtgaacag tgtgcttgtg 2160
gcgcaaaacg tgatcttgcc caaaggcgga acggtcaacg ggtagatct gagcgagtca 2220
acggtctatt tcaactgcaa gaatcgtcgg tgggataact tgaagttcga ttcggtggaa 2280
gtgttggaga atgtggtagc tcacgaaacg atcaacgggg tgaagcttga cctggcggaa 2340

```
ttggatgctc gattcaggca ggcaagtgaa gacatgtctg atgtgctggt aacggaaaat   2400
ctacaactag atggaagttt gtacgtccat agcataaatg gcgtaccgtg gagtgacatt   2460
atccatcgaa tcgtgctgaa gaaccgacct aatcggctgg ctgatctgaa gatcaacgga   2520
agtctgattc tgcagaacga caacgtgacg gtttaccatc tgaatgggct ggccttccca   2580
atggattatc tgctctccag cagtccgatg gagtcgatcg tgaccggcta caagaaattt   2640
gtgaacatta cgaacatcga agccatggac gtagaacgca cgatcaacgg agttgacctg   2700
caggacatta tcaccttgca cgacgatcag cacatccctg gtgacgttac catcggtgaa   2760
cttcacgtaa ccgaacggct ggaagtcaag ggagctatcc gcggcaagca cttggatgaa   2820
ttcctggaca acccaacgct gctgcaaacc acgtcgatca aagccgcgtg ccatttcaag   2880
cagctcttcg tcgacggacc ggtgatcgtg gaaggcaatc tcaacggcat ggatgtggac   2940
gcagtgctgt cggatgtggt ctacgacacg gagcacacgg tcacgatcga ggcttccaag   3000
cgaattgctt cggcagagtt ccgcgacaat gtcacgatca gttctaatat ggtcaacgag   3060
ttcaaactgg atcagtttgt gacgcgcagc accgagcagg agctgaacgt tcgggagatc   3120
aacggaaacg tatttatccg cgagttgcaa ttagatgggc tattcgatgg actgaatgcg   3180
acggctttgg atgtgagcgc ggtgaagttg tttggcgatc agtacacgga agcttcgttg   3240
atcttcaaga atcgggagaa tgctctgtac ccggacgtgg aagcaaacga gcttaagatt   3300
atgaaaactc tgaactccaa agcgagaagt gaatacaagg atacggatca agaagaactg   3360
gttctgaccg ggcagattag tctgaaccat ctacatgtag atcatttgct gttgaaggga   3420
tcgagcttag agggaccgtc caaaatgatc aacttggtgc acttaccgac cttcgacaac   3480
cttcgcttca gcttgacgag acctcaacag gtcacagcac cgttcatcgt gaacaaactt   3540
gtcgtgggaa gtcaaatagc ggcggcttac gttaatggac gagacttccg ggtctgaag    3600
gagagcatcg atcgcttgga caacttcaag aaccacctgc tacagggaag tattccgatt   3660
gagaatctcc acgttggagg cgatctgcag gtcaacatgt tgaacgacgt aaactttgat   3720
gcgttggtga agcaagtcat ctggttgaac cgcccccaaca ggataccggg aacgatccgg  3780
ttcctcgatc ctctgatgat cattggaaat ctaacggcac ggggacaggt caacaacgcc   3840
gttttcggag actttttgga agatgtgatc cggaaatcgg caggagtggc ggagtttcac   3900
ggttcaatta cattcatgaa cggtttggta gtcgaaggca acgtcaatac tgagagcatc   3960
aacaatatcc acatgagtga gctggcgttg agaaacgata cgatctactt gcaaggtgac   4020
gtggaaatct tgggagacct tttcgtggag catctacacg tcgagaacca tctgaatcag   4080
gagcccattc agaacctcct gaactcgtac agctatgacg attccaagga cgttcacacg   4140
gtcaaaagtg atatgtacct gtatggtgcc caaatcggag cgctgcacat cggaggaatg   4200
ctgaaccaga taccgaacgt tgacgcccac ttggcatcgg tcatccgcaa ggaccaaaac   4260
tacaacttca ccaagccgct gttgttcaag aacgaagtct tcttcgatca aggtttctcg   4320
gccacctacc tcaaccaaat tgatatttca aatatccagc aagacatcgt tcggatcaac   4380
gatccgaacc cggtagagat cgaagcggaa gtgatcacgt tcgccgaacc catctacgct   4440
gatcagttga ccatcaaagg ggatatgatc actacaaatc tcgttgggtg caatccggac   4500
atctggacga gcacaggaat catgatcaat agggacgccg agatctacgc gaaaacattc   4560
ttctcgccgg gagccttccg tacgaatcat ctccgcgtag actacatgaa cggacaaccg   4620
atgaacagcc tgatcacgct gaacaccgat cagacgatcg agacaacgct gctcattcac   4680
```

gagatgacaa ttacacagcc gatggatgtc ggtggatacg tcaacggagt tacgctaccg 4740
tacgaacgca agaatacgct catgacatac ggcaaccagc gggtccgcct accaacagtc 4800
ttccacacga tccgagtcct tcaatcgctc actctcccac caattctgaa cagtaaaccc 4860
ttcggaccac cggtcgcgat cggacccgaa atgataatcg agtcccccat ttccttccga 4920
catctcatcg ttgatcggct cgagacggaa gacatgatct ccggggtgga cttcaaccag 4980
tggtacgaga acagtttgtg gcgtaagggc cgcgatcacc agaccatcga agcgaagatt 5040
tcagcccgca atgtgcggtt caacggagac gtggaaggcg acggcaagat caacggagta 5100
gacatcgtgg acgtcgtgca gcgaatgaag gccgccaaga agaacgtgga agatcagcta 5160
ctggactacc ggtcggagat gcgatcgttc tgctccaaca ccaaacagct ggtggacaaa 5220
tcccagagcc ggatgtactt cttcaagtac ttcgtgcagc gacaggtgat caatgagcat 5280
ctaccgatcg tgtcgttcca cttcttcgat cacttggggt acaatttcct gggcgtgaac 5340
atgggatgcg agagccactt ctaccaatgg gatccgactg ggaaggcatt cgtgccgatt 5400
ttcaaatatt acacgggagt ggtgcaggaa tggaaccacg tggttaatgg cgaggaagct 5460
atcttcctgg tgacgcgatc gatcactgag cttacgcaat gtgaagttgc gggacttagc 5520
gtgtggttgt tcacgggcgt acagctgcag ctgatttgga atacggtgga caccgcctcg 5580
atgcaatcgg tagctgccga tcctgcgaag tcgacaagct tctatgtact aacgccggat 5640
gttgtggtgg agtacggcgt tgatggaagc actttggagc agtggagact tccaaagagc 5700
gctttgggtt acgaattcat ccccagtaag gtcggacttg gactggcctt aagcgatagt 5760
aagctactgg ttctgctttc gaatgtgaac aagactttcg aggaggattc gactgatctt 5820
gaaatggcgc tgttctcttc gcaatcgctg cacgatcgca tgaaaaagac gtattcggaa 5880
aagctattga attctacggt aagctcagaa gaagtcagcg acattatcca cccagaaaat 5940
atatcaccac tcgaagagca ctcacatttc aacaacgata cggtgatcta tgtggttgaa 6000
ccggagacaa tcgacatacc ggatccaccg gtaagtgaag atgaattgtc ttcggagaca 6060
ccgatcgcca gagacattcc ccacggagga atcctgattg ccgacaacca gcacttcccc 6120
gagagagcca aaggggacgt ggtggcattt tacgctggtc cgcacaacaa gaagcgccat 6180
ctggtggcgg tgtccactgt gattcacaca gtcatccaag gagatcagga cgcgatcaag 6240
atctacaccg acatccagac gggcaaactc taccaggttc taccctgtca ccgtccttcg 6300
catttgaccg ccctggaact gcgggacgag acgatcctcg ccttcctgga agcccggcag 6360
accgtgcaga tctacatcta ccggggcatg cagggtttcg tgcggctgag caacttcaag 6420
ctgacggctc cggccagggc catggccggg gtttcgctgc cgcagccgtt gacgattcga 6480
tgcaagctgc actacctggc gatcgccact gagcagaacg aactgatcat gctacgagcc 6540
aagacacaag gtgactgcgg actgctggtc caggtggact gcgatgatgt ggagtga 6597

<210> SEQ ID NO 193
<211> LENGTH: 7008
<212> TYPE: DNA
<213> ORGANISM: Aedes aegypti

<400> SEQUENCE: 193
atgccggaga ccgatctatt tgattgccag atgtgcgagc tcgcaaataa catcgatgat 60
atggtgcaat gtgagggatg tactaagtgg tcgcattatg gatgcgtcgg ctttgacgat 120
gggaaaaagg aagaaaactg gaggtgtgcc ggttgtattg cgaaatcatc ttccaatagc 180
accggcggag attccaatgt tcaagctacc gacggacagc agaagacaag aggctctaca 240

```
ggaggagcag aatccattag tgatctcgca cagcttaacc ttaaactgtt agaggagcgc    300
aaggccgtcc tgttgaggga gatcgaactg cagcactcaa ctcagttaga acaacgtaaa    360
cttcagctgg agaaggaggc atggcaagca aagtacgata ttctcaacgc gaaatgtgaa    420
tcaaccagta gcacggtagg aagcagcggt ctcggaaact ggataagccg tatgaatcag    480
gtcgctgtca gccagtacca acaaacatcc gtgtcggcaa gtacggtgac gacttcattg    540
aatcccagga tgagacagca gcacaccgct actggagaag gaaatgcgac atcagtagta    600
acgacgtcat cgcgaccagg ctgttcgctg tatggaagcg aatcgacatc ctttcttccg    660
caaattactt ctacgatcgc cttgtctgca aatcaaccat caagtacgta tgcggtggga    720
caagcaacca gttatatggg agacttccaa cctggagtag gagcgaatcg tccgggatca    780
tcgacgccag tgaccagtgt aaattgggtc aacccagggg cgaatccaac cagctccgcc    840
cagtgtttgc caccatacgt cagctcgatg gaacagctag gaggtcatcc gatgccatcg    900
ggatacgtaa gccacccgta ccaggtaacc agtagcttaa ataatttcgc accagtaggc    960
caggtagctt tttcacaata tgctcacagt agcgtagggt cagccgaaaa tcgctacctc   1020
aaaggtttcc gtgagcgagg atccataccg gttagctttc ccatcgatat ctgcttgctt   1080
aaagtgggac gctccgtttt cggtgcatca ctgcatattc ggaaatccaa ggagaactac   1140
aagaaccaaa ccatcgtaac gttctacaag agacagaagg gacagttcca caagtacaag   1200
gagtacttgg cggctcaagc acgacatttc gactgtattt cgcacgcttc gctcgggttt   1260
gtcgccgtgg tcaactacta cgacaatgcg gctaaccaag aattcccgga agctcatcca   1320
gggttcgacg aggggtcgcc cgtgtttcaa attcatgagg acggcaccac tgagattata   1380
caaaagtttc gacaatccaa tcagaatacg gttcacatgt ggactgcggg gaaccatttc   1440
tatctgacgc acacgtacat caatttgaac gaaagcgttg aaaacgtttg ccctctatat   1500
cgctggaccg ggtatcactt cgatgtgatc gatgagctgc cgtgctacaa ttccatcaac   1560
atagaaccgt tctcgatcga gcagaccctg tacatcgcca tcgccaatca gatgaacgat   1620
cagtccgtcg aagaggacac cttttccgac atctttcggt ttaactacga acagcagagg   1680
ttcgagttcc accagaagat ctacgtctac tccgtgtcgg atatagcgta cttcttcctg   1740
gagttgggcg acgttcgcga acactactta atcacgggaa attcgcgagc cggcaaggaa   1800
accgcgatcg ataagcttga ctacgatcag cattcgatcg tgtacaagtt cgtcgaggga   1860
tacttcgtgc cggtgcagaa gatcgaactg caccaggtga agatgttcct gcccgttacg   1920
cacgagaacg gtgatttcct gctactgatc cgctgcaaag gcaagcccct gttgatctac   1980
gagtacgatg gctataagtt tgtaccttcg cgaattgatt acacccggaa tgcctttagc   2040
acgggagtgt cgttcatgcg cgtctatcga cacattctga acaccagtct gatcgtgatc   2100
gccaacaagc aaagctacgg gactacggcg aacctgttca ctcctatcta cggcgttgag   2160
aatgatctcc gggatgtcta cggcagtttt atatcgtggt gtagcgaaac gacccatcag   2220
ttggagaacg tcaatctgga agaggtttat aacaaactgg ctgcgctgcc gaagatttcg   2280
ggtagcggtg caaggttcga gaaggatata gaagtcaagg actcgagtgt ggaaaagctg   2340
aggactaaag ttttacacac gaagcacttc atgttcaacc aagaagcgtt cgattatttg   2400
aacaatgtga atgcacagat gaaggcgttg aagcagaagg cgaagaaact tcgtagcttg   2460
atcgatgaca gcctgaagtt gagtgaagcg atggaagtcc gtggggacgt tagggtaccg   2520
caggtgatcg cggccgacgg attgataagg gatctagaag cgaagaatgt caacgatgag   2580
```

```
cgggtggttc ccagagttgc gaatcaaaca aaacacgaag atgtgatcaa tgtagatcga   2640
ctgatcattg aagacagatt ggcggtaaag ttcttgaacg gctatgccag tgaaacactg   2700
ttgcatacga cagatgatct tcgatctttg gaaggagtag acttgcatgc aaaagcggtt   2760
gaaatacgcg gagagttgtt cgtagataag gcaatcgatg gtgttcatgt gtctgcggac   2820
aatgttctac ttcgtggcgt ggatcaggta ttcacgggaa gaacactacg ggccacgaac   2880
tttacagtgg gtaatttggt ggcaaagcag cttaactcga cggatgttgg gatgatcatg   2940
tcgtacctgg atcgagtatc agagtacgac agcgcacaga aaagaacagt tgaaagttat   3000
ccgaaaaagt tcaaagaaat cagagttcaa gatctcgaag tcagcggtct tgtgaatgat   3060
gttgatatca aatatatcaa caagaacgct ttgaagatcg ttggagatca agtgattact   3120
ggtagcataa acttcgataa tatcgttaca aggaaacttg aaactcccaa caaacgacta   3180
tctggagtag atttgaacta cctagtcatg accgaaccga cgccggatca acaggatttc   3240
actgtacgac aagacgtaca gttcatcaac cctgtgtaca tggagaactt acacgtagat   3300
gatcgcatca accacatcaa cgtggttgac gatcagctgc aggtactgct gaaggaccca   3360
aaggaacctc aactcatcac cggtaccaag tcgttcgaca acgtccagct tctggggcca   3420
atctaccttc agggaaaaat caacagtagt agtttgagta aattgaatcc ggtttctacg   3480
atcacccaag acgtatatct ggaaggcgac tttgtaataa ccggagatgt atcgatcaga   3540
caactgttga acacctccaa catatacgga tcgagcaaaa cgttcaactt ctacgatttg   3600
tatcaccatg gccttccgct aagtgcagct tccgccaatc agaacttcgt cttcaaggaa   3660
cctcttgttg tgcatcacgc gttcgccaac aatctcaatg gtgtcaatcc gagcgacttc   3720
atcccaatac cttccaaaaa actgcagcgc attaccgggc ggaagatatt caacggagat   3780
ctaaccatac gtggtgatcg agttgatgct gccatgatca atgacattga tttaaagcac   3840
ttgaatcgaa cgatactgaa aaagactggc gatcaagtgg ttaagggaac gatccatttc   3900
aaggaattga tcgcatccac cgtagttgcg aagacgactc tgttcgagga acgacctctg   3960
agtacgctcc ttaccgtgaa taccaaccaa cgcatcaagt cgaaggtacg ctgcgtaaac   4020
tgtaaactga cgatccacgg agacctgagc gtcggtcgaa tggaaacgca caacaaatcc   4080
aggctattcg gttatgatct ggatttcctg ttttctgaca cactacacaa aagttacgct   4140
cagcctgatt cgattgcggt aactggcggc aagggcttct acaacgtaac cgttggggaa   4200
ctcatactgc tggatcaagc aaccatcaac ggagtggacc tgattgggct gaagaagatc   4260
aacgatcccc tcgagaagga tgtcattgtg gaggaaacgt tgattttgaa gaatcctcta   4320
cacgtacgca atgtgtactt caacggatcg atcaacggcg tcccggcgca agaattcgga   4380
cgcacgtggc tgttgaacga gtacaaccaa acgttcacgg cgccgcaggt cttcgagcac   4440
gtggcagccg aggggatgtt cgtcgatggg tatttcaatg gagtcaagct ggaggacttg   4500
gttcaggaca tctatttctt ggatcgaagc gaacatctac cggaggctat ctttcatgag   4560
gggattgtct cctatcagcc aatcaccgtc aagggtctcg tttccggttt gaacctggcc   4620
accgacgtgc tgttgaacta ctccccaaat cgtcaatatc tcaaggacgt acgaatcgat   4680
ggtaatctgc ttgtggccaa ccggatacac gtggagcata ctttgaacgg gatgaactac   4740
gctaaactac gggaatacgc aacatctagt ggcgttgaac gaccgatgaa cgtggaggtt   4800
caagggaacg ttcatttcca ccttcaaccg gacgtttctc agcttaatgg gtacagcttg   4860
gaacagcttc atcgggaaat ttggctgacg aatcgagatg aagtgctcac ggggtcatac   4920
cgcttcgaca acgttcactt cggcagctat gttcatacta agggtccggt gaaccagctg   4980
```

gatttggagg aaattgtaca cagctacctg agtgtatcga agccacaaaa cgtgactaca 5040
ccgctggttt tcaagggacc ggtggagctt cagaagatgg caacattcga tagtataaac 5100
ctggaaggac tgctgaaggg agcgaaggag tctcgaggaa taaatatcgt ggactttgat 5160
agatacgtcc tcaagaagaa cgtcgatcaa accattactg gaaaatgggt cttccatgat 5220
gctgaagttt acggaaacct caatttgacc accctaaacg gcctggacat cagacgggac 5280
atcctgttga accacgctga gcaggtaacg ttctctggag ccaaacgaat tgacaacctt 5340
cgagttcata acctccgatg tccggatcca tgcatcatcc aaggggtgga ctttagcgaa 5400
tggttcgcca actctgttcg tctggatcgg aaccataccg tcgagggcgt cacctatctg 5460
gaaggggcta ccatcctggg agacatcgaa tcccgtggcc cagtcaacaa tgttacgttt 5520
gatcctcaga gtttgcttct gaaatcggtt ccacaaacgc tggaaggtac cctgtacctt 5580
aaaaccaaat ttccagaaca caacttgatc taccagtcgt cgatcgaatc tttggaggtg 5640
aactccatca acggcaagga tttcaaccgg tttatggaca atctggcacg tgttgaggag 5700
ggtaaagtaa cgatagatac cccggtaacg ttggttcaga acttgaatgc caagaatgtc 5760
gatacgggcg atagtaagat gttcgatgtg aacatcaacc aacttctgca ggaagtggaa 5820
tacggcgatc agctgagcca atacgaaacg aagttgcgac ggttgcacat ggttggtcaa 5880
tccttggtgg aaacactcag taccaaaact ccttatctga gtcactatca accgataaag 5940
cctttgccgg gatacttccg tagcgtagtt actattacgt taccccttc accaatgccg 6000
atcgagttac tggctgcgca cgtggacgac ggaaatcgta cggccgttga gttctacagg 6060
tggaacaaga aggattcgca gttccatatt gctaaaggtt ttccacccat cacttatccg 6120
acccttcaga tcaccaagac gaaacgaatc gtcttgggtg gcgtgcagaa cctcttcgtt 6180
gaatactacg accacagccg tcatctgtat cgacagtcca tccttgacct cgaagcgccg 6240
gacttcacag cacctaagaa gacaccgaag ttcacctcga tctacgagtt caacagttca 6300
ctacccaggg atattgtggc actgaaggtc ttggatctgg actgcgtcgg actctactcg 6360
cctcacatcg atgggctaaa cgtgtactgc ctccagttgg agaatctggt gtactacttg 6420
aagttccatc aactgcttac cacgcccgcc gtcaatcaag ctcttcacct agacggacga 6480
ttgatcctac tgagcagaga tagcctattg caagtgtggc gaccacgggc cgactacaaa 6540
ctaggtctcc tgcagctaat caaaatagcc catccgactt cgctaaccgt agccaaattc 6600
gagcagcagc tgttcatcgc cattaattcg gaccaggcac tgaccgaggc gtccgcccat 6660
cacggttcca tagagatttg gcgcgatcta cgaccccagc atcacaacag caccttcaac 6720
aagtatcaaa ccatcctgac caagatgccc aagcagatcc agttctcggt cctggcaacc 6780
acttcggaac tgatgctgta cactttgacg gagaatccgt tccacccgtt ggtgatctac 6840
cgctacgagg gtgtggccgg attccgcgaa tatctgacga gcaacgcgct gcgaaccagc 6900
agtaagcggt tcacggtggt caaactggat cgcaaacagc gggaactgtt ggcgttggtg 6960
agcgatcggg aagtgacgtg gatcgaagct gtcataaagg ggaggtag 7008

<210> SEQ ID NO 194
<211> LENGTH: 5673
<212> TYPE: DNA
<213> ORGANISM: Aedes aegypti

<400> SEQUENCE: 194
atgattcttc caaagtggtt actgttgtcg gcgattgcgc ttcaggtggc gtggtgttgg 60

-continued

```
aatggattca gtgatggggg ctccgatttg gatgttctca tgcggcgaag gttggatctc    120
ttatcatccg agcgaaggac taggcaagct ccacaagcgc attcccgtga aactgataca    180
tctcagtatg atttaacatt gcaccgtgtt aaggtgaacc taaaccgtac tgctgctgat    240
catcaaatgt tgttcacacg agttcgaagc agcggaaatc tgtatctcta ctctggcaat    300
caaatctcac gggtcacggt tgccgaaaca gaggttaagc tggtgcctgt agctgcgact    360
tctgatatac acgaggaagt ttcagaattc cagattgagg aacttaaggc aattgacaac    420
aagacgacac tgatagtcac tgtctctctg ccggatcgga tgcatgttta tcaaatatcg    480
ggcaactcga aggggaaagt gttaacagtg aaagctatgc aaaggataaa gcgaccaggt    540
caaacccatc aatcagtttt ggtgcagtcg aaatccaatt tgttcctgat cagcggttat    600
tccgaagcac gtttcggaaa agtggtaatt tatcgttggt tggacttcca tttttcgttg    660
cgtgatgtca aggaagtgga tcgctgtgac aagcttttgg tattcagtgg tgatcaactc    720
gttattctcg tactggaaat ggctgaatat ccggaacgat cagtgaataa tattttcatg    780
cttaacgatg aattcaagtt ggttaaaacg caagaaatgt actttttgtt cgatcgacta    840
ccgcattatg aggtggaaaa tcagttctac attctgcgat gtcttgcgtt agatacgtgc    900
tttttatatc gatggaatgg tgagagcctt tttcgtcgag ccagcaaaat atcatacgat    960
cccaggaaca tcgacatcat ggcctcgggt catggaatga tagcaatgtc cctcgaaaga   1020
acactctact tctacgacaa tcagcccctg ttgaaaattg ctgcttcgta cgctatcgta   1080
aacagacgcg gcacagttac ggataaacct ttccagctcg atccacgagt tagcgacatg   1140
tttctttaca aggaggaagc aacggaaaaa ttgtatctct gcatcctgta caactctggt   1200
gccaaattgt tggatatggt cgagatacag ttgaataaag gaagaagcgc gcccagtcca   1260
ggtgagcagt ccaatttcaa cgctcttaaa acgtgccttt tccacatgaa agatttggcg   1320
aatattcgta aaaagtggat tgatttaatc aaataccaac tgagcaaaac gctgcgcagc   1380
tgcaaatcta caggtgtgct ttcgctggca tccaaagtgt tttagctga atccaataaa    1440
gttgatcgca tagaagttga cggaaatatc gaaaactctc cccaggatct attgaaagag   1500
tggagttcga ctaaaaaaag tttagctgaa atgcattcgc agtcgcaaaa tttgttctat   1560
ttgaaccgga tgaatactgt gcaatctaat atgaaaattc aaggaaattt gcgaacaaaa   1620
tcgacacgaa tgaaacacgt taaggtacac catcctcatt caggccgacc tgcttatgtg   1680
cgacccaaaa gggatctgca atcttcaaga gtgatcacct ccgccattgt caacgccaga   1740
gaagtagtat acaatggaaa aatgtttgct tatactctaa gtcgtaacaa cgtgaactac   1800
gtttcatctc ctgtccatgt tgcaaatcta catacgcaaa acgtgcacat cggtttgaat   1860
accattaacc gaatcccagt ggatcaaatg ttgtacaacg ctaccgataa attcgtagaa   1920
aaaggacaca aagttttcaa agcgatagac acaaatactc tcaaagttta tctcgtgaat   1980
ggggagaaaa caacacagca attctctagc ttgcgaaatt tcgtcgtaac ggccggatct   2040
gaagctcctg tgaaattgtc tggggcacgt ggcgtcacaa atttgatcgt cggtggaaag   2100
ctgaataacg tatccttaga tgatctatta catcagttat attacgtgga caaaaaatcg   2160
acaatcaacg gtaacgtttt cttgcgtgca ccttcataca tccgtaatgt atatgctcga   2220
agtctgaata gtttccctac cagcaacatt ttcgatttga ggacgaatca aacaatttct   2280
gccgttgtac atctctctca agtgtacgcc cgaaatgtgt atagtaaaac aataaatgga   2340
ataaacattc ctaaagatgt cgcactaata agctctgcga aaccattaa agcggcagtg    2400
gcatccaact tcgtcgtcaa gaaagatctc acactttccg ccgaagacca gcactttacc   2460
```

```
aaacatgttt tgggcacaaa ggtggaagat ttctcccaaa tttactcagg acgtgtttat   2520
ctgaaaggat ccctcaagtt gaaacagctt aacctggaga atcaaaaaag tcaactggtt   2580
ttgaatggtt tcacagccag tccggatgta caaaaccatt tctggatgaa acgtgtcgaa   2640
caggatatag gtaccttcac gttcaatcgc aacgttaagg ctagccatct ggtctgtgca   2700
aaactgaatt ataatccaac ggttagctat ttgaggggtg accattggcc atcgcatctg   2760
aaccttgaaa tgtcgaatgc ttatgtccga ggattcataa aaacctatgc taccaccccc   2820
actttcttac aacacatttc cactgaagcc gttctgcgtg gatccatgtc cactgtgtca   2880
ggccgtaaag tcttcactgg tcagcttcat accgatacct tggttgcaga tggagtcgat   2940
gcaatcaacg ttcaaagctt ggcaactgac ttcagcacta tggcgttcct agacggagtc   3000
aaagaaattg aacatttctc atcagaggaa tgttatatcg agctgctcgg tggattgaca   3060
ttgcaagagt accagaacgt ctccttcaac gctatagtgg agagcactgt aaatacgcac   3120
aacccgcaaa ctctggagta tttgtttctg ccggatataa aagttgaaca tttccgagca   3180
gcgctgatca atggagttaa cgcagaagat ttcataaccg aaatagataa ttttacgtat   3240
cgtgtagatc ccttcgcggc gcaatttaaa atcgataacc tcattgttaa gaaaaacgtg   3300
atttccacca gccaaatgtt catggactat ttgaacacaa tcgctgtgaa ggaatatttc   3360
aaactgctga ccctaaaggg tgatagtgac aaagcgcagc agtgggaaat cggaggcagc   3420
aaaaccttgc agaaaggcat ggccgtcgat ggaaaattga atgtggttca cgtaaatcgg   3480
ctaatcctag ttaacatact ctataattct gccaggaaaa caggtcctat gaatattgcg   3540
ggattatgga acataacgaa actggcgacg aagtacttgg cgaccaaaca aataaacgat   3600
ctaccaataa aacatttgca gaattccaat ttgaaaagct tcaaaattaa acacgacatt   3660
tcggttggaa cattggcgat ttctgcgaac atgcatggtc atctgtttcc aaatagttca   3720
tcagtttcga tgcccccaaa tatccagatg ctggccagtt tgactgtcca tggatcgttt   3780
ttgctggaac attggaagcc tggaacactc ttgttcgatg tgatgttatc agccgtaact   3840
ggttcaacga atgtttttga taagaagctt gttttccgag gacaccacgt tgaaattgag   3900
aagttacgaa acgaaggcaa aattttcagc aagagctgca attttgtcaa tttgctaatg   3960
gactcagtga agagaagaca acccaatctc gtattcagca gtctcggaaa aacgttcagg   4020
gaagtggttt gtcttggatc agtggcatct aatgatttag ttaccgcaac gctggtgaat   4080
ggaatcgatg taattcattt gaataggagc attcactcag ttggtcacca ccaggaaatg   4140
attaaatcga caaagtactt tgaagaagaa gtgaaggttg tgcagttgct ctgtcatgac   4200
caactggtgg acggtattta tcctagcaat ttggaccttt actcggacgc aagccagatg   4260
gtcaagaaac ggtatcagtt tgaaaaaccc atttcggtca tcgggaattt gtacgtcgat   4320
gcaatcaacg atttctcgtt gcaacacttc ctggcgactc gcgtggtgaa aaataggacg   4380
tatacgcagg aataccatca ggaaaagtct caacaagtaa caggatttat cacattttcg   4440
aacctggttt tatccggtga atacaacaca gttcacgtag tcaacggtat tcctgtaagc   4500
gagattgtat ccagatcgtc caatgagcat caggttatgg ttgagacaaa gcatttgaca   4560
ggcaccattc agcttattgg acctacatcg gtcatgaagt gtaacaacgt ctctttgttg   4620
gatgcataca aatctagctt taaagccaat tctgcagaga ttgctttcaa agacttgatt   4680
tttaattcta aaggtgtttt gcaaaatggt ttgaccattg aaaacaagct gaatggagta   4740
tcagtgcaga aaatgatgaa gcttcggcta tcgtcggtag aggagctgct gccattgatt   4800
```

```
ccaataatcc aagagcagat atcggtctcc aatagagcat acctaaccaa caaaccaaag   4860
gatttacaca tgttgtacat agaaaatatt ccgctggatg aaagaggcac catggtcgga   4920
aagagcgaag gtcaacggac caatgaagca tctgatactg ttaatttcga gaaatcctgc   4980
agtaatggca tatatcgttt caacgttact attcggcaga aatcgtccaa cggagatata   5040
agttctgcca gaaccgtatt ggatggagtg atgataaaat ccgattggat ggaaatagca   5100
aataacggcg aaatacaaac aatagtcgtg tcacaagtcg aaaagaatgc caagtacttc   5160
ctacttcttt acgtcaatcg caatggagaa ctcagtgttc aacaggaact tccattaagc   5220
tcatcggcgg ctgtattcta cttcgtacac gtaaacgatt cagcactttt gctggcagta   5280
tcagattcac accccttca actgggccat ttggcaccga aactcaaact attccgctat    5340
gatccggatg taatgcgctt cgtacatttc aaaacgctca gtggccatta caatgacgtt   5400
gttgctatcg atgtcgagga cgttataatg tttgcagttt cagagcaagg ttctaacatg   5460
gtggaaatat ttgtgctgga ccgttcctac tcggcgttat tccaaaagct tatcttcgat   5520
tcgactttgg cgtcaatgaa agcgttcaaa ttacaaggat ccccagttct acagatatca   5580
acggtcgata atttggtcta cgtttacaat tacagtattc ttgagggctg gcggcagttg   5640
tcgtacggca ggattccgtc tgacgtgaac taa                                 5673
```

<210> SEQ ID NO 195
<211> LENGTH: 5415
<212> TYPE: DNA
<213> ORGANISM: Aedes aegypti

<400> SEQUENCE: 195

```
atgaatgttc cactcaacat ccaaaatctt tccggaaaaa gaacaagtga cgatccggat     60
ctagaaggag ctcaactggt gtgtagcttc gtgggaccat cttccacgga gaaaccttta    120
gctgggaatg attcgatgat gttgcaatca tcacaggaat tgtttgtgag cagtacgagg    180
gctcgtggcc accatcggca ctgtcctcga ggcaaggttc cctgtgcaga tggcattcag    240
tgtgttctga gttcacattt gtgtgactcg cgggtggact gtttcgatgg aagtgacgaa    300
tcgcactgct cgtgtttgtc acggttggcg gacaaacggc gctgtgatgg ttacgtagac    360
tgtcctctcg cggaagatga gatgggctgc ttcggatgtg acaagttctc gttctcgtgt    420
ttcaatacgt tttttgagta tcaggcttcg catcattccg agacaaggtg ctttacgttg    480
atcgagaagt gtgatggctt caacaactgc atgaatcgga aggacgaaca ggattgtacg    540
atgttggtgc gagacttgag aagtcccctg gcgtttgcgg ttggccattc agtgggtgtc    600
ctgcatcgga actacaaggg taagtggtat ccggtttgtc acaatccgtt gaatctggca    660
cgagaggctt gtgaagcaga acttggacca gcggatcgcg atccggtgat tctgcagcac    720
catggagatc taccgggacc atttattcaa ccaagtccac gaagtcatca cgtgttccaa    780
ccggagttca ccgatacctg taacgggttg atcaactacg ttaagtgtcc ggcaccgaag    840
tgtggatcca gcaagcagaa cgagatggaa aatcttcgta ttaaaatccg tggaaagaga    900
aatgctacag agttagtgca gatcgttggc ggaacgaaag ctgaaccggc tgcttaccct    960
tttattgtgg gaatattcag agacgggaaa ttccattgcg gtggtagcat cttcaacgaa   1020
cgttggatcg taacggcagc tcactgctgt gacaacttcc caaggcacca ttacgaactg   1080
cgagcgggtc ttctccgtag acgtagcttc tctcctcagg tgcaggtttc aacggtaacc   1140
catgtgttca tacaccgagg atacagcgcg caaaagatga tcaacgacat cagtctgatg   1200
cattcggaca ggcctttcca gtacaaccga tgggtaaggc cgatctgtct acccgaccga   1260
```

```
cacatgacta ccaacgatcg ggattggatt tggggtccga aaccgggaac gatgtgtacg   1320
gctgttggtt ggggagcact cagggagcac ggtggatcac ctgatcattt gatgcaggtt   1380
acggtcccaa ttctaccgtt ctgtaaacat aaaaatgatc gcgatggact cgctatttgt   1440
gctgccgaaa tgagtggagg tcacgacgcc tgtcaaggtg actcgggagg tccatttgcc   1500
tgcattagtg tctccagtcc acatgagtgg tatctggcgg gagtggttag ccatggagag   1560
ggctgtgcta gaccaaacga gcctggcgtc tatacgagag ttgcactgtt caacgactgg   1620
atccaaagga aaactaggga agtgcttact tcgtcctcta cgcggcagga ttgtcccggc   1680
ttccagtgct cagttggggt atcgttctgc ataccgcggc agaagcggtg caacgggaag   1740
gtagattgtc ttggtggaga agatgaacta agctgttcgc tggatcaact gctagctgaa   1800
tcgatacagg aaacaaccat agcgacgaca ccaaagaata gtactgcgac aagttcaaca   1860
actgctgcag ctactacaga agctgtcact tcgaagatcg atttcctcgc ggagaattct   1920
gaagcatcgg atcctgctac taccgtgacg gaagcatcaa gcactgaaac tgctaatatt   1980
gaaactatat tgacaactat tgagacagta tctgctaaag atgtaagtga tggtattttc   2040
caagtatcaa ctgaggcaac tacagtggaa ataaatacta ccttagatat tagcagttca   2100
tcgcaaaatg tttcagcttc accagaaaaa gttgaagaat caacagtgga cgaaaccact   2160
tcatccacaa ctgaaacaag cttcacacat ccaacaacga ttgaatccga aactacagct   2220
gacagtgtaa ccgctctcat gtcggaaact acctcgccat ctctaccacc aaacgaaaac   2280
aacactacag tggactacac tgtcacaaga tctactgatc aaacaacaaa tacacctttt   2340
acaatatccc ctaccactga ttccttagat gactcatctg ctgcttactc atcatctgca   2400
aacgattcag aagtaaatca cagtacaacg atagaaccca agaacacaga aagtagcgta   2460
catgcaacga cagttataga actgatctcg gttgaatcta ctaccaatat cgaagcaacg   2520
tccttagcgg atccctcaaa tgcgtcaatc acaacgctat cctccgattt ggtcgaagaa   2580
acttcatcct cgtcaacaac cccgtccact ccagattcta cttcatcaac tcaacctgat   2640
tcctcccaca gcagcacctc aagcgctcct tggatgcaga ttaacgaagc tatcgcaaat   2700
ttgaaacctc gtccacctag cacggatcgc gatatggaga tgcgtcaact ggaattgggc   2760
gacagcgtcg cagcgactcg aacagacaac accacgtcga caactatctc tacagctccc   2820
agtgctgcaa ccgattccac cagttccaca ccgctgtcaa ccaccacggt ggaaagttcc   2880
agcacgaccc acggcgatct ggaacacagc gaaactcaaa tcgagcccgt tgaagccgaa   2940
gcgaccaatg cttctgtgga ggagcatcca tttttgcgcg aaattcacaa tctggtggag   3000
gagaaaaccc gtcggttgaa ccagttccgg ttgtccatgc actacctgca cacatcgctg   3060
aggaaccaaa cgcaggacgc gaacgaaact tcctaccaat accggcggtt caagtgttct   3120
aaaatccgac aatcgatcaa cattgcgcac cattgcgatc ggatcatcga ctgcgaagac   3180
ggtacggacg aattgcggtg cacgtgtcgc gattacctga aggataagta cgacttcctg   3240
atctgtgacg gcaaaacgga ttgtttggat ttgaccgatg aagcagattg cttttcttgc   3300
acggctggac agtttccttg ccgaatgagc aaagtctgca tcgacgagaa gaagctgtgc   3360
gatgcgattc cggattgtcc tctgcatgaa gatgagctgg attgtcttgc cctcacggat   3420
ggtcacaagg tctactttga tgcgaacaac ctctcggaat tcaaatacga agggctggtc   3480
actaagaaca ctaacggaac gtgggatctg atctgtggag cggagatcaa taacaaatct   3540
gtggaatcga ttggaaaaat ctgctctttc ttgggatttg ctgggtacga aagctactat   3600
```

caaaccgtcc taacaccact ggtgaacgaa acggtggatt tggatcatca gccgctgctg 3660
atcatgtcgt atcgcaatat ctcatcggag ccaaactgta aggccctcca tataacctgt 3720
gcgccattca tcaatgctac tgaacatgag atcagtcact tcgagaacca acataaggaa 3780
caaccagtgc aagtcaacat tcgtccaaca catccgatac agaatatcac ctctctaacg 3840
cacatcacct tccaagaaaa cgctcacatc gagttcatcg agaacttcgg cgatgactac 3900
gattggccat ggaacgccga catctacctg gaaggagtgt tcctgtgcag tgcgatcatc 3960
atcgaggtca actggatcgt ggtcgacagt tcctgcatga ggatgatcaa tctgaagaac 4020
gattacctct ccgtagtggc cggtggagcc aagtcatatc tgaagatctc cggaccatac 4080
gaacaggttg ttcgcgtgga ttgttatcac tttttgcccg aggcacgcgt tgtgatgctt 4140
catttggcga aaaacttgac cttcaccagg catgttctgc cgacattcat tccggaaaag 4200
aactataaca ttacggataa ccaatgcctc gccgttggtc aggacaagta tggaagaacg 4260
cgtacgttac gagtccacat gaacatgacg aattgcgaac cagaggacca tatctgttat 4320
cagctaaatc cagataacgg catataccat gcagatcact gctataccga aaatgcatca 4380
cgtactggag tcgtcgtttg taagtctaag gtctcgggat ggtatccagt gggcttctat 4440
cagaacaagc acggcctttg cgggttcaac gaagtcgtca aaatgatctc cctgaaggaa 4500
ttctacactg acattcaaca tgttttgagc cataagaaat gtgactacga atttcctgag 4560
ccgctttgcg atggagtgag gtgttggcat gggaaatgta ttggccattc tttggtttgt 4620
gataacaaaa tggactgcga cgacaacttt gacgagcgtc ccgaagcgtg caatgccata 4680
aacgatacgt caactgcctg tctaccgacg cagttccgtt gcgggagcca tcaatgcgtt 4740
gataagagca agttctgtga cgggcgaaac gattgcggtg atttgtcgga tgagccacac 4800
gaatgctctt gctacactta tctcaaggta accgatccat ctaagatatg cgatggcgtt 4860
cgcaactgtt gggacaaatc tgatgagaat ccacgactgt gcaagtgtgc aaaaacgagc 4920
ttcagatgcg gcgacagcga agtttgtatt ccttacgatc acgtctgcga cgacgagatc 4980
gactgccccg gagaagaaga cgaacgatac tgctatgctc tacagcagaa tccagcggag 5040
accaactacg gtgaagtgat gcaacaaagc tacggcatct ggcactcaaa gtgcttccct 5100
aaggacgata aatacgacga gcaaacgatc aaggaaatat gtcatcgcgt cggataccaa 5160
caggtccgga aggtctacgg cagaaaggtg cttccggagt cacgtctgag aacttccaat 5220
cggacacatg atcccgtcga taggttacgc ggcgcagcaa ccaaggcagt tgcgttcaac 5280
aaattcttca aagtgaatat caacgaaaaa caagcgatct tcatgaaacc cagtaggccg 5340
ttgtacactc tggtcaactg ggatgccgaa gacgagcaga agtgcgatcg gttagagatc 5400
aactgtggag attaa 5415

<210> SEQ ID NO 196
<211> LENGTH: 774
<212> TYPE: DNA
<213> ORGANISM: Aedes aegypti

<400> SEQUENCE: 196
atgaagaaac aactgctgtg gatactttct gcgctgatag tcgctgccgg agatattggc 60
gaacgagtgg atgagggtga tgttaccaat tttgacacat ttttgggcgc gtaccagaag 120
aaatacaaag ccaaataccg aatggaccga agaaagaggg ctttcaagaa gaatatgcag 180
gaaattgaag agcacaatgc taattacgag caaggcaaaa gcacattcca gatgggggtc 240
aacgaactgg ctgatatgga caaaagcagc tacctgaaga agatggtccg aatgacggac 300

```
gcgatcgacc accggaaatt ggacgtggac ttcaacgacg aaatgctaca agccacgaat    360

gccttcggcg aagaatttgt gcaagccaca cagaacagca tgccggacag tttggattgg    420

cgcgataaag gattcaccac gatggccgtc aaccagaaga cgtgtggttc ctgctatgct    480

ttcagcattg gacatgccct caatggacag attatgcgcc gtattggtcg ggttgagtat    540

gtcagtaccc agcagatggt cgattgttcg accagtgccg gcaataaggg atgtgctgga    600

ggatctctaa ggtttacgat gcagtacttg cagaatagcc agggtatcat gaggagttca    660

gattatccgt acacttcgtc ggtaagtatc attttcaggg tgttgttggt tttcctttct    720

catttcctgc aggccagagc agtaagcagt cggagtattt ccaagaagag gtaa          774
```

<210> SEQ ID NO 197
<211> LENGTH: 1653
<212> TYPE: DNA
<213> ORGANISM: Aedes aegypti

<400> SEQUENCE: 197

```
atgtggaaat cgtcggtggt gtgtttggcc cttctggggg tcctggggtc ggttagcgga     60

acgacgaaac tgcaggaacg ctacagctgg cgtcagttgg actttgtgtt cccgaaccag    120

cagctgaagc agcaggcctt ggccagcgga gactacgtgc ccacgaatgg actcccggtc    180

ggaatcgaac gctgggagaa caagctcttt gtgtcggtcc caagatggaa ggatggtatc    240

ccgtccaccc tgaactacat cgatatgaat cagaccccgt ccgggtcgcc accgctgatc    300

ccttacccaa gctgggccaa caacgtggcc ggagactgtc agaatggcct gtcgaccgtg    360

taccgtatca aggctgacaa gtgtggacgc ctctgggttc tggacaccgg taccgtcgga    420

atcggaaaca ccacccagca gctgtgcccg tacgcgttga acatctttga ccttaagacc    480

aacacccgtc tgcgtcggta tgaactgcgt gccgaagaca ccaaccagaa caccttcatc    540

gctaacattg ccatcgacat gggacgcagc tgcgaggaca ccttcgccta catgtccgat    600

gaactgggct acggactgat tgcctactca tttgagaaga acaagtcctg gcggttcgag    660

catagcttct tcttcccaga tcctctacgc ggagacttca acgttgccgg tctgaacttc    720

caatggggtg aggaaggtat cttcggaatg tcgctttccc ccctgcaatc cgatggcttc    780

cgcaccatgt acttctcccc gttggccagt caccgtgaat tcatggtctc cactcaggtc    840

ctgcgcgacg aagaaggtgc cgaagagagc ttccacaagt tcacctacct gaaggaacga    900

ggacccaaca gccatactac atcccgagtc atgagcgaaa ccggactgca gctattcaac    960

ttgattgacc agaacgccgt cggatgctgg cattcgtcgc tcccttacag ccctgaaaac   1020

catggaatcg tcgaccgtga tgatgtggaa ctggtcttcc cagctgacgt caagatcgat   1080

gccgaagaga acgtgtgggt catctccgac cgtatgccag tgttcctcat cgccgagctg   1140

gactacagtg atgtcaactt ccgcatcttc accgctcctc tgagcactct ggtcgctgga   1200

accgtctgcg acgttaggcc ttcgctccga ccaggtgcca tccagtccaa attcggtgga   1260

tccgatctgt ccacctatcc aggcaccacc cttctcccag ttggctacac tcaacccatc   1320

agctataccc cgtcctcgta cgccccaacc gttgcccctg tcaccaagta cacagccgct   1380

ccagcgtacg atcacccaac ctcccacatg tacacgaccc aggaatatcc gacgaccgcc   1440

aaggcgtacc acttcaacaa gtaccacaac gtagagtacc aatcgcatgg aaatggtcaa   1500

gctgactacc acttcggaca cggtggacac taccacgatc acgaccacgc ccatgaatac   1560

ggtcacgatc acggatacta cggcggtggt caacgccgtc attggggagc tggcgccaag   1620
```

aagcccgaag cctggaagca gcagctgtac tag 1653

<210> SEQ ID NO 198
<211> LENGTH: 1119
<212> TYPE: DNA
<213> ORGANISM: Aedes aegypti

<400> SEQUENCE: 198
atgcgaggta acatcctttg gctgttggct gcagtgacgc agctgacggt gaccagcgtt 60
acggcgttcg cgaacaattc aaatgctatc tacacctggg aaggtggccg catcgagtgg 120
ccatgcccga cgacaaagcg attggttaag gctgctgcaa agtacactcc taaggatatc 180
atcgcaatgg cttgcgcaag aagtggcgac aagaccctct gcgcgatgcc aagataccga 240
aatagtattc cgataaccct gggacaaatc tacgcaacaa aaaagggttg tgacgtcaag 300
ttcgaacctt tcccgtgctg gactgagcaa gaagagaaca actgcaattc gctacagtcg 360
gttattgaca tctacgctac cggtgacttc gtgtgggttc tggacaatgg tatacttaat 420
gcattgagaa gtcctattca aagatgccca gcgaagatcg tggtttatga agccaaaacg 480
gggaaaaaga tgaagacgat aaaccttggc cgatacgtga ccgagaagtc tcgtctccag 540
tatatgcagg tcgagtgctt gaagggtggc caatgtttcg tgtacatcag cgacgctgga 600
aacaatgcaa ttatcattta cgacgtgtct ggaggtcgtg gctatcgtgt agtactgccg 660
aaagctgtgc atcacggatg tagattccgc gacgttctgt acattttctt gtcgtatcac 720
aaggatggaa caaaactatt tttcacctat ctgggtggac gacgactatt cgccattgct 780
acggatcacc tacgaaaagg tcatggcggt aacattgaag atatcgggga aaagccaggg 840
tccttcattt acatcggacc agacggagca acaggtgtgt ttttcagaga ggaaggcgat 900
agcaatgtat tcttctggga cacaaaaaca tgtctcaaga agtcgaactt caaactggtg 960
ttcaagagca gtgagggatt atatgcaacg gatgtgttcc cggaccatga aatcaatcgg 1020
ttccttatat tggagtcaga ttttccaggt tatatggagg agaaagctgg atgtggtaca 1080
ctgcatcaga tctccctgct tgacggggct acttgttaa 1119

<210> SEQ ID NO 199
<211> LENGTH: 747
<212> TYPE: DNA
<213> ORGANISM: Aedes aegypti

<400> SEQUENCE: 199
atgtgggccc tcgactcagg catttgcaac tctttggagc aacccataaa acgctgcaca 60
gcaaaggtga tagcgtttga cctggaaaca gataaaacag tgaaaacggt ggatctaagc 120
gacattctga agccacactc cagaccacag taccttgtga cggattattc gcccaatgga 180
ttcccgtacg tctacattag cgacgctgaa ggtgccatca tcgtactgga catccaccac 240
aacaagatgt accgagtggt gctaccacgt gccatttctg ctggctgtgg cgaatcggat 300
gtcctatatt tactgctggt acgaagaccc aaaaaccaaa acatggtcat attctcgtat 360
ctgtgcggaa acaaggtcta cggtatcaaa tcggaatttc tgcgcacggg acgaggctcg 420
agtgctatcg tagagctcgg tagcaagact aagcattctg ttttgctcgg gacggacgga 480
agcaacggtg ttattctgag gtatagaagc gaaagcgaac tctacaaatg gaacactgat 540
caaccgtaca aggagtgtaa cttcgaattg gttcaacttg cggaggagtg tcgcttgagc 600
acgcatgtcg cccctggagg aaaagatgct ctgatgtact cattgtcatc caatgtggcc 660
gattacttaa atcacacctg tggcgcagga ggtgcttcag ctcgactcaa atatataagt 720
aaagaatgtg aagatgattg ttattaa 747

<210> SEQ ID NO 200
<211> LENGTH: 257
<212> TYPE: PRT
<213> ORGANISM: Aedes aegypti

<400> SEQUENCE: 200

Met Lys Lys Gln Leu Leu Trp Ile Leu Ser Ala Leu Ile Val Ala Ala
1 5 10 15

Gly Asp Ile Gly Glu Arg Val Asp Glu Gly Asp Val Thr Asn Phe Asp
20 25 30

Thr Phe Leu Gly Ala Tyr Gln Lys Lys Tyr Lys Ala Lys Tyr Arg Met
35 40 45

Asp Arg Arg Lys Arg Ala Phe Lys Lys Asn Met Gln Glu Ile Glu Glu
50 55 60

His Asn Ala Asn Tyr Glu Gln Gly Lys Ser Thr Phe Gln Met Gly Val
65 70 75 80

Asn Glu Leu Ala Asp Met Asp Lys Ser Ser Tyr Leu Lys Lys Met Val
85 90 95

Arg Met Thr Asp Ala Ile Asp His Arg Lys Leu Asp Val Asp Phe Asn
100 105 110

Asp Glu Met Leu Gln Ala Thr Asn Ala Phe Gly Glu Glu Phe Val Gln
115 120 125

Ala Thr Gln Asn Ser Met Pro Asp Ser Leu Asp Trp Arg Asp Lys Gly
130 135 140

Phe Thr Thr Met Ala Val Asn Gln Lys Thr Cys Gly Ser Cys Tyr Ala
145 150 155 160

Phe Ser Ile Gly His Ala Leu Asn Gly Gln Ile Met Arg Arg Ile Gly
165 170 175

Arg Val Glu Tyr Val Ser Thr Gln Gln Met Val Asp Cys Ser Thr Ser
180 185 190

Ala Gly Asn Lys Gly Cys Ala Gly Gly Ser Leu Arg Phe Thr Met Gln
195 200 205

Tyr Leu Gln Asn Ser Gln Gly Ile Met Arg Ser Ser Asp Tyr Pro Tyr
210 215 220

Thr Ser Ser Val Ser Ile Ile Phe Arg Val Leu Leu Val Phe Leu Ser
225 230 235 240

His Phe Leu Gln Ala Arg Ala Val Ser Ser Arg Ser Ile Ser Lys Lys
245 250 255

Arg

<210> SEQ ID NO 201
<211> LENGTH: 1376
<212> TYPE: PRT
<213> ORGANISM: Aedes albopictus

<400> SEQUENCE: 201

Met Glu Glu Ser Gln Gln Leu His Phe Pro Gly Arg His Asn Tyr Asn
1 5 10 15

Gly Val Gly Val Gly Ser Asn Asn Asn Asn Lys Pro Leu Asn Val Ser
20 25 30

Gly Gly Ala Asn Asp Gly Gln Leu Ala Asp Ser Gly Tyr Thr Ser Tyr
35 40 45

His Ser Ser Ile Asn Ala Ser Cys Ser Val Ala Arg Ser Val Leu Ala

```
    50                  55                  60

Thr Ile Glu Glu Asp Asn Glu Ala Asp Ser Ser Phe Glu Glu Ala Arg
65                  70                  75                  80

Ser Ser Glu Asp Ile Phe Gln Phe Gly Gly Ser Asn Val Leu Thr Pro
                85                  90                  95

Thr Thr Ala Ala Ser Ile Glu Arg Ile Ser Asn Phe His Leu Thr Thr
            100                 105                 110

Pro Asn Ser Thr Gly Lys Pro Val Ala Val Gln His Arg Ala Leu Val
        115                 120                 125

Arg Lys Pro Thr Phe Glu Asn Leu Phe Glu Gln Cys Thr Pro Lys Lys
    130                 135                 140

Ala Gly Phe Gly Ser Thr Gly Thr Pro Val Arg Ser Glu Arg Lys Leu
145                 150                 155                 160

Glu Leu Gly Ser Gln Thr Pro Arg Lys Asn Lys Ala Ser Ala Lys Arg
                165                 170                 175

Lys Leu Gly Glu Phe Arg Glu Lys Leu Tyr Ser Asp Gly Asp Ala Arg
            180                 185                 190

Glu Leu Ala Ala Ser Gly Asp Leu Asn Asp Ser Leu Glu Gly Ala Cys
        195                 200                 205

Lys Lys Leu Asp Gln Glu Asp Ile Ser Pro Ile Tyr His Ala Lys Arg
    210                 215                 220

Arg Arg Asn Ser Val Ile Asp Leu Ile Arg Ser Ser Thr Pro Lys Thr
225                 230                 235                 240

Ala Ser Leu Arg Ser Asn Phe His Val Glu Ala Arg Glu Asn Ile Asp
                245                 250                 255

Trp Asp Ala Val Gln Gln Glu Lys Ala Met Gly Gly Leu Arg Lys Ser
            260                 265                 270

Arg Ala Leu Arg Lys Phe Gln Ser Phe Ser Pro Ser Lys Met His Ser
        275                 280                 285

Tyr Lys Lys Arg Asp Ala Leu Gln Glu Lys Ser Val Leu Pro Asn Gly
    290                 295                 300

Arg Ala Pro Phe Gln Arg Gln Asp Ala Phe Arg Gln Ile Ser Ile Glu
305                 310                 315                 320

Gln Asp Phe Ser Lys Gln Ser Thr Pro Arg Lys Ser Ser Glu Ile Ser
                325                 330                 335

Leu Asp Ala Ser Phe Glu Leu Leu Pro Glu Ile Leu Ala Thr Pro Thr
            340                 345                 350

Lys Gln Ala Asn Met Asn Val Leu Leu Asp Ala Pro Ile Leu Leu Pro
        355                 360                 365

Thr Asn Ser Glu Ala Ala Leu Lys Thr Leu Asp Leu Glu Gln Gln Ile
    370                 375                 380

Ser Gln Ile Pro Ser Phe Gln Glu Cys Ser Tyr Pro Gln Thr Pro Ser
385                 390                 395                 400

Lys Gln Thr Leu Ser Leu Asp Asp Ser Gly Val Ile Arg His Ala Pro
                405                 410                 415

Val Cys Thr Glu Leu Asn Lys Ser Ile Pro Ser Ile Leu Gly Thr Glu
            420                 425                 430

Ser Pro Ser Phe Val Ser Leu Asn Ile Pro Lys Thr Pro Thr Ser Ala
        435                 440                 445

Asn Lys Ser Arg Thr Arg Leu Lys Arg Leu Ser Ser Thr Lys Lys Asp
    450                 455                 460

Lys Pro Arg Ser Lys Pro Pro Ser Pro Ile His Arg Ala Gln Pro Phe
465                 470                 475                 480
```

```
Ile Pro Gly Ser His Arg Arg Ser Tyr Glu Asn Val Glu Cys Leu Asn
                485                 490                 495

Ile Leu Lys Arg Leu Asn Glu His Asp Lys Asp Ala Leu Gly Ile Val
            500                 505                 510

Leu Asp Tyr Leu Thr Asp Ser Asp Leu Val Gln Val Val Ala Val Ser
        515                 520                 525

Arg Gly Trp Arg Ala Ile Ile Lys His His Gln Pro Ser Phe Lys Arg
    530                 535                 540

Leu Arg Ala His Leu Ala Arg Glu Ala Glu Cys Lys Glu Asn Leu Asp
545                 550                 555                 560

Arg Thr Val Ser Ser Ser Arg Glu Phe Ser Leu Leu Gly Lys Thr Gly
                565                 570                 575

Ala Ser Leu Ile Ser Ser Ser Phe Gly Asp Leu Gly Lys Glu Ile Ser
            580                 585                 590

Gly Thr Ser Val Val Val Ser Arg Gln Pro Phe Ser Leu Cys Asn Ser
        595                 600                 605

Ile Asp Gly Asn His Ser Thr Ala Ala Ala Gly Glu Leu Arg Arg Ser
    610                 615                 620

Gly Ser Val Gln Lys Ser Pro Pro Val Ser Pro Ser Lys Arg Lys Phe
625                 630                 635                 640

Arg Glu Asn Gln Lys Lys Asn Leu Ala Asn Phe Ser Gln Asn Met Ser
                645                 650                 655

Ser Ser Thr Arg Lys Ser Arg Thr Ser Phe Ile Glu Cys Trp Arg Asp
            660                 665                 670

Lys Ile Ala Val Leu Arg Asp Arg Asn Lys Leu Ser Thr Asn Ile Glu
        675                 680                 685

Asp Ile Glu Lys Ile Leu Ser Gly Phe Ser Asp Ser Thr Ile Glu Asp
    690                 695                 700

Asp Ile Asp Arg Gln Thr Tyr Thr Ile His Asp Cys Asn Asp Gln Ile
705                 710                 715                 720

Glu Pro Pro Gly Gln Leu Val Tyr Ser Glu Leu Ala Leu Asp Gln Glu
                725                 730                 735

Gln Thr Asn Ile Thr Phe Gln Thr Ala Val Glu Gln Pro Ala His Gln
            740                 745                 750

Glu Asp Ser Leu Arg Thr Asn Glu Phe Ala Leu Ala Leu Cys Pro Ser
        755                 760                 765

Ala Pro Pro Glu Glu Ser Val Gln Ser Glu Val Lys Pro Leu Phe Glu
    770                 775                 780

Ala Gln Asn Arg Leu Val Gln Ile Thr Lys Glu Tyr Val His Thr Asp
785                 790                 795                 800

Asp Glu Ala Gly Leu Val Phe Tyr Glu Lys Lys Phe Ile Ala Ala Glu
                805                 810                 815

Ser Val Ala Lys Gln Gln Pro Leu Asn Gly His Arg Asn Ala Ser Phe
            820                 825                 830

Ser Ser Gln Ser Thr Ala Leu Thr Leu Pro Pro Leu Asp Tyr Asp Thr
        835                 840                 845

Asp Val Leu Arg Ala Glu Leu Thr Asn Phe Gly Glu Pro Pro Gly Pro
    850                 855                 860

Ile Thr Lys His Thr Lys Lys Leu Tyr Leu Lys Lys Leu Val Lys Tyr
865                 870                 875                 880

Lys Arg Asp Pro Glu Arg Ala Leu Ala Gln Ile Lys Gly Lys Leu Asn
                885                 890                 895
```

```
Phe Ser Val Glu Leu Leu Ala Thr Ile Arg Ser Glu Asp Val Phe Ser
            900                 905                 910

Lys Ile Pro Gln Gln Gln Ala Leu Glu Thr Glu Met Ser Ser Glu Phe
        915                 920                 925

Ile Thr Thr Asn Asp Lys Thr Trp Arg Glu Gly His Leu Lys Lys Ser
    930                 935                 940

Phe Ile Tyr Leu Leu Ile Asp Pro Arg Val Ser Glu Asn Leu Pro Ala
945                 950                 955                 960

Gln Gln Thr Leu Phe Gln Gln His Asp Leu Trp Lys Arg Phe Leu Gln
                965                 970                 975

Ser Ile Phe Tyr Val Gly Lys Gly Lys Ser Ser Arg Pro Tyr Cys His
            980                 985                 990

Leu Tyr Asp Ala Met Lys Leu Tyr  Gln Gln Asn Ser Ser  Ser Ser Ser
        995                 1000                1005

Ala Leu  Lys Pro Pro Pro Asn  Gly Glu Leu Leu Glu  Leu Gln Val
    1010                 1015                1020

Glu Glu  Glu Gln Ile Ile Phe  Gln Ser Glu Glu Arg  Ile Glu Arg
    1025                 1030                1035

Val Cys  Arg Ala Thr Lys Ile  Leu Asn Arg Lys Gln  Met Asn Asp
    1040                 1045                1050

Ser Ala  Lys Leu Asn Arg Ile  Ile Asp Ile Trp Arg  Ala Gln Arg
    1055                 1060                1065

Gly Val  Ile Cys Leu His Val  Phe His Asn Ile Met  Pro Ala Glu
    1070                 1075                1080

Ala Phe  Thr Arg Glu Ala Ala  Ile Ile Asp Ala Leu  Gly Val Gln
    1085                 1090                1095

Asn Leu  Thr Asn Leu Lys Arg  Gly Asp Tyr Tyr Gly  Lys Ala Leu
    1100                 1105                1110

Ser Trp  Pro Met Lys Arg Arg  Lys Gln Leu Gly Ile  Leu Leu Leu
    1115                 1120                1125

Tyr Lys  Ala Leu Leu Ile Tyr  Leu Ala Glu Gly Glu  Thr Gln Leu
    1130                 1135                1140

Leu Pro  Ser Thr Ile Val Pro  Pro Thr Gly Leu Leu  Gln Leu Val
    1145                 1150                1155

Ile Ala  Ser His Leu Lys Lys  Ser Glu Arg Leu Lys  Pro Cys Pro
    1160                 1165                1170

Arg Cys  Glu Lys Pro Ser Arg  Val Val Leu Asn Lys  Ser Ser Ile
    1175                 1180                1185

Lys Leu  Ala Ile Ser Thr Gly  Ser Leu Asp Ser Ser  Thr Val Arg
    1190                 1195                1200

Thr Val  Ala Asn Gly Lys Leu  Asp Arg Ser Tyr Thr  Leu Pro Glu
    1205                 1210                1215

Ser Leu  Gly Ser Ser Ala Ser  Ser Met Ile Ala Ala  Thr Ala Leu
    1220                 1225                1230

Asp Cys  Thr Ser Thr Thr Ile  Ser Ser Pro Gln Ser  Pro Thr Asn
    1235                 1240                1245

Pro Asp  Arg Ile Arg Arg Asn  Leu Phe Ala Thr Ser  Leu Leu Pro
    1250                 1255                1260

Arg Ser  Gln Ser Val Asp Ala  Gln Thr Pro Gly Met  Thr Arg Ser
    1265                 1270                1275

Pro Arg  Arg Arg Asn Ser Thr  Asp Met Pro Gly Ser  Gly Ser Gly
    1280                 1285                1290

Ser Leu  Leu Glu Arg Lys Leu  Thr Thr Lys Asn Gly  Lys Thr Lys
```

1295 1300 1305

Ser Ala Glu Ala Ile Gln Cys Asp Tyr Ala Val Cys Ser Gly Lys
1310 1315 1320

Asn Cys Gly Phe Met Phe Cys Ile Lys Cys Leu Cys Glu Tyr His
1325 1330 1335

Pro Asn Ser Val Cys Lys Asp Leu Ala Pro Asn Ser Pro Ser Lys
1340 1345 1350

Glu Asp Glu Pro Ala His Asn Val Ala Cys Ser Lys Gln Ser Arg
1355 1360 1365

Arg Ser Leu Met Arg Leu Arg Lys
1370 1375

<210> SEQ ID NO 202
<211> LENGTH: 2203
<212> TYPE: PRT
<213> ORGANISM: Aedes albopictus

<400> SEQUENCE: 202

Met Asn Arg Leu Ala Phe Leu Phe Thr Thr Leu Phe Leu Val Ile Val
1 5 10 15

Ile Gln Ile Gln Ile Arg Thr Asn Ala Gln Val Val Gln Pro Ala His
20 25 30

Thr Leu Pro Asn Asp Gln Arg Pro Ser Gly Pro Lys Lys Pro Ala Gln
35 40 45

Asn Glu Arg Pro Gln Lys Lys Ile Pro Thr Thr Lys Ala Thr Pro Lys
50 55 60

Pro Ser Met Gly Asp Ala Ile Lys Asn Leu Lys Asp Arg Ile Leu Asn
65 70 75 80

Asp Thr Asp Thr Pro Gln Asp Met Leu Gln His Val Arg Asp Ser Ser
85 90 95

Phe Arg Asn Ala Phe His Glu Ala Ile Asp Ala Asn Ile Val Asn Pro
100 105 110

Gly Leu Ile Asn Thr Leu Ala Ser Val Ala Lys Pro Leu Val Asn Asp
115 120 125

Tyr Ser Arg Asp Thr Leu Leu Ile Asp Ser Ile Arg Glu Asp Ile Asn
130 135 140

Phe Thr Phe Gly Pro Asn Val Thr Trp Trp Lys Thr Leu Glu Leu Lys
145 150 155 160

Lys Asn Glu Gln His Val Ile Val Gly Leu Ser Asn Asp Ser Ile Val
165 170 175

Ile Leu Phe Glu His Phe Gly Glu Tyr Lys Leu Gln Gln Glu Val Leu
180 185 190

Met Glu Thr Ala Pro Thr Ala Phe Glu Ile Ile Thr Val Trp Asp Ser
195 200 205

Val Ala Glu Thr Pro Ile Ser Cys Leu Ile Val Ala Thr Glu Leu Gln
210 215 220

Leu Ile Trp Tyr Thr Met Arg Pro Asp Thr Asn Phe Glu Leu Thr Glu
225 230 235 240

Glu Trp Arg Trp Pro Leu Tyr Lys Met Thr Thr Leu Ile Lys Gly Phe
245 250 255

Lys Tyr Arg Asp Ile His Met Ile Leu Leu Val Gly Thr His Pro Asn
260 265 270

Lys His Lys Ser Val Ser Ala Thr Leu Tyr Glu Phe Asn Phe Glu Arg
275 280 285

```
Gln Gln Phe Trp Leu Leu Gln Arg Leu Asp Leu Ala Phe Pro Cys Ser
    290                 295                 300

Lys Val Gly Leu Val Arg Val Gly Arg Glu Phe Leu Val Thr Phe Pro
305                 310                 315                 320

Gln Asn Asp Thr Ala Met Ile Tyr Thr Leu Glu Ala Gly Glu Lys Tyr
                325                 330                 335

Arg Gly Arg Phe Asn Leu Ile Ala Asn Tyr Thr Ser Glu Met Val Gln
            340                 345                 350

Thr Val Gly Ala Phe Gln Val Gly Arg Tyr Ala Tyr Ile Ala Ile Gly
        355                 360                 365

Gly Arg Ser Pro Gln Ile Val Arg Tyr Ala Asn Gly Val Phe Thr Ser
    370                 375                 380

Gln Arg Ile Pro Met Glu Ala Met Glu Thr Val Glu Ala Tyr Tyr Glu
385                 390                 395                 400

Ile Pro Thr Pro Thr Tyr Arg Asp Asp Leu Ile Leu Leu Val Gln His
                405                 410                 415

Lys Met Leu Phe Ser Thr His Asp Leu Gln Arg Leu Asp Val Phe Val
            420                 425                 430

Trp Asn Gly Glu Ser Phe Asp Leu Arg Ser Asn Ile Pro Cys Tyr Val
        435                 440                 445

Glu Asp Glu Leu Met Asp Asn Glu Val Ser Cys Met Leu Asp Leu Tyr
    450                 455                 460

Arg Pro Thr Gly Ile Val Gly Ser Ala Ile Ile Leu Arg Gly Lys Lys
465                 470                 475                 480

Val Ser Met Ile Val Pro Arg Tyr Gln Thr His Ser Thr Leu Phe Asn
                485                 490                 495

Leu His Ile Glu Leu Leu Ser Ala Glu His Pro Ile Arg Gln Lys Thr
            500                 505                 510

Gln Glu Met Gln Asp Thr Ile Asp Ala Phe Thr Lys Ile Val His Tyr
        515                 520                 525

Gln Asp Glu Val Ile Ser Glu Gly Phe Ala Ala Ile Ala Glu Ala Asp
    530                 535                 540

Gln Leu Tyr Asp Val Pro Leu Leu Thr Leu Gln Asn Cys Ser Leu Gly
545                 550                 555                 560

Thr Ile Gln Ala Asp Leu Val Ile Gln Asp Ser His Phe Asn Trp Pro
                565                 570                 575

Asn Gly Thr Ile Val Val Gly Ser Lys Ile Trp Ser His Arg Asp Thr
            580                 585                 590

Ala Val Asn Val Pro Ala Ile Ala Gln Glu Ile Glu Ala Glu Thr Ala
        595                 600                 605

Leu Leu Ser Gln Leu Glu Gln Gln Leu Asn Tyr Thr Val Arg Arg His
    610                 615                 620

Asn Asp Ser Phe Ser Leu Asp Leu Asp Gln Pro Leu Tyr Val Gln Gly
625                 630                 635                 640

Arg Val Glu Val Gly Gly Ala Leu Val Thr Asp Asp Leu Tyr Val Arg
                645                 650                 655

Gln Leu Glu Glu Asp Pro Pro Leu Leu Arg Val Leu Arg Gln Thr Gly
            660                 665                 670

Asp Asp Ser Val Lys Glu Leu Arg Val Lys Asp Leu Lys Val Arg His
        675                 680                 685

Leu Asn Phe Glu Thr Val Asn Gly Ile Pro Ala Ser Asp Leu Val Phe
    690                 695                 700

Asn Thr Gly Glu Lys Ile Glu Leu Ala Asn Ala Leu Ile Val Asp Asn
```

```
705                 710                 715                 720

Val Val Val Ala Gln Asn Val Ile Leu Pro Lys Gly Gly Thr Val Asn
                725                 730                 735

Gly Val Asp Leu Ser Glu Ser Thr Val Tyr Phe Asn Cys Lys Asn Arg
            740                 745                 750

Arg Trp Asp Gly Leu Lys Phe Asp Ser Val Glu Val Leu Glu Asp Val
        755                 760                 765

Met Val Gln Glu Thr Ile Asn Gly Val Lys Leu Asp Leu Glu Glu Leu
    770                 775                 780

Asp Ala Arg Phe Arg Gln Ala Ser Asp Asp Met Thr Asp Val Leu Val
785                 790                 795                 800

Thr Glu Lys Leu Gln Leu Asp Gly Asn Leu Tyr Val His Ser Val Asn
                805                 810                 815

Gly Val Pro Trp Ser Asp Ile Ile His Arg Ile Val Leu Lys Asn Arg
            820                 825                 830

Pro Asn Arg Leu Ala Glu Val Arg Ile Asn Gly Ser Leu Ile Leu Glu
        835                 840                 845

Asn Asp Asn Val Thr Val Tyr His Leu Asn Gly Leu Ala Phe Pro Met
    850                 855                 860

Asp Tyr Leu Leu Ser Asn Ser Pro Ile Glu Ser Ile Val Thr Gly Tyr
865                 870                 875                 880

Lys Arg Phe Val Asn Phe Thr Asn Ile Asp Ala Leu Asp Ile Glu Arg
                885                 890                 895

Lys Ile Asn Gly Val Asp Leu Leu Asp Ile Val Thr Leu His Asp Asp
            900                 905                 910

Gln His Ile Pro Gly Asp Val Thr Phe Gly Glu Leu His Val Thr Glu
        915                 920                 925

Arg Leu Glu Val Lys Gly Ala Ile Arg Gly Lys His Leu Asp Glu Phe
    930                 935                 940

Leu Asp Asn Pro Ser Leu Leu Gln Thr Pro Leu Val Lys Ala Ala Cys
945                 950                 955                 960

His Phe Lys Gln Leu Phe Val Asp Gly Pro Val Ile Val Glu Asp Lys
                965                 970                 975

Leu Asn Gly Met Asp Val Asp Ala Val Leu Ser Asp Val Val Tyr Asp
            980                 985                 990

Ser Glu His Thr Val Thr Ile Glu  Ser Ala Lys Arg Ile  Ala Ser Val
        995                 1000                1005

Glu Phe  Gly Asp Lys Val Thr  Ile Gly Ser Gly Met  Val Asn Glu
    1010                1015                1020

Phe Lys  Leu Asp Gln Phe Val  Thr Arg Ser Thr Glu  Gln Glu Leu
    1025                1030                1035

Ser Val  Arg Glu Ile Asn Gly  Lys Val Phe Ile His  Asp Leu Met
    1040                1045                1050

Leu Asp  Gly Leu Phe Asp Gly  Leu Asn Ala Thr Ala  Leu Asp Val
    1055                1060                1065

Ser Ser  Val Lys Leu Phe Gly  Asp Gln Tyr Thr Glu  Thr Ser Leu
    1070                1075                1080

Ile Phe  Lys Asn Arg Glu Asn  Ala Leu Tyr Pro Asp  Val Glu Ala
    1085                1090                1095

Asn Glu  Leu Lys Ile Met Lys  Thr Leu Asn Ser Lys  Ala Arg Ser
    1100                1105                1110

Glu Tyr  Lys Asp Thr Glu Gln  Glu Glu Leu Val Leu  Ser Gly Gln
    1115                1120                1125
```

```
Ile Ser  Leu Ser His Leu His  Val Asn His Met Lys  Leu Thr Gly
    1130                 1135                 1140

Ser Ser  Leu Ser Gly Pro Ser  Lys Met Ile Asn Leu  Val His Leu
    1145                 1150                 1155

Pro Thr  Phe Asp Ser Leu Arg  Phe Ser Leu Ser Arg  Pro Gln Gln
    1160                 1165                 1170

Val Thr  Ala Pro Phe Tyr Val  Asn Lys Leu Val Val  Gly Ser Gln
    1175                 1180                 1185

Ile Ala  Thr Ala His Val Asn  Gly Arg Asp Ile Arg  Gly Leu Lys
    1190                 1195                 1200

Glu Ser  Phe Asp Arg Val Asp  Asn Phe Lys Thr His  Leu Leu Gln
    1205                 1210                 1215

Gly Ser  Ile Pro Ile Glu Asn  Leu Tyr Val Gly Gly  Asp Leu Gln
    1220                 1225                 1230

Val Asn  Met Leu Asn Asp Val  Asn Phe Asp Ala Leu  Ile Lys Gln
    1235                 1240                 1245

Val Ile  Trp Leu Asn Arg Pro  Asn Arg Ile Pro Gly  Thr Phe Arg
    1250                 1255                 1260

Phe Leu  Asp Pro Ile Gln Val  Glu Gly Asn Leu Thr  Ile Arg Gly
    1265                 1270                 1275

Gln Ile  Asn Asn Ala Asp Leu  Gly Asp Phe Leu Glu  Asp Val Val
    1280                 1285                 1290

Gln Lys  Ser Ala Gly Val Ala  Glu Phe His Gly Thr  Thr Val Phe
    1295                 1300                 1305

Met Asn  Gly Leu Val Val Glu  Gly Asn Val Asn Thr  Glu Ser Ile
    1310                 1315                 1320

Asn Asn  Ile His Met Ser Glu  Leu Ala Leu Arg Asn  Asp Thr Ile
    1325                 1330                 1335

Tyr Leu  Gln Gly Asp Val Glu  Ile Gln Gly Asp Ile  Phe Val Glu
    1340                 1345                 1350

His Leu  His Ile Glu Asn His  Leu Asn Gln Glu Pro  Ile Gln Asn
    1355                 1360                 1365

Leu Leu  Asn Ser Tyr Gly Tyr  Asp Glu Thr Lys Asp  Val His Thr
    1370                 1375                 1380

Ile Lys  Gly Asp Leu Tyr Leu  Tyr Gly Ala Gln Ile  Gly Ser Leu
    1385                 1390                 1395

Arg Ile  Ala Gly Met Met Asn  Gln Ile Pro Asn Val  Asp Ala His
    1400                 1405                 1410

Leu Ala  Ser Ile Ile Arg Lys  Asp Gln Asp Tyr Asn  Phe Thr Lys
    1415                 1420                 1425

Pro Leu  Leu Phe Lys Asn Glu  Val Phe Phe Asp Arg  Gly Phe Ser
    1430                 1435                 1440

Ala Thr  Tyr Leu Asn Gln Val  Asp Ile Ser Thr Ile  Gln Gln Asp
    1445                 1450                 1455

Ile Val  Arg Ile Asn Asp Gln  Ala Pro Val Glu Ile  Glu Ala Asp
    1460                 1465                 1470

Arg Ile  Val Phe Ala Glu Pro  Val Tyr Ala Asp Arg  Leu Ala Ile
    1475                 1480                 1485

Lys Gly  Asp Met Ile Ala Ala  Asn Leu Val Gly Cys  Asn Pro Asp
    1490                 1495                 1500

Val Trp  Met Ser Thr Gly Val  Met Ile Asn Arg Asp  Ala Glu Ile
    1505                 1510                 1515
```

```
Tyr Ala  Lys Thr Leu Phe Ser  Pro Gly Ala Phe Arg  Thr Asp His
    1520                 1525                 1530

Leu Arg  Val Asp Tyr Leu Asn  Gly Gln Pro Met Asn  Asn Leu Ile
    1535                 1540                 1545

Thr Leu  Asn Thr Asp Gln Thr  Ile Glu Thr Thr Leu  Phe Ile His
    1550                 1555                 1560

Glu Met  Thr Ile Thr Gln Pro  Met Glu Val Gly Gly  Tyr Val Asn
    1565                 1570                 1575

Gly Val  Thr Leu Pro Tyr Glu  Arg Lys Asn Thr Leu  Met Thr Tyr
    1580                 1585                 1590

Gly Asn  Gln Arg Val Arg Leu  Pro Thr Val Phe His  Ser Ile Arg
    1595                 1600                 1605

Val Leu  Gln Ser Phe Thr Leu  Pro Pro Val Leu Asn  Gly Lys Pro
    1610                 1615                 1620

Phe Gly  Pro Pro Val Ala Ile  Gly Pro Glu Met Val  Ile Glu Ser
    1625                 1630                 1635

Pro Ile  Ser Phe Arg His Leu  Ile Val Asp Arg Leu  Glu Thr Glu
    1640                 1645                 1650

Asp Met  Ile Ser Gly Val Asp  Phe Asp Arg Trp Tyr  Glu Asn Ser
    1655                 1660                 1665

Leu Trp  Ser Lys Gly Arg Asp  His Gln Thr Ile Glu  Ala Arg Ile
    1670                 1675                 1680

Ser Ala  Arg Asn Val Arg Phe  Asn Gly Asp Val Glu  Gly Asn Gly
    1685                 1690                 1695

Lys Ile  Asn Gly Val Asp Ile  Met Asp Val Val Gln  Arg Met Lys
    1700                 1705                 1710

Ala Ala  Lys Lys Asn Val Glu  Asp Gln Leu Gln Asp  Tyr Gln Ser
    1715                 1720                 1725

Glu Met  Arg Ser Phe Cys Ser  Asn Thr Lys Gln Leu  Val Asp Lys
    1730                 1735                 1740

Ser Gln  Ser Arg Met Tyr Phe  Phe Lys Tyr Phe Val  Gln Arg Gln
    1745                 1750                 1755

Val Ile  Asn Glu His Leu Pro  Ile Val Ser Phe His  Phe Phe Asp
    1760                 1765                 1770

His Leu  Gly Tyr His Phe Leu  Gly Val Asn Met Gly  Cys Glu Ser
    1775                 1780                 1785

His Phe  Tyr Gln Trp Asp Pro  Thr Gly Lys Ala Phe  Val Pro Ile
    1790                 1795                 1800

Phe Lys  Tyr Tyr Thr Gly Leu  Val Glu Glu Trp Ser  His Val Val
    1805                 1810                 1815

Asn Gly  Glu Glu Ala Ile Phe  Leu Val Thr Arg Ser  Ile Ser Glu
    1820                 1825                 1830

Ile Thr  Gln Cys Glu Val Thr  Gly Leu Ser Val Trp  Leu Phe Thr
    1835                 1840                 1845

Gly Val  Gln Leu Gln Leu Val  Trp Asn Thr Val Asp  Thr Ala Ser
    1850                 1855                 1860

Met Lys  Ser Val Ala Ala Asp  Pro Ala Lys Ser Thr  Ser Phe Tyr
    1865                 1870                 1875

Val Leu  Ser Pro Asp Val Val  Val Glu Tyr Ser Val  Asp Gly Ser
    1880                 1885                 1890

Thr Leu  Glu Gln Trp Arg Leu  Pro Lys Ser Ala Leu  Asp Tyr Glu
    1895                 1900                 1905

Phe Val  Pro Ser Arg Val Gly  Leu Gly Leu Ala Leu  Ser Asp Ser
```

```
    1910                1915                1920

Lys Leu  Leu Val Leu Leu Ser  Asn Val Asn Lys Thr  Val Asp Glu
    1925                1930                1935

Gly Pro  Thr Val Asn Ser Gly  Leu Glu Met Ala Leu  Phe Ser Ser
    1940                1945                1950

Gln Ser  Met His Asp Arg Met  Lys Lys Thr Tyr Ser  Glu Lys Leu
    1955                1960                1965

Leu Asn  Ser Thr Ile Glu Ser  Glu Glu Val Ser Asp  Ile Ile His
    1970                1975                1980

Pro Glu  Asn Leu Ser Pro Gln  Glu Glu Tyr Ser His  Phe Gly Asn
    1985                1990                1995

Asp Thr  Val Ile Val Val Glu  Pro Glu Ala Val Asp  Ile Pro Glu
    2000                2005                2010

Pro Pro  Ala Ser Glu Asp Gln  Leu Pro Thr Glu Thr  Pro Ile Ala
    2015                2020                2025

Arg Asp  Ile Pro His Gly Gly  Ile Met Ile Ala Asp  Asn Gln His
    2030                2035                2040

Phe Pro  Glu Arg Ser Lys Gly  Asp Val Val Ala Phe  His Ala Gly
    2045                2050                2055

Pro Gln  Asn Lys Lys Arg His  Leu Val Ala Val Ser  Thr Val Val
    2060                2065                2070

His Thr  Val Val Gln Gly Asp  Gln Asp Ala Ile Lys  Ile Tyr Thr
    2075                2080                2085

Asp Ile  Gln Thr Gly Lys Leu  Tyr Gln Val Leu Pro  Cys His Arg
    2090                2095                2100

Pro Ser  His Leu Thr Ala Leu  Glu Leu Arg Asp Glu  Thr Ile Leu
    2105                2110                2115

Ala Phe  Leu Glu Ala Gln Gln  Thr Val Gln Ile Tyr  Ile Tyr Arg
    2120                2125                2130

Gly Met  Gln Gly Phe Val Arg  Leu Ser Asn Phe Lys  Leu Thr Gly
    2135                2140                2145

Pro Ala  Arg Ala Met Ala Gly  Val Ser Leu Pro Gln  Pro Leu Met
    2150                2155                2160

Ile Arg  Cys Lys Leu His Tyr  Leu Ala Ile Ser Thr  Glu Gln Asn
    2165                2170                2175

Glu Leu  Ile Met Leu Arg Ala  Lys Thr Gln Gly Asp  Cys Gly Leu
    2180                2185                2190

Ala Val  Gln Val Asp Cys Asp  Asp Val Glu
    2195                2200
```

```
<210> SEQ ID NO 203
<211> LENGTH: 2132
<212> TYPE: PRT
<213> ORGANISM: Aedes albopictus
<220> FEATURE:
<221> NAME/KEY: misc_feature
<222> LOCATION: (607)..(607)
<223> OTHER INFORMATION: Xaa can be any naturally occurring amino acid

<400> SEQUENCE: 203

Met Leu Phe Leu Leu Asn Phe Val Leu Val Leu Val Leu Leu Thr Ala
1               5                   10                  15

Ile Lys Leu Pro Ser Tyr Ala Val Arg Cys Glu Asp Asp Arg Asp Val
            20                  25                  30

Pro Gln Ser Pro Ala Ala Gly Asp Asp Glu Leu Asp Gly Leu Lys Glu
        35                  40                  45
```

```
Val Phe Tyr Arg Asn Leu Met Ala Asp Met Arg Met Glu Ser Gly Gly
    50                  55                  60

Gln Pro Ile Ile Thr Pro Glu Leu Glu Asn Arg Met Glu Glu Arg Ile
65                  70                  75                  80

Gln Ser Phe Leu Ser Ala Thr Asp Gly Ser Thr Thr Gly Trp Val Arg
                85                  90                  95

Arg Arg Arg Gln Ala Met His Gly Gly Pro Met Gly Asn Glu Met Glu
            100                 105                 110

His His Ser Gly Pro Ser Met Ala Ser His Glu Glu Ile Tyr Ala Asp
        115                 120                 125

Thr Ala Asp Ala Glu His Arg Tyr Leu Lys Gly Phe Arg Glu Arg Gly
    130                 135                 140

Ser Val Pro Val Ser Phe Pro Ile Asp Ile Cys Leu Leu Lys Val Gly
145                 150                 155                 160

Arg Ser Ile Phe Ala Ala Ser Leu His Leu Arg Lys Ser Lys Glu Asn
                165                 170                 175

Tyr Lys Asn Gln Thr Ile Val Thr Phe Tyr Lys Arg Gln Lys Gly Gln
            180                 185                 190

Phe His Lys Tyr Met Glu Tyr Lys Ala Ala Gln Ala Arg Asn Phe Asp
        195                 200                 205

Cys Thr Ser His Ala Ser Leu Gly Phe Val Ala Val Val Asn Tyr Tyr
    210                 215                 220

Asp Asn Ser Gly Ser Gln Asp Phe Pro Glu Ala His Pro Gly Phe Asp
225                 230                 235                 240

Glu Gly Ser Pro Val Phe Gln Ile Arg Glu Asp Gly Thr Thr Asp Ile
                245                 250                 255

Ile Gln Lys Phe Arg Gln Ser Asn Gln Asn Thr Val His Met Trp Thr
            260                 265                 270

Ala Gly Asn His Phe Tyr Leu Thr His Thr Tyr Thr Asn Leu Asn Glu
        275                 280                 285

Ser Val Glu Asn Val Cys Pro Leu Tyr Arg Trp Thr Gly Tyr His Phe
    290                 295                 300

Asp Val Ile Asp Glu Leu Pro Cys Tyr Asn Ser Ile Tyr Ile Glu Pro
305                 310                 315                 320

Phe Ser Ile Glu Gln Thr Leu Tyr Ile Ala Ile Ala Asn Gln Met Asn
                325                 330                 335

Asp Lys Ser Val Glu Glu Asp Thr Phe Ser Asp Ile Phe Arg Phe Asn
            340                 345                 350

Tyr Glu Gln Gln Lys Phe Glu Phe His Gln Lys Ile Tyr Ile Tyr Ser
        355                 360                 365

Val Ser Asp Ile Ala Tyr Phe Phe Leu Glu Leu Gly Asp Val Arg Glu
    370                 375                 380

His Tyr Leu Ile Thr Gly Asn Ser Arg Ala Gly Lys Glu Thr Ala Val
385                 390                 395                 400

Asp Lys Leu Asp Tyr Asp Gln His Ser Ile Val Tyr Lys Phe Val Glu
                405                 410                 415

Gly Tyr Phe Val Pro Val Gln Lys Ile Glu Leu His Gln Val Lys Met
            420                 425                 430

Phe Leu Pro Val Met His Glu Asn Gly Glu Phe Leu Leu Leu Ile Arg
        435                 440                 445

Cys Arg Gly Lys Pro Leu Leu Ile Tyr Glu Tyr Asp Gly Tyr Lys Phe
    450                 455                 460
```

-continued

```
Val Pro Ser Arg Ile Asp Tyr Thr Arg Asn Ala Phe Ser Thr Gly Val
465                 470                 475                 480

Ser Phe Met Arg Val Tyr Arg His Ile Leu Asn Thr Ser Leu Ile Val
                485                 490                 495

Ile Ala Asn Lys Gln Ser Phe Gly Asn Thr Ala Asn Leu Phe Ser Pro
            500                 505                 510

Ile Tyr Gly Val Glu Asn Asn Leu Arg Asp Val Tyr Gly Gln Phe Ile
        515                 520                 525

Ser Trp Cys Ser Glu Thr Thr His Gln Leu Glu Asn Val Asn Leu Glu
    530                 535                 540

Glu Val Tyr Asn Lys Leu Val Glu Leu Pro Lys Val Ser Gly Ser Gly
545                 550                 555                 560

Ala Lys Leu Glu Lys Asp Val Glu Val Lys Asp Ser Ser Val Glu Thr
                565                 570                 575

Leu Lys Thr Lys Val Leu His Thr Gln His Phe Met Phe Asn Gln Glu
            580                 585                 590

Ala Phe Asp Tyr Leu Asn Asn Val His Gly Ser Cys Lys Thr Xaa Lys
        595                 600                 605

Glu Lys Ala Lys Lys Leu Arg Ser Lys Ile Asp Asp Ser Leu Lys Leu
    610                 615                 620

Ser Glu Ala Met Glu Val Arg Gly Asp Val Arg Val Pro Gln Val Ile
625                 630                 635                 640

Ala Ala Asp Gly Leu Ile Arg Asp Leu Glu Ala Lys Asn Val Asn Asp
                645                 650                 655

Glu Arg Val Val Pro Arg Val Ala Asn Gln Thr Lys His Glu Asp Val
            660                 665                 670

Ile Asn Val Asp Arg Leu Val Ile Glu Asp Arg Leu Ala Val Lys Phe
        675                 680                 685

Leu Asn Gly Tyr Ala Ser Glu Thr Leu Leu His Thr Thr Asp Asp Leu
    690                 695                 700

Arg Ser Leu Glu Gly Ala Asp Leu His Val Lys Gly Val Glu Ile Arg
705                 710                 715                 720

Gly Glu Leu Phe Val Asp Lys Leu Ile Asp Gly Ile His Val Ser Val
                725                 730                 735

Asp Asn Val Leu Leu Arg Gly Val Asp Gln Val Phe Ala Gly Arg Thr
            740                 745                 750

Leu Arg Ala Thr Asn Leu Thr Val Gly Asn Leu Met Ala Lys Lys Leu
        755                 760                 765

Asn Ser Thr Asp Val Gly Thr Val Met Ser Tyr Leu Asp Arg Ala Ser
    770                 775                 780

Glu Tyr Asp Asn Ala Gln Lys Arg Thr Val Glu Ser Tyr Pro Lys Lys
785                 790                 795                 800

Phe Lys Glu Ile Arg Val Gln Asp Leu Glu Ile Ser Gly Leu Val Asn
                805                 810                 815

Asp Val Asp Ile Lys Tyr Ile Asn Lys Asn Ala Leu Lys Ile Val Gly
            820                 825                 830

Asp Gln Val Ile Thr Gly Ser Val Asn Phe Asp Asn Ile Val Thr Lys
        835                 840                 845

Lys Leu Glu Thr Pro Asn Lys Arg Leu Ser Gly Val Asp Leu Asn Tyr
    850                 855                 860

Leu Val Met Thr Glu Pro Thr Pro Asp Gln Gln Asp Phe Thr Val Arg
865                 870                 875                 880

Gln Asp Val Gln Phe Ile Lys Pro Val Tyr Met Glu His Leu His Val
```

```
                885                 890                 895

Asp Glu Arg Ile Asn His Ile Asn Val Ile Asp Asp Gln Leu Gln Val
            900                 905                 910

Leu Leu Lys Asp Pro Lys Glu Pro Gln Leu Ile Thr Gly Thr Lys Ser
        915                 920                 925

Phe Asp Asn Val Gln Leu Leu Gly Pro Ile Tyr Leu Gln Gly Lys Val
    930                 935                 940

Asn Ser Ser Ser Leu Ser Lys Leu Asn Pro Val Ser Thr Ile Thr Gln
945                 950                 955                 960

Asp Val Tyr Leu Glu Gly Asp Phe Glu Ile Thr Gly Asp Val Met Ile
                965                 970                 975

Arg His Leu Leu Asn Thr Thr Asn Ile Tyr Gly Ala Ser Lys Thr Phe
            980                 985                 990

Asn Phe Tyr Asp Leu Tyr His His  Gly Leu Pro Leu Ser  Ala Ala Phe
        995                 1000                1005

Ala Asn  Gln Asn Phe Val Phe  Lys Gln Pro Leu Val  Ala His His
    1010                 1015                 1020

Ala Phe  Ala Asn Asn Leu Asn  Asp Val Asn Pro Arg  Asp Phe Ile
    1025                 1030                 1035

Pro Ile  Pro Ser Ser Lys Leu  Gln Arg Ile Thr Gly  Arg Lys Ile
    1040                 1045                 1050

Phe Asn  Gly Asp Leu Thr Ile  Arg Gly Asp Arg Val  Asp Ala Thr
    1055                 1060                 1065

Lys Ile  Asn Gly Ile Asp Leu  Lys Gln Leu Asn Gln  Thr Val Leu
    1070                 1075                 1080

Lys Lys  Thr Gly Asp Gln Val  Val Glu Gly Thr Ile  His Phe Lys
    1085                 1090                 1095

Glu Leu  Ile Ala Ser Thr Val  Val Ala Lys Lys Thr  Leu Phe Glu
    1100                 1105                 1110

Glu Arg  Pro Leu Ser Thr Leu  Leu Thr Val Asn Thr  Asn Gln Arg
    1115                 1120                 1125

Ile Lys  Ser Lys Val Arg Cys  Val Asn Cys Lys Leu  Thr Ile His
    1130                 1135                 1140

Gly Asp  Leu Ser Val Gly Arg  Leu Glu Ser Tyr Asn  Lys Ser Arg
    1145                 1150                 1155

Val Phe  Gly Tyr Asp Leu Asp  Phe Leu Phe Thr Asp  Thr Leu Arg
    1160                 1165                 1170

Lys Gly  His Ala Pro Asp Glu  Ser Ile Ala Val Thr  Gly Gly Lys
    1175                 1180                 1185

Gly Phe  Tyr Asn Val Ser Val  Gly Glu Leu Ile Leu  Leu Asp Gln
    1190                 1195                 1200

Ala Thr  Ile Asn Gly Val Asp  Leu Ile Gly Leu Lys  Lys Ile Asn
    1205                 1210                 1215

Asp Pro  Leu Glu Lys Asp Val  Ile Val Glu Glu Thr  Leu Ile Leu
    1220                 1225                 1230

Lys Asn  Pro Leu His Val Arg  Asn Val Tyr Phe Asn  Gly Ser Ile
    1235                 1240                 1245

Asn Gly  Val Gln Arg Glu Glu  Phe Gly His Ser Trp  Leu Leu Asn
    1250                 1255                 1260

Glu Tyr  Asn Gln Thr Phe Thr  Ala Pro Gln Val Phe  Glu His Val
    1265                 1270                 1275

Thr Ala  Glu Gly Met Val Val  Asp Gly Tyr Phe Asn  Gly Val Lys
    1280                 1285                 1290
```

```
Leu Glu  Glu Leu Val Gln Asp  Ile Tyr Phe Leu Asp  Arg Ser Glu
    1295                 1300                 1305

His Leu  Pro Glu Ala Val Phe  His Glu Gly Ile Val  Ser Tyr Gln
    1310                 1315                 1320

Pro Ile  Ile Val Lys Gly Leu  Val Ser Gly Leu Asn  Leu Ala Thr
    1325                 1330                 1335

Asp Val  Leu Leu Asn Tyr Ser  Pro Ser Arg Gln Tyr  Leu Lys Asp
    1340                 1345                 1350

Val Arg  Ile Asp Gly Asn Leu  Leu Val Thr Asn Arg  Ile His Val
    1355                 1360                 1365

Glu His  Thr Leu Asn Gly Met  Asn Tyr Ala Lys Leu  Arg Glu Tyr
    1370                 1375                 1380

Ala Thr  Ser Ser Gly Glu Glu  Arg Pro Leu Asn Val  Asp Val Gln
    1385                 1390                 1395

Gly Asn  Val His Phe His Leu  Gln Pro Asp Val Ser  Glu Leu Asn
    1400                 1405                 1410

Gly Tyr  Asn Leu Glu Gln Leu  His Arg Asp Val Trp  Leu Thr Asn
    1415                 1420                 1425

Arg Asp  Glu Val Leu Thr Gly  Ser Tyr Arg Phe Glu  Asn Val His
    1430                 1435                 1440

Phe Ala  Asn Tyr Val His Thr  Lys Gly Pro Val Asn  Gln Leu Asp
    1445                 1450                 1455

Leu Glu  Glu Ile Ile His Ser  Tyr Leu Ser Val Ser  Lys Pro Gln
    1460                 1465                 1470

Asn Val  Ser Thr Pro Leu Val  Phe Lys Gly Pro Val  Glu Phe Gln
    1475                 1480                 1485

Lys Met  Ala Thr Phe Asp Asn  Ile Ala Leu Glu Gly  Leu Leu Lys
    1490                 1495                 1500

Gly Ser  Lys Glu Ser Arg Gly  Ile Asn Ile Val Asp  Phe Asp Arg
    1505                 1510                 1515

Phe Val  Leu Lys Lys Asn Val  Asp Gln Thr Ile Thr  Gly Lys Trp
    1520                 1525                 1530

Val Phe  His Asp Val Glu Val  Tyr Gly Asn Leu Asn  Leu Thr Thr
    1535                 1540                 1545

Leu Asn  Gly Leu Asp Ile Arg  His Asp Ile Leu Leu  Asn His Ala
    1550                 1555                 1560

Glu Gln  Val Thr Phe Thr Gly  Ala Lys Arg Ile Asp  Asn Leu Arg
    1565                 1570                 1575

Val His  Asn Leu Arg Cys Pro  Glu Pro Cys Ile Ile  Gln Gly Val
    1580                 1585                 1590

Asp Phe  Ser Glu Trp Phe Ser  Asn Ser Val Arg Leu  Asp Arg Asn
    1595                 1600                 1605

His Thr  Val Glu Gly Val Thr  Tyr Leu Glu Gly Val  Thr Ile Leu
    1610                 1615                 1620

Gly Gly  Ile Glu Ser Leu Gly  Pro Val Asn Asn Val  Thr Phe Asp
    1625                 1630                 1635

Pro Gln  His Leu Leu Leu Lys  Ser Val Asn Gln Thr  Leu Glu Gly
    1640                 1645                 1650

Thr Leu  Tyr Leu Lys Thr Lys  Phe Pro Glu His Asn  Leu Ile Tyr
    1655                 1660                 1665

Gln Ser  Ser Ile Glu Thr Leu  Glu Val Asn Thr Ile  Asn Gly Lys
    1670                 1675                 1680
```

```
Asp Phe  Asn Glu Phe Met Asp  Asn Leu Ala Arg Asp  Glu Glu Gly
    1685                 1690                 1695

Thr Ile  Thr Ile Gly Thr Pro  Val Thr Leu Ala Gln  Asn Leu Lys
    1700                 1705                 1710

Ala Lys  Asn Val Arg Thr Ser  Asp Ser Lys Val Phe  Gly Val Asn
    1715                 1720                 1725

Ile Asn  Gln Leu Leu Gln Glu  Val Glu Tyr Gly Asp  Gln Leu Ser
    1730                 1735                 1740

Lys Tyr  Glu Thr Lys Leu Arg  Arg Leu His Met Val  Gly Gln Ser
    1745                 1750                 1755

Leu Val  Glu Thr Leu Ser Thr  Lys Thr Pro Tyr Leu  Ser His Tyr
    1760                 1765                 1770

Gln Pro  Ile Lys Ala Leu Pro  Gly Tyr Phe Arg Ser  Val Ala Thr
    1775                 1780                 1785

Ile Thr  Leu Pro Leu Ser Pro  Ala Ala Ile Glu Leu  Leu Ala Ala
    1790                 1795                 1800

His Val  Asp Asp Gly Asn Arg  Thr Ala Val Glu Phe  Tyr Arg Trp
    1805                 1810                 1815

Asn Lys  Lys Asp Ser Gln Phe  Arg Phe Ala Lys Gly  Phe Pro Ser
    1820                 1825                 1830

Ile Ser  Tyr Pro Thr Leu Arg  Ile Thr Lys Met Lys  Arg Ile Val
    1835                 1840                 1845

Leu Gly  Gly Ile Gln Asn Leu  Phe Val Glu Tyr Tyr  Asp His Ser
    1850                 1855                 1860

Arg Leu  Leu Tyr Arg Gln Ser  Ile Leu Asp Leu Glu  Ala Pro Asp
    1865                 1870                 1875

Phe Ser  Ala Pro Lys Lys Thr  Pro Lys Phe Thr Ser  Ile Tyr Glu
    1880                 1885                 1890

Phe Asn  Ser Thr His Pro Gln  Asp Ile Val Ala Leu  Lys Ile Leu
    1895                 1900                 1905

Asp Leu  Asp Cys Val Gly Leu  Tyr Ser Thr His Ile  Asp Gly Leu
    1910                 1915                 1920

Asn Val  Tyr Cys Leu Gln Leu  Glu Ser Leu Glu Tyr  Tyr Leu Lys
    1925                 1930                 1935

Phe His  Gln Pro Leu Thr Thr  Pro Ala Val Lys Gln  Ala Leu Phe
    1940                 1945                 1950

Leu Asp  Gly Arg Leu Ile Leu  Leu Ser Arg Asp Asn  Leu Leu Gln
    1955                 1960                 1965

Val Trp  Arg Ser Arg Ala Asp  Tyr Lys Leu Gly Leu  Phe Gln Leu
    1970                 1975                 1980

Ile Lys  Ile Ala His Pro Thr  Ser Leu Thr Val Ala  Lys Phe Glu
    1985                 1990                 1995

Gln Gln  Leu Phe Ile Ala Ile  Asn Ser Asp Gln Ala  Leu Thr Glu
    2000                 2005                 2010

Ala Ser  Ala His His Gly Ser  Ile Glu Ile Trp Arg  Asp Leu Arg
    2015                 2020                 2025

Pro Gln  His Arg Asn Ser Thr  Phe Thr Lys Tyr Gln  Thr Ile Leu
    2030                 2035                 2040

Thr Lys  Val Pro Lys Gln Ile  Gln Phe Ser Val Leu  Ser Thr Thr
    2045                 2050                 2055

Ser Glu  Leu Met Leu Tyr Thr  Leu Thr Glu Asn Pro  Phe His Pro
    2060                 2065                 2070

Leu Val  Ile Tyr Arg Tyr Glu  Gly Val Ala Gly Phe  Arg Glu Tyr
```

2075 2080 2085

Leu Thr Ser Asn Ala Leu Arg Thr Ser Ser Lys Arg Phe Ala Val
2090 2095 2100

Ile Lys Leu Asp His Lys Gln Arg Glu Leu Leu Ala Leu Ile Ala
2105 2110 2115

Asp Gln Gly Val Thr Trp Ile Glu Ala Val Ile Lys Gly Arg
2120 2125 2130

<210> SEQ ID NO 204
<211> LENGTH: 1890
<212> TYPE: PRT
<213> ORGANISM: Aedes albopictus

<400> SEQUENCE: 204

Met Ile Val Thr Met Trp Leu Tyr Phe Leu Leu Ile Leu Pro Gln Val
1 5 10 15

Thr Trp Cys Trp Ser Asp Phe Gly Asn Gly Gly Thr Glu Val Asp Leu
20 25 30

Phe Leu Arg Arg Lys Ile Asp Asp Leu Met Leu Glu Arg Arg Thr Arg
35 40 45

Gln Ala Ser Pro Ala Ala Arg Glu Ile Asp Thr Ser Gln Tyr Asp Leu
50 55 60

Thr Leu His Arg Val Lys Leu Ser Leu Asn Arg Thr Val Ile Gly Asp
65 70 75 80

His Gln Thr Phe Phe Ala Arg Val Arg Ser Ser Gly Asn Leu Tyr Leu
85 90 95

Phe Ser Gly Asn Gln Ile Ser Arg Ile Thr Val Asn Asp Ala Asp Val
100 105 110

Lys Leu Val Pro Ile Ala Thr Thr Pro Asp Val Arg Glu Glu Val Ala
115 120 125

Asp Phe Gln Ile Glu Glu Leu Gln Ile Ser Gly Asn Lys Thr Ile Leu
130 135 140

Val Ala Thr Val Cys Leu Gln Asp Arg Phe Lys Ile Tyr Gln Phe Pro
145 150 155 160

Asp His Ser Lys Gly Asn Ala Leu Thr Val Lys Ala Met Gln Arg Ile
165 170 175

Lys Arg Pro Gly Leu Asn Arg Arg Ser Val Leu Val Gln Phe Lys Ser
180 185 190

Asp Leu Phe Leu Ile Ser Gly Tyr Ser Glu Ala Gly Phe Gly Lys Val
195 200 205

Ala Ile Tyr Arg Trp Met Asp Tyr His Phe Ser Leu Arg Asp Val Lys
210 215 220

Glu Val Glu Arg Cys Asp Glu Leu Leu Val Phe Ser Gly Glu Gln Leu
225 230 235 240

Val Ile Leu Val Leu Glu Ile Ala Glu Tyr Pro Glu Arg Ser Val Asn
245 250 255

Asn Ile Tyr Met Leu Thr Asp Asp Phe Lys Leu Ile Lys Thr Gln Glu
260 265 270

Met Tyr Phe Leu His Asp Arg Leu Pro His Tyr Glu Val Asp Ser Gln
275 280 285

Phe Tyr Ile Leu Arg Cys Leu Ala Leu Asp Ala Cys Phe Leu Tyr Arg
290 295 300

Trp Asn Gly Glu Ser Leu Phe Arg Arg Ala Ser Lys Ile Gly Tyr Asp
305 310 315 320

```
Pro Arg Ser Ile Glu Met Met Ala Ser Gly Arg Asp Ile Ile Val Met
                325                 330                 335

Ser Leu Glu Lys Thr Leu Tyr Phe Tyr Asn Asn Gln Pro Leu Leu Lys
            340                 345                 350

Ile Ala Ala Ser Tyr Thr Met Val Asn Lys Arg Gly Thr Val Ala Asp
        355                 360                 365

Ala Pro Phe Gln Ile Asp Pro Arg Val Ser Lys Leu Phe Leu Tyr Lys
    370                 375                 380

Glu Ala Thr Thr Glu Lys Leu Tyr Leu Ser Ile Leu Tyr Ser Ser Gly
385                 390                 395                 400

Pro Lys Leu Leu Asp Met Val Glu Ile Gln Leu Asn Lys Gly Arg Ser
                405                 410                 415

Ala Pro Ser Pro Gly Glu Gln Ser Asn Phe Asn Ala Leu Lys Thr Cys
            420                 425                 430

Leu Phe His Ile Lys Asp Leu Val Asn Ile Arg Lys Lys Trp Ile Asp
        435                 440                 445

Met Ile Lys Tyr Gln Leu Ser Lys Thr Leu Arg Ser Cys Lys Ser Lys
    450                 455                 460

Gly Gln Leu Ser Leu Ala Ser Lys Val Tyr Leu Ala Glu Ser Asn Thr
465                 470                 475                 480

Val Asp Arg Ile Glu Val Asp Gly Asn Ile Glu Asn Ser Pro Gln Gly
                485                 490                 495

Leu Leu Asn Asp Trp Ser Ser Thr Arg Ser Ser Leu Ala Ala Ile His
            500                 505                 510

Ser Gln Ser Gln Asp Leu Phe Tyr Leu Asn Arg Met Asn Thr Val Gln
        515                 520                 525

Ser Asn Met Lys Ile Arg Gly Asn Leu Arg Ser Lys Ser Thr Arg Met
    530                 535                 540

Lys His Val Lys Val Gln His Pro His Ser Gly Arg Pro Ala Tyr Val
545                 550                 555                 560

Arg Pro Lys Arg Asp Leu Gln Ser Ser Lys Val Val Thr Ser Ala Ile
                565                 570                 575

Val Asn Ala Arg Glu Val Val Tyr Ser Gly Asn Met Phe Ala His Thr
            580                 585                 590

Leu Ser Arg Asn Asn Val Asn Tyr Val Ser Leu Pro Ile His Val Gly
        595                 600                 605

Asn Leu His Thr Pro Thr Val His Val Ser Leu Asn Thr Ile Asn Arg
    610                 615                 620

Ile Pro Ile Asp Glu Met Leu Tyr Asn Ala Thr Asn Lys Val Ile Glu
625                 630                 635                 640

Lys Gly His Lys Val Phe Lys Ser Met Asp Thr Asp Ala Leu Lys Val
                645                 650                 655

Tyr Leu Val Asn Gly Val Lys Thr Thr Gln Gln Phe Ser Ser Leu Arg
            660                 665                 670

Asn Phe Val Val Thr Ala Gly Thr Gly Ala Pro Val Lys Leu Thr Gly
        675                 680                 685

Ala Arg Gly Val Thr Asn Leu Ile Val Ser Gly Lys Leu Asn Asn Ile
    690                 695                 700

Pro Leu Asp Asp Leu Leu Gln Gln Leu Tyr Tyr Val Asp Lys Lys Ser
705                 710                 715                 720

Thr Ile Asn Gly Asn Val Phe Leu Arg Ala Pro Ser His Ile Arg Asn
                725                 730                 735

Val Tyr Val Arg His Leu Asn Asn Ile Pro Thr Ser Ser Phe Phe Asp
```

```
            740                 745                 750

Leu Arg Thr Asn Gln Thr Ile Ser Ala Val Val His Leu Ser Gln Val
        755                 760                 765

Tyr Ala Arg Thr Leu Tyr Ser Lys Thr Ile Asn Gly Ile Asn Ile Pro
    770                 775                 780

Asn Asp Val Thr Leu Ile Ser Ser Ala Lys Thr Ile Asn Ala Ala Leu
785                 790                 795                 800

Ala Ser Asn Phe Val Val Thr Lys Asp Leu Thr Leu Ser Ala Lys Asp
                805                 810                 815

Gln His Phe Thr Arg His Val Leu Gly Thr Lys Val Glu Asp Phe Ser
            820                 825                 830

Gln Ile Tyr Ser Gly Arg Val Tyr Leu Lys Gly Ser Leu Lys Val Lys
        835                 840                 845

Gln Leu Asn Leu Glu Ile Pro Lys Gly Gln Leu Ile Leu Gly Gly Leu
    850                 855                 860

Thr Val Ser Pro Asp Val Gln Lys His Phe Trp Met Lys His Val Glu
865                 870                 875                 880

Gln Asp Ile Gly Thr Phe Thr Phe Asn Arg Asn Val Glu Ala Ser His
                885                 890                 895

Leu Val Cys Ala Glu Leu Asn Tyr Asn Pro Thr Val Asn Tyr Leu Arg
            900                 905                 910

Gly Asp Gln Trp Pro Ser His Leu Asn Leu Glu Met Ser Asn Val Tyr
        915                 920                 925

Val Arg Gly Phe Ile Lys Thr Tyr Ala Ser Thr Pro Thr Phe Leu Gln
    930                 935                 940

Tyr Ile Asn Thr Glu Ala Val Gln Arg Gly Ser Met Ser Thr Val Ser
945                 950                 955                 960

Gly Arg Lys Ile Phe Thr Gly Gln Leu His Thr Asp Thr Leu Val Ser
                965                 970                 975

Asp Ala Val Asp Asn Ile Asn Ile Gln Ser Leu Ala Thr Asp Phe Ser
            980                 985                 990

Thr Met Ala Phe Leu Asp Gly Val  Lys Glu Ile Glu His  Phe Ser Ser
        995                 1000                 1005

Glu Glu  Ser Tyr Ile Glu Leu  Leu Gly Ala Leu Thr  Leu Gln Asp
    1010                 1015                 1020

Tyr Gln  Asn Thr Ser Phe Ser  Val Ile Val Asp Ser  Ser Val Asn
    1025                 1030                 1035

Thr His  Thr Met Gln Ser Leu  Glu Tyr Met Phe Leu  Pro Asp Ile
    1040                 1045                 1050

Lys Val  Glu His Phe Gln Ala  Ala Leu Ile Asn Gly  Val Asn Ala
    1055                 1060                 1065

Glu Asp  Phe Ile Ser Glu Ile  Asp Asn Phe Thr Tyr  Arg Val Asp
    1070                 1075                 1080

Pro Phe  Ala Thr Gln Phe Lys  Ile Asp Asn Leu Val  Val Lys Lys
    1085                 1090                 1095

Asn Val  Ile Ser Thr Ser Gln  Met Phe Met Asp Phe  Leu Asn Thr
    1100                 1105                 1110

Ile Gly  Val Lys Glu Tyr Phe  Lys Leu Leu Thr Leu  Lys Gly Val
    1115                 1120                 1125

Gly Asp  Lys Ala Gln Gln Trp  Glu Ile Gly Gly Ser  Lys Ile Phe
    1130                 1135                 1140

Gln Lys  Glu Met Ala Val Asp  Gly Lys Leu Asn Val  Val His Val
    1145                 1150                 1155
```

Asn Arg Leu Ile Leu Asp Asn Ile Leu Tyr Asn Ser Ala Arg Lys
1160 1165 1170

Thr Thr Pro Leu Asn Ile Ala Gly Leu Trp Ser Ile Thr Gln Leu
1175 1180 1185

Ala Thr Lys Tyr Leu Ala Thr Lys Gln Ile Asn Asp Val Pro Ile
1190 1195 1200

Lys His Leu Gln Asn Ser Asn Leu Lys Thr Phe Lys Ile Lys His
1205 1210 1215

Asp Val Ser Ile Gly Ser Leu Ser Val Ser Ser Ser Val His Gly
1220 1225 1230

His Met Phe Pro Asn Ser Ser Ser Val Leu Met Pro Pro Asn Ile
1235 1240 1245

Gln Leu Leu Ser Ser Leu Thr Val Gln Gly Ser Phe Leu Leu Glu
1250 1255 1260

His Trp Lys Pro Gly Thr Phe Leu Phe Asp Val Met Leu Ser Thr
1265 1270 1275

Val Thr Gly Ala Ser Asn Val Phe Asp Arg Lys Val Val Phe Arg
1280 1285 1290

Gly Asn His Val Glu Ile Val Lys Leu Arg Asn Glu Gly Lys Ile
1295 1300 1305

Phe Ser Lys Thr Cys Asn Phe Val Asn Leu Leu Met Asp Ser Val
1310 1315 1320

Lys Arg Lys Gln Pro Asn Leu Val Phe Ser Ser Leu Gly Lys Thr
1325 1330 1335

Phe Lys Glu Val Val Cys Leu Gly Thr Val Ala Ser Asp Asp Leu
1340 1345 1350

Val Thr Val Thr Leu Val Asn Gly Ile Asp Val Val His Leu Asn
1355 1360 1365

Arg Ser Ile His Ser Val Gly His His Gln Glu Met Ile Lys Ser
1370 1375 1380

Thr Lys Tyr Phe Glu Glu Glu Val Lys Val Val Gln Leu Leu Cys
1385 1390 1395

Asn Asp Gln Leu Val Asp Gly Ile Tyr Pro His His Leu Asp Leu
1400 1405 1410

Tyr Ser Glu Ala Ser Gln Leu Thr Lys Lys Arg Tyr Gln Phe Asp
1415 1420 1425

Lys Pro Ile Ser Val Ile Gly Asn Leu Tyr Val Asp Ala Val Asn
1430 1435 1440

Asp Tyr Ser Leu Gln His Phe Leu Ala Thr Arg Val Val Lys Asn
1445 1450 1455

Arg Thr Tyr Ala Gln Glu Tyr Gln Gln Glu Lys Ser Gln Gln Val
1460 1465 1470

Thr Gly Leu Ile Thr Phe Ser Asn Leu Val Leu Phe Gly Glu Tyr
1475 1480 1485

Asn Thr Val His Val Val Asn Gly Ile Pro Val Ser Glu Ile Val
1490 1495 1500

Ser Arg Ser Ser Asn Glu His Gln Val Met Val Lys Pro Lys His
1505 1510 1515

Leu Lys Gly Thr Ile Lys Leu Leu Gly Pro Thr Ser Val Met Lys
1520 1525 1530

Cys Asn Asp Val Asn Leu Leu Asp Val Tyr Lys Ser Ser Phe Leu
1535 1540 1545

Thr Ser Ser Pro Glu Ile Ala Phe Lys Asp Leu Val Phe Val Ser
1550 1555 1560

Glu Ser Thr Leu Gln Asn Gly Leu Ser Ile Asp Ser Arg Leu Asn
1565 1570 1575

Gly Val Ser Val Gln Lys Met Met Lys Leu Arg Leu Ser Ser Val
1580 1585 1590

Glu Asp Leu Leu Pro Met Ile Pro Val Ile Arg Glu Gln Ile Thr
1595 1600 1605

Val Ser Asn Arg Ala Tyr Val Ala Asn Ser Ala Lys Glu Ser Arg
1610 1615 1620

Met Leu Tyr Ile Glu Asn Val Pro Phe Asp Glu Arg Gly Thr Met
1625 1630 1635

Val Ser Lys Ser Glu Asn Arg Gln Ser Ser Glu Ala Ser Glu Asn
1640 1645 1650

Val Asn Phe Asp Lys Ser Cys His Asn Gly Ile Asn Arg Phe Asn
1655 1660 1665

Val Thr Ile Arg Gln Arg Ser Ser Asn Gly Asp Ile Ser Ser Ala
1670 1675 1680

Arg Ala Val Leu Asp Gly Val Leu Ile Arg Ser Glu Trp Lys Glu
1685 1690 1695

Leu Ala Tyr Asn Glu Glu Ile Glu Thr Leu Val Val Ser Gln Val
1700 1705 1710

Glu Arg Asn Ala Lys Pro Met Leu Leu Ile Tyr Val Asn Arg Asn
1715 1720 1725

Gly Glu Leu Ser Ile Gln Gln Glu Leu Pro Leu Ser Ser Ser Ala
1730 1735 1740

Ala Val Phe Tyr Met Val His Ile Asn Asp Ser Ala Leu Met Leu
1745 1750 1755

Ala Val Ala Asp Ser His Gln Leu His Leu Gly Ile Phe Ala His
1760 1765 1770

Lys Leu Lys Leu Phe Arg Tyr Asp Ser Asp Ala Ile Arg Phe Val
1775 1780 1785

His Leu Lys Thr Leu Ser Gly Ser Tyr Asn Asp Val Ala Ala Ile
1790 1795 1800

Asp Val Glu Asp Ala Ile Met Phe Ala Val Ser Glu Lys Gly Ser
1805 1810 1815

Asn Met Val Glu Ile Phe Ser Leu Glu Arg Ser Tyr Ser Ser Leu
1820 1825 1830

Tyr Gln Lys Leu Ile Phe Asp Ser Thr Val Asn Ser Met Lys Ala
1835 1840 1845

Phe Arg Leu Gln Gly Ser Pro Val Ile Gln Ile Ser Thr Ile Asp
1850 1855 1860

Asn Leu Val Tyr Val Tyr Ser Tyr Ser Thr Leu Glu Gly Trp Arg
1865 1870 1875

Gln Leu Ser Tyr Gly Arg Ile Pro Ser Asp Val Asn
1880 1885 1890

<210> SEQ ID NO 205
<211> LENGTH: 2569
<212> TYPE: PRT
<213> ORGANISM: Aedes albopictus

<400> SEQUENCE: 205

Met Asp Thr Arg Thr Glu Asn Met Tyr Glu Gln Leu Gln Arg Lys Pro
1 5 10 15

```
Trp Lys Gln Asn Val Leu His Arg Ile Gly Leu Leu Leu Leu Thr Ile
            20                  25                  30

Val Leu Val Leu Ala Val Thr Ile Ile Phe Thr Leu Leu Ile Gly Ala
        35                  40                  45

Val Thr Arg Ala Leu Ile Thr Pro Gln Thr Val Gln Val Val Tyr His
    50                  55                  60

Thr Glu Thr His His His Gly Asp Leu Leu Asp Thr Val Leu Lys Pro
65                  70                  75                  80

Met Lys Gln Leu Leu Ser Ser Thr Leu His Leu Met Gly Phe Glu Lys
                85                  90                  95

Glu His Lys Ser Arg Arg Lys Arg Asp Leu Asp Asp Asp Asp Asp Asn
            100                 105                 110

Arg Ile Gln Met Val Asp Asp Asn Met Leu Glu Lys Ser Glu Gln Ser
        115                 120                 125

Asp Glu Asp Leu Arg Thr Val Asp Phe Gly Ser Gly Ile Asp Gly Ala
    130                 135                 140

Leu Gln Arg Leu Thr His Lys Asn Leu Thr Leu Lys Ile Val Tyr Ala
145                 150                 155                 160

Pro Phe Gly Asn Glu Gly Asn Arg Asn Glu Ile Met Arg Ser Met Arg
                165                 170                 175

Arg Arg Arg Arg Arg Lys Arg Ser Ala Glu Ser Glu Lys Arg Lys Ala
            180                 185                 190

His Glu Tyr Gln Glu Leu Arg Arg Glu Tyr Ser Lys Arg Cys Lys Lys
        195                 200                 205

Glu Ala Pro Asn Glu Lys Asp Cys Ser Arg Tyr Cys Glu Lys Phe Glu
    210                 215                 220

Gln Phe Leu Lys Glu Thr Lys His Ser Tyr Lys Glu Ile Lys His Lys
225                 230                 235                 240

Leu Ser Gly Leu Leu Lys Asp Cys Lys Gly Lys His Gly Gly Asp Leu
                245                 250                 255

Lys Gly Asp Leu Ser Asp Ser Phe Pro Lys Arg Lys Glu Asn Lys Leu
            260                 265                 270

Ile Asp Leu Asp Ser Asp Glu Ser Ser Gly Lys Val Met Lys Lys Asp
        275                 280                 285

Lys Pro Ile Asp Gln Ala Thr Asp Ser Thr Thr Leu Asn Glu Asp Gln
    290                 295                 300

Val Thr Thr Val His Thr Glu Leu Glu Leu Thr Thr Val Thr Gly Asn
305                 310                 315                 320

Tyr Ser Asp Ala Ser Glu His Asp Lys Thr Asn Thr Gln Asn Pro Gly
                325                 330                 335

Lys Asp Thr Lys Asn Val Ser Thr Val Pro Pro Ile Glu Lys Thr Ser
            340                 345                 350

Tyr Asn Pro Leu Asn Ala Asp Phe Gln Glu Gln Ile Glu Gln Phe Ala
        355                 360                 365

Glu Asn Leu Val Asp Asp Thr Thr Trp Lys Val Leu Asn Thr Ala Ser
    370                 375                 380

Thr Lys Thr Pro Glu Thr Leu Ala Thr Thr Thr Val Val Val Thr Ser
385                 390                 395                 400

Thr Asp Gln Thr Ser Lys Asp Pro Thr Leu Asp Asp Leu Ile Glu Ser
                405                 410                 415

Leu Asn Lys Thr Ala Ser Asn Arg Thr Val Pro Gln Pro Phe Asp Ala
            420                 425                 430
```

```
Gln Arg His Asn Pro Val Glu Asp Asp Cys Val Lys Asn Leu Asp Asp
        435                 440                 445

Leu Leu Lys Lys Ile Pro Glu Phe Lys Thr Asp Asp Asp Glu Asp Leu
    450                 455                 460

Asp Cys Asn Glu Thr Thr Thr Gln Ser Pro Asp Glu Thr Leu Val Gly
465                 470                 475                 480

Gln Thr His Ile Ser His Phe Lys Lys Gln Asn Leu Lys Tyr Asn Pro
                485                 490                 495

Asp Glu His Arg Pro Lys Thr Val Glu Cys Ile Lys Asn Ile Asp Asp
            500                 505                 510

Leu Leu Glu Ala Val Asp Met Glu His Gly Gly Leu Lys Lys Pro Lys
        515                 520                 525

Asn Cys Lys Ile Ser Ser Ser Thr Val Ala Pro Ser Lys His Arg Ser
    530                 535                 540

Asp Ser Ser Ala Arg Thr Glu Asp Glu Glu Phe Asp Pro Val Gln Thr
545                 550                 555                 560

His Asp Glu Gln Leu Asp Gln Phe Ala Ser Ala Ala Glu Leu Pro Asp
                565                 570                 575

Phe Ile Lys Pro Pro Thr Pro Phe His Glu Glu Gln Phe Asp Gln Ser
            580                 585                 590

Thr Leu Pro Val Glu Val His Asp Phe Ile Met Gly Arg Ser Arg Asn
        595                 600                 605

Arg Glu Gln Phe Asn His Asp Ile Pro Ser Thr Ile Asp Ser Pro Asp
    610                 615                 620

Phe Arg Ala Ser Lys Tyr Ser Ala Gln Pro Thr Val Ala Ala Ser Gly
625                 630                 635                 640

Pro Phe Leu Asn Leu Cys Glu Gln Leu Arg Ser Gln Gln His Ala Ala
                645                 650                 655

Pro Ile Lys Thr Leu Ser Ser Asn Gln His His Phe Gln Ala Gln Gln
            660                 665                 670

Tyr Gly Gly Leu Gly Gln Thr Ser Ile Pro Val Thr Gly Glu Thr Leu
        675                 680                 685

Lys Ala Thr Ser Gln Val Leu Val Asn Ser Ala Tyr Gly Gly Phe Ala
    690                 695                 700

Pro Asn His Phe Cys Phe Tyr Gln Val Pro Pro Thr Tyr Gly Ala Met
705                 710                 715                 720

Arg Pro Val Tyr Ala Gly Gly Gln Asn Tyr Pro Ala Gly Ser Leu Lys
                725                 730                 735

Ile Phe Arg Gly Val Phe Ser Gly Leu Leu Asn Val Pro Leu Ser Ile
            740                 745                 750

Gln Lys Ser Ser Gly Arg Ser Thr Gly Asp Asp Pro Asp Leu Glu Gly
        755                 760                 765

Ala Lys Leu Leu Cys Ser Leu Val Val Pro Pro Ser Thr Glu Ser Pro
    770                 775                 780

Leu Ala Gly Asn Asp Ser Leu Ile Ser Gln Glu Val Leu Val Gly Gly
785                 790                 795                 800

Ala Arg Ala Arg Gly His His Arg His Cys Pro Arg Gly Lys Val Pro
                805                 810                 815

Cys Ala Asp Gly Ile Gln Cys Val Leu Ser Ser His Leu Cys Asp Ser
            820                 825                 830

Arg Val Asp Cys Phe Asp Gly Ser Asp Glu Ser His Cys Ser Cys Leu
        835                 840                 845

Ser Arg Leu Ser Gln Lys Arg Arg Cys Asp Gly Tyr Val Asp Cys Pro
```

```
    850                 855                 860

Leu Gly Glu Asp Glu Met Gly Cys Phe Gly Cys Asp Lys Phe Ser Phe
865                 870                 875                 880

Ser Cys Phe Asn Ser Phe Phe Glu His Gln Ala Ser His His Ser Glu
                885                 890                 895

Thr Arg Cys Tyr Thr Leu Ile Glu Lys Cys Asp Gly Phe Asn Asn Cys
            900                 905                 910

Val Asn Gly Lys Asp Glu Gln Asp Cys Thr Met Leu Val Arg Asp Leu
        915                 920                 925

Arg Ser Pro Leu Ala Phe Thr Val Gly His Ser Val Gly Val Leu His
    930                 935                 940

Arg Asn His Lys Gly Lys Trp Tyr Pro Val Cys His Asn Pro Leu Ser
945                 950                 955                 960

Leu Ala Arg Glu Ala Cys Glu Ala Glu Leu Gly Pro Ser Glu Arg Asp
                965                 970                 975

Pro Val Ile Val Gln His His Gly Asp Leu Pro Gly Pro Phe Ile Gln
            980                 985                 990

Pro Ser Pro Arg Ser His His Val  Phe Gln Pro Glu Phe  Thr Asp Thr
        995                 1000                1005

Cys Asn  Gly Leu Ile Asn Tyr  Val Lys Cys Pro Ala  Pro Lys Cys
    1010                 1015                 1020

Gly Ser  Ser Lys Gln Asn Glu  Met Glu His Ala Arg  Ile Lys Ile
    1025                 1030                 1035

Arg Gly  Lys Arg Asn Thr Thr  Glu Ile Val Gln Ile  Val Gly Gly
    1040                 1045                 1050

Thr Lys  Ala Glu Ala Ser Ala  Tyr Pro Phe Ile Val  Gly Ile Phe
    1055                 1060                 1065

Arg Asp  Gly Lys Phe His Cys  Gly Gly Ser Ile Phe  Asn Glu His
    1070                 1075                 1080

Trp Ile  Val Thr Ala Ala His  Cys Cys Asp Asn Phe  Pro Arg His
    1085                 1090                 1095

His Tyr  Glu Leu Arg Ala Gly  Leu Leu Arg Arg Arg  Ser Phe Ala
    1100                 1105                 1110

Pro Gln  Val Gln Val Ser Thr  Val Thr His Val Ile  Ile His Arg
    1115                 1120                 1125

Gly Tyr  Ser Ala Gln Lys Met  Ile Asn Asp Ile Ser  Leu Met His
    1130                 1135                 1140

Ser Asp  Arg Pro Phe Gln Tyr  Asn Arg Trp Val Arg  Pro Ile Cys
    1145                 1150                 1155

Leu Pro  Asn Arg His Met Thr  Thr Asn Asp Arg Asp  Trp Ile Trp
    1160                 1165                 1170

Gly Pro  Lys Pro Gly Thr Met  Cys Thr Ala Ile Gly  Trp Gly Ala
    1175                 1180                 1185

Leu Arg  Glu His Gly Gly Ser  Pro Asp His Leu Met  Gln Val Thr
    1190                 1195                 1200

Val Pro  Ile Leu Pro Phe Cys  Lys His Arg Asn Asp  Arg Asp Gly
    1205                 1210                 1215

Leu Ala  Ile Cys Ala Ala Glu  Pro Ser Gly Gly His  Asp Ala Cys
    1220                 1225                 1230

Gln Gly  Asp Ser Gly Gly Pro  Phe Ala Cys Ile Ser  Val Thr Ser
    1235                 1240                 1245

Pro His  Glu Trp Tyr Leu Ala  Gly Val Val Ser His  Gly Glu Gly
    1250                 1255                 1260
```

```
Cys Ala  Arg Pro Asn Glu Pro  Gly Val Tyr Thr Arg  Val Ala Leu
    1265                 1270                 1275

Phe Asn  Asp Trp Ile His Arg  Lys Thr Ser Glu Val  Leu Pro Pro
    1280                 1285                 1290

Ala Ser  Thr Arg Met Asp Cys  Pro Gly Phe Gln Cys  Ser Val Gly
    1295                 1300                 1305

Val Ser  Phe Cys Ile Pro Arg  Gln Lys Arg Cys Asn  Gly Lys Val
    1310                 1315                 1320

Asp Cys  Leu Gly Gly Glu Asp  Glu Leu His Cys Ser  Leu Asp Gln
    1325                 1330                 1335

Leu Leu  Ala Glu Thr Ile Lys  Glu Thr Ser Thr Val  Thr Val Ala
    1340                 1345                 1350

Ala Asn  Ser Thr Val Ala Ser  Ser Thr Thr Glu Ala  Ala Thr Thr
    1355                 1360                 1365

Ala Val  Thr Ser Lys Ile Asp  Phe Val Glu Glu Thr  Ala Glu Thr
    1370                 1375                 1380

Ser Glu  Lys Ser Thr Thr Val  Thr Thr Ala Ser Asn  Asp Glu Thr
    1385                 1390                 1395

Ser Thr  Ile Ala Thr Thr Ile  Glu Thr Thr Ser Val  Ser Thr Glu
    1400                 1405                 1410

Pro Lys  Pro Ala Lys Asp Leu  Asp Met Met Ser Asp  Ser Thr Ala
    1415                 1420                 1425

His Asn  Ile Thr Glu Val Thr  Thr Val Glu Pro Thr  Thr Thr Gln
    1430                 1435                 1440

Asp Glu  Asp Thr Ser Thr Ser  Ser Thr Thr Ser Glu  Tyr Ser Thr
    1445                 1450                 1455

Thr Glu  Thr Ser Phe Thr Asn  Gln Thr Lys Phe Glu  Ser Ser Thr
    1460                 1465                 1470

Thr Tyr  Glu Val Thr Thr Arg  Gln Val Leu Glu Asp  Ile Ser Ala
    1475                 1480                 1485

Ser Pro  Val Phe Asn Glu Thr  Thr Ser Thr Leu Glu  Tyr Asn Ala
    1490                 1495                 1500

Ala Met  Pro Thr Asp Pro Ser  Thr Ile Pro Thr Ser  Thr Leu Pro
    1505                 1510                 1515

Ala Thr  Ile Asp Ser Ile Asp  Ser Tyr Ser Ser Thr  Ala Asn His
    1520                 1525                 1530

Ser Ser  Val Asp Phe Ser Ile  Thr Thr Glu Pro Thr  Thr Glu Thr
    1535                 1540                 1545

Ser Leu  His Thr Thr Glu Ser  Val Thr Glu Leu Ser  Thr Ser Thr
    1550                 1555                 1560

Ala Glu  Thr Ser Ser Ile Glu  Thr Ser Thr Val Leu  Asp Thr Thr
    1565                 1570                 1575

Thr Ile  Met Glu Thr Thr Thr  Pro Leu Tyr Ser Ser  Lys Ile Tyr
    1580                 1585                 1590

Glu Thr  Thr Ser Met Thr His  Glu Thr Glu Ser Ser  Asp Thr Thr
    1595                 1600                 1605

Gln Ser  Ser Glu Leu Ala Thr  Thr Glu Ser Thr Thr  Ser Thr Thr
    1610                 1615                 1620

Thr Pro  Asp Glu Thr Thr Pro  Leu Val Thr Thr Glu  Ser Glu His
    1625                 1630                 1635

Ser Ser  Thr Thr Thr Ser Pro  Phe Trp Met Gln Val  Asn Glu Ala
    1640                 1645                 1650
```

```
Ile Ser  Lys Leu Lys Pro His  Phe Pro Ser Met His  Arg Glu Met
    1655                 1660                 1665

Glu Asp  Arg Asn Gln Gln Gln  Tyr Asp Ser Ile Arg  Ala Thr Leu
    1670                 1675                 1680

Ser Asp  Asn Ala Thr Ser Thr  Thr Thr Pro Ile Pro  Lys Thr Ser
    1685                 1690                 1695

Tyr Asp  Thr Ser Thr Thr Glu  Leu Ala Thr Ser Thr  Thr Asp Ser
    1700                 1705                 1710

Thr Ser  Ser Thr Ser Ile Ser  Pro Ser Thr Val Glu  Ser Ser Ser
    1715                 1720                 1725

Thr Val  Pro His Asp Gln Glu  Phe Ser Glu Thr Gln  Ile Glu Pro
    1730                 1735                 1740

Val Lys  Ala Glu Thr Thr Asn  Ala Thr Ala Glu Gln  His Pro Phe
    1745                 1750                 1755

Phe Arg  Glu Ile His Asp Leu  Val Glu Glu Lys Thr  Arg Arg Leu
    1760                 1765                 1770

Asn Gln  Phe Arg Leu Ser Met  His Tyr Leu His Thr  Ser Leu Lys
    1775                 1780                 1785

Asn Gln  Thr Leu Asp Thr Asn  Glu Thr Ser Tyr Arg  Tyr Lys Arg
    1790                 1795                 1800

Phe Val  Cys Ser Lys Ile Pro  Gln Thr Ile Asn Ile  Ala His His
    1805                 1810                 1815

Cys Asp  Arg Ile Ile Asp Cys  Glu Asp Gly Thr Asp  Glu Leu Arg
    1820                 1825                 1830

Cys Thr  Cys Arg Asp Tyr Leu  Lys Asp Lys Tyr Asp  Phe Leu Ile
    1835                 1840                 1845

Cys Asp  Gly Lys Thr Asp Cys  Leu Asp Leu Thr Asp  Glu Asp Asp
    1850                 1855                 1860

Cys Phe  Ser Cys Ala Thr Gly  Gln Tyr Pro Cys Arg  Met Ser Lys
    1865                 1870                 1875

Val Cys  Ile Asp Glu Lys Lys  Leu Cys Asp Asn Val  Pro Asp Cys
    1880                 1885                 1890

Pro Leu  His Glu Asp Glu Leu  Asp Cys Leu Ala Leu  Thr Asp Gly
    1895                 1900                 1905

His Lys  Val Tyr Phe Asp Ala  Asn Asn Leu Thr Glu  Phe Lys Tyr
    1910                 1915                 1920

Glu Gly  Leu Val Thr Lys Asn  Thr Asn Gly Thr Trp  Asp Leu Ile
    1925                 1930                 1935

Cys Gly  Ala Glu Val Asn Asn  Lys Ser Val Asp Ser  Ile Gly Lys
    1940                 1945                 1950

Ile Cys  Ser Phe Leu Gly Phe  Ala Gly Tyr Lys Ser  Tyr Tyr Gln
    1955                 1960                 1965

Thr Ile  Leu Thr Pro Leu Val  Asn Glu Thr Val Asp  Leu Glu His
    1970                 1975                 1980

Gln Pro  Leu Leu Ile Met Ser  Tyr Arg Asn Val Ser  Ser Glu Pro
    1985                 1990                 1995

Asn Cys  Lys Ala Leu His Ile  Thr Cys Val Pro Phe  Ile Asn Ala
    2000                 2005                 2010

Thr Glu  His Glu Ile Ser His  Tyr Glu Asn Gln His  Lys Glu Gln
    2015                 2020                 2025

Pro Val  Gln Val Asn Ile Arg  Pro Thr Asn Pro Ile  Lys Asn Ile
    2030                 2035                 2040

Ser Ser  Gln Ala Tyr Ile Thr  Phe Asn Glu Asn Ala  His Ile Glu
```

```
    2045                2050                2055

Phe Ile  Glu Asn Phe Gly Asp  Asp Tyr Asp Trp Pro  Trp Asn Ala
    2060                2065                2070

Asp Ile  Tyr Leu Glu Gly Val  Phe Leu Cys Ser Ala  Ile Ile Ile
    2075                2080                2085

Asp Val  Asn Trp Ile Val Val  Asp Ser Ser Cys Met  Arg Met Ile
    2090                2095                2100

Asn Leu  Lys Asn Asp Tyr Leu  Ser Val Val Ala Gly  Gly Ala Lys
    2105                2110                2115

Ser Tyr  Leu Lys Ile Ser Gly  Pro Tyr Asp Gln Val  Val Arg Val
    2120                2125                2130

Asp Cys  Tyr His Phe Leu Pro  Glu Pro Arg Val Val  Met Leu His
    2135                2140                2145

Leu Ala  Lys Asn Leu Thr Phe  Thr Arg His Val Leu  Pro Thr Phe
    2150                2155                2160

Ile Pro  Glu Gln Asn His Asn  Ile Glu Asp Asn Gln  Cys Leu Ala
    2165                2170                2175

Val Gly  Gln Asp Lys Tyr Gly  Arg Thr Arg Thr Leu  Arg Val His
    2180                2185                2190

Met Asn  Met Thr Asn Cys Glu  Pro Phe His Val Cys  Tyr Gln Leu
    2195                2200                2205

Asn Pro  Asp Arg Gly Ile Tyr  His Ala Asp His Cys  Tyr Ser Glu
    2210                2215                2220

Asn Ala  Ser Arg Thr Gly Val  Val Val Cys Lys Ser  Lys Ile Ser
    2225                2230                2235

Gly Trp  Tyr Pro Val Gly Phe  Tyr Gln Asn Lys His  Gly Leu Cys
    2240                2245                2250

Gly Phe  Asn Glu Val Val Lys  Met Ile Ser Leu Lys  Glu Tyr Tyr
    2255                2260                2265

Thr Asp  Ile Gln His Val Leu  Asn His Glu Lys Cys  Asn Glu Phe
    2270                2275                2280

Pro Glu  Pro Leu Cys Asp Gly  Leu Arg Cys Trp Leu  Gly Lys Cys
    2285                2290                2295

Ile Gly  His Ser Leu Val Cys  Asp Asn Lys Met Asp  Cys Asp Asp
    2300                2305                2310

Asn Ser  Asp Glu Arg Pro Glu  Ala Cys Asn Ala Ile  Asn Asp Thr
    2315                2320                2325

Ser Thr  Ala Cys Leu Pro Thr  Gln Phe Arg Cys Gly  Asn His Gln
    2330                2335                2340

Cys Val  Asp Lys Ser Lys Phe  Cys Asp Gly Arg Asn  Asp Cys Gly
    2345                2350                2355

Asp Leu  Ser Asp Glu Pro His  Glu Cys Ser Cys Tyr  Thr Tyr Leu
    2360                2365                2370

Lys Val  Thr Asn Pro Ser Lys  Ile Cys Asp Gly Val  Arg Asn Cys
    2375                2380                2385

Trp Asp  Lys Ser Asp Glu Asn  Pro Arg Leu Cys Lys  Cys Glu Gln
    2390                2395                2400

Thr Ser  Phe Val Cys Gly Asp  Ser Asp Ile Cys Ile  Pro Tyr Asp
    2405                2410                2415

His Val  Cys Asp Gly Glu Ile  Asp Cys Pro Gly Glu  Glu Asp Glu
    2420                2425                2430

His Tyr  Cys Tyr Ala Leu Gln  Gln Asn Pro Ala Glu  Thr Asn Tyr
    2435                2440                2445
```

Gly Glu Val Met Gln Gln Ser His Gly Ile Trp His Ser Met Cys
2450 2455 2460

Phe Pro Lys Asp Gly Gln Tyr Asp Glu Gln Lys Ile Lys Glu Ile
2465 2470 2475

Cys His Ser Ile Gly Tyr Arg Lys Ile Arg Lys Val Phe Gly Arg
2480 2485 2490

Lys Met Ile Gln Glu Ser Arg Leu Arg Thr Ser Asn Arg Thr His
2495 2500 2505

Asn Pro Val Asp Arg Met Arg Gly Ala Ala Thr Lys Ala Val Val
2510 2515 2520

Leu Asn Lys Phe Ser Lys Val Arg Ile Asn Gly Lys Gln Thr Phe
2525 2530 2535

Phe Met Lys Pro Ser Arg Pro Leu Tyr Thr Leu Val His Trp Asp
2540 2545 2550

Ala Glu Asp Glu Thr Arg Cys Asp Arg Leu Glu Ile Asn Cys Gly
2555 2560 2565

Asp

<210> SEQ ID NO 206
<211> LENGTH: 248
<212> TYPE: PRT
<213> ORGANISM: Aedes albopictus

<400> SEQUENCE: 206

Met Arg Lys Gln Leu Leu Trp Ile Leu Ser Val Leu Ile Val Ala Ala
1 5 10 15

Gly Asp Ile Gly Asn Arg Val Asp Asp Gly Asn Val Thr Asn Phe Asp
20 25 30

Ser Phe Leu Gly Thr Tyr Gln Lys Lys Tyr Lys Ala Lys Tyr Arg Met
35 40 45

Asp Arg Arg Lys Arg Ala Phe Lys Lys Asn Met Glu Glu Ile Glu Glu
50 55 60

His Asn Ala Asn Phe Gln Gln Gly Lys Ser Thr Phe Gln Met Gly Val
65 70 75 80

Asn Glu Leu Ala Asp Met Asp Lys Ser Ser Tyr Leu Lys Lys Met Val
85 90 95

Arg Met Thr Asp Ser Ile Asp His Arg Lys Leu Asp Val Asp Phe Asn
100 105 110

Asp Glu Met Leu Gln His Thr His Ser Phe Gly Glu Glu Ile Val Gln
115 120 125

Ser Thr Gln Asn Ser Met Pro Asp Ser Leu Asp Trp Arg Asp Lys Gly
130 135 140

Phe Thr Thr Ile Ala Val Asn Gln Lys Thr Cys Gly Ser Cys Tyr Ala
145 150 155 160

Phe Ser Val Gly His Ala Ile Asn Gly Gln Ile Met Arg Arg Ile Gly
165 170 175

Arg Ile Glu Tyr Val Ser Thr Gln Gln Met Val Asp Cys Ser Thr Ser
180 185 190

Ala Gly Asn Lys Gly Cys Ala Gly Gly Ser Leu Arg Tyr Thr Met Gln
195 200 205

Tyr Leu Gln Gly Ser Gly Gly Val Met Arg Asp Ser Asp Tyr Pro Tyr
210 215 220

Thr Ser Ala Val Ser Met Asn Glu Lys Gly Val Asp Gly Phe Ser Leu
225 230 235 240

Tyr Ser Leu Asn Glu Pro Val Gln
245

<210> SEQ ID NO 207
<211> LENGTH: 553
<212> TYPE: PRT
<213> ORGANISM: Aedes albopictus

<400> SEQUENCE: 207

Met Trp Lys Ser Val Val Cys Val Ala Leu Ile Gly Ala Phe Gly Ala
1 5 10 15

Val Ser Gly Thr Ser Lys Leu Gln Glu Arg Tyr Ser Trp Arg Gln Leu
20 25 30

Asp Phe Val Phe Pro Asn Gln Gln Leu Lys Gln Gln Ala Leu Ala Ser
35 40 45

Gly Asp Tyr Val Pro Thr Asn Gly Leu Pro Val Gly Ile Glu Arg Trp
50 55 60

Glu Asn Lys Leu Phe Val Ser Val Pro Arg Trp Lys Asp Gly Ile Pro
65 70 75 80

Ser Thr Leu Asn Tyr Ile Asp Met Asn Gln Thr Pro Ser Gly Ser Pro
85 90 95

Pro Leu Ile Pro Tyr Pro Ser Trp Ala Asn Asn Val Ala Gly Asp Cys
100 105 110

Gln Asn Gly Leu Ser Thr Val Tyr Arg Ile Lys Ala Asp Lys Cys Gly
115 120 125

Arg Leu Trp Val Leu Asp Thr Gly Thr Val Gly Ile Gly Asn Thr Thr
130 135 140

Gln Gln Leu Cys Pro Tyr Ala Leu Asn Ile Phe Asp Leu Lys Thr Asn
145 150 155 160

Thr Arg Leu Arg Arg Tyr Glu Leu Arg Ala Glu Asp Thr Asn Gln Asn
165 170 175

Thr Phe Ile Ala Asn Ile Ala Ile Asp Met Gly Arg Ser Cys Asp Asp
180 185 190

Thr Phe Ala Tyr Met Ser Asp Glu Leu Gly Tyr Gly Leu Ile Ala Tyr
195 200 205

Ser Phe Glu Lys Asn Lys Ser Trp Arg Phe Glu His Ser Phe Phe Phe
210 215 220

Pro Asp Pro Leu Arg Gly Asp Phe Asn Val Ala Gly Leu Asn Phe Gln
225 230 235 240

Trp Gly Glu Glu Gly Ile Phe Gly Met Ser Leu Ser Pro Met Gln Ala
245 250 255

Asp Gly Phe Arg Thr Met Tyr Phe Ser Pro Leu Ala Ser His Arg Glu
260 265 270

Phe Met Val Ser Thr Gln Val Leu Arg Asp Glu Glu Gly Ala Glu Glu
275 280 285

Ser Phe His Lys Phe Thr Tyr Leu Lys Glu Arg Gly Pro Asn Ser His
290 295 300

Thr Thr Ser Arg Val Met Ser Glu Thr Gly Leu Gln Leu Phe Asn Leu
305 310 315 320

Ile Asp Gln Asn Ala Val Gly Cys Trp His Ser Ser Leu Pro Tyr Ser
325 330 335

Pro Glu Asn His Gly Ile Val Asp Arg Asp Asp Val Glu Leu Val Phe
340 345 350

Pro Ala Asp Val Lys Ile Asp Phe Glu Glu Asn Val Trp Val Ile Ser

```
        355                 360                 365

Asp Arg Met Pro Val Phe Leu Ile Ala Glu Leu Asp Tyr Ser Asp Val
    370                 375                 380

Asn Phe Arg Ile Phe Thr Ala Pro Leu Ser Thr Leu Val Ser Gly Thr
385                 390                 395                 400

Val Cys Asp Val Ala Pro Ser Leu Arg Pro Gly Ala Ile Gln Ser Lys
                405                 410                 415

Phe Gly Gly Ser Asp Leu Thr Thr Tyr Pro Gly Thr Thr Leu Leu Pro
            420                 425                 430

Ala Gly Tyr Ser Gln Pro Ile Ser Tyr Thr Pro Thr Ser Tyr Ala Pro
        435                 440                 445

Thr Val Ala Pro Val Thr Lys Tyr Thr Ser Ala Pro Ala Ala Tyr Asp
    450                 455                 460

His Pro Thr Ser His Met Tyr Thr Thr Gln Glu Tyr Pro Thr Thr Ala
465                 470                 475                 480

Lys Ala Tyr His Phe Asn Lys Tyr His Asn Val Glu Tyr Gln Ser His
                485                 490                 495

Gly Asn Gly Gln Ala Asp Tyr His Phe Gly His Gly Gly His Tyr His
            500                 505                 510

Gly Gly His Asp His Gly Gly His Asp Tyr Gly His Asp His Gly Tyr
        515                 520                 525

Tyr Gly Gly Gly Glu His Arg Arg Tyr Trp Gly Ala Gly Pro Lys Lys
    530                 535                 540

Pro Glu Ala Trp Lys Gln Gln Leu Tyr
545                 550


<210> SEQ ID NO 208
<211> LENGTH: 373
<212> TYPE: PRT
<213> ORGANISM: Aedes albopictus

<400> SEQUENCE: 208

Met Arg Asp Asn Ile Leu Trp Leu Leu Ala Ala Leu Val Ala Leu Leu
1               5                   10                  15

Thr Val Thr Thr Val Thr Ala Phe Ala Asn Asn Ser Asn Ala Ile Tyr
            20                  25                  30

Thr Trp Glu Gly Gly Arg Ile Glu Trp Pro Cys Pro Thr Thr Lys Arg
        35                  40                  45

Leu Val Lys Ala Ala Ala Lys Tyr Thr Pro Lys Asp Ile Ile Ala Met
    50                  55                  60

Ala Cys Ala Arg Ser Gly Asp Lys Thr Leu Cys Ala Met Pro Arg Tyr
65                  70                  75                  80

Arg Asn Ser Ile Pro Ile Thr Leu Gly Gln Ile Tyr Ala Thr Lys Arg
                85                  90                  95

Gly Cys Asp Val Lys Phe Glu Pro Phe Pro Cys Trp Thr Glu Gln Glu
            100                 105                 110

Glu Asn Asn Cys Asn Ser Leu Gln Ser Val Ile Asp Ile Tyr Ala Thr
        115                 120                 125

Gly Asp Phe Val Trp Val Leu Asp Ser Gly Ile Leu Asn Ala Leu Arg
    130                 135                 140

Ser Pro Ile Gln Arg Cys Pro Ala Lys Ile Val Val Tyr Glu Ser Lys
145                 150                 155                 160

Thr Asn Lys Lys Met Lys Thr Ile Asn Leu Ala Arg Tyr Val Thr Glu
                165                 170                 175
```

```
Lys Ser Arg Leu Gln Tyr Met Gln Val Glu Cys Leu Lys Gly Gly Gln
            180                 185                 190

Cys Phe Val Tyr Ile Ser Asp Ala Gly Asn Asn Ala Ile Ile Val Tyr
        195                 200                 205

Asp Val Ser Gly Gly Arg Gly Tyr Arg Val Val Leu Pro Lys Ala Val
    210                 215                 220

His His Gly Cys Arg Phe Arg Asp Val Leu Tyr Ile Phe Leu Ser Tyr
225                 230                 235                 240

His Lys Glu Gly Thr Lys Leu Tyr Phe Thr Tyr Leu Gly Gly Arg Arg
                245                 250                 255

Leu Phe Ala Ile Arg Thr Asp His Leu Arg Lys Gly His Gly Gly Asn
            260                 265                 270

Ile Glu Asp Ile Gly Glu Lys Pro Gly Ser Tyr Ile Tyr Ile Gly Ser
        275                 280                 285

Asp Gly Ala Thr Gly Val Phe Phe Arg Glu Glu Gly Asp Ser Asn Val
    290                 295                 300

Phe Phe Trp Asp Thr Lys Gln Cys Leu Lys Lys Ser Asn Phe Lys Leu
305                 310                 315                 320

Val Phe Lys Ser Ser Glu Gly Leu Tyr Ala Thr Asp Val Phe Pro Asp
                325                 330                 335

His Glu Ile Asn Arg Phe Leu Ile Leu Glu Ser Asp Phe Pro Gly Tyr
            340                 345                 350

Met Glu Glu Lys Ala Gly Cys Gly Thr Leu His Gln Ile Ser Leu Leu
        355                 360                 365

Asp Gly Thr Ala Cys
    370
```

<210> SEQ ID NO 209
<211> LENGTH: 379
<212> TYPE: PRT
<213> ORGANISM: Aedes albopictus

<400> SEQUENCE: 209

```
Met Trp Phe Arg Ile Leu Ser Gly Ser Leu Leu Ala Val Leu Cys Leu
1               5                   10                  15

Ala Asp Val Lys Pro Cys Glu Tyr Met Asp Arg Ile Tyr Arg Ile Asn
            20                  25                  30

Gly Asn Ser Ile Asp Phe Pro Cys Glu Ser Thr Lys Asn Ile Phe Val
        35                  40                  45

Ser Thr Glu Arg Tyr Lys Pro Cys Ser Ile Ile Pro Met Arg Phe Gln
    50                  55                  60

Ile Asp Gly Asp Asn Glu Arg Cys Phe Val Val Met Thr Arg Leu Arg
65                  70                  75                  80

Thr Gly Asn Pro Val Thr Leu Gly Val Ile Asp Leu Thr Arg Pro Ser
                85                  90                  95

Cys Tyr Ala His Ile Lys Pro Tyr Pro Cys Trp Ser Tyr Gln Glu Glu
            100                 105                 110

Gly Asn Cys Asn Ala Phe Gln Ser Val Val Asp Ile Phe Val Asp Val
        115                 120                 125

Lys Lys Lys Met Trp Val Leu Asp Ser Gly Ile Cys Asn Ser Leu Glu
    130                 135                 140

Gln Pro Ile Lys Arg Cys Thr Ala Lys Val Val Ala Phe Asp Leu Glu
145                 150                 155                 160

Thr Asp Lys Thr Val Lys Thr Val Asp Leu Ser Asp Ile Leu Lys Pro
                165                 170                 175
```

Asn Ser Arg Pro Gln Tyr Leu Val Thr Asp Tyr Ser Pro Asn Gly Phe
180 185 190

Pro Tyr Val Tyr Ile Ser Asp Ala Glu Gly Ala Ile Ile Val Leu Asp
195 200 205

Ile His His Asn Lys Met Tyr Arg Val Val Leu Pro Arg Ala Ile Ser
210 215 220

Ala Gly Cys Gly Glu Ser Asp Val Leu Tyr Leu Leu Leu Val Arg Arg
225 230 235 240

Pro Lys Asn His Asn Leu Val Ile Phe Ser Tyr Leu Cys Gly Asn Lys
245 250 255

Val Tyr Gly Ile Lys Ser Glu Tyr Leu Arg Thr Gly Arg Gly Ser Ser
260 265 270

Ala Ile Val Glu Leu Gly Ser Lys Thr Arg His Ser Val Leu Leu Gly
275 280 285

Thr Asp Gly Ser Asn Ser Val Ile Leu Arg Tyr Arg Ser Glu Ser Glu
290 295 300

Leu Tyr Lys Trp Asn Thr Asp Gln Pro Tyr Lys Glu Cys Asn Phe Glu
305 310 315 320

Leu Val Gln Leu Ala Glu Glu Cys Arg Leu Ser Thr His Val Ala Pro
325 330 335

Gly Gly Lys Asp Asp Leu Met Tyr Ser Leu Ser Ser Asn Val Ala Asp
340 345 350

Tyr Leu Asn His Thr Cys Gly Ala Gly Gly Ala Ser Ala Arg Leu Lys
355 360 365

Tyr Ile Ser Lys Asp Cys Glu Asp Asp Cys Tyr
370 375

<210> SEQ ID NO 210
<211> LENGTH: 827
<212> TYPE: PRT
<213> ORGANISM: Anopheles gambiae

<400> SEQUENCE: 210

Asp Gly Gly Gln Ser Phe Gly Gln Asp Ser Gly Tyr Thr Ser Tyr Gln
1 5 10 15

Ala Thr Thr Pro Asn Asn Thr Phe Asn Leu Ser Ser Arg His Gly Ile
20 25 30

Ser Ser Val Thr Leu Ala Thr Ile Asp Glu Ala Gly Glu His Asp Cys
35 40 45

Ser Met Asn Asp Thr Gly Gly Gly Gly Ser Pro Thr Gly Ala Ile Asn
50 55 60

Leu Thr Pro Lys Thr Ala Ala Ser Met Val Leu Leu Ser Asn Ile His
65 70 75 80

Ile Asn Thr Pro Lys Ser Thr Asp Arg Ala Lys Arg Ile Arg Arg Pro
85 90 95

Ile Ala Phe Asp Tyr Asp Gly Ser Gly Gly Ser Cys Ser Ser Ser Phe
100 105 110

Leu Ala Pro Ser Thr Pro Glu Arg Leu Pro Gly Leu Ser Arg Ser Val
115 120 125

Ser Phe Glu Leu Pro Glu Thr Pro Leu Arg Thr Gly Asn Arg Ser Ala
130 135 140

Ser Gln Pro Ser Ser Gln Leu Thr Pro His Lys Ala Arg Gly Gly Ser
145 150 155 160

Leu Lys Arg Lys His Ser Thr Phe Arg Glu Lys Leu Tyr Ser Asp Ala

```
                165                 170                 175

Asp Gly Val Ala Leu Pro Ala Asp Glu Asn Asp Pro Arg Asp Leu Asn
            180                 185                 190

Asp Ser Leu Asp Ala Asp Cys Arg Arg Leu Glu Asp Ile Ser Pro Ile
        195                 200                 205

Leu Asn Val Lys Arg Arg Lys His Gln Asp Arg Gly Ile Glu Asp Leu
    210                 215                 220

Met Arg Ser Ser Thr Pro Lys Thr Ala Ser Ser Gln Pro Thr Phe Leu
225                 230                 235                 240

Gln Val Gly Ala Ala Ala Gly Arg Asn Pro Pro Leu Gly Ala Lys Arg
                245                 250                 255

Thr Phe Arg Lys Phe Gln Ser Phe Ser Pro Ser Lys Met Gln Pro Asn
            260                 265                 270

Ala Thr Arg Pro Leu Leu Arg Gln Asn Ala Ile Arg Ala Leu Glu His
        275                 280                 285

Thr Pro Glu Lys Arg Lys Glu Gln Arg Val Leu Ala Glu Ile His Pro
    290                 295                 300

Gln Pro Ala Val Ala Asp Ala Val Leu Pro Pro Leu Asp Leu Ala Ala
305                 310                 315                 320

Leu Leu Asp Ala Pro Ile Leu Gly Glu Pro Ser Arg Gln Leu Glu Gln
                325                 330                 335

Thr Val Thr Thr Val Pro Ser Leu Asp Asp Phe Ser Leu Thr Pro Ser
            340                 345                 350

Lys Ala Asn Leu Ile Asp Leu Glu Leu Met Ala Pro Ala Ala Asp Gly
        355                 360                 365

Pro Phe Ala Thr Asp Asp Tyr Leu Val Arg His Ala Ser Asn Phe Ser
    370                 375                 380

Tyr Ala Pro Thr Leu Asn Ser Ile Leu Glu Glu Ser Pro Ile Lys Ala
385                 390                 395                 400

Ala Ala Ala Phe Leu Pro Gly Lys Leu Pro Leu Pro Lys Thr Pro Pro
                405                 410                 415

Ser Val Thr Lys Ser Gly Arg Lys Leu Lys Arg Leu Gly Thr Asn Ser
            420                 425                 430

Gly Ser Ala Ala Arg Ala Ser Val Ser Pro Lys Ala Thr Arg Arg Leu
        435                 440                 445

His Gly Ala Gln Pro His Asn Cys Arg Leu Lys Thr Ala Gln Pro Tyr
    450                 455                 460

Ser Phe Cys Gly Cys Glu Tyr Ile Asn Ile Leu His Gln Leu Ser Met
465                 470                 475                 480

Arg Asn Pro Asp Ala Leu Glu Thr Leu Leu Asp Tyr Leu Ala Asp Thr
                485                 490                 495

Asp Leu Val Gln Val Val Arg Val Ser Arg Gly Trp Lys Ala Ile Ile
            500                 505                 510

Gln Asn His Lys Lys Ser Trp Arg Arg Leu Gln Arg Phe Leu Lys Gln
        515                 520                 525

Gln Glu Glu His Lys Glu Asn Cys His Gly Ser Arg Trp Glu Asn Gly
    530                 535                 540

Ser Phe Ala Ser Ser Leu Asn Ala Gly Ser Ser Gln Leu Gly Thr Ala
545                 550                 555                 560

Leu Pro Glu Leu Leu Ser Gly Thr Phe Gly Lys Asp Ser Asn Ala Gly
                565                 570                 575

Gly Gly Leu Gly Thr Arg Leu Pro Phe Lys Val Cys Asn Thr Leu Asp
            580                 585                 590
```

Asn Ser Gln Ala Ser Ala Gly Asn Ala Ser Phe Ala His Gly Ser Phe
595 600 605

Ala Asn Ser Pro Pro Val Ser Pro Ser Met Arg Lys Phe Val Thr Asn
610 615 620

Gln Lys Ile Ala Ser His Leu Lys Gln Ser Glu Gln Leu Arg Pro Cys
625 630 635 640

Pro Arg Cys Glu Gln Pro Ser Arg Ile Ile Leu Ser Arg Ala Ser Lys
645 650 655

Ser Ser Lys Ser Arg Ser Ser Ala Arg Cys Ser Ala Val Gly Ala Arg
660 665 670

Leu Glu Lys Ser Tyr Thr Leu Pro Asp Pro Glu Thr Val Thr Ala Ser
675 680 685

Gly His Arg His Ser Gly Ser Asn Asn Thr His Ser Ser Thr Ile Glu
690 695 700

Thr Val Arg Ser Ser Asn Leu Ser Thr Asp Thr Ile Thr Thr Thr His
705 710 715 720

Arg Asn Asn Asn His Tyr Gly Glu Pro Ser Pro Glu Arg Val Arg Lys
725 730 735

Asn Leu Leu Asp Cys Ser Ser Thr Ala Ala Met His Pro Ala Gly Gly
740 745 750

Glu Asp Thr Leu Gly Val Arg Asp Ser Lys Cys Asp Tyr Ala Ile Cys
755 760 765

Ser Gly Ala Phe Cys Gly Phe Arg Phe Cys Ile Lys Cys Leu Cys Glu
770 775 780

Tyr His Pro Asp Thr Val Cys Ala Asp Leu Ala Ala Asn Ser Pro Thr
785 790 795 800

Lys Glu Glu Glu Arg Gly Arg Pro Asn Met Ala Cys Ser Arg Gln Ser
805 810 815

Arg Arg Ser Leu Gln Arg Leu Cys Arg Lys Leu
820 825

<210> SEQ ID NO 211
<211> LENGTH: 2113
<212> TYPE: PRT
<213> ORGANISM: Anopheles gambiae

<400> SEQUENCE: 211

Met Pro Asn Met Gln Cys Ser Ser Tyr Leu Val Leu Ser Phe Val Leu
1 5 10 15

Ser Ile Glu Leu Val Leu Val Val His Ser Asp Gly Glu Lys Asn Pro
20 25 30

Leu Asp Pro Gln Gly Gln Met Arg Gly Pro Ala Thr Phe Pro Lys Gln
35 40 45

Glu Pro His Asn Thr Thr His Asp Ser Ala Thr Glu Ser Ala Thr Pro
50 55 60

Ser Ala Tyr Glu Leu Lys Arg Gln Gln Leu Leu Glu His Pro Asp Gly
65 70 75 80

Phe Asp Glu Ala Glu Leu Lys Pro Leu Arg Glu Thr His Ile Asn Val
85 90 95

Leu His Glu Ala Ile Asp Ala Lys Leu Ile Asp Pro Ser Phe Ile Arg
100 105 110

Thr Leu Gly Ala Val Ser Glu Pro Pro Lys Val His Asp Ala Thr Arg
115 120 125

Asp Thr Leu Ser Ile Arg Ser Ile Glu Glu Asp Val Asn Phe Thr Leu

```
    130                 135                 140

Gly Glu Arg Val Val Arg Trp Lys Thr Met Ser Ala Ile Asn Val Asp
145                 150                 155                 160

Arg His Val Val Val Gly Leu Thr Ala Ala Ser Ala Val Val Leu Leu
                165                 170                 175

Glu Arg Asp Gly Gln Tyr Val Leu Ser Gln Glu Leu Leu Leu Glu Ser
            180                 185                 190

Ala Pro Ile Ala Phe Glu Val Leu Ser Phe Trp Asp Thr Glu His Ala
        195                 200                 205

Ser Ala Val Gly Cys Val Val Ile Ser Met Gly Asn Phe Leu Val Trp
    210                 215                 220

Tyr Thr Leu Arg Glu Gln Ser Glu Tyr Lys Leu Glu Glu Glu Trp Arg
225                 230                 235                 240

Trp Pro Leu His Lys Thr Ile Thr Gln Ile Lys Phe Phe Arg Gln Lys
                245                 250                 255

Glu Val Asp Ala Leu Leu Leu Ile Gly Arg His Pro Asn Arg His Glu
            260                 265                 270

Ser Val Ser Ala Thr Val Tyr Glu Phe Ser Phe Asn Asp Arg Gln Phe
        275                 280                 285

Trp Leu Met Gln Lys Leu Gly Leu Lys His Pro Cys Pro Ser Val Gly
    290                 295                 300

Leu Val Ala Ala Gly Glu Glu Tyr Leu Val Ala Phe Pro Gln Asn Thr
305                 310                 315                 320

Thr Val Glu Leu Tyr Thr Phe Arg Val Gly Asp Gln Asn Arg Arg Lys
                325                 330                 335

Phe Lys Ala Val Gly Asn Tyr Ser Ser Glu Ala Leu Arg Ser Val Tyr
            340                 345                 350

Ala Phe Gln Ile Gly Arg Tyr Ala Tyr Val Ala Ile Ser Gly Lys Thr
        355                 360                 365

Pro Ala Val Leu Arg Tyr Lys Arg Gly Lys Phe Tyr Glu Gln Lys Ile
    370                 375                 380

Pro Thr Glu Ala Leu Glu Ile Val Glu Ala Phe Phe Glu Ile Pro Ala
385                 390                 395                 400

Arg Thr Tyr Arg Asp Asp Met Val Leu Leu Val Gln His Arg Met Ile
                405                 410                 415

Phe Ala Thr His Glu Ile Gln Arg Leu Glu Ala Leu Val Trp Asn Gly
            420                 425                 430

Val Ser Phe Asp Leu Ala Thr Asn Ile Pro Cys Met Val Gly Asn Glu
        435                 440                 445

Val Ile Asp Asn Glu Ala Ser Cys Met Leu Asp Leu Asp Arg Thr Asp
    450                 455                 460

Gly Leu Phe Gly Ala Thr Ile Ala Gln Arg Gly Lys Ser Ile Ser Ile
465                 470                 475                 480

Ile Val Pro Arg His Glu Ala His Ser Ser Leu Tyr Arg Met Ser Ile
                485                 490                 495

Glu Leu Leu Ser Gly Glu His Pro Ile Leu Met Lys Ile Gln Glu Ile
            500                 505                 510

Gln Glu Thr Met Asp Ala Phe Thr Lys Ile Ile Asp Tyr Gln Asn Ala
        515                 520                 525

Val Ile Glu Gln Ala Gln Ser Tyr Val Glu Leu Met Glu Ser Asp Pro
    530                 535                 540

Val Val Leu Lys Arg Gln Asn Leu Ser Ser Val Asn Thr Pro Leu Val
545                 550                 555                 560
```

```
Arg Phe Ala Glu Asp Phe Asp Leu Ala Gly Val Lys Met Thr Ile Gly
                565                 570                 575

Gln Asn Ser Trp Arg Glu Ala Asp Leu Gln Ala Asp Leu Thr Ala Thr
            580                 585                 590

Val Lys Thr Val Gln Asp Val Glu Leu Ser Val Asp Ala Met Leu Ser
        595                 600                 605

Glu Leu Gln Tyr Ser Val Arg Arg Asp Ala Arg Ser His Asp Leu Gln
    610                 615                 620

Ile Asn Gly Thr Val Gln Val Thr Gly Arg Leu Tyr Ile Asp Gly Ala
625                 630                 635                 640

Leu His Ala Asp Asp Met Tyr Ile Gln Arg Phe Glu Gln Pro Arg Met
                645                 650                 655

Asp His Leu Val Arg Phe Gly Arg Asp Val His Gly Gln Glu Val Pro
            660                 665                 670

Thr Met Gln Glu Leu His Leu Lys Glu Leu Asn Val Glu Gln Leu Gln
        675                 680                 685

Phe Asp Arg Phe Asn Gly Ile Pro Ala Glu Glu Leu Leu Tyr Asp Val
    690                 695                 700

Asp Gly Lys Val Val Leu Asp Gly Glu Leu Val Leu Gly Gly Asp Leu
705                 710                 715                 720

Tyr Thr Asn Thr Val Leu Leu Pro Glu Gly Gly Thr Val Asn Gly Ile
                725                 730                 735

Asp Leu Ser Glu Ala Leu Ile Tyr Phe Asn Cys Lys Asn Arg Arg Trp
            740                 745                 750

Arg Asn Leu Thr Leu Asp Ser Leu Glu Val Ile Asp Asp Val Gln Val
        755                 760                 765

Ala Asn Lys Val Asn Gly Ala Arg Ile Asn Leu Gln Glu Ala Glu Ser
    770                 775                 780

Ser Leu Arg Asn Ala Ile Asp Glu His Gly Arg Val Leu Arg Ser Lys
785                 790                 795                 800

Ser Leu His Ile Glu Gly Asp Leu Ser Phe Glu Arg Ile Asn Gly Val
                805                 810                 815

Pro Trp Lys Thr Phe Tyr Asp Gly Leu Val Phe Lys Asp Gln Pro Met
            820                 825                 830

Arg Leu Gly Ile Leu Asn Val Glu Gly Asn Val Thr Phe Ala Ser Gln
        835                 840                 845

Thr Thr Val Gln Phe Leu Asn Arg Leu Arg Phe Pro Glu Asp Tyr Val
    850                 855                 860

Leu Arg Ser Gly Pro Arg Glu Ser Ile Ile Thr Gly Gln Lys Tyr Phe
865                 870                 875                 880

Lys Asp Ser Leu Thr Met Asp Ala Leu Asp Ile Asp Gly Phe Val Asn
                885                 890                 895

Gly Ile Asn Pro Phe Asp Phe Ile Thr Leu His Asp Asp Gln Tyr Ile
            900                 905                 910

Pro Gly Asn Val Thr Phe Asp Ser Leu Glu Ile Glu Glu Ser Leu Asp
        915                 920                 925

Val Arg Gly Ala Val His Gly Lys His Met Asp Lys Phe Leu Asp Asn
    930                 935                 940

Pro Ser Leu Leu Gln Thr Lys Leu Leu Glu Ala Ala Cys Glu Phe Asn
945                 950                 955                 960

Glu Val Val Val Asn Gly Pro Ile Tyr Val Asp Gln Leu Asp Gly Tyr
                965                 970                 975
```

```
Asp Leu Asp His Phe Leu Arg Ser Val Val Tyr Val Asp Glu Pro Tyr
            980                 985                 990

Val Glu Ile Asn Ala Ser Lys His  Tyr Arg Ser Leu His  Phe Tyr Glu
        995                 1000                 1005

Pro Ile  Arg Ile Glu Ser Asn  Met Ile Gly Glu Ile  His Leu Asp
    1010                 1015                 1020

Glu Leu  Leu Thr Lys Ser Thr  Asp Gln Thr Ile Asn  Val Ser Met
    1025                 1030                 1035

Val Leu  Gly Asn Val Phe Phe  Asn Arg Val Gln Val  His Gly Leu
    1040                 1045                 1050

Phe Gly  Gly Ile Asn Val Thr  Glu Trp Asp Thr Asn  Ser Ile Lys
    1055                 1060                 1065

Ile Phe  Gly Asp Gln His Thr  Gln Ala Thr Leu Glu  Phe Cys Pro
    1070                 1075                 1080

Gln Tyr  Ser Leu Leu Tyr Ala  Lys Asn Leu Glu Ile  Val Gly Thr
    1085                 1090                 1095

Leu Asn  Gly Gln Pro Arg Ala  Ala Phe Tyr Asp Met  Glu Glu Glu
    1100                 1105                 1110

Ile Val  Phe Arg Asp Gln Ser  Ile Tyr Met Ser Glu  Leu Tyr Ala
    1115                 1120                 1125

Ser Tyr  Leu Ser Leu Ala Gly  Ser Glu Ile Asp Gly  Pro Thr Asn
    1130                 1135                 1140

Met Leu  Asn Asp Val His Leu  Pro Thr Phe Asp Ala  Tyr Arg Phe
    1145                 1150                 1155

Ser Leu  Ser Gln Pro Gln Thr  Ile Gln His Asp Val  Leu Val Asp
    1160                 1165                 1170

Ala Leu  Tyr Val Ser Asn Ala  Phe Ala Ala Arg Tyr  Leu Asn Gly
    1175                 1180                 1185

Leu Asp  Val Val Arg Leu Gln  Glu Asn Val Glu Thr  Tyr Leu Asn
    1190                 1195                 1200

Asp Asp  Tyr Met Leu Ser Gly  Arg His Val Leu Asp  Thr Leu His
    1205                 1210                 1215

Ile Asp  Gly Ser Val Glu Ile  Gly Thr Leu Asn Gly  Val Asp Leu
    1220                 1225                 1230

Thr Gln  Phe Leu Asn Asn Val  Ile Trp Leu Asp Arg  Pro Asn Ala
    1235                 1240                 1245

Val Gln  Ser Ala Leu His Phe  Leu His Pro Leu His  Val Asp Gly
    1250                 1255                 1260

Asp Val  Ser Val Asp Gly Ala  Leu Asn Glu Ile Pro  Phe Val Ser
    1265                 1270                 1275

Phe Leu  Arg Asn Val Val Tyr  Arg Thr Asp Gly Ala  Ala Val Glu
    1280                 1285                 1290

Phe Thr  Gly Ser Lys Leu Phe  Thr Gln Gly Phe Asp  Val Val Gly
    1295                 1300                 1305

Asp Leu  His Thr Pro Thr Ile  Asn Asn Val Pro Val  Lys Asp Leu
    1310                 1315                 1320

Val Leu  Lys Asn Glu Ser Ile  Thr Phe Pro Gly Arg  Val Leu Thr
    1325                 1330                 1335

Thr Gly  Arg Val Tyr Val Lys  Glu Met Ile Val Ser  Gly Thr Ile
    1340                 1345                 1350

Asn Gly  Lys Ser Phe Lys Pro  Ile Glu Ala Tyr Tyr  Ala Tyr Asp
    1355                 1360                 1365

Asn Ala  Thr Asp Thr His Ile  Ile Lys Gly Asp Leu  Arg Leu Gln
```

```
    1370                1375                1380

Gly Gln  Gln Thr Ile His Ser  Leu Glu Ala Tyr Gly  Gly Trp Asn
    1385                1390                1395

Glu Leu  Met Asn Val Thr His  Lys Leu Ala Ser Leu  Ile Arg Thr
    1400                1405                1410

Asn Gln  Asp Tyr Tyr Phe Lys  Gly His Tyr Val Leu  Gln Glu Glu
    1415                1420                1425

Val His  Phe Lys His Gly Phe  Thr Val Asp Phe Val  Asn Gly Tyr
    1430                1435                1440

Asn Val  Ser Asn Val Gln Asn  Glu Ile Val Tyr Tyr  Asp Gln Gln
    1445                1450                1455

Glu Leu  Ile Val Phe Ser Glu  Pro Val Glu Phe Tyr  Gly Asn Val
    1460                1465                1470

Trp Gly  Gly Pro Leu His Ile  Ala Gly Asp Met Ile  Gly Lys Asn
    1475                1480                1485

Leu Met  Gly Ile Asp Pro Asp  Thr Leu Leu Gln Gln  Thr Leu Leu
    1490                1495                1500

Ile Asn  Lys Asp Tyr Glu Ile  Val Asp Lys Ile Val  Phe Leu Pro
    1505                1510                1515

Gly Ala  Phe Lys Cys Asp His  Leu Val Ala Ala Ser  Ile Asn Gly
    1520                1525                1530

Leu Pro  Thr Ser Gly Leu Ile  Thr Leu His Thr Glu  Gln Thr Ile
    1535                1540                1545

Asp Gln  Pro Val Tyr Val Lys  Gln Ile Val Ile His  His Pro Leu
    1550                1555                1560

Gln Val  Glu Gly Leu Val Asn  Gly Arg Asp Leu Arg  Val Glu Arg
    1565                1570                1575

Ala Asn  Thr Val Met Arg Tyr  Gly Glu Gln Thr Ile  Asp Ala Pro
    1580                1585                1590

Ser Val  Phe Asn Ser Ile Arg  Val Leu Asn Ser Ala  Thr Leu Pro
    1595                1600                1605

Lys Ile  Leu Asn Gly Val Pro  Phe Gly Glu Pro Val  Gln Leu Thr
    1610                1615                1620

Asp Asp  Met Thr Ile Ser Ser  Pro Leu Thr Phe Tyr  Lys Ile Ala
    1625                1630                1635

Ala Asn  Asp Val Tyr Thr Asn  Asp Thr Ile Gly Gly  Ile Asp Phe
    1640                1645                1650

Asp His  Trp Tyr Glu Arg Ala  Leu Trp Thr Asp Gly  Arg Glu His
    1655                1660                1665

Gln Ala  Tyr Trp Gly Arg Leu  Arg Ser Arg Lys Phe  Val Phe Arg
    1670                1675                1680

Asp Ser  Ile His Gly Asn Gly  Thr Ile Asn Gly Leu  Pro Ile Asn
    1685                1690                1695

Glu Ile  Val Arg Lys Leu His  Ser Glu Lys Gln Phe  Val Glu Gly
    1700                1705                1710

Glu Leu  Ala Lys Arg Arg Ala  Asn Tyr Arg Ala Ser  Cys Arg Glu
    1715                1720                1725

Thr Gln  Ala Leu Ile Asn Gly  Thr Gln Lys Gly Val  Tyr Phe Phe
    1730                1735                1740

Asn Tyr  Phe Val Gln Arg Gln  Thr Ile Arg Val Gln  Gln Pro Ile
    1745                1750                1755

Gln Ser  Phe Trp Thr Phe Gln  His Gln Gly Asn His  Phe Leu Ala
    1760                1765                1770
```

Leu Asn Tyr Gly Cys Gly Ser Lys Phe Phe Gln Trp Asn Pro Gln
1775 1780 1785

Asp Arg Val Phe Val Gly Leu Phe Lys Ala His Thr Gly Tyr Val
1790 1795 1800

Phe Glu Trp Gln Thr Val Ala Ala Gln Asp Glu Lys Leu Tyr Leu
1805 1810 1815

Val Thr Arg Ser Ala Pro Thr Asp Glu Gln Cys Asn Val Thr Gly
1820 1825 1830

Leu Ala Ile Trp Glu Phe Gln Gly Leu Ser Leu Glu Leu Val Lys
1835 1840 1845

Ala Met Pro Asp Lys Asp Thr Asp Ser Leu Phe Val Asp Pro Ser
1850 1855 1860

Thr Ser Gly Arg Phe Tyr Val Leu Glu Arg Thr Thr Val Leu Glu
1865 1870 1875

Tyr Asp Val Thr Gly Lys Val Gln Glu Glu Trp Asp Leu Ser Arg
1880 1885 1890

Ile Phe Glu Ala Ala Ser Phe Val Pro Ser Ser Leu Gly Val Gly
1895 1900 1905

Leu Ala Leu Ala Asp Gly Lys Arg Ile Ala Val Leu Ser Arg Ala
1910 1915 1920

Glu Gly Thr Ile Lys Pro Ser Arg Ser Lys Arg Ser His Asp Asp
1925 1930 1935

Pro Leu Val Asn Leu Ala Leu Phe Ala Ser Pro Ile Thr Val Tyr
1940 1945 1950

Asn Gln Met Gln Arg Asn Ser Ser Tyr Tyr Arg Thr Asp Asp Thr
1955 1960 1965

Pro Asp Glu Tyr Thr Gln Glu Val Ser Leu Leu Thr Gln Pro Asp
1970 1975 1980

Pro Leu Asn Glu Ile Gly Thr Ile Gln Glu Ser Asn Asp Thr Val
1985 1990 1995

Ile Ile Thr Arg Gln Thr Gln Thr Asp Leu Met Glu Pro Leu Glu
2000 2005 2010

Pro Leu Pro Glu Pro Arg Ile Ala Lys Val Val Pro Leu Gly Arg
2015 2020 2025

Ile Ser Thr Thr Glu Asn Ser His Phe Pro Asp Pro Ala Thr Gly
2030 2035 2040

Glu Leu Leu Thr Phe His Val Gly Leu Arg Gly Glu Ala Arg Arg
2045 2050 2055

Leu Leu Val Ala Val Thr Asp Thr Val Asn Thr Ile Ile Gln Gly
2060 2065 2070

Asn His Asp Thr Val Arg Ile Tyr Ser Asp Ile Leu Gln Gly His
2075 2080 2085

Leu Phe Gln Ile Ile Ser Cys His Arg Pro Ala Gln Leu Ala Val
2090 2095 2100

Leu Glu Val Arg Asp Glu Thr Ile Leu Ala
2105 2110

<210> SEQ ID NO 212
<211> LENGTH: 2015
<212> TYPE: PRT
<213> ORGANISM: Anopheles gambiae

<400> SEQUENCE: 212

Ser Ala Arg Gln Leu Tyr Leu Lys Gly Phe Arg Glu Arg Gly His Val

-continued

```
1               5                   10                  15

Pro Val Asn Phe Pro Val Asp Ile Cys Leu Leu Arg Val Gly Lys Thr
            20                  25                  30

Ile Phe Ala Ala Ala Leu His Gln Ser Glu Thr Ser Asn Arg Thr Met
        35                  40                  45

Asn Ala Thr Ala Val Ser Phe Tyr Arg Arg Val Lys Gly Lys Phe Glu
    50                  55                  60

Lys Tyr Leu Glu His Gln Thr Val Thr Ala Arg His Phe Asp Cys Val
65                  70                  75                  80

Ser Ile Ala His Leu Gly Phe Val Ala Val Val Asn Tyr His Asp Gln
                85                  90                  95

Glu Leu Asn Val Phe Gly Asp Gly Ser Pro Val Phe Gln Ile His Glu
            100                 105                 110

Asp Gly Arg Thr Glu Leu Val Gln Thr Phe Gly Gln Pro Asn Gln Asn
        115                 120                 125

Thr Val His Leu Trp Val His Gly Lys His Val Tyr Leu Ala His Thr
    130                 135                 140

Tyr Ile Asn Leu Asp Ala Glu Arg Gly Ser Thr Ala Asn Val Cys Pro
145                 150                 155                 160

Leu Tyr Arg Trp Ala Gly Gln Tyr Phe Asp Val Ile Asp Gln Met Pro
                165                 170                 175

Cys Tyr Ser Ser Val His Ile Glu Ala Phe Ser Ile Glu Gln Gln Met
            180                 185                 190

Phe Val Ala Val Ala Asn Gln Met Ser Pro Ala Gln Gly Lys Asp Thr
        195                 200                 205

Phe Ser Asp Ile Phe Leu Leu Asn Pro Asp Thr Gln Lys Leu Val Leu
    210                 215                 220

His Gln Arg Ile Tyr Ile Tyr Ser Val Ser His Met Ala Tyr Phe Phe
225                 230                 235                 240

Phe Glu Ala Arg Asn Gly Arg Arg Glu His Phe Leu Ile Thr Gly Asn
                245                 250                 255

Ser Val Asp Glu Glu Gly Gly Lys Glu Gly Gly Asp Gly Pro Arg Pro
            260                 265                 270

Ser Asn Gly Ile Lys Ser Arg Thr Val Glu Arg Ser Ser Ile Val Tyr
        275                 280                 285

Lys Phe Val Asp Gly Tyr Phe Val Pro Phe Gln Asn Leu Glu Leu Thr
    290                 295                 300

Gly Val Lys Met Phe Leu Pro Val Val His Glu Asn Gly Glu Phe Leu
305                 310                 315                 320

Leu Leu Val His Cys His Asp Gln Pro Leu Leu Ile Tyr Glu Tyr Asp
                325                 330                 335

Gly Trp Lys Leu Ala Pro Ser Arg Ile Asp Tyr Thr Gly Glu Ala Phe
            340                 345                 350

Ala Ala Gly Val Ser His Met Arg Val Tyr Arg His Ile Val Asn Ala
        355                 360                 365

Ser Val Ile Val Ile Ala Asn Ser Asn Leu Phe Gly Lys Ser Ile Asn
    370                 375                 380

Leu Phe Thr Pro Gln Tyr Gly Val Gln Asn Asp Leu Arg Arg Val Tyr
385                 390                 395                 400

Ala His Phe Ile Glu Trp Cys Glu Arg Met His Asp Gln Leu Gly Gln
                405                 410                 415

Val Asn Leu Glu Gln Leu Tyr Asn Lys Leu Val Gly Leu Pro Asp Asn
            420                 425                 430
```

```
Ala Pro Asp Gly Ala Arg Ile Val Glu Lys Asp Leu Val Leu Gln Asp
        435                 440                 445

Ser Ala Val Arg Thr Ile Lys Ala Lys Thr Ile Ala Thr Lys His Gly
    450                 455                 460

Leu Val Asp Asp Ala Leu Leu Ser Tyr Val Ile Glu Val Asn Glu Tyr
465                 470                 475                 480

Val Gln Arg Val Gln Glu Lys Met Asp Leu Val Glu Gln Thr Ile His
                485                 490                 495

Gly Ser Val Leu Thr Asn Asp Thr Val Arg Trp Asn Gly Asp Leu Ala
            500                 505                 510

Val Ser Glu Leu Ile Ala Pro Ala Gly Gln Met Lys Gln Leu Asp Val
        515                 520                 525

Lys Val Leu Asn Asn Ala Ala His Lys Thr Arg His Thr Glu Gln Gln
    530                 535                 540

Gly Arg Arg Gly Asp Val Pro Glu Asp Asp Val Ile Thr Val Asp Arg
545                 550                 555                 560

Leu Ile Val Asp Arg Ile Gly Ser Val Gln Phe Phe Asn Gly His Ala
                565                 570                 575

Ala Glu Ser Leu Leu Leu Val Asp Asp Pro Pro Ala Lys Trp Lys Thr
            580                 585                 590

Leu Ser Leu Ser Ala Lys Lys Val Val Val Gly Gly Asn Leu Phe Val
        595                 600                 605

Asn Lys Leu Ile Asp Gly Val Phe Phe His Pro Gly Asn Val Leu Leu
    610                 615                 620

Pro Asn Val Asn Gln Met Phe Pro Ala Lys Ser Leu Met Val Lys Asp
625                 630                 635                 640

Leu Ser Val Asn Arg Leu Thr Ser Lys Arg Leu Asn Ala Thr Asp Ala
                645                 650                 655

Val Ala Val Gln Arg Met Met Asp Gln Ser Arg Thr Leu Leu Ala Lys
            660                 665                 670

Ala Arg Gly Ala Met Pro Arg Glu Tyr Gly Ser Asp Phe Glu Ser Ile
        675                 680                 685

Asp Ala Asp Asp Leu Lys Leu Thr Gly Leu Leu Asn Asp Ile Asp Pro
    690                 695                 700

Arg Ala Leu Ser Asp His Val Leu Leu Asp Glu Ala Ala Glu Gln Gln
705                 710                 715                 720

Leu Ser Gly Lys Leu Val Val Asp Gln Leu Val Ala His Asn Val Val
                725                 730                 735

Val Ser Asp Ala Lys Leu Ser Asp Val Pro Leu Ala Asn Val Ala Arg
            740                 745                 750

Thr Thr Gly Lys Gln Gln Ile Leu Gln Asp Leu Gln Phe Val Gln Pro
        755                 760                 765

Met Val Val Glu His Leu His Leu Gln Asp Arg Leu Asn His Ile Pro
    770                 775                 780

Val Ile Glu Gly Lys Leu Gln Val Leu His Leu Ser Ser Asp Glu Ile
785                 790                 795                 800

Gln Pro Ile Thr Gly Thr Lys Thr Phe Asp Tyr Val Thr Leu Leu His
                805                 810                 815

Pro Ile Glu Leu Gln Gly Lys Ile Asn Gly Ala Ser Leu Ser Lys Met
            820                 825                 830

Asn Pro Ile Val Thr Val Gly Asp Asp Leu Val Leu Asp Gly Asp Tyr
        835                 840                 845
```

```
Thr Ile His Gly Asn Val Thr Phe Asn Gly Gly Leu Trp Ala His Asn
    850                 855                 860

Ile Leu Ser Ala Gly Gly Thr Arg Asn Leu His Arg Val Ala Thr His
865                 870                 875                 880

Gly Leu Gln Val Gln Ala Ala Pro Pro Pro Gly Gln Val Leu Lys Phe
                885                 890                 895

Leu Gln Pro Val Phe Val Glu His Leu Arg Ala Asp Gln Ile Asn Glu
            900                 905                 910

Leu Ser Val Asn Asp Leu Val Pro Gln Ala Ala Gly Gly Glu Val Gln
        915                 920                 925

Tyr Leu Thr Gly Arg Lys Thr Phe Val Ser Glu Leu Lys Ile Asp Gly
    930                 935                 940

Val Ala Asp Ala Asn Glu Ile Asn Lys Val Asp Leu Asn Leu Leu Asn
945                 950                 955                 960

Arg Thr Met Leu Gln Arg Ala Gly Ala Glu Gln Gln Ile Glu Gly Thr
                965                 970                 975

Ile His Phe Asp Thr Val Ile Ala Pro Ile Val Asn Ser Lys Asn Val
            980                 985                 990

Leu Phe Glu Ser Lys Arg Leu Asp  Arg Leu Leu Arg Leu  Asp Val Pro
        995                 1000                1005

Gln Asn  Val Ser Ala Ala Val  Arg Phe Glu Asn Cys  Thr Ile Tyr
    1010                1015                1020

Ala Ser  Asn Ala Ile Val Thr  Glu Glu Leu His Ala  Asp Arg Gln
    1025                1030                1035

Ser Thr  Ile Tyr Gly Tyr Asp  Leu Glu Tyr Leu Leu  Gln Asp Thr
    1040                1045                1050

Leu Met  Leu Asp Ala Asp Glu  Ala Asn Val Pro Thr  Val Gln Gly
    1055                1060                1065

Leu Lys  Ser Phe Arg Asn Leu  Thr Ile Gly Gln Leu  Ile Leu His
    1070                1075                1080

Ser Glu  Ala Thr Leu Asn Ser  Ile Pro Val Glu Asn  Leu Lys His
    1085                1090                1095

Ile Ile  Ala Ala Gly Asp Asn  Arg Thr Ile Ile Lys  Asn Glu Pro
    1100                1105                1110

Tyr Ser  Phe Gln Ser Asp Ile  Thr Val Asn His Leu  Leu Phe Glu
    1115                1120                1125

Gly Ser  Ile Asn Gly Val Pro  Lys Asp Ala Phe Cys  Arg Ala Trp
    1130                1135                1140

Leu Met  Tyr Ser Gly Asn Gln  Thr Phe Thr Ala Gly  Gln Ser Ile
    1145                1150                1155

Asp His  Leu Ala Thr Glu Gln  Leu Phe Val Thr Gly  Lys Leu Asn
    1160                1165                1170

Asn Val  Thr Met Glu Gln Leu  Val Glu Asn Ala Tyr  Arg Thr Asp
    1175                1180                1185

Arg Glu  Glu Tyr Ile Glu Arg  Ala Val Phe His Gln  Gly Ile Val
    1190                1195                1200

Thr Tyr  Asp Pro Cys Ser Val  Gly Gly Leu Val Ser  Gly Leu Asn
    1205                1210                1215

Val Ser  Ser Asp Val Leu Leu  Lys Gln Ser Pro Glu  Met Gln Thr
    1220                1225                1230

Leu Gly  Thr Val His Val Leu  Gly Thr Leu Glu Ala  Lys Gly Glu
    1235                1240                1245

Leu His  Ile Leu Ser Gln Leu  Asn Gly Ile Asn Phe  Pro Lys Met
```

```
    1250                1255                1260

Met Glu  Phe Phe Ser Ala Pro  Gly Glu Asn Ala Glu  Gly Arg Glu
    1265                1270                1275

Ser Val  Pro Val Gly Ile Glu  Thr His Gly Asn Val  Tyr Phe Glu
    1280                1285                1290

His Asp  Pro Thr Val Ile His  Leu Asn Gly His Asn  Val Gln Lys
    1295                1300                1305

Leu Tyr  Gly Glu Val Trp Leu  Pro His Arg Pro Thr  Val Leu Thr
    1310                1315                1320

Gly Arg  Tyr Gln Phe Glu Ser  Val Glu Phe Val Lys  Pro Leu His
    1325                1330                1335

Thr Lys  Asp Gln Pro Ile Asn  His Leu Asn Trp Asp  Glu Val Glu
    1340                1345                1350

Ala Arg  Cys Leu Ser Gly Lys  Arg Ala Gln Asn Ile  Thr Ala Pro
    1355                1360                1365

Val Gln  Phe Leu Gly Asp Val  Thr Val His Ala Gly  Ala Ala Phe
    1370                1375                1380

Gln Asp  Val Asn Leu Gln Gly  Ser Leu Lys Ser Thr  His Ser Ser
    1385                1390                1395

Ala Gly  Leu Asn Val Val Glu  Tyr Asp Lys Tyr Ala  Leu Arg Tyr
    1400                1405                1410

His Glu  Pro Gln Glu Ile Thr  Gly Lys Trp Leu Phe  His His Ala
    1415                1420                1425

Glu Val  His Gly Asn Phe Asp  Val Glu Thr Leu Asn  Gly Tyr Asn
    1430                1435                1440

Val Lys  Thr Asp Leu Leu Arg  Asn Asp Ala Pro Ser  Gly Asn Phe
    1445                1450                1455

Thr Ala  Ala Lys Arg Phe Thr  Gln Leu His Val Glu  Ser Ile Val
    1460                1465                1470

Cys Ala  Pro Pro Cys Val Ile  Gln Asp Val Asp Met  Asp Glu Trp
    1475                1480                1485

Tyr Ala  Asn Gly Leu Arg Leu  Arg Gly Asn Gln Thr  Ile Glu Gly
    1490                1495                1500

Thr Leu  His Ile Arg Asn Gly  Ile Val Thr Gly Asn  Leu Glu Val
    1505                1510                1515

Leu Gly  Thr Val Asn Gly Met  Arg Phe Asp Ala Glu  His Leu Met
    1520                1525                1530

Leu Lys  Ser Leu Pro Gln His  Val Asn Gly Thr Leu  Arg Leu Val
    1535                1540                1545

Thr Lys  Phe Pro Lys Glu Asn  Lys Ile Tyr Pro Leu  Val Phe Glu
    1550                1555                1560

Ala Leu  Gln Ala Asn Ala Ile  Asn Gly Lys Asp Val  Glu Gln Phe
    1565                1570                1575

Leu Lys  Asn Val Ala Leu Ala  Gly Gln Asn Pro Leu  Thr Val Asn
    1580                1585                1590

Ile Pro  Val Thr Phe Val Gln  Pro Leu Glu Ala Asp  Glu Thr Val
    1595                1600                1605

Phe Glu  Gly Asp Met Val Phe  Gly Val Asn Val Thr  Gln Leu Leu
    1610                1615                1620

Gln Ser  Thr Ser Tyr Arg Lys  Asp Ile Asn Glu Leu  Ala Ser Gln
    1625                1630                1635

Val Arg  Ser Leu Asn Ser Val  Asn Asp Lys Leu Ala  Glu Ser Val
    1640                1645                1650
```

Phe Glu Asn Ser Pro Val Phe Ser His Phe Asp Lys Met Lys Pro
1655 1660 1665

Leu Ala Val Gln Ala Val Arg Met Leu Val Leu Asn Leu Pro Val
1670 1675 1680

His Pro Gly Pro Met Asp Leu Ile Ala Val His Ser Ala Glu Pro
1685 1690 1695

Asn Arg Pro Ser Ala Ile Asp Phe Tyr His Trp Ser Thr Gly Asn
1700 1705 1710

Lys Gly Pro Gly Leu Val Pro Ala Gln Ala Phe Pro Ser Ile Val
1715 1720 1725

Gly Arg Asp Arg Thr Ile Val Asn Val Lys Arg Leu Asn Leu Gly
1730 1735 1740

Pro Lys Gln His Leu Phe Val Glu Phe Glu Glu His Gly Ser Gly
1745 1750 1755

Lys His Phe Val Gln Gln Ile Leu Asp Leu Ser His Glu Ser Thr
1760 1765 1770

Gly Met Tyr Lys Phe Ile Pro Leu Tyr Val Met Asn Ser Thr Gln
1775 1780 1785

Ser Arg Glu Ala Ile Gly Met Lys Ile Val Lys Leu Asp Cys Ile
1790 1795 1800

Val Met Tyr Ser Lys Gly Lys Pro Asp Val Glu Val Arg Cys Leu
1805 1810 1815

Arg Glu His Asn Leu Leu Gln Ile Leu Asp Val Arg Gln Met Glu
1820 1825 1830

Glu Thr Ile Val Pro Leu Gln Ile Val Ala Leu Glu Asn His Leu
1835 1840 1845

Ile Val Leu Asp Ser Asn Glu Arg Ile Gln Ile Trp Arg Ser Thr
1850 1855 1860

Ala Ser Phe Tyr Leu Lys His His Gln Thr Ile Thr Val Ser His
1865 1870 1875

Pro Ser Tyr Leu Thr Val Ala Arg Tyr Glu Asn Gln Leu Met Leu
1880 1885 1890

Ala Ile Asn Ser Glu Asn Thr Pro Asn Thr Ala His His Gly Ser
1895 1900 1905

Ile Glu Val Trp Arg Lys Gly Leu Thr Gly Asn Gly Thr Phe Val
1910 1915 1920

Gln His Gln Leu Ile Leu Thr Lys Leu Pro Lys Gln Leu Gln Leu
1925 1930 1935

Ser Val Leu Pro Ser Lys Glu Met Leu Leu Tyr Thr Leu Thr Glu
1940 1945 1950

Asn Trp Leu His Pro Leu Val Val Tyr Arg Tyr Glu Gly Val Thr
1955 1960 1965

Gly Phe Arg Glu Ile Leu Thr Thr Asn Thr Ile Arg Gln Lys Ala
1970 1975 1980

Lys Arg Met Ser Val Leu Lys Leu Arg Leu Ala Arg Lys Glu Ile
1985 1990 1995

Ile Ala Ile Val Gly Pro Glu Ser Thr Asp Phe Val Glu Val Val
2000 2005 2010

Phe Val
2015

<210> SEQ ID NO 213

<400> SEQUENCE: 213

000

<210> SEQ ID NO 214
<211> LENGTH: 2275
<212> TYPE: PRT
<213> ORGANISM: Anopheles gambiae

<400> SEQUENCE: 214

Met Ala Asp His Asp Gln Thr Val Leu Asp Glu Glu Leu Ala Thr Ile
1               5                   10                  15

Asn Ser Thr Arg Met Gln Gln Leu Val Gly Ala Gly Arg Thr Asn Trp
            20                  25                  30

Leu Cys Leu Met Met Thr Ala Ile Gly Gly Val Ile Val Met Ala Ala
        35                  40                  45

Ile Ala Phe Gly Phe Tyr Leu Thr Ile Pro Ala Ser Ala Leu Ser Gln
    50                  55                  60

Gln Pro Ser Asn Leu Ile Glu Leu Glu Pro Ile Glu Val Gln Ser Pro
65                  70                  75                  80

Glu Glu Leu Glu Thr Ile Arg Glu Thr Tyr Phe Lys Ala Glu Ala His
                85                  90                  95

Asp Ile Leu Met Gly Ser Leu Glu Leu Leu Glu Leu Leu Asn Asp Leu
            100                 105                 110

Asp Pro Leu Leu Gln Arg His Arg Ser Arg Arg Glu Ala Phe Gly Ala
        115                 120                 125

Glu Pro Val Pro Asn Arg Ile Ser Arg Gly Asp Asp Arg Ser Gly Glu
    130                 135                 140

Ile Thr Tyr Gly Val Arg Lys Arg Val Gln Arg Glu Phe Asp Leu Gly
145                 150                 155                 160

Thr Val Pro Ile Asp Tyr Arg Gly Ile Leu Val Gly Ser Glu Ser Pro
                165                 170                 175

Arg Ala Pro Arg Lys Arg Arg His Thr Asp Ile Ser Leu Asp Glu Leu
            180                 185                 190

Glu Arg Ala Lys Arg Ser Ala Gln Lys Asp Tyr Gln Arg Leu Glu Lys
        195                 200                 205

Glu Tyr Asn Arg Cys Arg Lys Glu Ala Pro Asn Gly Lys Leu Cys Asp
    210                 215                 220

Gln Ile Tyr Glu Lys Leu Gln Arg Leu Ser Glu Glu Val Asn Ala Arg
225                 230                 235                 240

Phe Leu Glu Met Ala Asn Leu Leu Gln Gly Phe Ser Glu Met Gly Pro
                245                 250                 255

Ala Lys Glu Lys Thr Thr Pro Gln Tyr Glu Glu Met Tyr Tyr Ser Ser
            260                 265                 270

Thr Glu Arg Ser Thr Ser Tyr Arg Pro Glu Met His Ala Pro Lys Asn
        275                 280                 285

Asp Pro Lys Ile Thr Thr Val Glu Gln Leu Val Asn Gln Met Asn Ile
    290                 295                 300

Thr Gln Ala Ile Pro Lys Glu Lys Leu Arg Thr Ser Ala Glu Asp Glu
305                 310                 315                 320

Met Val Thr Thr Thr Pro Met Leu Pro Val Phe Asp Pro Ser Leu His
                325                 330                 335

Lys Pro Ile Glu Asn Ser Ser Ile Arg Ser Leu Asp Asp Leu Phe Asp
            340                 345                 350

His Met Arg Leu Ser Gly Glu Asp Ala Ser Thr Thr Glu Trp Thr Thr

```
        355                 360                 365

Glu Arg Arg Glu Leu Phe Glu Phe Glu Ile Asp Ser Thr Ser Thr Ser
    370                 375                 380

Pro Val Thr Val Lys Pro Ser Thr Gln Pro Thr Ser Lys Arg Arg Thr
385                 390                 395                 400

Thr Thr Lys Ser Pro Leu Gln Ala Ala Arg Asn Leu His Asp Val Val
                405                 410                 415

His Gln Leu Gln Leu Ala Gln Met Leu Gln Pro His Pro Phe His Glu
            420                 425                 430

Asp Leu Val Met Ser Pro Pro Glu Asn Ile Asn Glu Phe Val Met Ser
        435                 440                 445

Arg Ser Arg Asn Arg Glu Glu Met His His Asp Thr Thr Pro Ser Pro
    450                 455                 460

Met Arg Ala Val Val His Gln Gln His Gln His Leu Gln His Gln Thr
465                 470                 475                 480

Gln Pro Gln Ser Pro His Gln Pro Leu Val Val Gly Pro Ser Ala Pro
                485                 490                 495

Phe Leu Asn Leu Cys Asp Gln Leu Arg Ser Ala Ala Gly Asn Gly His
            500                 505                 510

Leu Lys Pro Thr His Pro Gly Ala Thr Phe Gln His Ser Pro Gly Ile
        515                 520                 525

Pro Ile Thr Gly Glu Ala Thr Lys Ala Ser Ser Gln Ile Ile Val Asn
    530                 535                 540

Ser Ala Phe Gly Ala Gly Tyr Val Pro Asn Thr Val Cys Phe Tyr Gln
545                 550                 555                 560

Asn Ala Pro Pro Val Gly Ala Gln Pro Thr Ala Tyr Gly Phe Arg Pro
                565                 570                 575

Ala Gly Ser Gly Ala Pro Tyr Val Tyr Pro Asn Ala Pro Gly Tyr Pro
            580                 585                 590

Pro Tyr Gln Pro His Gln Gln Gln Pro Tyr His Gln Gln His His His
        595                 600                 605

His His Pro Gly Ala Gly Ala Met Ile Asn Met Pro Val Ser Ile Gln
    610                 615                 620

Asn Leu His Gln Ala Gly Ala Arg Thr Ser Glu Leu Pro Ala Asp Gln
625                 630                 635                 640

Asn Gly Pro Ile Leu Leu Cys Ser Met Met Gln Asn Val Glu Gln Pro
                645                 650                 655

Thr Arg His His Ala Gly Asn Glu Thr His Pro Glu Asp Ala Glu Glu
            660                 665                 670

Glu Leu Asp Glu Asn Leu Asp Thr Met Phe Ala Ala Gly Arg Ser Leu
        675                 680                 685

Ala Ala Arg Ala Lys Gly Arg His His Cys Arg Arg Gly Ser Val Pro
    690                 695                 700

Cys Phe Ser Ser His Gln Cys Val Lys Arg Ser Ser Trp Cys Asp Ser
705                 710                 715                 720

Lys Thr Asp Cys Met Asp Gly Ser Asp Glu Ser Ala Cys Ser Cys Val
                725                 730                 735

Ser Arg Leu Pro Lys Arg Lys Leu Cys Asp Gly Tyr Ala Asp Cys Pro
            740                 745                 750

Leu Gly Met Asp Glu Met Gly Cys Phe Gly Cys Glu Lys Phe Ser Phe
        755                 760                 765

Ser Cys Phe His Thr Glu Ala Glu Tyr Arg Ser Ala His Arg Ser Gly
    770                 775                 780
```

```
Ser Met Cys Tyr Ser Leu Leu Glu Lys Cys Asp Gly Phe Asp Asn Cys
785                 790                 795                 800

Leu Asn Arg Lys Asp Glu Gln Asp Cys Thr Met Leu Val Arg Asp Leu
                805                 810                 815

Gly His Tyr Leu Ala Tyr Ser Val Pro His Ser Thr Gly Val Leu His
            820                 825                 830

Arg Asn Tyr Arg Gly Lys Trp Tyr Pro Val Cys His Asn Pro Thr Gln
        835                 840                 845

Trp Ala Arg Glu Ala Cys Glu Thr Glu Leu Gly Pro Leu Asp Arg Glu
    850                 855                 860

Pro Leu Leu Ser His Gly His Gly Ser Leu Pro Gly Pro Tyr Ile Ser
865                 870                 875                 880

Gln Arg Ala Asn Ser Ala Val Pro Gln Pro Glu Phe Ser Glu Ala Cys
                885                 890                 895

Asn Gly Val Tyr Val His Val Lys Cys Pro Ala Val Arg Cys Gly Thr
            900                 905                 910

Ser Arg Met His Glu Gln His Ala Ala Arg Ile Asn Val Arg Thr Arg
        915                 920                 925

Arg Glu Ala Asn Glu Ser Glu Ile Val Glu Ser Val Arg Ile Val Gly
    930                 935                 940

Gly Ser His Ala Asp Pro Glu Ala Tyr Pro Phe Ile Val Gly Ile Phe
945                 950                 955                 960

Arg Asp Gly Lys Tyr His Cys Gly Gly Ser Ile Tyr Asn Glu His Trp
                965                 970                 975

Ile Ile Ser Ala Ala His Cys Cys Asp Asn Phe Asp Gln His Tyr Phe
            980                 985                 990

Glu Val Arg Ser Gly Met Leu Arg  Lys Arg Ser Phe Ala  Pro Gln Val
        995                 1000                1005

Gln Ile  Thr Arg Val Thr His  Met Ile Val His His  Ala Tyr Ser
    1010                1015                1020

Ser Ser  Leu Met Ala Asn Asp  Ile Ala Leu Met Arg  Val Glu His
    1025                1030                1035

Pro Phe  His Tyr Asn Arg Trp  Val Arg Pro Ile Cys  Met Pro Glu
    1040                1045                1050

Arg His  Arg Thr Thr Asp Asp  Arg Asp Trp Ile Trp  Gly Pro Lys
    1055                1060                1065

Ala Gly  Thr Val Cys Thr Ala  Ile Gly Trp Gly Ala  Leu Arg Glu
    1070                1075                1080

Arg Gly  Gly Ala Pro Asp His  Leu Met Gln Val Ser  Val Pro Ile
    1085                1090                1095

Leu Gly  Tyr Cys Lys His Lys  Ser Asp Arg Asp Ser  Leu Gln Ile
    1100                1105                1110

Cys Ala  Ala Glu Glu Asp Gly  Gly His Asp Ala Cys  Gln Gly Asp
    1115                1120                1125

Ser Gly  Gly Pro Phe Val Cys  Gln Ser Lys Ser Asn  Pro Phe Glu
    1130                1135                1140

Trp Tyr  Leu Ala Gly Val Val  Ser His Gly Glu Gly  Cys Ala Arg
    1145                1150                1155

Ala His  Glu Pro Gly Val Tyr  Thr Arg Val Ala Leu  Phe Ile Asp
    1160                1165                1170

Trp Ile  Ala Glu Lys Val Asn  Ala Pro Leu Pro Ala  Arg Thr Ala
    1175                1180                1185
```

```
Arg Ala  Asp Cys Pro Gly Met  Arg Cys Ile Trp Gly  Gly Gly Ile
    1190                 1195                 1200

Cys Leu  Pro Pro Gly Lys Lys  Cys Asn Gly Tyr Val  Asn Cys Leu
    1205                 1210                 1215

Gly Gly  Glu Asp Glu Ser Gly  Cys Gly Met Asp Gln  Met Leu Arg
    1220                 1225                 1230

Ser Met  Ser Gln Arg Gly Glu  Glu Glu Ser Glu Glu  Glu Gly Gly
    1235                 1240                 1245

Ser Ala  Thr Gln Arg Ala Ser  Asp Val Asp Thr Thr  Glu Ala Glu
    1250                 1255                 1260

Thr Thr  Val Leu Phe Thr Ser  Glu Glu Thr Thr Thr  Leu Ser Val
    1265                 1270                 1275

Pro Glu  Glu Ala Ser Val Glu  Ala Gln Glu Ser Met  Ile Met Thr
    1280                 1285                 1290

Asn Thr  Ala Gln Thr Glu Pro  Ile Thr Thr Thr Thr  Ser Thr Val
    1295                 1300                 1305

Ala Thr  Thr Thr Pro Gln Leu  Glu Leu Ser Thr Ala  Glu Glu Ser
    1310                 1315                 1320

Thr Thr  Glu Asp Ser Ser Thr  Ser Ala Ser Thr Ser  Glu Asp Ala
    1325                 1330                 1335

Pro Thr  Glu Ala Ser Thr Ser  Pro Glu Ser Thr Thr  Leu Glu Val
    1340                 1345                 1350

Thr Thr  Asp Leu Ser Thr Glu  Pro Ser Ser Thr Thr  Asn Glu Pro
    1355                 1360                 1365

Thr Thr  Thr Phe Thr Ser Thr  Thr Asp Ser Ala Ile  Ile Phe Pro
    1370                 1375                 1380

Ile His  Asp His Glu Gln Asp  Arg Pro Lys Gln Asp  Phe Glu Phe
    1385                 1390                 1395

Ile Ala  Pro Ile Thr Ser Ser  Thr Thr Glu Val Ile  Trp Lys Ala
    1400                 1405                 1410

Leu Glu  Lys Ala Val Lys Glu  Val Arg Gly Gln Val  Arg Thr Gly
    1415                 1420                 1425

Asn Gly  Thr Ser Val Val Asn  Ala Thr Thr Glu Pro  Met Glu Val
    1430                 1435                 1440

Phe Ser  Thr Glu Leu Pro Leu  Glu Ala Thr Ser Glu  Asp Pro Leu
    1445                 1450                 1455

Glu Asp  Ser Ser Asp His Pro  Phe Leu Val Glu Leu  Asp Val Met
    1460                 1465                 1470

Gln Gln  Gln Lys His Lys Arg  Val Ala Gln Phe Arg  Met Thr Val
    1475                 1480                 1485

His Asn  Val His Thr Asn Thr  Lys Val Gln Thr Met  Leu Pro Asn
    1490                 1495                 1500

Asp Thr  Ala Gln Tyr Arg Gln  Phe Ser Cys Arg Asn  Ile Thr Gln
    1505                 1510                 1515

Lys Ile  Asn Val Ala His Arg  Cys Asp Arg Ile Val  Asp Cys Glu
    1520                 1525                 1530

Asp Gly  Ser Asp Glu Leu Asn  Cys Thr Cys Arg Asp  Phe Leu Lys
    1535                 1540                 1545

Asp Lys  Phe Asp Phe Leu Ile  Cys Asp Gly Lys Thr  Asp Cys Leu
    1550                 1555                 1560

Asp Gln  Thr Asp Glu Leu Gly  Cys Met Asn Cys Gln  Ala Gly Gln
    1565                 1570                 1575

Tyr Ala  Cys Arg Ile Ser Gln  Val Cys Ile Pro Gly  Val Gln Val
```

-continued

```
    1580                1585                1590

Cys Asn  Gly His Pro Asp Cys  Pro Met His Glu Asp  Glu Leu Asp
    1595                1600                1605

Cys Leu  Ala Leu Thr Asp Gly  His Arg Val Tyr Phe  Asp Ala Asn
    1610                1615                1620

Asn Leu  Thr Leu Phe His Asn  Thr Gly Ile Val Thr  Lys Asn Thr
    1625                1630                1635

Asn Gly  Thr Trp Glu Ile Leu  Cys Gly Ala Val Leu  Thr Ala Lys
    1640                1645                1650

Thr Glu  His Ala Val Glu Lys  Ile Cys Ser Phe Leu  Gly Phe Ala
    1655                1660                1665

Gly His  Arg Asn Tyr Ser Leu  Leu Ser Leu Ala Pro  Thr Asp Leu
    1670                1675                1680

Pro Val  Gly Leu Leu Ala Asn  Pro Asn Asn Leu His  Tyr Val Asn
    1685                1690                1695

Leu Thr  Leu His Ala Pro Cys  Gln Ala Leu Arg Val  Ser Cys Val
    1700                1705                1710

Gln His  Ile Asn Ala Thr Glu  His Asp Ile Ala His  Phe Glu His
    1715                1720                1725

Asn His  Lys Gln Asp Pro Val  Gln Val Asn Ile Arg  Pro Leu Asn
    1730                1735                1740

Pro Ile  Asn Arg Pro His His  Met Pro Gln Ile Val  Phe Gln Glu
    1745                1750                1755

Asn Ala  His Ile Glu Leu Val  Glu Asn Phe Gly Asp  Asp Tyr Asp
    1760                1765                1770

Trp Pro  Trp Asn Thr Asn Ile  Tyr Leu Asp Gly Val  Met Ile Cys
    1775                1780                1785

Ser Gly  Leu Ile Ile Asp Ala  Ser Trp Ile Ile Val  Ser Gly Ser
    1790                1795                1800

Cys Thr  Arg Leu Val Asn Leu  Arg His Gln Tyr Leu  Ala Val Val
    1805                1810                1815

Ala Gly  Gly Ala Lys Ser Tyr  Leu His Ile Glu Gly  Pro Tyr Glu
    1820                1825                1830

Gln Val  Val Arg Val Asp Cys  Tyr His Tyr Ile Pro  Glu Ala Glu
    1835                1840                1845

Thr Val  Met Leu His Leu Ala  Thr Lys Leu Ser Phe  Ser Arg His
    1850                1855                1860

Val Leu  Pro Thr Phe Val Pro  Glu Asn Glu Asn Leu  Thr Asp Ser
    1865                1870                1875

Glu Cys  Leu Ala Val Gly Gln  Asp Lys Tyr Gly Arg  Thr Lys Thr
    1880                1885                1890

Leu Arg  Val His Leu Asn Thr  Thr Asn Cys Pro Gly  Glu Arg Val
    1895                1900                1905

Arg Cys  Tyr His Lys Asp Leu  Lys Gln Pro Tyr Tyr  His His Glu
    1910                1915                1920

Ser Cys  Tyr Thr Pro Glu Ala  Thr Arg Ser Gly Val  Ile Val Cys
    1925                1930                1935

Lys Thr  Ser Arg Ser Gly Trp  Tyr Pro Val Gly Phe  Tyr Gln His
    1940                1945                1950

Lys Arg  Gly Leu Cys Gly Phe  Asn Glu Val Val Arg  Val Thr Ser
    1955                1960                1965

Leu Val  Glu Ser Tyr His Arg  Ile Gln Asn Val Leu  His Lys Glu
    1970                1975                1980
```

Gln Cys Gly Asp Gln Leu Tyr Glu Glu Pro His Cys Gly Gly Lys
    1985                1990                1995

Arg Cys Arg Tyr Gly Lys Cys Val Gly Glu Lys Leu Leu Cys Asp
    2000                2005                2010

Arg Lys Pro Asp Cys Ser Asp Gly Ser Asp Glu Glu Pro Ala Met
    2015                2020                2025

Cys Ala Ser Arg Asn Gln Thr Gly Asn Cys Leu Pro His Gln Leu
    2030                2035                2040

Arg Cys Ala Asn Glu Arg Cys Ile Asp Lys Ser Ser Phe Cys Asp
    2045                2050                2055

Arg Lys Asn Asp Cys Gly Asp Ser Thr Asp Glu Pro His Asp Cys
    2060                2065                2070

Ser Cys Tyr Thr Tyr Leu Lys Ile Thr Asp Pro Gly Lys Ile Cys
    2075                2080                2085

Asp Gly Val Arg Asn Cys Trp Asp Lys Ser Asp Glu Asn Pro Arg
    2090                2095                2100

Val Cys Arg Cys His Ser Thr Ser Phe Arg Cys Gly Glu Ser Asp
    2105                2110                2115

Ile Cys Val Pro Tyr Asp Phe Val Cys Asp Lys Glu Arg Asp Cys
    2120                2125                2130

Pro Asn Gly Glu Asp Glu Leu Tyr Cys Tyr Ala Leu Gln Gln Asn
    2135                2140                2145

Ser Tyr Glu Ala Gly Tyr Gly Glu Leu Met Glu Gln Ser Tyr Gly
    2150                2155                2160

Ile Trp His Ser Lys Cys Phe Pro Thr Thr Thr Gln Phe Asp Asp
    2165                2170                2175

Glu Tyr Met Lys Arg Ile Cys Glu Gln Leu Gly Tyr Ser Gln Val
    2180                2185                2190

Arg Lys Ile Phe Gly Arg Ala Ile Val Gln Gly Ala Arg Leu Arg
    2195                2200                2205

Thr Ala Asn Gln Thr Glu Thr Pro Val Asp Lys Leu Arg Arg Ser
    2210                2215                2220

Ala Thr Lys Ala Ile Val Gln Asn Lys Phe Ser Lys Val Val Ile
    2225                2230                2235

Asn Gln Asn His Thr Phe Tyr Met Lys Pro Ser Arg Pro Met Phe
    2240                2245                2250

Lys Val Ile Asn Trp Asn Tyr Glu Asp Glu Gln Asn Cys His Arg
    2255                2260                2265

Leu Glu Leu Leu Cys Ala Pro
    2270                2275

<210> SEQ ID NO 215
<211> LENGTH: 302
<212> TYPE: PRT
<213> ORGANISM: Anopheles gambiae

<400> SEQUENCE: 215

Met His Ile Arg His Ser His Leu Ile Leu Tyr Leu Ala Ala Val Gly
1               5                   10                  15

Gly Phe Val Val Ala Ala Asp Phe Pro Pro Gln Arg His Thr Pro Ser
            20                  25                  30

Ala Arg Glu Glu Met Arg Arg Ala Arg Lys Gln Ser Gln Thr Ala Ile
        35                  40                  45

Leu Gln Ser Val Gly Lys Arg Ser His Gly Asn Arg Asp Ala Leu Val

```
    50                  55                  60

Ser Leu Ser Glu Glu Leu Glu Met Val Ala Ala Ala Glu Ala Thr Thr
65                  70                  75                  80

Val Ser Ser Lys Lys Ala Ser Pro Ala Ala Val Ala Thr Pro Gly Asn
                85                  90                  95

Ala Thr Ala Ala Ala Ala Ala Pro Val Ile Thr Thr Thr Thr Glu Ser
            100                 105                 110

Asp Leu Phe Arg Ser Tyr Met Gln Thr His Arg Lys Lys Tyr Tyr Ala
        115                 120                 125

Lys Tyr Arg Ala Asp Arg Arg Arg Ser Ala Leu Met Glu Asn Met Gln
    130                 135                 140

Glu Ile Gln Glu His Asn Lys Ala Tyr Glu Ala Gly Ser Asn Arg Phe
145                 150                 155                 160

Arg Met Ala Pro Asn Ala Phe Ala Asp Met His Asn Ser Glu Tyr Arg
                165                 170                 175

Lys Arg Leu Val Arg Leu Lys Thr Asp Pro His Arg Lys Val Glu Pro
            180                 185                 190

Ala Val Ala Asp Glu Ile Val Ser Ser Ser Asn Glu Leu Pro Ala Glu
        195                 200                 205

Leu Asp Trp Arg Glu Lys Gly Phe Lys Thr Ala Pro Ala Asn Gln Lys
    210                 215                 220

Ser Cys Gly Ser Cys Tyr Ala Phe Ser Val Ala Tyr Ala Ile Ser Ala
225                 230                 235                 240

Gln Leu Met Lys His Ile Gly Arg Val Glu Leu Val Ser Glu Gln Gln
                245                 250                 255

Met Val Asp Cys Ser Thr Ala Asn Gly Asn Leu Gly Cys Gly Gly Gly
            260                 265                 270

Ser Leu Arg Asn Thr Leu Lys Tyr Leu Glu Gln Ala Gly Gly Val Met
        275                 280                 285

Arg Glu Val Asp Tyr Pro Tyr Thr Ser Ser Val Ser Val Gly
    290                 295                 300


<210> SEQ ID NO 216
<211> LENGTH: 549
<212> TYPE: PRT
<213> ORGANISM: Anopheles gambiae

<400> SEQUENCE: 216

Met Tyr Gly Gly Met Leu Leu Met Val Ala Cys Leu Val Ala Ala Gly
1               5                   10                  15

Ser Val Ser Gly Thr Gln Lys Leu Gln Glu Arg Tyr Ser Trp Gln Gln
            20                  25                  30

Leu Asp Phe Val Phe Pro Asn Gln Arg Leu Lys Gln Gln Ala Leu Ala
        35                  40                  45

Arg Gly Asp Tyr Val Pro Thr Asn Gly Leu Pro Val Gly Ile Glu Arg
    50                  55                  60

Trp Glu Asn Lys Leu Phe Val Ser Val Pro Arg Trp Lys Asp Gly Ile
65                  70                  75                  80

Pro Ser Thr Leu Asn Tyr Ile Asp Met Asn Gln Thr Pro Ser Gly Ser
                85                  90                  95

Pro Ala Leu Ile Pro Tyr Pro Asp Trp Ser Ser Asn Val Ala Gly Asp
            100                 105                 110

Cys Ala Asn Gly Leu Ser Thr Val Tyr Arg Ile Lys Ala Asp Lys Cys
        115                 120                 125
```

```
Gly Arg Leu Trp Ala Leu Asp Thr Gly Thr Val Gly Ile Gly Asn Thr
    130                 135                 140

Thr Gln Gln Leu Cys Pro Tyr Ala Leu Asn Val Trp Asp Leu Lys Thr
145                 150                 155                 160

Asn Arg Arg Leu Arg Arg Tyr Glu Leu Arg Pro Glu Asp Thr Asn Ala
                165                 170                 175

Asn Thr Phe Ile Ala Asn Ile Ala Ile Asp Met Gly Arg Ser Cys Asp
            180                 185                 190

Asp Thr Phe Ala Tyr Met Ser Asp Glu Leu Gly Tyr Gly Leu Ile Val
        195                 200                 205

Tyr Ser Phe Glu Gln Asn Lys Ser Trp Arg Phe Ala His Ser Phe Phe
    210                 215                 220

Phe Pro Asp Pro Leu Arg Gly Asp Phe Asn Val Ala Gly Leu Asn Phe
225                 230                 235                 240

Gln Trp Gly Glu Glu Gly Ile Phe Gly Met Ser Leu Thr Pro Pro Gln
                245                 250                 255

Ala Asp Gly Phe Arg Thr Leu Tyr Phe Ser Pro Leu Ala Ser His Arg
            260                 265                 270

Glu Phe Thr Val Ser Thr Arg Ile Leu Arg Asp Glu Thr Lys Val Glu
        275                 280                 285

Glu Ser Phe His Asp Phe Gln Tyr Leu Lys Glu Arg Gly Pro Asn Ser
    290                 295                 300

His Thr Thr Ser Arg Val Met Ser Glu Thr Gly Leu Gln Leu Phe Asn
305                 310                 315                 320

Leu Ile Asp Gln Asn Ala Val Gly Cys Trp His Ser Ser Leu Pro Tyr
                325                 330                 335

Ser Pro Glu Tyr His Gly Val Val Asp Arg Asp Asp Val Glu Leu Val
            340                 345                 350

Phe Pro Ala Asp Val Lys Ile Asp Asp Glu Glu Thr Val Trp Val Ile
        355                 360                 365

Ser Asp Arg Met Pro Val Phe Leu Ile Ala Asp Leu Asp Tyr Ser Asp
    370                 375                 380

Val Asn Phe Arg Ile Phe Ser Ala Pro Leu Ser Thr Leu Val Ala Gly
385                 390                 395                 400

Thr Val Cys Asp Val Gln Ala Gly Gln Phe Gly Ala Ile Gln Pro Lys
                405                 410                 415

Phe Gly Gly Asp Ala Ala Asp Leu Ser Thr Thr Tyr Asn Thr Asp Thr
            420                 425                 430

Thr Leu Leu Pro Thr Thr Tyr Ser Gln Pro Leu Ser Gly Gly Tyr Thr
        435                 440                 445

Pro Ser Leu Ser Phe Ala Pro Thr Val Ala Pro Gln Val His Lys Phe
    450                 455                 460

Thr Gln Gly Tyr Asp Thr Pro Thr Ser His Met Tyr Ser Thr Gln Ser
465                 470                 475                 480

Tyr Pro Thr Thr Ala Lys Ala Tyr Ala Tyr Asn Lys Tyr His Gly Val
                485                 490                 495

Glu Phe His Ala His Gly Ala Pro His His Gly His Gly Tyr His His
            500                 505                 510

Gly Pro Gln His Gly His Asp Glu Gln Glu Gln Gln Gly Gly Tyr Ser
        515                 520                 525

Gly His Arg Gly Tyr Trp Asn Gly Gly His Lys Lys Gln Asp Ser Trp
    530                 535                 540

Lys Gln Phe Phe Tyr
```

545

<210> SEQ ID NO 217
<211> LENGTH: 380
<212> TYPE: PRT
<213> ORGANISM: Anopheles gambiae

<400> SEQUENCE: 217

Met Pro Thr Ala Ala Leu Leu Pro Leu Leu Val Gly Leu Leu Ser Leu
1 5 10 15

Ala Val Ala Val Gln Gly Ala Cys Ser Ser Ser Asp Asn Cys Thr Arg
20 25 30

Thr Ile Tyr Thr Trp Glu Gly Gly Arg Ile Val Trp Pro Cys Pro Thr
35 40 45

Thr Lys Arg Leu Ile Thr Ser Thr Gly Lys Tyr Lys Pro Arg Asp Leu
50 55 60

Ile Ala Met Arg Cys Gln Arg Ser Gly Thr His Thr Leu Cys Val Phe
65 70 75 80

Pro Arg Tyr Lys Ser Ser Asn Pro Ile Thr Leu Ser Lys Val Tyr Ala
85 90 95

Thr Lys Lys Gly Cys Asp Val Lys Phe Glu Pro Phe Pro Cys Trp Asn
100 105 110

Glu Gln Glu Glu Gly Asn Cys Asn Ala Leu Gln Ser Ala Ile Asp Leu
115 120 125

His Ser Asp Gly Glu Tyr Val Trp Val Leu Asp Ser Gly Val Thr Gln
130 135 140

Ser Gln Arg Thr Pro Val Gln Arg Cys Pro Pro Lys Val Val Val Tyr
145 150 155 160

Cys Ser Lys Thr Gly Lys Lys Leu Lys Thr Ile Asn Leu Ala Arg Phe
165 170 175

Val Thr Glu Lys Ser Arg Leu Gln Tyr Ile Gln Val Glu Cys Leu Lys
180 185 190

Gly Gly Arg Cys Tyr Val Tyr Val Ser Asp Pro Gly Asn Asn Ala Ile
195 200 205

Ile Val Tyr Asp Val Tyr Asn Gly Arg Gly Tyr Arg Val Ile Leu Pro
210 215 220

Lys Ala Val His Met Gly Cys Arg Tyr Arg Asp Met Leu Tyr Ile Phe
225 230 235 240

Leu Ser Lys His Lys Glu Gly Thr Arg Leu Tyr Phe Thr Tyr Leu Gly
245 250 255

Gly Asn Arg Leu Phe Ala Ile Lys Thr Glu His Leu Arg Lys Gly His
260 265 270

Gly Gly Asn Ile Ile Asp Ile Gly Glu Lys Pro Val Val Pro Val Phe
275 280 285

Leu Gly Thr Asp Gly Gly His Gly Val Phe Phe Arg Glu Glu Gly Glu
290 295 300

Met Asn Ile Tyr Tyr Trp Asp Thr Asn Thr Cys Trp Lys Lys Thr Asn
305 310 315 320

Phe Lys Leu Val Tyr Lys Ser Thr Leu Gly Leu Tyr Ala Thr His Val
325 330 335

Phe Pro Asp Leu Lys Leu Asn Arg Leu Leu Val Leu Glu Asn Asp Phe
340 345 350

Pro Ser Tyr Val Lys Asp His Ala Gly Cys Gly Thr Leu His Gln Ile
355 360 365

```
Ser Ile Leu Asp Gly Ser Cys Lys Cys Asn Ser Gly
    370                 375                 380
```

<210> SEQ ID NO 218
<211> LENGTH: 380
<212> TYPE: PRT
<213> ORGANISM: Anopheles gambiae

<400> SEQUENCE: 218

```
Met Ser Cys Arg Val Thr Gly Leu Pro Leu Ala Leu Leu Phe Val Leu
1               5                   10                  15

Val Ser Ala Leu Ala Ser Thr Asp Asp Leu Glu Tyr Cys Asn Ile Val
            20                  25                  30

Tyr Arg Ile Asn Gly Asn Ser Ile Asp Phe Pro Cys Leu Ser Thr Lys
        35                  40                  45

Asn Ile Tyr Ile Ser Ala His Arg Tyr Gln Pro Arg Asn Val Met Pro
    50                  55                  60

Val Arg Cys Gln Tyr Asp Asn Gln Arg Met Leu Met Ala Leu Pro Arg
65                  70                  75                  80

Leu Arg Ser Gly Val Pro Thr Thr Leu Gly Gln Ile Asp Leu Asn Lys
                85                  90                  95

Pro Asn Cys Tyr Ala His Ile Lys Pro Tyr Pro Cys Trp Ala Tyr Gln
            100                 105                 110

Glu Glu Gly Asn Cys Asn Ser Leu Gln Ser Val Ile Asp Leu Tyr Val
        115                 120                 125

Asp Val Lys Arg Ile Ala Trp Val Leu Asp Ser Gly Ile Thr Asn Phe
    130                 135                 140

Leu Glu Gln Pro Ile Lys Arg Cys Pro Pro Lys Val Tyr Ala Phe Asn
145                 150                 155                 160

Leu Ser Asn Asp Lys Thr Val Lys Thr Ile Asp Leu Ser Glu Ile Val
                165                 170                 175

Lys Ser Ser Ser Arg Leu Gln Tyr Leu Val Thr Asp Tyr Asn Glu Leu
            180                 185                 190

Gly His Pro Phe Val Tyr Ile Ser Asp Gly Asp Gly Ala Ile Ile Val
        195                 200                 205

Leu Asp Val Asn Asn Asn Lys Ser Phe Arg Val Val Leu Pro Arg Ala
    210                 215                 220

Ile Ser Ala Gly Cys Gly Asp Ser Asp Val Leu Tyr Leu Leu Leu Ile
225                 230                 235                 240

Pro Lys Pro Lys Gly Gln Ser Leu Val Ile Phe Ser Tyr Leu Cys Gly
                245                 250                 255

Gln Lys Val Tyr Ser Ile Lys Ser Glu His Leu Arg Ser Gly Lys Gly
            260                 265                 270

Ser Ser Ala Ile Val Glu Leu Gly Thr Lys Arg Lys His Ser Val Leu
        275                 280                 285

Leu Gly Thr Asp Gly Gly Lys Gly Val Val Leu Arg Tyr Arg Gly Glu
    290                 295                 300

Ala Glu Leu Tyr Leu Trp Asp Ser Asp Gln Pro Tyr Arg Glu Cys Asn
305                 310                 315                 320

Phe Glu Leu Ile Gln Asn Ala Asp Glu Cys Arg Leu Ser Thr His Val
                325                 330                 335

Val Val Gly Lys Asn Glu His Leu Leu Ser Leu Ser Ser Asn Leu Ser
            340                 345                 350

Asp Phe Leu Asn Asn Thr Cys Gly Val Gly Gly Ala Ser Ser Arg Leu
        355                 360                 365
```

Lys Tyr Val Cys Lys Glu Cys Asp Asp Asp Cys Tyr
    370                 375                 380

<210> SEQ ID NO 219
<211> LENGTH: 651
<212> TYPE: PRT
<213> ORGANISM: Unknown
<220> FEATURE:
<223> OTHER INFORMATION: Culex quinquefasciatus

<400> SEQUENCE: 219

Met Glu Glu Ser Ser Gln Gln Leu Gln His Pro Ser Pro Val Arg His
1               5                   10                  15

His Ser Tyr Ser Gly Ala Ser Gln Gln Gln His Lys Leu Leu Lys Asp
            20                  25                  30

Asn Ser Ala Asp Gly Ser Gly His Leu Ala Asp Ser Gly Tyr Asn Ser
        35                  40                  45

Tyr His Ser Ile Asn Ala Ser Cys Ser Val Val Arg Ser Val Leu Ala
    50                  55                  60

Thr Ile Glu Glu Asp Asn Glu Thr Ala Asp Ser Ser Phe Glu Glu Pro
65                  70                  75                  80

Ala Ser Ala Arg Lys Val Val Thr Gly Ser Val Leu Thr Pro Thr Thr
                85                  90                  95

Thr Val Ser Met Glu Leu Ile Ser Asn Phe His Leu Thr Thr Pro Lys
            100                 105                 110

Glu Asn Val Val Ala Gln Arg Arg Thr Leu Ala Arg Lys Pro Thr Cys
        115                 120                 125

Gln Asn Leu Phe Ala Leu Arg Thr Pro Glu Lys Ser Ser Gly Ser Gly
    130                 135                 140

Ser Val Glu Thr Pro Val Arg Ser Gly Arg Lys Ser Ala Glu Leu Gly
145                 150                 155                 160

Ile Leu Thr Pro Arg Lys Asn Lys Thr Ser Ala Lys Arg Lys His Ala
                165                 170                 175

Ser Phe Arg Glu Lys Leu Tyr Ser Asp Gly Asp Ala Glu Ser Leu Glu
            180                 185                 190

Asn Asp Cys Lys Lys Leu Asp Gln Glu Asp Ile Ser Pro Ile Phe His
        195                 200                 205

Asn Lys Arg Arg Arg Asn Ser Val Ile Asp Asp Phe Ile Arg Ser Ser
    210                 215                 220

Thr Pro Lys Thr Ala Ser Phe Lys Ser Asn Phe His Val Glu Ala Gln
225                 230                 235                 240

Glu Asn Gln Lys Pro Ala Asn Arg Lys Ala Leu Val Leu Arg Lys Phe
                245                 250                 255

Gln Ser Phe Ser Pro Ser Lys Met His Ser Tyr Arg Lys Arg Asp Thr
            260                 265                 270

Val Leu Gln Glu Lys Ser Val Leu Thr Asn Arg Lys Ala Pro Leu Gln
        275                 280                 285

Arg Gln Asn Ala Ile Gln Ser Thr Thr Pro Gln Lys Pro Ser Leu Glu
    290                 295                 300

Ala Ser Leu Glu Leu Ser Phe Glu Pro Thr Pro Glu Leu Pro Asn Pro
305                 310                 315                 320

Thr Pro Thr Phe Gly Leu Gly Ala Leu Leu Asp Ala Pro Ile Leu Pro
                325                 330                 335

Gln Ser Ser Asp Asp Leu Lys Val Asp Leu Asn Glu Glu Val Ser Gln
            340                 345                 350

Leu Pro Ser Phe Asp Asp Cys Ser Thr Phe Thr Pro Thr Lys Pro Cys
355 360 365

Ser Leu Pro Thr Glu Pro Asp Ser Val Leu Arg Asp Ala Ser Val Ala
370 375 380

Thr Arg Arg Arg Ser Ile Pro Gln Ile Leu Asp Gln Gln Leu Glu Ser
385 390 395 400

Pro Ile Leu Phe Ser Pro Asn Ile Pro Arg Thr Pro Lys Ser Thr Arg
405 410 415

Lys Leu Lys Arg Leu Asn Ser Ser Thr Lys Lys Asp Lys Gln Pro Arg
420 425 430

Ser Lys Pro Ala Ser Pro Lys Arg Tyr Pro Val Ile Pro Gly Ala Tyr
435 440 445

Arg Arg His Tyr Asp Gly Ile Glu Arg Leu Asn Ile Leu Lys Arg Leu
450 455 460

Asn Glu His Asp Lys Gly Ala Leu Glu Ile Val Leu Gly Tyr Leu Ala
465 470 475 480

Asp Ser Asp Leu Val Arg Val Val Ala Val Ser Arg Gly Trp Arg Ser
485 490 495

Ile Ile Glu Ser Asp Trp Arg Leu Ala Arg Arg Leu Arg Ala Tyr Leu
500 505 510

Ala Arg Glu Ala His Ser Lys Glu Asn Leu Asp Arg Ser Glu Ser Leu
515 520 525

Arg Glu Asp Ser Ser Lys Ile Gly Cys Glu Ala Val Val Val Gly Lys
530 535 540

Leu Val Gln Gln Ser Ala Ser Val Thr Arg Gln Pro Phe Ser Leu Cys
545 550 555 560

Asn Ser Ile Asp Ala Gly Asn His Ser Val Met Asn Thr Thr Val Pro
565 570 575

Lys Ser Pro Pro Val Ser Pro Ser Arg Arg Lys Phe His Glu Asn Gln
580 585 590

Lys Phe Trp Gln Arg Cys Arg Glu Gln Met Ser Arg Ile Ala Val Val
595 600 605

Asn Lys Ile Pro Val Val Gly Val Trp Leu Ser Ala Leu Ser Val Asp
610 615 620

Met Leu Gln His Asp Ser Ser Leu Ser Ala Met Arg Leu Thr Asp Ile
625 630 635 640

Gly Ala Ser Ile Glu Asn Phe Pro Ser Leu Trp
645 650

<210> SEQ ID NO 220
<211> LENGTH: 2862
<212> TYPE: DNA
<213> ORGANISM: Aedes albopictus

<400> SEQUENCE: 220
aacactgctg acagtaaaca aaacagtaac tgtttcgcta gtgacaaaac aacaacattg 60
catttcggga gtgctcggaa aatcgctcgg actctcaggc tcggactaat gaccgccgta 120
ctatcatcac cgtcatcatc attatcatcg attccgcttc tccagctgag tccagccgaa 180
cgcagaatga gagggaaatt tttcaaactg tcactgtggc tttggtggtg tgcgtgagat 240
cgcacgttgc cgttctgtgc tgatgtgaag gctacgtgca gtttgtttgg gcgtcctccg 300
gttcatttat tttgattcaa tttgtatacc tatctattgt ccgcgattcc cttaccggca 360
atgcttgttt tttttcacaa gtcgtttgtt gggaatttaa agtgccaaaa aagtgcctag 420

```
tgtgagatta agttcaaagt gttgcattat aatgtctaga gcggatagct acctagcgct    480
gtgtctgttg gatgcccttg atgatcaaaa tttggagtcg ttgcgagttc tgctggagaa    540
gcacaaggcc aaccccaatg ctattgtgct ggagaagaat gtggcaccgg tacatttggt    600
gcagggagcg gaaagcgaac ggtttgccga gcaagcgact agcctgatgc tacggtacgg    660
agcggatccg aacttgcggt ccgacgagga aggaatgaca ccgttacatg tggcggccaa    720
tttgggacga ccgcggttgg tcgagatgtt gctcaaggcg ggagccgata tggatgtgga    780
ggatggagag ggcaaaatag cagtggaata tgcgattgag gagggacatt ttgaggtggt    840
gaaggtgatg caaaatttg ttttcgagaa aaagtttgag actaagcgga aggaattgat    900
acagaaggaa caacaaaatg ggaatagcag cggagggtta gtgaaatgtt ttggcggtta    960
cctgagactg gacactccaa ccaagaagag cgtattgatg gatgaatcca aattgacgcc   1020
aaaccgagta cattacaatt tcgacgcaac gtcaccttat tatatcaaca ttacccaccg   1080
gaggaaaact agtcctaaaa ggacgaagga tgactacaat cgggctgtgc tgcatttgca   1140
agacaccctt gatggaacaa agctaagtga tgacgatgat attgttgttg ctcgtaagaa   1200
tttatttgag ctgacggaga aaaacttggc aaatttcagt caaaatatgt cgagttcaac   1260
gcgaaaaagt cgaacatctt ttatcgaatg ctggagggat aaaatagccg tcctgcgtga   1320
tcgcaacaag ttaagcacaa acatcgagga tatcgaaaaa attttgtctg gattctccga   1380
tagcactatt gaagatgaca ttgataggca aacatatacc atacacgatt gtaatgatca   1440
aatcgaaccc ccaggtcagt tggtctacag tgaactggcc ctcgatcagg aacaaacaaa   1500
catcacattc caaacagctg ttgagcaacc ggcccaccaa gaagacagcc tacgaacaaa   1560
cgagtttgct ctagcccttt gtccatcgcc accgccagag gaatcagtgc aatcagaagt   1620
taagccttta ttcgaggcac agaaccgact ggttcaaatt acgaaagaat acgtccacac   1680
ggacgatgaa gccggtctgg tattttacga gaaaaaattc attgccgccg agtccgttgc   1740
gaagcagcaa ccattaaacg gtcatcgaaa tgcttccttc tccagtcaat cgacggcgct   1800
cacgttgcca ccgctggatt acgatacgga tgtgcttcgt gcagaattga ccaattttgg   1860
cgaaccgcca gggcccatta cgaagcacac gaaaaagttg tatctgaaga agctggtcaa   1920
atacaagcgg gatccggagc gggccctggc tcagattaag gggaaattaa atttctccgt   1980
tgagcttctg gcgactatcc ggagtgaaga tgtcttcagc aaaataccc aacagcaagc    2040
actcgaaacc gaaatgtcca gcgagtttat cacaaccaac gacaaaacgt ggcgagaagg   2100
tcacctaaag aaaagcttca tctacctgct gatcgatccg agggtatcgg aaaatttacc   2160
ggcccagcag acgttgttcc agcagcatga cctgtggaaa cgattcctgc agtcgatctt   2220
ctacgtcggc aagggcaaaa gcagtcgacc ctactgtcac ctgtacgatg caatgaagtt   2280
gtaccagcaa aagtccagtt cctccagtgc gttgaaaccg cctccgaacg gagagctgct   2340
ggaactgcag gtagaagaag agcaaatcat cttccaaagc gaggaacgca tcgagcgggt   2400
ttgtcgtgcc accaagatcc tgaaccggaa acagatgaac gacagcgcca agttgaacag   2460
gatcattgac atctggcgcg cacagcgagg cgtgatttgt ttgcacgtgt tccacaacat   2520
aatgccggcg gaagcgttca cccgggaggc ggccattatc gatgctttgg gcgttcaaaa   2580
tttgaccaat ctgaagcggg gtgattacta tgggaaggct ctgtcttggc ccatgaaacg   2640
tcggaaacag ctggggatat tgctgctgta caaggcgctg ttgatctatc tggccgaggg   2700
cgaaacgcaa ctgctgccga gtgatttgat ttgaatagct aaaggtgatt ttgtttcttt   2760
```

gggtgatctc agaaagtgtg ttcaaattat ttggatatgt gatattttta tacaaacatg 2820
aataaattgt gatcaataaa taattcggat aggtgtttca aa 2862

<210> SEQ ID NO 221
<211> LENGTH: 6754
<212> TYPE: DNA
<213> ORGANISM: Aedes albopictus

<400> SEQUENCE: 221
ttagatccac cgtgctttct accacgtcga agcaactgaa acccgtgcag cgtgatcgcc 60
gcattttttt ttaccattgg ccattgttct ctgtgcgtgc ccttgttctt ctgtagtcca 120
gctccacaag catgcataaa ccatgaatag gttagccttt ctttttacga cgctttttct 180
ggttatagtg attcagatcc agatcaggac caacgcgcag gtcgttcaac cggcgcacac 240
tctcccgaat gaccaacggc caagcggtcc gaagaaaccc gctcaaaatg agcgcccgca 300
caagcaaatc cccacgacca aggcaacgcc caagcccagc atgggtgacg cgatcaagaa 360
cctgaaagat cgcatcctga acgacacgga caccccgcag gatatgcttc agcacgtccg 420
ggatagctcc ttccgaaacg cattccacga ggcgatcgat gccaacatcg tcaatccagg 480
gctgatcaat acgctggcgt cggtcgccaa gccgttggtc aacgactaca gccgagatac 540
gctgctgatc gattccattc gggaggacat aaacttcacg ttcggaccga acgtgacctg 600
gtggaagacg ctggagctca agaagaacga acagcacgtg atcgtgggtt tgagtaacga 660
cagtattgtg atcttgtttg aacacttcgg ggagtataag ctgcaacagg aggtattgat 720
ggagacggct ccgacggctt tcgagatcat cacggtctgg gactcggtgg cggagactcc 780
gatcagctgc ttgatcgtgg caaccgagct gcagctgatt tggtacacga tgaggcccga 840
tacgaacttt gagctgacgg aggagtggcg atggccactg tacaagatga cgacgttgat 900
caaggggttc aaataccggg atatccacat gatcttgctg gtggggacgc atccgaacaa 960
gcacaagtcc gtttcggcaa cgctgtacga gttcaacttt gaacgacagc agttttggct 1020
gctgcagagg ctggatcttg ctttcccttg tagcaaagtc gggttggtaa gggtcggaag 1080
ggagtttctg gtgacattcc cgcagaacga tacggccatg atctatacgc tggaagctgg 1140
agagaaatac cgcggaaggt tcaatttgat cgcgaattac acgtcggaga tggtccaaac 1200
ggtgggggct ttccaggttg gcaggtacgc gtatatagcg atcggaggac gatcgccaca 1260
gatcgtacgt tacgcaaatg gtgtgtttac gtcccagcgt atcccaatgg aggctatgga 1320
gactgttgaa gcgtattatg aaattccgac tccaacctac cgagatgatc tgatcctgct 1380
ggttcagcac aagatgctct tctcgacgca cgatctgcag aggttggacg tcttcgtgtg 1440
gaacggcgag tccttcgatc tccgaagtaa tatcccatgc tacgtggagg acgaactgat 1500
ggacaacgaa gtttcatgca tgctggattt gtaccgacct accggcatcg tcgggtccgc 1560
gatcatcctt cgcggcaaga aggtttcgat gatcgttccc cggtaccaga ctcattccac 1620
tctgttcaat ctacacatag aactgctttc agcggagcat ccaatccggc agaagactca 1680
ggagatgcag gacacgatcg atgcattcac caagatcgtc cagtaccagg acgaggtaat 1740
cagcgaaggc ttcgcggcga tcgccgaagc agatcagttg tatgatgtcc ccctgttaac 1800
gctgcagaat tgttcgctgg gaacgatcca tgcggacttg gtcattcaag attcgcactt 1860
caattggccg aatggtacga tcgtggttgg tagcaagatt tggtcacatc gggacacggc 1920
ggtcaacgta ccggcgatcg cgcaagagat cgaggtggag acggcgctac taagccaatt 1980
ggaacagcag ctgaactaca cggttcgacg acacaacgac agcttttcgc ttgatttgga 2040

```
ccagccgttg tacgttcagg gtagagtgga ggtcggagga gctttggtca cggatgatct   2100
atacgttcgg caactggagg aggatccacc gcttcttcgg gtgcttcgac aaaccggcga   2160
tgatagtgtt aaagagcttc gggtgaaaga tctaaaagta cgccacttga attttgaaac   2220
tgtgaacgga atcccggcga gtgatctggt gttcaacacg ggcgagaaga tcgagcttgc   2280
caatgcgctg atcgtggata atgtggttgt ggcacaaaat gtgatcttgc cgaaaggagg   2340
tacggtgaat ggggtagatt tgagcgaatc tacggtgtat ttcaactgta agaatcgtcg   2400
gtgggatgga ttgaagtttg attcggtcga agtactggaa gacgtgatgg ttcaggagac   2460
gatcaacggt gtgacgttgg atctggaaga gttggatgcc cggttcagac aagctagcga   2520
tgacatgacg gatgttttag ttacggaaaa gctacaactg gacggcaact tgtacgtgca   2580
cagcgtcaac ggagtaccgt ggagcgatat aatccatcga attgtgctga agaatcgacc   2640
gaatcgactg gctgaagtga ggatcaatgg aagcttgata ctagagaacg acaacgtgac   2700
ggtttaccat ctgaatggac tggccttccc gatggactat ttgctgtcca acagccccat   2760
agagtcgatc gtaaccgggt acaagcggtt tgtgaacttt acaaatattg acgccctgga   2820
cattgaacgt aaaatcaacg gggttgacct gcaggacatt gtgaccttgc acgatgatca   2880
gcacatcccc ggtgacgtaa ccttcggcga attacacgtg accgagcgtc tcgaagtgaa   2940
gggagccatc cgcgggaaac atttggacga attcctcgat aacccgtcac tacttcaaac   3000
cccattggtc aaggccgcct gccacttcaa gcagctcttt gtcgacgggc cagtggtcgt   3060
ggagggcaaa ctcaacggca tggatgtgga cgctgtccta tcggatgtgg tctacgactc   3120
ggagcacacg gtgacgatcg aggcggccaa gcggatcgct tcggtggaat tcggtgataa   3180
ggttaccatc ggctccggca tggtcaacga gttcaagctg gatcagtttg tgacgcgaag   3240
caccgagcag gagttgagcg tacgggagat caatggaaat gtgttcatcc acgatttgaa   3300
gctggacggg ctgtttgatg gactgaacgc gacggccttg gatgtaagct cggtgaagtt   3360
gttcggcgat cagtacacgg agacttcgtt gatctttaag aaccgggaga acgctctgta   3420
tccagacgtg gaagcgaatg agttgaagat catgaaaaca ctgaactcga aagccaggag   3480
cgagtacaaa gatacggaac aggaagaact ggtgctctcg ggacagatca gcttgagtca   3540
tttgcacgta aatcacatga agttgacagg gtcgagcttg agcgggcctt cgaaaatgat   3600
caacttggtg catctaccaa cattcgacag cctccgattc agtttatcaa ggcctcagca   3660
ggtcactgcg ccgttctacg tgaacaaact ggtcgtgggc agtcaaatag cgacggctca   3720
cgtgaatgga cgagacatcc gcggtttgaa ggagagtttc gatcgcgtgg acaatttcaa   3780
gactcatcta ctgcagggca gtattcctat tgagaatctc tacgtgggag gtgacctgca   3840
ggtcaacatg ctgaatgacg tgaacttcga tgctttagtc aagcaggtca tctggttgaa   3900
ccgcccgaac aggatacctg gaacgtttcg gttcctcgat cctatacagg ttgaaggaaa   3960
tttgacaata cgaggacaga tcaacaacgc cgatctcgga gactttttgg aagacgtggt   4020
tcggaaatcg gccggagtgg cggagttcca tggtacgacc gtgttcatga acggtttggt   4080
agtcgagggg aacgtcaata cagagagcat caacaacatt cacatgagtg agctggcatt   4140
gagaaacgac acgatctacc tgcaaggtga tgtggagatt cagggagata tcttcgtaga   4200
gcacctgcat attgagaacc acttaaacca agagcctatc cagaacctcc tgaactcgta   4260
cggctacgac gaaaccaaag acgtccacac gatcaaaggt gatctctacc tgtacggtgc   4320
ccaaatcgga tcgcttcgca tcgcaggcat gatgaatcaa atcccgaacg tagacgccca   4380
```

```
cctggcgtcg atcatccgca aggaccagga ctacaacttc accaagccgt tgctgttcaa   4440
gaacgaggtc ttcttcgatc ggggcttctc ggctacgtac ctcaatcagg tggacatttc   4500
caccatccag caggacatcg tacggattaa cgatcagggc ccggtggaga tcgaagcgga   4560
ccggatcgtg tttgccgaac cggtctacgc ggatcgattg gcgatcaagg gcgatatgat   4620
tgcggcgaat ctggttggat gcaatccgga cgtttggatg agcaccgggg tcatgatcaa   4680
ccgggatgcg gagatctacg caaaaaccct cttctcaccg ggagccttcc gcacggatca   4740
cctccgcgtg gactacctga acggacaacc gatgaacaat ctgatcacgc tgaacaccga   4800
tcagacgatc gagaccaccc tgttcatcca cgagatgacc atcacccaac cgatggaggt   4860
cggtggctac gtcaacggag ttacgctacc gtacgagcgc aagaataccc ttatgaccta   4920
cggcaaccag cgagtccggc ttccgacggt cttccacacg atccgcgtcc ttcaatcgct   4980
caccctcccg ccggttctga atgggaaacc tttcggaccc ccggtcgcca tcgggcccga   5040
aatggtgatc gagtcaccca tctccttccg gcatctgatc gtcgatcgtc tggagacgga   5100
ggatatgatc tccggcgtgg actttgaccg ctggtacgag aacagcctgt ggagcaaggg   5160
tcgcgatcac caaaccatcg aagcgaggat ttccgcgaga aatgttcggt tcagcgggga   5220
cgtggaaggt aatggtaaga tcaacggagt tgacatcatg gacgtcgtcc agcgaatgaa   5280
ggccgccaag aagaacgtgg aggatcagtt gcaagactac cagtcggaga tgcgatcgtt   5340
ctgctccaac accaaacagt tggtggacaa atcacagagt cggatgttct tcttcaagta   5400
cttcgtgcag cggcaagtga tcaacgagca tctaccgatc gtgtcgttcc acttcttcga   5460
tcacttgggg taccatttcc tgggggtgaa catgggatgt gaaagtcact tctatcagtg   5520
ggatccaaca gggaaggcgt ttgtaccgat atttaaatac tacactggat tggtcgagga   5580
atggaatcac gtggtaaatg gcgaggaagc gattttcttg gtgacacgat caatcagcga   5640
gatcacgcaa tgtgaagtct cgggtctcag cgtatggttg ttcacgggag ttcaactgca   5700
gctggtgtgg aatacgattg acaccgcgtc gatgcaatcc gtagttgctg atccggtaaa   5760
gtcctacaag tttatgtact gtacgccaga tgtcgtggtg gagtacagcg ttgatggaag   5820
caccttggaa cagtggaggc ttccgaagag tgccctaggc tacgagttta tccccagtag   5880
agttggactt ggattggcct tgagtgacag taagctgctt gtgttgctgt cgaatgtaaa   5940
caagactgtt gatgaaggcc caaccgtaaa cagtggcctt gaaatggcgc tattctcgtc   6000
acaatcgatg cacgatcgta tgaaaaagac gtactctgaa aagttgctga attccacgat   6060
cgaatcagcg gaggtcagtg atatcatcca ccccgagaac ctatctccac aagaagaata   6120
caaccacttc ggcaacgata cagtgatcgt tgttgagccg gaagcagttg acataccgga   6180
acctccggta agcgaagatc aactgcccac ggagactccg atcgctcggg atattccaca   6240
cggaggaatt atgatcgccg acaatcagca cttccccgaa agatccaaag gcgatgtggt   6300
ggcgttccac gcaggtccac acaacaagaa gcgccatctg gtggcggttt ccaccgtggt   6360
ccacaccgtc gtccaaggag atcaagacgc gatcaagatc tacaccgaca tccaaactgg   6420
taagctgtac caggttcttc cctgtcaccg tccatcgcac ctaaccgccc tggaactccg   6480
ggatgaaacg atcctcgcct tccttgaggc acggcaaacc gtccagatct acatctaccg   6540
cgggatgcag ggtttcgtgc ggctcagcaa ctttaaactg acaggtccgg ccagggccat   6600
ggccgaagtt tcgctaccgc agccgttgat gatccgctgc aagctgcact acctggcgat   6660
ctcgaccgag cagaacgaac tgatcatgtt gcgtgccaag acgcaaggcg attgcggact   6720
ggcggtccag gtggactgcg atgatgtgga gtag                               6754
```

<210> SEQ ID NO 222
<211> LENGTH: 6533
<212> TYPE: DNA
<213> ORGANISM: Aedes albopictus

<400> SEQUENCE: 222
cgatctttat ccttccgaga aaaaatgtct tgttgaaccg tgaaaatgtt atttctttta 60
aattttgtgc ttgtgcttgt tttgctaacg gccataaaac tgcccagcta tgctgtgcga 120
tgtgaggacg accgggatgt cccccagtca ccagcagccg gtgacgatga actggatgga 180
ctcaaggagg tattctaccg taacctaatg gcggacatgc gcatggaatc gggaggacag 240
ccgatcatca ccccggagct agaaaaccgc atggaggaac ggattcaaag ctttctgagc 300
gctacggatg ggtcgacgac gggttgggtt cgtcgacggc gacaggccat gcacggtgga 360
cccatgggta acgaaatgga gcaccattcg ggtccaagca tggcttcgca tgaggaaatt 420
tacgctgaca ctgctgatgc cgagcatcgc tacctaaagg gcttccgcga gcgaggctcc 480
gtaccggtaa gcttccccat cgatatctgc ctactaaaag tgggccgatc cattttcgcg 540
gcatcgctac atctacgaaa atccaaagag aactacaaga accaaactat cgtcaccttt 600
tacaaacggc aaaaggggca gttccacaag tacatggagt acaaggcagc tcaggcacgt 660
aactttgact gcacctcgca cgcttcgcta ggattcgttg ccgtggttaa ctactacgac 720
aactccggca gccaagactt cccggaagct catcctgggt tcgacgaagg atcacccgtg 780
tttcaaatcc gtgaggatgg caccaccgac ataatacaga agttccgcca atccaaccag 840
aacacggttc acatgtggac tgccggaaac cacttctatc taacgcacac gtacacgaat 900
ttgaacgaaa gcgttgaaaa cgtttgccca ctgtaccgct ggaccgggta ccacttcgac 960
gtgatcgacg aactgccgtg ctacaactcg atctacatag aaccgttctc gatcgaacag 1020
acactgtaca tcgccatcgc caaccagatg aacgataaat ctgtcgaaga ggacaccttc 1080
tcggacatct tccggttcaa ctatgagcag cagaagttcg agttccatca gaagatctac 1140
atctactccg tgtcggacat agcgtacttc tttctggagt tgggtgacgt gcgggagcat 1200
tacttgatca cgggaaactc gcgagccggg aaggagaccg ccgtcgataa actggactac 1260
gatcagcatt cgatcgtgta caagttcgtc gagggatatt tcgtgccggt gcagaagatc 1320
gaactgcacc aggtgaagat gttccttccg gttatgcacg aaaacggcga attcctgcta 1380
ctgatccgct gcagaggcaa acccctgttg atctacgagt acgacggtta caaatttgtt 1440
ccctcgagaa tcgactacac gcggaacgcc ttcagtacgg gagtgtcgtt catgcgtgtc 1500
taccggcaca tcctgaacac cagcttgatc gtgattgcca acaagcagag cttcggcaac 1560
acagcgaatc tgttctcgcc gatctacgga gtggaaaaca acctgcggga tgtgtacggg 1620
cagttcatat cgtggtgcag cgaaacgacc catcagttgg agaacgtcaa cttggaagaa 1680
gtttacaaca agctggttga gttgccgaag gtttccggaa gtggggctaa gctcgagaag 1740
gacgtggaag tgaaggactc aagtgtggaa acgttgaaga ctaaggtgtt gcatacgcag 1800
cacttcatgt tcaaccagga agcgtttgac tatctgaaca acgtacatgg aagctgcaag 1860
acgtgaaagg agaaggcgaa gaagctacgt agtaagatcg atgacagtct caaactaagt 1920
gaagcgatgg aagtccgtgg agacgtcagg gtaccgcagg tgatcgcagc cgatggattg 1980
ataagggatc ttgaggctaa gaacgtcaac gatgagcggg tggttcctag ggtggcgaat 2040
caaacgaagc atgaagatgt tatcaacgta gacagactgg tgatcgagga caggttggct 2100
gtgaagtttc tcaatggcta tgccagtgaa acgctactgc atactacgga tgatttacga 2160
tctttggaag gcgcagacct gcatgtgaaa ggtgttgaaa tacgcggaga attgttcgta 2220
gataaattga tcgatggtat tcatgtgtca gtggacaatg ttttacttcg tggcgtggat 2280
caagtgtttg caggacggac tctacgggcc acaaacctta cggtaggtaa tcttatggcg 2340
aagaaactca actcgacgga tgttggcacg gttatgtcgt acctcgatcg agcatcggag 2400
tatgataacg cacaaaaacg aacggttgaa agttatccga agaaattcaa ggaaatccgg 2460
gttcaagatc ttgaaatcag cggtcttgtg aatgatgttg acatcaaata tatcaacaag 2520
aatgctctga agatcgtggg agatcaagtt attaccggta gcgtaaactt tgataatatt 2580
gttacgaaga aactagaaac ccccaacaaa agattatctg gagtagattt gaactactta 2640
gtgatgaccg agccgacgcc ggatcaacag gacttcacag ttcgacagga tgtacaattc 2700
atcaaaccgg tttacatgga acacctgcat gtcgatgagc gtattaacca catcaacgtg 2760
atcgacgatc aacttcaggt tctgctgaaa gatccaaagg agcctcagct tattaccggg 2820
accaagtcct tcgataacgt ccagcttctg ggtccgattt acctgcaggg caaagtcaac 2880
agcagcagtc tgagcaaatt gaaccctgtt tccacgatca ctcaggacgt atacctggaa 2940
ggcgactttg aaataactgg tgatgtcatg atcagacacc ttttgaacac tacgaatatc 3000
tatggagcaa gcaaaacttt caatttctat gatttgtacc accacggcct tccgctaagt 3060
gcagcttttg caaaccagaa cttcgtcttc aaacaaccgc ttgttgcgca tcatgccttc 3120
gccaacaacc tcaacgatgt caatccgaga gacttcattc cgatcccgtc cagcaaactg 3180
caacgtataa ccgggcgaaa gatattcaac ggtgacctta ccatccgcgg cgatcgagtg 3240
gatgctacca agatcaacgg aatcgatttg aagcaactga atcaaacggt actcaaaaag 3300
accggtgatc aggtcgttga aggaacgatc catttcaagg agctgatcgc atcgaccgtg 3360
gtggcgaaga agaccttgtt cgaagaacga cctctcagta cgctcctaac cgtgaatacc 3420
aaccagcgta tcaagtccaa ggtacgctgc gtgaactgca agctgaccat tcacggtgat 3480
ctgagcgtcg gtcgactgga gtcgtacaac aaatccaggg tattcggcta tgacttggat 3540
tttctcttta ccgacactct gcggaaaggt cacgcaccgg atgaatcgat cgcggtaacc 3600
ggcggaaagg gtttctacaa cgtgagcgtt ggggaactga tcctactgga tcaggcaacc 3660
atcaacggag tggacctgat tgggctgaag aagatcaacg acccccctgga gaaggatgtc 3720 atcgtggagg aaacgttgat cctgaagaat cctctgcacg ttcgcaacgt gtacttcaac 3780
ggatcgatca acggagttca gcgggaagaa tttggacact cgtggctgtt gaacgagtac 3840
aaccaaacgt ttacggctcc gcaggtgttc gaacacgtta cggcggaggg gatggtcgtc 3900
gatgggtact tcaatggagt caagttggag gagttggttc aggatatcta cttcttggat 3960
cgcagtgaac acctaccgga agcggtattc cacgaaggga tcgtgtcata ccaaccaatt 4020
atcgtcaagg gacttgtgtc aggtttgaat ctggccaccg acgttctgtt gaactactct 4080
ccgagtcgtc aatatctcaa agacgtgaga atcgatggta acctgctggt gactaaccga 4140
atacacgttg agcacacttt gaacggaatg aactacgcca aactgcgaga gtatgcgact 4200
tcgagtggcg aagaacggcc gttgaacgtg gacgttcagg ggaacgttca cttccacctt 4260
caaccggacg tttccgagtt gaacggctac aatctggaac agcttcatcg ggacgtctgg 4320
ttaactaacc gggacgaagt cctaactggg tcttatcgct ttgagaatgt tcatttcgcc 4380
aactatgtcc ataccaaggg tcccgtaaac caactggact tggaggagat tatccacagc 4440
tacttgagtg tgtcaaagcc acaaaacgtg tccacgccgc tggtttttaa gggacctgtc 4500

```
gagttccaga aaatggccac gttcgacaac atagccctgg aaggtctcct caagggatcg   4560
aaggaatccc gaggaatcaa catcgtagac ttcgatagat ttgtgctgaa aaagaacgta   4620
gaccaaacta ttacaggaaa atgggttttc cacgatgttg aagtgtacgg caacctcaac   4680
ttgaccaccc tcaacggtct ggacatccga cacgacatcc tgttgaacca cgccgagcag   4740
gtgaccttta ccggtgccaa acggatcgac aaccttcggg ttcacaatct tcgttgcccg   4800
gagccgtgca tcatccaagg ggtggatttt agcgaatggt tcagcaactc cgtgcggctt   4860
gaccgaaacc ataccgtgga aggcgtcacc tacctagaag gggtcaccat cctgggaggc   4920
atcgaatccc tcggtccggt caacaacgtt acgttcgacc cacagcattt actgctcaag   4980
tcggttaatc agacgctgga aggcactctc tacctgaaaa ccaaattccc agagcacaac   5040
ttgatctatc aatcgtcgat cgaaactttg gaggtgaaca caatcaacgg caaagatttc   5100
aacgagttca tggacaatct ggcacgtgat gaagagggta cgattacgat tgggacaccg   5160
gttacgttgg ctcagaattt gaaggccaag aatgtgcgta ccagcgatag taaggtattt   5220
ggtgtgaata tcaatcagct tctgcaggag gtggaatatg gtgatcagtt gagtaaatat   5280
gaaaccaagt tgcggaggct gcatatggtt ggacaatcct tggtggaaac actcagtacc   5340
aaaactccgt atcttagtca ctatcaaccg ataaaggccc tgccgggata cttccgtagt   5400
gtagcaacca ttacgttacc gttatcacct gcagcaatag aactactggc ggcacatgtg   5460
gatgatggaa atcgaacggc cgttgagttc tacaggtgga ataagaagga ctcacagttt   5520
cgttttgcta aaggttttcc atccatcagt tatccgactc tacggatcac caaaatgaaa   5580
cgaatcgtcc tgggtggaat ccagaacctc ttcgtcgaat actacgacca cagccgtcta   5640
ctctatcgac agtctatcct tgaccttgaa gcaccggact tttctgctcc caagaagact   5700
cccaaattca cttctatcta cgagttcaac agcacacatc cccaagacat tgttgcactc   5760
aagatactcg acttggactg cgtaggcctg tactcaacac acatcgacgg tctgaatgtg   5820
tactgtcttc aattggagag cctggagtac tacctgaagt tccaccaacc cctcacaaca   5880
ccagcagtca aacaggccct tttcctggac ggacgcctga tcttactgag cagagataat   5940
ctgctgcaag tctggcgctc ccgtgccgac tacaagctcg gtctcttcca actaatcaag   6000
atagcccacc caacttccct gaccgtggcc aagttcgagc aacagctctt catcgccatc   6060
aattcggacc aagcccttac ggaagcttcc gctcatcatg gatcgataga aatctggcgc   6120
gatctgcgac cccagcatcg gaacagtaca ttcaccaagt accagaccat cttgaccaag   6180
gttcccaagc agatccagtt ctcggtcctg tcgaccacgt cggaactgat gctgtacacc   6240
ctgacggaga atccgttcca cccgttggtg atctaccggt acgagggtgt ggccggattc   6300
cgggagtact tgacgagcaa cgccctgcgg accagcagta aacggtttgc ggtgatcaaa   6360
ctggatcaca aacagcggga actgttggcg ttgatcgccg accaaggagt cacttggatc   6420
gaagccgtta taaagggcag ataggtttgc tgttgatttg tatacattcg tgtataaagt   6480
tttgtttttg ttgttatgtt tgtaatgaaa tttgcgtgtt ttttttcaaa atc         6533
```

<210> SEQ ID NO 223
<211> LENGTH: 6009
<212> TYPE: DNA
<213> ORGANISM: Aedes albopictus

<400> SEQUENCE: 223

```
atcacaatcg agttgctctc ggcgcgaaag aacaggaagt cccactgtca tttctttgct     60
```

cgccggggat tgaacttctg gatgactacg gatccggccg atgcggatat ttctttctca 120
gtgaacatga tagtgacaat gtggatgtat ttcctgctga ttttgccaca gcaggtgact 180
tggtgttgga gcgattttgg caatggcggg accgaggtgg atctgttcct gcggcgaaag 240
attgacgacc tcatgttgga acgaagaacc agacaagcta gtccggccgc acgtgaaatt 300
gacacatcgc agtatgattt aacattgcat cgagttaaat tgagcctaaa tcgtaccgtc 360
attggtgacc atcagacatt tttcgcacgc gttcgcagca gcggaaacct gtaccttttc 420
tccggtaatc aaatttcgcg catcacggta aacgacgcag acgttaaact ggttccgatc 480
gctacaactc ccgacgtacg cgaagaagtg gcagatttcc agattgaaga gctgcatatt 540
tctggaaaca aaaccatcct ggtggcaact gtgtgtctac aggatcgctt caagatttat 600
caaattccgg atcactcgaa gggaaatgcg ctgactgtca aagctatgca gaggatttaa 660
acgtccaggt ctcaatcggc gatcggtttt ggtccaattc aaatcggatt tgttcttgat 720
caccggatac tcggaggccg gttttgggaa agtagcgatt tatcgatgga tggactatca 780
ttttctttgc gtgatgttaa agaagtggag cgttgcgacg agctgctggt atttagtggc 840
gaacaactag ttattctcgt gctcgaaatt gctgaatatc ctgaacgatc ggtgaacaat 900
atatacatgc ttaccgatga tttcaagtta atcaaaacac aggaaatgta ctttttacac 960
gatcgcttgc cgcattatga agtggacagc caattttaca tactgcgatg ccttgcctta 1020
gatgcatgct tcttgtaccg gtggaatggc gaaagtcttt tccgccgagc cagcaaaata 1080
ggatacgacc caaggagcat tgaaatgatg gcatcaggcc gtgacattat agtaatgtct 1140
ttggaaaaaa cactctactt ctataacaat caacccttgc taaaaattgc cgcttcgtac 1200
accatggtta acaaacgtgg cactgtggcc gacgctccct tccaaattga tcctcgagtt 1260
agcaagttgt ttctttacaa ggaagcaaca acggagaagc tgtacctcag catcctatat 1320
agctctggtc caaagcttct ggacatggtt gaaatacagc tcaacaaagg caggagcgcc 1380
cccagtccag gtgagcagtc aaattttaat gctcttaaaa cgtgtctttt tcacataaaa 1440
gatttggtaa acattcgcaa aaagtggatc gatatgatta aataccagtt aagcaaaaca 1500
ctgcgtagct gtaaatccaa agggcaacta tcgttggcat ccaaggtgta cctagctgaa 1560
tcgaatacag tagacaggat agaagttgat ggaaatatcg agaactctcc ccagggcttg 1620
ctaaacgatt ggagctcgac gagaagcagt ttagctgcaa ttcactcaca atcgcaggat 1680
ctgttctatt tgaaccgaat gaataccgtg cagtccaata tgaaaatccg gggaaatttg 1740
cgatcgaaat cgacacgaat gaaacacgtt aaagtacagc atcctcattc gggaagacca 1800
gcctacgtgc gacccaagag ggatctacag tcatcaaagg tagtgacatc cgccatagtc 1860
aacgctcgag aagtggttta cagtgggaac atgtttgcac atacacttag tcgtaacaat 1920
gtaaactacg tttcgttgcc cattcatgtc ggcaatcttc atacaccaac ggttcatgta 1980
agtttgaata caatcaaccg gatcccaatc gatgaaatgc tgtacaatgc gaccaataaa 2040
gttatagaaa agggtcacaa agtgttcaaa tctatggaca cagacgccct caaagtgtac 2100
ctggtgaatg gagttaaaac aacacagcaa ttttctagtc taagaaattt cgttgtgaca 2160
gtcggcactg gagctcctgt aaaactgacc ggagctcgtg gcgttacaaa tctgatcgtg 2220
agtggtaaat tgaacaacat tcctttggat gatctgctac aacagctgta ctatgtggat 2280
aaaaaatcaa caatcaatgg gaatgttttt ctacgggcac cttcacacat acggaatgta 2340
tacgttcgac acctgaataa tattcctacc agcagctttt tcgatttaag aacgaatcaa 2400
accatttctg ccgttgtgca tttatcacaa gtgtatgctc gaactttgta cagtaaaaca 2460

```
atcaatggaa ttaacattcc caacgatgtc acgctgataa gctcggcaaa aaccataaac   2520
gcggcactgg catccaattt tgtcgtcacg aaagatctca cactttcggc aaaggatcaa   2580
cactttacca ggcatgtact gggaaccaag gttgaagatt tctctcaaat ctactcggga   2640
cgtgtatatt tgaaaggttc tctgaaggta aaacaactta atatggaaat cccgaaaggt   2700
caacttattt gggtggactc acggctagtc cggatgtgca gaaacatttt tggatgaaac   2760
acgtcgagca ggatatagga acctttacct tcaaccgcaa tgtcgaggca agtcatctgg   2820
tttgtgccga attgaactac aaccccacgg taaactacct gaggggtgac cagtggccgt   2880
cgcatctgaa tcttgagatg tctaacgtct atgttcgagg tttcataaaa acttatgctt   2940
ccactcctac tttcctgcaa tacattaaca ccgaggcagt tcagcgcgga tccatgtcca   3000
ctgtatcagg tcgtaagatc ttcactggcc agctacacac cgatacactc gtctcagatg   3060
ccgtggataa tatcaacata cagagcttgg caaccgactt cagtacgatg gcgttcctcg   3120
atggagtcaa ggaaattgaa catttctcat cggaggaaag ttatatcgaa ttgctcggtg   3180
cgttgacttt acaggactac cagaatactt cgttcagcgt tatcgtggac agcagtgtaa   3240
atacgcacac catgcaaagt ttggagtata tgttcctacc ggatataaaa gtagaacatt   3300
tccaagcagc gctaatcaat ggggtgaacg cagaagattt tatatccgaa attgataatt   3360
ttacgtaccg cgtggatccc tttgccacgc agttcaagat agacaatctg gttgtgaaga   3420
agaacgtcat ttcaactagc caaatgttta tggacttttt aaacactatc ggcgtgaagg   3480
aatatttcaa attgttgacc ctgaagggtg tcggtgacaa agcgcaacag tgggaaatcg   3540
gcggtagtaa aattttttcaa aaagaaatgg cagtcgatgg gaagttgaac gtggtgcacg   3600
tcaatcgttt gatcctggac aacattctct acaattcagc tcggaaaaca cctcctttga   3660
acatcgctgg tttatggagc ataacgcaac ttgcgacgaa gtatttagcg acaaagcaaa   3720
taaatgatgt cccaatcaag catttgcaaa attccaactt gaaaacattc aaaataaaac   3780
acgatgtttc cattggttcg ctgtcggtat ctagtagtgt acacggtcac atgtttccga   3840
atagttcatc agtgctgatg cctccaaata ttcagctgct ctccagcttg accgtccaag   3900
gatcgttttt actagagcac tggaagcctg gaacgttctt attcgatgtg atgttatcaa   3960
ccgtgacggg tgcatcaaac gttttcgata gaaaggttgt tttccgagga aaccatgtag   4020
agattgtgaa gctacgaaac gaaggcaaaa tttttagcaa aacttgcaat tttgtcaact   4080
tgctaatgga ctcggtaaag aggaaacaac ccaatctcgt tttcagcagt cttggaaaaa   4140
acgttcaaag aagtagtttg tctcggcacg gtggcttctg atgatcttgt tacagtaaca   4200
ttggtcaacg gaatagatgt ggttcatttg aatcggagca ttcactcagt tggacaccac   4260
caggaaatga tcaagtcgac caagtatttt gaagaggaag tcaaagttgt acaactgctc   4320
tgcaacgatc agctggtcga cggcatttat ccgcatcatt tagatcttta ctccgaggca   4380
agccaattga ccaagaaacg ataccaattt gataaaccta tttccgttat cggaaacttg   4440
tacgtcgatg ccgtcaacga ctattcgctt caacatttct tggcaactcg cgtggttaag   4500
aacaggacgt acgcacagga gtaccaacag gaaaagtctc aacaagtaac aggattaatt   4560
acgttctcaa acttggtcct tttcggagaa tataacacag tccatgtagt taacggtatt   4620
ccggtaagcg agattgtgtc cagatcgtcc aacgagcatc aggttatggt taagccaaaa   4680
catttgaaag gaaccatcaa gctgcttgga cctacctcgg tcatgaaatg caacgacgtg   4740
aatttgttag atgtctacaa atccagcttt ttgaccagct cgcctgaaat cgcttttaaa   4800
```

gatctggttt ttgtatccga gagcactttg caaaatggat tatcaattga cagtagactg 4860
aatggtgttt ctgttcagaa aatgatgaaa cttcggctgt cctcagtgga ggacctgttg 4920
ccaatgattc cggtaatcag agagcagata actgtatcta acagagcata cgttgccaat 4980
agtgcgaagg agtcccgcat gttgtacatt gagaatgttc cgtttgatga aagaggtact 5040
atggtcagca aaagtgaaaa taggcagtca agtgaagcgt ccgaaaatgt aaattttgac 5100
aaatcctgcc acaacggaat taatcgcttc aacgttacca tacgtcagag gtcatcgaac 5160
ggagatataa gttctgccag ggccgtacta gatggagtat tgataagatc ggaatggaaa 5220
gaacttgcgt ataacgaaga aattgaaaca ctcgtagttt cacaggtcga gagaaatgcc 5280
aagccgatgc tacttattta cgtcaacaga aatggagaac tcagtattca gcaggagctt 5340
ccgctgagct catcggcagc agtattctat atggtgcaca ttaatgattc agcgcttatg 5400
ttggctgtag cggactccca tcagcttcac ctaggcatct ttgcccataa gctcaaatta 5460
ttccgctatg attcggatgc gatgcgcttt gtgcatttaa aacgctcagt ggtagctata 5520
atgatgtggc ggctattgat gtcgaggatg cgataatgtt tgcagtttcc gagaagggct 5580
ccaacatggt ggaaatattt tccctggaac gttcgtattc atcgctgtat caaaagttga 5640
ttttcgattc tactgtgaac tccatgaagg cgttcaggct acaagggtct ccggttatcc 5700
agatatcgac tattgacaat ttagtctacg tttacagtta tagtactctt gagggctggc 5760
ggcaactatc gtacggcagg ataccgtctg atgtgaacta ggctgggctt tgattttgtt 5820
tttatcattt taatatgata tctctaagct agttgttggt tatgttcttt gtgttattct 5880
gtatgttttt tgagaactgc aaatatgttt gccaattgat cgaaaacgta gtatatgtgt 5940
tattacaaaa ttaattgttt cgaatatatg catctttatc tttggggtaa ttacaatccc 6000
cgttcccga 6009

<210> SEQ ID NO 224
<211> LENGTH: 7764
<212> TYPE: DNA
<213> ORGANISM: Aedes albopictus

<400> SEQUENCE: 224
gcaattataa aaaaagaatt ggaagcagca tttgtaactt ctcatctcta aaacatggat 60
accagaacag aaaatatgta tgaacaactc caacggaagc catggaaaca aaacgtcctc 120
caccggattg gcctactgct tttgacaata gtgctggtgc ttgccgtgac gatcatattc 180
acgcttctca ttggagctgt gacacgagct ttaatcactc ctcaaactgt gcaggtggtt 240
taccacacgg aaactcacca tcatggggat ctcttggata ccgtgctgaa gcctatgaag 300
caactactat cgagcactct acatttgatg ggatttgaaa aggaacacaa atctcggcgg 360
aaacgagatt tggacgacga cgacgacaat cgtattcaga tggtggacga caatatgttg 420
gagaagagtg aacaatccga tgaggatttg agaacggtag atttcggaag cggaatcgat 480
ggagcgttgc agagattgac gcacaagaat ttgacactca agatagtgta cgcacctttt 540
ggcaatgagg gtaacaggaa cgagattatg cggtcgatgc ggaggagaag gaggcgaaag 600
cgaagtgccg agagtgagaa gcgaaaggcg catgaatacc aagagttaag gcgggagtat 660
agtaaacggt gcaagaagga agctcccaac gagaaggact gttcaagata ctgcgagaag 720
tttgaacagt ttctgaagga gaccaagcat agttataagg agatcaagca taaattaagt 780
gggctgctga aggattgcaa aggaaaacac ggcggagact tgaaagggga tctaagtgat 840
agtttcccga agaggaaaga gaacaagttg attgatctag actcggatga aagctcaggg 900

```
aaagtaatga agaaggataa accaattgat caagcaacag acagtacgac gttgaatgag    960
gatcaagtaa ctacagtgca tactgagttg gaactgacta ccgtgactgg gaattacagt   1020
gatgccagtg aacacgacaa aacaaatact caaaatcctg gcaaagatac gaaaaacgtg   1080
tcaacagtgc caccaatcga aaaaacttct tacaatccgt tgaacgcgga ttttcaggaa   1140
caaatagaac aatttgcaga aaatttggtg gatgatacaa cgtggaaagt tttgaacaca   1200
gcgtctacga aaacacctga aacattagca acaactaccg tcgttgttac ttccacagat   1260
caaaccagta aagatccaac cttagacgat cttattgaat cgttaaataa aaccgcatcc   1320
aatcgtacag tgccacagcc ttttgatgcc caaaggcaca acccagttga agatgactgt   1380
gtcaagaact tggacgacct gctgaagaag attcccgagt tcaaaacaga cgacgatgag   1440
gacttggact gcaacgagac cacaacgcaa tcgcccgatg aaactttagt cgggcagacg   1500
cacattagcc acttcaaaaa gcaaaatttg aagtacaatc cagatgaaca tcggcctaaa   1560
actgttgaat gtatcaaaaa catcgacgac cttctggagg cggttgacat ggagcatggg   1620
ggtttgaaga aacctaaaaa ttgtaaaatt tcgtcctcaa cggttgctcc cagtaaacac   1680
cgttcagatt cgtcagccag gaccgaagat gaagagttcg atccagttca aacccatgac   1740
gaacagttgg atcaatttgc atctgctgca gagctgcccg acttcatcaa acctccaact   1800
ccattccacg aggaacaatt cgatcaatcc actcttcccg tagaagttca cgacttcatc   1860
atgggcagat ctcgtaatcg ggagcaattc aaccatgaca taccctccac aatcgattct   1920
ccggatttca gagcctccaa atactcagcg cagccaacgg tagctgccag tggtccgttc   1980
ttgaatctct gcgaacagct acgaagtcag cagcatgccg ctccgataaa aactctctcc   2040
agcaatcaac accacttcca ggctcagcag tacggtggat tggggcagac cagcattccg   2100
gttacgggtg aaacgttgaa agcgacatct caggtcctgg tcaactccgc gtacggaggt   2160
ttcgctccga accatttctg cttctatcaa gttccgccaa cttacggcgc catgcggccg   2220
gtctatgctg gaggccagaa ctacccggca ggctcactaa agatctttcg tggtgtcttt   2280
tcaggtttgt tgaatgttcc actcagcatt cagaagtcat ctggacgaag caccggtgac   2340
gatccggatc ttgaaggtgc caagctgctg tgtagtctgg ttgtgccacc ttccacggaa   2400
tcaccgttag cgggcaatga ctctttgata tcgcaggaag tcttagtggg gggtgcgaga   2460
gcacgtggtc accatcggca ctgtcctcgg ggcaaggttc cttgcgcaga tggaatccag   2520
tgcgttctga gctcacacct gtgtgactcc agggtggatt gtttcgacgg aagtgacgaa   2580
tcgcactgct cgtgcttgtc acggttgtcg caaaaaacgac gttgcgatgg ttatgtagac  2640
tgtcctctag gggaggatga gatgggttgt ttcggctgcg acaagttctc gttttcgtgc   2700
ttcaattcgt tcttcgaaca ccaggcttct catcactccg agacgaggtg ttataccttg   2760
attgagaagt gcgatgggtt caacaactgt gtgaatggga aggacgaaca ggattgtacg   2820
atgttggtgc gagacctgag gagtcccttg gcgttcacgg ttgggcattc ggtaggagtt   2880
cttcatcgga accacaaggg caagtggtat ccggtttgtc ataacccgtt gtcgttggcg   2940
agagaagctt gcgaagcgga acttggacca tcggagaggg atccggtgat tgtgcagcac   3000
catggagatc taccaggacc gttcattcaa ccgagtcccc gaagtcatca cgtattccaa   3060
ccggagttca cggatacctg taatgggttg atcaactacg tcaagtgtcc agctccaaag   3120
tgtggctctt caaagcagaa tgagatggaa cacgcccgta tcaagattcg tgggaagagg   3180
aatactacgg agattgtaca gatcgttggc ggaacgaaag ctgaagcgtc cgcttatccg   3240
```

```
tttatcgttg gtatattcag agatggcaag ttccattgcg gcggaagcat cttcaatgaa   3300
cattggatcg taacggcagc tcactgctgt gataactttc cgagacacca ctacgagctg   3360
agggcgggtc ttctccgtcg gcgcagcttc gcaccgcagg ttcaggtatc cacagtaact   3420
cacgtgatca ttcaccgtgg atacagtgcg cagaagatga tcaacgacat cagcttgatg   3480
cattcggaca ggccgttcca gtacaatcga tgggtaaggc caatctgtct accgaatcgg   3540
cacatgacga ccaacgatcg ggactggatt tggggaccga agccgggaac catgtgtact   3600
gccataggct ggggagcact ccgagagcat ggaggatcac cggatcatct aatgcaagtc   3660
acagtgccga tcctgccgtt ctgcaaacac aggaacgatc gcgatggtct cgctatttgc   3720
gctgccgaac cgagtggggg tcacgacgcc tgccagggag actcgggagg tccgttcgcc   3780
tgcattagtg tcaccagtcc acatgagtgg tacctggcag gcgtggtaag tcacggagaa   3840
ggttgcgccc gacctaacga acctggggtg tatactagag tggcactgtt caacgactgg   3900
atccacagaa agaccagtga ggtgcttcca ccagcctcta cgcggatgga ttgtcccggc   3960
ttccagtgct cggttggagt ttcgttctgt attccaaggc agaaacgctg caacggaaag   4020
gttgattgtc ttggtggaga agatgaattg cattgttcgc tggatcaact gctggccgaa   4080
acgatcaagg aaacttctac cgtgacggtg gcagctaaca gcactgtagc cagttcaaca   4140
acggaggctg ctacgacagc tgtaacttca aagatcgatt ttgtcgagga gacagccgaa   4200
acttcagaga agtctactac tgttacaact gcttccaacg atgagacaag tacgatagca   4260
actaccatcg aaacaacatc ggtttctacg gaaccaaagc ctgcgaaaga ccttgatatg   4320
atgagtgaca gcactgcgca caatattact gaagtaacta ctgttgaacc tacaactacc   4380
caggatgagg atacgtctac ttcttcaaca acatctgagt attcaacaac tgaaacaagc   4440
tttacaaatc aaacaaagtt tgaatccagt actacatacg aggtgacgac acgtcaagta   4500
cttgaagaca tttcagcatc cccggtattt aacgaaacaa cttccacttt ggaatacaat   4560
gcagcaatgc ccaccgatcc ctcaacaatc cccactagta ctttaccagc taccattgat   4620
tccatagata gctattcttc aacagcaaat cattcatcgg tagattttag tataacgacg   4680
gaacccacaa ccgaaaccag tctccataca accgaatcag tgaccgaatt gtcaacaagc   4740
actgctgaaa cttcatcaat agaaactagc actgtgttgg acacaacgac cattatggaa   4800
acaaccactc cattgtattc atcgaaaatt tatgaaacga catcaatgac gcatgaaacc   4860
gaatctagtg atacaacaca gtcctccgag ttggccacaa cagagtccac aacatctacg   4920
actaccccag atgaaacaac ccctttggta actactgagt cagaacattc gtcaactaca   4980
acatctcctt tctggatgca ggtcaacgaa gccatctcca agttgaaacc acattttcca   5040
agtatgcatc gcgagatgga ggaccgcaac cagcaacagt acgacagtat cagagcaact   5100
ctgtcggata acgctacgtc aacaacaacg cccataccta aaacctccta tgatacttct   5160
acaactgaac ttgccacttc tacaaccgat tctaccagtt ctacatctat ttcgccatct   5220
accgtggaga gttctagcac tgttccccac gatcaggaat tcagtgaaac ccaaatagaa   5280
cccgtgaaag ctgaaactac gaacgcgaca gctgaacagc atcccttttt ccgagaaatt   5340
cacgacctag tcgaagagaa aacccgccgg ctgaaccagt tccgattgtc catgcactac   5400
ctgcacactt cgttgaagaa ccaaacgctg gacacgaacg aaacctccta ccggtacaag   5460
cggttcgtct gttccaaaat tccccaaacg atcaacattg cgcatcactg cgatcgcatc   5520
atcgactgcg aagacggtac ggacgagttg cggtgcacgt gtcgcgacta tctcaaggac   5580
aagtacgact tcctgatctg cgatgggaaa accgattgct tggatttgac cgatgaggac   5640
```

gactgctttt cttgcgccac cggtcagtac ccttgccgaa tgagcaaagt ctgcatcgac 5700
gagaagaaac tgtgcgataa cgttccggat tgtccgttgc atgaagatga gctcgattgc 5760
cttgccctta ccgatggtca caaggtctac tttgatgcga acaacctcac agagttcaag 5820
tacgaaggct tggtcaccaa gaatacgaac ggaacgtggg atctaatctg tggagcggaa 5880
gttaacaaca agtcagttga ttcgatcggg aaaatatgct cttttctggg atttgcaggt 5940
tacaagagct actaccaaac catcctgacg ccgctggtca acgaaacggt tgatttggaa 6000
caccaacctc tgttgatcat gtcgtatcgg aacgtttcat ccgagccgaa ctgcaaggcc 6060
cttcacataa cctgcgtacc attcatcaat gccaccgaac acgaaatcag tcactacgag 6120
aaccaacaca aggaacaacc agtgcaagta aacattcgtc caacgaatcc aatcaagaac 6180
atttcctccc aagcatacat aaccttcaac gaaaatgctc acatcgagtt cattgagaac 6240
ttcggcgatg actacgattg gccgtggaat gcggacatct atctggaagg cgtcttcctg 6300
tgcagtgcga tcattatcga cgtcaactgg atcgtagtgg acagttcctg tatgcgaatg 6360
atcaacttga agaatgatta cctctcggtg gtggccggag gagccaagtc atacctgaag 6420
atttcgggac cgtacgatca ggttgtccga gtggattgct atcacttttt accggagccg 6480
agagttgtaa tgcttcactt ggcgaaaaat ttgaccttca ctcgacatgt cttgccgacc 6540
ttcataccgg aacagaacca taacatcgag gacaatcagt gcctggccgt tgggcaggac 6600
aaatacggcc ggacccgaac gttgcgagtc cacatgaaca tgacgaattg cgaaccattc 6660
catgtttgct accagctcaa tcctgacagg ggcatatacc atgctgatca ctgctattca 6720
gaaaatgcat cacggaccgg agtcgtcgtt tgtaagtcta aaatctccgg ttggtaccca 6780
gtgggtttct atcagaacaa gcatggtctc tgtgggttca acgaggtcgt caaaatgata 6840
tccctcaagg agtactacac cgatattcag cacgttctga accacgagaa atgcaacgaa 6900
tttccggagc cactttgcga tggtctgcgc tgttggctgg gcaaatgtat cggacattcg 6960
ttggtctgtg ataacaagat ggactgcgac gataactccg atgagcgccc cgaagcgtgc 7020
aatgcaataa acgacacgtc cactgcctgt ctaccgacgc agttccggtg cggaaatcat 7080
cagtgcgtgg acaagagcaa gttctgcgat gggcggaacg attgcggtga cttgtcggat 7140
gaacctcacg agtgctcttg ctacacgtat ctcaaagtta ccaatccatc caagatttgc 7200
gacggcgttc gcaactgttg ggataagtct gacgagaatc cgcgtctctg caagtgcgag 7260
caaaccagct tcgtgtgtgg tgacagcgat atttgcatcc catacgatca cgtctgcgat 7320
ggcgagatcg actgtcccgg agaggaagat gaacactatt gctatgccct gcagcaaaat 7380
ccagcggaga ccaactacgg tgaagttatg cagcaaagcc acggcatttg gcactccatg 7440
tgcttcccca aggacggcca gtatgacgag caaaagatca aggaaatatg ccacagcatc 7500
ggttatcgaa agattcgaaa agtcttcggc aggaaaatga ttcaagagtc ccgactgcgg 7560
acttccaacc gtacgcacaa tccggtcgat aggatgcgcg gggcagcaac caaagcggtt 7620
gtactgaaca aattttccaa agtgaggatc aatgggaagc agacgttctt catgaaaccc 7680
agtaggccgt tgtataccct ggttcactgg gatgccgaag atgagacgcg gtgcgatcga 7740
ctggagatca attgtggaga ttaa 7764

<210> SEQ ID NO 225
<211> LENGTH: 1694
<212> TYPE: DNA
<213> ORGANISM: Aedes albopictus

<400> SEQUENCE: 225
tgacccaagc aattgtggaa cgtggtgaca caattaaaac atcacacctg ctgcacgcgt 60
atcgccaccc gtagcgttca gttcgcgaaa gacggtgtcg gtggttactt caatcgcgtt 120
acgtgtgtgt tctttactgg aagtcgcggt cgtttcgtcc gaataacgaa atgaggaaac 180
aactgttgtg gatactttcg gtgttaatcg ttgctgccgg agacatagga aatcgagtcg 240
atgatggaaa tgttaccaat tttgattcgt ttttgggtac atatcagaag aagtacaaag 300
ccaaataccg aatggatcga aggaaaagag cgttcaagaa gaatatggag gaaatcgaag 360
agcacaatgc caatttccag cagggcaaaa gtacgttcca gatgggggtc aacgaactgg 420
cggatatgga caaaagcagc tacctgaaga aaatggttcg gatgacggac tctattgacc 480
atcgcaaact ggacgtagac ttcaacgatg aaatgctaca gcatacgcac tcctttgggg 540
aagaaatcgt tcagtccacc cagaacagca tgccggacag tttggattgg cgcgacaagg 600
gatttacgac aattgccgtc aaccagaaga cgtgtggttc ctgttatgcg ttcagtgttg 660
ggcatgccat caatggacag ataatgcgtc gtatcggacg gatagagtac gtcagtacgc 720
aacagatggt ggattgctcg acgagtgccg gaaataaggg atgtgctgga ggttccttga 780
ggtataccat gcagtatctg cagggcagcg ggggcgtcat gagggattcg gattatccat 840
acacgtcggc ggtaagtatg aatgagaagg gggtggatgg attttctctt tacagcttga 900
atgagccagt gcagtaagca gtcgaacaac ttcgaagaac aggtaatctc ttctgtgaac 960
acgttaatcg ccaaaaacaa gttctcaaac acgctaataa atttcaactt agaaaaggaa 1020
ttggttttac cctgcaaaaa ccagtgatat tcgaacattt tttaaagatt atgttatgtt 1080
cgattcaaaa gtttgtttct aatttttagt aaagccaaag tagaaattca ttaccgtcaa 1140
tatcaaacag cattacagga ccaagttgat cggaaagcat gtaacagtaa caattggcaa 1200
catgcaaagt gccgacaaag ttggtgacta gttttcgtgt agttcacacc tacggagcaa 1260
ttctcagtaa acggcggcgg ccttcctgcc ctatcgccaa tttgccattc gaacttcaag 1320
aatggggggc aatcgtgtcg tcgtcgtcag cgagtggtgt ttccccaaaa gggcaacttt 1380
gtcgtgcggc gagtcatttc ggtttcgttg aagagcgctg aataatggtg gaaaatttgt 1440
ttcgtttttt ttttcttcgg gcgcactttc ttggaggtag caaggaggaa caaggcgctt 1500
ttcgtgttaa agagttgtta aagcacctac cctttgttgg actcataatg gccggatgga 1560
agcaacatgg ttagtaggaa ttgattgctg ttggaatgaa ctgaaacaac gcggtgattt 1620
gatgtatctt ttctttttac aggcaagcga cgggtgttaa tgtgagcaaa taaagttaat 1680
ttgaccttcg tgta 1694

<210> SEQ ID NO 226
<211> LENGTH: 2043
<212> TYPE: DNA
<213> ORGANISM: Aedes albopictus

<400> SEQUENCE: 226
gttgtcgcgg tcgtcgtact cggtctcgtt gatataaccg gcgtgggttg atcctccggt 60
cgtcagtcgc ggtagttggt acctcggatc aggacggttc accgaaaaac gaaccgggcg 120
cgcggtcgag attgtgtgtt gtattcccgt tttttgtgca aatagaggaa gagttttttt 180
tatcccgaca gaaggaagaa tagcaatgtg gaagtcggtg gtctgcgtgg cgttgatcgg 240
tgccttcggg gccgtcagcg gaacgtccaa gctgcaggaa cgctacagct ggcgccagtt 300
ggactttgtg ttcccgaacc agcagctcaa acagcaggcc ctggccagtg gggactacgt 360
gccgaccaac ggactcccgg tcggaatcga acggtgggag aacaagctct ttgtgtcggt 420
gccaagatgg aaggatggta tcccatctac cctgaactac atcgacatga atcagacgcc 480
gtcgggatcg cccccgctga tcccgtatcc aagctgggcc aacaacgtgg ccggagactg 540
tcagaacggt ctgtcgaccg tgtaccgtat caaggctgac aagtgcggac gcctctgggt 600
tctggacacc ggtaccgttg gaatcggaaa caccacccag cagctgtgcc cgtacgcgct 660
gaacatcttt gacctcaaga ccaacacccg tctgcgacga tacgaactgc gcgctgaaga 720
caccaaccag aacaccttca tcgccaacat tgccatcgac atgggacgca gctgcgacga 780
cacctttgcc tacatgtccg acgaactggg ctacggattg attgcctact cgtttgagaa 840
gaacaagtcc tggcggttcg agcacagctt cttcttcccg gatcctctgc gtggagactt 900
caacgtcgcc ggtctgaact tccaatgggg tgaggaaggt atcttcggaa tgtcgctgtc 960
cccaatgcaa gccgacggtt tccgtaccat gtacttctcg ccactggcta gccaccgtga 1020
attcatggtc tccactcagg tcctccgcga tgaagaaggc gctgaagaga gcttccacaa 1080
gttcacctat ctgaaggaac gaggacccaa cagccacact acatcccgag tgatgagcga 1140
gaccggactg caactgttca acctgatcga ccagaacgcc gtcggatgct ggcattcgtc 1200
gctgccttac agccccgaga accacggaat cgttgaccgc gacgatgtcg aactggtctt 1260
ccctgctgac gtcaagatcg atttcgaaga aaacgtctgg gtcatctccg accgtatgcc 1320
tgtgttcctc atcgccgagc tggactacag cgatgttaac ttccgcatct tcaccgctcc 1380
tctgagcacc ctggtctctg gaaccgtctg cgacgtcgct ccatcgctcc gaccaggtgc 1440
catccaatcc aaattcggtg gatccgattt gacgacctac ccaggaacca ccctgctccc 1500
agccggctac agccagccca tcagctacac ccccaacctcc tacgccccga ccgttgcccc 1560
agtgaccaag tacacatccg ccccggcagc gtacgatcac cccacatccc acatgtacac 1620
aacccaggaa tatccgacga ccgcgaaggc atatcacttc aacaagtacc acaacgtgga 1680
gtaccaatcg cacggaaacg gccaagccga ctaccacttc ggccacggag gacactacca 1740
cggtggtcat gaccatggcg gtcatgacta cggccacgat cacggatact acggcggcgg 1800
agagcaccgc cggtactggg gagctggccc caagaagccc gaagcctgga agcagcagct 1860
gtactagtag aacccaccac ccccgatact gcggactagc cgcacagttt tcgttttaga 1920
gaaatttagg taaattattt gtcagtgtaa aagtgcagta ctctcgtcaa gtgtcttaag 1980
tttaagtatc taagatcgaa cgaaccaact caagtcgaat aaagtaagat gtttgttacg 2040
aaa 2043

<210> SEQ ID NO 227
<211> LENGTH: 1329
<212> TYPE: DNA
<213> ORGANISM: Aedes albopictus

<400> SEQUENCE: 227
gcatacagtg taaattagag ggtgtgttcg ttacgatttg atttcgaacc acccaaaaag 60
atgcgagata acatactttg gctgttggct gcactcgtgg ccctactgac ggtgaccacc 120
gttacggcgt tcgcgaataa ttcaaatgcg atctacacct gggagggcgg tcgcatcgag 180
tggccatgtc caacgacaaa acgattggtt aaggctgctg cgaagtacac tccgaaggat 240
atcatcgcaa tggcttgcgc gagaagtggc gataagaccc tttgcgcaat gcctcgatac 300
cggaatagca ttccgataac cctggggcaa atttacgcta cgaagagggg ttgtgatgtg 360

```
aagtttgaac cattcccgtg ttggaccgaa caggaagaga acaactgcaa ttcgctgcag    420

tcggttattg atatctacgc caccggtgac ttcgtatggg tcctggatag tggaatactc    480

aacgcattga ggagtcccat tcaaagatgc ccagccaaga tcgtagtcta tgaatccaaa    540

acaaacaaaa agatgaaaac gatcaacctg gccaggtacg ttactgaaaa gtctcgtctt    600

cagtacatgc aggtcgaatg cctgaagggt ggccaatgct tcgtgtacat cagcgatgct    660

ggaaacaatg ccattatcgt ttatgatgta tccggaggtc gcggttatcg ggtagttctg    720

ccgaaagccg ttcatcatgg ttgtcgcttc cgagatgttt tgtacatttt cttgtcatat    780

cacaaggaag gtacgaagct ctatttcacc tatctcggcg gacgaagact attcgctatc    840

cgcactgatc acctacggaa aggacatggt ggtaatattg aagatattgg agaaaagccc    900

ggttcctaca tttacatagg atcggacgga gccacggggg tatttttccg ggaggaaggt    960

gacagcaatg ttttcttctg ggacacgaag cagtgtctga agaaatccaa cttcaaactg   1020

gtgttcaaga gtagcgaggg attgtacgca acggatgtgt tcccagacca cgagatcaac   1080

cgcttcctca tactggaatc ggatttcccc ggttacatgg aggaaaaggc tggatgtggt   1140

acgctgcatc aaatctcgct gctggatgga actgcttgtt gaacatattg tgctttggag   1200

tataactcat taactacaat gcagttgtta aaagagcagc actcacgttg tgatggtgtt   1260

taggataagt agtacataga tcccaagtaa gatacaataa atcgaaaaaa aaaaaaaaaa   1320

aaaaaaaaa                                                           1329
```

```
<210> SEQ ID NO 228
<211> LENGTH: 1338
<212> TYPE: DNA
<213> ORGANISM: Aedes albopictus

<400> SEQUENCE: 228

ccagtcgttc tacatccgcc ggtgaaattt ttagtcgcgg ttcgcgtggt ggtggaggct     60

atcgttaagt gatcaagtga tcgtggttga ttccccgcgg tacaatgtgg tttcggatat    120

tgtccggaag cctgttggct gtgctgtgcc tagccgatgt caaaccctgt gaatacatgg    180

acagaatcta tcgaatcaac ggaaactcga tcgactttcc gtgtgaatcg acgaagaaca    240

tttttgtgtc taccgaacgg tacaaaccgt gcagtatcat accgatgcgg tttcaaatcg    300

acggagacaa cgaaaggtgt tttgtggtga tgacccgact gcgtaccggc aatccagtga    360

cgctgggagt gatcgatctg acgcgtccga gctgctatgc gcatatcaaa ccttatccgt    420

gctggtcgta ccaagaggag ggcaattgca atgccttcca gtcggtggtg gatatattcg    480

tggatgtgaa gaaaaagatg tgggtcctgg actcaggtat ttgcaactct ttggaacaac    540

cgatcaagcg atgcacggca aaggtggtgg catttgacct ggaaaccgac aaaaccgtca    600

aaaccgttga tttgagtgac attctgaagc caaactccag gccacagtac ctcgtgacgg    660

actattcgcc caacggattc ccgtacgttt atatcagcga cgcagaggga gctatcatcg    720

tactggacat ccatcataat aagatgtacc gagtagtgct accacgtgcc atatccgccg    780

gatgcggcga atcggatgtc ctatatctgc tgctcgttcg tagacccaag aatcacaatt    840

tggtcatatt ctcgtatctg tgtggaaaca aggtgtacgg aatcaaatcg gaatacctgc    900

gcacgggacg gggttccagt gccattgtgg aacttggcag taagactagg cattccgttc    960

tgcttggcac agacggaagc aacagtgtca tcctgcgata tcgaagcgaa agcgaactct   1020

acaagtggaa caccgatcaa ccatataagg agtgcaactt tgagctggtg caacttgcag   1080

aggagtgtcg attgagcacg catgttgcac ccggaggaaa agacgatctg atgtactcat   1140
```

tgtcatcgaa tgtggccgat tatctgaatc acacttgcgg cgcaggaggt gcttctgctc 1200
gactgaaata tattagtaaa gattgtgaag atgattgtta ctaagttagt atgtaatatg 1260
tgattaagaa ttgtaatata agaaaacacc cagatcaaca gtcttacaag tttagttcaa 1320
aaatatattt taacattt 1338

<210> SEQ ID NO 229
<211> LENGTH: 2484
<212> TYPE: DNA
<213> ORGANISM: Anopheles gambiae

<400> SEQUENCE: 229
gacggtgggc aatcgttcgg ccaggacagt ggctacacat cctaccaggc caccacgccg 60
aacaacacgt ttaacctgtc ctcgcgccac ggcatctcgt ccgtaacgct ggccacgatc 120
gacgaggccg gcgagcacga ctgcagcatg aacgatacgg gcggcggcgg cagtccgacg 180
ggtgcgatca acctcacgcc caagacggcc gccagcatgg tgctgctgtc gaacattcat 240
ataaacacgc cgaaaagcac ggaccgagcg aagcgcatcc ggcgaccgat cgcgttcgat 300
tacgacgggt ccggcggcag ctgctcgtcc tcctttcttg caccgtccac cccggaacgg 360
ctgcccgggc tgtctcgctc cgtttcgttc gagctgccgg aaacgccgct ccgcaccggg 420
aaccgctccg ccagccagcc gagcagccag ctcacgccgc acaaagcgcg gggcggctcg 480
ctcaagcgca aacactccac cttccgcgag aagctctact ccgatgcgga cggcgtggcg 540
ctgccggcgg acgagaacga tccgcgcgat ctgaacgact cgctcgatgc ggactgccgc 600
cggctggagg acatctcgcc catcctcaac gtgaagcgcc gcaagcacca ggaccgcggc 660
atcgaggatc tgatgcgctc cagcacgccg aaaacggcca gctcgcagcc aacgtttctg 720
caggtggggg cggctgcagg gcgcaacccg cccctcggcg cgaagcgaac gttccgcaag 780
tttcaaagct tcagcccgag caaaatgcag ccgaacgcaa cgcggccact gctgcggcaa 840
aatgcgatcc gcgcgctcga acacacgccg gaaaagcgga aggagcagcg cgtgctcgct 900
gaaatccatc cccagccggc ggtggcggac gccgtgctgc caccgctcga tctggccgcc 960
ctgctcgacg caccgatact gggcgagccg tcgcggcaac tggagcaaac cgtcaccacc 1020
gtaccctcgt tggatgactt cagcctgacg ccgtccaagg cgaacctgat cgacctggaa 1080
ctgatggcac cggccgccga tggtccgttc gcgaccgacg actacctggt gcggcacgcg 1140
tccaactttt cctacgcacc gaccctcaac tccatcctgg aggaatcgcc gatcaaggcg 1200
gcggcggcct tcctgcccgg caagctgccg ctaccgaaaa cgccaccctc ggtgaccaag 1260
tccggccgca agcttaaacg gctcggtacg aacagcggat cggccgcacg tgcttcagtt 1320
tcgccgaagg cgacgcgccg cctgcacggt gcccaaccgc acaactgtcg cctgaaaacg 1380
gcccaaccgt acagcttctg tggctgcgag tacattaaca tactgcacca gctgagcatg 1440
cgcaatccgg acgcgctcga gacgctgctc gactacctgg ccgatacgga cctggtgcag 1500
gtggtgcgcg tgtcccgcgg ctggaaagcg atcatccaga accacaagaa gagctggagg 1560
cggctgcagc gcttcctcaa gcagcaggag gagcacaagg aaaactgcca tggcagtcgg 1620
tgggaaaatg ggtcgttcgc gtcgagcctg aacgccggca gttcccagct gggcaccgca 1680
ctgcccgagc tgctgagcgg aacttttggc aaggatagca atgcaggagg cgggctggga 1740
acgcggctac cgtttaaggt gtgcaacacg ctcgataaca gtcaggcgag cgcgggcaac 1800
gcatcgtttg cgcatggttc gtttgcgaac tcgccaccgg ttagcccctc gatgcgcaag 1860
tttgtcacta accagaagat tgcatcccat ctgaaacaat cggaacagct gcgaccctgt 1920
ccacggtgcg agcagccgag ccgtatcatc ctctcgcggg cctccaagtc cagcaaatct 1980
cgctcctccg cccggtgcag tgcggtcgga gcacggctag agaagtccta cacgttacct 2040
gatccggaga cagtcactgc ttcggggcac cgtcacagcg gcagtaacaa tactcattcc 2100
tccaccatcg aaacggtacg atcgtcgaac ctttccaccg ataccatcac caccacacac 2160
cgtaacaaca accattatgg tgaaccatcg ccggaacggg tacgcaagaa cctcctggac 2220
tgctcgtcca ctgccgcgat gcatccggct ggcggggagg atacgctcgg tgtgcgtgac 2280
tccaagtgcg actatgccat ctgtagcggc gcgttctgtg ggttccggtt ctgcatcaag 2340
tgtctgtgcg agtatcatcc ggacacggtg tgcgctgatt tggccgcgaa ctcgcccacc 2400
aaagaggagg agcgcggacg gccgaatatg gcctgcagcc ggcagagtcg ccgctcgctg 2460
cagcgtctct gccggaagct gtag 2484

<210> SEQ ID NO 230
<211> LENGTH: 6341
<212> TYPE: DNA
<213> ORGANISM: Anopheles gambiae

<400> SEQUENCE: 230
atgcctaaca tgcagtgtag ctcgtatcta gtgctttcct ttgtgctctc tattgagctg 60
gtgcttgtag tgcatagtga tggggaaaaa aatccgctcg atccacaggg gcaaatgcga 120
gggccggcca cctttccgaa acaggaacct cacaacacaa cgcacgattc cgcgacggaa 180
tcagctaccc cttccgcgta cgaactaaag cgccaacagt tgctagaaca tccggacggg 240
ttcgacgagg cggagctgaa accgctgcgc gaaacacaca tcaacgtgct gcacgaagcg 300
atcgatgcga agctgatcga tccaagcttc atccgtacgt tgggcgccgt atcggaaccg 360
ccgaaggtgc acgatgccac ccgggatacg ctttcgatac ggtccatcga ggaggacgtt 420
aactttacgc tcggcgagcg ggtagtgcgc tggaagacga tgagtgcgat caacgtcgat 480
cggcacgtgg tcgtggggct aacggcggcc agtgcggtgg tgctgctgga gcgcgacggc 540
cagtacgtcc tgagccagga gctgctgctc gagtcggccc cgattgcctt cgaggtgtta 600
agcttctggg acacggagca tgcgtcagcg gtcgggtgtg tggtcatatc gatgggcaac 660
tttctcgtct ggtacacgct gcgcgaacag tcggagtaca agctggagga ggaatggcgc 720
tggccgctgc acaaaacaat tacgcaaatt aaattctttc gccagaagga ggttgatgcg 780
ctgctgctga taggtcggca tccgaatcgg cacgagtcgg tgtcggccac cgtgtacgag 840
ttttccttca acgatcgaca gttttggttg atgcagaagc tcggcctaaa gcatccctgc 900
ccatcggtag ggctagtggc cgccggggaa gagtatttag ttgcgtttcc gcagaatacg 960
accgtagagc tgtacacgtt ccgtgtcggc gatcagaacc gtaggaagtt taaagccgta 1020
ggtaactaca gctcggaagc gctccgctcg gtgtacgcct ttcaaatagg acgctacgcg 1080
tacgttgcta tcagcggcaa aacgccggcc gttttgcgct acaagcgggg taagttttac 1140
gagcagaaga tccccaccga ggcgctggag atagtggaag cgttctttga gataccggcc 1200
cgaacgtacc gggacgatat ggtgctgctg gtgcagcatc gtatgatttt tgccacgcac 1260
gaaatacagc gcctggaagc gctcgtgtgg aacggtgtgt cgttcgacct ggccaccaac 1320
ataccgtgca tggtagggaa cgaggtgatc gacaacgagg ccagctgcat gctggatctc 1380
gaccgcacgg acgggttgtt cggtgcgacg atagcgcagc gcggcaaatc catatcgatc 1440
attgtgccgc gccacgaggc acactccagt ctgtaccgca tgtcgatcga gctgctgtcc 1500
ggggagcatc cgattttgat gaaaattcaa gaaatccagg aaacgatgga cgcgttcacg 1560
aagataatcg actaccagaa tgcggtaatt gagcaggcgc agtcgtacgt tgagctgatg 1620
gaaagcgatc cggtagtgtt gaagcgccag aaccttagct cggtcaatac gccgctggtg 1680
cgctttgcgg aggatttcga tctggccggg gtgaaaatga cgatcggaca aaacagctgg 1740
cgcgaggcag acttgcaggc cgatctgacc gccactgtta aaacggtgca ggacgtcgag 1800
ctgagtgtgg atgcaatgct gtccgagttg cagtacagcg tgcgacggga tgcccgctcg 1860
cacgatcttc aaatcaacgg tacggtacag gtgacgggac ggctgtatat cgacggggcg 1920
ctgcacgcgg acgatatgta catacagcgc tttgaacagc cacgcatgga ccatctcgta 1980
cggttcggtc gcgatgtgca cggccaggag gtaccgacga tgcaagagct acacctgaag 2040
gagttgaacg tggagcagct tcagttcgat cgtttcaatg gcataccggc ggaagagcta 2100
ctgtacgacg tagacggcaa ggtggtgctc gatggggagc tggtcctcgg cggtgatctc 2160
tacacaaaca ccgtgctgct ccccgagggg ggcacagtga atgggatcga tctaagcgag 2220
gcgttgattt acttcaactg caaaaataga cgctggcgga acctgacgct cgattcgctg 2280
gaagtcatcg acgatgtgca ggtggcgaac aaagtcaacg gggcccgcat caatctgcag 2340
gaagcggaaa gctcgctgcg caatgcaatc gatgagcatg ggcgtgtgct gcggtcaaag 2400
tctttgcaca tcgagggtga tctaagcttc gagcgcatca acggtgtccc ttggaaaacg 2460
ttttacgatg ggctcgtttt taaggatcaa ccgatgcggc ttggaattct taatgtggaa 2520
gggaatgtga cgtttgctag ccaaacaacg gtacagttct tgaacagatt acgcttcccg 2580
gaggattatg tgctacgatc aggaccgcgt gaatcgatca ttactggcca gaagtatttc 2640
aaggactcgt taacaatgga tgcactcgac attgacgggt ttgtgaacgg tatcaatccg 2700
ttcgatttca tcacactaca cgacgatcag tatatcccgg gcaatgtgac attcgactca 2760
ctcgagatag aagaatcact cgatgttcgc ggtgccgtcc atggcaagca tatggataaa 2820
tttctcgaca atccatccct tctccaaaca aagctcctcg aagcggcctg cgagtttaac 2880
gaggtagtcg ttaacggacc aatctacgtc gatcagctcg atggttacga tctggaccac 2940
ttcctgcgga gcgttgtgta cgtagacgaa ccgtacgtgg aaattaacgc atcgaaacac 3000
tatcgcagtc tacactttta cgaaccgatc cggatcgagt cgaacatgat cggcgagata 3060
catctggacg agctgctgac caagagcacg gatcagacga tcaacgtgag catggtgctg 3120
ggcaacgtgt ttttcaaccg cgtacaggtg cacggcctgt tcggtggcat taacgtgacg 3180
gagtgggata cgaattcgat caaaaatattc ggcgaccagc acacgcaggc gacgctagag 3240
ttctgccctc agtattcctt gctgtacgca aagaaccttg agatagtggg aaccctcaat 3300
ggtcaaccgc gggccgcgtt ctacgacatg gaggaggaaa tcgtcttccg cgatcaatcc 3360
atctacatga gcgaactgta cgcgagctac ctatcgcttg cgggcagcga gatcgatggt 3420
ccaacgaaca tgttgaacga cgtccatctg cccacgtttg atgcgtaccg gttcagctta 3480
agccaaccgc aaacgataca gcacgatgtg ctcgtcgacg cactgtacgt tagtaacgcg 3540
tttgctgcac gttaccttaa cggcttggat gtagtacggc tccaggagaa tgtggagacg 3600
tacctgaacg atgattacat gctcagcggt aggcatgtgc tcgatacgct gcatatcgat 3660
ggaagcgtcg agatcggtac cctgaatgga gttgatttga cgcagtttct gaacaacgtc 3720
atatggttgg accgaccgaa tgctgtccag agtgcattgc actttttgca tcccttgcac 3780
gtagacggag atgtgtcggt cgatggagcc ttgaatgaga taccttttgt cagcttcttg 3840

```
agaaacgtgg tttacagaac ggatggggcg gcggtggagt tcaccggatc aaagctgttc   3900
acacaagggt tcgatgtggt gggcgatctg cacacaccaa ccatcaacaa tgtgccggta   3960
aaggatctgg tgctcaaaaa tgaatcgatc acttttcccg gccgcgtgct aacgacgggc   4020
agagtgtacg tgaaagagat gattgtcagt ggcaccatca acgggaagtc gttcaaacca   4080
atcgaagcgt actacgcgta cgataacgct accgacacgc acatcatcaa gggtgatctg   4140
cgtctgcaag gacagcagac cattcacagc ctagaggcgt acggtggctg gaatgagctg   4200
atgaatgtga cgcacaagct tgcatcgctc atccgcacga accaggacta ctacttcaag   4260
gggcattacg tcctacagga ggaggttcat ttcaagcatg gttttacggt tgatttcgta   4320
aacgggtaca atgtgtcgaa cgtgcagaac gagatcgtat actacgatca gcaggaactg   4380
atcgttttta gcgaaccagt agaattctat ggaaatgtgt ggggaggacc attgcatatt   4440
gcgggtgata tgattgggaa aaatttgatg ggcatcgatc cggacacgct gttgcagcaa   4500
acattgctga taaacaagga ttatgagatt gtggataaga tagtgttcct tccgggagcc   4560
ttcaaatgtg accatctagt ggctgcttct atcaatggcc taccgacgag cggactaatt   4620
accctgcaca cggaacaaac gatcgaccag ccagtttatg tgaagcaaat cgtcattcac   4680
catcctctac aagtggaagg tcttgtaaat gggcgagatc ttcgcgtgga acgagcaaat   4740
accgtcatgc gttacggcga acaaacgatc gacgcaccgt cagtgttcaa ctccatacgc   4800
gtgctgaaca gtgccacgct gcccaagatt ctgaacggtg tgccgtttgg cgaaccggta   4860
cagctgaccg acgacatgac catctcgtca ccgttaacgt tctacaaaat tgccgccaac   4920
gatgtgtaca ctaacgacac gatcgggggg atcgatttcg atcactggta cgagcgcgcc   4980
ctctggaccg atgggcgtga gcatcaagcg tactggggta ggctacgctc tcgtaaattc   5040
gtcttccgtg acagcatcca cggcaatggt acgatcaacg ggttgcccat taacgagatc   5100
gtacgcaagc tccactccga gaaacagttc gtcgagggtg agctggctaa acgtcgcgcc   5160
aactatcgcg cctcttgtcg cgaaacgcaa gccctcatca atggtacgca gaagggtgtg   5220
tacttcttta actacttcgt gcagcggcaa actattcgcg tgcagcaacc catccagtcg   5280
ttctggacgt tccagcacca gggcaaccat ttccttgcgc tcaactacgg ctgcggtagt   5340
aagttcttcc agtggaaccc acaggaccga gtgttcgtgg gactgttcaa ggcgcacacg   5400
ggatacgttt ttgagtggca aactgtggct gcgcaggatg agaagcttta tctagtaacg   5460
cgatcggcac cgacggatga gcagtgcaat gtgacggggc tggcgatatg ggagttccag   5520
ggactttcgc tggagctggt gaaggccatg ccggataagg ataccgatag cttgtttgta   5580
gatccttcca ccagtggacg gttctacgtc ttggagcgca cgaccgtgct cgagtatgat   5640
gtgactggta aggtgcagga agaatgggac ctgtcacgca tctttgaagc agcaagcttt   5700
gtaccgagct cacttggtgt tggactggct ttggccgatg ggaaacgaat tgcggttctg   5760
tctagagccg aaggcaccat caaaccctca cgctccaagc gctcacacga tgatccactc   5820
gtaaatctgg ccctgttcgc ctccccccata acggtgtaca atcaaatgca aaggaacagc   5880
tcgtactacc gcacggatga tactccggac gaatacacgc aggaggtgtc gctactcacc   5940
caacccgatc cgctgaacga aatcggaacg atacaggaaa gcaacgatac cgtcataata   6000
acgcgtcaaa cacaaacgga cctgatggaa cctctcgaac cactacccga accacggata   6060
gccaaggtag taccgctcgg acgcatcagc accacggaaa acagccactt ccctgatcct   6120
gccaccggcg aactgcttac cttccacgtt ggtctgcggg gtgaagcgcg ccggctacta   6180
gtggcagtca ccgacacggt caacacgatc atccagggca accacgacac ggtccgcatc   6240
```

tacagcgaca tactgcaggg tcacctgttc cagatcatat cctgccaccg gccggcacag 6300
cttgcggtgc tagaggttcg ggacgaaacg atactggcat t 6341

<210> SEQ ID NO 231
<211> LENGTH: 6048
<212> TYPE: DNA
<213> ORGANISM: Anopheles gambiae

<400> SEQUENCE: 231
tcagcacgac agctctatct caagggattc cgtgagcggg gccacgtgcc ggttaacttt 60
ccggtcgaca tttgcttgct gcgcgttggc aaaacgatct ttgctgcggc cctgcaccaa 120
agcgaaacca gcaaccggac gatgaatgcc acggccgtgt ccttctatcg cagggtgaag 180
ggaaagtttg aaaagtatct cgaacatcaa accgttaccg cccgccactt tgactgtgtg 240
tcgatcgcgc acctgggctt tgtggcggtc gtcaactacc acgaccagga gctgaacgtg 300
ttcggggacg gttcgcccgt ctttcaaatc cacgaggacg gccgcaccga gctggtgcaa 360
acgttcggcc agccgaacca gaacacggta cacctgtggg tgcacggcaa gcacgtctat 420
ctagcgcaca cgtacatcaa tctggacgcg gagcgcggca gcacagccaa cgtctgtcca 480
ctgtaccgct gggccggcca atactttgac gtgatcgatc aaatgccgtg ctacagttcc 540
gtgcacatcg aagcgttctc gatcgagcag cagatgttcg tggcggtggc aaaccaaatg 600
tcaccggcgc agggcaagga cacgttctcc gacatcttcc tgctgaaccc ggacacgcag 660
aagctcgtgc tgcaccagcg catctacatc tactccgtgt cgcatatggc gtactttttc 720
ttcgaagcgc gaaacgggcg gcgggaacac tttctcatta ctggcaactc ggttgatgag 780
gaaggtggca aggagggtgg tgatggtccg aggccatcga acggcatcaa atcgcgcact 840
gtcgagcgga gctcgatcgt gtacaagttt gtggacggat actttgtgcc gttccaaaac 900
ctggagctta cgggtgtgaa gatgtttctg ccggttgtgc acgaaaatgg cgaatttttg 960
ctgctcgtcc actgtcacga ccagccgctg ctgatttacg agtacgacgg ttggaagctg 1020
gcaccgtccc gtatcgacta caccggcgaa gcgtttgcgg ccggcgtgtc ccacatgcgc 1080
gtctaccggc acatcgtgaa cgcgagcgtc atcgtgatcg cgaacagcaa tctgttcggc 1140
aagtcgatca atctgttcac cccccagtac ggggtgcaga acgatctgcg ccgcgtgtac 1200
gcccacttta tcgagtggtg cgagcgcatg cacgaccagc ttgggcaggt gaatctggag 1260
cagctgtaca acaagctggt cgggctgccg gacaatgccc cggacggggc gcgcatcgtc 1320
gagaaggatc tggtgctgca ggattcggcg gtgaggacga tcaaagccaa aaccatcgcg 1380
acgaagcacg gcctggtgga cgatgcgttg ctgtcgtacg tgatcgaggt gaacgagtac 1440
gtgcagcgcg tccaggagaa gatggacctg gtcgagcaaa cgattcacgg cagtgtgctg 1500
accaacgaca cggtccgctg gaacggtgat ctggccgttt cggagctgat agcaccggcc 1560
gggcagatga agcagctcga tgtgaaggtg ctgaacaatg cggcacacaa gacgcgccac 1620
acggagcaac agggcagaag gggggatgtt cccgaggacg atgtgatcac ggtcgatcgg 1680
ctcatagtgg accgtatcgg cagtgtgcag tttttcaatg gacatgcggc cgaaagtttg 1740
ctgctagttg atgatccacc ggcgaagtgg aaaacgcttt ccctgtcggc caaaaaagtc 1800
gtcgtcggag gcaatctgtt cgtgaacaag ctgatcgacg gcgttttctt ccacccgggc 1860
aacgtactgc tgccgaacgt gaatcaaatg ttccccgcca aaagcttgat ggtgaaggat 1920
ctaagcgtga accggctgac gagcaagcgg ctcaacgcaa ccgatgccgt cgccgtccag 1980

```
cgcatgatgg atcagtcccg cacgttgctg gccaaggcac ggggcgcaat gccccgcgag   2040
tacgggagcg atttcgaaag catcgatgcg gacgacctca agctgaccgg gctgctgaac   2100
gatatcgatc cgcgcgctct ctccgaccac gtgctgctgg acgaagcagc agagcaacag   2160
cttagcggca aactcgtcgt cgatcagctg gttgcgcaca atgtcgtcgt aagtgatgcg   2220
aagctgtccg acgtgccgct tgcaaacgtt gcccgcacga cgggcaaaca gcaaatccta   2280
caagacctac agttcgtgca accgatggtg gtagagcacc tgcacctgca ggatcgtctc   2340
aaccacatac ccgtgatcga aggaaagctg caggtgctgc acctatcgtc ggacgaaatt   2400
caacccatca cgggcacgaa aacgttcgac tacgtcacgc tgctgcaccc gatcgagctg   2460
cagggcaaaa tcaacggcgc aagcttaagc aagatgaacc ccatcgtgac ggtcggggac   2520
gatctcgtgc tggacgggga ctacacgatc cacggcaacg tcacgttcaa cggcggactg   2580
tgggcgcaca acattctcag tgccggcggt acacgcaacc ttcaccgggt ggcaacgcac   2640
ggtttgcagg tgcaggcggc accaccgccc ggccaggtgc ttaaattttt gcagcccgtt   2700
ttcgtggagc atctgcgggc ggatcaaatt aacgagctga gcgtcaacga tctcgtaccg   2760
caagcggccg gcggggaggt tcagtatcta acggggagga aaacgttcgt ctcggagctg   2820
aagattgacg gcgtggccga tgcgaacgaa atcaacaagg tggatctgaa tctgctcaat   2880
cgcaccatgc tgcagcgagc aggggccgaa cagcagatcg aaggaacgat ccacttcgac   2940
acggttattg cgccgattgt gaacagcaaa aacgtccttt ttgaatcgaa acgactcgac   3000
cgattgctcc ggctggacgt gccgcaaaac gtaagcgcag cggtacggtt cgaaaactgt   3060
accatctacg caagcaacgc gatcgttacg gaagaactac acgcggatcg gcagtcgacg   3120
atttacgggt acgatttgga gtacctgctg caggatacgc tcatgctcga cgcggacgaa   3180
gcaaacgtac cgaccgtgca ggggttgaaa agtttccgca atctaacgat tgggcagttg   3240
attttgcaca gcgaggcaac gctgaattcc atcccggtgg agaacttgaa gcacattatc   3300
gctgccggcg ataatcgaac catcatcaag aatgaaccgt acagcttcca gagcgacatt   3360
acggtcaacc atctgctgtt cgagggttcc atcaacggtg taccgaagga tgcgttttgt   3420
cgtgcgtggt taatgtacag cggcaatcaa acgttcactg cagggcaatc gatcgaccat   3480
cttgcaacgg aacagttgtt cgttaccggc aaactgaaca acgttacgat ggagcagctg   3540
gtggagaatg cgtatcgaac cgatcgggag gaatacatcg agcgggcagt gtttcatcaa   3600
ggcattgtta cctacgaccc gtgctccgtg ggtggtttag tctcggggct taacgtgagt   3660
agcgacgtac tgttgaagca gtcgcccgaa atgcaaacgc tcggcaccgt gcacgtcctg   3720
ggcacactgg aagcgaaggg cgagctacac attctgagcc aactgaacgg tatcaatttc   3780
cccaagatga tggaattttt cagcgccccg ggtgaaaacg ccgaaggtcg ggaaagtgta   3840
ccggtcggca tcgaaacaca cggtaacgtg tactttgagc acgatccaac cgtcatccac   3900
ctgaacgggc acaacgtgca gaagctgtac ggtgaggtgt ggcttcccca ccggccaacg   3960
gtactgactg gccggtatca gtttgagagc gttgagttcg tgaaaccgct ccacacgaag   4020
gatcaaccga ttaaccacct caactgggac gaagtggaag cacgatgttt gagcgggaag   4080
cgagcacaaa acattacggc cccggtacag tttctgggcg atgtgacagt ccatgcgggt   4140
gccgcgtttc aagacgttaa cctgcaagga tcactgaaaa gcacgcacag ctctgctgga   4200
ttaaatgtgg tggagtacga taagtatgct ttgcggtatc acgaaccgca ggaaattacc   4260
ggaaaatggc ttttccacca tgcggaagta cacggaaact tcgatgtgga aaccctcaac   4320
ggctacaacg tcaagacaga cttgctgaga aacgatgctc cgagcgggaa ctttaccgct   4380
```

```
gcaaagcgtt tcacccagct gcacgtagaa agcatcgtct gtgctccgcc ctgtgtcata   4440

caggacgtcg atatggatga gtggtacgcg aacgggcttc gtttgagagg caaccaaacg   4500

atagaaggga cgcttcacat tcgcaatggt atcgttaccg gcaatctgga agtgctcggc   4560

acagtgaacg gcatgcggtt tgatgcggag catttgatgc ttaaatcgct tccgcagcat   4620

gtcaatggca cgctgcggct ggtcacaaaa ttccccaagg agaacaaaat ctacccgctg   4680

gtgtttgaag ccctgcaagc gaatgccatc aacggaaagg atgtggagca gtttttgaag   4740

aacgttgctt tggcgggcca aaacccattg acggtgaaca ttccggtcac gtttgtgcag   4800

ccactggaag cggatgaaac ggtgtttgag ggagacatgg tgtttggtgt gaacgtgacc   4860

cagcttctgc agagtacttc ctatcgtaaa gatataaatg aactggcatc gcaggtacgg   4920

tcgcttaaca gcgtcaacga caagctagcg gaaagcgtgt ttgaaaatag tcccgtattt   4980

agccactttg ataaaatgaa acccttggca gtgcaagcgg tgcgtatgct tgtcctgaac   5040

ttgccagtac atccggggcc gatggatttg atagctgttc acagtgccga acccaacaga   5100

ccgtccgcca ttgatttcta tcattggagt accggcaaca agggaccagg tttagtgcct   5160

gcccaagcgt tcccttcgat cgttggacgc gatcgcacga tcgtgaacgt gaagcggctt   5220

aacctgggcc ccaaacagca cctgttcgtt gagttcgagg agcatggtag cggcaaacac   5280

tttgtgcaac aaattctaga cctaagccac gaatcgacgg gcatgtacaa attcatcccc   5340

ctgtacgtga tgaacagtac ccagtccagg gaagcgatcg ggatgaaaat tgttaagcta   5400

gactgtatcg tgatgtactc gaagggaaag ccggatgtcg aagttcgctg tctgcgtgaa   5460

cacaatctgc tgcaaatact ggacgtacgg caaatggaag aaacgatcgt tccccttcaa   5520

attgttgccc tcgaaaacca tctcatcgtg ctggacagta acgagcggat ccagatttgg   5580

cgctcgacgg ccagcttcta tctaaaacac catcaaacca taactgtatc gcacccatcg   5640

tacctcactg ttgcgaggta cgaaaatcag cttatgcttg cgatcaattc agaaaacaca   5700

ccgaacacgg cgcaccacgg atcgattgaa gtctggcgca aggggctgac tgggaatggt   5760

acgttcgtgc agcatcagct catactgacc aagctgccca agcagctcca gctttccgtg   5820

ctaccctcga aggagatgct gctgtacacg ctgacggaaa attggctgca tccgctggtg   5880

gtgtatcggt acgaaggggt gaccggattc agggagatac tgaccacgaa cactatccgg   5940

cagaaggcga aacgcatgtc ggtgctgaag ctgcgcctgg cacggaaaga gatcatcgca   6000

atcgtaggcc cagagtctac cgattttgtg gaggttgtgt ttgtttga                6048
```

<210> SEQ ID NO 232

<400> SEQUENCE: 232

000

<210> SEQ ID NO 233
<211> LENGTH: 6828
<212> TYPE: DNA
<213> ORGANISM: Anopheles gambiae

<400> SEQUENCE: 233

```
atggcggatc acgatcaaac tgtgctagat gaagagttgg caacgatcaa ctcgacgaga     60

atgcagcaat tggtgggtgc tggcaggacg aactggctct gcctgatgat gacggcgatc    120

ggtggagtga tcgtgatggc tgcgatcgcg ttcggtttct acctaaccat acccgcatca    180

gctctctccc aacaaccatc taacctgatt gagctagaac ctatcgaagt acaaagcccc    240
```

```
gaagagctgg aaaccatccg cgaaacgtac ttcaaagcgg aagcacatga catcctgatg    300
ggatcactgg aattgctgga actgttaaac gatcttgatc cactgctcca acgtcaccgc    360
tcgcgccgag aagcctttgg agcagaaccc gtcccgaacc gtatctcccg cggagacgat    420
cgttccggcg agattacgta cggtgtgcga aagcgcgtac agcgtgagtt cgatctcggt    480
acagtaccga tcgactaccg gggtatactg gtcggttctg agtctccccg tgcgccacgt    540
aagcgacgcc acaccgacat ctcgctcgac gagctggagc gtgcaaagcg cagtgcacag    600
aaagactacc agcggctgga gaaggagtac aaccggtgtc ggaaggaagc accgaacggg    660
aagctgtgcg atcagatcta cgaaaagctg caacgtctgt cggaggaagt gaatgcacgc    720
tttctcgaga tggcgaacct gctgcagggg ttcagcgaga tgggtccagc caaagagaag    780
acgacgccac agtatgagga gatgtactat agtagcaccg agcgaagtac aagttatcga    840
ccggagatgc acgctccgaa aaacgatccc aagataacga ctgttgagca gcttgtgaat    900
cagatgaaca ttacacaggc catccccaag gagaagctaa ggacgagtgc ggaggatgag    960
atggtcacca ccactcccat gctaccggtg tttgatccga gcctgcataa accgatcgag   1020
aatagttcta tacggagttt ggatgatctg ttcgatcata tgagactgag cggagaggac   1080
gcttccacca ccgagtggac tacagagcgg cgtgagctgt ttgagttcga aatcgactcc   1140
acttccacgt cgcctgtcac cgtgaagcca tcaacccaac cgacgagtaa gcgacgaaca   1200
acaaccaaaa gcccactgca agcggctcgc aatctccacg atgttgtcca tcaactgcaa   1260
ctagcacaga tgcttcagcc acaccccttc cacgaggatc ttgtgatgag tccaccggaa   1320
aacattaacg agtttgtcat gtcacgatcg cgcaatcggg aggaaatgca tcacgacacg   1380
acccccagtc cgatgcgtgc cgtcgtccat caacaacatc aacatctgca gcatcagact   1440
caacctcaat cacctcacca accgttggtc gttggtccaa gtgctccctt tctgaatctg   1500
tgcgatcaac ttcgatcggc agcaggaaat ggccacctga agccaacaca ccctggggca   1560
acattccaac actcaccagg cattccgatc acgggtgaag caacgaaagc ctcctcccag   1620
atcattgtca actcggcgtt tggggctggg tatgtgccga atacggtttg cttctaccag   1680
aacgcaccac cagtaggggc acaaccaacg gcgtacggct ttcgtcctgc cggttccggt   1740
gctccttacg tgtatccgaa cgcgccaggg tatccaccgt accagccaca ccagcaacag   1800
ccttatcatc aacaacacca ccatcatcat ccgggtgccg gagctatgat caacatgccc   1860
gttagcatac agaaccttca tcaagccggt gctcgtacct cggagctgcc ggccgatcag   1920
aacggtccca tcctcctctg ctcaatgatg cagaacgtgg agcaaccgac gcgacatcac   1980
gccgggaatg aaacgcaccc agaggacgcc gaagaagagc tggacgaaaa tctagacacg   2040
atgtttgcgg cgggacgctc actggcagca cgggccaagg gacgccacca ctgccgacgg   2100
ggctcggtac cgtgctttag ctcgcatcag tgcgtcaaac gcagcagctg gtgtgactcc   2160
aagacggact gtatggatgg tagtgacgag agtgcgtgct cctgcgtttc gcgcctcccc   2220
aagcgcaagc tctgcgatgg ttatgccgac tgtccgctcg gtatggacga gatgggatgc   2280
tttgggtgtg aaaagttctc cttctcctgc ttccacacgg aggcggagta ccgttcggct   2340
caccggtctg ggtcgatgtg ctacagtctg ctcgaaaagt gcgacggttt cgataactgt   2400
ctgaacagga aggatgaaca ggactgtacg atgttggtgc gtgatctggg gcactatttg   2460
gcgtactcgg tcccgcactc tactggggtg ttgcatcgga actatcgcgg gaagtggtac   2520
ccggtgtgtc ataatcctac gcagtgggca agggaagctt gcgagacgga gctcgggcca   2580
```

```
ctcgatcgtg agccactgtt gagccacggc catggcagtc ttcccggacc gtacattagc   2640
cagcgagcga acagtgccgt accgcagccc gagtttagtg aagcttgtaa tggggtttac   2700
gtacacgtga agtgtccggc ggtgcgatgt ggtacgagtc ggatgcacga acagcacgcc   2760
gcccgaatca atgtgcggac aaggcgtgag gcgaacgaga gtgaaattgt ggagagtgtt   2820
cgcatcgttg gaggatcaca tgccgatccg gaagcgtacc cgttcatcgt cggtatcttc   2880
cgggatggga agtatcactg tggtggcagc atttacaacg aacattggat catttctgcc   2940
gctcattgct gtgacaactt cgaccagcac tacttcgagg tacggtcggg catgctgcgc   3000
aagcggagct ttgcgccgca ggttcaaatt acacgcgtca cgcacatgat cgttcatcac   3060
gcgtacagct cgtcgttgat ggcgaacgat attgcgctga tgcgggtaga gcatccgttc   3120
cactacaatc gatgggtgcg tccgatctgt atgccggagc gccatcgtac cacggacgat   3180
cgggattgga tctggggacc aaaggctggc actgtctgca ccgctattgg atggggtgca   3240
ctgcgggagc gtggtggagc acccgatcat ctgatgcagg tttcggtgcc gatcttaggc   3300
tactgcaagc acaaatccga tcgtgacagt ctgcagatct gtgcggcaga agaagacggc   3360
ggtcatgatg cgtgccaggg tgattccggt ggaccgtttg tgtgtcagag caagtcgaac   3420
ccgttcgagt ggtatctggc cggtgtggta agtcacgggg agggatgtgc gcgtgcacac   3480
gaacccggtg tctacacgcg agtggcactg tttatcgatt ggattgcgga gaaggtaaat   3540
gcgccactgc cagcacgtac tgcgcgggct gactgtccgg ggatgcgatg tatctggggt   3600
ggagggatct gtctaccacc gggcaagaag tgtaacggat acgttaactg tcttggtggt   3660
gaggatgagt cgggctgtgg gatggatcag atgctacgat cgatgtcgca gcgaggtgag   3720
gaagaaagtg aggaggaggg tggtagtgcc acacagagag cttcggatgt ggatacaacg   3780
gaagctgaga ctaccgtatt gttcacatcg gaagaaacga cgacgttaag cgtgccggaa   3840
gaagcgagtg tagaagcgca ggagagtatg atcatgacga acacagcaca gacggaaccg   3900
atcactacta ctacaagtac agttgccact accacacctc agcttgagct atctactgct   3960
gaagaaagca caacggagga cagctctacc tcagcaagta cctcagaaga tgcacctacg   4020
gaagcttcta cctcgccgga gtcaaccaca ttggaggtca caacagacct cagtacagag   4080
ccatcttcca ctacgaatga accaacaaca accttcacat caacaaccga ctctgcgatc   4140
atcttcccca tacacgatca cgaacaggat cgtcctaagc aagactttga attcattgca   4200
ccgatcacct cctccacaac ggaagtcatt tggaaggcgt tggaaaaggc agtcaaagag   4260
gtacgtggac aggtacgcac tgggaatggc acttcagtgg tgaacgccac aacggaacca   4320
atggaagtgt tctctacgga actgccactg gaagccacgt ccgaagatcc gctggaagat   4380
tcttccgacc atccattctt ggtggagttg gacgtgatgc agcagcagaa acacaagcga   4440
gtggcccaat tccgcatgac ggtgcacaat gtgcacacga acacgaaggt gcagacgatg   4500
ctgccgaatg atacggcaca gtacaggcag ttttcctgca ggaatatcac ccagaagatc   4560
aatgtggcac accggtgcga tcggatcgta gactgtgaag atggcagtga tgagctgaac   4620
tgtacctgtc gcgacttcct gaaggataag tttgatttcc tgatctgcga cggcaagacg   4680
gactgtctcg atcaaacgga tgagctgggt tgtatgaact gtcaggctgg tcagtatgcg   4740
tgccggatca gccaggtttg cattcccggg gtgcaggtct gcaacggtca tccagactgt   4800
ccgatgcatg aagatgagct ggattgcttg gctctaacgg atggacatcg tgtgtacttc   4860
gatgcaaaca atctcaccct cttccacaac acgggcattg tgacgaaaaa cacgaacgga   4920
acttgggaga tactgtgtgg agcggttctc acggcaaaga cggaacatgc tgtggagaag   4980
```

atctgttcct tcttgggatt tgctggtcat cgaaactact cactgctctc actcgcaccg 5040
accgatctgc ctgttgggct gcttgcaaat ccaaacaatc tacactacgt caaccttacg 5100
ctccatgctc cctgtcaagc gttgcgtgtc tcctgcgtcc agcacatcaa cgctaccgag 5160
cacgacattg cacactttga gcacaaccac aagcaagacc cggtacaggt taacattcgc 5220
ccactgaacc cgatcaaccg gccccatcac atgccccaga tcgtgttcca ggagaacgct 5280
cacattgagc tggtggaaaa ctttggcgat gattacgatt ggccctggaa tacgaacatc 5340
tatctcgatg gagtaatgat ctgcagtggg ctgatcatcg atgcgagctg gatcattgtg 5400
tcggggagct gtacacggtt ggtgaacctg cggcatcagt atctggcggt ggtggcgggc 5460
ggtgccaagt cgtacctaca cattgaaggg ccgtacgagc aggtggtgcg ggtcgattgc 5520
taccactaca taccggaggc ggaaacggtg atgctgcatc tggcgacgaa gctaagcttt 5580
agccggcacg tgctgccgac gtttgtgccg gagaatgaaa acctaacgga cagtgagtgt 5640
cttgcggtgg gacaggataa gtacggaaga acgaaaacgc tgcgggtgca tctcaacacc 5700
accaactgcc caggcgaacg ggtgcgatgc taccataagg atctgaagca gccctactat 5760
catcatgaat cttgttacac accagaagcg acacgatcag gtgtgatcgt gtgcaaaaca 5820
agtcgctccg gttggtatcc agtcggattc taccagcaca agcgtggtct gtgcggattc 5880
aacgaagtgg tgcgtgttac gagcctggta gaatcgtacc acaggatcca gaacgtgcta 5940
cacaaggaac agtgcggtga tcagctgtac gaggaacctc attgcggagg aaagcgctgt 6000
cgctatggaa agtgtgtcgg tgagaagttg ctgtgcgatc gcaaaccgga ctgttccgat 6060
ggatcggatg aggaaccggc aatgtgtgcc tcacgcaatc aaactggaaa ttgtctgcca 6120
catcaactac gttgcgcgaa tgaacggtgt attgacaagt ctagtttctg cgatcgcaag 6180
aacgattgtg gagactcgac cgatgaaccg cacgattgct cctgctacac ctatcttaaa 6240
attaccgacc caggcaagat ctgcgacgga gtgcgcaact gttgggacaa atcggacgag 6300
aatccacgcg tctgtcggtg ccactcgacg agcttccggt gtggcgagtc cgacatctgc 6360
gtgccgtatg attttgtgtg cgacaaggaa cgggactgtc cgaatgggga ggatgagctg 6420
tactgttacg cactgcagca gaactcttat gaagctgggt acggtgagct gatggagcaa 6480
agctacggca tctggcactc aaaatgcttc cccacgacga cccagttcga cgacgagtac 6540
atgaagcgca tctgcgagca gttgggctac agtcaggtgc gcaaaatctt tggccgagcg 6600
atcgtgcaag gtgctcggtt gcgtacggcc aaccagacgg aaacgcccgt tgataagctg 6660
cgtcgttcgg cgaccaaagc gatcgtgcag aacaagttct ccaaggtcgt tattaaccag 6720
aaccatacgt tttacatgaa accgagtcgg cccatgttta aggtgatcaa ctggaactat 6780
gaggacgagc aaaactgcca tcggttggag ttgctgtgtg ccccgtga 6828

<210> SEQ ID NO 234
<211> LENGTH: 1583
<212> TYPE: DNA
<213> ORGANISM: Anopheles gambiae

<400> SEQUENCE: 234
atgcacattc gccacagtca tttaatcctg taccttgccg ccgtcggtgg gtttgtggtt 60
gccgccgatt ttccacccca gcggcacacc ccgtcggcgc gggaggaaat gagacgcgcc 120
cggaagcaat cgcaaaccgc gatcctgcaa tcggtcggta agcgatcgca cggtaaccga 180
gacgcgttgg tttcgctgtc cgaggagctg gagatggtgg ctgccgcaga agcgacgacc 240

```
gtctccagca agaaagcatc gccagcggcg gttgcaacgc ccgggaatgc caccgcagca    300
gcagcagcac ctgtcatcac gaccacaacg gaaagtgatt tgtttcggtc gtacatgcaa    360
acgcaccgca agaagtacta cgccaagtat cgggccgacc ggagacggtc cgcgctgatg    420
gaaaacatgc aggagatcca ggagcacaac aaagcgtacg aggccggcag caatcgattc    480
cgcatggcac cgaacgcgtt cgccgacatg cacaacagcg agtaccgcaa gcgcctggta    540
cggctgaaga cggacccgca ccggaaggtg gagccggcgg tcgcggacga gatcgtcagc    600
agcagcaacg agctgccggc ggagctcgac tggcgcgaga agggcttcaa aacggcaccg    660
gccaatcaaa agtcctgcgg ctcctgttac gccttcagcg tggcgtacgc catatcggcc    720
cagctaatga aacacatcgg ccgggtggag ctggtgagcg agcagcagat ggtggactgt    780
tccaccgcga acggcaactt gggctgcggt ggtggttcgc tgcgaaacac gctaaagtat    840
ctggagcagg cgggcggggt gatgcgcgag gtggactatc cgtacacgtc ttcggtaagt    900
gtggggtaaa caggccgtaa gcagaggccg gggtaaaggt ggtatatcaa aacggggtca    960
tcattgtatt tgaaatcaga aaacatttgc tcagttttgg tgtgttgttg tgctgtgctg   1020
aagaagaggt tcctcgtcaa cacaacacac accctggggg ggcaaaagta acacttttca   1080
gctaatttgc ctatgtcgcg gttggacagc aacctacctg aatgcacttc acgcaagtgg   1140
tggcgcccga tgcaaagggg caaacaacaa atgagcgcat catttattta ctgcattttt   1200
tgtcgagtgc taattgccac ttgactgtac tgaccacacc atccaccgct gaggacggac   1260
tcggtagtga tgggtggtgg aggacgtgaa gctgcacttt aagatgaacg actgcagcgg   1320
gacaagtcag caaagaaaca acggaaagag acaaagagtt atggccgtac cgattccacc   1380
gaattgcatc attgtgtcgc ttatcgtaat tgatgatatt cgtaagtact ttccttcgac   1440
atgatcttgc gcgagacaat aacctacaca cacacacaca cgcacactta taaatatatc   1500
ttaaacactt tgcagggtga gagagagaca gagagttgtg gcgtagcaac ggggtaaatt   1560
atgaacccga agttctcatc att                                           1583
```

<210> SEQ ID NO 235
<211> LENGTH: 1896
<212> TYPE: DNA
<213> ORGANISM: Anopheles gambiae

<400> SEQUENCE: 235

```
gaagtggcgc gccgagcagt gtgtgagatc cggagaagct accccgaagc caagtttttg     60
ggaccaagtt gtgcacagaa gttccttagt ggcagaagcg aacaaacaca caatcagaaa    120
cagaaacgtt tgaacaaaaa ggacacgatg tacggtggaa tgttgctgat ggtagcgtgc    180
ctggtggccg ccggcagtgt cagtggaacg cagaagctcc aggagcgcta tagctggcag    240
cagctggact ttgtcttccc caatcaacgc ctcaagcaac aggcactggc gcggggcgac    300
tacgtgccca cgaacggtct gccggtcggt atcgagcgct gggagaacaa gctgttcgtc    360
tcggtaccaa gatggaagga tggtatcccc tcgacgctta actacattga catgaaccag    420
acaccgtccg gttcgccggc cctcatcccc tacccggact ggtcctcgaa cgtggcgggc    480
gactgtgcca acggtctgtc caccgtgtac cgcatcaagg cggacaagtg cggtcgactg    540
tgggccctcg acaccggtac cgtcggcatc ggcaacacta cgcagcaact ctgcccgtac    600
gcgctgaacg tttgggatct gaagacgaac cgtcggctgc gccggtacga gctccgcccg    660
gaggacacca acgccaacac gttcatcgcc aacattgcca tcgatatggg acgcagctgc    720
gacgacacgt tcgcgtacat gtcggacgag ctcgggtacg ggctgatcgt gtactcgttc    780
```

gagcagaaca aatcgtggcg cttcgcccac agcttcttct tcccggatcc gctccgcggg 840
gactttaacg tcgccgggct caacttccag tggggcgagg agggcatctt cggcatgtcg 900
ctgacgccgc cgcaggctga cggcttccgc acgttgtact tctcgccgct ggccagccac 960
cgcgagttca ccgtgtcgac gcgcatcctg cgcgacgaga cgaaggtgga ggaaagcttc 1020
cacgacttcc agtacctgaa ggagcgcgga ccgaacagcc acacgacgtc gcgcgtgatg 1080
agcgaaactg ggctgcagct gttcaacctg atcgaccaga acgcggtcgg ctgctggcat 1140
tcgtcgctgc cgtacagccc ggagtaccac ggcgtggtcg accgggacga cgtggagctg 1200
gtcttcccgg cggacgtgaa gattgacgac gaggagacgg tgtgggtcat ctccgaccgg 1260
atgccggtgt tcctgattgc cgacctggac tacagcgatg tgaacttccg catcttctcc 1320
gccccgctgt cgacgctcgt cgccggcacg gtgtgtgacg tgcaggcggg ccagttcggc 1380
gcaatccagc ccaagtttgg cggcgatgcg gccgacctgt cgaccaccta caacaccgac 1440
acgacgctgc tgccgacgac ctactcgcag ccgctgtccg gcgggtacac gccgtcgctg 1500
agcttcgcgc cgaccgtggc gccccaggtg cacaagttta cgcagggcta cgatacgccg 1560
acctcgcaca tgtactccac ccagtcctac ccgacgacgg ccaaggcgta cgcatacaac 1620
aagtaccacg gcgtagagtt ccatgcgcac ggtgcgccgc accacggtca cggctaccac 1680
cacgggccgc agcacgggca cgacgagcag gagcagcagg gcggatacag cggccatcgc 1740
ggctactgga acggtggcca caagaagcag gactcgtgga agcagttctt ctactaaaag 1800
agaggcacac actaagccac accgacgcgc acccacagac ctctgttaaa tctgttttat 1860
tggtcgttca ataatacata cacatacaca aacacc 1896

<210> SEQ ID NO 236
<211> LENGTH: 1274
<212> TYPE: DNA
<213> ORGANISM: Anopheles gambiae

<400> SEQUENCE: 236
ttggtgctgg tgctgctctg gatagtagca agaaacgtta tcaatttagc gctccgttaa 60
gcttatatta ctttttacgt acaaaaaacc tcctggaggt gatgcggtct aaagtgtgtt 120
ccggcggcat gatgccgaca gcggctctcc ttccgcttct cgtcggtctg ctgtcgctgg 180
ccgtggcggt gcagggcgcc tgcagctctt cggacaactg tacgcgcacg atctacacct 240
gggaaggggg ccggatcgtt tggccctgcc cgaccacgaa gcggctcatc accagcaccg 300
gcaagtacaa gccacgtgat ctgatcgcga tgcgctgcca gcgcagcggt acgcacacgc 360
tgtgcgtatt tccgcgctac aagagcagca acccgatcac gctgagcaag gtgtacgcaa 420
cgaagaaggg ctgcgacgtc aagttcgaac cgttcccgtg ctggaacgag caggaggagg 480
gcaactgcaa tgcgctccag tcggccatcg atctgcacag cgatggcgag tacgtgtggg 540
tgctggacag tggggtgacg cagtcgcagc gcacaccggt ccagcgctgc ccgccgaagg 600
tcgtggtgta ctgtagcaag accggcaaga aactgaaaac gatcaatctg gcccggtttg 660
tgacggaaaa gtcgcgcctg cagtacatcc aggtagagtg tctgaagggc ggccggtgct 720
acgtgtacgt gagcgacccg ggcaacaatg cgatcatcgt gtacgacgtg tacaatgggc 780
gcggatatcg ggtgatcctg ccgaaggctg tccacatggg ctgccgctac cgggacatgc 840
tgtacatctt cctgtcgaag cacaaggaag gtacgcggct gtactttacc tatctcggcg 900
gtaatcgact gtttgcgatc aagacggagc atctgcgcaa gggacacggt ggcaacatta 960
tagacattgg cgagaaaccg gtggtgcccg tcttcctcgg cacggacggt ggccatggag 1020
tgttcttcag ggaggagggc gagatgaaca tctactactg ggacaccaac acctgctgga 1080
aaaagaccaa ctttaagctg gtgtacaaga gcacgctcgg cctgtacgcc acgcacgtgt 1140
tccccgatct gaagctgaac cggctgctgg tgctggagaa cgatttcccg agctacgtaa 1200
aggaccacgc cggctgtgga acgctccatc agatctcgat cctcgatgga agctgcaagt 1260
gtaattcggg ctag 1274

<210> SEQ ID NO 237
<211> LENGTH: 1212
<212> TYPE: DNA
<213> ORGANISM: Anopheles gambiae

<400> SEQUENCE: 237
cgcgtttgtt cttcgttgtg gatcacgggt ttgtgttggc gctggggata aacgaacgca 60
cagaacacga tgagttgccg cgtgacgggg ctaccgcttg ccctgctgtt tgtgctggtg 120
tccgcgctcg ctagcacgga cgatctcgag tactgcaaca tcgtgtaccg gatcaatggc 180
aattcgatcg actttccctg cctttcgacc aagaacatct acatctccgc acatcgctac 240
cagccacgca atgtgatgcc ggtgcggtgc cagtacgaca atcaacgcat gctgatggca 300
ctgccaagat tgcgctcggg cgttcctacc acgcttgggc agatcgatct gaacaaaccg 360
aactgctacg cgcacattaa gccgtaccct tgctgggcct atcaggagga gggcaattgc 420
aactcgctcc aatccgtcat cgatctgtac gtggatgtga agcgcatcgc gtgggtgctg 480
gactcgggca tcaccaactt cctggagcaa ccgatcaagc gctgcccgcc gaaggtgtat 540
gccttcaact tgagcaacga caagacggtc aagacgatcg acctgtcgga gattgtgaaa 600
tccagctcgc ggctccagta tctcgtcact gattacaacg agctcggcca tccgtttgtc 660
tacatttccg atggcgatgg tgcaatcatt gtgctggacg tgaacaacaa caagagcttc 720
cgcgtggtgc taccgcgtgc catctcggct ggctgcggcg attcggacgt gctctacctg 780
ctgctcatcc cgaaaccgaa gggccagagc ctggtgatct tcagctatct gtgcggccag 840
aaggtttact cgatcaagtc ggaacatctg cgcagcggca agggttcgag cgcgatcgtc 900
gagctcggca ccaagcgcaa acactccgtc ctgctcggca cggacggtgg caagggggtg 960
gtgctgcggt accgtggcga ggccgagctg tacctctggg acagcgatca gccgtacagg 1020
gagtgtaact ttgagctgat tcagaacgcg gacgagtgcc ggctgtcgac gcacgtggtc 1080
gtgggcaaga acgagcatct actgtcgctg tcgtcgaact tgagcgattt tctcaacaac 1140
acgtgcggcg ttggtggcgc ctcgtcccgg ttgaagtacg tttgcaagga gtgtgacgat 1200
gattgttact aa 1212

<210> SEQ ID NO 238
<211> LENGTH: 1956
<212> TYPE: DNA
<213> ORGANISM: Unknown
<220> FEATURE:
<223> OTHER INFORMATION: Culex quinquefasciatus

<400> SEQUENCE: 238
atggaagagt cgtcgcaaca gctgcagcac ccttctccgg ttcggcacca cagttacagt 60
ggtgccagcc agcagcagca caaactgttg aaggataatt ccgccgacgg gagtgggcac 120
ttggccgaca gcggctacaa ctcgtaccac tcgatcaatg cgtcctgctc ggtggtccga 180
tcggtgctgg ccacgatcga ggaggacaat gagacggcgg actcgagctt tgaggagccg 240
gcttccgcgc ggaaggtcgt caccggcagc gtcctgactc cgacgaccac ggtaagcatg 300
gaactcatct cgaacttcca cctgaccacg ccgaaggaga acgtggtggc ccagcggcga 360
acgctggccc ggaagcccac ctgccagaac ttgtttgcgc tgcgaacccc ggaaaagtct 420
tctggaagcg gttccgtcga aacgccggtt cgctcggggc gcaaatccgc cgagctgggc 480
attctaactc cgagaaagaa caagacttcc gccaagcgca aacatgccag cttccgggag 540
aagctgtact ccgacgggga cgcggaatca ctcgaaaacg actgcaaaaa gctcgatcag 600
gaggacattt ccccgatctt tcacaacaag cgccgtcgca actcggtcat cgacgacttt 660
atccggtcca gcacgccgaa aacggccagc tttaagtcca acttccacgt tgaagcgcag 720
gagaaccaaa aacccgccaa ccggaaggca ctcgtactgc gcaagttcca gtccttcagc 780
cccagcaaga tgcacagcta tcgcaagcgg gacacggttc tgcaggaaaa gtccgtccta 840
accaatcgca aggcaccact tcagcgccag aacgcaatcc aatccacaac ccctcaaaaa 900
ccgtcgctcg aagcctccct agaactcagc ttcgaaccaa ccccggagct ccccaaccca 960
actccaacct tcggtctcgg cgccctcctg gacgccccga tcctgcccca atccagcgac 1020
gacctcaagg tcgacctcaa cgaggaagtg tcccagctgc cgtccttcga cgactgcagc 1080
accttcaccc ccaccaaacc gtgctctctc ccaacggagc cggactccgt cctccgtgac 1140
gcgtccgtcg caacgcgacg ccgctccatc ccccaaatcc tcgaccagca actggaatcc 1200
cccatcctct tctccccgaa catcccccgc acccccaaat ccacccgcaa gctcaagcgc 1260
ctcaactcgt caaccaaaaa ggacaaacaa ccccgcagca agcccgcgtc ccccaagcgc 1320
taccccgtca tccccggtgc ctaccgccgc cactacgacg gcatcgagcg gctcaacatt 1380
ctgaagcgcc tgaacgagca cgacaagggc gcgctggaaa tagtcctggg ttatctcgcc 1440
gattcggacc tggtccgggt ggtggccgtt tcgcgcggct ggcgctccat catcgagtcg 1500
gattggcggc tggcgcgacg cttgcgtgcg tatctggcac gggaggcgca ctccaaggag 1560
aatctcgatc gaagtgagtc gttgcgggag gatagcagca agattgggtg tgaagcagtg 1620
gtggtgggaa agttggtgca gcagtcggcg tcggtgacgc gtcagccgtt tagtctgtgc 1680
aactcgatcg acgccgggaa ccactcggtg atgaacacga cggtgcccaa gtcgccgccg 1740
gttagcccgt ccagaaggaa gtttcacgag aatcagaagt tctggcaacg ctgccgcgaa 1800
cagatgtcgc gaatcgcggt tgtaaacaaa attcccgttg ttggtgtttg gctctctgct 1860
ctctctgttg acatgttgca acatgacagc tcgctctccg ctatgcgcct caccgacatc 1920
ggagcgagca tagaaaactt cccatcgctg tggtag 1956

<210> SEQ ID NO 239
<211> LENGTH: 3476
<212> TYPE: DNA
<213> ORGANISM: Aedes aegypti

<400> SEQUENCE: 239
ttgcggatcg cgaaaaaaaa aaaagaaagc caccatcatt ctcgcgagct aacaaaagtg 60
gccacagctg aatgagtttc gttcgcgctc ggccatcagc agcccaaacg acgtagaaat 120
ccagaaaaga acaatcattc gcgagtgttt tagtgttgtg tgttgtttta tcggaataaa 180
ttaaaaacga atgcctagat gcgcgaatct tagctgaagt aagaaacctt tttttttttt 240
cgttccatgg agcgctagga gtagcggttt ttcgtccgtc gaaatttgag aaatcgctca 300
tgttttcctc cgcctgatgc ttgatgatgt agaggacact tttcgttttt tttttttcgt 360

-continued

```
tgcgtttcct ctcgagaatc cttgtgtgtg atgtgctgtc cgtgaaaaaa gagggaaaga    420
atatcgataa gagtgttgaa taataattgc gttggattgt tgttgcatca gttattgtca    480
ggcggaagtt ttatgtaaga aaaggaaata accaaggatc ccaaagaggc gttcaaagaa    540
tcgtaacatt tatctatgca tgttgaagaa gttgcaggat tttgcatgtt ttgcggacag    600
tgagggaaag agaaagaggg aaacaacatg gaagagtccc aacagctgca atttcccatc    660
cgtggcaaca acaacaataa accgctcaat gtcagcggag ggaatgacgg aagtggacag    720
ttcaccgata gcggatacac gtcgtatcat tcgataagtg cttccggttc ggttgcccgg    780
tcggtgctgg ccacaatcga ggaggataat gaagcggaca gtagcttcga ggaggctcga    840
tcctcggaag atatcttcca gatgggtggg ggcagtaatg tcctgacccc taccactgcg    900
gccagtatcg agagaatctc aaatttccac cttaccacac cgaacagtac gggaaaaccg    960
gttggacaac atcgaggtct tgtccggaaa ccgacatttg ataatctgtt tgagcaatac   1020
actccgaaga aagctgatta tggacctcct tgcagaacca ctcaaacccc tgttcgatca   1080
gatcggaaag ttgagcttgg cagtcaaaca ccccgcaaaa ataaggcttc agccaaacgc   1140
aagctcggag aattcagaga gaagctttac tccgatgggg atgcactgga attggcacct   1200
cctcgtgacc tcaatgattc cctggaagga gattgtaaga agctggatca agaggacatt   1260
tcaccgatct accatacaaa acgtcgcaga agctccgtca ttgatttgat tcgctccagt   1320
actccgaaga cggcaagtct cagatctaac ttccacgtag aagtccgaga gaacatcgat   1380
tgggatgcag tgcagcaggg aaaagcttcc gggcgcgggg gtaaatctcg cgccttacgc   1440
aagtttcaga gcttcagtcc cagcaaaatg cacagctata agaagcgaga tgtgctgcag   1500
gaaaaatcgg tcatagcgaa tcgcagagcc ccatttcaac ggcaggacgc cttacggcag   1560
gtttccctgg agcaagattt gtccaaacaa tccactccac aaaaagcaca agaatcctca   1620
ttggacaaat cttttgaatt gcctctcgag ggactcatca ctccgtcgaa gcaatccaat   1680
ctcggcgttc tgctggacgc tccgattttg gttcagccgt cttccgaggc ggacttcaag   1740
gaatccgacc ttgagcagca aatatcgcaa ataccttcgt tcgaagaatg tgcctatcct   1800
cagactccca gcaagcaaac cctttcgttg gatgattccg gcgtcattcg acatgctccc   1860
gtgtgcactg aggtcaacaa gtccattccg tcgattcttg gcaccgaatc tccatctttc   1920
gtctctctaa gcatccccaa aacgccaaca tcaaccaaca aatctcgcaa ccgtctcaag   1980
cgtctctctt cgacgaaaaa ggacaaaccc cgtagcaagc cgccttcgcc aatccatcgc   2040
gcccagccat tcattcccgg aacgtatcgt cgtccatcct acgtgaacgt tgagcgtctc   2100
aacattctca agtggctcaa cgagcatgac aaggatgcgc tggggatagt cctggattat   2160
ctgaacgaca gcgatctggt tcgggtggtg cgcgtttcca ccgggtggcg tgacattatc   2220
gaacaccatc ggccatccta tcggcgtctt cgagcgcatt ttgctcggga aaaggaagtc   2280
aaggagaatc tcagttttcc gtcgtttgta tcgcgcgaag gcagcctcct ggggaaaacc   2340
ggaggaagtc tgctgagtag cttcggcgac tcgtcgaagg agattgcggt atcgcttcct   2400
cgtcagccgt tcagtttgtg taactcgatc gacagcaacc aatcggttgg cggcgagctg   2460
agacgttcgg ggtcggtaca gaggtcgcca ccggtcagcc cgtccaagag gaagttccgg   2520
gagaaccaga agattgcatc ccatctgaag aaatcggaaa gactgaaacc ttgccctcgc   2580
tgtgaaaagc ccagccgggt ggtactgacc aaatcgtcca tcaagctggc catggccacg   2640
ggatcgctag actcgtctac cacccgaacc gtggccagcg gaaagttgga tcgctcctat   2700
acgttacctg attccctcat gggctcgtcg gcgacaagca tgatcgccgc tgcggcactc   2760
```

gactgtacct caaccaccat cggcagtccc cagtcaccta ccaatccgga tcgcatccgt 2820
aggaatttgt tctcgaccag tttgctgccc cggtcccagt ctgtcgacgc gagaactccg 2880
gtgactcgga gtccgcgtcg gcgcaggtcc acagatgttc agggaacgtc tgtgtccctg 2940
ctggagcgta aaaatggtaa gactaaatcc gccgaagcga tccaatgtga ttatgccgtg 3000
tgcagtggca aaaactgcgg cttcatgttc tgtattaagt gtttgtgtga gtaccatccg 3060
agttcggtgt gcaaggactt ggccccaaat tcgcctagta aagaggacga accggcgcac 3120
aatgtggcat gtagcaagca aagccgccga tcgttactgc gactgcgaaa gtagtgagac 3180
tgcaacaact aaagcatact atacaaacgg tattttttct agtgttttaa gcagtgacag 3240
taatttatta ctaattgtag aataggctta ataccatgtt ccgaattttg cccagttatt 3300
cttattcgtt tatttttgta tgcttttctt ttttaaagtg tttttaaaaa tacgtaatga 3360
gattagaatt ttaattttat atatgcacga ttttggtatc acttatgtaa gaaaaagtcc 3420
ccaaaaattt caagttaata tataattaca atacatttcc tgatgatcat tcctaa 3476

<210> SEQ ID NO 240
<211> LENGTH: 6872
<212> TYPE: DNA
<213> ORGANISM: Aedes aegypti

<400> SEQUENCE: 240
cgtgcgctcc agtcagtaaa ttcaatccca tcagtcatca ctccgcattg ctttcctacc 60
gagaaacgac aaatcgctct tcacccgtgt gcctcgatcg ctaaccacat tgtggggcca 120
ttgttctctg tgcgtgacct tgctcttctt tggccagctc tcaagcatgc atgaaccatg 180
aataggttaa gctttctttt ttcgacgctt ttcgtgattg cagcgattca gattaagatc 240
gagactaacg cgcaggtcgt ccaaccagcg catacccttc cttcaaacga gcgaccaaca 300
agtggtccaa caaaacccgc caaaaatggt tccccgccgc ttaaaatccc aacggccaaa 360
cctagtctcg gtgacgcgat caagagcctc aatgatcgca tcctgaatga cacggacact 420
ccgcaggata tgctccaaca cgtccgagat agttcgttcc gaaacgtttt ccacgaggcg 480
atcgacgcca agatcgtcaa tccggatctc atcagaacgc tggcttcggt cggcaaaccg 540
ttggtcaatg actacacccg ggacaccctg ctgatcgagt cgatcaggga agacattaac 600
ttcacattcg ggcctaatgt cacttggtgg gaaacactgg agctcaagaa gaacgagcag 660
cacgtgatcg tggggttgag caatagcagt atcgttattc tgtttgagca ctttggcgag 720
ttcaagctac agcaggaggt tctgatggag acggcgccga cggctttcga gatcatcacg 780
gtttgggact cggtggcgga gactccggtc agctgtttga tcgtggcgac cgagttgcag 840
ctcatttggt acacgatgcg accggatacg aatttcgttc tgacggagga gtggcgttgg 900
ccgctttata agatgacgac gttgattcgg ggattcaagt accgggatat tcacatgatc 960
ttgctggtgg ggacgcaccc gaacaaacaa aaatccgttt cggcaactct ttatgagttc 1020
aattttgaga agcagcagtt ttggcttctg cagcggttgg atcttgcaca tgcttgtagt 1080
acggttggac tggtgagggt tggacgggag tttttggtgg cttttccgca gcatgataag 1140
gccatgattt acactctgga agccggtgag aaatatcgcg gaaggttcaa tttggtagcg 1200
aactacacgt cggagttggt tcagacggtg ggggcttttc aggtcggaag gtatgcctat 1260
attgcgatcg gggggagatc gccacagatc gtgcgctatg ccaatggagt gttcgtgtcc 1320
cagcgtattc caatggaggc gatggagacg gttgaggcat actttgaaat accgactcct 1380
acctatcggg atgacttcat tctgctggtg cagcacaaaa tgcttttctc aacgcacgat 1440
cttcagcggt tggatatttt tgtgtggaac ggggagtcgt ttgatctccg aagtaacatc 1500
ccttgctacg tggaagacga actaatggac aacgaagttt cgtgcatgct ggatctgtac 1560
cggccgaccg gtatcgtcgg gtctgcgatc atacttcggg gcaagcaggt ttcgatgatc 1620
gttcctcgct atcagactca ttcgacgctg ttcaacttgc gtatcgagct gctgtccgca 1680
gagcacccga tcaggcagaa gactcaggag atgcgggaca cgatcgatgc gtttaccaaa 1740
atcttccact accaagacga ggtgatcagc gaagcgtatg cggcgatcgc cgaagcggag 1800
cagacatatg atgttccact gctaacgctg cagaactgtt ctctggggac agttcaggcg 1860
gacttggttg tgcaagattc ggacttccgg tggccgagcg ggaagatcat ggttggtaac 1920
aggacatggt cgcatcgtga cacggcggtt gacgttccag cgatcgcgcg agaattagag 1980
gcggagatgg cgctgttgag tgagttggag caacagctga actacacggt tcgacgacac 2040
aacgatagct tctcgctgga tttggatcag ccgttgtacg tgcagggtcg agtcgaggtc 2100
ggaggagctc tggttacgga tgatctgtac gtaaggcagc tggaagaaga tccaccgttg 2160
ttgcgggtgg tccggcaaac cggcgatgat ggtatgcagg agttgcgggt caaagatctc 2220
aaagttcgtc atctgaattt tgaaaccgtg aacggaattc tggcgagtga tctcgtctac 2280
aatacgggcg agaagatcga gttggccaac gcgctggttg tgaacagtgt gcttgtggcg 2340
caaaacgtga tcttgcccaa aggcggaacg gtcaacgggg tagatctgag cgagtcaacg 2400
gtctatttca actgcaagaa tcgtcggtgg gataacttga agttcgattc ggtggaagtg 2460
ttggagaatg tggtagctca cgaaacgatc aacggggtga agcttgacct ggcggaattg 2520
gatgctcgat tcaggcaggc aagtgaagac atgtctgatg tgctggtaac ggaaaatcta 2580
caactagatg gaagtttgta cgtccatagc ataaatggcg taccgtggag tgacattatc 2640
catcgaatcg tgctgaagaa ccgacctaat cggctggctg atctgaagat caacggaagt 2700
ctgattctgc agaacgacaa cgtgacggtt taccatctga atgggctggc cttcccaatg 2760
gattatctgc tctccagcag tccgatggag tcgatcgtga ccggctacaa gaaatttgtg 2820
aacattacga acatcgaagc catggacgta gaacgcacga tcaacggagt tgacctgcag 2880
gacattatca ccttgcacga cgatcagcac atccctggtg acgttaccat cggtgaactt 2940
cacgtaaccg aacggctgga agtcaaggga gctatccgcg gcaagcactt ggatgaattc 3000
ctggacaacc caacgctgct gcaaaccacg tcgatcaaag ccgcgtgcca tttcaagcag 3060
ctcttcgtcg acggaccggt gatcgtggaa ggcaatctca acggcatgga tgtggacgca 3120
gtgctgtcgg atgtggtcta cgacacggag cacacggtca cgatcgaggc ttccaagcga 3180
attgcttcgg cagagttccg cgacaatgtc acgatcagtt ctaatatggt caacgagttc 3240
aaactggatc agtttgtgac gcgcagcacc gagcaggagc tgaacgttcg ggagatcaac 3300
ggaaacgtat ttatccgcga gttgcaatta gatgggctat tcgatggact gaatgcgacg 3360
gctttggatg tgagcgcggt gaagttgttt ggcgatcagt acacggaagc ttcgttgatc 3420
ttcaagaatc gggagaatgc tctgtacccg gacgtggaag caaacgagct taagattatg 3480
aaaactctga actccaaagc gagaagtgaa tacaaggata cggatcaaga agaactggtt 3540
ctgaccgggc agattagtct gaaccatcta catgtagatc atttgctgtt gaagggatcg 3600
agcttagagg gaccgtccaa aatgatcaac ttggtgcact taccgacctt cgacaacctt 3660
cgcttcagct tgacgagacc tcaacaggtc acagcaccgt tcatcgtgaa caaacttgtc 3720
gtgggaagtc aaatagcggc ggcttacgtt aatggacgag acttccgggg tctgaaggag 3780

```
agcatcgatc gcttggacaa cttcaagaac cacctgctac agggaagtat tccgattgag   3840
aatctccacg ttggaggcga tctgcaggtc aacatgttga acgacgtaaa ctttgatgcg   3900
ttggtgaagc aagtcatctg gttgaaccgc cccaacagga taccgggaac gatccggttc   3960
ctcgatcctc tgatgatcat tggaaatcta acggcacggg gacaggtcaa caacgccgtt   4020
ttcggagact ttttggaaga tgtgatccgg aaatcggcag gagtggcgga gtttcacggt   4080
tcaattacat tcatgaacgg tttggtagtc gaaggcaacg tcaatactga gagcatcaac   4140
aatatccaca tgagtgagct ggcgttgaga aacgatacga tctacttgca aggtgacgtg   4200
gaaatcttgg gagacctttt cgtggagcat ctacacgtcg agaaccatct gaatcaggag   4260
cccattcaga acctcctgaa ctcgtacagc tatgacgatt ccaaggacgt tcacacggtc   4320
aaaagtgata tgtacctgta tggtgcccaa atcggagcgc tgcacatcgg aggaatgctg   4380
aaccagatac cgaacgttga cgcccacttg gcatcggtca tccgcaagga ccaaaactac   4440
aacttcacca agccgctgtt gttcaagaac gaagtcttct tcgatcaagg tttctcggcc   4500
acctacctca accaaattga tatttcaaat atccagcaag acatcgttcg gatcaacgat   4560
ccgaacccgg tagagatcga agcggaagtg atcacgttcg ccgaacccat ctacgctgat   4620
cagttgacca tcaaagggga tatgatcact acaaatctcg ttgggtgcaa tccggacatc   4680
tggacgagca caggaatcat gatcaatagg gacgccgaga tctacgcgaa aacattcttc   4740
tcgccgggag ccttccgtac gaatcatctc cgcgtagact acatgaacgg acaaccgatg   4800
aacagcctga tcacgctgaa caccgatcag acgatcgaga caacgctgct cattcacgag   4860
atgacaatta cacagccgat ggatgtcggt ggatacgtca acggagttac gctaccgtac   4920
gaacgcaaga atacgctcat gacatacggc aaccagcggg tccgcctacc aacagtcttc   4980
cacacgatcc gagtccttca atcgctcact ctcccaccaa ttctgaacag taaacccttc   5040
ggaccaccgg tcgcgatcgg acccgaaatg ataatcgagt cccccatttc cttccgacat   5100
ctcatcgttg atcggctcga gacggaagac atgatctccg gggtggactt caaccagtgg   5160
tacgagaaca gtttgtggcg taagggccgc gatcaccaga ccatcgaagc gaagatttca   5220
gcccgcaatg tgcggttcaa cggagacgtg gaaggcgacg gcaagatcaa cggagtagac   5280
atcgtggacg tcgtgcagcg aatgaaggcc gccaagaaga acgtggaaga tcagctactg   5340
gactaccggt cggagatgcg atcgttctgc tccaacacca aacagctggt ggacaaatcc   5400
cagagccgga tgtacttctt caagtacttc gtgcagcgac aggtgatcaa tgagcatcta   5460
ccgatcgtgt cgttccactt cttcgatcac ttggggtaca atttcctggg cgtgaacatg   5520
ggatgcgaga gccacttcta ccaatgggat ccgactggga aggcattcgt gccgattttc   5580
aaatattaca cgggagtggt gcaggaatgg aaccacgtgg ttaatggcga ggaagctatc   5640
ttcctggtga cgcgatcgat cactgagctt acgcaatgtg aagttgcggg acttagcgtg   5700
tggttgttca cgggcgtaca gctgcagctg atttggaata cggtggacac cgcctcgatg   5760
caatcggtag ctgccgatcc tgcgaagtcg acaagcttct atgtactaac gccggatgtt   5820
gtggtggagt acggcgttga tggaagcact ttggagcagt ggagacttcc aaagagcgct   5880
ttgggttacg aattcatccc cagtaaggtc ggacttggac tggccttaag cgatagtaag   5940
ctactggttc tgctttcgaa tgtgaacaag actttcgagg aggattcgac tgatcttgaa   6000
atggcgctgt tctcttcgca atcgctgcac gatcgcatga aaaagacgta ttcggaaaag   6060
ctattgaatt ctacggtaag ctcagaagaa gtcagcgaca ttatccaccc agaaaatata   6120
```

```
tcaccactcg aagagcactc acatttcaac aacgatacgg tgatctatgt ggttgaaccg   6180

gagacaatcg acataccgga tccaccggta agtgaagatg aattgtcttc ggagacaccg   6240

atcgccagag acattcccca cggaggaatc ctgattgccg acaaccagca cttccccgag   6300

agagccaaag ggacgtggt ggcattttac gctggtccgc acaacaagaa gcgccatctg   6360

gtggcggtgt ccactgtgat tcacacagtc atccaaggag atcaggacgc gatcaagatc   6420

tacaccgaca tccagacggg caaactctac caggttctac cctgtcaccg tccttcgcat   6480

ttgaccgccc tggaactgcg ggacgagacg atcctcgcct tcctggaagc ccggcagacc   6540

gtgcagatct acatctaccg gggcatgcag ggtttcgtgc ggctgagcaa cttcaagctg   6600

acggctccgg ccagggccat ggccggggtt tcgctgccgc agccgttgac gattcgatgc   6660

aagctgcact acctggcgat cgccactgag cagaacgaac tgatcatgct acgagccaag   6720

acacaaggtg actgcggact gctggtccag gtggactgcg atgatgtgga gtgacggatt   6780

ttgatgtact gtttttgatg ttgtacaatg tttgtttgat tgtatgaata attgttattg   6840

ttgaaagtat agaaattttt atatggaatt ta                                 6872
```

<210> SEQ ID NO 241
<211> LENGTH: 6613
<212> TYPE: DNA
<213> ORGANISM: Aedes aegypti

<400> SEQUENCE: 241

```
tgagctgaac aatggcacac agccataaac agttggacca agttcaaggt caattcgaat     60

ccccactcgc caacacgttg ccgcagtaca tcttcattct tttaagaaac atgtcgtgtt    120

agatcgttga aatgttgttt cttttaaatt gtttgctcgt gctcgtctta ctaacgacgt    180

taaaactgcc cagttatatg gtgcgatgtg agctaccaca agaaccggac agtgatcccc    240

aaccagccag tgatgatgat ctcgacgggc tgaaagaagt gttctaccgc aatctaatgg    300

cggacatgcg catgggagaa tccgggaaac cgctggtcat caccccagag ttggaaaacc    360

gcgtggagcg acgcattcaa agcttcctca gtgcaacgga tggctccagt tgggttcggc    420

gacgtcgcca agccgttcat ggtggaccga taaccggcga gatggaatat caatcagtgg    480

agaatactgc ttctcatgcg gacatttacg ctgaaacggc tgaagccgaa aatcgctacc    540

tcaaaggttt ccgtgagcga ggatccatac cggttagctt tcccatcgat atctgcttgc    600

ttaaagtggg acgctccgtt ttcggtgcat cactgcatat tcggaaatcc aaggagaact    660

acaagaacca aaccatcgta acgttctaca agagacagaa gggacagttc cacaagtaca    720

aggagtactt ggcggctcaa gcacgacatt tcgactgtat ttcgcacgct tcgctcgggt    780

ttgtcgccgt ggtcaactac tacgacaatg cggctaacca agaattcccg gaagctcatc    840

cagggttcga cgaggggtcg cccgtgtttc aaattcatga ggacggcacc actgagatta    900

tacaaaagtt tcgacaatcc aatcagaata cggttcacat gtggactgcg gggaaccatt    960

tctatctgac gcacacgtac atcaatttga acgaaagcgt tgaaaacgtt tgccctctat   1020

atcgctggac cgggtatcac ttcgatgtga tcgatgagct gccgtgctac aattccatca   1080

acatagaacc gttctcgatc gagcagaccc tgtacatcgc catcgccaat cagatgaacg   1140

atcagtccgt cgaagaggac accttttccg acatctttcg gtttaactac gaacagcaga   1200

ggttcgagtt ccaccagaag atctacgtct actccgtgtc ggatatagcg tacttcttcc   1260

tggagttggg cgacgttcgc gaacactact taatcacggg aaattcgcga gccggcaagg   1320

aaaccgcgat cgataagctt gactacgatc agcattcgat cgtgtacaag ttcgtcgagg   1380
```

gatacttcgt gccggtgcag aagatcgaac tgcaccaggt gaagatgttc ctgcccgtta 1440
cgcacgagaa cggtgatttc ctgctactga tccgctgcaa aggcaagccc ctgttgatct 1500
acgagtacga tggctataag tttgtacctt cgcgaattga ttacacccgg aatgccttta 1560
gcacgggagt gtcgttcatg cgcgtctatc gacacattct gaacaccagt ctgatcgtga 1620
tcgccaacaa gcaaagctac gggactacgg cgaacctgtt cactcctatc tacggcgttg 1680
agaatgatct ccgggatgtc tacgggcagt ttatatcgtg gtgtagcgaa acgacccatc 1740
agttggagaa cgtcaatctg gaagaggttt ataacaaact ggctgcgctg ccgaagattt 1800
cgggtagcgg tgcaaggttc gagaaggata tagaagtcaa ggactcgagt gtggaaaagc 1860
tgaggactaa agttttacac acgaagcact tcatgttcaa ccaagaagcg ttcgattatt 1920
tgaacaatgt gaatgcacag atgaaggcgt tgaagcagaa ggcgaagaaa cttcgtagct 1980
tgatcgatga cagcctgaag ttgagtgaag cgatggaagt ccgtggggac gttagggtac 2040
cgcaggtgat cgcggccgac ggattgataa gggatctaga agcgaagaat gtcaacgatg 2100
agcgggtggt tcccagagtt gcgaatcaaa caaaaacacga agatgtgatc aatgtagatc 2160
gactgatcat tgaagacaga ttggcggtaa agttcttgaa cggctatgcc agtgaaacac 2220
tgttgcatac gacagatgat cttcgatctt tggaaggagt agacttgcat gcaaaagcgg 2280
ttgaaatacg cggagagttg ttcgtagata aggcaatcga tggtgttcat gtgtctgcgg 2340
acaatgttct acttcgtggc gtggatcagg tattcacggg aagaacacta cgggccacga 2400
actttacagt gggtaatttg gtggcaaagc agcttaactc gacggatgtt gggatgatca 2460
tgtcgtacct ggatcgagta tcagagtacg acagcgcaca gaaaagaaca gttgaaagtt 2520
atccgaaaaa gttcaaagaa atcagagttc aagatctcga agtcagcggt cttgtgaatg 2580
atgttgatat caaatatatc aacaagaacg ctttgaagat cgttggagat caagtgatta 2640
ctggtagcat aaacttcgat aatatcgtta caaggaaact tgaaactccc aacaaacgac 2700
tatctggagt agatttgaac tacctagtca tgaccgaacc gacgccggat caacaggatt 2760
tcactgtacg acaagacgta cagttcatca accctgtgta catggagaac ttacacgtag 2820
atgatcgcat caaccacatc aacgtggttg acgatcagct gcaggtactg ctgaaggacc 2880
caaaggaacc tcaactcatc accggtacca agtcgttcga caacgtccag cttctggggc 2940
caatctacct tcagggaaaa atcaacagta gtagtttgag taaattgaat ccggtttcta 3000
cgatcaccca agacgtatat ctggaaggcg actttgtaat aaccggagat gtatcgatca 3060
gacaactgtt gaacacctcc aacatatacg gatcgagcaa aacgttcaac ttctacgatt 3120
tgtatcacca tggccttccg ctaagtgcag cttccgccaa tcagaacttc gtcttcaagg 3180
aacctcttgt tgtgcatcac gcgttcgcca acaatctcaa tggtgtcaat ccgagcgact 3240
tcatcccaat accttccaaa aaactgcagc gcattaccgg gcggaagata ttcaacggag 3300
atctaaccat acgtggtgat cgagttgatg ctgccatgat caatgacatt gatttaaagc 3360
acttgaatcg aacgatactg aaaaagactg gcgatcaagt ggttaaggga acgatccatt 3420
tcaaggaatt gatcgcatcc accgtagttg cgaagacgac tctgttcgag gaacgacctc 3480
tgagtacgct ccttaccgtg aataccaacc aacgcatcaa gtcgaaggta cgctgcgtaa 3540
actgtaaact gacgatccac ggagacctga gcgtcggtcg aatggaaacg cacaacaaat 3600
ccaggctatt cggttatgat ctggatttcc tgttttctga cacactacac aaaagttacg 3660
ctcagcctga ttcgattgcg gtaactggcg gcaagggctt ctacaacgta accgttgggg 3720

```
aactcatact gctggatcaa gcaaccatca acggagtgga cctgattggg ctgaagaaga   3780
tcaacgatcc cctcgagaag gatgtcattg tggaggaaac gttgattttg aagaatcctc   3840
tacacgtacg caatgtgtac ttcaacggat cgatcaacgg cgtcccggcg caagaattcg   3900
gacgcacgtg gctgttgaac gagtacaacc aaacgttcac ggcgccgcag gtcttcgagc   3960
acgtggcagc cgaggggatg ttcgtcgatg ggtatttcaa tggagtcaag ctggaggact   4020
tggttcagga catctatttc ttggatcgaa gcgaacatct accggaggct atctttcatg   4080
aggggattgt ctcctatcag ccaatcaccg tcaagggtct cgtttccggt ttgaacctgg   4140
ccaccgacgt gctgttgaac tactccccaa atcgtcaata tctcaaggac gtacgaatcg   4200
atggtaatct gcttgtggcc aaccggatac acgtggagca tactttgaac gggatgaact   4260
acgctaaact acgggaatac gcaacatcta gtggcgttga acgaccgatg aacgtggagg   4320
ttcaagggaa cgttcatttc caccttcaac cggacgtttc tcagcttaat gggtacagct   4380
tggaacagct tcatcgggaa atttggctga cgaatcgaga tgaagtgctc acggggtcat   4440
accgcttcga caacgttcac ttcggcagct atgttcatac taagggtccg gtgaaccagc   4500
tggatttgga ggaaattgta cacagctacc tgagtgtatc gaagccacaa aacgtgacta   4560
caccgctggt tttcaaggga ccggtggagc ttcagaagat ggcaacattc gatagtataa   4620
acctggaagg actgctgaag ggagcgaagg agtctcgagg aataaatatc gtggactttg   4680
atagatacgt cctcaagaag aacgtcgatc aaaccattac tggaaaatgg gtcttccatg   4740
atgctgaagt ttacggaaac ctcaatttga ccaccctaaa cggcctggac atcagacggg   4800
acatcctgtt gaaccacgct gagcaggtaa cgttctctgg agccaaacga attgacaacc   4860
ttcgagttca taacctccga tgtccggatc catgcatcat ccaaggggtg gactttagcg   4920
aatggttcgc caactctgtt cgtctggatc ggaaccatac cgtcgagggc gtcacctatc   4980
tggaaggggc taccatcctg ggagacatcg aatcccgtgg cccagtcaac aatgttacgt   5040
ttgatcctca gagtttgctt ctgaaatcgg ttccacaaac gctggaaggt accctgtacc   5100
ttaaaaccaa atttccagaa cacaacttga tctaccagtc gtcgatcgaa tctttggagg   5160
tgaactccat caacggcaag gatttcaacc ggtttatgga caatctggca cgtgttgagg   5220
agggtaaagt aacgatagat accccggtaa cgttggttca gaacttgaat gccaagaatg   5280
tcgatacggg cgatagtaag atgttcgatg tgaacatcaa ccaacttctg caggaagtgg   5340
aatacggcga tcagctgagc caatacgaaa cgaagttgcg acggttgcac atggttggtc   5400
aatccttggt ggaaacactc agtaccaaaa ctccttatct gagtcactat caaccgataa   5460
agcctttgcc gggatacttc cgtagcgtag ttactattac gttacccctt tcaccaatgc   5520
cgatcgagtt actggctgcg cacgtggacg acggaaatcg tacggccgtt gagttctaca   5580
ggtggaacaa gaaggattcg cagttccata ttgctaaagg ttttccaccc atcacttatc   5640
cgacccttca gatcaccaag acgaaacgaa tcgtcttggg tggcgtgcag aacctcttcg   5700
ttgaatacta cgaccacagc cgtcatctgt atcgacagtc catccttgac ctcgaagcgc   5760
cggacttcac agcacctaag aagacaccga agttcacctc gatctacgag ttcaacagtt   5820
cactacccag ggatattgtg gcactgaagg tcttggatct ggactgcgtc ggactctact   5880
cgcctcacat cgatgggcta aacgtgtact gcctccagtt ggagaatctg gtgtactact   5940
tgaagttcca tcaactgctt accacgcccg ccgtcaatca agctcttcac ctagacggac   6000
gattgatcct actgagcaga gatagcctat tgcaagtgtg gcgaccacgg gccgactaca   6060
aactaggtct cttgcagcta atcaaaatag cccatccgac ttcgctaacc gtagccaaat   6120
```

```
tcgagcagca gctgttcatc gccattaatt cggaccaggc actgaccgag gcgtccgccc   6180
atcacggttc catagagatt tggcgcgatc tacgacccca gcatcacaac agcaccttca   6240
acaagtatca aaccatcctg accaagatgc ccaagcagat ccagttctcg gtcctggcaa   6300
ccacttcgga actgatgctg tacactttga cggagaatcc gttccacccg ttggtgatct   6360
accgctacga gggtgtggcc ggattccgcg aatatctgac gagcaacgcg ctgcgaacca   6420
gcagtaagcg gttcacggtg gtcaaactgg atcgcaaaca gcgggaactg ttggcgttgg   6480
tgagcgatcg ggaagtgacg tggatcgaag ctgtcataaa ggggaggtag ggaatttatg   6540
tagatttgta cgcacgtaca aaacctggtt ttgttgatta gttttgtaat aaaatgtttc   6600
gttctacgtt cga                                                      6613
```

<210> SEQ ID NO 242
<211> LENGTH: 3185
<212> TYPE: DNA
<213> ORGANISM: Aedes aegypti

<400> SEQUENCE: 242

```
ctagccatct ggtctgtgca aaactgaatt ataatccaac ggttagctat ttgaggggtg     60
accattggcc atcgcatctg aaccttgaaa tgtcgaatgc ttatgtccga ggattcataa    120
aaaacctatg ctaccacccc cactttcttt acaacacatt tccactgaag ccgttctgcg    180
tggatccatg tccactgtgt caggccgtaa agtcttcact ggtcagcttc ataccgatac    240
cttggttgca gatggagtcg atgcaatcaa cgttcaaagc ttggcaactg acttcagcac    300
tatggcgttc ctagacggag tcaaagaaat tgaacatttc tcatcagagg aatgttatat    360
cgagctgctc ggtggattga cattgcaaga gtaccagaac gtctccttca acgctatagt    420
ggagagcact gtaaatacgc acaacccgca aactctggag tatttgtttc tgccggatat    480
aaaagttgaa catttccgag cagcgctgat caatggagtt aacgcagaag atttcataac    540
cgaaatagat aattttacgt atcgtgtaga tcccttcgcg gcgcaattta aaatcgataa    600
cctcattgtt aagaaaaacg tgatttccac cagccaaatg ttcatggact atttgaacac    660
aatcgctgtg aaggaatatt tcaaactgct gaccctaaag ggtgatagtg acaaagcgca    720
gcagtgggaa atcggaggca gcaaaacctt gcagaaaggc atggccgtcg atggaaaatt    780
gaatgtggtt cacgtaaatc ggctaatcct agttaacata ctctataatt ctgccaggaa    840
aacaggtcct atgaatattg cgggattatg gaacataacg aaactggcga cgaagtactt    900
ggcgaccaaa caaataaacg atctaccaat aaaacatttg cagaattcca atttgaaaag    960
cttcaaaatt aaacacgaca tttcggttgg aacattggcg atttctgcga acatgcatgg   1020
tcatctgttt ccaaatagtt catcagtttc gatgccccca aatatccaga tgctggccag   1080
tttgactgtc catggatcgt tttgctggga acattggaag cctggaacac tcttgttcga   1140
tgtgatgtta tcagccgtaa ctggttcaac gaatgttttt aataagaagc ttgttttccg   1200
aggacaccac gttgaaattg agaagttacg aaacgaaggc aaaattttca gcaagagctg   1260
caattttgtc aatttgctaa tggactcagt gaagagaaga caacccaatc tcgtattcag   1320
cagtctcgga aaaacgttca gggaagtggt ttgtcttgga tcagtggcat ctaatgattt   1380
agttaccgca acgctggtga atggaatcga tgtaattcat ttgaatagga gcattcactc   1440
agttggtcac caccaggaaa tgattaaatc gacaaagtac tttgaagaag aagtgaaggt   1500
tgtgcagttg ctctgtcatg accaactggt ggacggtatt tatcctagca atttggacct   1560
```

ttactcggac gcaagccaga tggtcaagaa acggtatcag tttgaaaaac ccatttcggt 1620
catcgggaat ttgtacgtcg atgcaatcaa cgatttctcg ttgcaacact tcctggcgac 1680
tcgcgtggtg aaaaatagga cgtatacgca ggaataccat caggaaaagt ctcaacaagt 1740
aacaggattt atcacatttt cgaacctggt tttatccggt gaatacaaca cagttcacgt 1800
agtcaacggt attcctgtaa gcgagattgt atccagatcg tccaatgagc atcaggttat 1860
ggttgagaca aagcatttga caggcaccat tcagcttatt ggacctacat cggtcatgaa 1920
gtgtaacaac gtctctttgt tggatgcata caaatctagc tttaaagcca attctgcaga 1980
gattgctttc aaagacttga tttttaattc taatggtgtt ttgcaaaatg gtttgaccat 2040
tgaaaacaag ctgaatggag tatcagtgca gaaaatgatg aagcttcggc tatcgtcggt 2100
agaggagctg ctgccattga ttccaataat ccgagagcag atatcggtct ccaatagagc 2160
atacctaacc aacaaaccaa aggatttaca catgttgtac atagaaaata ttccgctgga 2220
tgaaagaggc accatggtcg gaaagagcga aggtcaacgg accaatgaag catctgatac 2280
tgttaatttc gagaaatcct gcagtaatgg catatatcgt ttcaacgtta ctattcggca 2340
gaaatcgtcc aacggagata taagttctgc cagaaccgta ttggatggag tgatgataaa 2400
atccgattgg atggaaatag caaataacgg cgaaatacaa acaatagtcg tgtcacaagt 2460
cgaaaagaat gccaagtact tcctacttct ttacgtcaat cgcaatggag aactcagtgt 2520
tcaacaggaa cttccattaa gctcatcggc ggctgtattc tacttcgtac acgtaaacga 2580
ttcagcactt ttgctggcag tatcagattc acaccccctt caactgggcc atttggcacc 2640
gaaactcaaa ctattccgct atgatccgga tgtaatgcgc ttcgtacatt tcaaaacgct 2700
cagtggccat tacaatgacg ttgttgctat cgatgtcgag gacgttataa tgtttgcagt 2760
ttcagagcaa ggttctaaca tggtggaaat atttgtgctg gaccgttcct actcggcgtt 2820
attccaaaag cttatcttcg attcgacttt ggcgtcaatg aaagcgttca aattacaagg 2880
atccccagtt ctacagatat caacggtcga taatttggtc tacgtttaca attacagtat 2940
tcttgagggc tggcggcagt tgtcgtacgg caggattccg tctgacgtga actaagctgt 3000
ttcttattaa attttatcat tttaaatgat attttctatg tttattgtgt tattcatgtt 3060
gtgaatattt tgttctagta tttgtagtta gcaatattgt gttctaaaaa atatttcttc 3120
accttcactt aagccgtata ccactcatat gattatctag ggcaattaaa attgagtcaa 3180
cttta 3185

<210> SEQ ID NO 243
<211> LENGTH: 5441
<212> TYPE: DNA
<213> ORGANISM: Aedes aegypti

<400> SEQUENCE: 243
tgaatgtccc actcaacatc caaaatcttt ccggaaaaag aacaagtgac gatccggatc 60
tagaaggagc tcaactggtg tgtagcttcg tggggccatc atccacggag aaacctttag 120
ctgggaatga ttcgatgatg ttgcaatcat cacaggaatt gtttgtgggt agtacgaggg 180
ctcgtggcca ccatcggcac tgtcctcgag gcaaggttcc ctgtgcagat ggcattcagt 240
gtgttctgag ttcacatttg tgtgactcgc gggtggactg tttcgatgga agtgacgaat 300
cgcactgctc gtgtttgtca cggttggcgg gcaaacggcg ctgtgatggt tacgtagact 360
gccctctcgc ggaagatgag atgggctgct tcggatgtga caagttctcg ttctcgtgtt 420
tcaatacgtt ttttgagtat caggcttcgc atcattccga gacaaggtgc tttacgttga 480
tcgagaagtg tgatggcttc aacaactgca tgaatcggaa ggacgaacag gattgtacga 540
tgttggtacg agacttgaga agtcccctgg cgtttgcggt tggccattca gtgggtgtcc 600
tgcatcggaa ctacaagggt aagtggtatc cggtttgtca caatccgttg aatctggcac 660
gagaggcttg tgaagcagaa cttggaccag cggatcgcga tccggtgatt ctgcagcacc 720
atggagatct accgggacca ttcattcaac caagtccacg aagtcatcac gtgttccaac 780
cggagttcac cgatacctgt aacgggttga taaactatgt taagtgtccg gcaccgaagt 840
gtggatccag caagcagaac gagatggaaa atcttcgtat taaaatccgt ggaaagagaa 900
atgctacaga gttagtgcag atcgttggcg gaacgaaagc tgaaccggct gcttacccat 960
tcattgtggg aatcttcaga gacgggaaat tccattgcgg tggtagcatc ttcaatgaac 1020
attggatcgt aacggcagct cactgttgtg acaacttccc aaggcaccat tacgagctgc 1080
gagcgggtct tctccgtaga cgtagcttct ctcctcaggt gcaggtttca acggtaactc 1140
atgtgttcat acaccgagga tacagcgcgc aaaagatgat caacgacatc agtctgatgc 1200
attcggacag accattccag tacaaccgat gggtaaggcc gatctgtcta cccgaccgac 1260
acatgactac caacgatcgg gattggattt ggggtccgaa accgggaacg atgtgtacgg 1320
ctgttggttg gggagcactc agagagcatg gtggatcacc tgatcatttg atgcaggtta 1380
cggtcccaat tctaccgttc tgcaaacata aaaatgatcg cgatggactc gctatttgtg 1440
ctgccgaaat gagtggaggt cacgacgcct gtcaaggtga ctcgggaggt ccatttgcct 1500
gcattagtgt ctccagtcca catgagtggt atctggcggg agtggtaagc catggagagg 1560
gctgcgctag accaaacgag cctggcgtct atacgagagt tgcactgttc aacgactgga 1620
tccaaaggaa aactagggaa gtgcttactt cgtcctctac gcgtcaggat tgtcccggct 1680
tccagtgctc agttggggta tcgttctgca taccaaggca gaagcggtgc aacgggaagg 1740
tagattgtct tggcggagaa gatgaactaa gctgttcgct ggatcaactg ctagctgaat 1800
cgatacagga aacaaccata gcgacgacac caaagaatag tactgcgaca agttcaacaa 1860
ctgctgcagc tactacagaa gctgtcactt cgaagatcga tttcctcgcg gagaattctg 1920
aagcatcgga tcctgctact accgtgacgg aagcatcaag cactgaaact gctactattg 1980
aaacaatgtc ggcaacttta gagacagtat ctgcgaaaga tttgagtgat gatattgctc 2040
aaatatccac tgcggcaact acagtagaac cgaatactac cttagatatg actgtcagca 2100
gctcaacgca aagtgtttca acttctccgg aaaaagttga agaatcaaca atggatgaaa 2160
gcacgtcatc cacaactgaa acaagcttca cacatccaac aacgatgaac tccgaaacta 2220
caactaacaa tgcaaccact ctcatttcgg aaactacctt gccatctctg tcaacaaaag 2280
aagacaacgc tacttcagtg gactacagtg ccacgatatc tactgatcaa acaacacata 2340
caccttgcac aacatcccct gccgctgatt ccttagacga ctcatcttct gctcattcct 2400
caccggcaaa cgattcagaa cccagcacag aaagtagcgt acatgcaacg acagaattca 2460
ccacgacagt tatagaactg acctcggtag aatctactac caatatcgaa gcaacatcct 2520
tagcggatcc ctcaaatgcg tcaatcacaa cgctaccctc cgatttggtc gaagaaactt 2580
catcctcgtc aacaaccccg accactccag actctacctc atcaactcaa cctgattcct 2640
cccacagcag cacctcaagc gctccttgga tgcagattaa cgaagctatc gcaaatttga 2700
aacctcgtcc acctagtttg gatcgcgata tggagatgcg tcaactggaa ttgggcgaca 2760
gcgtcgcagc gactcgaaca gacaacgcta cgtcgacaac tatctctaca gcttccagtg 2820
gtacaaccga tttcaccagt tctacaccga tgtcaaccac cacggtggaa agttccagca 2880
cgacccacgg cgatctggaa cacagcgaaa ctcaaatcga gcccgttgaa gccgaagcga 2940
ccaatgcttc tgtggaggag catccatttt tgcgcgaaat tcacaatctg gtggaggaga 3000
aaacccgtcg gttgaaccag ttccggttgt ccatgcacta cctgcacaca tcgctgagga 3060
accaaacgca ggacgcgaac gaaacttcct accaataccg gcggttcaag tgttccaaaa 3120
tccgacaatc gatcaacgtt gcgcaccatt gcgatcggat catcgactgc gaagacggta 3180
cggacgaatt gcggtgcacg tgtcgcgact acctgaagga taagtacgac ttcctgatct 3240
gtgacggcaa aacggattgt ttggatttga ccgatgaagc agattgcttt tcttgcacgg 3300
ctggacagta tccttgccga atgagcaaag tctgcatcga cgagaagaag ctgtgcgatg 3360
cggttccgga ttgtcctctg catgaagatg agctggattg tcttgccctc acggatggtc 3420
acaaggtcta ctttgatgcg aacaacctct cggaattcaa atacgaaggg ctggtcacta 3480
agaacactaa cggaacgtgg gatctgatct gtggagcgga gatcaataac aaatctgtgg 3540
aatcgattgg aaaaatctgc tctttcttgg gatttgctgg gtacgaaagc tactatcaaa 3600
ccgtcctaac accactggtg aacgaaacgg tggatttgga tcatcagccg ctgctgatca 3660
tgtcgtatcg caatatctca tcggagccaa actgtaaggc cctccatata acctgtgcgc 3720
cattcatcaa tgctactgaa catgagatca gtcacttcga gaaccaacat aaggaacaac 3780
cagtgcaagt caacattcgt ccaacacatc cgatacagaa tatcacctct ctaacgcaca 3840
tcaccttcca agaaaacgct cacatcgagt tcatcgagaa cttcggcgat gactacgatt 3900
ggccatggaa cgccgacatc tacctggaag gagtgttcct gtgcagtgcg atcatcatcg 3960
aggtcaactg gatcgtggtc gacagttcct gcatgaggat gatcaatctg aagaacgatt 4020
acctctccgt agtggccggt ggagccaagt catatctgaa gatctccgga ccatacgaac 4080
aggttgttcg cgtggattgt tatcactttt tgcccgaggc acgcgttgtg atgcttcatt 4140
tggcgaaaaa cttgaccttc accaggcatg ttctgccgac attcattccg gaaaagaact 4200
ataacattac ggataaccaa tgcctcgccg ttggtcagga caagtatgga agaacgcgta 4260
cgttacgagt ccacatgaac atgacgaatt gcgaaccaga ggaccatatc tgttatcagc 4320
taaatccaga taacggcata taccatgcag atcactgcta taccgaaaat gcatcacgta 4380
ctggagtcgt cgtttgtaag tctaaggtct cgggatggta tccagtgggc ttctatcaga 4440
acaagcacgg cctttgcggg ttcaacgaag tcgtcaaaat gatctccctg aaggaattct 4500
acactgacat tcaacatgtt ttgagccata agaaatgtga ctacgaattt cctgagccgc 4560
tttgcgatgg agtgaggtgt tggcatggga aatgtattgg ccattctttg gtttgtgata 4620
acaaaatgga ctgcgacgac aactttgacg agcgtcccga agcgtgcaat gccataaacg 4680
atacgtcaac tgcctgtcta ccgacgcagt tccgttgcgg gagccatcaa tgcgttgata 4740
agagcaagtt ctgtgacggg cgaaacgatt gcggtgattt gtcggatgag ccacacgaat 4800
gctcttgcta cacttatctc aaggtaaccg atccatctaa gatatgcgat ggcgttcgca 4860
actgttggga caaatctgat gagaatccac gactgtgcaa gtgtgcaaaa acgagcttca 4920
gatgcggcga cagcgaagtt tgtattcctt acgatcacgt ctgcgacgac gagatcgact 4980
gccccggaga agaagacgaa cgatactgct atgctctaca gcagaatcca gcggagacca 5040
actacggtga agtgatgcaa caaagctacg gcatctggca ctcaaagtgc ttccctaagg 5100
acgataaata cgacgagcaa acgatcaagg aaatatgtca tcgcgtcgga taccaacagg 5160
tccggaaggt ctacggcaga aaggtgcttc cggagtcacg tctgagaact tccaatcgga 5220
cacatgatcc cgtcgatagg ttacgcggcg cagcaaccaa ggcagttgcg ttcaacaaat 5280
tcttcaaagt gaatatcaac gaaaaacaag cgatcttcat gaaacccagt aggccgttgt 5340
acactctggt caactgggat gccgaagacg agcagaagtg cgatcggtta gagatcaact 5400
gtggagatta atttttgaaa taaattattt gtaaaccgca a 5441

<210> SEQ ID NO 244
<211> LENGTH: 2095
<212> TYPE: DNA
<213> ORGANISM: Aedes aegypti

<400> SEQUENCE: 244
ttgcacgggt tttccaccct cattctggac ctatcgccgg gaacctgtat ctaataataa 60
aatcgccaga tttatgacag cttggcagac aaactccgag catgcttcgg agctcgacaa 120
ggtgcaaaca atgaatcaca tttttaaatt attgcgattc ttttgctgtt tggtggcgtc 180
tacaatgtct gccccactct gttagatagg atcgaaaaat acttcgactc attgaacaac 240
ttttcaagat cctattattt ccgttgtggt gacatcgtta tgatgatgcc gatacagtgc 300
aaggggtggc atagtgttgg caatcacgaa gtgcaaactt ggtttattgc aatcactttc 360
gtcgtgggaa tgcgttctgt gattcgattg cagtgttgtg cctctaagga agtgaaggtt 420
taccgtcgca cagcctgcag tcaaggtctt ggaaaagtgt catcaaccga aactacaatt 480
tgacatccac accttccagt caatatgagg ctcaatcact gaatgaacaa actccaatgc 540
gaaatgccga ggatgccgtt acacttccag tcatcgaatc gtactcgact ctgttatgat 600
gacccaagca actgttttgt gtggtgacac aattaaaacc aaacaccagc tagaatcata 660
agccgctgaa gtgcgttgcc gttcacccac tgcattcagt tcgcgtaaga cggtctcggt 720
agatagttta attacgtgtg agttcgcggt gttaattgaa agttcctcgt gtgacagggt 780
ttacggcaac aatatgaaga aacaactgct gtggatactt tctgcgctga tagtcgctgc 840
cggagatatt ggcgaacgag tggatgaggg tgatgttacc aattttgaca catttttggg 900
cgcgtaccag aagaaataca aagccaaata ccgaatggac cgaagaaaga gggctttcaa 960
gaagaatatg caggaaattg aagagcacaa tgctaattac gagcaaggca aaagcacatt 1020
ccagatgggg gtcaacgaac tggctgatat ggacaaaagc agctacctga agaagatggt 1080
ccgaatgacg gacgcgatcg accaccggaa attggacgtg gacttcaacg acgaaatgct 1140
acaagccacg aatgccttcg gcgaagaatt tgtgcaagcc acacagaaca gcatgccgga 1200
cagtttggat tggcgcgata aaggattcac cacgatggcc gtcaaccaga agacgtgtgg 1260
ttcctgctat gctttcagca ttggacatgc cctcaatgga cagattatgc gccgtattgg 1320
tcgggttgag tatgtcagta cccagcagat ggtcgattgt tcgaccagtg ccggcaataa 1380
gggatgtgct ggaggatctc taaggtttac gatgcagtac ttgcagaata gccagggtat 1440
catgaggagt tcagattatc cgtacacttc gtcggtaagt atcattttca gggtgttgtt 1500
ggttttcctt tctcatttcc tgcaggccag agcagtaagc agtcggagta tttccaagaa 1560
gaggtaatca cttccgcaaa ctttaatcga caaaacaaat tcccaacacg gcgtgcaggg 1620
acgagttgga cagaaagctt gtaagcaaca attggcatca tgcaaggcac cagcaacaaa 1680
gttggtgact agtttagtgt gtagatcaca cccaatcaag cagttctcgg tttccgactc 1740
ggttcaagaa tgggccgtgt tggacgtcgt cagtggtgtt tccccaaagg agcaactttg 1800
tcgtgtgacg gcgagtcata cagtttcgtt gaagaatgct gaatgatggt ggaaaatttg 1860

```
tttctttttt ttcgggtgct ttggaagtcg gcacggaacg aggagaagtt cgtgttaaag   1920

agttgttaaa atatctgccc ttttaagtca tagtttgagg agcaacatgg ttagtatgag   1980

ttgactactg ttgaaataaa ctgggtcgac gcgtgatttg atgtactctt tctttttat    2040

agtcaagcag ctggtgttaa tgtgagcaaa taaacttaaa ttgaccttcg tgtaa        2095


<210> SEQ ID NO 245
<211> LENGTH: 1969
<212> TYPE: DNA
<213> ORGANISM: Aedes aegypti

<400> SEQUENCE: 245

gttgatcctc cggtcgtcag tcgcggtagt ttgtgcctcg gaacaggacg gttcacttag     60

agaagaagga agaaccgggt gcgcggtcga gaactcttga ttttagcgtg tgtcgtcccg    120

ttttggtgaa gttacagata gattatacag aacatgtgga attcgtcggt ggtgtgtttg    180

gcccttctgg gggtcctggg gtcggttagc ggaacgacga aactgcagga acgctacagc    240

tggcgtcagt tggactttgt gttcccgaac cagcagctga agcagcaggc cttggccagc    300

ggagactacg tgcccacgaa tggactcccg gtcggaatcg aacgctggga gaacaagctc    360

tttgtgtcgg tcccaagatg gaaggatggt atcccgtcta ccctgaacta catcgatatg    420

aatcagactc cgtccgggtc gccaccgctg atcccttacc caagctgggc caacaacgtg    480

gccggagact gtcagaatgg cctgtcgacc gtgtaccgta tcaaggctga caagtgcgga    540

cgcctctggg ttctggacac cggtaccgtc ggaatcggaa acaccaccca gcagctgtgc    600

ccgtacgcgt tgaacatctt tgacctcaag accaacaccc gtctgcgtcg gtatgaactg    660

cgtgccgaag acaccaacca gaacaccttc atcgccaaca ttgccatcga catgggacgc    720

agctgcgagg acaccttcgc ctacatgtcc gatgaactgg gctacggact gattgcctac    780

tcattcgaga agaacaagtc ctggcggttc gagcatagtt tcttcttccc agatcctctg    840

cgcggagact tcaacgttgc cggcctgaac ttccaatggg gtgaggaagg catcttcgga    900

atgtcgcttt ccccattgca gtccgatggc ttccgcacca tgtacttctc ccattggcc     960

agtcaccgtg aattcatggt ctccactcaa gtcctacgcg acgaagaagg tgccgaagag   1020

agcttccaca agttcaccta cctgaaggaa cgaggaccca acagtcacac tacatcccga   1080

gtcatgagcg aaaccggact gcagctattc aacttgattg accagaacgc cgtcggatgc   1140

tggcattcgt cgctccctta cagccccgaa aaccatggaa tcgtcgaccg tgatgatgtg   1200

gaactggtct tccccgctga cgtcaagatc gatgccgaag agaacgtgtg ggtcatctcc   1260

gaccgtatgc cagtgttcct catcgccgag ctggactaca gcgatgtcaa cttccgcatc   1320

ttcaccgctc ctctgagcac cctggtcgct ggaaccgtct gcgacgttag gccttcgctc   1380

cgaccaggtg ccatccagtc caagttcggt ggatccgatc tggccaccta tccaggcacc   1440

accctgctcc cagtcgggta cacacaaccc atcagctata ccccgtcctc gtacgcccca   1500

accgttgccc ctgtcaccaa gtacacagcc gctccagcgt acgaccatcc cacatcccac   1560

atgtacacga cccaagaata tccgacgacc gccaaggcgt accacttcaa caagtaccac   1620

aacgtagagt atcaatcgca tggaaatggt caagctgact accacttcgg acacggtgga   1680

cactaccacg atcacgacca cgcccatgac tacggtcacg atcacggata ctacggtggt   1740

ggccaacgcc gccattgggg agcaggcgcc aagaagcccg aagcctggaa gcagcagctg   1800

tactagaatc gagagaatgc accatactag agatgtaacc gcacaatttt cgttttagag   1860

aaatttaggt aaattatttg tcagtgtaaa agtacccgtc aagtttctta tgtttaagtg   1920
```

ctaagatcga acgaaccaac tcaagtcgaa taaagtaaga tttttgtta 1969

<210> SEQ ID NO 246
<211> LENGTH: 2665
<212> TYPE: DNA
<213> ORGANISM: Aedes aegypti

<400> SEQUENCE: 246
ttgaaatttt tgaagagagc aaagtgatta ttggaaaaaa aaatgtagta gttttttctt 60
attaatccat atacgagcag catttgtgct agatgtattt ggataaaaat atccttgtta 120
aataaatgtt ggaattcttt gtcgaatgta atgtgtacaa tttaaaacct ctcggttatc 180
ttcctggatg aacctctgga ttgttttctg aagagactcg ttagagaatt atattaagga 240
atattttgct tctagagcat tgtttcccca acttctttga ctttcatccc cttgttcaat 300
attctttgga attaacctct cagatatgta attttagcat taatattgaa ctctataatt 360
ttttgaattt cttatcaata tcttgaaaca ttattgagtt cactagtgtg gtacttagaa 420
cttgctgaaa atgttgaaga tatgtggtgt tgaagcctat gcacgccaaa caatgttctc 480
gattcgcata tctatatacc ttagcgtaac tgaagaacca tcaatcagct ttaatgaacc 540
caagataacc tcggatgcac ttccaatttt gttcaaattc tctcgtgatg tatctctata 600
atttgttgag cttagaaaaa gcgtttttag acctaaaggg gtccccatgg atccactttc 660
tttcgtattc aagtaagctc caagccttgt ggaaaattta ttttctcaca ctaactctac 720
atatgtgtct gagtaattca ctcaattacc aattaaattc ctgattacca ttcacttgct 780
cgtcatgtaa aaacacagac aagctagcta tgatgctaat gagttacttg gttgaaagat 840
catggttagg gtaatgttgt ccttgtccgt actgatattc agaatgagtt cgcgggccgc 900
ataaaacgaa ggcggtacga gaccgttggc catagtttgg taactactgc aacatttcaa 960
acatagagca agtcttgcaa aactgatgct ttatttgtac ggcgtctatg cttgacgcaa 1020
tagctccatg gtttgcctaa ataagtcacc atttttacaa cagccagtct acgccaaata 1080
cagcgagttg cgtaattgca gcaaaaagga cataagcatg tccagcttta cgcaatagct 1140
cgtggtatgc attgcatcga ggttctcgac catttattca cgtatttgga caacattgag 1200
ctcatcgcac gtgttccagt gaccgaactt ttctcagctt tcagttgcaa aggtcaattg 1260
tctgccgttg ctaaatattt ggcattgatg aatgttctga agaacaaaca cttctttagt 1320
tggtagcttt gctgttatta ctttcagtag caggttataa aagctgctaa ttcggaacga 1380
gttcatccag tttaatttag ggggtgtgtt cgttgctatt tggatgcgga ccgcacaaag 1440
aggtacgtac ggaggatagg cgaacttcat agctgagtct gctgagaaat tcgttctaat 1500
cttgctgaac atccacagat gcgaggtaac atcctttggc tgttggctgc agtgacgcag 1560
ctgacggtga ccagcgttac ggcgttcgcg aacaattcaa atgctatcta cacctgggaa 1620
ggtggccgca tcgagtggcc atgcccgacg acaaagcgat tggttaaggc tgctgcaaag 1680
tacactccta aggatatcat cgcaatggct tgcgcaagaa gtggcgacaa gaccctctgc 1740
gcgatgccaa gataccgaaa tagtattccg ataaccttgg gacaaatcta cgcaacaaag 1800
aagggctgtg acgtcaagtt cgaacctttc ccgtgctgga ctgagcaaga agagaacaac 1860
tgcaattcgc tacagtccgt tattgacatc tacgctaccg gtgacttcgt gtgggttctg 1920
gacaatggta tacttaatgc attgagaagt cctattcaaa gatgcccagc gaagatcgtg 1980
gtttatgaag ccaaaacggg gaaaaagatg aagacgataa accttggccg atacgtgacc 2040

```
gagaagtctc gtctccagta tatgcaggtc gagtgcttga agggtggcca atgcttcgtg   2100

tacatcagcg acgctggaaa caatgcaatt atcatttacg acgtgtctgg aggtcgtggc   2160

tatcgtgtag tactgccgaa agctgtgcat cacggatgta gattccgcga cgttctgtac   2220

attttcttgt cgtatcacaa ggatggaaca aaactatttt tcacctatct gggtggacga   2280

cgactattcg ccattgctac ggatcaccta cgaaaaggtc atggcggtaa cattgaagat   2340

atcggggaaa agccagggtc cttcatttac atcggaccag acggagcaac aggtgtgttt   2400

ttcagagagg aaggcgacag caatgtattc ttctgggaca caaaaacatg tctcaagaag   2460

tcgaacttca aactggtgtt caagagcagt gagggattat atgcaacgga tgtgttcccg   2520

gaccatgaaa tcaatcggtt ccttatattg gagtcagatt ttccaggtta tatggaggag   2580

aaagctggat gtggtacact gcatcagatc tccctgcttg acggggctac ttgttaatat   2640

agaaatttc ctgtgtagtt ttaaa                                         2665
```

<210> SEQ ID NO 247
<211> LENGTH: 1545
<212> TYPE: DNA
<213> ORGANISM: Aedes aegypti

<400> SEQUENCE: 247

```
ttcaaatgcc atactgaact ttgcatcttg ctgtgcgcag atcattggca caattggcat     60

gaacggtcaa tgtttagccc tttcgtcatt acttctacgt actggtcaaa tgtggataac    120

atctaacaac aagattgagt aagtttgcct aaacctgttg ataaaacaac tgccactgtt    180

tcgaaaacaa cagagcttat aaaaccttgt tgttaccaaa ccttttccca gtcgctatac    240

atccgtcggt gtatgtttga ttcgcgttcg cgttgtgcga tagttaattt ccctagtgat    300

cgaagacttt tagatacctt acgacatgtg gtttcggata ctctccggaa gcctactggc    360

tgcgatttgc ctagccgaaa tcaaaccctg cgagtacatg gacagaatct accgaatcaa    420

cggaaactcg atcgactttc cttgtgaatc gacaaagaac atttttatca ctaccgagcg    480

gtacaaaccg tgcagtatca taccgatgcg gtttcaaatc gacggagaca acgagaggtg    540

ttttgtggtg ttaactcgac ttcgaagcgg aaatccagtg acgctgggag tgatcgacct    600

gacccgtccg agctgctatg cgcatatcaa accttacccg tgttggtctt accaggaaga    660

aggcaactgc aatgcgttcc agtccgtggt ggatatattc attgatgtta aaaaaaagat    720

gtgggccctc gactcaggca tttgcaactc tttggagcaa cccataaaac gctgcacagc    780

aaaggtgata gcgtttgacc tggaaacaga taaaacagtg aaaacggtgg atctaagcga    840

cattctgaag ccacactcca gaccacagta ccttgtgacg gattattcgc ccaatggatt    900

cccgtacgtc tacattagcg acgctgaagg tgccatcatc gtactggaca tccaccacaa    960

caagatgtac cgagtagtgc taccacgtgc catttctgct ggctgtggcg aatcggatgt   1020

cctatatttg ctactggtac gaagacccaa aaaccaaaac atggtcatat tctcgtatct   1080

gtgcggtaac aaggtctacg gtatcaaatc ggaatttctg cgcacgggac gaggctcgag   1140

tgctatcgtg gagctcggta gcaagactaa gcattccgtt ttgctcggga cggacggaag   1200

caacggtgtt attttgaggt atagaagcga aagcgaactc tacaaatgga acactgatca   1260
```

-continued

| | |
|---|---|
| accgtacaag gagtgtaact tcgaattggt tcaacttgcg gaggagtgtc gcttgagcac | 1320 |
| gcatgtcgcc cctggaggaa aagatgctct gatgtactca ttgtcatcca atgtggccga | 1380 |
| ttacttaaat cacacctgtg gcgcaggagg tgcttcagct cgactcaaat atataagtaa | 1440 |
| agaatgtgaa gatgattgtt attaaaataa taattgaaac ctagtaatta acatagtgta | 1500 |
| agaaaatcaa actactcaga tctactaaat aaaaactaaa aaata | 1545 |